United States Patent
Payan et al.

(10) Patent No.: US 9,511,058 B2
(45) Date of Patent: *Dec. 6, 2016

(54) METHODS FOR USING CARBOXAMIDE, SULFONAMIDE AND AMINE COMPOUNDS

(71) Applicant: Rigel Pharmaceuticals, Inc., South San Francisco, CA (US)

(72) Inventors: Donald Payan, Hillsborough, CA (US); Yasumichi Hitoshi, Brisbane, CA (US); Todd Kinsella, Redwood City, CA (US)

(73) Assignee: Rigel Pharmaceuticals Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/325,012

(22) Filed: Jul. 7, 2014

(65) Prior Publication Data

US 2014/0323460 A1 Oct. 30, 2014

Related U.S. Application Data

(63) Continuation of application No. 13/077,539, filed on Mar. 31, 2011, now Pat. No. 8,796,254.

(60) Provisional application No. 61/319,864, filed on Mar. 31, 2010.

(51) Int. Cl.
| | | |
|---|---|---|
| A61K 31/5377 | (2006.01) | |
| A61K 31/4545 | (2006.01) | |
| A61K 31/506 | (2006.01) | |
| A61K 31/454 | (2006.01) | |
| A61K 31/496 | (2006.01) | |
| A61P 29/00 | (2006.01) | |
| A61P 35/00 | (2006.01) | |
| A61P 11/00 | (2006.01) | |
| A61P 11/06 | (2006.01) | |
| A61P 9/10 | (2006.01) | |
| A61P 25/00 | (2006.01) | |
| A61P 39/06 | (2006.01) | |
| A61K 31/437 | (2006.01) | |
| A61K 31/4427 | (2006.01) | |
| A61K 31/4525 | (2006.01) | |
| A61K 31/4709 | (2006.01) | |

(52) U.S. Cl.
CPC ......... *A61K 31/437* (2013.01); *A61K 31/4427* (2013.01); *A61K 31/454* (2013.01); *A61K 31/4525* (2013.01); *A61K 31/4545* (2013.01); *A61K 31/4709* (2013.01); *A61K 31/496* (2013.01); *A61K 31/506* (2013.01); *A61K 31/5377* (2013.01)

(58) Field of Classification Search
USPC ........... 514/210.2, 316, 318, 23.5, 258, 320, 514/292, 253.01
See application file for complete search history.

(56) References Cited

U.S. PATENT DOCUMENTS

| | | |
|---|---|---|
| 2009/0163511 A1 | 6/2009 | Darwish et al. |
| 2009/0170829 A1 | 7/2009 | Hong et al. |
| 2009/0186894 A1 | 7/2009 | Singh et al. |
| 2009/0275609 A1 | 11/2009 | Yu et al. |
| 2010/0190802 A1 | 7/2010 | Darwish et al. |

FOREIGN PATENT DOCUMENTS

WO 2009/065131 5/2009

OTHER PUBLICATIONS

D.W. Kitzman and L. Groban, "Exercise Intolerance," Heart Fail. Clin., 4, 99-115 (2008).
M. Mancuso et al, "Fatigue and exercise intolerance in mitochondrial diseases, Literature revision and experience of the Italian Network of mitochondrial diseases," Neuromuscular disorders, 22, S226-S229 (2012).
Toye, "A genetic and physiological study of impaired glucose homeostasis control in C57BL/6J mice," Diabetologiz (2005) 48, pp. 675-686.
Yokota, Oxidative stress in skeletal muscle impairs mitochondrial respiration and limits exercise capacity in type 2 diabetic mice, Am Journal Physiol Heart Circ Physiol, 297, 2009, pp. H1069-H1076.

*Primary Examiner* — Kathrien Cruz
(74) *Attorney, Agent, or Firm* — McDonnell Boehnen Hulbert & Berghoff LLP; Travis Young

(57) ABSTRACT

Disclosed are uses of carboxamide, sulfonamide and amine compounds for the treatment and amelioration of disorders and conditions related to oxidative stress, mitochondrial dysfunction, free radical damage and metabolic inefficiency, among others. Also described are methods for increasing exercise endurance, exercise efficiency and aerobic workload using the compounds described herein.

25 Claims, No Drawings

METHODS FOR USING CARBOXAMIDE, SULFONAMIDE AND AMINE COMPOUNDS

CROSS-REFERENCE TO RELATED APPLICATIONS

This application is a continuation of U.S. patent application Ser. No. 13/077,539, filed Mar. 31, 2011, which claims the benefit of the earlier filing date of U.S. Provisional Patent Application Ser. No. 61/319,864, filed Mar. 31, 2010, each of which is incorporated herein by reference.

BACKGROUND

Field

This disclosure relates generally to compounds, pharmaceutical compositions and methods of use of the compounds and compositions containing them. This disclosure relates more particularly to certain carboxamide compounds and pharmaceutical compositions thereof, and to methods of treating and ameliorating disorders and conditions related to oxidative stress, mitochondrial dysfunction, free radical damage and metabolic inefficiency, among others.

Background

Adiponectin is a protein hormone exclusively expressed in and secreted from adipose tissue and is the most abundant adipose-specific protein. Adiponectin has been implicated in the modulation of glucose and lipid metabolism in insulin-sensitive tissues. Decreased circulating adiponectin levels have been demonstrated in some insulin-resistant states, such as obesity and type 2 diabetes mellitus and also in patients with coronary artery disease, atherosclerosis and hypertension. Adiponectin levels are positively correlated with insulin sensitivity, HDL (high density lipoprotein) levels and insulin stimulated glucose disposal and inversely correlated with adiposity and glucose, insulin and triglyceride levels. Thiazolidinedione drugs, which enhance insulin sensitivity through activation of the peroxisome proliferator-activated receptor-γ, increase endogenous adiponectin production in humans.

Adiponectin binds its receptors in liver and skeletal muscle and thereby activates the 5'-AMP-activated protein kinase (AMPK) pathway. Adiponectin receptors 1 and 2 are membrane-bound proteins found in skeletal muscle and liver tissue. Being a multi-substrate enzyme, AMPK regulates a variety of metabolic processes, such as glucose transport, glycolysis and lipid metabolism. It acts as a sensor of cellular energy homeostasis and is activated in response to certain hormones and muscle contraction as well as to intracellular metabolic stress signals such as exercise, ischemia, hypoxia and nutrient deprivation. Once activated, AMPK switches on catabolic pathways (such as fatty acid oxidation and glycolysis) and switches off ATP-consuming pathways (such as lipogenesis). Adiponectin improves insulin sensitivity by directly stimulating glucose uptake in adipocytes and muscle and by increasing fatty acid oxidation in liver and muscle, resulting in reduced circulating fatty acid levels and reduced intracellular triglyceride contents. Moreover, adiponectin decreases glycogen concentration by reducing the activity of glycogen synthase. Adiponectin also plays a protective role against inflammation and atherosclerosis. It suppresses the expression of adhesion molecules in vascular endothelial cells and cytokine production from macrophages, thus inhibiting the inflammatory processes that occur during the early phases of atherosclerosis.

SUMMARY

One aspect of the disclosure relates to methods of treating or ameliorating disorders and conditions related to oxidative stress, mitochondrial dysfunction, free radical damage and metabolic inefficiency, using a compound having any of structural formula (1-I), (2-I), (3-I), (4-I), (5-I) and (5-XVII):

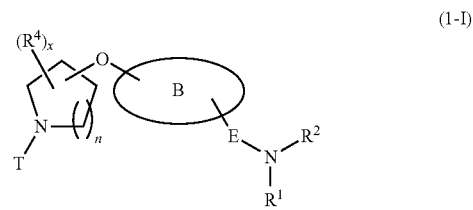

(1-I)

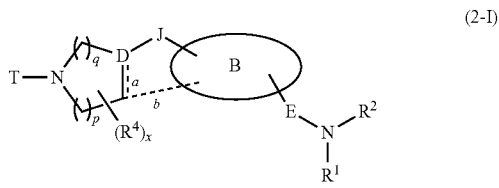

(2-I)

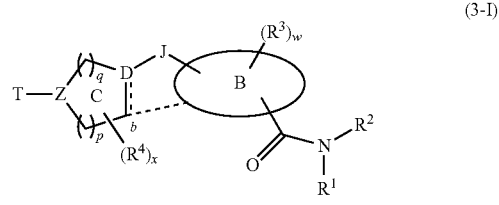

(3-I)

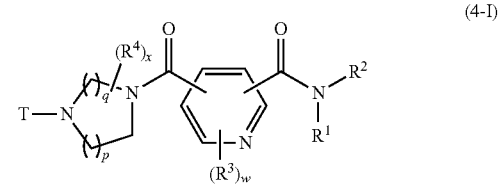

(4-I)

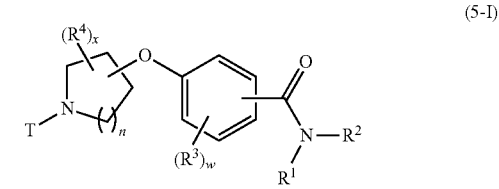

(5-I)

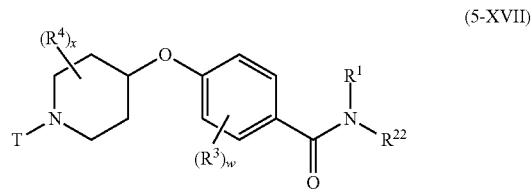

(5-XVII)

or a pharmaceutically acceptable salt, prodrug or N-oxide thereof (or solvate or hydrate thereof), wherein the variables are as described herein.

Another aspect of the present disclosure relates to methods for increasing exercise endurance, exercise efficiency and aerobic workload in subjects using the compounds described herein.

Another aspect of the present disclosure relates to methods for using the compounds described herein as exercise mimetics.

Another aspect of the present disclosure relates to methods for increasing fiber oxidative capacity of muscle fiber using the compounds described herein.

DETAILED DESCRIPTION

One aspect of the disclosure provides a method for treating or ameliorating a disorder or condition related to oxidative stress, mitochondrial dysfunction, free radical damage and/or metabolic inefficiency in a subject, the method including administering to the subject an effective amount of a compound having structural formula (1-I):

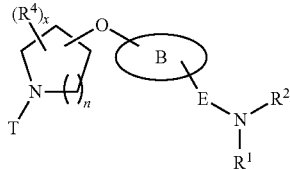

(1-I)

or a pharmaceutically acceptable salt, solvate, hydrate, or N-oxide thereof (or a solvate or hydrate thereof), wherein "B" represents -(aryl or heteroaryl)- substituted by w $R^3$ and k $R^{14}$;

E is —C(O)—, —S(O)$_2$— or a single bond, provided that when "B" is phenyl, E is not —C(O)—;

$R^1$ is H, —(C$_1$-C$_4$ alkyl) or —C(O)O—(C$_1$-C$_4$ alkyl);

$R^2$ is -Hca, -Cak-N(R$^9$)-G-R$^{22}$ or —(C$_2$-C$_8$ alkyl)-N(R$^9$)—R$^{24}$ in which one or two carbons of the (C$_2$-C$_8$ alkyl) are optionally replaced by —O—, —S— or —N(R$^9$)— and R$^{24}$ is —R$^{23}$, -G-R$^{23}$, or —C(O)O—(C$_1$-C$_6$ alkyl);

each $R^3$ is substituted on a benzo or pyrido carbon of the ring system denoted by "B" and is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN;

w is 0, 1, 2 or 3;

each $R^{14}$ is substituted on a non-benzo, non-pyrido carbon of the ring system denoted by "B", and is independently selected from —(C$_1$-C$_6$ alkyl), —(C$_1$-C$_6$ halooalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN;

k is 0, 1 or 2;

each $R^4$ is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, and two $R^4$ on the same carbon optionally combine to form oxo;

x is 0, 1, 2, 3 or 4;

n is 0, 1, 2 or 3;

T is —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$ or

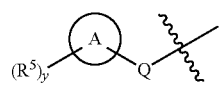

in which

Q is —(C$_0$-C$_3$ alkyl)-, in which each carbon of the —(C$_0$-C$_3$ alkyl)- is optionally and independently substituted with one or two R$^{16}$, or —S(O)$_2$—;

the ring system denoted by "A" is heteroaryl, aryl, cycloalkyl or heterocycloalkyl;

each $R^5$ is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, —(C$_0$-C$_6$ alkyl)-C(O)R$^{10}$, -halogen, —NO$_2$ and —CN; and y is 0, 1, 2, 3 or 4;

in which each L is independently selected from —NR$^9$C(O)O—, —OC(O)NR$^9$—, —NR$^9$C(O)—NR$^9$—, —NR$^9$C(O)S—, —SC(O)NR$^9$—, —NR$^9$C(O)—, —C(O)—NR$^9$—, —NR$^9$C(S)O—, —OC(S)NR$^9$—, —NR$^9$C(S)—NR$^9$—, —NR$^9$C(S)S—, —SC(S)NR$^9$—, —NR$^9$C(S)—, —C(S)NR$^9$—, —SC(O)NR$^9$—, —NR$^9$C(S)—, —S(O)$_{0-2}$—, —C(O)O, —OC(O)—, —C(S)O—, —OC(S)—, —C(O)S—, —SC(O)—, —C(S)S—, —SC(S)—, —OC(O)O—, —SC(O)O—, —OC(O)S—, —SC(S)O—, —OC(S)S—, —NR$^9$C(NR$^2$)NR$^9$—, —NR$^9$SO$_2$—, —SO$_2$NR$^9$— and —NR$^9$SO$_2$NR$^9$—, each $R^6$, $R^7$, $R^8$ and $R^{10}$ is independently selected from H, —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-(C$_0$-C$_6$ alkyl), —(C$_0$-C$_6$ alkyl)-NR$^9$—(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl) and —(C$_0$-C$_6$ alkyl)-S(O)$_{0-2}$—(C$_0$-C$_6$ alkyl), each $R^9$ is independently selected from —H, —(C$_1$-C$_4$ alkyl) and —C(O)O—(C$_1$-C$_4$ alkyl), each G is independently —(C$_0$-C$_3$ alkyl)-, in which each carbon of the —(C$_0$-C$_3$ alkyl)- is optionally and independently substituted with one or two R$^{16}$, or —S(O)$_2$—, each $R^{16}$ is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, and optionally two of R$^{16}$ on the same carbon combine to form oxo, each $R^{20}$, $R^{22}$ and $R^{23}$ is independently Ar or Het, each Ar is an optionally substituted aryl, each Het is an optionally substituted heteroaryl, each Cak is an optionally substituted cycloalkyl, each Hca is an optionally substituted heterocycloalkyl, and each alkyl is optionally substituted.

Various embodiments of compounds of structural formula (1-I) suitable for use in the methods described herein are described below. Information regarding these compounds can also be found in U.S. Patent Application Publication no. 2009/0170829, which is hereby incorporated by reference in its entirety.

In certain embodiments of the presently disclosed compounds of structural formula (1-I), the ring system denoted by "B" is

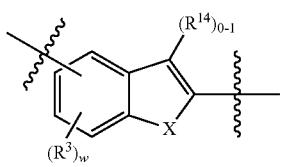

in which X is O or S, and E is —C(O)—. In certain such embodiments, one $R^{14}$ can be substituted on the furano or thieno carbon. In one such embodiment, $R^{14}$ is selected from —($C_1$-$C_6$ alkyl), —($C_1$-$C_6$ haloalkyl) (e.g., trifluoromethyl), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, in which each $R^7$, $R^8$ and $R^{10}$ is independently selected from H, —($C_1$-$C_2$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl), and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, $R^{14}$ is selected from —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. $R^{14}$ can be, for example, halo (e.g., —Cl or —F), cyano, or unsubstituted —($C_1$-$C_4$ alkyl) (e.g., methyl or ethyl), unsubstituted —($C_1$-$C_4$ haloakyl) (e.g., trifluoromethyl). In other embodiments, no $R^{14}$ is substituted on the furano or thieno carbon. In certain embodiments, $R^{14}$ is H or methyl; in others, $R^{14}$ is halo (e.g., Cl). In other embodiments, no $R^{14}$ is substituted on the furano or thieno carbon.

In one embodiment of the presently disclosed compounds of structural formula (1-I), X is O.

In certain embodiments of the presently disclosed compounds of structural formula (1-I), the ring system denoted by "B" is

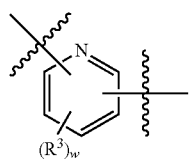

and E is —C(O)— or —S(O)$_2$—.

In certain embodiments of the presently disclosed compounds of structural formula (1-I), the ring system denoted by "B" is

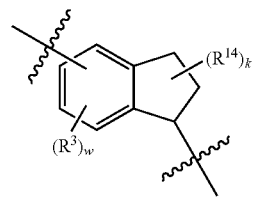

and E is a single bond. In one embodiment, k is 0. In another embodiment, k is 1 or 2. In certain embodiments, In each $R^{14}$ is independently selected from —($C_1$-$C_6$ alkyl), —($C_1$-$C_6$ haloalkyl) (e.g., trifluoromethyl), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl), and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^{14}$ is independently selected from —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. Each $R^{14}$ can be, for example, halo (e.g., —Cl or —F), cyano, unsubstituted —($C_1$-$C_4$ alkyl) (e.g., methyl or ethyl) or unsubstituted —($C_1$-$C_4$ haloakyl) (e.g., trifluoromethyl).

In certain embodiments of the presently disclosed compounds of structural formula (1-I), T is

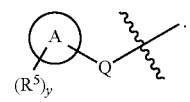

In such embodiments, Q is —S(O)$_2$— or —($C_0$-$C_3$ alkyl)- in which each carbon of the ($C_0$-$C_3$ alkyl) is optionally and independently substituted with one or two $R^{16}$, in which each $R^{16}$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, and optionally two of $R^{16}$ on the same carbon combine to form oxo. In certain embodiments, each $R^{16}$ is independently selected from —($C_1$-$C_6$ alkyl), —($C_1$-$C_6$ haloalkyl) (e.g., trifluoromethyl), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, and two $R^{16}$ on the same carbon optionally combine to form an oxo, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—(C$_0$-C$_6$ alkyl), —(C$_0$-C$_6$ alkyl)-C(O)—(C$_0$-C$_6$ alkyl), and —(C$_0$-C$_6$ alkyl)-S(O)$_{0-2}$—(C$_0$-C$_6$ alkyl), and in which no alkyl or haloalkyl is substituted with an aryl-, heteroaryl-, cycloalkyl- or heterocycloalkyl-containing group. For example, in particular compounds, each R$^{16}$ is —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN, and two R$^{16}$ on the same carbon optionally combine to form an oxo, in which each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group. In certain embodiments, Q has at most one R$^{16}$ or an oxo substituted thereon. Q can be, for example, an unsubstituted —(C$_0$-C$_3$ alkyl)-. In other embodiments, Q is a (C$_1$-C$_3$ alkyl) having as its only substitution a single oxo group. For example, in certain embodiments, Q is —CH$_2$—; a single bond; —S(O)$_2$—; —C(O)—; or —CH(CH$_3$)—.

In certain embodiments of the presently disclosed compounds of structural formula (1-I), the

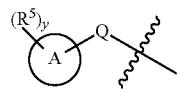

moiety is

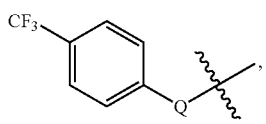

for example, p-(trifluoromethyl)phenyl. In other embodiments, the

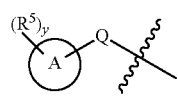

moiety is

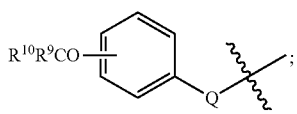

in one such embodiment, Q is a single bond.

The number of substituents on the ring system denoted by "A", y, is 0, 1, 2, 3 or 4. For example, in some embodiments, y is 0, 1, 2 or 3, for example 1. In one embodiment, y is not zero and at least one R$^5$ is halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ or —C(O)-Hca in which the Hca contains a ring nitrogen atom through which it is bound to the —C(O)—, and in which no alkyl, haloalkyl or heterocycloalkyl is substituted by an aryl, heteroaryl, cycloalkyl or heterocycloalkyl-containing group.

In certain embodiments of the presently disclosed compounds of structural formula (1-I), each R$^5$ is independently selected from —(C$_1$-C$_6$ alkyl), —(C$_1$-C$_6$ haloalkyl) (e.g., trifluoromethyl), —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, in which each R$^7$, R$^8$ and R$^{10}$ is independently selected from H, —(C$_1$-C$_6$ alkyl), —(C$_1$-C$_6$ haloalkyl) (e.g., trifluoromethyl), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl) and —(C$_0$-C$_6$ alkyl)-S(O)$_{0-2}$—(C$_0$-C$_6$ alkyl), and in which no alkyl or haloalkyl is substituted with an aryl-, heteroaryl-, cycloalkyl- or heterocycloalkyl-containing group. For example, in one embodiment, each R$^5$ is —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN, in which each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group.

In one embodiment of the compounds of structural formula (1-I), y is 0.

In the presently disclosed compounds, the ring system denoted by "A" is heteroaryl, aryl, cycloalkyl or heterocycloalkyl. For example, in one embodiment, the ring system denoted by "A" is an aryl or a heteroaryl. The ring system denoted by "A" can be, for example, a monocyclic aryl or heteroaryl. In one embodiment, when the "A" ring system is aryl, Q is a —(C$_0$-C$_3$ alkyl)- optionally substituted with oxo, and optionally substituted with one or more R$^{16}$. For example, Q can be a —(C$_1$-C$_3$ alkyl)- having its only substitution a single oxo, or an unsubstituted —(C$_0$-C$_3$ alkyl)-. For example, in certain embodiments, Q is —CH$_2$—; a single bond; —S(O)$_2$—; —C(O)—; or —CH(CH$_3$)—.

For example, in certain embodiments of the presently disclosed compounds, the ring system denoted by "A" is a phenyl. In one embodiment, y is 1 and R$^5$ is attached to the phenyl para to Q. In another embodiment, y is 1 and R$^5$ is selected from the group consisting of halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, and in which no (C$_0$-C$_4$ alkyl) or (C$_1$-C$_4$ alkyl) is substituted by an aryl, heteroaryl, cycloalkyl or heterocycloalkyl-containing group. R$^5$ can be, for example, —Cl, —F, cyano, —C(O)CH$_3$, —C(O)OH, —C(O)NH$_2$, trifluoromethyl, difluoromethyl, difluoromethoxy or trifluoromethoxy. In another embodiment, the

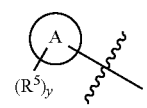

moiety is a 3,4-dihalophenyl.

In another embodiment of the presently disclosed compounds of structural formula (1-I), the ring system denoted by "A" is a heteroaryl. For example, in certain embodiments, the ring system denoted by "A" is a pyridyl, a thienyl, or a furanyl. In one embodiment, when the "A" ring system is heteroaryl, Q is a —($C_0$-$C_3$ alkyl)- optionally substituted with oxo, and optionally substituted with one or more $R^{16}$. For example, Q can be a —($C_1$-$C_3$ alkyl)- having its only substitution a single oxo, or an unsubstituted —($C_0$-$C_3$ alkyl)-. In certain embodiments, Q is —$CH_2$—; a single bond; —$S(O)_2$—; —$C(O)$—; or —$CH(CH_3)$—.

In one embodiment of the presently disclosed compounds, the compound has structural formula (1-II):

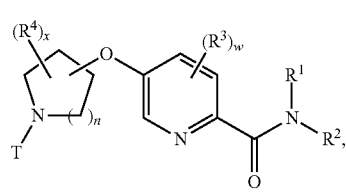

(1-II)

in which the variables are defined as described above with reference to structural formula (1-I).

In another embodiment of the presently disclosed compounds, the compound has structural formula (1-III):

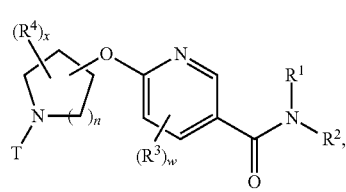

(1-III)

in which the variables are defined as described above with reference to structural formula (1-I).

In another embodiment of the presently disclosed compounds, the compound has structural formula (1-IV):

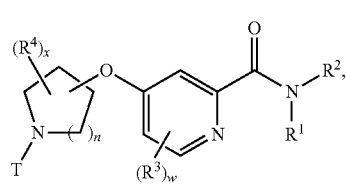

(1-IV)

in which the variables are defined as described above with reference to structural formula (1-I).

In another embodiment of the presently disclosed compounds, the compound has structural formula (1-V):

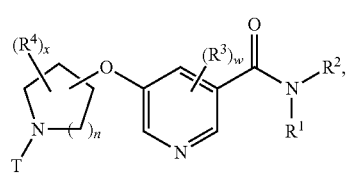

(1-V)

in which the variables are defined as described above with reference to structural formula (1-I).

In another embodiment of the presently disclosed compounds, the compound has structural formula (1-VI):

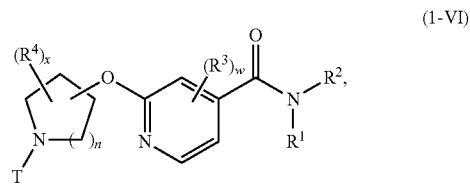

(1-VI)

in which the variables are defined as described above with reference to structural formula (1-I).

In another embodiment of the presently disclosed compounds, the compound has structural formula (1-VII):

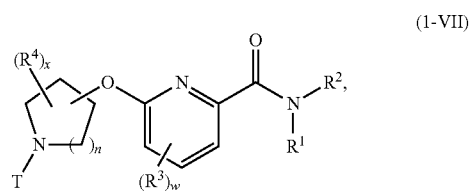

(1-VII)

in which the variables are defined as described above with reference to structural formula (1-I).

In another embodiment of the presently disclosed compounds, the compound has structural formula (1-VIII):

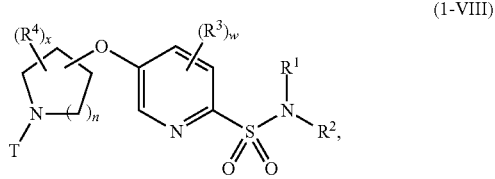

(1-VIII)

in which the variables are defined as described above with reference to structural formula (1-I).

In another embodiment of the presently disclosed compounds, the compound has structural formula (1-IX):

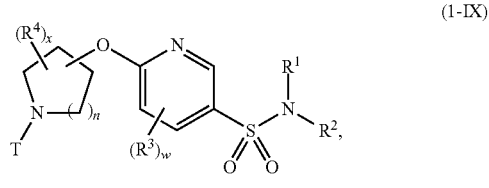

(1-IX)

in which the variables are defined as described above with reference to structural formula (1-I).

In another embodiment of the presently disclosed compounds, the compound has the structural formula (1-X):

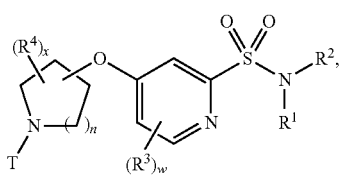

(1-X)

in which the variables are defined as described above with reference to structural formula (1-I).

In another embodiment of the presently disclosed compounds, the compound has structural formula (1-XI):

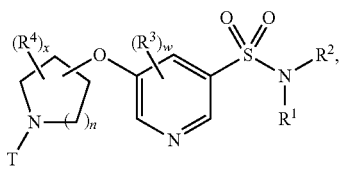

(1-XI)

in which the variables are defined as described above with reference to structural formula (1-I).

In another embodiment of the presently disclosed compounds, the compound has structural formula (1-XII):

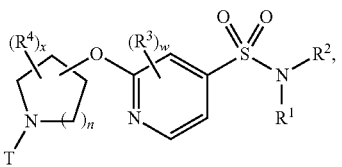

(1-XII)

in which the variables are defined as described above with reference to structural formula (1-I).

In another embodiment of the presently disclosed compounds, the compound has structural formula (1-XIII):

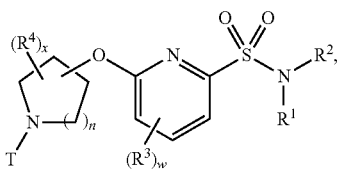

(1-XIII)

in which the variables are defined as described above with reference to structural formula (1-I).

In one embodiment of the presently disclosed compounds, the compound has structural formula (1-XIV):

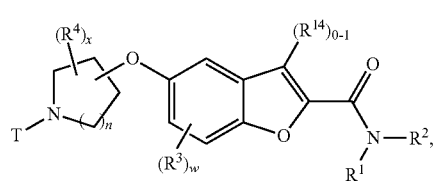

(1-XIV)

in which the variables are defined as described above with reference to structural formula (1-I). In certain embodiments, one $R^{14}$ is substituted on the furano carbon. In other embodiments, no $R^{14}$ is substituted on the furano carbon.

In another embodiment of the presently disclosed compounds, the compound has structural formula (1-XV):

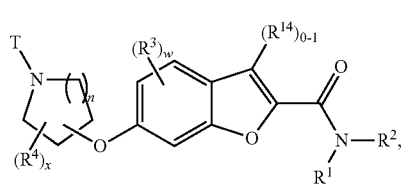

(1-XV)

in which the variables are defined as described above with reference to structural formula (1-I). In certain embodiments, one $R^{14}$ is substituted on the furano carbon. In other embodiments, no $R^{14}$ is substituted on the furano carbon.

In one embodiment of the presently disclosed compounds, the compound has structural formula (1-XVI):

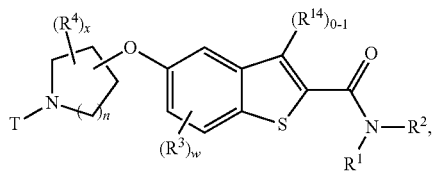

(1-XVI)

in which the variables are defined as described above with reference to structural formula (1-I). In certain embodiments, one $R^{14}$ is substituted on the thieno carbon. In other embodiments, no $R^{14}$ is substituted on the thieno carbon.

In another embodiment of the presently disclosed compounds, the compound has structural formula (1-XVII):

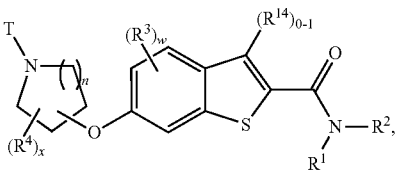

(1-XVII)

in which the variables are defined as described above with reference to structural formula (1-I). In certain embodiments, one $R^{14}$ is substituted on the thieno carbon. In other embodiments, no $R^{14}$ is substituted on the thieno carbon.

The presently disclosed compounds include S-oxidized forms of the benzothiophene compounds described (e.g., with reference to structural formulae (1-XVI) and (1-XVII). S-oxides include, for example, sulfoxides (—SO—) and sulfones (—SO$_2$—). Such compounds may be oxidized chemically or upon administration to e.g. a human subject, may be oxidized biologically. Chemically oxidized compounds may also be biologically reduced to the benzothiophene form.

In one embodiment of the presently disclosed compounds, the compound has structural formula (1-XVIII):

(1-XVIII)

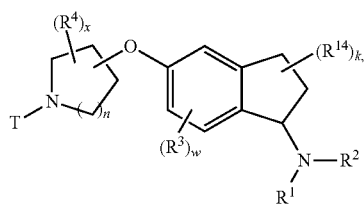

in which the variables are defined as described above with reference to structural formula (1-I).

In another embodiment of the presently disclosed compounds, the compound has structural formula (1-XIX):

(1-XIX)

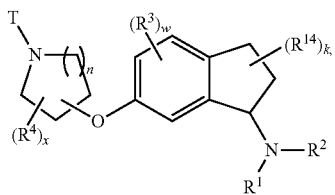

in which the variables are defined as described above with reference to structural formula (1-I).

In certain embodiments of the compounds disclosed with respect to structural formulae (1-I)-(1-XIX), n is 1 or 2. For example, in one embodiment, n is 2. In another embodiment, n is 1.

In one embodiment of the presently disclosed compounds, the compound has the structural formula (1-XX):

(1-XX)

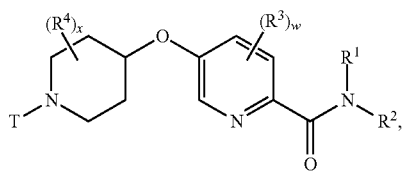

in which the variables are defined as described above with reference to structural formula (1-I).

In another embodiment of the presently disclosed compounds, the compound has structural formula (1-XXI):

(1-XXI)

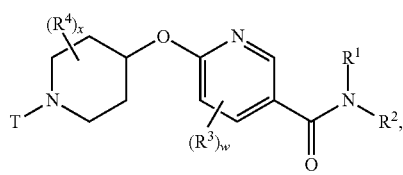

in which the variables are defined as described above with reference to structural formula (1-I).

In another embodiment of the presently disclosed compounds, the compound has structural formula (1-XXII):

(1-XXII)

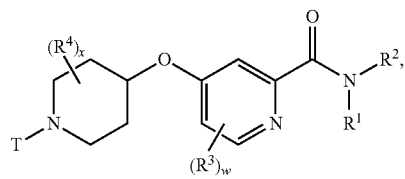

in which the variables are defined as described above with reference to structural formula (1-I).

In another embodiment of the presently disclosed compounds, the compound has structural formula (1-XXIII):

(1-XXIII)

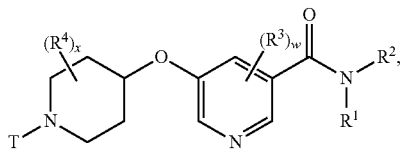

in which the variables are defined as described above with reference to structural formula (1-I).

In another embodiment of the presently disclosed compounds, the compound has structural formula (1-XXIV):

(1-XXIV)

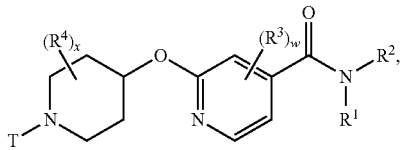

in which the variables are defined as described above with reference to structural formula (1-I).

In another embodiment of the presently disclosed compounds, the compound has structural formula (1-XXV):

(1-XXV)

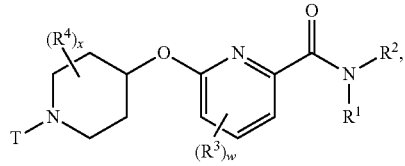

in which the variables are defined as described above with reference to structural formula (1-I).

In one embodiment of the presently disclosed compounds, the compound has structural formula (1-XXVI):

(1-XXVI)

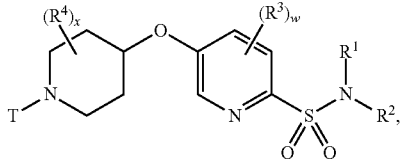

in which the variables are defined as described above with reference to structural formula (1-I).

In another embodiment of the presently disclosed compounds, the compound has structural formula (1-XXVII):

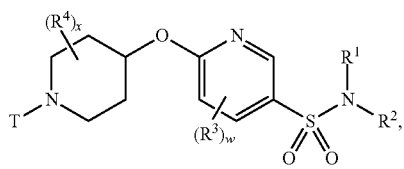

(1-XXVII)

in which the variables are defined as described above with reference to structural formula (1-I).

In another embodiment of the presently disclosed compounds, the compound has structural formula (1-XXVIII):

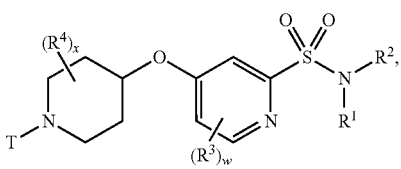

(1-XXVIII)

in which the variables are defined as described above with reference to structural formula (1-I).

In another embodiment of the presently disclosed compounds, the compound has structural formula (1-XXIX):

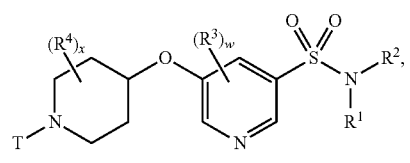

(1-XXIX)

in which the variables are defined as described above with reference to structural formula (1-I).

In another embodiment of the presently disclosed compounds, the compound has structural formula (1-XXX):

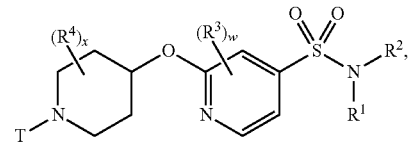

(1-XXX)

in which the variables are defined as described above with reference to structural formula (1-I).

In another embodiment of the presently disclosed compounds, the compound has structural formula (1-XXXI):

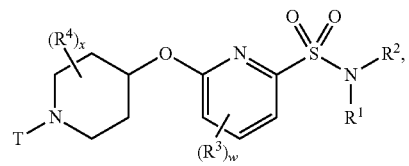

(1-XXXI)

in which the variables are defined as described above with reference to structural formula (1-I).

In one embodiment of the presently disclosed compounds, the compound has structural formula (1-XXXII):

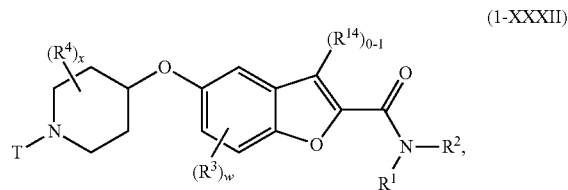

(1-XXXII)

in which the variables are defined as described above with reference to structural formula (1-I). In certain embodiments, one $R^{14}$ is substituted on the furano carbon. In other embodiments, no $R^{14}$ is substituted on the furano carbon.

In another embodiment of the presently disclosed compounds, the compound has structural formula (1-XXXIII):

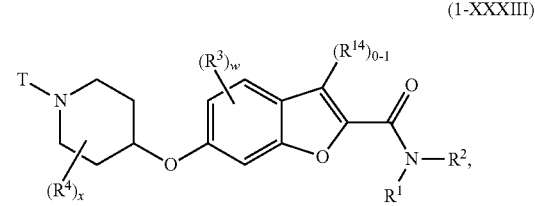

(1-XXXIII)

in which the variables are defined as described above with reference to structural formula (1-I). In certain embodiments, one $R^{14}$ is substituted on the furano carbon. In other embodiments, no $R^{14}$ is substituted on the furano carbon.

In one embodiment of the presently disclosed compounds, the compound has structural formula (1-XXXIV):

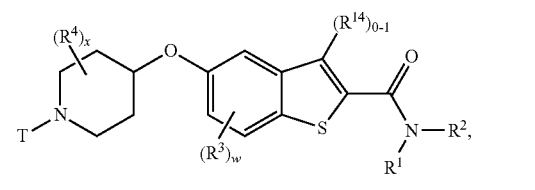

(1-XXXIV)

in which the variables are defined as described above with reference to structural formula (1-I). In certain embodiments, one $R^{14}$ is substituted on the thieno carbon. In other embodiments, no $R^{14}$ is substituted on the thieno carbon.

In another embodiment of the presently disclosed compounds, the compound has structural formula (1-XXXV):

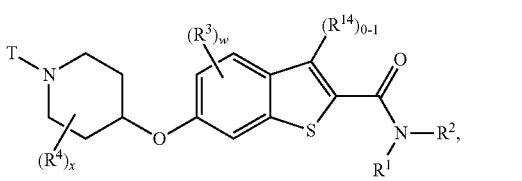

(1-XXXV)

in which the variables are defined as described above with reference to structural formula (1-I). In certain embodiments, one $R^{14}$ is substituted on the thieno carbon. In other embodiments, no $R^{14}$ is substituted on the thieno carbon.

In one embodiment of the presently disclosed compounds, the compound has structural formula (1-XXXVI):

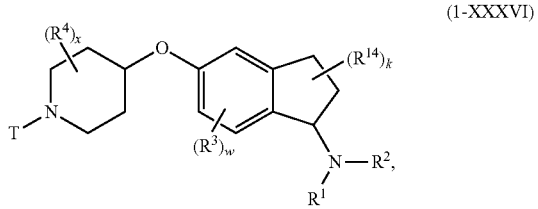

(1-XXXVI)

in which the variables are defined as described above with reference to structural formula (1-I).

In another embodiment of the presently disclosed compounds, the compound has structural formula (1-XXXVII):

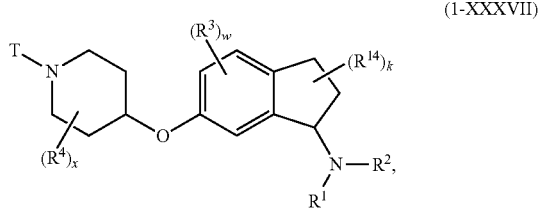

(1-XXXVII)

in which the variables are defined as described above with reference to structural formula (1-I).

In certain embodiments of the presently disclosed compounds of any of structural formulae (1-I)-(1-XXXVII), $R^1$ is —H. In other embodiments, $R^1$ is ($C_1$-$C_4$ alkyl), for example methyl, ethyl, n-propyl or isopropyl.

In certain embodiments of the presently disclosed compounds of any structural formulae (1-I)-(1-XXXVII), $R^2$ is -Hca. In certain embodiments, $R^2$ is an optionally-substituted monocyclic heterocycloalkyl. In another embodiment, $R^2$ is not an oxo-substituted heterocycloalkyl.

In certain particular compounds disclosed herein having any of structural formulae (1-I)-(1-XXXVII), $R^2$ is -(optionally-substituted azetidinyl), -(optionally-substituted pyrrolidinyl), -(optionally-substituted piperidinyl), or -(optionally-substituted azepanyl). For example, $R^2$ can be -(optionally substituted piperidinyl) or -(optionally substituted pyrrolidinyl). In one embodiment, $R^2$ is -(optionally substituted piperidinyl). In another embodiment, $R^2$ is -(optionally substituted pyrrolidinyl).

In particular embodiments of the presently disclosed compounds of any of structural formulae (1-I)-(1-XXXVII), $R^2$ is -(optionally-substituted azetidin-3-yl), -(optionally substituted piperidin-4-yl), -(optionally substituted pyrrolidin-3-yl) or -(optionally-substituted azepan-4-yl). For example, in one embodiment, $R^2$ is -(optionally substituted piperidin-4-yl). In another embodiment, $R^2$ is -(optionally substituted pyrrolidin-3-yl).

In certain embodiments of the presently disclosed compounds of any of structural formulae (1-I)-(1-XXXVII), the azetidinyl, pyrrolidinyl, piperidinyl and azepanyl $R^2$ moieties described above are substituted at their 1-positions. For example, in one embodiment, $R^2$ is substituted at its 1-position with —($C_0$-$C_3$ alkyl)-Ar or —($C_0$-$C_3$ alkyl)-Het, for example -(unsubstituted $C_0$-$C_3$ alkyl)-Ar or -(unsubstituted $C_0$-$C_3$ alkyl)-Het. For example, in one particular embodiment, the azetidinyl, pyrrolidinyl, piperidinyl or azepanyl $R^2$ moiety is substituted at its 1-position with an optionally substituted benzyl or an optionally substituted phenyl. In another embodiment, the azetidinyl, pyrrolidinyl, piperidinyl or azepanyl $R^2$ moiety is substituted at its 1-position with a benzyl substituted with an electron withdrawing group; or with a pyridinylmethyl optionally substituted with an electron withdrawing group. For example, the benzyl or pyridinylmethyl can be substituted with an electron withdrawing group selected from the group consisting of halo, cyano, —($C_1$-$C_4$ fluoroalkyl), —O—($C_1$-$C_4$ fluoroalkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), —S(O)$_2$O—($C_0$-$C_4$ alkyl), $NO_2$ and —C(O)-Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group. In other embodiments, the azetidinyl, pyrrolidinyl, piperidinyl or azepanyl $R^2$ moiety is substituted at its 1-position with an unsubstituted benzyl or an unsubstituted phenyl.

In other embodiments of the compounds disclosed herein having any of structural formulae (1-I)-(1-XXXVII), the azetidinyl, pyrrolidinyl, piperidinyl or azepanyl $R^2$ moiety is substituted at its 1-position with an optionally substituted pyridinylmethyl, an optionally substituted furanylmethyl or an optionally substituted thienylmethyl. For example, the azetidinyl, pyrrolidinyl, piperidinyl or azepanyl $R^2$ moiety can be substituted with an unsubstituted pyridinylmethyl, an unsubstituted furanylmethyl, or an unsubstituted thienylmethyl.

In other embodiments of the presently disclosed compounds of any of structural formulae (1-I)-(1-XXXVII), the azetidinyl, pyrrolidinyl, piperidinyl or azepanyl $R^2$ moiety is substituted at its 1-position with —C(O)—O—($C_0$-$C_6$ alkyl), —C(O)—Het, —C(O)—Ar, —S(O)$_2$-Het, —S(O)$_2$—Ar or —S(O)$_2$—O($C_0$-$C_6$ alkyl).

In certain embodiments of the compounds of any of structural formulae (1-I)-(1-XXXVII), $R^2$ is -Cak-N($R^9$)-G-$R^{22}$, as described above. For example, in one embodiment, $R^2$ has the structure

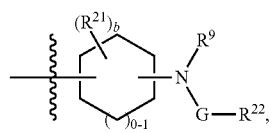

in which b is 0, 1, 2, 3 or 4, and each $R^{21}$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0\text{-}2}R^{10}$, -halogen, —$NO_2$ and —CN, and two $R^{21}$ on the same carbon optionally combine to form oxo. In certain embodiments of the presently disclosed compounds, each $R^{21}$ is independently selected from —($C_1$-$C_6$ alkyl), —($C_1$-$C_6$ haloalkyl) (e.g., trifluoromethyl), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0\text{-}2}R^{10}$, -halogen, —$NO_2$ and —CN and two $R^{21}$ on the same carbon optionally combine to form oxo, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0\text{-}2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^{21}$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0\text{-}2}R^{10}$, -halogen, —$NO_2$ and —CN and two $R^{21}$ on the same carbon optionally combine to form oxo, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0\text{-}2}$—($C_0$-$C_2$ alkyl), and in which no alkyl or haloalkyl is substituted with an aryl-, heteroaryl-, cycloalkyl- or heterocycloalkyl-containing group. In certain embodiments, b is 1 or 2. In other embodiments, b is 0. In certain embodiments, $R^9$ is H. In certain embodiments, G is a single bond.

In one embodiment of compounds of any of structural formulae (1-I)-(1-XXXVII), $R^2$ has the structure

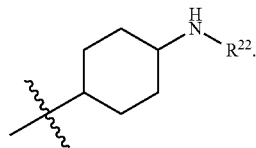

In certain embodiments of the compounds of any of structural formulae (1-I)-(1-XXXVII), $R^2$ is —($C_2$-$C_8$ alkyl)-N($R^9$)—$R^{24}$ in which one or two carbons of the ($C_2$-$C_8$ alkyl) are optionally replaced by —O— or —N($R^9$)— and $R^{24}$ is —$R^{23}$, -$GR^{23}$, or —C(O)O—($C_1$-$C_6$ alkyl). In certain embodiments, the ($C_2$-$C_8$ alkyl) is unsubstituted and no carbon is replaced by —O— or —N($R^9$)—. For example, in one embodiment, $R^2$ is —$CH_2$—$CH_2$—$CH_2$—N($R^9$)—$R^{24}$ or —$CH_2$—$CH_2$—$CH_2$—$CH_2$—N($R^9$)—$R^{24}$. In other embodiments, the ($C_2$-$C_8$ alkyl) is substituted and/or one or two carbons are replaced by —O— or —N($R^9$)—. For example, in one embodiment, $R^2$ is —$CH_2$—$CH_2$—O—$CH_2$—$CH_2$—N($R^9$)—$R^{24}$; —$CH_2$—CH($CH_3$)—N($R^9$)—$R^{24}$; or —$CH_2$—$CH_2$—O—$CH_2$—C(O)—N($R^9$)—$R^{24}$. In certain embodiments, $R^9$ is H. In certain embodiments, $R^{24}$ is Ar or Het. In certain embodiments, the ($C_2$-$C_8$ alkyl) is a ($C_2$-$C_5$ alkyl).

In the compounds of any of structural formulae (1-I)-(1-XXXVII), w is 0, 1, 2 or 3. For example, in one embodiment, w is 0, 1 or 2. In another embodiment, w is 0. In other embodiments, w is at least 1, and at least one $R^3$ is selected from the group consisting of halo, cyano, —($C_1$-$C_4$ fluoroalkyl), —O—($C_1$-$C_4$ fluoroalkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), —S(O)$_2$O—($C_0$-$C_4$ alkyl), $NO_2$ and —C(O)-Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group. In certain embodiments, an $R^3$ is substituted on the "B" ring system at a benzo or pyrido ring position meta to the alicyclic ethereal oxygen.

In certain embodiments of the compounds of any of structural formulae (1-I)-(1-XXXVII), each $R^3$ is independently selected from —($C_1$-$C_6$ alkyl), —($C_1$-$C_6$ haloalkyl) (e.g., trifluoromethyl), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_0$ alkyl)-C(O)$R^{10}$, —($C_0$-$C_6$ alkyl)-S(O)$_{0\text{-}2}R^{10}$, -halogen, —$NO_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl), and —($C_0$-$C_6$ alkyl)-S(O)$_{0\text{-}2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^3$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0\text{-}2}R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0\text{-}2}$—($C_0$-$C_2$ alkyl), and in which no alkyl or haloalkyl is substituted with an aryl-, heteroaryl-, cycloalkyl- or heterocycloalkyl-containing group.

In certain embodiments of the compounds of any of structural formulae (1-I)-(1-XXXVII), w is at least one, and at least one $R^3$ is —$NR^8R^9$. For example, in one embodiment, w is 1. In certain such embodiments, $R^3$ is substituted on the "B" ring system at a benzo or pyrido ring position meta to the alicyclic ethereal oxygen.

In other embodiments of the compounds of any of structural formulae (1-I)-(1-XXXVII), w is at least one, and at least one $R^3$ is —($C_0$-$C_3$ alkyl)-$Y^1$—($C_1$-$C_3$ alkyl)-$Y^2$—($C_0$-$C_3$ alkyl), in which each of $Y^1$ and $Y^2$ is independently L, —O—, —S— or —$NR^9$—. For example, in one embodiment, w is 1. In certain such embodiments, $R^3$ is substituted on the "B" ring system at a benzo or pyrido ring position meta to the alicyclic ethereal oxygen. In one particular embodiment, $R^3$ is —$CH_2$—$N(CH_3)$—$CH_2$—$C(O)$—$OCH_3$.

In the presently disclosed compounds of any of structural formulae (1-I)-(1-XXXVII), the number of substituents on the azacycloalkyl ring, x, is 0, 1, 2, 3 or 4. In one embodiment, x is 0, 1, 2 or 3. For example, x can be 0, or can be 1 or 2.

In certain embodiments of the presently disclosed compounds of any of structural formula (1-I)-(1-XXXVII), two $R^4$s combine to form an oxo. The oxo can be bound, for example, at the position alpha to the nitrogen of the azacycloalkyl ring. In other embodiments, no two $R^4$s combine to form an oxo.

In certain embodiments of the presently disclosed compounds of any of structural formulae (1-I)-(1-XXXVII), when x is 4, not all four $R^4$ moieties are ($C_1$-$C_6$ alkyl).

In certain embodiments of the presently disclosed compounds of any of structural formulae (1-I)-(1-XXXVII), each $R^4$ is independently selected from —($C_1$-$C_6$ alkyl), —($C_1$-$C_6$ haloalkyl) (e.g., trifluoromethyl), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-$C(O)R^{10}$, —($C_0$-$C_6$ alkyl)-$S(O)_{0-2}R^{10}$, -halogen, —$NO_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-$S(O)_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^4$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-$C(O)R^{10}$, —($C_0$-$C_3$ alkyl)-$S(O)_{0-2}R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-$S(O)_{0-2}$—($C_0$-$C_2$ alkyl), and in which no alkyl or haloalkyl is substituted with an aryl-, heteroaryl-, cycloalkyl- or heterocycloalkyl-containing group.

In certain embodiments, the presently disclosed compounds have the structural formula (1-XXXVIII):

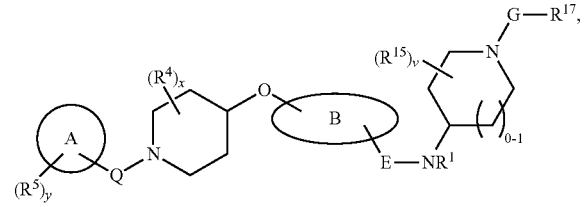

(1-XXXVIII)

in which Q and G are each independently a bond, —$CH_2$—, —$C(H)(R^{16})$—, —$C(R^{16})_2$— or —$S(O)_2$—; v is 0, 1, 2, 3 or 4; each $R^{15}$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-$C(O)R^{10}$, —($C_0$-$C_6$ alkyl)-$S(O)_{0-2}R^{10}$, -halogen, —$NO_2$ and —CN, and two $R^{15}$ on the same carbon optionally combine to form oxo; $R^{17}$ is Het or Ar, and all other variables are defined as described above with reference to structural formulae (1-I)-(1-XXXVII). In one embodiment, Q is a single bond. In another embodiment, Q is —$CH_2$—. In other embodiments, Q is —C(O)— or —$S(O)_2$—. In certain embodiments, G is —$CH_2$—. In other embodiments, G is —C(O)— or —$S(O)_2$—. In other embodiments, G is —$CH(CH_3)$—. For example, in one embodiment, Q is a single bond and G is —$CH_2$— or —C(O)—. As described above, in certain embodiments, the ring system denoted by "A" is aryl or heteroaryl. In one embodiment, the ring system denoted by "A" is substituted with one or more electron-withdrawing groups. In another embodiment, $R^{17}$ is substituted with one or more electron-withdrawing groups. In certain embodiments, the ring system denoted by "A", $R^{17}$ or both are not substituted with an aryl, heteroaryl, cycloalkyl or heterocycloalkyl-containing group.

In the presently disclosed compounds of structural formula (1-XXXVIII), v is 0, 1, 2, 3 or 4. In one embodiment, v is 0, 1, 2 or 3. For example, v can be 0, or can be 1 or 2.

In certain embodiments of the presently disclosed compounds of structural formula (1-XXXVIII), two $R^{15}$s combine to form an oxo. The oxo can be bound, for example, at the position alpha to the nitrogen of the azacycloalkyl ring. In other embodiments, no two $R^{15}$s combine to form an oxo.

In certain embodiments of the presently disclosed compounds of structural formula (1-XXXVIII), when v is 4, not all four $R^{15}$ moieties are ($C_1$-$C_6$ alkyl).

In certain embodiments of the presently disclosed compounds of structural formula (1-XXXVIII), each $R^{15}$ is independently selected from —($C_1$-$C_6$ alkyl), —($C_1$-$C_6$ haloalkyl) (e.g., trifluoromethyl), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-$C(O)R^{10}$, —($C_0$-$C_6$ alkyl)-$S(O)_{0-2}R^{10}$, -halogen, —$NO_2$ and —CN and two $R^{15}$ on the same carbon optionally combine to form oxo, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-$S(O)_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^{15}$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-$C(O)R^{10}$, —($C_0$-$C_3$ alkyl)-$S(O)_{0-2}R^{10}$, -halogen, —$NO_2$ and —CN and two $R^{15}$ on the same carbon optionally combine to form oxo, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-$S(O)_{0-2}$—($C_0$-$C_2$ alkyl), and in which no alkyl or haloalkyl is substituted with an aryl-, heteroaryl-, cycloalkyl- or heterocycloalkyl-containing group. In some embodiments, one $R^{15}$ is —$C(O)NR^9R^7$, which can be bound, for example, at a position alpha to the piperidine nitrogen, or at the position linked to the —$N(R^1)$—.

In certain embodiments of the presently disclosed compounds of structural formula (1-XXXVIII), $R^{17}$ is an unsubstituted aryl or heteroaryl. In other embodiments, the $R^{17}$ Ar or Het is substituted with 1, 2 or 3 substituents independently selected from —($C_1$-$C_6$ alkyl), —($C_1$-$C_6$ haloalkyl) (e.g., trifluoromethyl), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, the $R^{17}$ Ar or Het is substituted with 1, 2 or 3 substituents independently selected from —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. In certain embodiments, $R^{17}$ is substituted with 1, 2 or 3 substituents selected from halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca. $R^{17}$ can be substituted with, for example, one such substituent, or two such substituents.

In certain embodiments, the presently disclosed compounds have the structural formula (1-XXXIX):

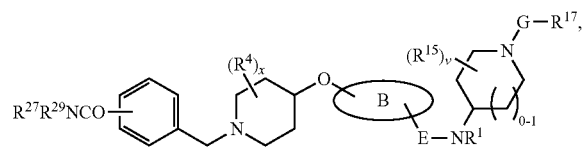

(1-XXXIX)

in which $R^{27}$ is selected from H, —($C_1$-$C_6$ alkyl), —($C_1$-$C_6$ haloalkyl) (e.g., trifluoromethyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with respect to structural formulae (1-I) and (1-XXXVIII).

In certain embodiments, the presently disclosed compounds have the structural formula (1-XL):

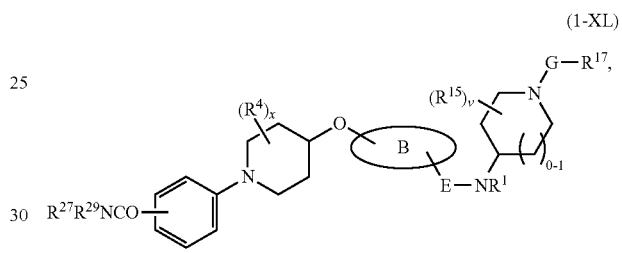

(1-XL)

in which $R^{27}$ is selected from H, —($C_1$-$C_6$ alkyl), —($C_1$-$C_6$ haloalkyl) (e.g., trifluoromethyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with respect to structural formulae (1-I) and (1-XXXVIII).

In certain embodiments, the presently disclosed compounds have the structural formula (1-XLI):

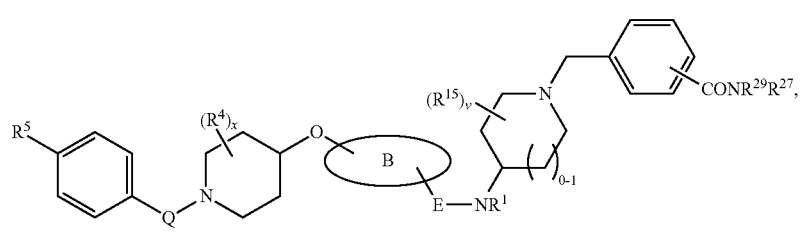

(1-XLI)

in which $R^{27}$ is selected from H, —($C_1$-$C_6$ alkyl), —($C_1$-$C_6$ haloalkyl) (e.g., trifluoromethyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with respect to structural formulae (1-I) and (1-XXXVIII).

In certain embodiments, the presently disclosed compounds have the structural formula (1-XLII):

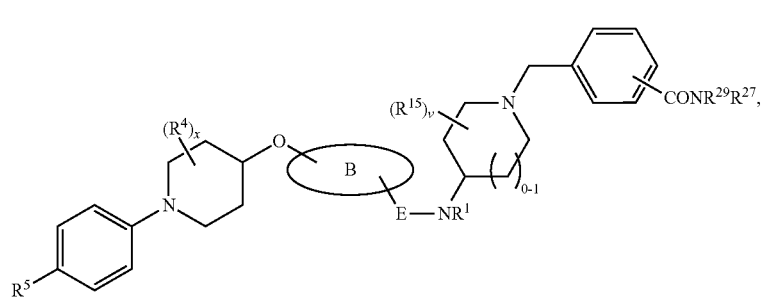

(1-XLII)

in which $R^{27}$ is selected from H, —($C_1$-$C_6$ alkyl), —($C_1$-$C_6$ haloalkyl) (e.g., trifluoromethyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with respect to structural formulae (1-I) and (1-XXXVIII).

In certain embodiments, the presently disclosed compounds have the structural formula (1-XLIII):

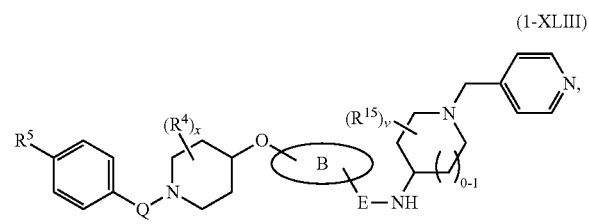

(1-XLIII)

in which all variables are as described above with respect to structural formulae (1-I) and (1-XXXVIII).

In certain embodiments, the presently disclosed compounds have the structural formula (1-XLIV):

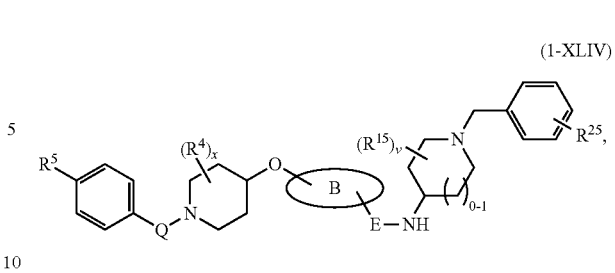

(1-XLIV)

in which $R^{25}$ is selected from halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, in which no alkyl or haloalkyl is substituted by an aryl, heteroaryl, cycloalkyl or heterocycloalkyl-containing group; and all other variables are as described above with respect to structural formulae (1-I) and (1-XXXVIII). $R^{25}$ can be, for example, —Cl, —F, cyano, —C(O)$CH_3$, —C(O)OH, —C(O)$NH_2$, trifluoromethyl, difluoromethyl, difluoromethoxy or trifluoromethoxy.

In certain embodiments, the presently disclosed compounds have the structural formula (1-XLV):

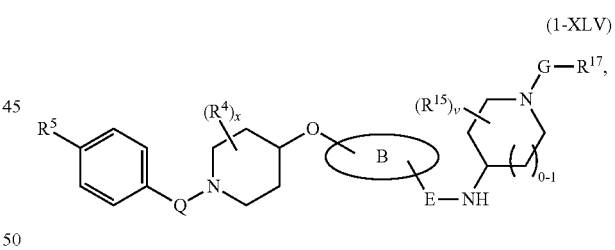

(1-XLV)

in which G is —C(O)— or —S(O)$_2$— and all other variables are as described above with respect to structural formulae (1-I) and (1-XXXVIII).

In certain embodiments, the presently disclosed compounds have the structural formula (1-XLVI):

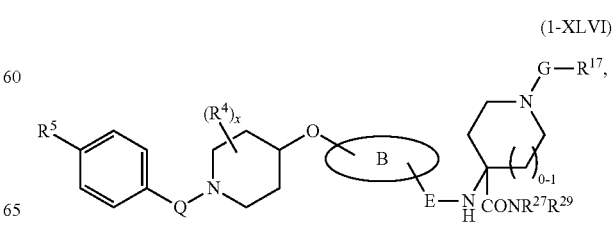

(1-XLVI)

in which $R^{27}$ is selected from H, —($C_1$-$C_6$ alkyl), —($C_1$-$C_6$ haloalkyl) (e.g., trifluoromethyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with respect to structural formulae (1-I) and (1-XXXVIII). In some embodiments, the compounds of structural formula (1-XLVI) are present as racemic mixtures or scalemic mixtures. In other embodiments, the compounds of structural formula (1-XLVI) are present in an enantiomerically-enriched form, for example as a substantially pure stereoisomer.

In certain embodiments, the presently disclosed compounds have the structural formula (1-XLVII):

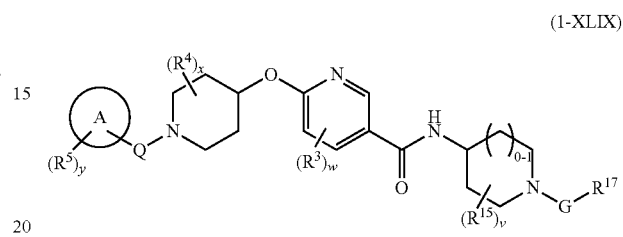

(1-XLVII)

in which $R^{27}$ is selected from H, —($C_1$-$C_6$ alkyl), —($C_1$-$C_6$ haloalkyl) (e.g., trifluoromethyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with respect to structural formulae (1-I) and (1-XXXVIII). In some embodiments, the compounds of structural formula (1-XLVII) are present as racemic mixtures or scalemic mixtures. In other embodiments, the compounds of structural formula (1-XLVII) are present in an enantiomerically-enriched form, for example as a substantially pure stereoisomer.

In certain embodiments, the presently disclosed compounds have the structural formula (1-XLVIII):

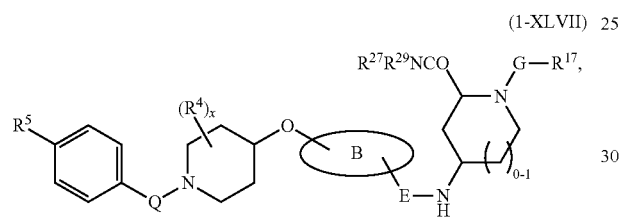

(1-XLVIII)

in which G, v, $R^{15}$ and $R^{17}$ are defined as described above with reference to structural formula (1-XXXVIII), and all other variables are defined as described above with reference to structural formulae (1-I) and (1-XXXVIII). $R^5$, v, $R^{15}$, $R^{17}$, Q, G and the ring denoted by "A" can be defined, for example, as described with respect to any of structural formulae (1-XXXIX)-(1-XLVII).

In certain embodiments, the presently disclosed compounds have the structural formula (1-XLIX):

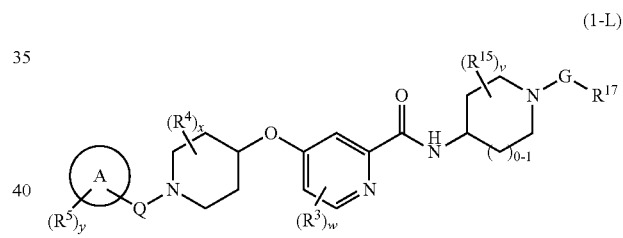

(1-XLIX)

in which G, v, $R^{15}$ and $R^{17}$ are defined as described above with reference to structural formula (1-XXXVIII), and all other variables are defined as described above with reference to structural formulae (1-I) and (1-XXXVIII). $R^5$, v, $R^{15}$, $R^{17}$, Q, G and the ring denoted by "A" can be defined, for example, as described with respect to any of structural formulae (1-XXXIX)-(1-XLVII).

In certain embodiments, the presently disclosed compounds have the structural formula (1-L):

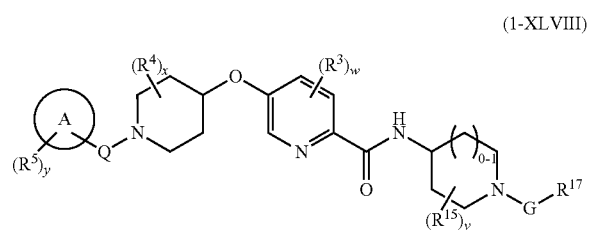

(1-L)

in which G, v, $R^{15}$ and $R^{17}$ are defined as described above with reference to structural formula (1-XXXVIII), and all other variables are defined as described above with reference to structural formulae (1-I) and (1-XXXVIII). $R^5$, v, $R^{15}$, $R^{17}$, Q, G and the ring denoted by "A" can be defined, for example, as described with respect to any of structural formulae (1-XXXIX)-(1-XLVII).

In certain embodiments, the presently disclosed compounds have the structural formula (1-LI):

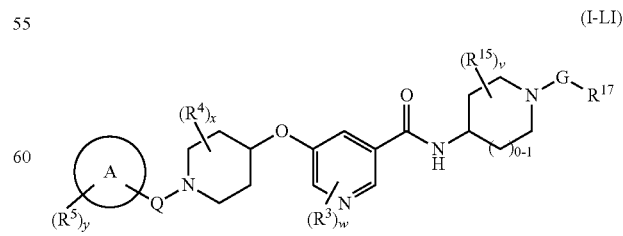

(1-LI)

in which G, v, $R^{15}$ and $R^{17}$ are defined as described above with reference to structural formula (1-XXXVIII), and all other variables are defined as described above with reference to structural formulae (1-I) and (1-XXXVIII). $R^5$, v, $R^{15}$, $R^{17}$, Q, G and the ring denoted by "A" can be defined, for example, as described with respect to any of structural formulae (1-XXXIX)-(1-XLVII).

In certain embodiments, the presently disclosed compounds have the structural formula (1-LII):

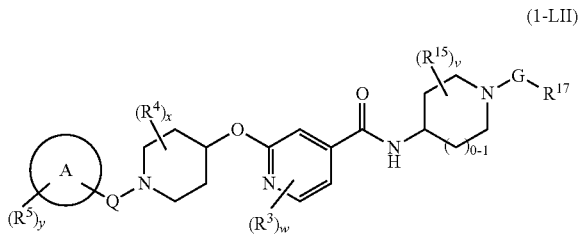

(1-LII)

in which G, v, $R^{15}$ and $R^{17}$ are defined as described above with reference to structural formula (1-XXXVIII), and all other variables are defined as described above with reference to structural formulae (1-I) and (1-XXXVIII). $R^5$, v, $R^{15}$, $R^{17}$, Q, G and the ring denoted by "A" can be defined, for example, as described with respect to any of structural formulae (1-XXXIX)-(1-XLVII).

In certain embodiments, the presently disclosed compounds have the structural formula (1-LIII):

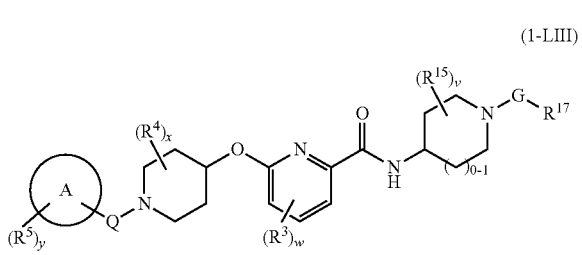

(1-LIII)

in which G, v, $R^{15}$ and $R^{17}$ are defined as described above with reference to structural formula (1-XXXVIII), and all other variables are defined as described above with reference to structural formulae (1-I) and (1-XXXVIII). $R^5$, v, $R^{15}$, $R^{17}$, Q, G and the ring denoted by "A" can be defined, for example, as described with respect to any of structural formulae (1-XXXIX)-(1-XLVII).

In certain embodiments, the presently disclosed compounds have the structural formula (1-LIV):

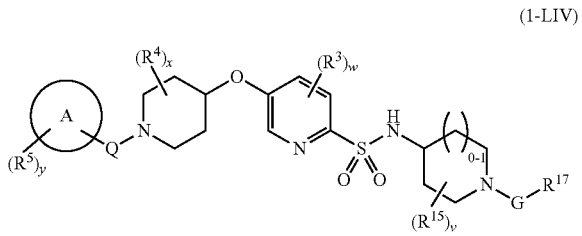

(1-LIV)

in which G, v, $R^{15}$ and $R^{17}$ are defined as described above with reference to structural formula (1-XXXVIII), and all other variables are defined as described above with reference to structural formulae (1-I) and (1-XXXVIII). $R^5$, v, $R^{15}$, $R^{17}$, Q, G and the ring denoted by "A" can be defined, for example, as described with respect to any of structural formulae (1-XXXIX)-(1-XLVII).

In certain embodiments, the presently disclosed compounds have the structural formula (1-LV):

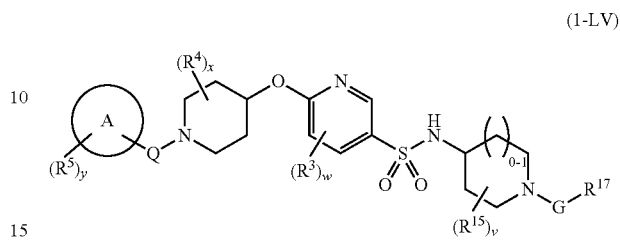

(1-LV)

in which G, v, $R^{15}$ and $R^{17}$ are defined as described above with reference to structural formula (1-XXXVIII), and all other variables are defined as described above with reference to structural formulae (1-I) and (1-XXXVIII). $R^5$, v, $R^{15}$, $R^{17}$, Q, G and the ring denoted by "A" can be defined, for example, as described with respect to any of structural formulae (1-XXXIX)-(1-XLVII).

In certain embodiments, the presently disclosed compounds have the structural formula (1-LVI):

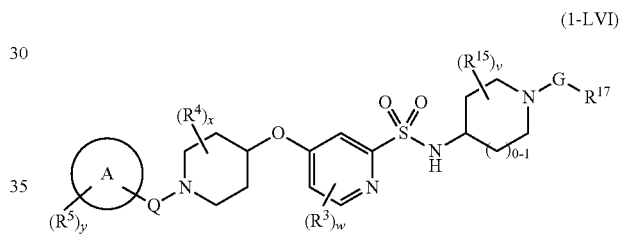

(1-LVI)

in which G, v, $R^{15}$ and $R^{17}$ are defined as described above with reference to structural formula (1-XXXVIII), and all other variables are defined as described above with reference to structural formulae (1-I) and (1-XXXVIII). $R^5$, v, $R^{15}$, $R^{17}$, Q, G and the ring denoted by "A" can be defined, for example, as described with respect to any of structural formulae (1-XXXIX)-(1-XLVII).

In certain embodiments, the presently disclosed compounds have the structural formula (1-LVII):

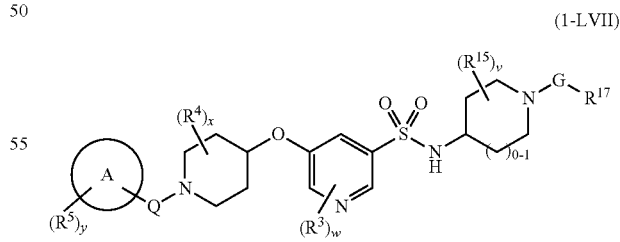

(1-LVII)

in which G, v, $R^{15}$ and $R^{17}$ are defined as described above with reference to structural formula (1-XXXVIII), and all other variables are defined as described above with reference to structural formulae (1-I) and (1-XXXVIII). $R^5$, v, $R^{15}$, $R^{17}$, Q, G and the ring denoted by "A" can be defined, for example, as described with respect to any of structural formulae (1-XXXIX)-(1-XLVII).

In certain embodiments, the presently disclosed compounds have the structural formula (1-LVIII):

(1-LVIII)

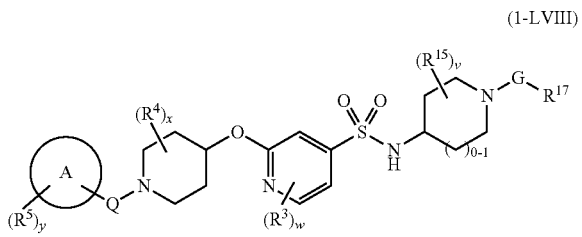

in which G, v, $R^{15}$ and $R^{17}$ are defined as described above with reference to structural formula (1-XXXVIII), and all other variables are defined as described above with reference to structural formulae (1-I) and (1-XXXVIII). $R^5$, v, $R^{15}$, $R^{17}$, Q, G and the ring denoted by "A" can be defined, for example, as described with respect to any of structural formulae (1-XXXIX)-(1-XLVII).

In certain embodiments, the presently disclosed compounds have the structural formula (1-LIX):

(1-LIX)

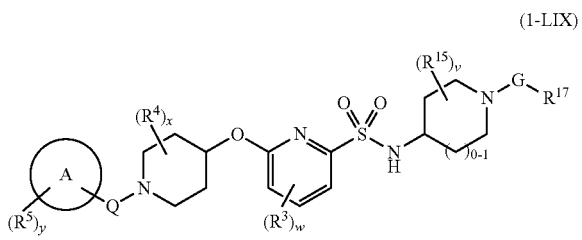

in which G, v, $R^{15}$ and $R^{17}$ are defined as described above with reference to structural formula (1-XXXVIII), and all other variables are defined as described above with reference to structural formulae (1-I) and (1-XXXVIII). $R^5$, v, $R^{15}$, $R^{17}$, Q, G and the ring denoted by "A" can be defined, for example, as described with respect to any of structural formulae (1-XXXIX)-(1-XLVII).

In certain embodiments, the presently disclosed compounds have the structural formula (1-LX):

(1-LX)

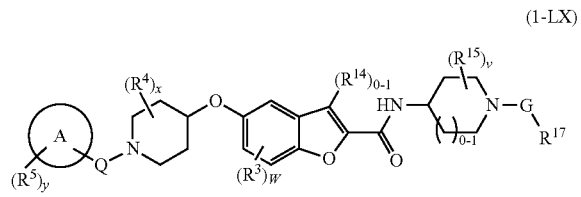

in which G, v, $R^{15}$ and $R^{17}$ are defined as described above with reference to structural formula (1-XXXVIII), and all other variables are defined as described above with reference to structural formulae (1-I) and (1-XXXVIII). $R^5$, v, $R^{15}$, $R^{17}$, Q, G and the ring denoted by "A" can be defined, for example, as described with respect to any of structural formulae (1-XXXIX)-(1-XLVII). In certain embodiments, one $R^{14}$ is substituted on the furano carbon. $R^{14}$ can be, for example, as described above with reference to structural formula (1-I). For example, in one embodiment $R^{14}$ is halo (e.g., —Cl or —F), cyano unsubstituted —($C_1$-$C_4$ alkyl) (e.g., methyl or ethyl), unsubstituted —($C_1$-$C_4$ haloakyl) (e.g., trifluoromethyl). In other embodiments, no $R^{14}$ is substituted on the furano carbon.

In certain embodiments, the presently disclosed compounds have the structural formula (1-LXI):

(1-LXI)

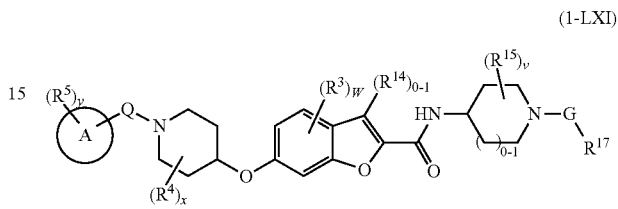

in which G, v, $R^{15}$ and $R^{17}$ are defined as described above with reference to structural formula (1-XXXVIII), and all other variables are defined as described above with reference to structural formulae (1-I) and (1-XXXVIII). $R^5$, v, $R^{15}$, $R^{17}$, Q, G and the ring denoted by "A" can be defined, for example, as described with respect to any of structural formulae (1-XXXIX)-(1-XLVII). In certain embodiments, one $R^{14}$ is substituted on the furano carbon. $R^{14}$ can be, for example, as described above with reference to structural formula (1-I). For example, in one embodiment $R^{14}$ is halo (e.g., —Cl or —F), cyano unsubstituted —($C_1$-$C_4$ alkyl) (e.g., methyl or ethyl), unsubstituted —($C_1$-$C_4$ haloakyl) (e.g., trifluoromethyl). In other embodiments, no $R^{14}$ is substituted on the furano carbon.

In certain embodiments, the presently disclosed compounds have the structural formula (1-LXII):

(1-LXII)

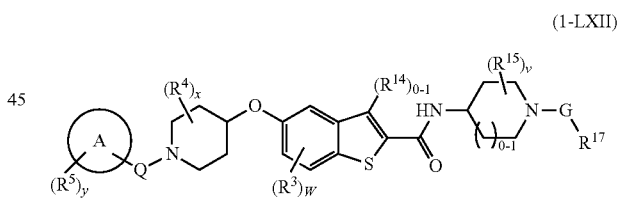

in which G, v, $R^{15}$ and $R^{17}$ are defined as described above with reference to structural formula (1-XXXVIII), and all other variables are defined as described above with reference to structural formulae (1-I) and (1-XXXVIII). $R^5$, v, $R^{15}$, $R^{17}$, Q, G and the ring denoted by "A" can be defined, for example, as described with respect to any of structural formulae (1-XXXIX)-(1-XLVII). In certain embodiments, one $R^{14}$ is substituted on the thieno carbon. $R^{14}$ can be, for example, as described above with reference to structural formula (1-I). For example, in one embodiment $R^{14}$ is halo (e.g., —Cl or —F), cyano unsubstituted —($C_1$-$C_4$ alkyl) (e.g., methyl or ethyl), unsubstituted —($C_1$-$C_4$ haloakyl) (e.g., trifluoromethyl). In other embodiments, no $R^{14}$ is substituted on the thieno carbon.

In certain embodiments, the presently disclosed compounds have the structural formula (1-LXIII):

(1-LXIII)

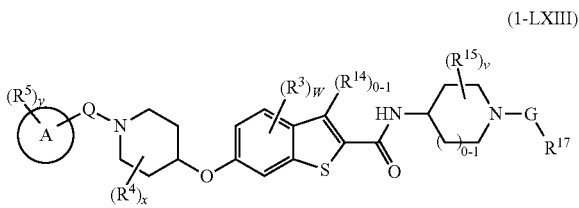

in which G, v, $R^{15}$ and $R^{17}$ are defined as described above with reference to structural formula (1-XXXVIII), and all other variables are defined as described above with reference to structural formulae (1-I) and (1-XXXVIII). $R^5$, v, $R^{15}$, $R^{17}$, Q, G and the ring denoted by "A" can be defined, for example, as described with respect to any of structural formulae (1-XXXIX)-(1-XLVII). In certain embodiments, one $R^{14}$ is substituted on the thieno carbon. $R^{14}$ can be, for example, as described above with reference to structural formula (1-I). For example, in one embodiment $R^{14}$ is halo (e.g., —Cl or —F), cyano unsubstituted —($C_1$-$C_4$ alkyl) (e.g., methyl or ethyl), unsubstituted —($C_1$-$C_4$ haloakyl) (e.g., trifluoromethyl). In other embodiments, no $R^{14}$ is substituted on the thieno carbon.

In certain embodiments, the presently disclosed compounds have the structural formula (1-LXIV):

(1-LXIV)

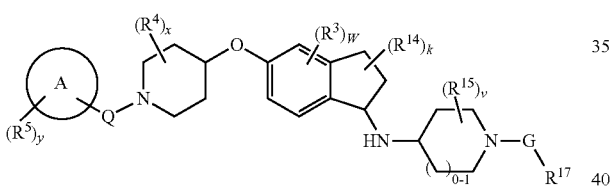

in which Q, G, v, $R^{15}$ and $R^{17}$ are defined as described above with reference to structural formula (1-XXXVIII), and all other variables are defined as described above with reference to structural formula (1-I). $R^5$, $R^{15}$, $R^{17}$, Q, G and the ring denoted by "A" can be defined, for example, as described with respect to any of structural formulae (1-XXXIX)-(1-XLVII).

In certain embodiments, the presently disclosed compounds have the structural formula (1-LXV):

(1-LXV)

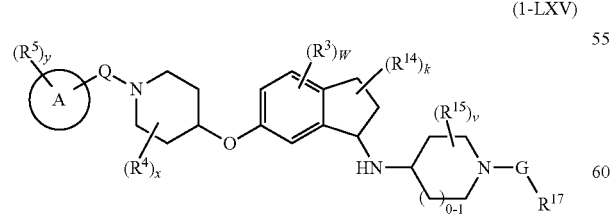

in which Q, G, v, $R^{15}$ and $R^{17}$ are defined as described above with reference to structural formula (1-XXXVIII), and all other variables are defined as described above with reference to structural formula (1-I). $R^5$, $R^{15}$, $R^{17}$, Q, G and the ring denoted by "A" can be defined, for example, as described with respect to any of structural formulae (1-XXXIX)-(1-XLVII).

In certain embodiments of compounds having structural formulae (1-XXXVIII)-(1-LXV), the

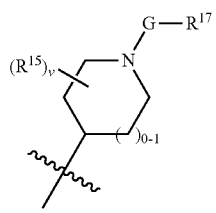

moiety has the structure

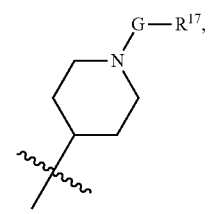

in which G is —$CH_2$—, —$CH(CH_3)$—, —C(O)— or —$S(O)_2$—. For example, in one embodiment, G is —$CH_2$—. In another embodiment, G is —C(O)— or —$S(O)_2$—.

In other embodiments of compounds having structural formulae (1-XXXVIII)-(1-LXV), the

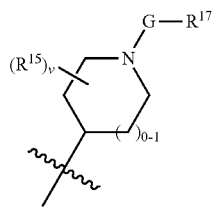

moiety has the structure

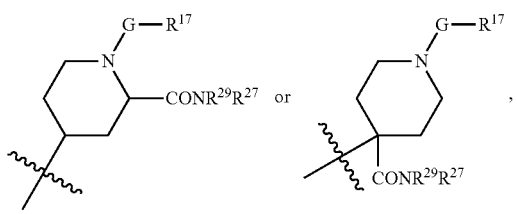

in which G is —$CH_2$—, —C(O)— or —$S(O)_2$—. In such embodiments, the compounds of structural formula (1-XLVII) can be present as racemic mixtures or scalemic mixtures, or in an enantiomerically-enriched form, for example as a substantially pure stereoisomer.

In other embodiments of compounds having structural formulae (1-XXXVIII)-(1-LXV), the moiety has the structure

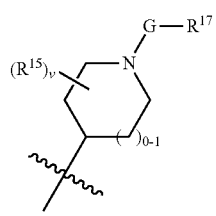

in which G is —CH$_2$—, —C(O)— or —S(O)$_2$—.

In certain embodiments of compounds having structural formulae (1-XXXVIII)-(1-LXV), the R$^{17}$ moiety has the structure

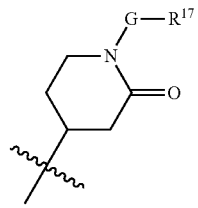

in which R$^{27}$ is selected from H, —(C$_1$-C$_6$ alkyl), —(C$_1$-C$_6$ haloalkyl) (e.g., trifluoromethyl), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl)-(C$_0$-C$_6$ alkyl)-S(O)$_{0-2}$—(C$_0$-C$_6$ alkyl), in which no heterocycloalkyl, alkyl or haloalkyl is substituted with an aryl-, heteroaryl-, cycloalkyl- or heterocycloalkyl-containing group, and R$^{29}$ is —H, —(C$_1$-C$_4$ alkyl) or —CO—O—(C$_1$-C$_4$ alkyl) in which no (C$_1$-C$_4$ alkyl) is substituted by an aryl, heteroaryl, cycloalkyl or heterocycloalkyl-containing group, or R$^{27}$ and R$^{29}$ together with the nitrogen to which they are bound form Hca.

In certain embodiments described above, each R$^{27}$ is selected from —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN and two R$^{21}$ on the same carbon optionally combine to form oxo, in which each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group, and each R$^{29}$ is H, methyl or ethyl, or R$^{27}$ and R$^{29}$ together with the nitrogen to which they are bound form Hca.

In certain embodiments of compounds having structural formulae (1-XXXVIII)-(1-LXV), the

moiety is p-(trifluoromethyl)phenyl.

In one embodiment, the presently disclosed compounds have the structural formula (1-LXVI):

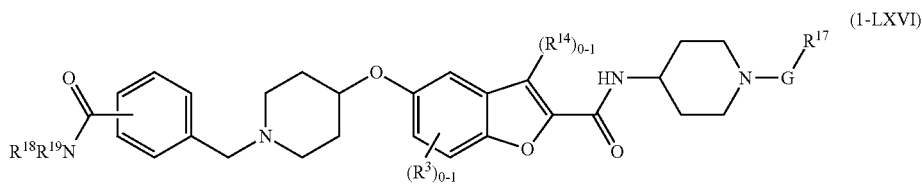

(1-LXVI)

in which G, R$^3$ and R$^{17}$ are as described above with respect to structural formula (1-XXXVIII); R$^{18}$ is H, —(C$_1$-C$_6$ alkyl), —(C$_1$-C$_6$ haloalkyl) (e.g., trifluoromethyl), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl) and —(C$_0$-C$_6$ alkyl)-S(O)$_{0-2}$—(C$_0$-C$_6$ alkyl), in which no alkyl or haloalkyl is substituted with an aryl-, heteroaryl-, cycloalkyl- or heterocycloalkyl-containing group and R$^{19}$ is —H, —(C$_1$-C$_4$ alkyl) or —CO—O—(C$_1$-C$_4$ alkyl) in which no alkyl is substituted by an aryl, heteroaryl, cycloalkyl or heterocycloalkyl-containing group, or R$^{18}$ and R$^{19}$ together with the nitrogen to which they are bound form Hca; and R$^{20}$ is Ar or Het. In certain embodiments, R$^{18}$ is H or (C$_1$-C$_4$ alkyl), and R$^{19}$ is —H. In certain embodiments, one R$^{14}$ is substituted on the furano carbon. R$^{14}$ can be, for example, as described above with reference to structural formula (1-I). For example, in one embodiment R$^{14}$ is halo (e.g., —Cl or —F), cyano unsubstituted —(C$_1$-C$_4$ alkyl) (e.g., methyl or ethyl), unsubstituted —(C$_1$-C$_4$ haloakyl) (e.g., trifluoromethyl). In other embodiments, no R$^{14}$ is substituted on the furano carbon.

In certain embodiments of compounds of structural formula (1-LXVI), w is 1, and R$^3$ is —NR$^8$R$^9$. In certain such embodiments, R$^3$ is substituted at a benzo or pyrido ring position meta to the alicyclic ethereal oxygen.

In other embodiments of compounds of structural formula (1-LXVI), w is 1, and R$^3$ is —(C$_0$-C$_3$ alkyl)-Y$^1$—(C$_1$-C$_3$ alkyl)-Y$^2$—(C$_0$-C$_3$ alkyl), in which each of Y$^1$ and Y$^2$ is independently L, —O—, —S— or —NR$^9$—. In certain such embodiments, R$^3$ is substituted at a benzo or pyrido ring position meta to the alicyclic ethereal oxygen.

In another embodiment, the presently disclosed compounds have the structural formula (1-LXVII):

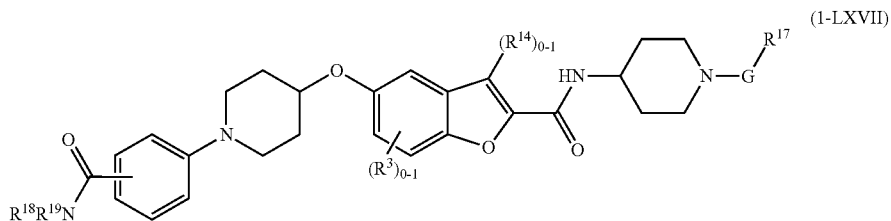

in which $R^3$ and $R^{14}$ are defined as described above with reference to structural formulae (1-I) and (1-XXXVIII); G and $R^{17}$ are defined as described above with reference to structural formula (1-XXXVIII); and $R^{18}$ and $R^{19}$ are defined as described above with reference to structural formula (1-LXVI).

In another embodiment, the presently disclosed compounds have the structural formula (1-LXVIII):

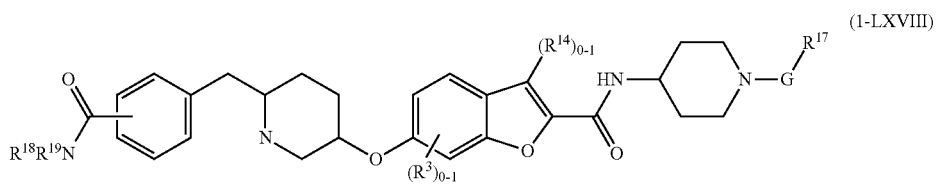

in which $R^3$ and $R^{14}$ are defined as described above with reference to structural formulae (1-I) and (1-XXXVIII); G and $R^{17}$ are defined as described above with reference to structural formula (1-XXXVIII); and $R^{18}$ and $R^{19}$ are defined as described above with reference to structural formula (1-LXVI).

In another embodiment, the presently disclosed compounds have the structural formula (1-LXIX):

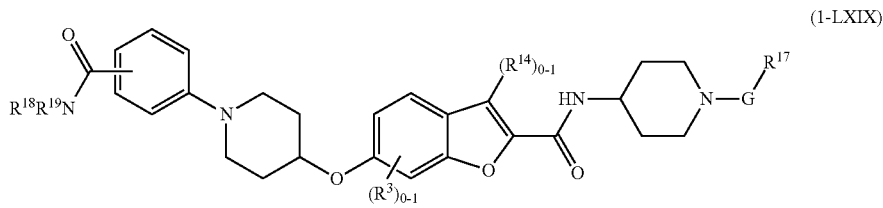

in which $R^3$ and $R^{14}$ are defined as described above with reference to structural formulae (1-I) and (1-XXXVIII); G and $R^{17}$ are defined as described above with reference to structural formula (1-XXXVIII); and $R^{18}$ and $R^{19}$ are defined as described above with reference to structural formula (1-LXVI).

In another embodiment, the presently disclosed compounds have the structural formula (1-LXX):

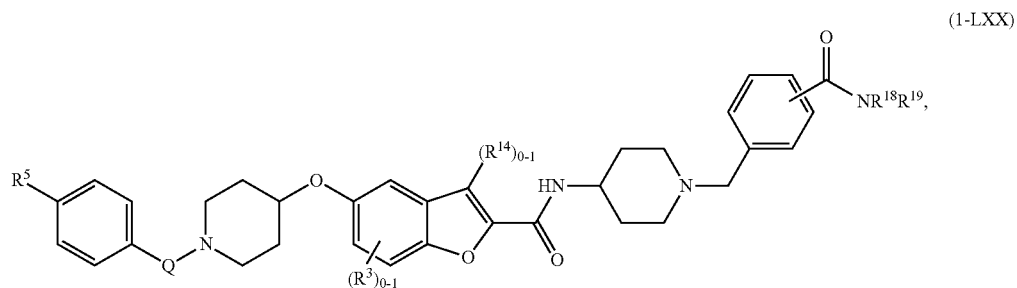
(1-LXX)

in which Q, $R^3$, $R^5$ and $R^{14}$ are defined as described above with reference to structural formulae (1-I) and (1-XXXVIII); and $R^{18}$ and $R^{19}$ are defined as described above with reference to structural formula (1-LXVI).

In another embodiment, the presently disclosed compounds have the structural formula (1-LXXI):

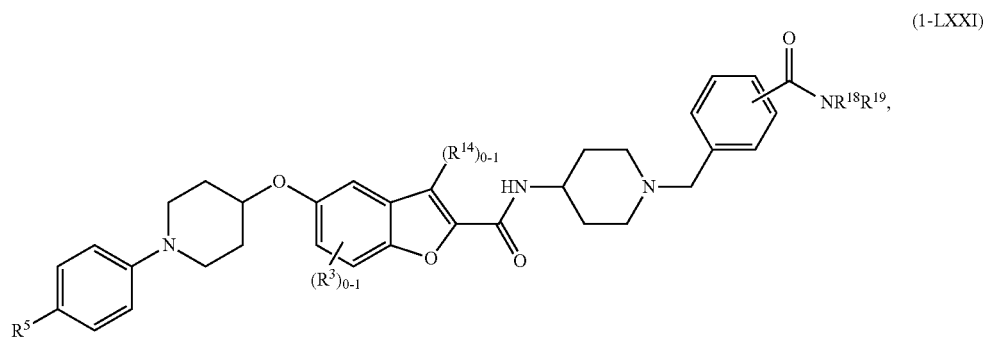
(1-LXXI)

in which $R^3$, $R^5$ and $R^{14}$ are defined as described above with reference to structural formulae (1-I) and (1-XXXVIII); and $R^{18}$ and $R^{19}$ are defined as described above with reference to structural formula (1-LXVI).

In another embodiment, the presently disclosed compounds have the structural formula (1-LXXII):

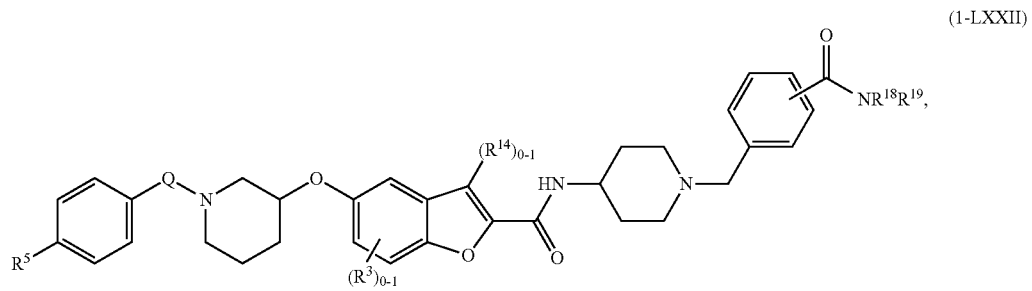
(1-LXXII)

in which Q, $R^3$, $R^5$ and $R^{14}$ are defined as described above with reference to structural formulae (1-I) and (1-XXXVIII); and $R^{18}$ and $R^{19}$ are defined as described above with reference to structural formula (1-LXVI).

In another embodiment, the presently disclosed compounds have the structural formula (1-LXXIII):

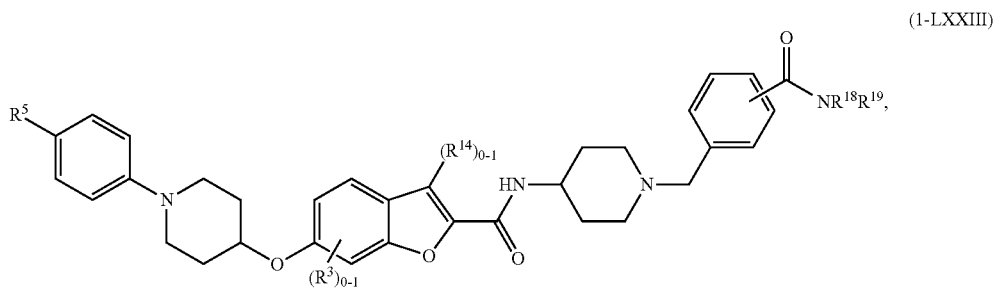

(1-LXXIII)

in which $R^3$, $R^5$ and $R^{14}$ are defined as described above with reference to structural formulae (1-I) and (1-XXXVIII); and $R^{18}$ and $R^{19}$ are defined as described above with reference to structural formula (1-LXVI).

In another embodiment, the presently disclosed compounds have the structural formula (1-LXXIV):

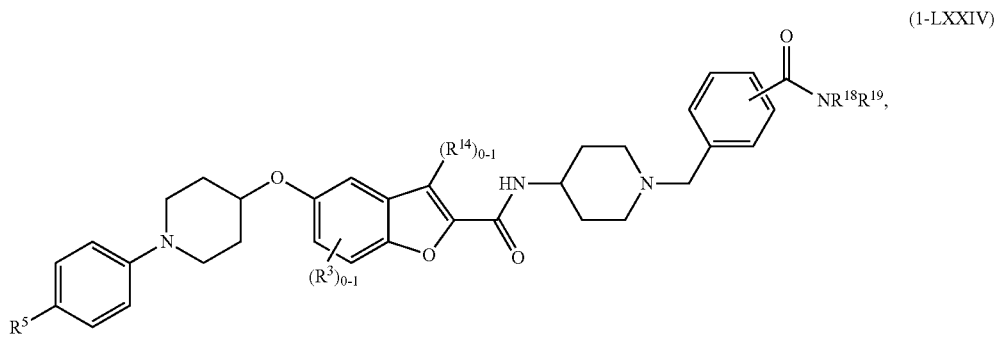

(1-LXXIV)

in which $R^3$, $R^5$ and $R^{14}$ are defined as described above with reference to structural formulae (1-I) and (1-XXXVIII); and $R^{18}$ and $R^{19}$ are defined as described above with reference to structural formula (1-LXVI).

In one embodiment, the presently disclosed compounds have the structural formula (1-LXXV):

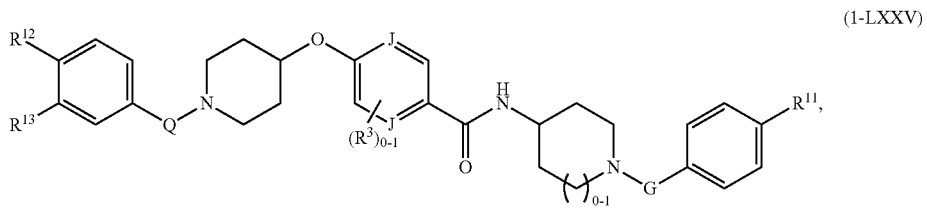

(1-LXXV)

in which one J is N and the other is CH; Q is —CH$_2$— or a single bond; G is CH$_2$ or C(O); $R^3$ is as described above with respect to structural formulae (1-I) and (1-XXXVIII) (e.g., absent or halo); and $R^{11}$, $R^{12}$ and $R^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H.

In certain embodiments, the presently disclosed compounds have the structural formula (1-LXXVI):

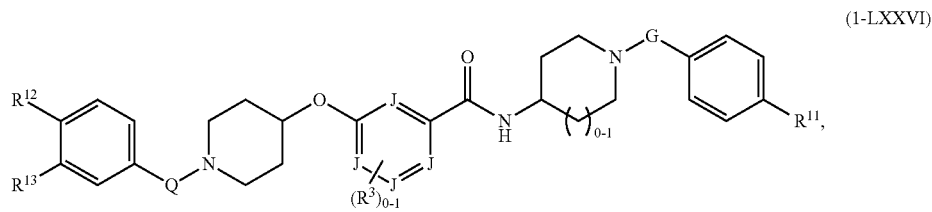

(1-LXXVI)

in which one J is N and the other is CH; Q is —CH₂— or a single bond; G is CH₂ or C(O); R³ is as described above with respect to structural formulae (1-I) and (1-XXXVIII) (e.g., absent or halo); and R¹¹, R¹² and R¹³ are independently selected from H, halo, cyano, —(C₁-C₄ haloalkyl), —O—(C₁-C₄ haloalkyl), —(C₁-C₄ alkyl), —O—(C₁-C₄ alkyl), —C(O)—(C₀-C₄ alkyl), —C(O)O—(C₀-C₄ alkyl), —C(O)N(C₀-C₄ alkyl)(C₀-C₄ alkyl), NO₂ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R¹² and R¹³ is not H.

In certain embodiments, the presently disclosed compounds have the structural formula (1-LXXVII):

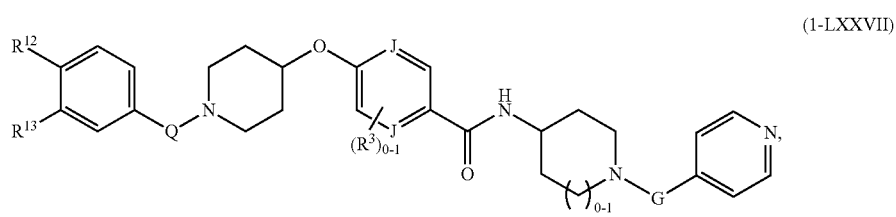

(1-LXXVII)

in which one J is N, and the other is CH; Q is —CH₂— or a single bond; G is CH₂ or C(O); R³ is as described above with respect to structural formulae (1-I) and (1-XXXVIII) (e.g., absent or halo); and R¹² and R¹³ are independently selected from H, halo, cyano, —(C₁-C₄ haloalkyl), —O—(C₁-C₄ haloalkyl), —(C₁-C₄ alkyl), —O—(C₁-C₄ alkyl), —C(O)—(C₀-C₄ alkyl), —C(O)O—(C₀-C₄ alkyl), —C(O)N(C₀-C₄ alkyl)(C₀-C₄ alkyl), NO₂ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R¹¹, R¹² and R¹³ is not H.

In certain embodiments, the presently disclosed compounds have the structural formula (1-LXXVIII):

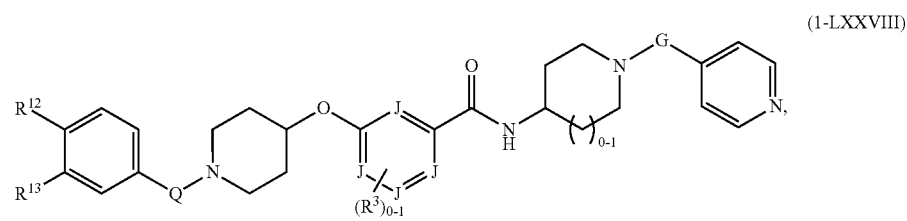

(1-LXXVIII)

in which one J is N, and the other three are CH; Q is —CH$_2$— or a single bond; G G is CH$_2$ or C(O); R$^3$ is as described above with respect to structural formulae (1-I) and (1-XXXVIII) (e.g., absent or halo); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H.

In certain embodiments, the presently disclosed compounds have the structural formula (1-LXXIX):

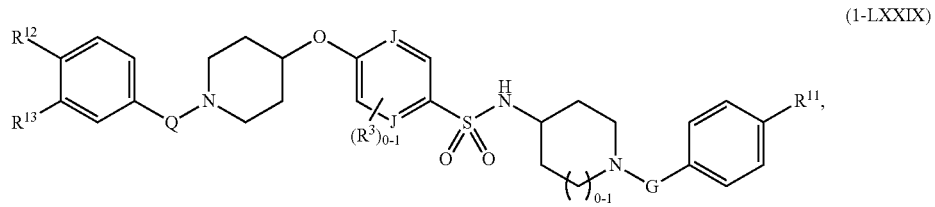

(1-LXXIX)

in which one J is N and the other is CH; Q is —CH$_2$— or a single bond G is CH$_2$ or C(O); R$^3$ is as described above with respect to structural formulae (1-I) and (1-XXXVIII) (e.g., absent or halo); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H.

In certain embodiments, the presently disclosed compounds have the structural formula (1-LXXX):

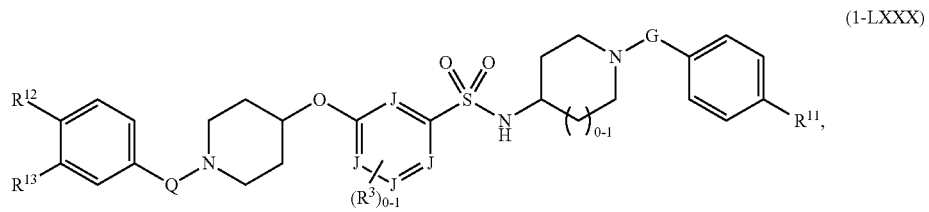

(1-LXXX)

in which one J is N, and the other three are CH; Q is —CH$_2$— or a single bond; G is CH$_2$ or C(O); R$^3$ is as described above with respect to structural formulae (1-I) and (1-XXXVIII) (e.g., absent or halo); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H.

In certain embodiments, the presently disclosed compounds have the structural formula (1-LXXXI):

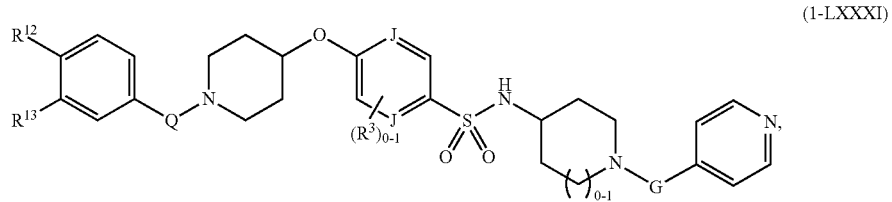

(1-LXXXI)

in which one J is N, and the other is CH; Q is —CH₂— or a single bond; G is CH₂ or C(O); R³ is as described above with respect to structural formulae (1-I) and (1-XXXVIII) (e.g., absent or halo); and R¹² and R¹³ are independently selected from H, halo, cyano, —(C₁-C₄ haloalkyl), —O—(C₁-C₄ haloalkyl), —(C₁-C₄ alkyl), —O—(C₁-C₄ alkyl), —C(O)—(C₀-C₄ alkyl), —C(O)O—(C₀-C₄ alkyl), —C(O)N(C₀-C₄ alkyl)(C₀-C₄ alkyl), NO₂ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R¹¹, R¹² and R¹³ is not H.

In certain embodiments, the presently disclosed compounds have the structural formula (1-LXXXII):

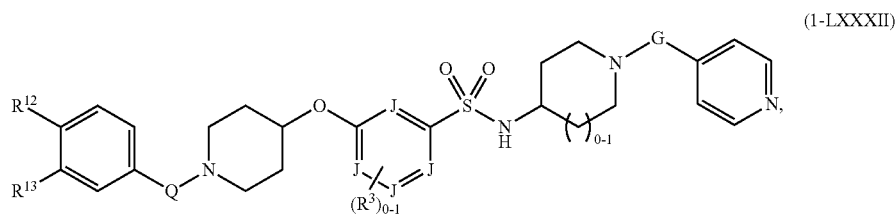

(1-LXXXII)

in which one J is N, and the other three are CH; Q is —CH₂— or a single bond; G is CH₂ or C(O); R³ is as described above with respect to structural formulae (1-I) and (1-XXXVIII) (e.g., absent or halo); and R¹² and R¹³ are independently selected from H, halo, cyano, —(C₁-C₄ haloalkyl), —O—(C₁-C₄ haloalkyl), —(C₁-C₄ alkyl), —O—(C₁-C₄ alkyl), —C(O)—(C₀-C₄ alkyl), —C(O)O—(C₀-C₄ alkyl), —C(O)N(C₀-C₄ alkyl)(C₀-C₄ alkyl), NO₂ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R¹² and R¹³ is not H.

In certain embodiments, the presently disclosed compounds have the structural formula (1-LXXXIII):

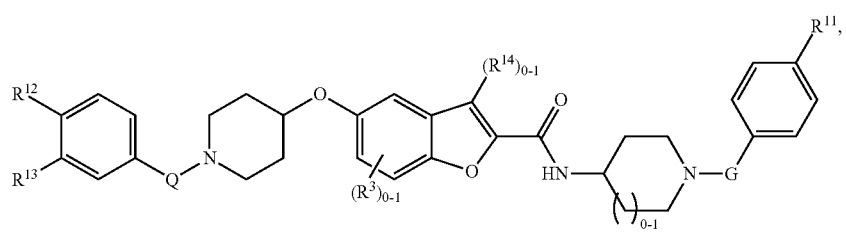

(1-LXXXIII)

in which Q is —CH$_2$— or a single bond; G is CH$_2$ or C(O); R$^3$ is as described above with respect to structural formulae (1-I) and (1-XXXVIII) (e.g., absent or halo); R$^{14}$ is as described above with respect to structural formulae (1-I) and (1-LX) (e.g., absent, methyl or halo); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H.

In certain embodiments, the presently disclosed compounds have the structural formula (1-LXXXIV):

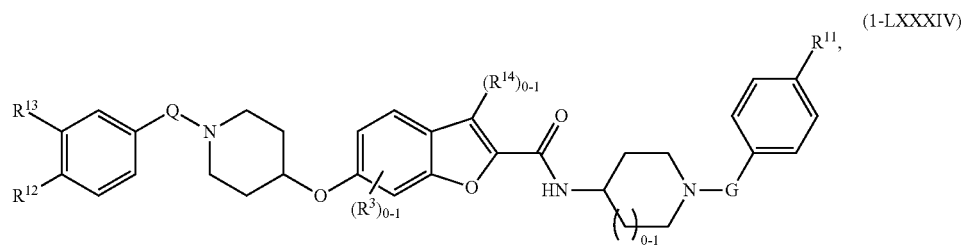

(1-LXXXIV)

in which Q is —CH$_2$— or a single bond; G is CH$_2$ or C(O); R$^3$ is as described above with respect to structural formulae (1-I) and (1-XXXVIII) (e.g., absent or halo); R$^{14}$ is as described above with respect to structural formulae (1-I) and (1-LXI) (e.g., absent, methyl or halo); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H.

In certain embodiments, the presently disclosed compounds have the structural formula (1-LXXXV):

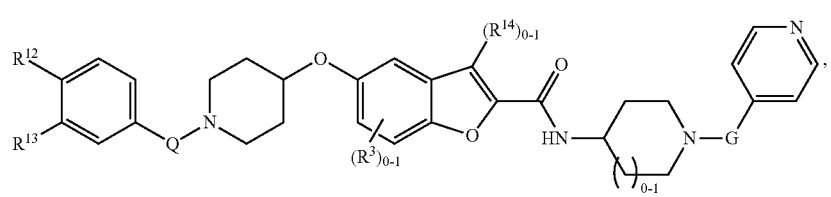

(1-LXXXV)

in which Q is —CH₂— or a single bond; G is CH₂ or C(O); R³ is as described above with respect to structural formulae (1-I) and (1-XXXVIII) (e.g., absent or halo); R¹⁴ is as described above with respect to structural formulae (1-I) and (1-LX) (e.g., absent, methyl or halo); and R¹² and R¹³ are independently selected from H, halo, cyano, —(C₁-C₄ haloalkyl), —O—(C₁-C₄ haloalkyl), —(C₁-C₄ alkyl), —O—(C₁-C₄ alkyl), —C(O)—(C₀-C₄ alkyl), —C(O)O—(C₀-C₄ alkyl), —C(O)N(C₀-C₄ alkyl)(C₀-C₄ alkyl), NO₂ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R¹² and R¹³ is not H.

In certain embodiments, the presently disclosed compounds have the structural formula (1-LXXXVI):

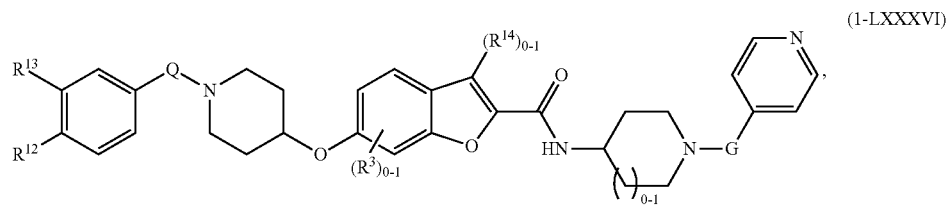

(1-LXXXVI)

in which Q is —CH₂— or a single bond; G is CH₂ or C(O); R³ is as described above with respect to structural formulae (1-I) and (1-XXXVIII) (e.g., absent or halo); R¹⁴ is as described above with respect to structural formulae (1-I) and (1-LXI) (e.g., absent, methyl or halo); and R¹² and R¹³ are independently selected from H, halo, cyano, —(C₁-C₄ haloalkyl), —O—(C₁-C₄ haloalkyl), —(C₁-C₄ alkyl), —O—(C₁-C₄ alkyl), —C(O)—(C₀-C₄ alkyl), —C(O)O—(C₀-C₄ alkyl), —C(O)N(C₀-C₄ alkyl)(C₀-C₄ alkyl), NO₂ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R¹² and R¹³ is not H.

In certain embodiments, the presently disclosed compounds have the structural formula (1-LXXXVII):

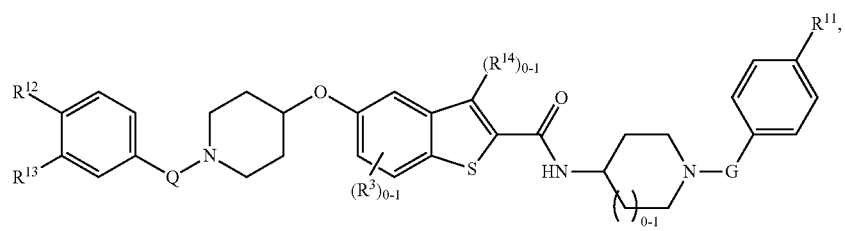

(1-LXXXVII)

in which Q is —CH₂— or a single bond; G is CH₂ or C(O); R³ is as described above with respect to structural formulae (1-I) and (1-XXXVIII) (e.g., absent or halo); R¹⁴ is as described above with respect to structural formulae (1-I) and (1-LXII) (e.g., absent, methyl or halo); and R¹¹, R¹² and R¹³ are independently selected from H, halo, cyano, —(C₁-C₄ haloalkyl), —O—(C₁-C₄ haloalkyl), —(C₁-C₄ alkyl), —O—(C₁-C₄ alkyl), —C(O)—(C₀-C₄ alkyl), —C(O)O—(C₀-C₄ alkyl), —C(O)N(C₀-C₄ alkyl)(C₀-C₄ alkyl), NO₂ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H.

In certain embodiments, the presently disclosed compounds have the structural formula (1-LXXXVIII):

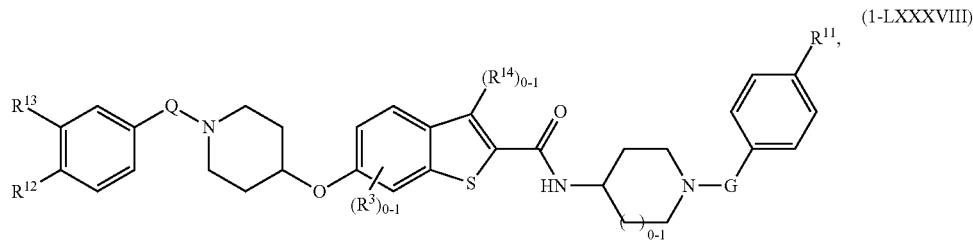

(1-LXXXVIII)

in which Q is —CH$_2$— or a single bond; G is CH$_2$ or C(O); $R^3$ is as described above with respect to structural formulae (1-I) and (1-XXXVIII) (e.g., absent or halo); $R^{14}$ is as described above with respect to structural formulae (1-I) and (1-LXIII) (e.g., absent, methyl or halo); and $R^{11}$, $R^{12}$ and $R^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H.

In certain embodiments, the presently disclosed compounds have the structural formula (1-LXXXIX):

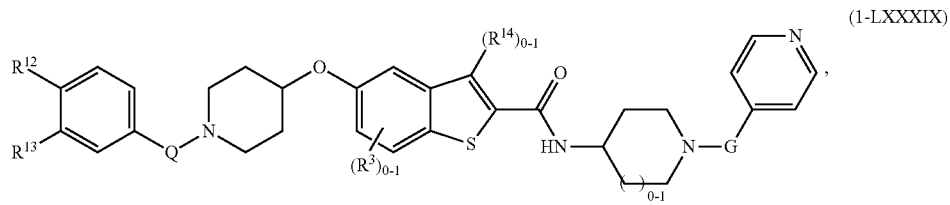

(1-LXXXIX)

in which Q is —CH$_2$— or a single bond; G is CH$_2$ or C(O); $R^3$ is as described above with respect to structural formulae (1-I) and (1-XXXVIII) (e.g., absent or halo); $R^{14}$ is as described above with respect to structural formulae (1-I) and (1-LXII) (e.g., absent, methyl or halo); and $R^{12}$ and $R^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H.

In certain embodiments, the presently disclosed compounds have the structural formula (1-XC):

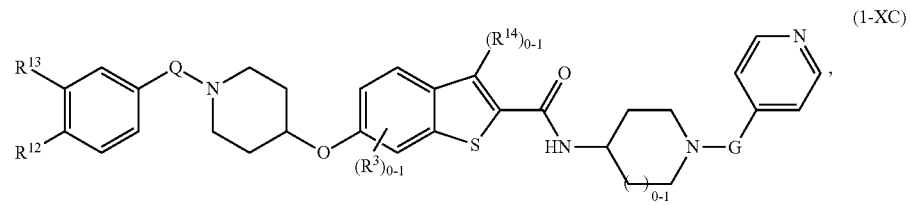

(1-XC)

in which Q is —CH$_2$— or a single bond; G is CH$_2$ or CO; G is CH$_2$ or C(O); R$^3$ is as described above with respect to structural formulae (1-I) and (1-XXXVIII) (e.g., absent or halo); R$^{14}$ is as described above with respect to structural formulae (1-I) and (1-LXIII) (e.g., absent, methyl or halo); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H.

In certain embodiments, the presently disclosed compounds have the structural formula (1-XCI):

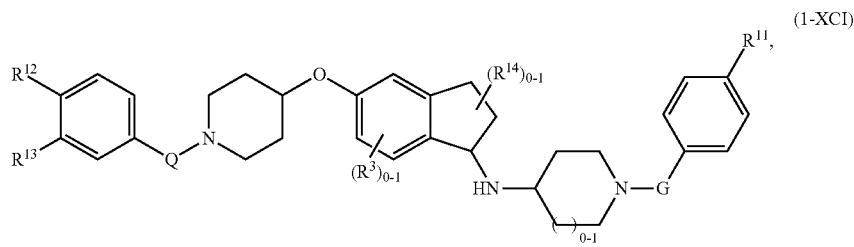

(1-XCI)

in which Q is —CH$_2$— or a single bond; G is CH$_2$ or C(O); R$^3$ is as described above with respect to structural formulae (1-I) and (1-XXXVIII) (e.g., absent or halo); R$^{14}$ is as described above with respect to structural formula (1-I) (e.g., absent, methyl or halo); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H.

In certain embodiments, the presently disclosed compounds have the structural formula (1-XCII):

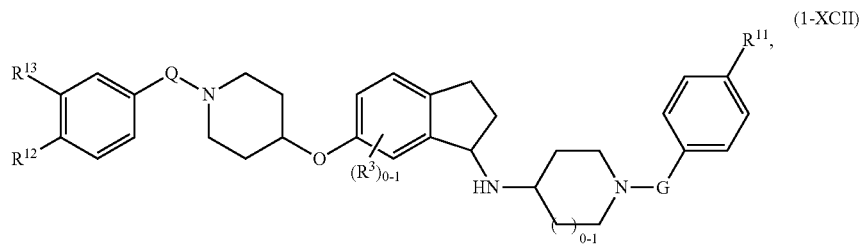

(1-XCII)

in which Q is —CH$_2$— or a single bond; G is CH$_2$ or C(O); R$^3$ is as described above with respect to structural formulae (1-I) and (1-XXXVIII) (e.g., absent or halo); R$^{14}$ is as described above with respect to structural formula (1-I) (e.g., absent, methyl or halo); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H.

In certain embodiments, the presently disclosed compounds have the structural formula (1-XCIII):

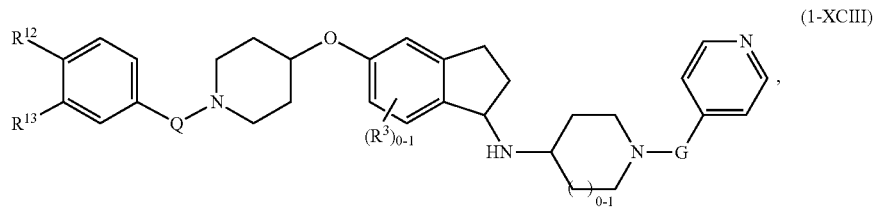

(1-XCIII)

in which Q is —CH₂— or a single bond; G is CH₂ or C(O); R³ is as described above with respect to structural formulae (1-I) and (1-XXXVIII) (e.g., absent or halo); R¹⁴ is as described above with respect to structural formula (1-I) (e.g., absent, methyl or halo); and R¹² and R¹³ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), NO₂ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R¹¹, R¹² and R¹³ is not H.

In certain embodiments, the presently disclosed compounds have the structural formula (1-XCIV):

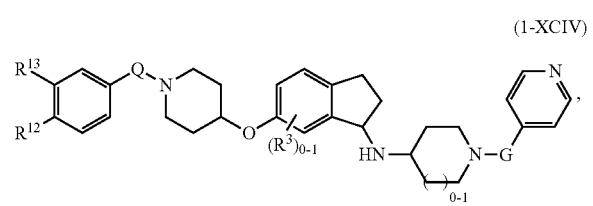

(1-XCIV)

in which Q is —CH₂— or a single bond; G is CH₂ or C(O); R³ is as described above with respect to structural formulae (1-I) and (1-XXXVIII) (e.g., absent or halo); R¹⁴ is as described above with respect to structural formula (1-I) (e.g., absent, methyl or halo); and R¹² and R¹³ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), NO₂ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R¹¹, R¹² and R¹³ is not H.

Examples of compounds presently disclosed for use as described herein include those described in U.S. patent application Ser. No. 11/963,742, filed Dec. 21, 2007, Ser. No. 12/272,581, filed Nov. 17, 2008, Ser. No. 12/334,201, filed Dec. 12, 2008, Ser. No. 12/428,334, filed Apr. 22, 2009, and Ser. No. 12/695,861, filed Jan. 28, 2010, each of which are hereby incorporated herein by reference in their entireties. Further examples of compounds for use as disclosed herein include those according to structural formula (1-I) illustrative examples of which are listed in Table 1. These compounds can be made, for example using a procedure analogous to those described in U.S. Patent Application Publications nos. 2009/0163511, 2009/0170829, 2009/0186894 and 2009/0275609, and in U.S. patent application Ser. No. 12/695,861, each of which is hereby incorporated by reference in its entirety.

TABLE 1

| No. | Name | Structure |
|---|---|---|
| 1-1 | 5-(1-(4-cyanophenyl)piperidin-4-yloxy)-N-(1-(pyridin-4-ylmethyl)piperidin-4-yl)picolinamide | 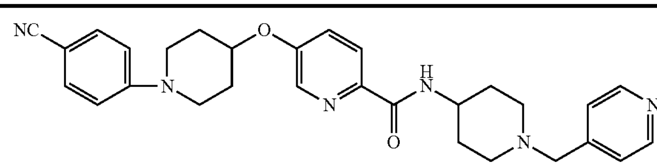 |
| 1-2 | N-(1-(4-cyanobenzyl)piperidin-4-yl)-5-(1-(4-cyanophenyl)piperidin-4-yloxy)picolinamide | 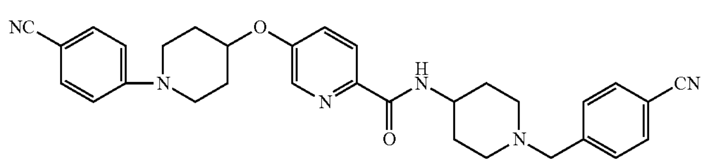 [SMILES: N#Cc1ccc(CN2CCC(NC(=O)c3ccc(OC4CCN(c5ccc(C#N)cc5)CC4)cn3)CC2)cc1] |
| 1-3 | N-(1-(pyridin-4-ylmethyl)piperidin-4-yl)-5-(1-(4-(trifluoromethyl)phenyl)piperidin-4-yloxy)picolinamide | 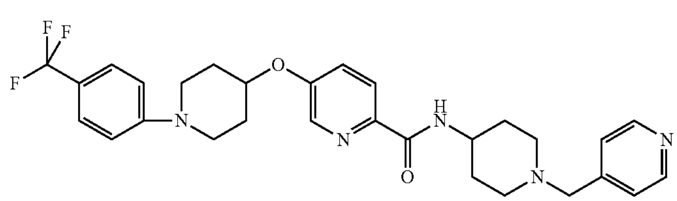 [SMILES: O=C(NC1CCN(Cc2ccncc2)CC1)c1ccc(OC2CCN(c3ccc(C(F)(F)F)cc3)CC2)cn1] |

TABLE 1-continued

| No. | Name | Structure |
|---|---|---|
| 1-4 | N-(1-(4-cyanobenzyl)piperidin-4-yl)-5-(1-(4-(trifluoromethyl)phenyl)piperidin-4-yloxy)picolinamide | 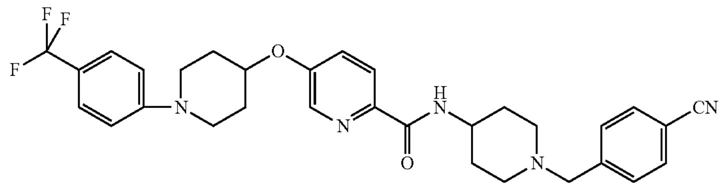 [SMILES: N#Cc1ccc(CN2CCC(NC(=O)c3ccc(OC4CCN(c5ccc(C(F)(F)F)cc5)CC4)cn3)CC2)cc1] |
| 1-5 | N-(1-(pyridin-3-ylmethyl)piperidin-4-yl)-5-(1-(4-(trifluoromethyl)phenyl)piperidin-4-yloxy)picolinamide | 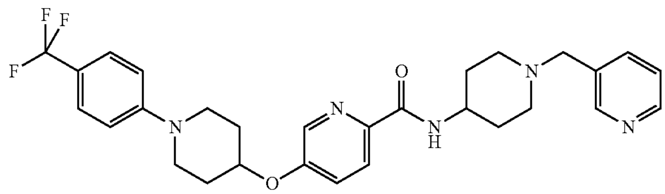 [SMILES: O=C(NC1CCN(Cc2cccnc2)CC1)c1ccc(OC2CCN(c3ccc(C(F)(F)F)cc3)CC2)cn1] |
| 1-6 | N-(1-(pyridin-3-ylmethyl)piperidin-4-yl)-5-(1-(4-cyanophenyl)piperidin-4-yloxy)picolinamide | 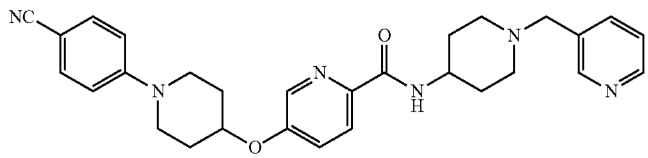 [SMILES: N#Cc1ccc(N2CCC(Oc3ccc(C(=O)NC4CCN(Cc5cccnc5)CC4)nc3)CC2)cc1] |
| 1-7 | methyl 4-((4-(5-(1-(4-cyanophenyl)piperidin-4-yloxy)picolinamido)piperidin-1-yl)methyl)benzoate | 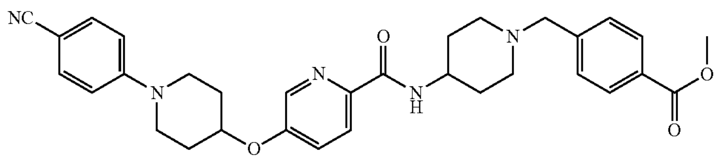 [SMILES: COC(=O)c1ccc(CN2CCC(NC(=O)c3ccc(OC4CCN(c5ccc(C#N)cc5)CC4)cn3)CC2)cc1] |
| 1-8 | methyl 4-((4-(5-(1-(4-(trifluoromethyl)phenyl)piperidin-4-yloxy)picolinamido)piperidin-1-yl)methyl)benzoate | 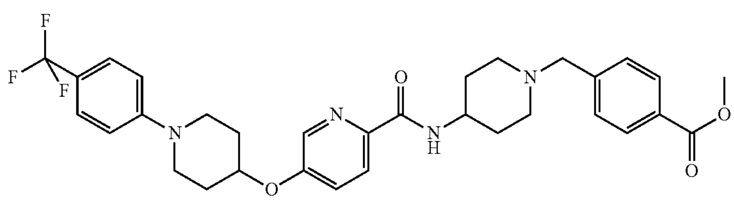 [SMILES: COC(=O)c1ccc(CN2CCC(NC(=O)c3ccc(OC4CCN(c5ccc(C(F)(F)F)cc5)CC4)cn3)CC2)cc1] |
| 1-9 | tert-butyl 4-(6-(1-(4-(trifluoromethyl)phenyl)piperidin-4-yloxy)nicotinamido)piperidine-1-carboxylate | 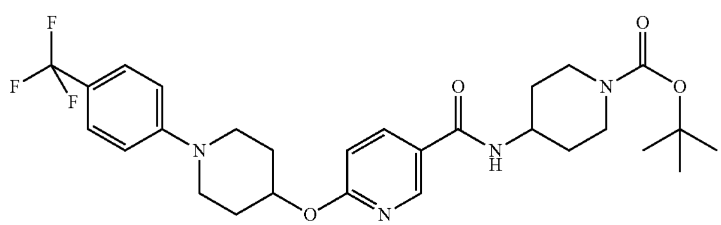 [SMILES: CC(C)(C)OC(=O)N1CCC(NC(=O)c2ccc(OC3CCN(c4ccc(C(F)(F)F)cc4)CC3)nc2)CC1] |
| 1-10 | N-(1-(pyridin-4-ylmethyl)piperidin-4-yl)-6-(1-(4-(trifluoromethyl)phenyl)piperidin-4-yloxy)nicotinamide | 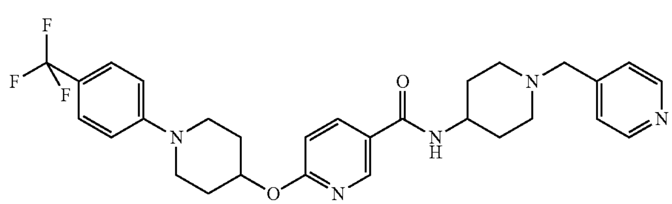 [SMILES: O=C(NC1CCN(Cc2ccncc2)CC1)c1ccc(OC2CCN(c3ccc(C(F)(F)F)cc3)CC2)nc1] |
| 1-11 | N-(1-(4-fluorobenzyl)piperidin-4-yl)-6-(1-(4-(trifluoromethyl)phenyl)piperidin-4-yloxy)nicotinamide | 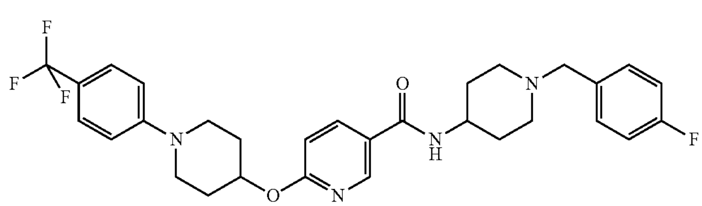 [SMILES: O=C(NC1CCN(Cc2ccc(F)cc2)CC1)c1ccc(OC2CCN(c3ccc(C(F)(F)F)cc3)CC2)nc1] |

TABLE 1-continued

| No. | Name | Structure |
|---|---|---|
| 1-12 | tert-butyl 4-(4-(1-(4-(trifluoromethyl)phenyl)piperidin-4-yloxy)picolinamido)piperidine-1-carboxylate | 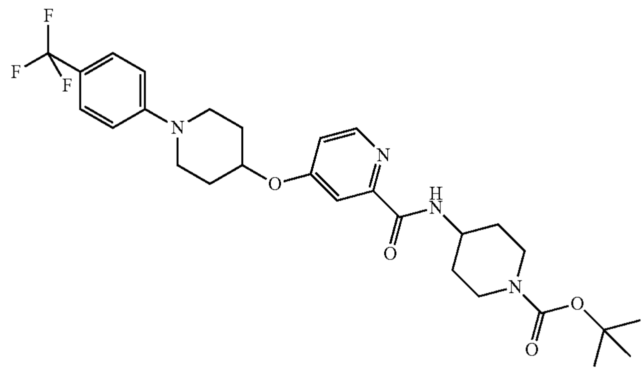 [SMILES: CC(C)(C)OC(=O)N1CCC(NC(=O)c2cc(OC3CCN(c4ccc(C(F)(F)F)cc4)CC3)ccn2)CC1] |
| 1-13 | N-(1-(pyridin-4-ylmethyl)piperidin-4-yl)-4-(1-(4-(trifluoromethyl)phenyl)piperidin-4-yloxy)picolinamide | 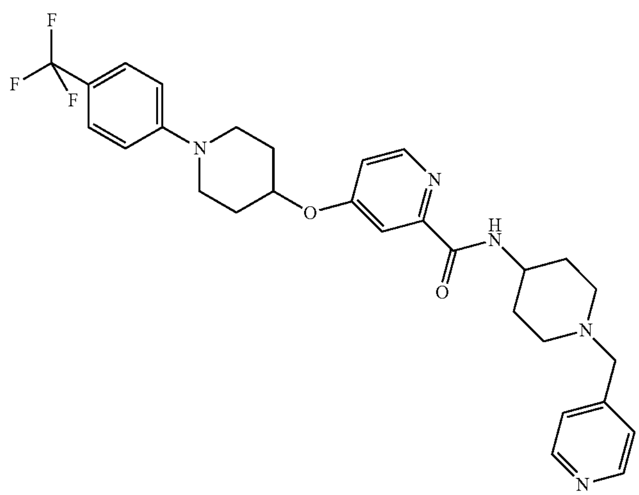 [SMILES: O=C(NC1CCN(Cc2ccncc2)CC1)c1cc(OC2CCN(c3ccc(C(F)(F)F)cc3)CC2)ccn1] |
| 1-14 | N-(1-(pyridin-4-ylmethyl)piperidin-4-yl)-5-(1-(4-(trifluoromethyl)phenyl)piperidin-4-yloxy)nicotinamide | 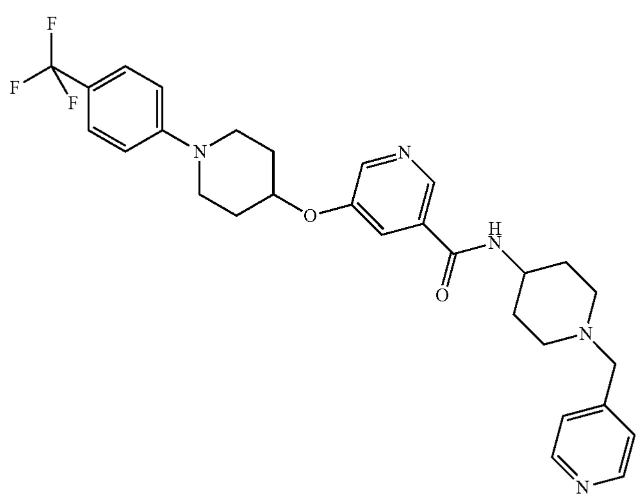 [SMILES: O=C(NC1CCN(Cc2ccncc2)CC1)c1cncc(OC2CCN(c3ccc(C(F)(F)F)cc3)CC2)c1] |

TABLE 1-continued

| No. | Name | Structure |
|---|---|---|
| 1-15 | tert-butyl 4-(2-(1-(4-(trifluoromethyl)phenyl)piperidin-4-yloxy)isonicotinamido)piperidine-1-carboxylate | 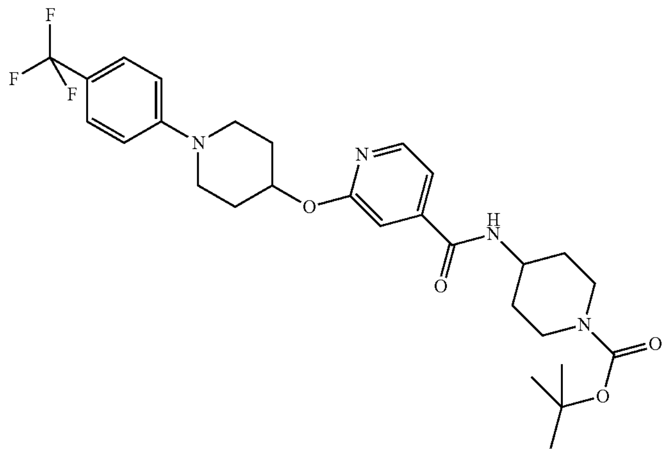 [SMILES: CC(C)(C)OC(=O)N1CCC(NC(=O)c2ccnc(OC3CCN(c4ccc(C(F)(F)F)cc4)CC3)c2)CC1] |
| 1-16 | N-(1-(4-fluorobenzyl)piperidin-4-yl)-5-(1-(4-(trifluoromethyl)phenyl)piperidin-4-yloxy)nicotinamide | 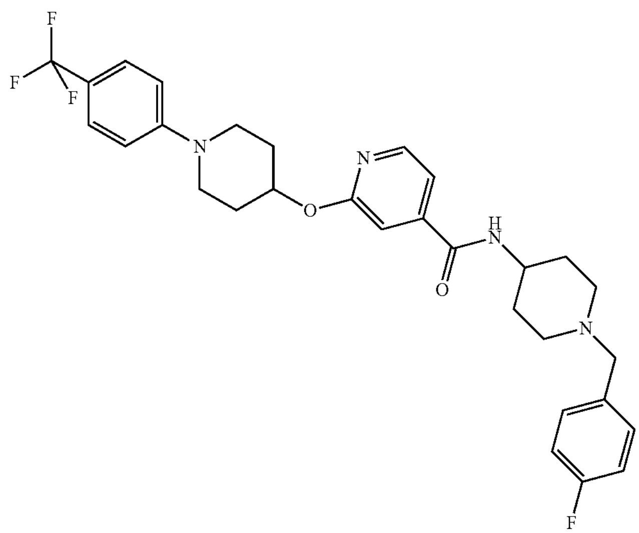 [SMILES: O=C(NC1CCN(Cc2ccc(F)cc2)CC1)c1ccnc(OC2CCN(c3ccc(C(F)(F)F)cc3)CC2)c1] |
| 1-17 | N-(1-(4-cyanobenzyl)piperidin-4-yl)-5-(1-(4-(trifluoromethyl)phenyl)piperidin-4-yloxy)nicotinamide | 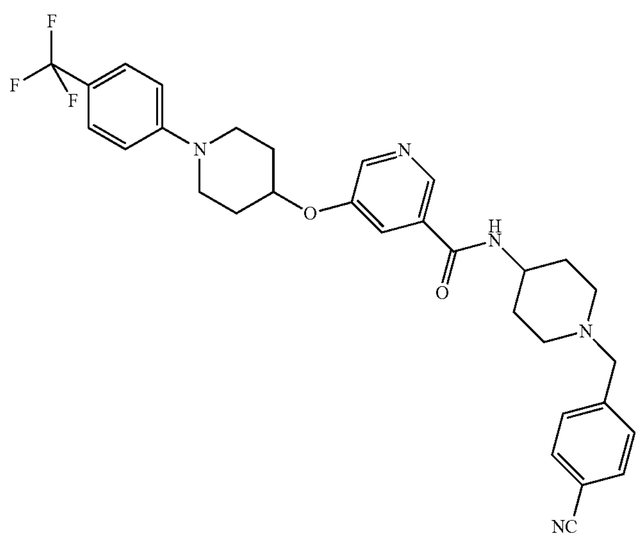 [SMILES: N#Cc1ccc(CN2CCC(NC(=O)c3cncc(OC4CCN(c5ccc(C(F)(F)F)cc5)CC4)c3)CC2)cc1] |

TABLE 1-continued
| No. | Name | Structure |
|---|---|---|
| 1-18 | N-(1-(pyridin-3-ylmethyl)piperidin-4-yl)-5-(1-(4-(trifluoromethyl)phenyl)piperidin-4-yloxy)nicotinamide | 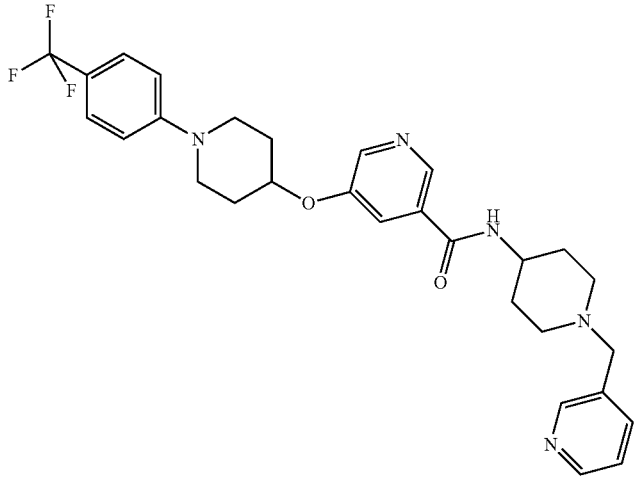 [SMILES: O=C(NC1CCN(Cc2cccnc2)CC1)c1cncc(OC2CCN(c3ccc(C(F)(F)F)cc3)CC2)c1] |
| 1-19 | N-(piperidin-4-yl)-2-(1-(4-(trifluoromethyl)phenyl)piperidin-4-yloxy)isonicotinamide | 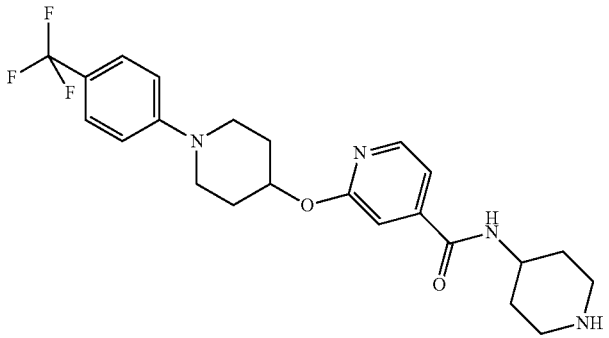 [SMILES: O=C(NC1CCNCC1)c1ccnc(OC2CCN(c3ccc(C(F)(F)F)cc3)CC2)c1] |
| 1-20 | N-(1-(pyridin-4-ylmethyl)piperidin-4-yl)-2-(1-(4-(trifluoromethyl)phenyl)piperidin-4-yloxy)isonicotinamide | 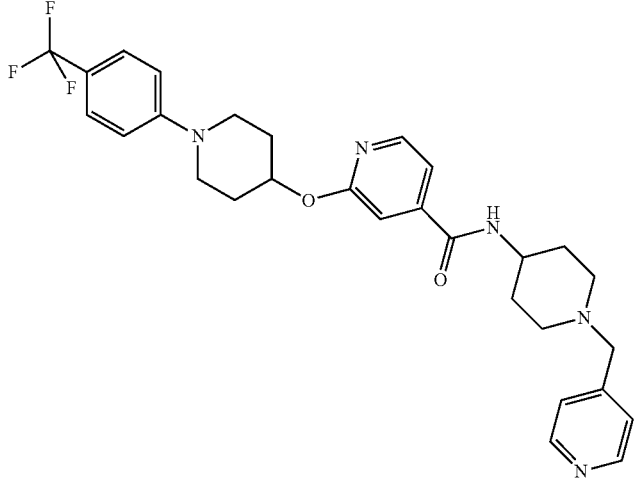 |

TABLE 1-continued

| No. | Name | Structure |
|---|---|---|
| 1-21 | N-(1-(4-cyanobenzyl)piperidin-4-yl)-2-(1-(4-(trifluoromethyl)phenyl)piperidin-4-yloxy)isonicotinamide | 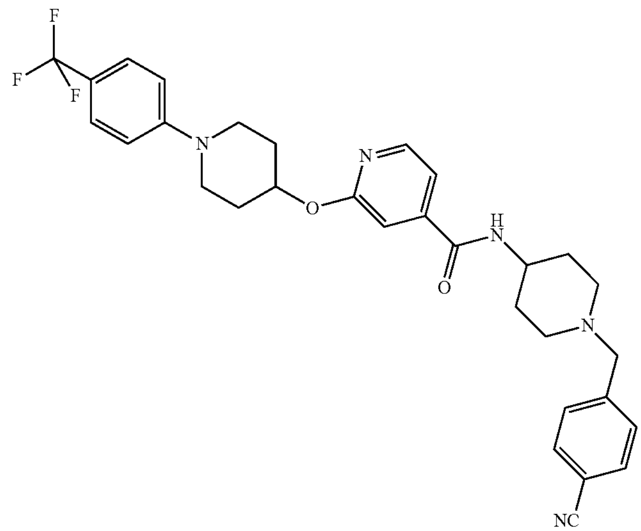 |
| 1-22 | N-(1-(4-fluorobenzyl)piperidin-4-yl)-2-(1-(4-(trifluoromethyl)phenyl)piperidin-4-yloxy)isonicotinamide | 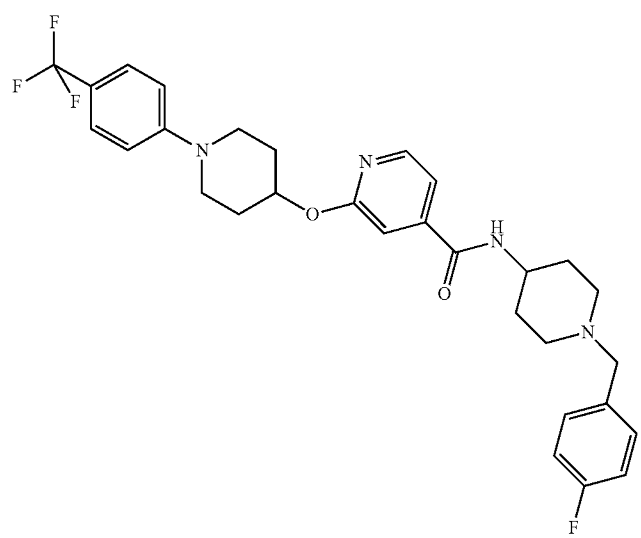 [SMILES: O=C(NC1CCN(Cc2ccc(F)cc2)CC1)c1ccnc(OC2CCN(c3ccc(C(F)(F)F)cc3)CC2)c1] |
| 1-23 | (R)-tert-butyl 3-(5-(1-(4-(trifluoromethyl)phenyl)piperidin-4-yloxy)picolinamido)pyrrolidine-1-carboxylate | 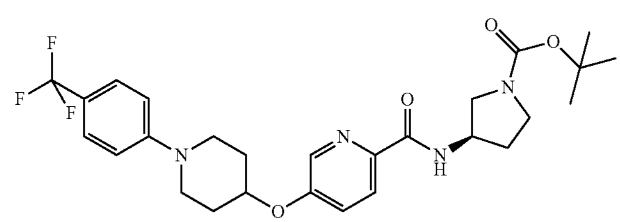 [SMILES: CC(C)(C)OC(=O)N1CC[C@@H](NC(=O)c2ccc(OC3CCN(c4ccc(C(F)(F)F)cc4)CC3)cn2)C1] |
| 1-24 | (R)-N-(pyrrolidin-3-yl)-5-(1-(4-(trifluoromethyl)phenyl)piperidin-4-yloxy)picolinamide | 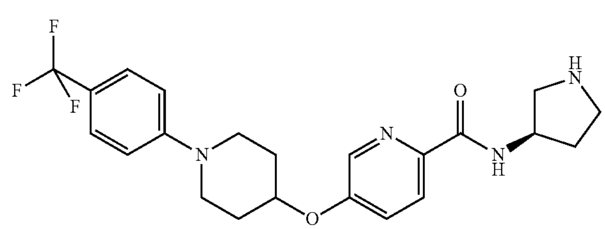 [SMILES: O=C(N[C@@H]1CCNC1)c1ccc(OC2CCN(c3ccc(C(F)(F)F)cc3)CC2)cn1] |

TABLE 1-continued

| No. | Name |
|---|---|
| 1-25 | (R)-N-(1-(pyridin-4-ylmethyl)pyrrolidin-3-yl)-5-(1-(4-(trifluoromethyl)phenyl)piperidin-4-yloxy)picolinamide |
| 1-26 | (S)-tert-butyl 3-(5-(1-(4-(trifluoromethyl)phenyl)piperidin-4-yloxy)picolinamido)pyrrolidine-1-carboxylate |
| 1-27 | (S)-N-(pyrrolidin-3-yl)-5-(1-(4-(trifluoromethyl)phenyl)piperidin-4-yloxy)picolinamide |
| 1-28 | N-(1-(4-cyanobenzyl)piperidin-4-yl)-4-(1-(4-(trifluoromethyl)phenyl)piperidin-4-yloxy)picolinamide |

TABLE 1-continued

| No. | Name | Structure |
|---|---|---|
| 1-29 | N-(1-(4-fluorobenzyl)piperidin-4-yl)-4-(1-(4-(trifluoromethyl)phenyl)piperidin-4-yloxy)picolinamide | 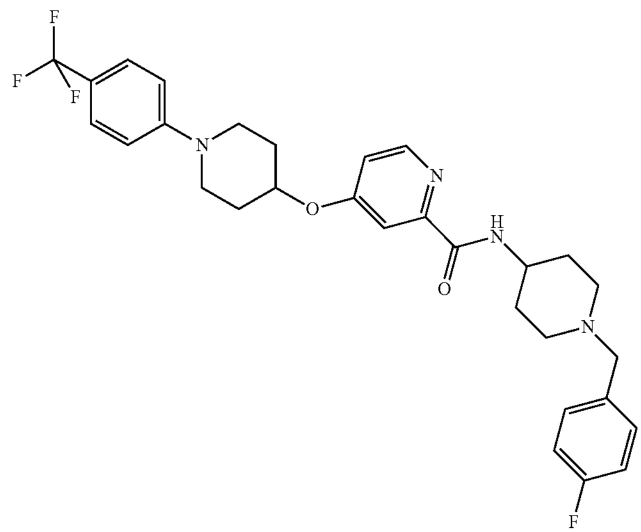 |
| 1-30 | (S)-N-(1-(pyridin-4-ylmethyl)pyrrolidin-3-yl)-5-(1-(4-(trifluoromethyl)phenyl)piperidin-4-yloxy)picolinamide | 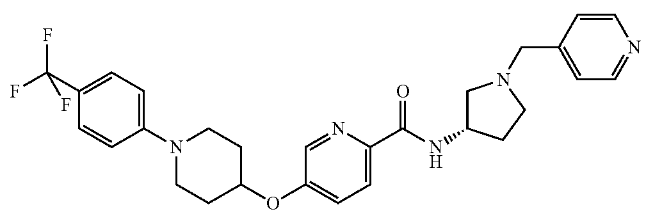 [SMILES: O=C(N[C@H]1CCN(Cc2ccncc2)C1)c1ccc(OC2CCN(c3ccc(C(F)(F)F)cc3)CC2)cn1] |
| 1-31 | (S)-N-(1-(4-cyanobenzyl)pyrrolidin-3-yl)-5-(1-(4-(trifluoromethyl)phenyl)piperidin-4-yloxy)picolinamide | 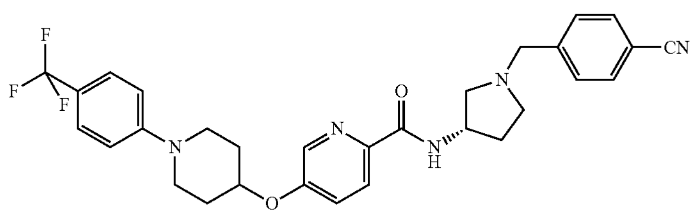 [SMILES: N#Cc1ccc(CN2CC[C@H](NC(=O)c3ccc(OC4CCN(c5ccc(C(F)(F)F)cc5)CC4)cn3)C2)cc1] |
| 1-32 | (S)-N-(1-(4-fluorobenzyl)pyrrolidin-3-yl)-5-(1-(4-(trifluoromethyl)phenyl)piperidin-4-yloxy)picolinamide | 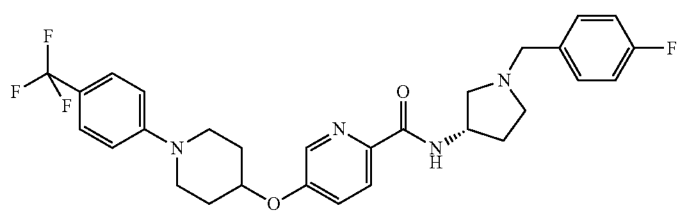 [SMILES: O=C(N[C@H]1CCN(Cc2ccc(F)cc2)C1)c1ccc(OC2CCN(c3ccc(C(F)(F)F)cc3)CC2)cn1] |
| 1-33 | (R)-N-(1-(4-cyanobenzyl)pyrrolidin-3-yl)-5-(1-(4-(trifluoromethyl)phenyl)piperidin-4-yloxy)picolinamide | 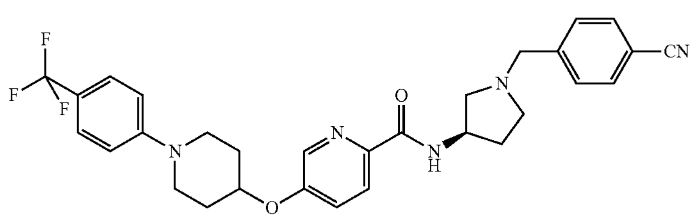 [SMILES: N#Cc1ccc(CN2CC[C@@H](NC(=O)c3ccc(OC4CCN(c5ccc(C(F)(F)F)cc5)CC4)cn3)C2)cc1] |
| 1-34 | (R)-N-(1-(4-fluorobenzyl)pyrrolidin-3-yl)-5-(1-(4-(trifluoromethyl)phenyl)piperidin-4-yloxy)picolinamide | 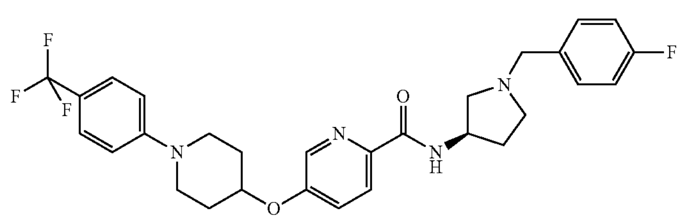 [SMILES: O=C(N[C@@H]1CCN(Cc2ccc(F)cc2)C1)c1ccc(OC2CCN(c3ccc(C(F)(F)F)cc3)CC2)cn1] |

TABLE 1-continued

| No. | Name |
|---|---|
| 1-35 | N-(1-(4-cyanobenzyl)piperidin-4-yl)-6-(1-(4-(trifluoromethyl)phenyl)piperidin-4-yloxy)nicotinamide |
| 1-36 | N-(1-phenethylpiperidin-4-yl)-5-(1-(4-(trifluoromethyl)phenyl)piperidin-4-yloxy)picolinamide |
| 1-37 | N-(1-(naphthalen-2-ylmethyl)piperidin-4-yl)-5-(1-(4-(trifluoromethyl)phenyl)piperidin-4-yloxy)picolinamide |
| 1-38 | N-(1-benzylpiperidin-4-yl)-5-(1-(4-(trifluoromethyl)phenyl)piperidin-4-yloxy)picolinamide |
| 1-39 | N-(1-(4-(dimethylamino)benzyl)piperidin-4-yl)-5-(1-(4-(trifluoromethyl)phenyl)piperidin-4-yloxy)picolinamide |
| 1-40 | N-(1-(4-morpholinobenzyl)piperidin-4-yl)-5-(1-(4-(trifluoromethyl)phenyl)piperidin-4-yloxy)picolinamide |
| 1-41 | N-(1-(4-cyanobenzyl)azetidin-3-yl)-5-(1-(4-(trifluoromethyl)phenyl)piperidin-4-yloxy)picolinamide |
| 1-42 | N-(1-(pyridin-4-ylmethyl)azetidin-3-yl)-5-(1-(4-(trifluoromethyl)phenyl)piperidin-4-yloxy)picolinamide |

TABLE 1-continued

| No. | Name | Structure |
|---|---|---|
| 1-43 | N-(1-(pyridin-4-ylmethyl)piperidin-4-yl)-6-(1-(4-(trifluoromethyl)phenyl)piperidin-4-yloxy)picolinamide | 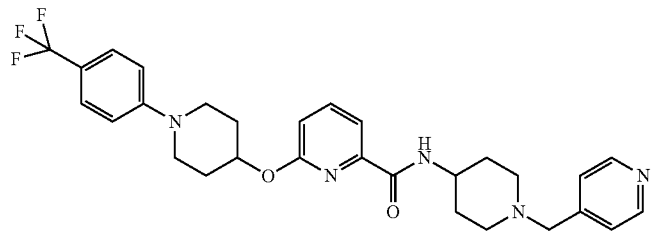 [SMILES: O=C(NC1CCN(Cc2ccncc2)CC1)c1cccc(OC2CCN(c3ccc(C(F)(F)F)cc3)CC2)n1] |
| 1-44 | N-(1-(pyrimidin-5-ylmethyl)piperidin-4-yl)-5-(1-(4-(trifluoromethyl)phenyl)piperidin-4-yloxy)picolinamide | 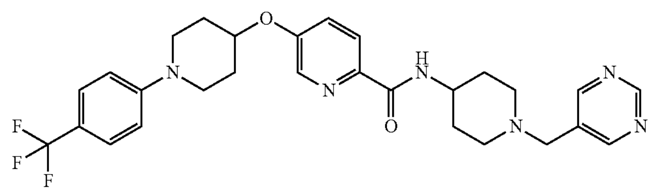 [SMILES: O=C(NC1CCN(Cc2cncnc2)CC1)c1ccc(OC2CCN(c3ccc(C(F)(F)F)cc3)CC2)cn1] |
| 1-45 | methyl 4-((4-(6-(1-(4-(trifluoromethyl)phenyl)piperidin-4-yloxy)nicotinamido)piperidin-1-yl)methyl)benzoate | 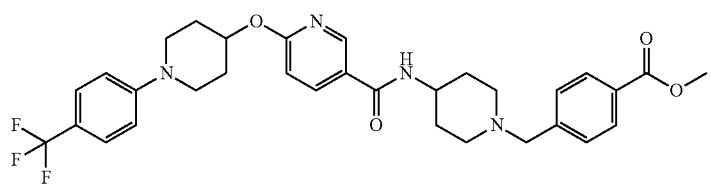 [SMILES: COC(=O)c1ccc(CN2CCC(NC(=O)c3ccc(OC4CCN(c5ccc(C(F)(F)F)cc5)CC4)nc3)CC2)cc1] |
| 1-46 | 4-((4-(6-(1-(4-(trifluoromethyl)phenyl)piperidin-4-yloxy)nicotinamido)piperidin-1-yl)methyl)benzoic acid | 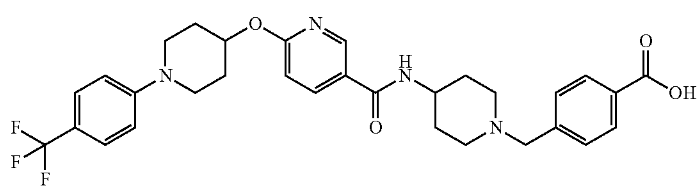 [SMILES: O=C(O)c1ccc(CN2CCC(NC(=O)c3ccc(OC4CCN(c5ccc(C(F)(F)F)cc5)CC4)nc3)CC2)cc1] |
| 1-47 | 5-(1-(4-(trifluoromethyl)phenyl)piperidin-4-yloxy)-N-(1-((1-trityl-1H-imidazol-4-yl)methyl)piperidin-4-yl)picolinamide | 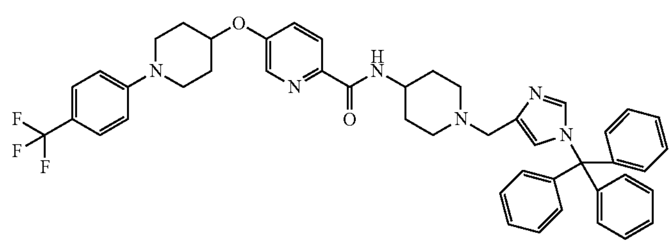 [SMILES: O=C(NC1CCN(Cc2cn(C(c3ccccc3)(c3ccccc3)c3ccccc3)cn2)CC1)c1ccc(OC2CCN(c3ccc(C(F)(F)F)cc3)CC2)cn1] |
| 1-48 | N-(1-((1H-imidazol-4-yl)methyl)piperidin-4-yl)-5-(1-(4-(trifluoromethyl)phenyl)piperidin-4-yloxy)picolinamide | 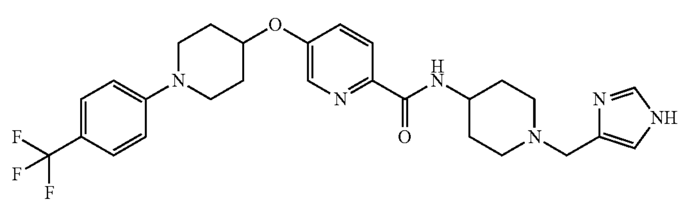 [SMILES: O=C(NC1CCN(Cc2c[nH]cn2)CC1)c1ccc(OC2CCN(c3ccc(C(F)(F)F)cc3)CC2)cn1] |
| 1-49 | tert-butyl 3-(5-(1-(4-(trifluoromethyl)phenyl)piperidin-4-yloxy)picolinamido)propylcarbamate | 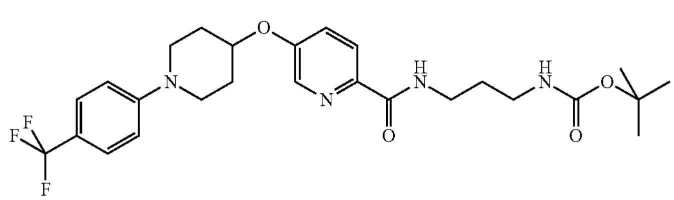 [SMILES: CC(C)(C)OC(=O)NCCCNC(=O)c1ccc(OC2CCN(c3ccc(C(F)(F)F)cc3)CC2)cn1] |

TABLE 1-continued

| No. | Name |
|---|---|
| 1-50 | N-(3-(pyridin-4-ylmethylamino)propyl)-5-(1-(4-(trifluoromethyl)phenyl)piperidin-4-yloxy)picolinamide |
| 1-51 | N-(1-(pyridin-4-ylmethyl)piperidin-4-yl)-6-(1-(4-(trifluoromethyl)phenyl)piperidin-4-yloxy)pyridine-3-sulfonamide |
| 1-52 | N-(1-(pyridin-4-ylmethyl)piperidin-4-yl)-6-(1-(4-cyanophenyl)piperidin-4-yloxy)pyridine-3-sulfonamide |
| 1-53 | 6-(1-(4-cyanobenzyl)piperidin-4-yloxy)-N-(1-(pyridin-4-ylmethyl)piperidin-4-yl)pyridine-3-sulfonamide |
| 1-54 | tert-butyl 4-(6-(1-(4-(trifluoromethyl)phenyl)piperidin-4-yloxy)pyridine-3-sulfonamido)piperidine-1-carboxylate |
| 1-55 | N-(piperidin-4-yl)-6-(1-(4-(trifluoromethyl)phenyl)piperidin-4-yloxy)pyridine-3-sulfonamide |
| 1-56 | N-(1-(4-cyanobenzyl)piperidin-4-yl)-6-(1-(4-(trifluoromethyl)phenyl)piperidin-4-yloxy)pyridine-3-sulfonamide |
| 1-57 | N-(1-(3-cyanobenzyl)piperidin-4-yl)-6-(1-(4-(trifluoromethyl)phenyl)piperidin-4-yloxy)pyridine-3-sulfonamide |
| 1-58 | N-(1-(4-(trifluoromethyl)benzyl)piperidin-4-yl)-6-(1-(4-(trifluoromethyl)phenyl)piperidin-4-yloxy)pyridine-3-sulfonamide |

TABLE 1-continued

| No. | Name | Structure |
|---|---|---|
| 1-59 | N-(1-(3-(trifluoromethyl)benzyl)piperidin-4-yl)-6-(1-(4-(trifluoromethyl)phenyl)piperidin-4-yloxy)pyridine-3-sulfonamide | 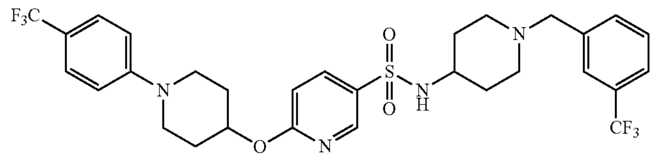 [SMILES: O=S(=O)(NC1CCN(Cc2cccc(C(F)(F)F)c2)CC1)c1ccc(OC2CCN(c3ccc(C(F)(F)F)cc3)CC2)nc1] |
| 1-60 | N-(1-(4-fluorobenzoyl)piperidin-4-yl)-6-(1-(4-(trifluoromethyl)phenyl)piperidin-4-yloxy)pyridine-3-sulfonamide | 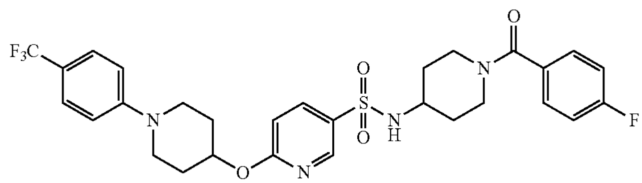 [SMILES: O=C(c1ccc(F)cc1)N1CCC(NS(=O)(=O)c2ccc(OC3CCN(c4ccc(C(F)(F)F)cc4)CC3)nc2)CC1] |
| 1-61 | tert-butyl 4-(3-methyl-6-(1-(4-(trifluoromethyl)phenyl)piperidin-4-yloxy)benzofuran-2-carboxamido)piperidine-1-carboxylate | 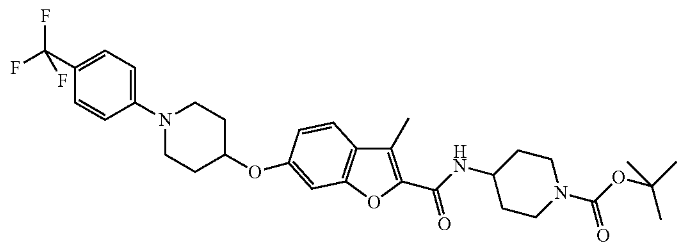 [SMILES: Cc1c(C(=O)NC2CCN(C(=O)OC(C)(C)C)CC2)oc2cc(OC3CCN(c4ccc(C(F)(F)F)cc4)CC3)ccc12] |
| 1-62 | 3-methyl-N-(piperidin-4-yl)-6-(1-(4-(trifluoromethyl)phenyl)piperidin-4-yloxy)benzofuran-2-carboxamide | 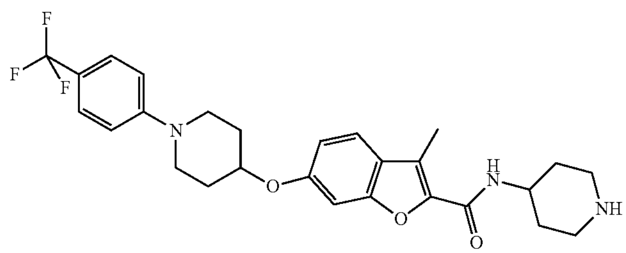 [SMILES: Cc1c(C(=O)NC2CCNCC2)oc2cc(OC3CCN(c4ccc(C(F)(F)F)cc4)CC3)ccc12] |
| 1-63 | N-(1-(4-fluorobenzyl)piperidin-4-yl)-3-methyl-6-(1-(4-(trifluoromethyl)phenyl)piperidin-4-yloxy)benzofuran-2-carboxamide | 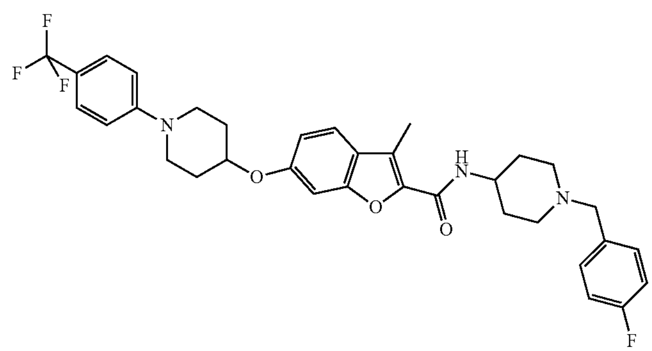 [SMILES: Cc1c(C(=O)NC2CCN(Cc3ccc(F)cc3)CC2)oc2cc(OC3CCN(c4ccc(C(F)(F)F)cc4)CC3)ccc12] |
| 1-64 | N-(1-(4-cyanobenzyl)piperidin-4-yl)-3-methyl-6-(1-(4-(trifluoromethyl)phenyl)piperidin-4-yloxy)benzofuran-2-carboxamide | 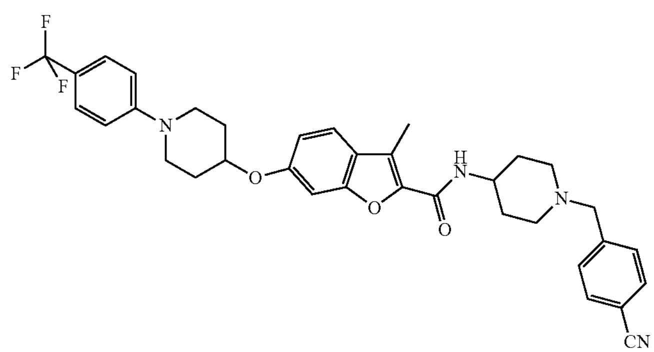 [SMILES: Cc1c(C(=O)NC2CCN(Cc3ccc(C#N)cc3)CC2)oc2cc(OC3CCN(c4ccc(C(F)(F)F)cc4)CC3)ccc12] |

TABLE 1-continued

| No. | Name |
|---|---|
| 1-65 | 3-methyl-N-(1-(pyridin-4-ylmethyl)piperidin-4-yl)-6-(1-(4-(trifluoromethyl)phenyl)piperidin-4-yloxy)benzofuran-2-carboxamide |
| 1-66 | N-(1-(3-cyanobenzyl)piperidin-4-yl)-3-methyl-6-(1-(4-(trifluoromethyl)phenyl)piperidin-4-yloxy)benzofuran-2-carboxamide |
| 1-67 | N-(1-(2-cyanobenzyl)piperidin-4-yl)-3-methyl-6-(1-(4-(trifluoromethyl)phenyl)piperidin-4-yloxy)benzofuran-2-carboxamide |
| 1-68 | 3-methyl-N-(1-(pyridin-2-ylmethyl)piperidin-4-yl)-6-(1-(4-(trifluoromethyl)phenyl)piperidin-4-yloxy)benzofuran-2-carboxamide |
| 1-69 | 3-methyl-N-(1-(pyridin-3-ylmethyl)piperidin-4-yl)-6-(1-(4-(trifluoromethyl)phenyl)piperidin-4-yloxy)benzofuran-2-carboxamide |
| 1-70 | N-(1-benzylpiperidin-4-yl)-5-(1-(4-cyanobenzyl)piperidin-4-yloxy)benzofuran-2-carboxamide |
| 1-71 | N-(1-benzylpiperidin-4-yl)-5-(1-(4-cyanophenyl)piperidin-4-yloxy)benzofuran-2-carboxamide |

TABLE 1-continued

| No. | Name | Structure |
|---|---|---|
| 1-72 | N-(1-benzylpiperidin-4-yl)-5-(1-(4-chlorobenzyl)piperidin-4-yloxy)benzofuran-2-carboxamide | 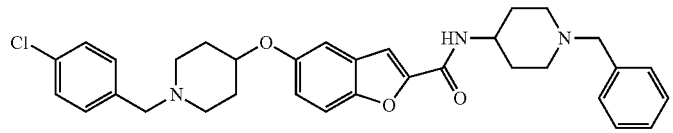 [SMILES: O=C(NC1CCN(Cc2ccccc2)CC1)c1cc2cc(OC3CCN(Cc4ccc(Cl)cc4)CC3)ccc2o1] |
| 1-73 | N-(1-benzylpiperidin-4-yl)-5-(1-(3-(trifluoromethyl)benzyl)piperidin-4-yloxy)benzofuran-2-carboxamide | 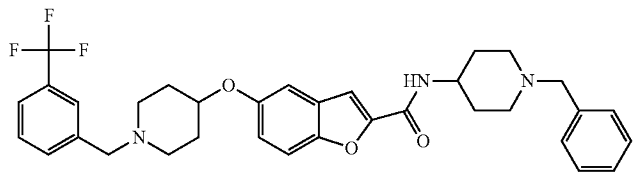 [SMILES: O=C(NC1CCN(Cc2ccccc2)CC1)c1cc2cc(OC3CCN(Cc4cccc(C(F)(F)F)c4)CC3)ccc2o1] |
| 1-74 | N-(1-benzylpiperidin-4-yl)-5-(1-(3,4-difluorobenzyl)piperidin-4-yloxy)benzofuran-2-carboxamide | 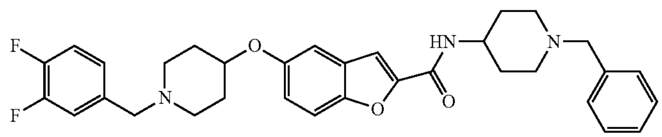 [SMILES: O=C(NC1CCN(Cc2ccccc2)CC1)c1cc2cc(OC3CCN(Cc4ccc(F)c(F)c4)CC3)ccc2o1] |
| 1-75 | N-(1-benzylpiperidin-4-yl)-5-(1-(4-(trifluoromethyl)phenyl)piperidin-4-yloxy)benzofuran-2-carboxamide | 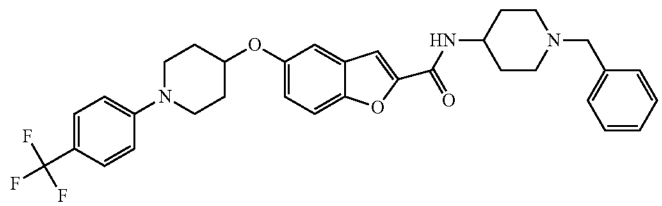 [SMILES: O=C(NC1CCN(Cc2ccccc2)CC1)c1cc2cc(OC3CCN(c4ccc(C(F)(F)F)cc4)CC3)ccc2o1] |
| 1-76 | N-(1-(pyridin-4-ylmethyl)piperidin-4-yl)-5-(1-(4-(trifluoromethyl)phenyl)piperidin-4-yloxy)benzofuran-2-carboxamide | 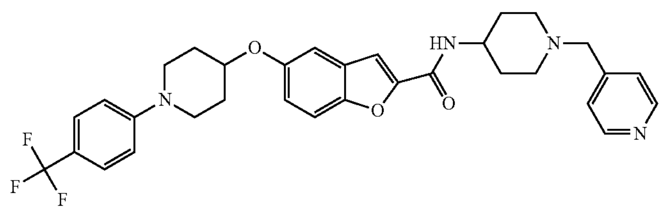 [SMILES: O=C(NC1CCN(Cc2ccncc2)CC1)c1cc2cc(OC3CCN(c4ccc(C(F)(F)F)cc4)CC3)ccc2o1] |
| 1-77 | 5-(1-(4-chlorobenzyl)piperidin-4-yloxy)-N-(1-(pyridin-4-ylmethyl)piperidin-4-yl)benzofuran-2-carboxamide | 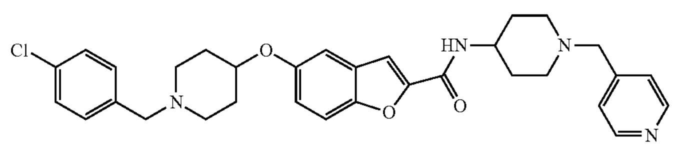 [SMILES: O=C(NC1CCN(Cc2ccncc2)CC1)c1cc2cc(OC3CCN(Cc4ccc(Cl)cc4)CC3)ccc2o1] |
| 1-78 | N-(1-(pyridin-4-ylmethyl)piperidin-4-yl)-5-(1-(4-(trifluoromethoxy)phenyl)piperidin-4-yloxy)benzofuran-2-carboxamide | 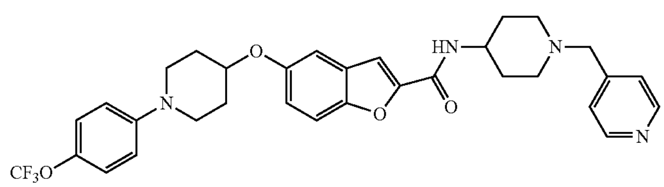 |
| 1-79 | 5-(1-(4-cyanobenzyl)piperidin-4-yloxy)-N-(1-(pyridin-4-ylmethyl)piperidin-4-yl)benzofuran-2-carboxamide | 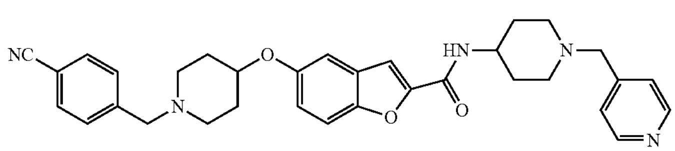 [SMILES: N#Cc1ccc(CN2CCC(Oc3ccc4oc(C(=O)NC5CCN(Cc6ccncc6)CC5)cc4c3)CC2)cc1] |
| 1-80 | N-(1-benzylpiperidin-4-yl)-5-(1-(4-(trifluoromethoxy)phenyl)piperidin-4-yloxy)benzofuran-2-carboxamide | 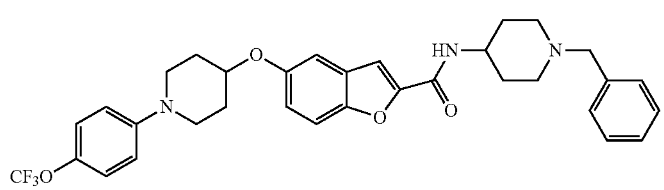 |

TABLE 1-continued

| No. | Name | Structure |
|---|---|---|
| 1-81 | tert-butyl 4-(6-(1-(4-(trifluoromethoxy)phenyl)piperidin-4-yloxy)benzofuran-2-carboxamido)piperidine-1-carboxylate | 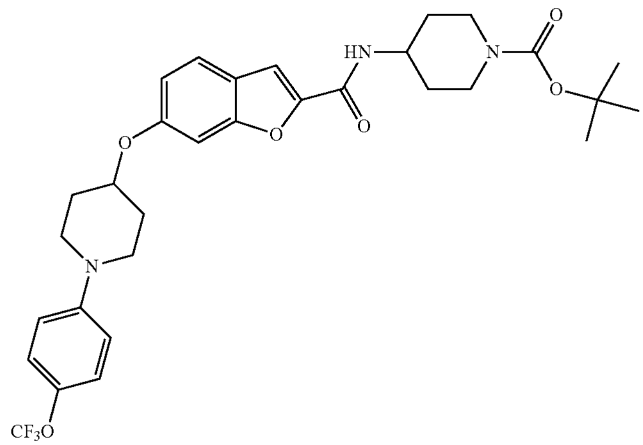 |
| 1-82 | tert-butyl 4-(6-(1-(4-(trifluoromethyl)phenyl)piperidin-4-yloxy)benzofuran-2-carboxamido)piperidine-1-carboxylate | 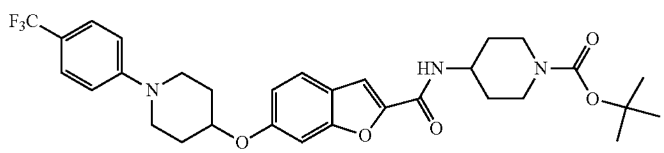 |
| 1-83 | N-(piperidin-4-yl)-6-(1-(4-(trifluoromethoxy)phenyl)piperidin-4-yloxy)benzofuran-2-carboxamide | 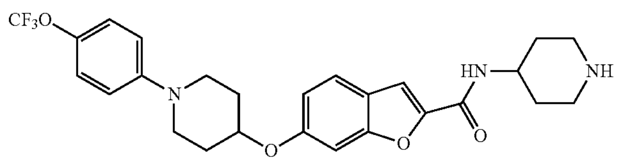 |
| 1-84 | N-(piperidin-4-yl)-6-(1-(4-(trifluoromethyl)phenyl)piperidin-4-yloxy)benzofuran-2-carboxamide | 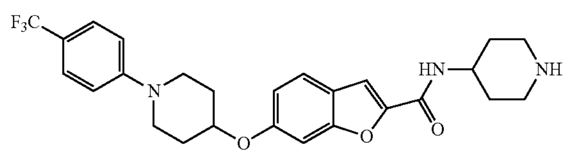 [SMILES: O=C(NC1CCNCC1)c1cc2ccc(OC3CCN(c4ccc(C(F)(F)F)cc4)CC3)cc2o1] |
| 1-85 | tert-butyl 4-(5-(1-(4-(trifluoromethyl)phenyl)piperidin-4-yloxy)benzofuran-2-carboxamido)piperidine-1-carboxylate | 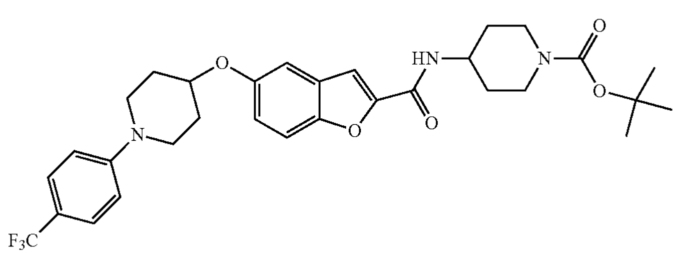 [SMILES: CC(C)(C)OC(=O)N1CCC(NC(=O)c2cc3cc(OC4CCN(c5ccc(C(F)(F)F)cc5)CC4)ccc3o2)CC1] |
| 1-86 | N-(piperidin-4-yl)-5-(1-(4-(trifluoromethyl)phenyl)piperidin-4-yloxy)benzofuran-2-carboxamide | 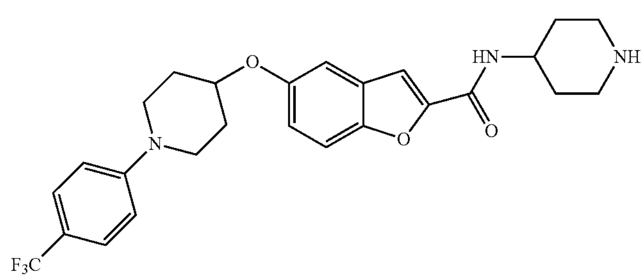 [SMILES: O=C(NC1CCNCC1)c1cc2cc(OC3CCN(c4ccc(C(F)(F)F)cc4)CC3)ccc2o1] |

TABLE 1-continued

| No. | Name | Structure |
|---|---|---|
| 1-87 | N-(1-(pyridin-4-ylmethyl)piperidin-4-yl)-6-(1-(4-(trifluoromethyl)phenyl)piperidin-4-yloxy)benzofuran-2-carboxamide | 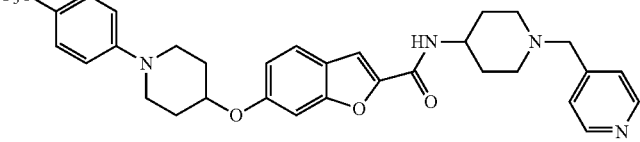 |
| 1-88 | N-(1-(pyridin-4-ylmethyl)piperidin-4-yl)-6-(1-(4-(trifluoromethoxy)phenyl)piperidin-4-yloxy)benzofuran-2-carboxamide | 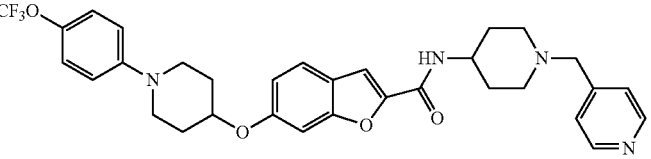 |
| 1-89 | N-(1-(4-cyanobenzyl)piperidin-4-yl)-6-(1-(4-(trifluoromethoxy)phenyl)piperidin-4-yloxy)benzofuran-2-carboxamide | 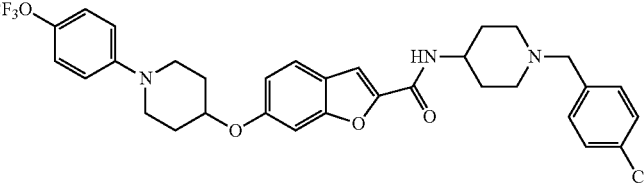 [SMILES: O=C(NC1CCN(Cc2ccc(F)cc2)CC1)c1cc2ccc(OC3CCN(c4ccc(C(F)(F)F)cc4)CC3)cc2o1] |
| 1-90 | N-(1-(4-cyanobenzyl)piperidin-4-yl)-6-(1-(4-(trifluoromethyl)phenyl)piperidin-4-yloxy)benzofuran-2-carboxamide | 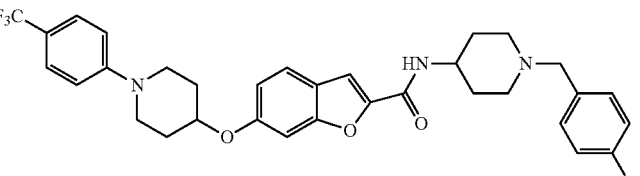 |
| 1-91 | N-(1-(4-fluorobenzyl)piperidin-4-yl)-6-(1-(4-(trifluoromethyl)phenyl)piperidin-4-yloxy)benzofuran-2-carboxamide | 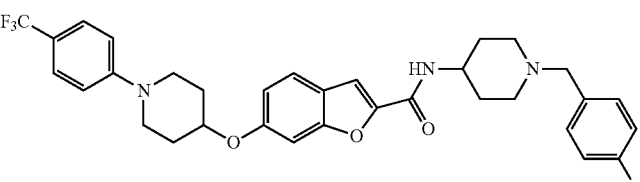 |
| 1-92 | N-(1-(pyridin-2-ylmethyl)piperidin-4-yl)-6-(1-(4-(trifluoromethoxy)phenyl)piperidin-4-yloxy)benzofuran-2-carboxamide | 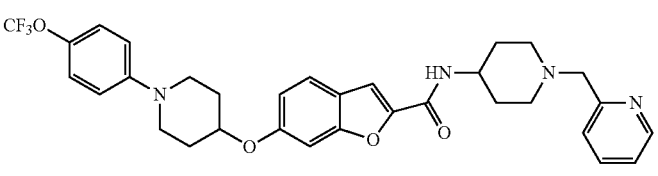 |
| 1-93 | N-(1-(pyridin-2-ylmethyl)piperidin-4-yl)-6-(1-(4-(trifluoromethyl)phenyl)piperidin-4-yloxy)benzofuran-2-carboxamide | 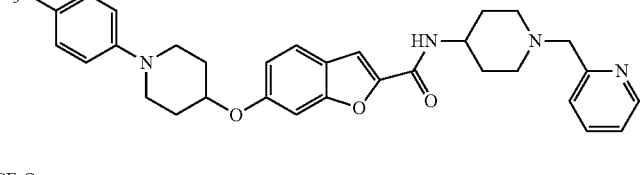 |
| 1-94 | N-(1-(4-fluorobenzyl)piperidin-4-yl)-6-(1-(4-(trifluoromethoxy)phenyl)piperidin-4-yloxy)benzofuran-2-carboxamide | 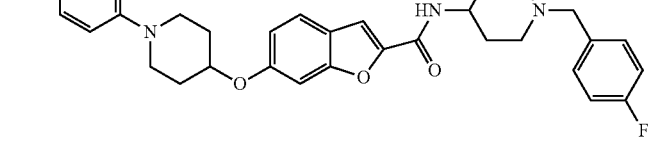 |

TABLE 1-continued

| No. | Name |
|---|---|
| 1-95 | N-(1-(pyridin-3-ylmethyl)piperidin-4-yl)-6-(1-(4-(trifluoromethoxy)phenyl)piperidin-4-yloxy)benzofuran-2-carboxamide |
| 1-96 | N-(1-(pyridin-3-ylmethyl)piperidin-4-yl)-6-(1-(4-(trifluoromethyl)phenyl)piperidin-4-yloxy)benzofuran-2-carboxamide |
| 1-97 | N-(1-(2-cyanobenzyl)piperidin-4-yl)-6-(1-(4-(trifluoromethoxy)phenyl)piperidin-4-yloxy)benzofuran-2-carboxamide |
| 1-98 | N-(1-(2-cyanobenzyl)piperidin-4-yl)-6-(1-(4-(trifluoromethyl)phenyl)piperidin-4-yloxy)benzofuran-2-carboxamide |
| 1-99 | N-(1-(4-(trifluoromethyl)benzyl)piperidin-4-yl)-6-(1-(4-(trifluoromethyl)phenyl)piperidin-4-yloxy)benzofuran-2-carboxamide |
| 1-100 | N-(1-(4-(trifluoromethyl)benzyl)piperidin-4-yl)-5-(1-(4-(trifluoromethyl)phenyl)piperidin-4-yloxy)benzofuran-2-carboxamide |
| 1-101 | N-(1-(pyridin-3-ylmethyl)piperidin-4-yl)-5-(1-(4-(trifluoromethyl)phenyl)piperidin-4-yloxy)benzofuran-2-carboxamide |
| 1-102 | tert-butyl 4-(N-methyl-5-(1-(4-(trifluoromethyl)phenyl)piperidin-4-yloxy)benzofuran-2-carboxamido)piperidine-1-carboxylate |

TABLE 1-continued

| No. | Name | Structure |
|---|---|---|
| 1-103 | N-methyl-N-(piperidin-4-yl)-5-(1-(4-(trifluoromethyl)phenyl)piperidin-4-yloxy)benzofuran-2-carboxamide | 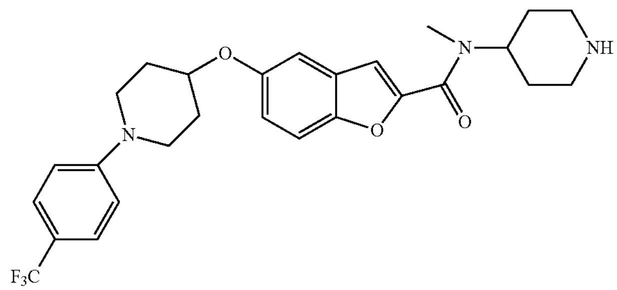 [SMILES: CN(C(=O)c1cc2cc(OC3CCN(c4ccc(C(F)(F)F)cc4)CC3)ccc2o1)C1CCNCC1] |
| 1-104 | N-methyl-N-(1-(pyridin-4-ylmethyl)piperidin-4-yl)-5-(1-(4-(trifluoromethyl)phenyl)piperidin-4-yloxy)benzofuran-2-carboxamide | 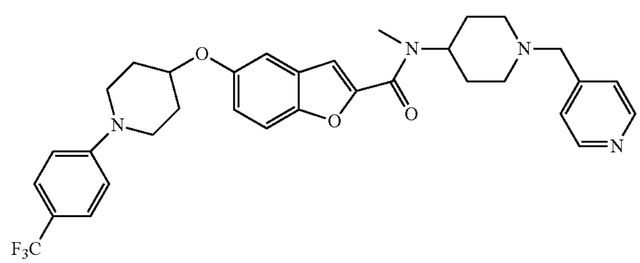 [SMILES: CN(C(=O)c1cc2cc(OC3CCN(c4ccc(C(F)(F)F)cc4)CC3)ccc2o1)C1CCN(Cc2ccncc2)CC1] |
| 1-105 | N-(1-(pyridin-4-ylmethyl)piperidin-4-yl)-5-(1-(4-(trifluoromethyl)phenyl)piperidin-4-yloxy)benzofuran-2-carboxamide, formate salt | 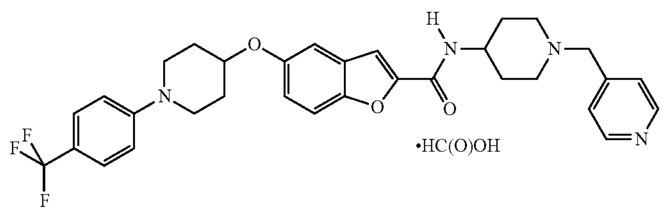 |
| 1-106 | N-(1-(pyridin-3-ylsulfonyl)piperidin-4-yl)-6-(1-(4-(trifluoromethyl)phenyl)piperidin-4-yloxy)benzofuran-2-carboxamide | 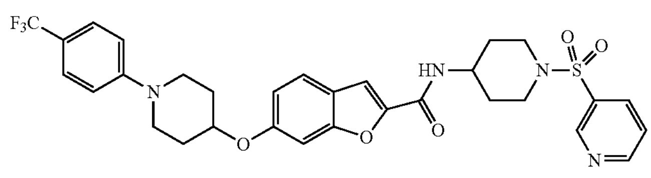 [SMILES: O=C(NC1CCN(S(=O)(=O)c2cccnc2)CC1)c1cc2ccc(OC3CCN(c4ccc(C(F)(F)F)cc4)CC3)cc2o1] |
| 1-107 | N-(1-(4-cyanobenzyl)piperidin-4-yl)-N-methyl-5-(1-(4-(trifluoromethyl)phenyl)piperidin-4-yloxy)benzofuran-2-carboxamide | 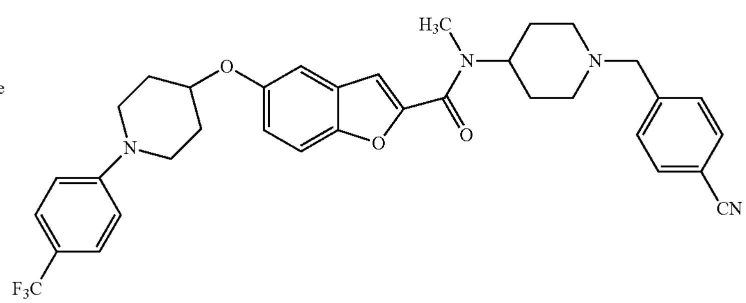 |
| 1-108 | N-(1-(pyridin-3-ylsulfonyl)piperidin-4-yl)-6-(1-(4-(trifluoromethoxy)phenyl)piperidin-4-yloxy)benzofuran-2-carboxamide | 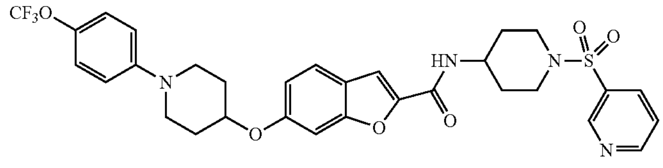 |

TABLE 1-continued

| No. | Name | Structure |
|---|---|---|
| 1-109 | N-methyl-N-(1-(pyridin-3-ylmethyl)piperidin-4-yl)-5-(1-(4-(trifluoromethyl)phenyl)piperidin-4-yloxy)benzofuran-2-carboxamide | 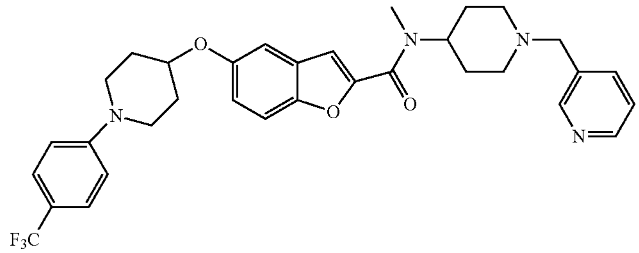 [SMILES: CN(C(=O)c1cc2cc(OC3CCN(c4ccc(C(F)(F)F)cc4)CC3)ccc2o1)C1CCN(Cc2cccnc2)CC1] |
| 1-110 | N-(1-(3-cyanobenzyl)piperidin-4-yl)-N-methyl-5-(1-(4-(trifluoromethyl)phenyl)piperidin-4-yloxy)benzofuran-2-carboxamide | 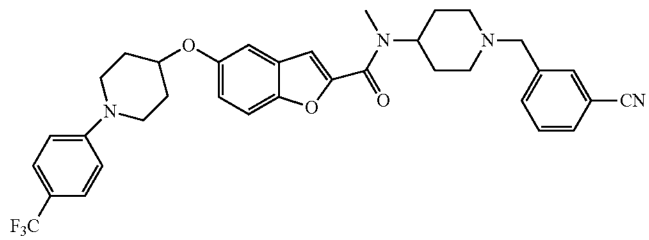 [SMILES: CN(C(=O)c1cc2cc(OC3CCN(c4ccc(C(F)(F)F)cc4)CC3)ccc2o1)C1CCN(Cc2cccc(C#N)c2)CC1] |
| 1-111 | N-(1-(2-cyanobenzyl)piperidin-4-yl)-N-methyl-5-(1-(4-(trifluoromethyl)phenyl)piperidin-4-yloxy)benzofuran-2-carboxamide | 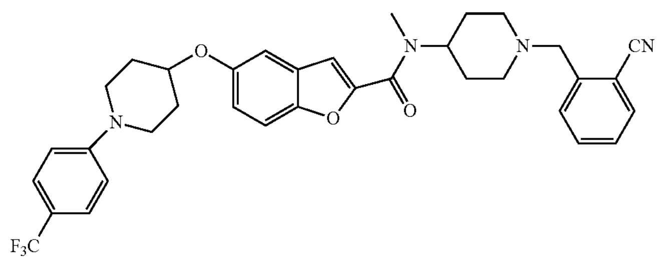 [SMILES: CN(C(=O)c1cc2cc(OC3CCN(c4ccc(C(F)(F)F)cc4)CC3)ccc2o1)C1CCN(Cc2ccccc2C#N)CC1] |
| 1-112 | N-(1-isonicotinoylpiperidin-4-yl)-6-(1-(4-(trifluoromethyl)phenyl)piperidin-4-yloxy)benzofuran-2-carboxamide | 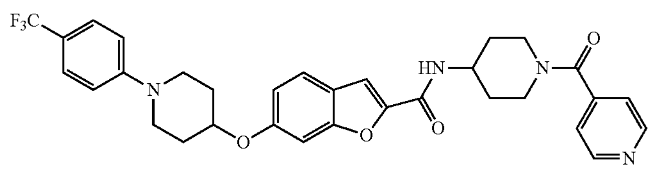 [SMILES: O=C(NC1CCN(C(=O)c2ccncc2)CC1)c1cc2ccc(OC3CCN(c4ccc(C(F)(F)F)cc4)CC3)cc2o1] |
| 1-113 | tert-butyl 4-(5-(1-(4-cyanobenzyl)piperidin-4-yloxy)benzofuran-2-carboxamido)piperidine-1-carboxylate | 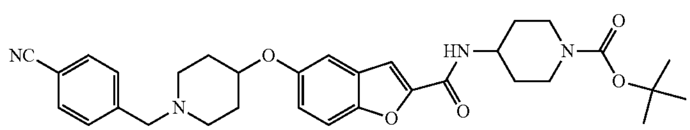 [SMILES: CC(C)(C)OC(=O)N1CCC(NC(=O)c2cc3cc(OC4CCN(Cc5ccc(C#N)cc5)CC4)ccc3o2)CC1] |
| 1-114 | N-(1-benzylpiperidin-4-yl)-5-(1-(4-cyanobenzyl)piperidin-4-yloxy)benzofuran-2-carboxamide | 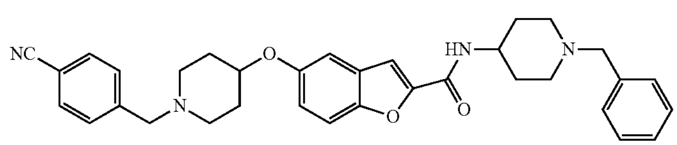 [SMILES: N#Cc1ccc(CN2CCC(Oc3ccc4oc(C(=O)NC5CCN(Cc6ccccc6)CC5)cc4c3)CC2)cc1] |
| 1-115 | N-(1-isonicotinoylpiperidin-4-yl)-5-(1-(4-(trifluoromethyl)phenyl)piperidin-4-yloxy)benzofuran-2-carboxamide | 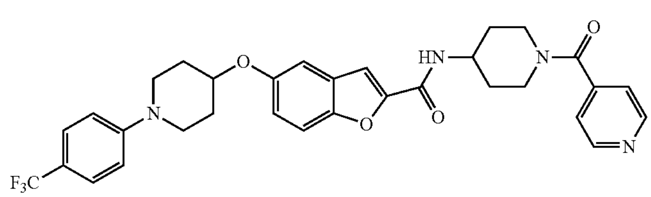 [SMILES: O=C(NC1CCN(C(=O)c2ccncc2)CC1)c1cc2cc(OC3CCN(c4ccc(C(F)(F)F)cc4)CC3)ccc2o1] |
| 1-116 | N-(1-benzylpiperidin-4-yl)-5-(1-(4-carbamoylbenzyl)piperidin-4-yloxy)benzofuran-2-carboxamide | 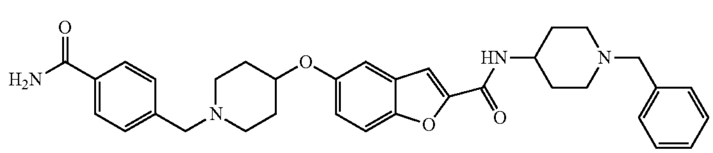 [SMILES: NC(=O)c1ccc(CN2CCC(Oc3ccc4oc(C(=O)NC5CCN(Cc6ccccc6)CC5)cc4c3)CC2)cc1] |

TABLE 1-continued

| No. | Name | Structure |
|---|---|---|
| 1-117 | N-methyl-N-(1-(pyridin-2-ylmethyl)piperidin-4-yl)-5-(1-(4-(trifluoromethyl)phenyl)piperidin-4-yloxy)benzofuran-2-carboxamide | 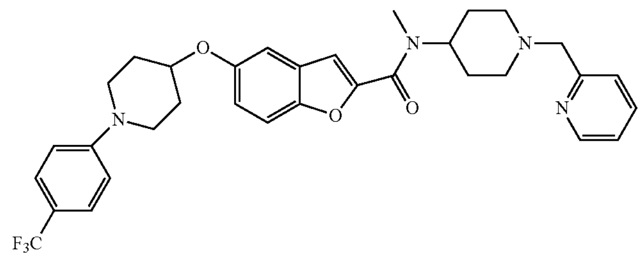 [SMILES: CN(C(=O)c1cc2cc(OC3CCN(c4ccc(C(F)(F)F)cc4)CC3)ccc2o1)C1CCN(Cc2ccccn2)CC1] |
| 1-118 | N-(1-isonicotinoylpiperidin-4-yl)-N-methyl-5-(1-(4-(trifluoromethyl)phenyl)piperidin-4-yloxy)benzofuran-2-carboxamide | 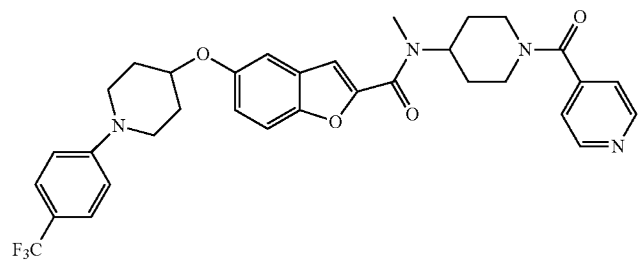 [SMILES: CN(C(=O)c1cc2cc(OC3CCN(c4ccc(C(F)(F)F)cc4)CC3)ccc2o1)C1CCN(C(=O)c2ccncc2)CC1] |
| 1-119 | N-methyl-N-(1-(4-(trifluoromethyl)benzyl)piperidin-4-yl)-5-(1-(4-(trifluoromethyl)phenyl)piperidin-4-yloxy)benzofuran-2-carboxamide | 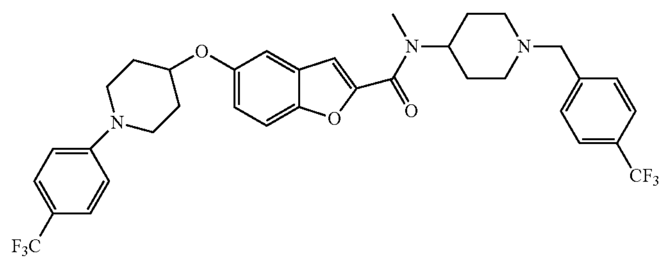 [SMILES: CN(C(=O)c1cc2cc(OC3CCN(c4ccc(C(F)(F)F)cc4)CC3)ccc2o1)C1CCN(Cc2ccc(C(F)(F)F)cc2)CC1] |
| 1-120 | (R)-tert-butyl 3-(5-(1-(4-(trifluoromethyl)phenyl)piperidin-4-yloxy)benzofuran-2-carboxamido)pyrrolidine-1-carboxylate | 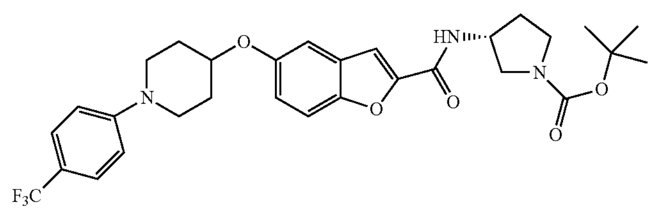 [SMILES: CC(C)(C)OC(=O)N1CC[C@@H](NC(=O)c2cc3cc(OC4CCN(c5ccc(C(F)(F)F)cc5)CC4)ccc3o2)C1] |
| 1-121 | (R)-N-(pyrrolidin-3-yl)-5-(1-(4-(trifluoromethyl)phenyl)piperidin-4-yloxy)benzofuran-2-carboxamide | 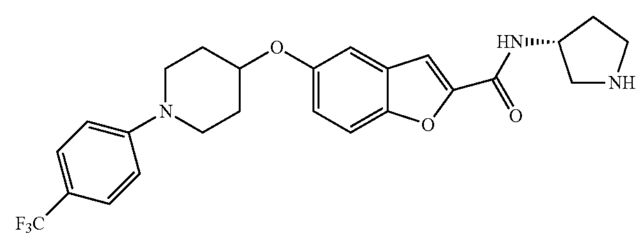 [SMILES: O=C(N[C@@H]1CCNC1)c1cc2cc(OC3CCN(c4ccc(C(F)(F)F)cc4)CC3)ccc2o1] |
| 1-122 | (R)-N-(1-(pyridin-4-ylmethyl)pyrrolidin-3-yl)-5-(1-(4-(trifluoromethyl)phenyl)piperidin-4-yloxy)benzofuran-2-carboxamide | 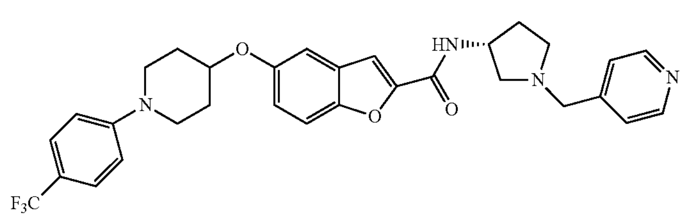 [SMILES: O=C(N[C@@H]1CCN(Cc2ccncc2)C1)c1cc2cc(OC3CCN(c4ccc(C(F)(F)F)cc4)CC3)ccc2o1] |

TABLE 1-continued

| No. | Name |
|---|---|
| 1-123 | (R)-N-(1-(pyridin-3-ylmethyl)pyrrolidin-3-yl)-5-(1-(4-(trifluoromethyl)phenyl)piperidin-4-yloxy)benzofuran-2-carboxamide |
| 1-124 | (R)-N-(1-(pyridin-2-ylmethyl)pyrrolidin-3-yl)-5-(1-(4-(trifluoromethyl)phenyl)piperidin-4-yloxy)benzofuran-2-carboxamide |
| 1-125 | (R)-N-(1-isonicotinoylpyrrolidin-3-yl)-5-(1-(4-(trifluoromethyl)phenyl)piperidin-4-yloxy)benzofuran-2-carboxamide |
| 1-126 | (R)-N-(1-(pyridin-3-ylsulfonyl)pyrrolidin-3-yl)-5-(1-(4-(trifluoromethyl)phenyl)piperidin-4-yloxy)benzofuran-2-carboxamide |
| 1-127 | (S)-tert-butyl 3-(5-(1-(4-chlorobenzyl)piperidin-4-yloxy)benzofuran-2-carboxamido)pyrrolidine-1-carboxylate |
| 1-128 | (S)-5-(1-(4-chlorobenzyl)piperidin-4-yloxy)-N-(pyrrolidin-3-yl)benzofuran-2-carboxamide |
| 1-129 | (S)-5-(1-(4-chlorobenzyl)piperidin-4-yloxy)-N-(1-(pyridin-4-ylmethyl)pyrrolidin-3-yl)benzofuran-2-carboxamide |
| 1-130 | (S)-5-(1-(4-chlorobenzyl)piperidin-4-yloxy)-N-(1-(pyridin-3-ylmethyl)pyrrolidin-3-yl)benzofuran-2-carboxamide |
| 1-131 | 5-(1-(4-carbamoylbenzyl)piperidin-4-yloxy)-N-(1-(pyridin-4-ylmethyl)piperidin-4-yl)benzofuran-2-carboxamide |

TABLE 1-continued

| No. | Name | Structure |
|---|---|---|
| 1-132 | 5-(1-(4-carbamoylbenzyl)piperidin-4-yloxy)-N-(1-isonicotinoylpiperidin-4-yl)benzofuran-2-carboxamide | 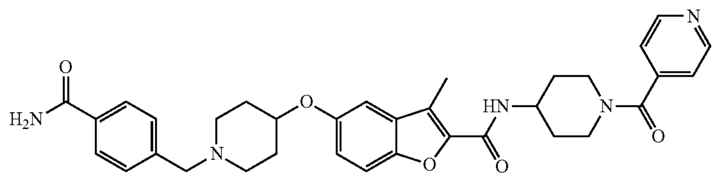 [SMILES: Cc1c(C(=O)NC2CCN(C(=O)c3ccncc3)CC2)oc2ccc(OC3CCN(Cc4ccc(C(N)=O)cc4)CC3)cc12] |
| 1-133 | 5-(1-(4-carbamoylbenzyl)piperidin-4-yloxy)-N-(1-(4-cyanobenzyl)piperidin-4-yl)benzofuran-2-carboxamide | 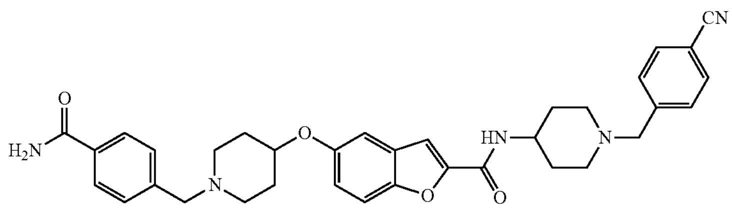 [SMILES: N#Cc1ccc(CN2CCC(NC(=O)c3cc4cc(OC5CCN(Cc6ccc(C(N)=O)cc6)CC5)ccc4o3)CC2)cc1] |
| 1-134 | 5-(1-(4-carbamoylphenyl)piperidin-4-yloxy)-N-(1-(pyridin-4-ylmethyl)piperidin-4-yl)benzofuran-2-carboxamide | 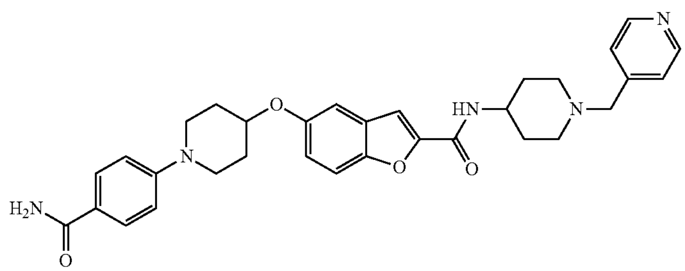 [SMILES: NC(=O)c1ccc(N2CCC(Oc3ccc4oc(C(=O)NC5CCN(Cc6ccncc6)CC5)cc4c3)CC2)cc1] |
| 1-135 | 5-(1-(4-carbamoylphenyl)piperidin-4-yloxy)-N-(1-isonicotinoylpiperidin-4-yl)benzofuran-2-carboxamide | 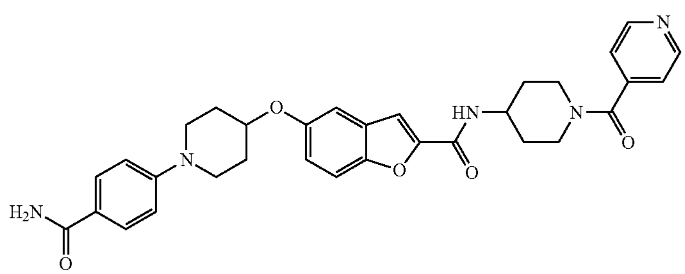 [SMILES: NC(=O)c1ccc(N2CCC(Oc3ccc4oc(C(=O)NC5CCN(C(=O)c6ccncc6)CC5)cc4c3)CC2)cc1] |
| 1-136 | 5-(1-(4-carbamoylphenyl)piperidin-4-yloxy)-N-(1-(4-cyanobenzyl)piperidin-4-yl)benzofuran-2-carboxamide | 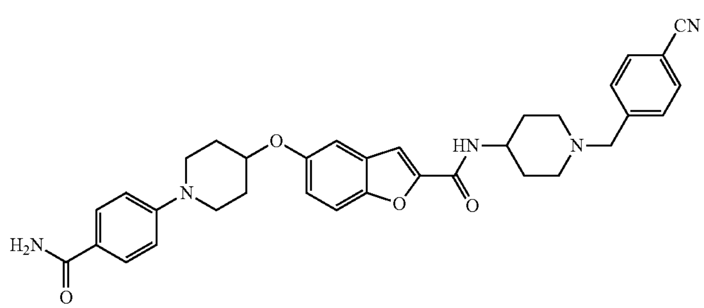 [SMILES: N#Cc1ccc(CN2CCC(NC(=O)c3cc4cc(OC5CCN(c6ccc(C(N)=O)cc6)CC5)ccc4o3)CC2)cc1] |
| 1-137 | N-(1-(pyridin-4-ylmethyl)piperidin-4-yl)-5-(1-(4-(trifluoromethoxy)phenyl)piperidin-4-yloxy)benzo[b]thiophene-2-carboxamide | 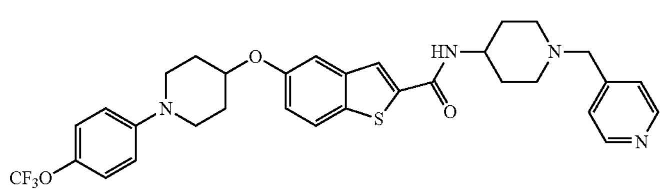 |

TABLE 1-continued

| No. | Name | Structure |
|---|---|---|
| 1-138 | N-(1-(pyridin-4-ylmethyl)piperidin-4-yl)-5-(1-(4-(trifluoromethyl)phenyl)piperidin-4-yloxy)benzo[b]thiophene-2-carboxamide | 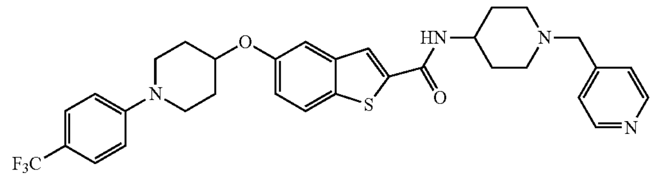 [SMILES: O=C(NC1CCN(Cc2ccncc2)CC1)c1cc2cc(OC3CCN(c4ccc(C(F)(F)F)cc4)CC3)ccc2s1] |
| 1-139 | N-(1-(pyridin-4-ylmethyl)piperidin-4-yl)-5-(1-(4-chlorophenyl)piperidin-4-yloxy)benzo[b]thiophene-2-carboxamide | 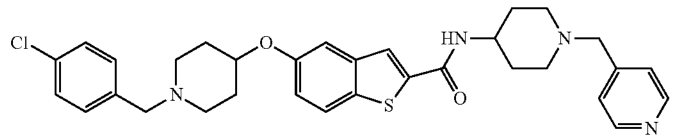 [SMILES: O=C(NC1CCN(Cc2ccncc2)CC1)c1cc2cc(OC3CCN(Cc4ccc(Cl)cc4)CC3)ccc2s1] |
| 1-140 | tert-butyl 4-(6-(1-(4-(trifluoromethyl)phenyl)piperidin-4-yloxy)benzo[b]thiophene-2-carboxamido)piperidine-1-carboxylate | 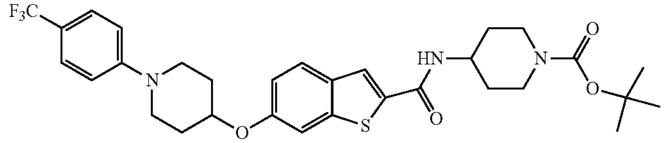 [SMILES: CC(C)(C)OC(=O)N1CCC(NC(=O)c2cc3ccc(OC4CCN(c5ccc(C(F)(F)F)cc5)CC4)cc3s2)CC1] |
| 1-141 | N-(piperidin-4-yl)-6-(1-(4-(trifluoromethyl)phenyl)piperidin-4-yloxy)benzo[b]thiophene-2-carboxamide | 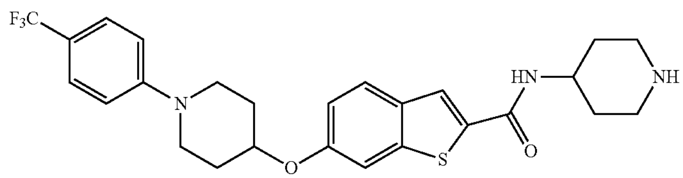 [SMILES: O=C(NC1CCNCC1)c1cc2ccc(OC3CCN(c4ccc(C(F)(F)F)cc4)CC3)cc2s1] |
| 1-142 | N-(1-(pyridin-4-ylmethyl)piperidin-4-yl)-6-(1-(4-(trifluoromethyl)phenyl)piperidin-4-yloxy)benzo[b]thiophene-2-carboxamide | 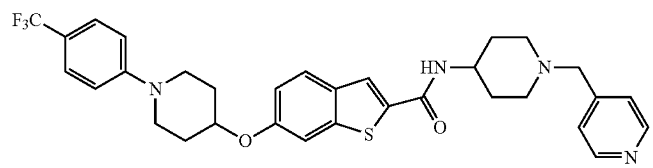 |
| 1-143 | N-(1-(pyridin-2-ylmethyl)piperidin-4-yl)-6-(1-(4-(trifluoromethyl)phenyl)piperidin-4-yloxy)benzo[b]thiophene-2-carboxamide | 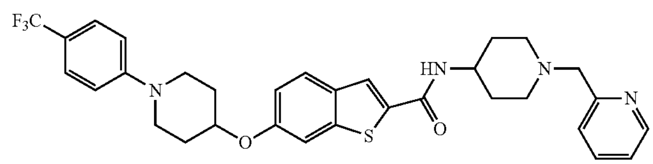 [SMILES: O=C(NC1CCN(Cc2ccccn2)CC1)c1cc2ccc(OC3CCN(c4ccc(C(F)(F)F)cc4)CC3)cc2s1] |
| 1-144 | N-(1-(4-cyanobenzyl)piperidin-4-yl)-6-(1-(4-(trifluoromethyl)phenyl)piperidin-4-yloxy)benzo[b]thiophene-2-carboxamide | 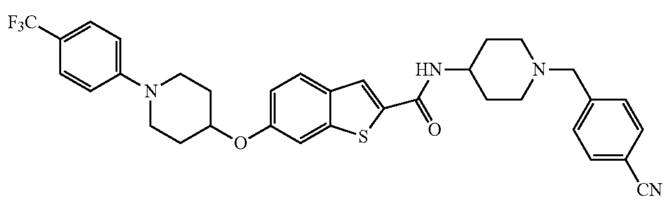 |
| 1-145 | N-(1-(3-cyanobenzyl)piperidin-4-yl)-6-(1-(4-(trifluoromethyl)phenyl)piperidin-4-yloxy)benzo[b]thiophene-2-carboxamide | 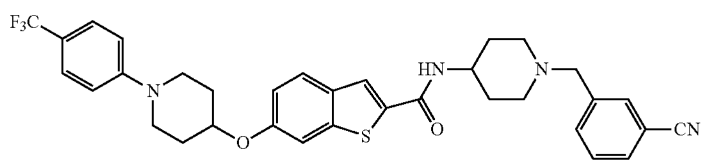 [SMILES: N#Cc1cccc(CN2CCC(NC(=O)c3cc4ccc(OC5CCN(c6ccc(C(F)(F)F)cc6)CC5)cc4s3)CC2)c1] |
| 1-146 | N-(1-(2-cyanobenzyl)piperidin-4-yl)-6-(1-(4-(trifluoromethyl)phenyl)piperidin-4-yloxy)benzo[b]thiophene-2-carboxamide | 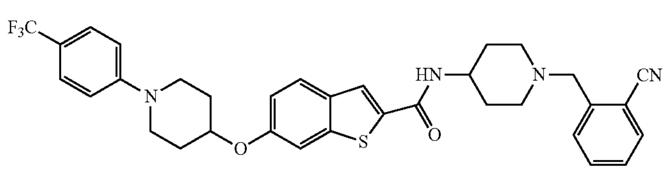 |

TABLE 1-continued

| No. | Name | Structure |
|---|---|---|
| 1-147 | tert-butyl 4-(3-chloro-6-(1-(4-(trifluoromethyl)phenyl)piperidin-4-yloxy)benzo[b]thiophene-2-carboxamido)piperidine-1-carboxylate | 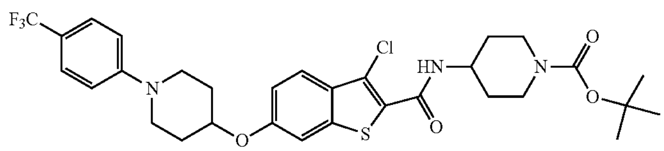 [SMILES: CC(C)(C)OC(=O)N1CCC(NC(=O)c2sc3cc(OC4CCN(c5ccc(C(F)(F)F)cc5)CC4)ccc3c2Cl)CC1] |
| 1-148 | 3-chloro-N-(piperidin-4-yl)-6-(1-(4-(trifluoromethyl)phenyl)piperidin-4-yloxy)benzo[b]thiophene-2-carboxamide | 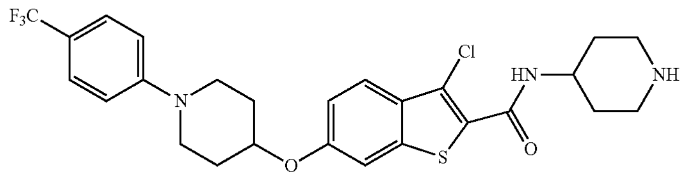 [SMILES: O=C(NC1CCNCC1)c1sc2cc(OC3CCN(c4ccc(C(F)(F)F)cc4)CC3)ccc2c1Cl] |
| 1-149 | tert-butyl 4-(5-(1-(4-(trifluoromethyl)phenyl)piperidin-4-yloxy)benzo[b]thiophene-2-carboxamido)piperidine-1-carboxylate | 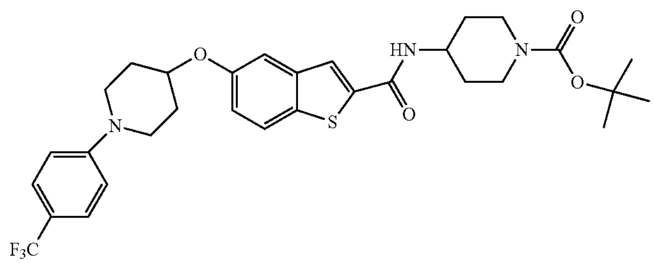 [SMILES: CC(C)(C)OC(=O)N1CCC(NC(=O)c2cc3cc(OC4CCN(c5ccc(C(F)(F)F)cc5)CC4)ccc3s2)CC1] |
| 1-150 | N-(piperidin-4-yl)-5-(1-(4-(trifluoromethyl)phenyl)piperidin-4-yloxy)benzo[b]thiophene-2-carboxamide | 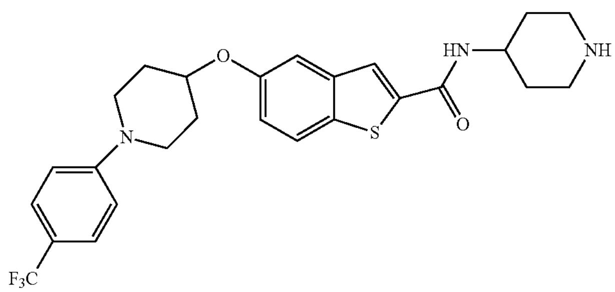 |
| 1-151 | 3-chloro-N-(1-(pyridin-4-ylmethyl)piperidin-4-yl)-6-(1-(4-(trifluoromethyl)phenyl)piperidin-4-yloxy)benzo[b]thiophene-2-carboxamide | 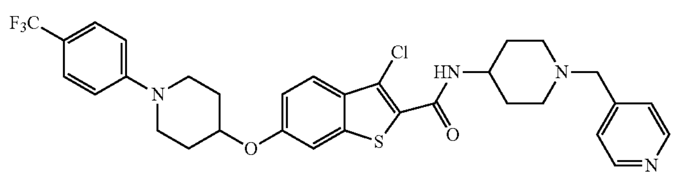 [SMILES: O=C(NC1CCN(Cc2ccncc2)CC1)c1sc2cc(OC3CCN(c4ccc(C(F)(F)F)cc4)CC3)ccc2c1Cl] |
| 1-152 | 3-chloro-N-(1-(pyridin-3-ylmethyl)piperidin-4-yl)-6-(1-(4-(trifluoromethyl)phenyl)piperidin-4-yloxy)benzo[b]thiophene-2-carboxamide | 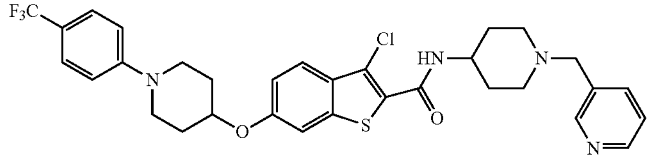 [SMILES: O=C(NC1CCN(Cc2cccnc2)CC1)c1sc2cc(OC3CCN(c4ccc(C(F)(F)F)cc4)CC3)ccc2c1Cl] |
| 1-153 | 3-chloro-N-(1-(pyridin-2-ylmethyl)piperidin-4-yl)-6-(1-(4-(trifluoromethyl)phenyl)piperidin-4-yloxy)benzo[b]thiophene-2-carboxamide | 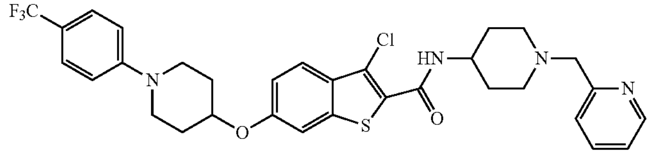 [SMILES: O=C(NC1CCN(Cc2ccccn2)CC1)c1sc2cc(OC3CCN(c4ccc(C(F)(F)F)cc4)CC3)ccc2c1Cl] |

TABLE 1-continued

| No. | Name | Structure |
|---|---|---|
| 1-154 | 3-chloro-N-(1-(4-cyanobenzyl)piperidin-4-yl)-6-(1-(4-(trifluoromethyl)phenyl)piperidin-4-yloxy)benzo[b]thiophene-2-carboxamide | 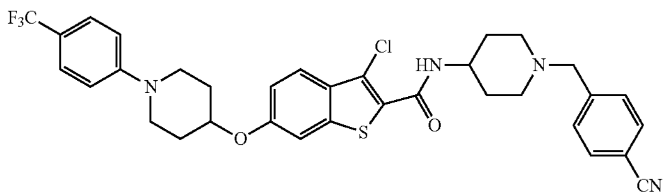 [SMILES: N#Cc1ccc(CN2CCC(NC(=O)c3sc4cc(OC5CCN(c6ccc(C(F)(F)F)cc6)CC5)ccc4c3Cl)CC2)cc1] |
| 1-155 | 3-chloro-N-(1-isonicotinoylpiperidin-4-yl)-6-(1-(4-(trifluoromethyl)phenyl)piperidin-4-yloxy)benzo[b]thiophene-2-carboxamide | 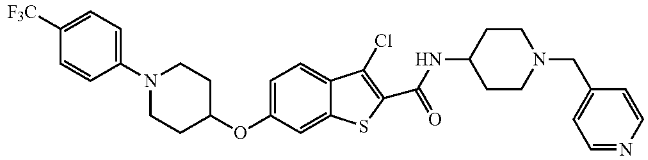 |
| 1-156 | tert-butyl 4-(5-(1-(4-(trifluoromethyl)phenyl)piperidin-4-yloxy)-2,3-dihydro-1H-inden-1-ylamino)piperidine-1-carboxylate | 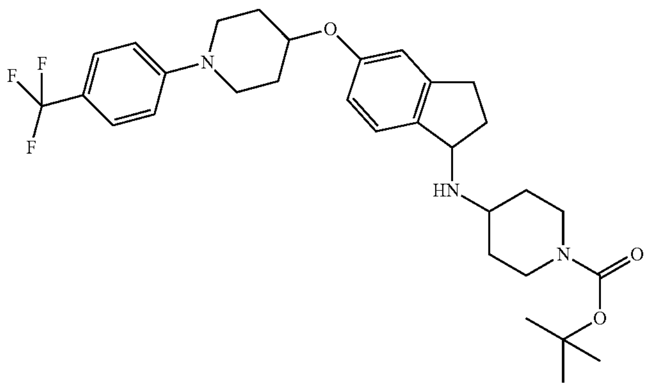 [SMILES: CC(C)(C)OC(=O)N1CCC(NC2CCc3cc(OC4CCN(c5ccc(C(F)(F)F)cc5)CC4)ccc32)CC1] |
| 1-157 | N-(5-(1-(4-(trifluoromethyl)phenyl)piperidin-4-yloxy)-2,3-dihydro-1H-inden-1-yl)piperidin-4-amine | 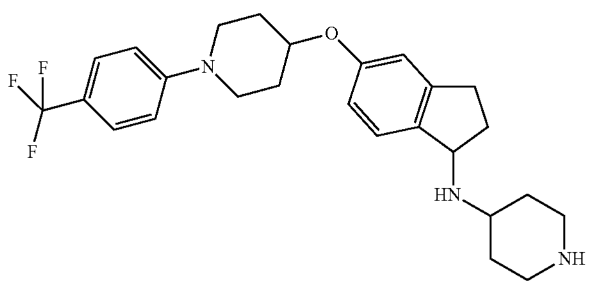 [SMILES: FC(F)(F)c1ccc(N2CCC(Oc3ccc4c(c3)CCC4NC3CCNCC3)CC2)cc1] |
| 1-158 | 1-(pyridin-4-ylmethyl)-N-(5-(1-(4-(trifluoromethyl)phenyl)piperidin-4-yloxy)-2,3-dihydro-1H-inden-1-yl)piperidin-4-amine | 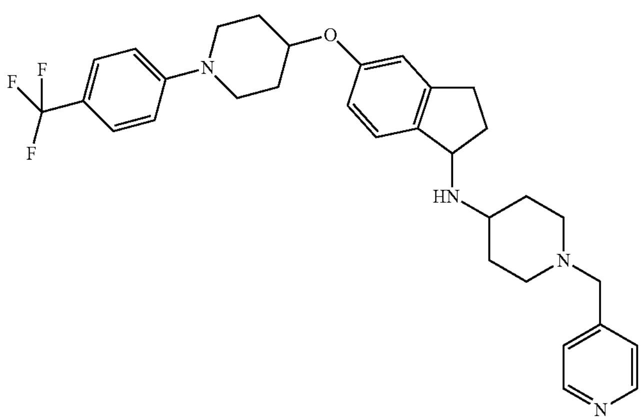 [SMILES: FC(F)(F)c1ccc(N2CCC(Oc3ccc4c(c3)CCC4NC3CCN(Cc4ccncc4)CC3)CC2)cc1] |

TABLE 1-continued

| No. | Name | Structure |
|---|---|---|
| 1-159 | 1-(4-fluorobenzyl)-N-(5-(1-(4-(trifluoromethyl)phenyl)piperidin-4-yloxy)-2,3-dihydro-1H-inden-1-yl)piperidin-4-amine | 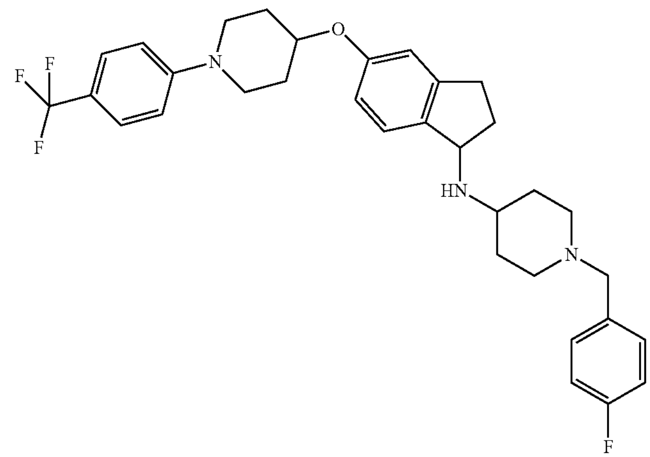 [SMILES: Fc1ccc(CN2CCC(NC3CCc4cc(OC5CCN(c6ccc(C(F)(F)F)cc6)CC5)ccc43)CC2)cc1] |
| 1-160 | 4-((4-(5-(1-(4-(trifluoromethyl)phenyl)piperidin-4-yloxy)-2,3-dihydro-1H-inden-1-ylamino)piperidin-1-yl)methyl)benzonitrile | 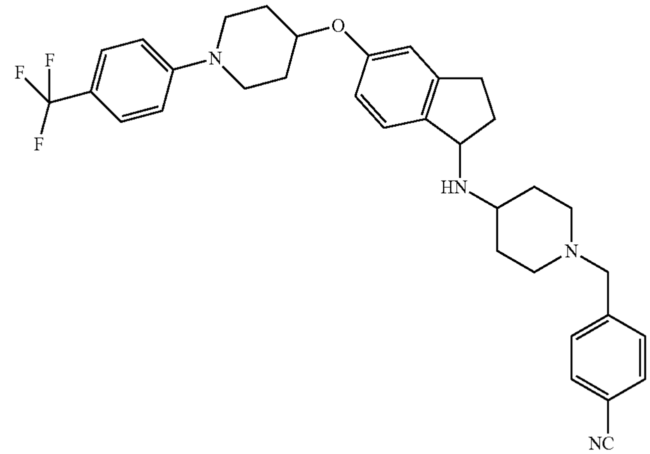 [SMILES: N#Cc1ccc(CN2CCC(NC3CCc4cc(OC5CCN(c6ccc(C(F)(F)F)cc6)CC5)ccc43)CC2)cc1] |

Another aspect of the disclosure provides a method for treating or ameliorating a disorder or condition related to oxidative stress, mitochondrial dysfunction, free radical damage and/or metabolic inefficiency in a subject, the method including administering to the subject an effective amount of a compound having structural formula (2-I):

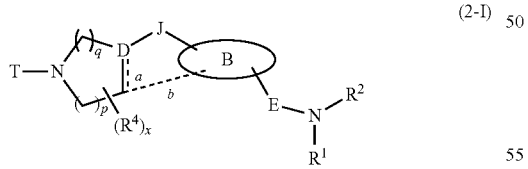

(2-I)

or a pharmaceutically acceptable salt, solvate, hydrate, or N-oxide thereof (or a solvate or hydrate thereof), wherein
"B" represents -(aryl or heteroaryl)- substituted by w $R^3$ and k $R^{14}$;
the dotted line denoted by "b" is absent, a single bond or a double bond;
the dotted line denoted by "a" is a bond or absent, provided that if the dotted line denoted by "b" is a double bond, then the dotted line denoted by "a" is absent;

D is a carbon or N when the dotted line denoted by "a" is absent, and a carbon when the dotted line denoted by "a" is a bond;
J is —O—, —N($R^{38}$)—, —CH$_2$—, —CH($R^{26}$)— or —C($R^{26}$)$_2$—;
E is —C(O)—, —S(O)$_2$— or a single bond, provided that when "B" is phenyl, J is —O— and D is a carbon, E is not —C(O)—;
$R^1$ is H, —(C$_1$-C$_4$ alkyl), —C(O)—(C$_1$-C$_4$ alkyl) or —C(O)O—(C$_1$-C$_4$ alkyl);
$R^2$ is -Hca, -Cak-N($R^9$)-G-$R^{22}$ or —(C$_2$-C$_8$ alkyl)-N($R^9$)—$R^{24}$ in which one or two carbons of the (C$_2$-C$_8$ alkyl) are optionally replaced by —O—, —S— or —N($R^9$)— and $R^{24}$ is —$R^{23}$, G-$R^{23}$, or —C(O)O—(C$_1$-C$_6$ alkyl), provided that two consecutive carbons of the (C$_2$-C$_8$ alkyl) are not replaced by —O—;
each $R^3$ is substituted on a benzo, pyrido or pyrazino carbon of the ring system denoted by "B" and is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-$R^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN;
w is 0, 1, 2 or 3;
each $R^{14}$ is substituted on a non-benzo, non-pyrido, non-pyrazino carbon of the ring system denoted by "B", and is independently selected from —($C_1$-$C_6$ alkyl), —($C_1$-$C_6$ halooalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN;

k is 0, 1 or 2;

each $R^4$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, and two $R^4$ on the same carbon optionally combine to form oxo;

x is 0, 1, 2, 3 or 4;

p is 0, 1, 2, 3 or 4;

q is 0, 1, 2, 3 or 4;

the sum of p and q is 1, 2, 3 or 4;

T is —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$ or

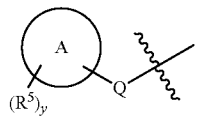

in which

Q is —S(O)$_2$—, L or —($C_0$-$C_3$ alkyl)-, in which each carbon of the —($C_0$-$C_3$ alkyl)- is optionally and independently substituted with one or two $R^{16}$;

the ring system denoted by "A" is heteroaryl, aryl, cycloalkyl or heterocycloalkyl;

each $R^5$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, —($C_0$-$C_6$ alkyl)-C(O)$R^{10}$, -halogen, —$NO_2$ and —CN; and y is 0, 1, 2, 3 or 4;

in which each L is independently selected from —$NR^9$C(O)O—, —OC(O)$NR^9$—, —$NR^9$C(O)—$NR^9$—, —$NR^9$C(O)S—, —SC(O)$NR^9$—, —$NR^9$C(O)—, —C(O)$NR^9$—, —$NR^9$C(S)O—, —OC(S)$NR^9$—, —$NR^9$C(S)—$NR^9$—, —$NR^9$C(S)S—, —SC(S)$NR^9$—, —$NR^9$C(S)—, —C(S)$NR^9$—, —SC(O)$NR^9$—, —$NR^9$C(S)—, —S(O)$_{0-2}$—, —C(O)O, —OC(O)—, —C(S)O—, —OC(S)—, —C(O)S—, —SC(O)—, —C(S)S—, —SC(S)—, —OC(O)O—, —SC(O)O—, —OC(O)S—, —SC(S)O—, —OC(S)S—, —$NR^9$C($NR^2$)$NR^9$—, —$NR^9$SO$_2$—, —SO$_2$$NR^9$— and —$NR^9$SO$_2$$NR^9$—, each $R^6$, $R^7$, $R^8$ and $R^{10}$ is independently selected from H, —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-($C_0$-$C_6$ alkyl), —($C_0$-$C_6$ alkyl)-$NR^9$—($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), each $R^9$ is independently selected from —H, —($C_1$-$C_4$ alkyl), —C(O)—($C_1$-$C_4$ alkyl) and —C(O)O—($C_1$-$C_4$ alkyl), each G is independently —S(O)$_2$—, L or —($C_0$-$C_3$ alkyl)-, in which each carbon of the —($C_0$-$C_3$ alkyl)- is optionally and independently substituted with one or two $R^{16}$, or each $R^{16}$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, and optionally two of $R^{16}$ on the same carbon combine to form oxo, each $R^{26}$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, and optionally two of $R^{26}$ on the same carbon combine to form oxo, each $R^{38}$ is independently selected from —H, —($C_1$-$C_4$ alkyl), —C(O)—($C_1$-$C_4$ alkyl) and —C(O)O—($C_1$-$C_4$ alkyl), each $R^{22}$ and $R^{23}$ is independently Ar or Het, each Ar is an optionally substituted aryl, each Het is an optionally substituted heteroaryl, each Cak is an optionally substituted cycloalkyl, each Hca is an optionally substituted heterocycloalkyl, and each alkyl is optionally substituted.

Various embodiments of compounds of structural formula (2-I) suitable for use in the methods described herein are described below. Information regarding these compounds can also be found in U.S. Patent Application Publication no. 2009/0163511, which is hereby incorporated by reference in its entirety.

In certain embodiments of the presently disclosed compounds of structural formula (2-I), the compound is not
5-methyl-N,2-bis(tetrahydro-2H-pyran-4-yl)-2,3,4,5-tetrahydro-1H-pyrido[4,3-b]indole-8-carboxamide or
5-methyl-2-(tetrahydro-2H-pyran-4-yl)-N-(tetrahydrothiophen-2-yl)-2,3,4,5-tetrahydro-1H-pyrido[4,3-b]indole-8-carboxamide S,S-dioxide.

In certain embodiments of the presently disclosed compounds of structural formula (2-I), J is —O— or —N($R^{38}$)—. In certain such embodiments, D can be, for example, a carbon (for example, it is CH or C substituted with one of the x $R^4$ groups when the bond denoted by "a" is absent, or C when the bond denoted by "a" is present). In other embodiments of the presently disclosed compounds of structural formula (2-I), J is —CH$_2$—, —CH($R^{26}$)— or —C($R^{26}$)$_2$—, for example, —CH$_2$—. In certain such embodiments, D can be, for example, N.

In certain embodiments of the presently disclosed compounds of structural formula (2-I), $R^{38}$ is —H. In other embodiments, $R^{38}$ is —($C_1$-$C_4$ alkyl), for example methyl, ethyl or propyl. In other embodiments, $R^{38}$ is —C(O)—($C_1$-$C_4$ alkyl), for example acetyl. In other embodiments, $R^{38}$ is —C(O)—O—($C_1$-$C_4$ alkyl)-, for example —C(O)—O-t-butyl. In certain embodiments, no alkyl of $R^{38}$ is substituted with an aryl-, heteroaryl-, cycloalkyl- or heterocycloalkyl-containing group.

In certain embodiments of the presently disclosed compounds of structural formula (2-I), each $R^{26}$ is independently selected from —(C$_1$-C$_6$ alkyl), —(C$_1$-C$_6$ haloalkyl) (e.g., difluoromethyl, trifluoromethyl and the like), —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, in which each R$^7$, R$^8$ and R$^{10}$ is independently selected from H, —(C$_1$-C$_6$ alkyl), —(C$_1$-C$_6$ haloalkyl), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl), and —(C$_0$-C$_6$ alkyl)-S(O)$_{0-2}$—(C$_0$-C$_6$ alkyl), and in which no alkyl or haloalkyl is substituted with an aryl-, heteroaryl-, cycloalkyl- or heterocycloalkyl-containing group. For example, in one embodiment, each R$^{26}$ is independently selected from —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN, in which each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group. In certain embodiments, each R$^{26}$ is methyl, ethyl, propyl, or two R$^{26}$ come together to form oxo.

In certain embodiments of the presently disclosed compounds of structural formula (2-I) as described above, the dotted line denoted by "b" is absent. In other embodiments, the dotted line denoted by "b" is a single bond; in one such embodiment, the dotted line denoted by "a" is a bond (thereby forming a double bond between D and the adjacent carbon).

In certain embodiments of the presently disclosed compounds of structural formula (2-I), E is —C(O)—. In other embodiments, E is —S(O)$_2$—

In certain embodiments of the presently disclosed compounds of structural formula (2-I), "B" represents

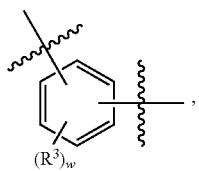

the dotted line denoted by "b" is a single bond, the dotted line denoted by "a" is a bond, k is 0, J is —N(R$^{38}$)— and D is a carbon. In one such embodiment, E is —C(O)—.

In other embodiments of the presently disclosed compounds of structural formula (2-I), "B" represents

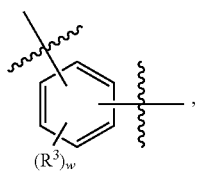

the dotted line denoted by "b" is absent, the dotted line denoted by "a" is absent, k is 0, J is —N(R$^{38}$)— and D is a carbon. In one such embodiment, E is —C(O)—.

In other embodiments of the presently disclosed compounds of structural formula (2-I), "B" represents

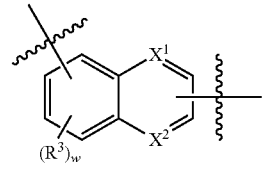

in which X$^1$ and X$^2$ are independently a carbon (for example, CH or C substituted with one of the w R$^3$ groups) or N, and k is 0. In one such embodiment, E is —C(O)—. In certain embodiments, one of X$^1$ and X$^2$ is N and the other is a carbon. In other embodiments, both X$^1$ and X$^2$ are a carbon. Floating bonds indicate attachment on any carbon of the ring system. In some embodiments, for example, the J moiety is on one ring of the ring system, and the E moiety is on the other ring of the naphthalene, and any R$^3$ groups can be on either ring of the fused ring system.

In other embodiments of the presently disclosed compounds of structural formula (2-I), "B" represents

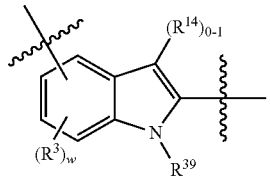

in which R$^{39}$ is H, —(C$_1$-C$_4$ alkyl), —C(O)—(C$_1$-C$_4$ alkyl) or —C(O)O—(C$_1$-C$_4$ alkyl). In certain such embodiments, E is —C(O)—. In certain embodiments, one R$^{14}$ can be substituted on the pyrrolo carbon. In one such embodiment, R$^{14}$ is selected from —(C$_1$-C$_6$ alkyl), —(C$_1$-C$_6$ haloalkyl) (e.g., difluoromethyl, trifluoromethyl and the like), —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, in which each R$^7$, R$^8$ and R$^{10}$ is independently selected from H, —(C$_1$-C$_6$ alkyl), —(C$_1$-C$_6$ haloalkyl), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl), and —(C$_0$-C$_6$ alkyl)-S(O)$_{0-2}$—(C$_0$-C$_6$ alkyl), and in which no alkyl or haloalkyl is substituted with an aryl-, heteroaryl-, cycloalkyl- or heterocycloalkyl-containing group. For example, in one embodiment, R$^{14}$ is selected from —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN, in which each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group. R$^{14}$ can be, for example, halo (e.g., —Cl or —F), cyano, unsubstituted —(C$_1$-C$_4$ alkyl) (e.g., methyl or ethyl), or unsubstituted —(C$_1$-C$_4$ haloakyl) (e.g., difluoromethyl, trifluoromethyl and the like). In certain embodiments, R$^{14}$ is H or methyl; in others, R$^{14}$ is halo (e.g., Cl). In other embodiments, no R$^{14}$ is substituted on the pyrrolo carbon.

In certain embodiments of the presently disclosed compounds of structural formula (2-I), T is

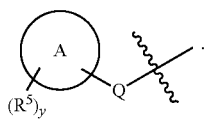

In such embodiments, Q is —S(O)$_2$—, L or —(C$_0$-C$_3$ alkyl)- in which each carbon of the (C$_0$-C$_3$ alkyl) is optionally and independently substituted with one or two R$^{16}$, in which each R$^{16}$ is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, and optionally two of R$^{16}$ on the same carbon combine to form oxo. In certain embodiments, each R$^{16}$ is independently selected from —(C$_1$-C$_6$ alkyl), —(C$_1$-C$_6$ haloalkyl) (e.g., difluoromethyl, trifluoromethyl and the like), —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, and two R$^{16}$ on the same carbon optionally combine to form an oxo, in which each R$^7$, R$^8$ and R$^{10}$ is independently selected from H, —(C$_1$-C$_6$ alkyl), —(C$_1$-C$_6$ haloalkyl), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl), and —(C$_0$-C$_6$ alkyl)-S(O)$_{0-2}$—(C$_0$-C$_6$ alkyl), and in which no alkyl or haloalkyl is substituted with an aryl-, heteroaryl-, cycloalkyl- or heterocycloalkyl-containing group. For example, in particular compounds, each R$^{16}$ is —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN, and two R$^{16}$ on the same carbon optionally combine to form an oxo, in which each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group. In certain embodiments, Q has at most one R$^{16}$ or an oxo substituted thereon. Q can be, for example, an unsubstituted —(C$_0$-C$_3$ alkyl)-. In other embodiments, Q is a (C$_1$-C$_3$ alkyl) having as its only substitution a single oxo group. For example, in certain embodiments, Q is —CH$_2$—; a single bond; —S(O)$_2$—; —C(O)—; or —CH(CH$_3$)—.

In certain embodiments of the compounds of structural formula (2-I), the

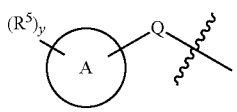

moiety is

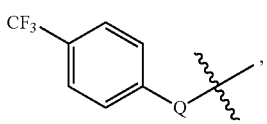

for example, p-(trifluoromethyl)phenyl. In other embodiments, the

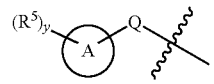

moiety is

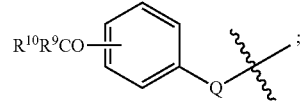

in one such embodiment, Q is a single bond.

The number of substituents on the ring system denoted by "A", y, is 0, 1, 2, 3 or 4. For example, in some embodiments of the presently disclosed compounds of structural formula (2-I), y is 0, 1, 2 or 3, such as 1. In one embodiment, y is not zero and at least one R$^5$ is halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ or —C(O)-Hca wherein the Hca contains a ring nitrogen atom through which it is bound to the —C(O)—, and wherein no alkyl, haloalkyl or heterocycloalkyl is substituted by an aryl, heteroaryl, cycloalkyl or heterocycloalkyl-containing group.

In certain embodiments of the presently disclosed compounds of structural formula (2-I), each R$^5$ is independently selected from —(C$_1$-C$_6$ alkyl), —(C$_1$-C$_6$ haloalkyl) (e.g., difluoromethyl, trifluoromethyl and the like), —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, in which each R$^7$, R$^8$ and R$^{10}$ is independently selected from H, —(C$_1$-C$_6$ alkyl), —(C$_1$-C$_6$ haloalkyl) (e.g., difluoromethyl, trifluoromethyl and the like), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl) and —(C$_0$-C$_6$ alkyl)-S(O)$_{0-2}$—(C$_0$-C$_6$ alkyl), and in which no alkyl or haloalkyl is substituted with an aryl-, heteroaryl-, cycloalkyl- or heterocycloalkyl-containing group. For example, in one embodiment, each R$^5$ is —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN, in which each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group.

In one embodiment of the compounds of structural formula (2-I), y is 0.

In the presently disclosed compounds of structural formula (2-I), the ring system denoted by "A" is heteroaryl, aryl, cycloalkyl or heterocycloalkyl. For example, in one embodiment, the ring system denoted by "A" is an aryl or a heteroaryl. The ring system denoted by "A" can be, for example, a monocyclic aryl or heteroaryl. In one embodiment, when the "A" ring system is aryl, Q is a —(C$_0$-C$_3$ alkyl)- optionally substituted with oxo, and optionally substituted with one or more $R^{16}$. For example, Q can be a —($C_1$-$C_3$ alkyl)- having its only substitution a single oxo, or an unsubstituted —($C_0$-$C_3$ alkyl)-. For example, in certain embodiments, Q is —$CH_2$—; a single bond; —$S(O)_2$—; —C(O)—; or —$CH(CH_3)$—.

For example, in certain embodiments of the presently disclosed compounds of structural formula (2-I), the ring system denoted by "A" is a phenyl. In one embodiment, y is 1 and $R^5$ is attached to the phenyl in the para position relative to Q. In another embodiment, y is 1 and $R^5$ is selected from the group consisting of halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, and in which no ($C_0$-$C_4$ alkyl) or ($C_1$-$C_4$ alkyl) is substituted by an aryl, heteroaryl, cycloalkyl or heterocycloalkyl-containing group. $R^5$ can be, for example, —Cl, —F, cyano, —C(O)$CH_3$, —C(O)OH, —C(O)$NH_2$, trifluoromethyl, difluoromethyl, difluoromethoxy or trifluoromethoxy. In another embodiment, the

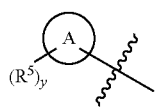

moiety is a 3,4-dihalophenyl.

In another embodiment of the presently disclosed compounds of structural formula (2-I), the ring system denoted by "A" is a heteroaryl. For example, in certain embodiments, the ring system denoted by "A" is a pyridyl, a thienyl, or a furanyl. In one embodiment, when the "A" ring system is heteroaryl, Q is a —($C_0$-$C_3$ alkyl)- optionally substituted with oxo, and optionally substituted with one or more $R^{16}$. For example, Q can be a —($C_1$-$C_3$ alkyl)- having its only substitution a single oxo, or an unsubstituted —($C_0$-$C_3$ alkyl)-. In certain embodiments, Q is —$CH_2$—; a single bond; —$S(O)_2$—; —C(O)—; or —$CH(CH_3)$—.

In one embodiment of the presently disclosed compounds, the compound has structural formula (2-II):

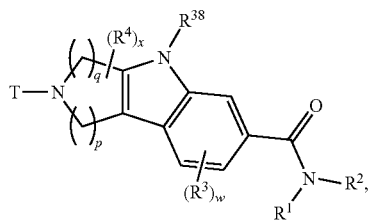

(2-II)

in which the variables are defined as described above with reference to structural formula (2-I). In certain embodiments, $R^{38}$ is not H. For example, $R^{38}$ can in one embodiment be methyl, ethyl or propyl. In another embodiment, $R^{38}$ can be acetyl. In other embodiments, $R^{38}$ is H.

In one embodiment of the presently disclosed compounds, the compound has structural formula (2-III):

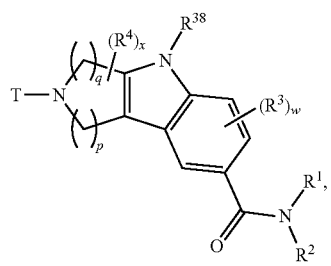

(2-III)

in which the variables are defined as described above with reference to structural formula (2-I). In certain embodiments, $R^{38}$ is not H. For example, $R^{38}$ can in one embodiment be methyl, ethyl or propyl. In another embodiment, $R^{38}$ can be acetyl. In other embodiments, $R^{38}$ is H.

In another embodiment of the presently disclosed compounds, the compound has structural formula (2-IV):

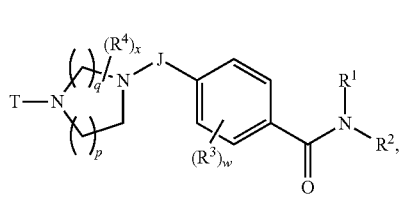

(2-IV)

in which k is 0, q is 1, 2, 3 or 4, J is —$CH_2$—, —$CH(R^{26})$— or —$C(R^{26})_2$— (e.g., —$CH_2$—), and all other variables are defined as described above with reference to structural formula (2-I).

In another embodiment of the presently disclosed compounds, the compound has structural formula (2-V):

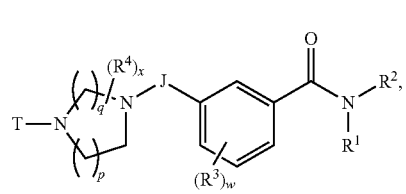

(2-V)

in which k is 0, q is 1, 2, 3 or 4, J is —$CH_2$—, —$CH(R^{26})$— or —$C(R^{26})_2$— (e.g., —$CH_2$—), and all other variables are defined as described above with reference to structural formula (2-I).

In certain embodiments according to structural formulae (2-I)-(2-V), the sum of p and q is 2 or 3. For example, in one embodiment, the sum of p and q is 2 (e.g., p is 1 and q is 1). In another embodiment, the sum of p and q is 3 (e.g., p is 1 and q is 2).

In another embodiment of the presently disclosed compounds, the compound has structural formula (2-VI):

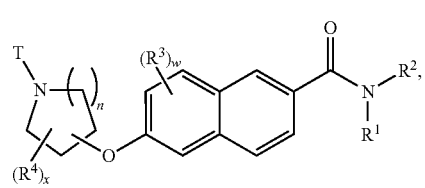

(2-VI)

in which k is 0, n is 0, 1, 2 or 3, and all other variables are defined as described above with reference to structural formula (2-I).

In another embodiment of the presently disclosed compounds, the compound has structural formula (2-VII):

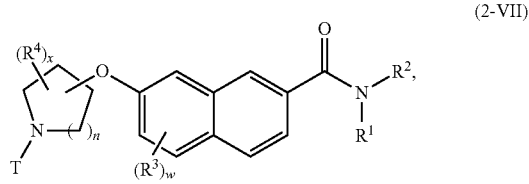

(2-VII)

in which k is 0, n is 0, 1, 2 or 3, and all other variables are defined as described above with reference to structural formula (2-I).

In another embodiment of the presently disclosed compounds, the compound has structural formula (2-VIII):

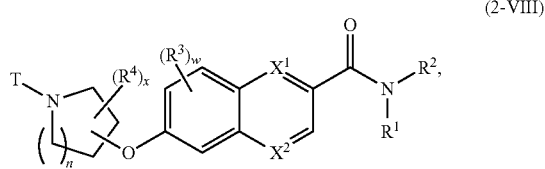

(2-VIII)

in which k is 0, n is 0, 1, 2 or 3, one of $X^1$ and $X^2$ is N and the other is a carbon, and all other variables are defined as described above with reference to structural formula (2-I). In one embodiment, for example, $X^1$ is N and $X^2$ is a carbon. In another embodiment, $X^1$ is a carbon, and $X^2$ is N.

In another embodiment of the presently disclosed compounds, the compound has structural formula (2-IX):

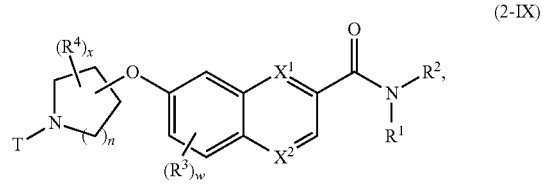

(2-IX)

in which k is 0, n is 0, 1, 2 or 3, one of $X^1$ and $X^2$ is N and the other is a carbon, and all other variables are defined as described above with reference to structural formula (2-I). In one embodiment, for example, $X^1$ is N and $X^2$ is a carbon. In another embodiment, $X^1$ is a carbon, and $X^2$ is N.

In one embodiment of the presently disclosed compounds, the compound has structural formula (2-X):

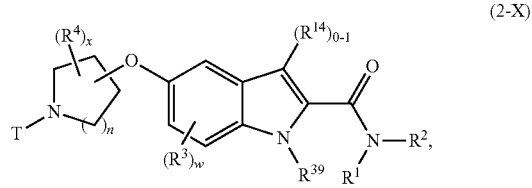

(2-X)

in which n is 0, 1, 2 or 3 and all other variables are defined as described above with reference to structural formula (2-I). In certain embodiments, one $R^{14}$ is substituted on the pyrrolo carbon. In other embodiments, no $R^{14}$ is substituted on the pyrrolo carbon.

In another embodiment of the presently disclosed compounds, the compound has structural formula (2-XI):

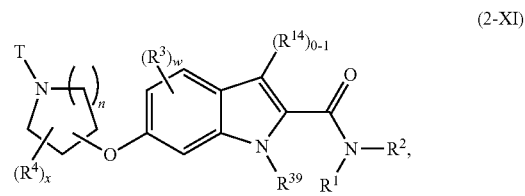

(2-XI)

in which the variables are defined as described above with reference to structural formula (2-I). In certain embodiments, one $R^{14}$ is substituted on the pyrrolo carbon. In other embodiments, no $R^{14}$ is substituted on the pyrrolo carbon.

In certain embodiments of the compounds disclosed with reference to structural formulae (2-VI)-(2-XI), n is 1 or 2. For example, in one embodiment, n is 2. In another embodiment, n is 1.

In one embodiment of the presently disclosed compounds, the compound has the structural formula (2-XII):

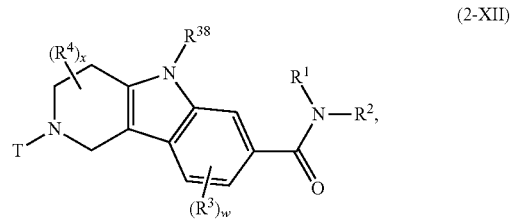

(2-XII)

in which the variables are defined as described above with reference to structural formulae (2-I) and (2-II).

In another embodiment of the presently disclosed compounds, the compound has structural formula (2-XIII):

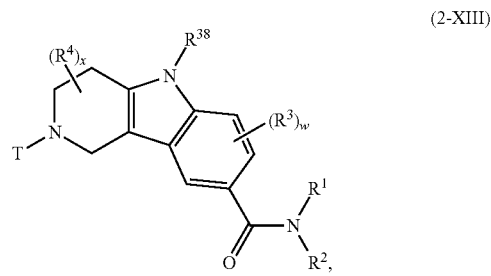

(2-XIII)

in which the variables are defined as described above with reference to structural formulae (2-I) and (2-III).

In another embodiment of the presently disclosed compounds, the compound has structural formula (2-XIV):

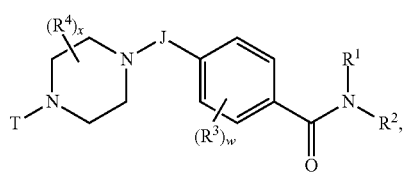

(2-XIV)

in which J is —CH$_2$—, —CH(R$^{26}$)— or —C(R$^{26}$)$_2$— (e.g., —CH$_2$—), and all other variables are defined as described above with reference to structural formulae (2-I) and (2-IV).

In another embodiment of the presently disclosed compounds, the compound has structural formula (2-XV):

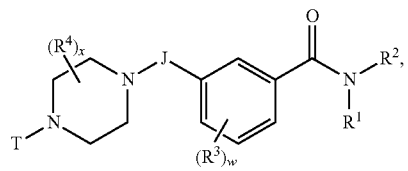

(2-XV)

in which J is —CH$_2$—, —CH(R$^{26}$)— or —C(R$^{26}$)$_2$— (e.g., —CH$_2$—), and all other variables are defined as described above with reference to structural formulae (2-I) and (2-V).

In another embodiment of the presently disclosed compounds, the compound has structural formula (2-XVI):

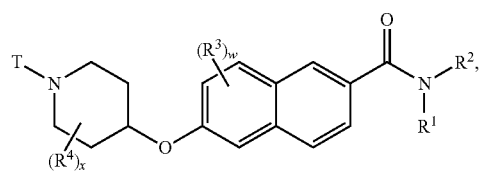

(2-XVI)

in which the variables are defined as described above with reference to structural formulae (2-I) and (2-VI).

In another embodiment of the presently disclosed compounds, the compound has structural formula (2-XVII):

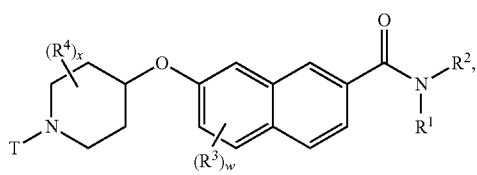

(2-XVII)

in which the variables are defined as described above with reference to structural formulae (2-I) and (2-VII).

In one embodiment of the presently disclosed compounds, the compound has structural formula (2-XVIII):

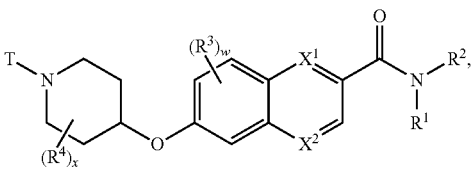

(2-XVIII)

in which one of X$^1$ and X$^2$ is N, and the other is a carbon; and the other variables are defined as described above with reference to structural formulae (2-I) and (2-VIII). In one embodiment, for example, X$^1$ is N and X$^2$ is a carbon. In another embodiment, X$^1$ is a carbon, and X$^2$ is N.

In another embodiment of the presently disclosed compounds, the compound has structural formula (2-XIX):

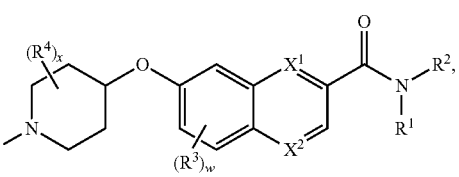

(2-XIX)

in which one of X$^1$ and X$^2$ is N, and the other is a carbon; and the other variables are defined as described above with reference to structural formulae (2-I) and (2-IX). In one embodiment, for example, X$^1$ is N and X$^2$ is a carbon. In another embodiment, X$^1$ is a carbon, and X$^2$ is N.

In one embodiment of the presently disclosed compounds, the compound has structural formula (2-XX):

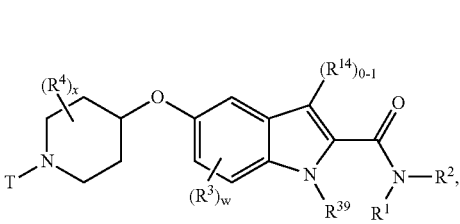

(2-XX)

in which the variables are defined as described above with reference to structural formulae (2-I) and (2-X). In certain embodiments, one R$^{14}$ is substituted on the pyrrolo carbon. In other embodiments, no R$^{14}$ is substituted on the pyrrolo carbon.

In another embodiment of the presently disclosed compounds, the compound has structural formula (2-XXI):

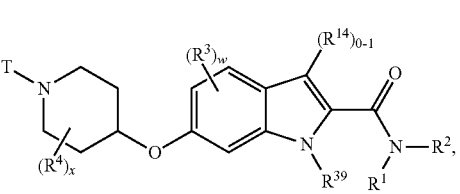

(2-XXI)

in which the variables are defined as described above with reference to structural formulae (2-I) and (2-XI). In certain embodiments, one $R^{14}$ is substituted on the pyrrolo carbon. In other embodiments, no $R^{14}$ is substituted on the pyrrolo carbon.

In certain embodiments of the presently disclosed compounds of any of structural formulae (2-I)-(2-XXI), $R^1$ is —H. In other embodiments, $R^1$ is ($C_1$-$C_4$ alkyl), for example methyl, ethyl, n-propyl or isopropyl.

In certain embodiments of the presently disclosed compounds of any structural formulae (2-I)-(2-XXI), $R^2$ is -Hca. In certain embodiments, $R^2$ is an optionally-substituted monocyclic heterocycloalkyl. In another embodiment, $R^2$ is not an oxo-substituted heterocycloalkyl. In certain embodiments (e.g., when the compound has structural formula (2-II) or (2-III)), $R^2$ is not tetrahydro-2H-pyran-4-yl moiety or a tetrahydrothiophene S,S-dioxide moiety.

In certain of the presently disclosed compounds of any structural formulae (2-I)-(2-XXI), $R^2$ is -(optionally-substituted azetidinyl), -(optionally-substituted pyrrolidinyl), -(optionally-substituted piperidinyl), or -(optionally-substituted azepanyl). For example, $R^2$ can be -(optionally substituted piperidinyl) or -(optionally substituted pyrrolidinyl). In one embodiment, $R^2$ is -(optionally substituted piperidinyl). In another embodiment, $R^2$ is -(optionally substituted pyrrolidinyl).

In certain particular embodiments of the presently disclosed compounds of any of structural formulae (2-I)-(2-XXI), $R^2$ is -(optionally-substituted azetidin-3-yl), -(optionally substituted piperidin-4-yl), -(optionally substituted pyrrolidin-3-yl) or -(optionally-substituted azepan-4-yl). For example, in one embodiment, $R^2$ is -(optionally substituted piperidin-4-yl). In another embodiment, $R^2$ is -(optionally substituted pyrrolidin-3-yl).

In certain embodiments of the presently disclosed compounds of any of structural formulae (2-I)-(2-XXI), the azetidinyl, pyrrolidinyl, piperidinyl and azepanyl $R^2$ moieties described above are substituted at their 1-positions. For example, in one embodiment, $R^2$ is substituted at its 1-position with —($C_0$-$C_3$ alkyl)-Ar or —($C_0$-$C_3$ alkyl)-Het, for example -(unsubstituted $C_0$-$C_3$ alkyl)-Ar or -(unsubstituted $C_0$-$C_3$ alkyl)-Het. For example, in one particular embodiment, the azetidinyl, pyrrolidinyl, piperidinyl or azepanyl $R^2$ moiety is substituted at its 1-position with an optionally substituted benzyl or an optionally substituted phenyl. In another embodiment, the azetidinyl, pyrrolidinyl, piperidinyl or azepanyl $R^2$ moiety is substituted at its 1-position with a benzyl substituted with an electron withdrawing group; or with a pyridinylmethyl optionally substituted with an electron withdrawing group. For example, the benzyl or pyridinylmethyl can be substituted with an electron withdrawing group selected from the group consisting of halo, cyano, —($C_1$-$C_4$ fluoroalkyl), —O—($C_1$-$C_4$ fluoroalkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), —S(O)$_2$O—($C_0$-$C_4$ alkyl), NO$_2$ and —C(O)-Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group. In other embodiments, the azetidinyl, pyrrolidinyl, piperidinyl or azepanyl $R^2$ moiety is substituted at its 1-position with an unsubstituted benzyl or an unsubstituted phenyl.

In other embodiments of the compounds disclosed herein having any of structural formulae (2-I)-(2-XXI), the azetidinyl, pyrrolidinyl, piperidinyl or azepanyl $R^2$ moiety is substituted at its 1-position with an optionally substituted pyridinylmethyl, an optionally substituted furanylmethyl, an optionally substituted thienylmethyl, an optionally substituted oxazolylmethyl, or an optionally substituted imidazolylmethyl. For example, the azetidinyl, pyrrolidinyl, piperidinyl or azepanyl $R^2$ moiety can be substituted with an unsubstituted pyridinylmethyl, an unsubstituted furanylmethyl, an unsubstituted thienylmethyl, an unsubstituted oxazolylmethyl, or an unsubstituted imidazolylmethyl. In other embodiments, the azetidinyl, pyrrolidinyl, piperidinyl or azepanyl $R^2$ moiety can be substituted with an pyridinylmethyl, furanylmethyl, thienylmethyl, oxazolylmethyl or imidazolylmethyl substituted with an electron withdrawing group as described above.

In certain embodiments of the compounds disclosed herein having any of structural formulae (2-I)-(2-XXI), the azetidinyl, pyrrolidinyl, piperidinyl or azepanyl $R^2$ moiety is substituted at its 1-position with -L-Ar or -L-Het, in which Ar and Het can be, for example, as described above with reference to —($C_0$-$C_3$ alkyl)-Ar or —($C_0$-$C_3$ alkyl)-Het. In one such embodiment, L is —C(O)—NR$^9$—, such as —C(O)—NH—.

In other embodiments of the presently disclosed compounds of any of structural formulae (2-I)-(2-XXI), the azetidinyl, pyrrolidinyl, piperidinyl or azepanyl $R^2$ moiety is substituted at its 1-position with —C(O)—O($C_0$-$C_6$ alkyl), —C(O)—Het, —C(O)—Ar, —S(O)$_2$-Het, —S(O)$_2$—Ar or —S(O)$_{2-0}$($C_0$-$C_6$ alkyl), in which Ar and Het can be, for example, as described above with reference to —($C_0$-$C_3$ alkyl)-Ar or —($C_0$-$C_3$ alkyl)-Het. In one embodiment, the azetidinyl, pyrrolidinyl, piperidinyl or azepanyl $R^2$ moiety is substituted at its 1-position with —C(O)—Het or —C(O)—Ar; in another embodiment, it is substituted at its 1-position with —S(O)$_2$-Het or —S(O)$_2$—Ar. For example, in certain embodiments, the azetidinyl, pyrrolidinyl, piperidinyl or azepanyl $R^2$ moiety is substituted at its 1-position with an optionally-substituted benzoyl (e.g., substituted with an electron withdrawing group as described above); or with an optionally-substituted nicotinyl, isonicotinyl or picolinyl (e.g., optionally substituted with an electron withdrawing group as described above). In other embodiments, the azetidinyl, pyrrolidinyl, piperidinyl or azepanyl $R^2$ moiety is substituted at its 1-position with an unsubstituted benzoyl; or an unsubstituted nicotinoyl, isonicotinoyl or picolinoyl.

In certain embodiments of the compounds of any of structural formulae (2-I)-(2-XXI), $R^2$ is -Cak-N(R$^9$)-G-R$^{22}$, as described above. For example, in one embodiment of the disclosed compounds, $R^2$ has the structure

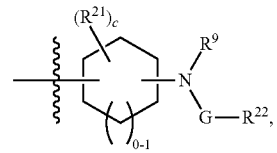

in which c is 0, 1, 2, 3 or 4, and each $R^{21}$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-R$^7$, —($C_0$-$C_6$ alkyl)-NR$^8$R$^9$, —($C_0$-$C_6$ alkyl)-OR$^{10}$, —($C_0$-$C_6$ alkyl)-C(O)R$^{10}$, —($C_0$-$C_6$ alkyl)-S(O)$_{0-2}$R$^{10}$, -halogen, —NO$_2$ and —CN, and two R$^{21}$ on the same carbon optionally combine to form oxo. In certain embodiments of the presently disclosed compounds, each $R^{21}$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-R$^7$, —($C_0$-$C_6$ alkyl)-NR$^8$R$^9$, —($C_0$-$C_6$ alkyl)-OR$^{10}$, ($C_0$-$C_6$ alkyl)-C(O)R$^{10}$, —($C_0$-$C_6$ alkyl)-S(O)$_{0-2}$R$^{10}$, -halogen, —NO$_2$ and —CN and two R$^{21}$ on the same carbon optionally combine to form oxo, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^{21}$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}R^{10}$, -halogen, —NO$_2$ and —CN and two $R^{21}$ on the same carbon optionally combine to form oxo, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. In certain embodiments, c is 1 or 2. In other embodiments, c is 0. In certain embodiments, $R^9$ is H. In certain embodiments, G is a single bond. In certain embodiments of the presently disclosed compounds, each $R^{22}$ is not substituted with an aryl-, heteroaryl-, cycloalkyl- or heterocycloalkyl-containing group. In certain embodiments of the presently disclosed compounds, each $R^{23}$ is not substituted with an aryl-, heteroaryl-, cycloalkyl- or heterocycloalkyl-containing group.

In one embodiment of compounds of any of structural formulae (2-I)-(2-XXI), $R^2$ has the structure

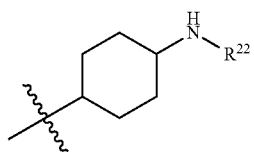

In certain embodiments of the compounds of any of structural formulae (2-I)-(2-XXI), $R^2$ is —($C_2$-$C_8$ alkyl)-N($R^9$)—$R^{24}$ in which one or two carbons of the ($C_2$-$C_8$ alkyl) are optionally replaced by —O— or —N($R^9$)— and $R^{24}$ is —$R^{23}$, -G$R^{23}$ or —C(O)O—($C_1$-$C_6$ alkyl). In certain embodiments, the ($C_2$-$C_8$ alkyl) is unsubstituted and no carbon is replaced by —O— or —N($R^9$)—. For example, in one embodiment, $R^2$ is —CH$_2$—CH$_2$—CH$_2$—N($R^9$)—$R^{24}$ or —CH$_2$—CH$_2$—CH$_2$—CH$_2$—N($R^9$)—$R^{24}$. In other embodiments, the ($C_2$-$C_8$ alkyl) is substituted and/or one or two carbons are replaced by —O— or —N($R^9$)—. For example, in one embodiment, $R^2$ is —CH$_2$—CH$_2$—O—CH$_2$—CH$_2$—N($R^9$)—$R^{24}$; —CH$_2$—CH(CH$_3$)—N($R^9$)—$R^{24}$; or —CH$_2$—CH$_2$—O—CH$_2$—C(O)—N($R^9$)—$R^{24}$. In certain embodiments, $R^9$ is H. In certain embodiments, $R^{24}$ is Ar or Het. In certain embodiments, $R^{24}$ is not substituted with an aryl-, heteroaryl-, cycloalkyl- or heterocycloalkyl-containing group. In certain embodiments, the ($C_2$-$C_8$ alkyl) is a ($C_2$-$C_5$ alkyl).

In the compounds of any of structural formulae (2-I)-(2-XXI), the number of substituents on benzo, pyrido or pyrazino carbons of the ring system represented by "B", w, is 0, 1, 2 or 3. For example, in one embodiment, w is 0, 1 or 2. In another embodiment, such as when the ring system represented by "B" does not include a benzo, pyrido or pyrazino moiety, w is 0. In other embodiments, w is at least 1, and at least one $R^3$ is selected from the group consisting of halo, cyano, —($C_1$-$C_4$ fluoroalkyl), —O—($C_1$-$C_4$ fluoroalkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), —S(O)$_2$O—($C_0$-$C_4$ alkyl), NO$_2$ and —C(O)-Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group. For example, in certain embodiments, at least one $R^3$ is halo (e.g., chloro) or —($C_1$-$C_4$ alkyl) (e.g., methyl, ethyl or propyl). In certain embodiments, an $R^3$ is substituted on the "B" ring system at a benzo, pyrido or pyrazino ring position in the meta position relative to the J moiety.

In certain embodiments of the compounds of any of structural formulae (2-I)-(2-XXI), each $R^3$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —NO$_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl), and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^3$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}R^{10}$, -halogen, —NO$_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. For example, in certain embodiments, each $R^3$ is halo (e.g., chloro) or —($C_1$-$C_4$ alkyl) (e.g., methyl, ethyl or propyl).

In certain embodiments of the compounds of any of structural formulae (2-I)-(2-XXI), w is at least one, and at least one $R^3$ is —$NR^8R^9$. For example, in one embodiment, w is 1. In certain such embodiments, $R^3$ is substituted on the "B" ring system at a benzo, pyrido or pyrazino ring position in the meta position relative to the J moiety.

In other embodiments of the compounds of any of structural formulae (2-I)-(2-XXI), w is at least one, and at least one $R^3$ is —($C_0$-$C_3$ alkyl)-$Y^1$—($C_1$-$C_3$ alkyl)-$Y^2$—($C_0$-$C_3$ alkyl), in which each of $Y^1$ and $Y^2$ is independently L, —O—, —S— or —$NR^9$—. For example, in one embodiment, w is 1. In certain such embodiments, $R^3$ is substituted on the "B" ring system at a benzo, pyrido or pyrazino ring position in the meta position relative to the J moiety. In one particular embodiment, $R^3$ is —CH$_2$—N(CH$_3$)—CH$_2$—C(O)—OCH$_3$.

In the compounds of structural formula (2-I), the number of substituents on non-benzo, non-pyrido, non-pyrazino carbons, k, is 0, 1 or 2. For example, in one embodiment, k is 1. In other embodiments, such as when the ring system represented by "B" contains only benzo, pyridino and/or piperazino carbons, k is 0. In certain embodiments of the compounds of structural formula (2-I), each $R^{14}$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —NO$_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl), and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^{14}$ is independently selected from —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. Each $R^{14}$ can be, for example, halo (e.g., —Cl or —F), cyano unsubstituted —($C_1$-$C_4$ alkyl) (e.g., methyl or ethyl) or unsubstituted —($C_1$-$C_4$ haloakyl) (e.g., difluoromethyl, trifluoromethyl and the like).

In the presently disclosed compounds of any of structural formulae (2-I)-(2-XXI), the number of substituents on the azacycloalkyl ring, x, is 0, 1, 2, 3 or 4. In one embodiment, x is 0, 1, 2 or 3. For example, x can be 0, or can be 1 or 2.

In certain embodiments of the presently disclosed compounds of any of structural formula (2-I)-(2-XXI), two $R^4$ groups combine to form an oxo. The oxo can be bound, for example, at the position alpha to the nitrogen of the azacycloalkyl ring. In other embodiments, no two $R^4$ groups combine to form an oxo.

In certain embodiments of the presently disclosed compounds of any of structural formulae (2-I)-(2-XXI), when x is 4, not all four $R^4$ groups are ($C_1$-$C_6$ alkyl).

In certain embodiments of the presently disclosed compounds of any of structural formulae (2-I)-(2-XXI), each $R^4$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-$NR^8R^9$, ($C_0$-$C_6$ alkyl)-$OR^{10}$, ($C_0$-$C_6$ alkyl)-C(O)$R^{10}$, —($C_0$-$C_6$ alkyl)-S(O)$_{0-2}R^{10}$, -halogen, —$NO_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^4$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, ($C_0$-$C_3$ alkyl)-$OR^{10}$, —($C_0$-$C_3$ alkyl)-C(O)$R^{10}$, —($C_0$-$C_3$ alkyl)-S(O)$_{0-2}R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group.

In certain embodiments, the presently disclosed compounds have the structural formula (2-XXII):

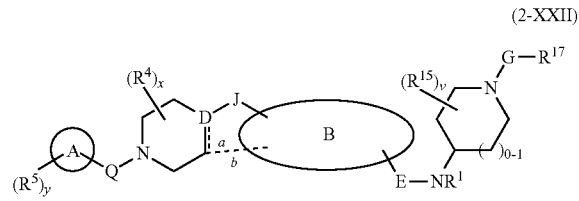

(2-XXII)

in which Q and G are each independently a bond, —$CH_2$—, —C(H)($R^{16}$)—, —C($R^{16}$)$_2$—, L (e.g., —C(O)—$NR^9$— or —$NR^9$—C(O)—) or —S(O)$_2$—; v is 0, 1, 2, 3 or 4; each $R^{15}$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, and two $R^{15}$ on the same carbon optionally combine to form oxo; $R^{17}$ is Het or Ar, and all other variables are defined as described above with reference to any of structural formula (2-I)-(2-XXI). In one embodiment, Q is a single bond. In another embodiment, Q is —$CH_2$—. In other embodiments, Q is —C(O)— or —S(O)$_2$—. In certain embodiments, G is —$CH_2$—. In other embodiments, G is —C(O)— or —S(O)$_2$—. In other embodiments, G is —CH($CH_3$)—. In other embodiments, G is —C(O)—NH—. The above-recited Q and G moieties can be combined in any possible combination. For example, in one embodiment, Q is a single bond and G is —$CH_2$— or —C(O)—. As described above, in certain embodiments, the ring system denoted by "A" is aryl or heteroaryl. In one embodiment, the ring system denoted by "A" is substituted with one or more electron-withdrawing groups as described above. In another embodiment, $R^{17}$ is substituted with one or more electron-withdrawing groups as described above. In certain embodiments, the ring system denoted by "A", $R^{17}$ or both are not substituted with an aryl, heteroaryl, cycloalkyl or heterocycloalkyl-containing group. In certain embodiments, the azacycloalkyl to which -G-$R^{17}$ is bound is a piperidinyl; in other embodiments, it is a pyrrolidinyl.

In the presently disclosed compounds of structural formula (2-XXII), v is 0, 1, 2, 3 or 4. In one embodiment, v is 0, 1, 2 or 3. For example, v can be 0, or can be 1 or 2.

In certain embodiments of the presently disclosed compounds of structural formula (2-XXII), two $R^{15}$ groups combine to form an oxo. The oxo can be bound, for example, at the position alpha relative to the nitrogen of the azacycloalkyl ring. In other embodiments, no two $R^{15}$ groups combine to form an oxo.

In certain embodiments of the presently disclosed compounds of structural formula (2-XXII), when v is 4, not all four $R^{15}$ moieties are ($C_1$-$C_6$ alkyl).

In certain embodiments of the presently disclosed compounds of structural formula (2-XXII), each $R^{15}$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN and two $R^{15}$ on the same carbon optionally combine to form oxo, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^{15}$ is —($C_1$-$C_3$ alkyl), —($C_1$-$C_3$ haloalkyl), —($C_0$-$C_3$ alkyl)-L-$R^7$, —($C_0$-$C_3$ alkyl)-NR$^8$R$^9$, —(C$_0$-C$_3$ alkyl)-OR$^{10}$, —(C$_0$-C$_3$ alkyl)-C(O) R$^{10}$, (C$_0$-C$_3$ alkyl)-S(O)$_{0-2}$R$^{10}$, -halogen, —NO$_2$ and —CN and two R$^{15}$ on the same carbon optionally combine to form oxo, in which each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group. In some embodiments, one R$^{15}$ is —C(O)NR$^9$R$^7$, which can be bound, for example, at a position alpha relative to the piperidine nitrogen, or at the position linked to the —N(R$^1$)—.

In certain embodiments of the presently disclosed compounds of structural formula (2-XXII), R$^{17}$ is an unsubstituted aryl or heteroaryl. In other embodiments, the R$^{17}$ Ar or Het is substituted with 1, 2 or 3 substituents independently selected from —(C$_1$-C$_6$ alkyl), —(C$_1$-C$_6$ haloalkyl) (e.g., difluoromethyl, trifluoromethyl and the like), —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, in which each R$^7$, R$^8$ and R$^{10}$ is independently selected from H, —(C$_1$-C$_6$ alkyl), —(C$_1$-C$_6$ haloalkyl), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl) and —(C$_0$-C$_6$ alkyl)-S(O)$_{0-2}$—(C$_0$-C$_6$ alkyl), and in which no alkyl or haloalkyl is substituted with an aryl-, heteroaryl-, cycloalkyl- or heterocycloalkyl-containing group. For example, in one embodiment, the R$^{17}$ Ar or Het is substituted with 1, 2 or 3 substituents independently selected from —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, (C$_0$-C$_3$ alkyl)-C(O)R$^{10}$, —(C$_0$-C$_3$ alkyl)-S(O)$_{0-2}$R$^{10}$, -halogen, —NO$_2$ and —CN, in which each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group. In certain embodiments, R$^{17}$ is substituted with 1, 2 or 3 substituents selected from halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca. R$^{17}$ can be substituted with, for example, one such substituent, or two such substituents.

In certain embodiments, the presently disclosed compounds have the structural formula (2-XXIII):

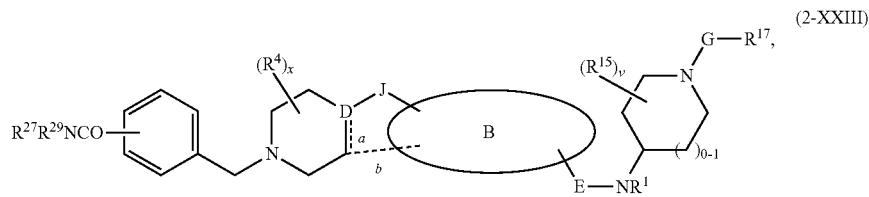

in which R$^{27}$ is selected from H, —(C$_1$-C$_6$ alkyl), —(C$_1$-C$_6$ haloalkyl) (e.g., difluoromethyl, trifluoromethyl and the like), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl)-(C$_0$-C$_6$ alkyl)-S(O)$_{0-2}$—(C$_0$-C$_6$ alkyl), in which no heterocycloalkyl, alkyl or haloalkyl is substituted with an aryl-, heteroaryl-, cycloalkyl- or heterocycloalkyl-containing group, and R$^{29}$ is —H, —(C$_1$-C$_4$ alkyl), —C(O)—(C$_1$-C$_4$ alkyl) or —C(O)—O—(C$_1$-C$_4$ alkyl) in which no (C$_1$-C$_4$ alkyl) is substituted by an aryl, heteroaryl, cycloalkyl or heterocycloalkyl-containing group, or R$^{27}$ and R$^{29}$ together with the nitrogen to which they are bound form Hca, and all other variables are as described above with reference to any of structural formulae (2-I)-(2-XXII). In one embodiment, R$^{27}$ and R$^{29}$ are both H.

In certain embodiments, the presently disclosed compounds have the structural formula (2-XXIV):

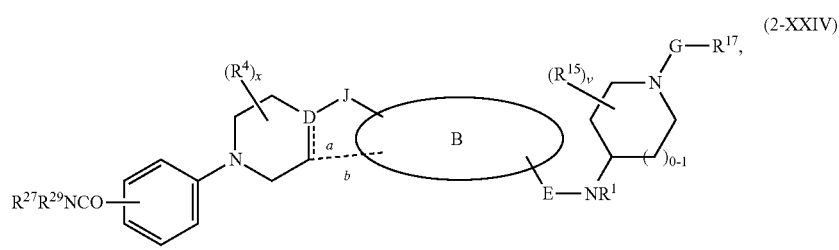

in which R$^{27}$ is selected from H, —(C$_1$-C$_6$ alkyl), —(C$_1$-C$_6$ haloalkyl) (e.g., difluoromethyl, trifluoromethyl and the like), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl)-(C$_0$-C$_6$ alkyl)-S(O)$_{0-2}$—(C$_0$-C$_6$ alkyl), in which no heterocycloalkyl, alkyl or haloalkyl is substituted with an aryl-, heteroaryl-, cycloalkyl- or heterocycloalkyl-containing group, and R$^{29}$ is —H, —(C$_1$-C$_4$ alkyl), —CO—O—(C$_1$-C$_4$ alkyl) or —CO—O—(C$_1$-C$_4$ alkyl) in which no (C$_1$-C$_4$ alkyl) is substituted by an aryl, heteroaryl, cycloalkyl or heterocycloalkyl-containing group, or R$^{27}$ and R$^{29}$ together with the nitrogen to which they are bound form Hca, and all other variables are as described above with reference to any of structural formulae (2-I)-(2-XXII). In one embodiment, R$^{27}$ and R$^{29}$ are both H.

In certain embodiments, the presently disclosed compounds have the structural formula (2-XXV):

(2-XXV)

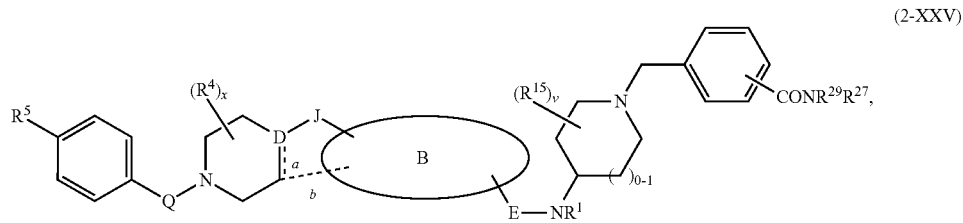

in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —CO—O—($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (2-I)-(2-XXII). In one embodiment, $R^{27}$ and $R^{29}$ are both H.

In certain embodiments, the presently disclosed compounds have the structural formula (2-XXVI):

(2-XXVI)

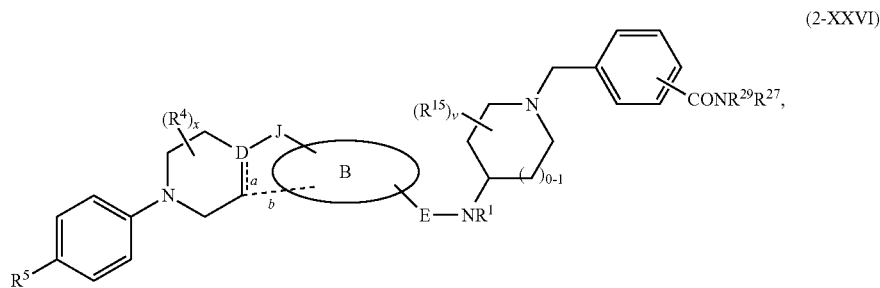

in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —CO—O—($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (2-I)-(2-XXII). In one embodiment, $R^{27}$ and $R^{29}$ are both H.

In certain embodiments, the presently disclosed compounds have the structural formula (2-XXVII):

(2-XXVII)

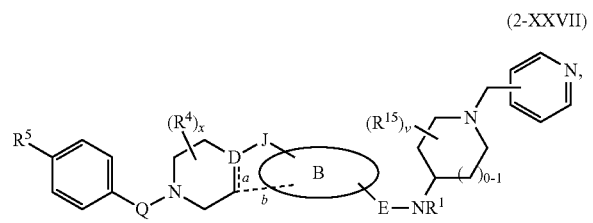

in which all variables are as described above with reference to any of structural formulae (2-I)-(2-XXII).

In certain embodiments, the presently disclosed compounds have the structural formula (2-XXVIII):

(2-XXVIII)

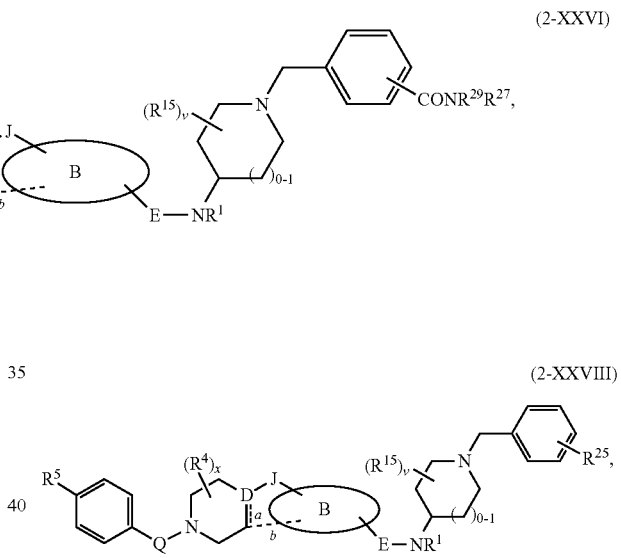

in which $R^{25}$ is selected from halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, in which no alkyl or haloalkyl is substituted by an aryl, heteroaryl, cycloalkyl or heterocycloalkyl-containing group; and all other variables are as described above with reference to any of structural formulae (2-I)-(2-XXII). $R^{25}$ can be, for example, —Cl, —F, cyano, —C(O)$CH_3$, —C(O)OH, —C(O)$NH_2$, trifluoromethyl, difluoromethyl, difluoromethoxy or trifluoromethoxy.

In certain embodiments, the presently disclosed compounds have the structural formula (2-XXIX):

(2-XXIX)

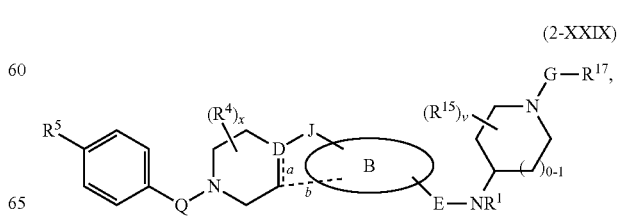

in which G is —C(O)—, —S(O)$_2$— or —C(O)—NH— and all other variables are as described above with reference to any of structural formulae (2-I)-(2-XXII).

In certain embodiments, the presently disclosed compounds have the structural formula (2-XXX):

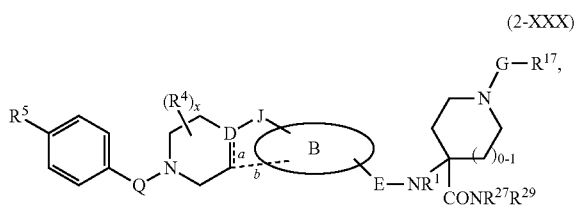

(2-XXX)

in which R$^{27}$ is selected from H, —(C$_1$-C$_6$ alkyl), —(C$_1$-C$_6$ haloalkyl) (e.g., difluoromethyl, trifluoromethyl and the like), —(C$_0$-C$_6$ alkyl)-L-(C$_0$-C$_6$ alkyl), —(C$_0$-C$_6$ alkyl)-NR$^9$ (C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl)-(C$_0$-C$_6$ alkyl)-S(O)$_{0-2}$—(C$_0$-C$_6$ alkyl), in which no heterocycloalkyl, alkyl or haloalkyl is substituted with an aryl-, heteroaryl-, cycloalkyl- or heterocycloalkyl-containing group, and R$^{29}$ is —H, —(C$_1$-C$_4$ alkyl), —CO—O—(C$_1$-C$_4$ alkyl) or —CO—O—(C$_1$-C$_4$ alkyl) in which no (C$_1$-C$_4$ alkyl) is substituted by an aryl, heteroaryl, cycloalkyl or heterocycloalkyl-containing group, or R$^{27}$ and R$^{29}$ together with the nitrogen to which they are bound form Hca, and all other variables are as described above with reference to any of structural formulae (2-I)-(2-XXII). In one embodiment, R$^{27}$ and R$^{29}$ are both H. In some embodiments, the compounds of structural formula (2-XXX) are present as racemic mixtures or scalemic mixtures. In other embodiments, the compounds of structural formula (2-XXX) are present in an enantiomerically-enriched form, for example as a substantially pure stereoisomer.

In certain embodiments, the presently disclosed compounds have the structural formula (2-XXXI):

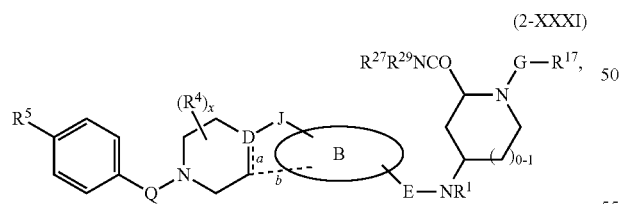

(2-XXXI)

in which R$^{27}$ is selected from H, —(C$_1$-C$_6$ alkyl), —(C$_1$-C$_6$ haloalkyl) (e.g., difluoromethyl, trifluoromethyl and the like), —(C$_0$-C$_6$ alkyl)-L-(C$_0$-C$_6$ alkyl), —(C$_0$-C$_6$ alkyl)-NR$^9$ (C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl)-(C$_0$-C$_6$ alkyl)-S(O)$_{0-2}$—(C$_0$-C$_6$ alkyl), in which no heterocycloalkyl, alkyl or haloalkyl is substituted with an aryl-, heteroaryl-, cycloalkyl- or heterocycloalkyl-containing group, and R$^{29}$ is —H, —(C$_1$-C$_4$ alkyl), —CO—O—(C$_1$-C$_4$ alkyl) or —CO—O—(C$_1$-C$_4$ alkyl) in which no (C$_1$-C$_4$ alkyl) is substituted by an aryl, heteroaryl, cycloalkyl or heterocycloalkyl-containing group, or R$^{27}$ and R$^{29}$ together with the nitrogen to which they are bound form Hca, and all other variables are as described above with reference to any of structural formulae (2-I)-(2-XXII). In one embodiment, R$^{27}$ and R$^{29}$ are both H. In some embodiments, the compounds of structural formula (2-XXXI) are present as racemic mixtures or scalemic mixtures. In other embodiments, the compounds of structural formula (2-XXXI) are present in an enantiomerically-enriched form, for example as a substantially pure stereoisomer.

In certain embodiments, the presently disclosed compounds have the structural formula (2-XXXII):

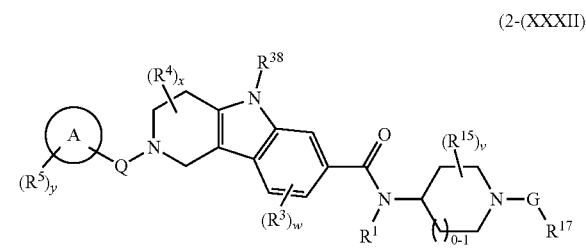

(2-(XXXII)

in which G, v, R$^{15}$ and R$^{17}$ are defined as described above with reference to structural formula (2-XXII), and all other variables are defined as described above with reference to structural formulae (2-I) or (2-II). R$^5$, y, v, R$^{15}$, R$^{17}$, Q, G and the ring denoted by "A" can be defined, for example, as described with reference to any of structural formulae (2-XXIII)-(2-XXXI).

In certain embodiments, the presently disclosed compounds have the structural formula (2-XXXIII):

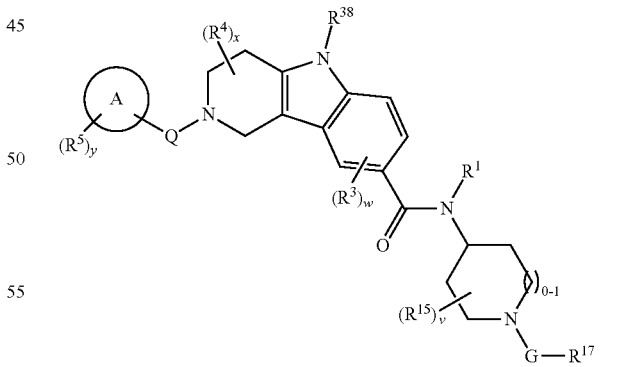

(2-XXXIII)

in which G, v, R$^{15}$ and R$^{17}$ are defined as described above with reference to structural formula (2-XXII), and all other variables are defined as described above with reference to structural formulae (2-I) or (2-III). R$^5$, y, v, R$^{15}$, R$^{17}$, Q, G and the ring denoted by "A" can be defined, for example, as described with reference to any of structural formulae (2-XXIII)-(2-XXXI).

In certain embodiments, the presently disclosed compounds have the structural formula (2-XXXIV):

(2-XXXIV)

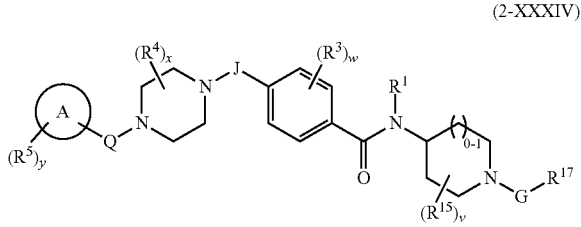

in which J is —CH$_2$—, —CH(R$^{26}$)— or —C(R$^{26}$)$_2$— (e.g., —CH$_2$—), G, v, R$^{15}$ and R$^{17}$ are defined as described above with reference to structural formula (2-XXII), and all other variables are defined as described above with reference to structural formulae (2-I) or (2-IV). R$^5$, y, v, R$^{15}$, R$^{17}$, Q, G and the ring denoted by "A" can be defined, for example, as described with reference to any of structural formulae (2-XXIII)-(2-XXXI).

In certain embodiments, the presently disclosed compounds have the structural formula (2-XXXV):

(2-XXXV)

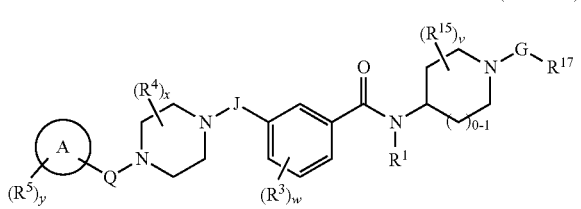

in which J is —CH$_2$—, —CH(R$^{26}$)— or —C(R$^{26}$)$_2$— (e.g., —CH$_2$—), G, v, R$^{15}$ and R$^{17}$ are defined as described above with reference to structural formula (2-XXII), and all other variables are defined as described above with reference to structural formulae (2-I) or (2-V). R$^5$, y, v, R$^{15}$, R$^{17}$, Q, G and the ring denoted by "A" can be defined, for example, as described with reference to any of structural formulae (2-XXIII)-(2-XXXI).

In certain embodiments, the presently disclosed compounds have the structural formula (2-XXXVI):

(2-XXXVI)

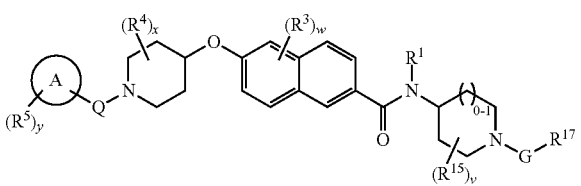

in which G, v, R$^{15}$ and R$^{17}$ are defined as described above with reference to structural formula (2-XXII), and all other variables are defined as described above with reference to structural formulae (2-I) or (2-VI). R$^5$, y, v, R$^{15}$, R$^{17}$, Q, G and the ring denoted by "A" can be defined, for example, as described with reference to any of structural formulae (2-XXIII)-(2-XXXI).

In certain embodiments, the presently disclosed compounds have the structural formula (2-XXXVII):

(2-XXXVII)

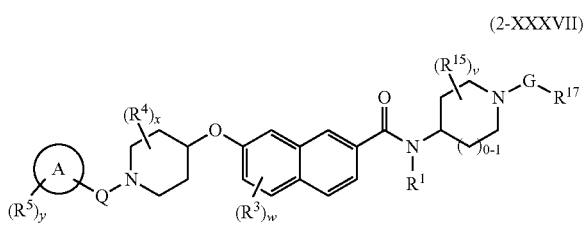

in which G, v, R$^{15}$ and R$^{17}$ are defined as described above with reference to structural formula (2-XXII), and all other variables are defined as described above with reference to structural formulae (2-I) or (2-VII). R$^5$, y, v, R$^{15}$, R$^{17}$, Q, G and the ring denoted by "A" can be defined, for example, as described with reference to any of structural formulae (2-XXIII)-(2-XXXI).

In certain embodiments, the presently disclosed compounds have the structural formula (2-XXXVIII):

(2-XXXVIII)

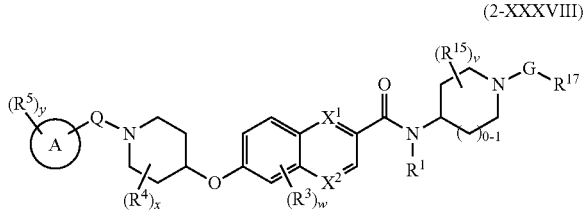

in which one of X$^1$ and X$^2$ is N, and the other is a carbon; G, v, R$^{15}$ and R$^{17}$ are defined as described above with reference to structural formula (2-XXII), and all other variables are defined as described above with reference to structural formulae (2-I) or (2-VIII). R$^5$, y, v, R$^{15}$, R$^{17}$, Q, G and the ring denoted by "A" can be defined, for example, as described with reference to any of structural formulae (2-XXIII)-(2-XXXI). In one embodiment, for example, X$^1$ is N and X$^2$ is a carbon. In another embodiment, X$^1$ is a carbon, and X$^2$ is N.

In certain embodiments, the presently disclosed compounds have the structural formula (2-XXXIX):

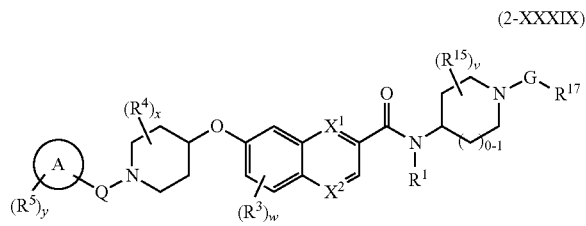

(2-XXXIX)

in which in which one of $X^1$ and $X^2$ is N, and the other is a carbon; G, v, $R^{15}$ and $R^{17}$ are defined as described above with reference to structural formula (2-XXII), and all other variables are defined as described above with reference to structural formulae (2-I) or (2-IX). $R^5$, y, v, $R^{15}$, $R^{17}$, Q, G and the ring denoted by "A" can be defined, for example, as described with reference to any of structural formulae (2-XXIII)-(2-XXXI). In one embodiment, for example, $X^1$ is N and $X^2$ is a carbon. In another embodiment, $X^1$ is a carbon, and $X^2$ is N.

In certain embodiments, the presently disclosed compounds have the structural formula (2-XL):

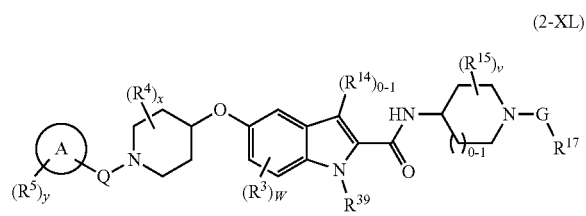

(2-XL)

in which G, v, $R^{15}$ and $R^{17}$ are defined as described above with reference to structural formula (2-XXII), and all other variables are defined as described above with reference to structural formulae (2-I) or (2-X). $R^5$, y, v, $R^{15}$, $R^{17}$, Q, G and the ring denoted by "A" can be defined, for example, as described with reference to any of structural formulae (2-XXIII)-(2-XXXI). In certain embodiments, one $R^{14}$ is substituted on the pyrrolo carbon. $R^{14}$ can be, for example, as described above with reference to structural formula (2-I). For example, in one embodiment $R^{14}$ is halo (e.g., —Cl or —F), cyano unsubstituted —($C_1$-$C_4$ alkyl) (e.g., methyl or ethyl), unsubstituted —($C_1$-$C_4$ haloakyl) (e.g., difluoromethyl, trifluoromethyl and the like). In other embodiments, no $R^{14}$ is substituted on the pyrrolo carbon.

In certain embodiments, the presently disclosed compounds have the structural formula (2-XLI):

in which G, v, $R^{15}$ and $R^{17}$ are defined as described above with reference to structural formula (2-XXII), and all other variables are defined as described above with reference to structural formulae (2-I) or (2-XI). $R^5$, y, v, $R^{15}$, $R^{17}$, Q, G and the ring denoted by "A" can be defined, for example, as described with reference to any of structural formulae (2-XXIII)-(2-XXXI). In certain embodiments, one $R^{14}$ is substituted on the pyrrolo carbon. $R^{14}$ can be, for example, as described above with reference to structural formula (2-I). For example, in one embodiment $R^{14}$ is halo (e.g., —Cl or —F), cyano unsubstituted —($C_1$-$C_4$ alkyl) (e.g., methyl or ethyl), unsubstituted —($C_1$-$C_4$ haloakyl) (e.g., difluoromethyl, trifluoromethyl and the like). In other embodiments, no $R^{14}$ is substituted on the pyrrolo carbon.

In certain embodiments of compounds having structural formulae (2-XXII)-(2-XLI), the

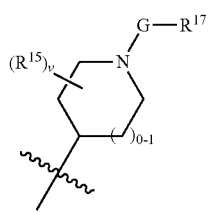

moiety has the structure

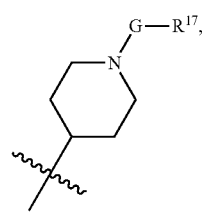

in which G is —$CH_2$—, —$CH(CH_3)$—, —C(O)—, —$S(O)_2$— or —C(O)—NH—. For example, in one embodiment, G is —$CH_2$—. In another embodiment, G is —C(O)— or —$S(O)_2$—. In another embodiment, G is —C(O)—NH—.

In other embodiments of compounds having structural formulae (2-XXII)-(2-XLI), the

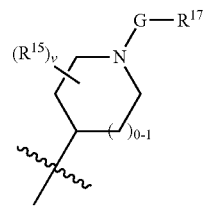

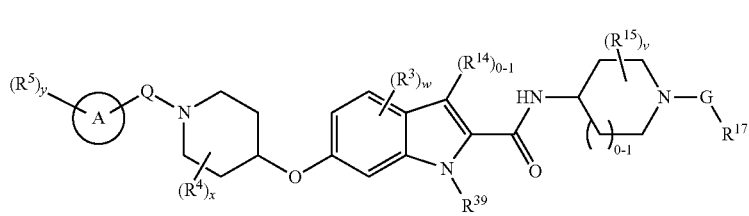

(2-XLI)

moiety has the structure

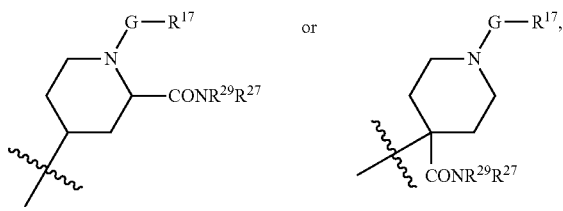

in which G is —$CH_2$—, —C(O)—, —$S(O)_2$— or —C(O)—NH—, $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-$S(O)_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —CO—($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca. In such embodiments, the compounds can be present as racemic mixtures or scalemic mixtures, or in an enantiomerically-enriched form, for example as a substantially pure stereoisomer.

In other embodiments of compounds having structural formulae (2-XXII)-(2-XLI), the

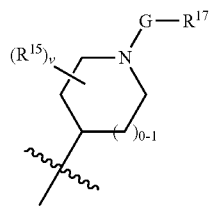

moiety has the structure

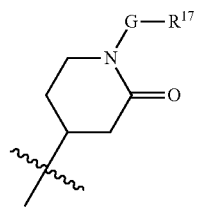

in which G is —$CH_2$—, —C(O)—, —$S(O)_2$— or —C(O)—NH—.

In certain embodiments of compounds having structural formulae (2-XXII)-(2-XLI), the $R^{17}$ moiety has the structure

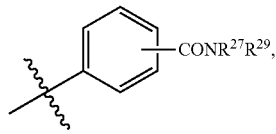

in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-$S(O)_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —CO—($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca.

In certain embodiments of compounds having structural formulae (2-XXII)-(2-XLI), w is 1, and $R^3$ is —$NR^8R^9$. In certain such embodiments, $R^3$ is substituted at a benzo, pyrido or pyrazino ring position in the meta position relative to the J moiety.

In other embodiments of compounds having structural formulae (2-XXII)-(2-XLI), w is 1, and $R^3$ is —($C_0$-$C_3$ alkyl)-$Y^1$—($C_1$-$C_3$ alkyl)-$Y^2$—($C_0$-$C_3$ alkyl), in which each of $Y^1$ and $Y^2$ is independently L, —O—, —S— or —$NR^9$—. In certain such embodiments, $R^3$ is substituted at a benzo, pyrido or pyrazino ring position in the meta position relative to the J moiety.

In certain embodiments described above, each $R^{27}$ is selected from —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-$S(O)_{0-2}R^{10}$, -halogen, —$NO_2$ and —CN and two $R^{21}$ on the same carbon optionally combine to form oxo, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-$S(O)_{0-2}$—($C_0$-$C_2$ alkyl), and in which no alkyl or haloalkyl is substituted with an aryl-, heteroaryl-, cycloalkyl- or heterocycloalkyl-containing group, and each $R^{29}$ is H, methyl or ethyl, or $R^{27}$ and $R^{29}$ together with the nitrogen to which they are bound form Hca.

In certain embodiments of compounds having structural formulae (2-XXII)-(2-XLI), at least one $R^5$ moiety is a haloalkyl group, and in exemplary embodiments of these formulae the

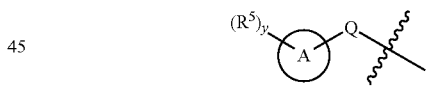

moiety is p-(trifluoromethyl)phenyl. By way of further illustration, certain exemplary compounds including such

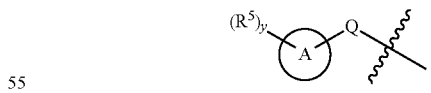

moieties have structural formula (2-XLII) or (2-XLIII):

(2-XLII)

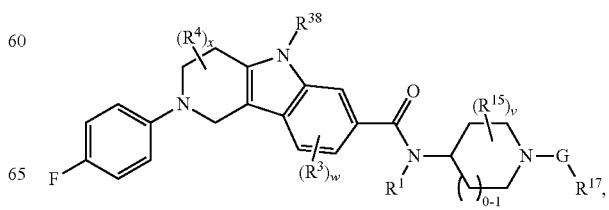

(2-XLIII)

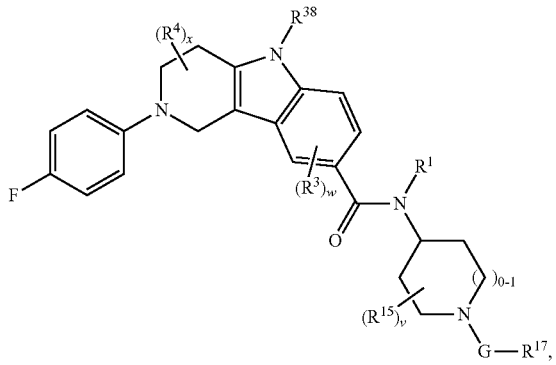

in which all variables are as described above with reference to structural formulae (2-XXXII) or (2-XXXIII).

In one embodiment, the presently disclosed compounds have the structural formula (2-XLIV):

(2-XLIV)

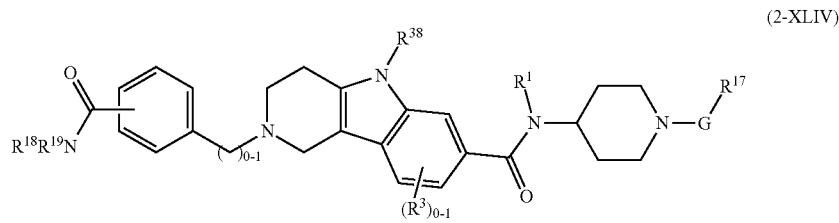

in which G, $R^1$, $R^3$, $R^{17}$ and $R^{38}$ are as described above with reference to any of structural formulae (2-I), (2-II), (2-XII) or (2-XXII), $R^{18}$ is H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), in which no alkyl or haloalkyl is substituted with an aryl-, heteroaryl-, cycloalkyl- or heterocycloalkyl-containing group and $R^{19}$ is —H, —($C_1$-$C_4$ alkyl), —CO—($C_1$-$C_4$ alkyl) or —CO—O—($C_1$-$C_4$ alkyl) in which no alkyl is substituted by an aryl, heteroaryl, cycloalkyl or heterocycloalkyl-containing group, or $R^{18}$ and $R^{19}$ together with the nitrogen to which they are bound form Hca. In one embodiment, $R^{18}$ and $R^{19}$ are both H.

In one embodiment, the presently disclosed compounds have the structural formula (2-XLV):

(2-XLV)

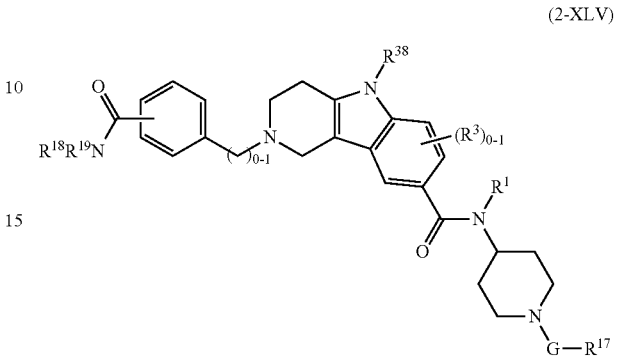

in which G, $R^1$, $R^3$, $R^{17}$ and $R^{38}$ are as described above with reference to any of structural formulae (2-I), (2-III), (2-XIII) and (2-XXII), and $R^{18}$ and $R^{19}$ are defined as described above with reference to structural formula (2-XLIV).

In another embodiment, the presently disclosed compounds have the structural formula (2-XLVI):

(2-XLVI)

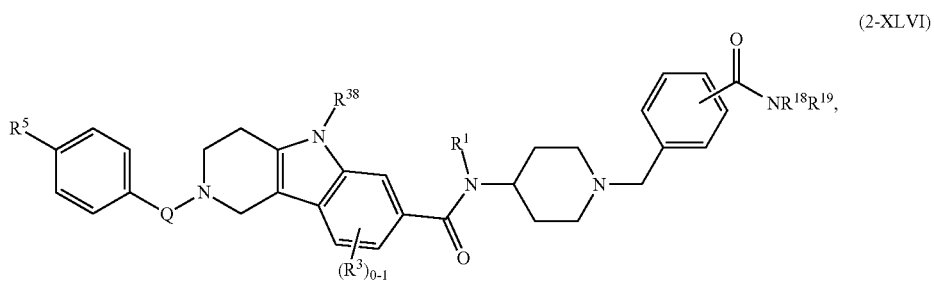

in which Q, $R^1$, $R^3$, $R^5$ and $R^{38}$ are defined as described above with reference to any of structural formulae (2-I), (2-II), (2-XII) and (2-XXII), and $R^{18}$ and $R^{19}$ are defined as described above with reference to structural formula (2-XLIV).

In another embodiment, the presently disclosed compounds have the structural formula (2-XLVII):

(2-XLVII)

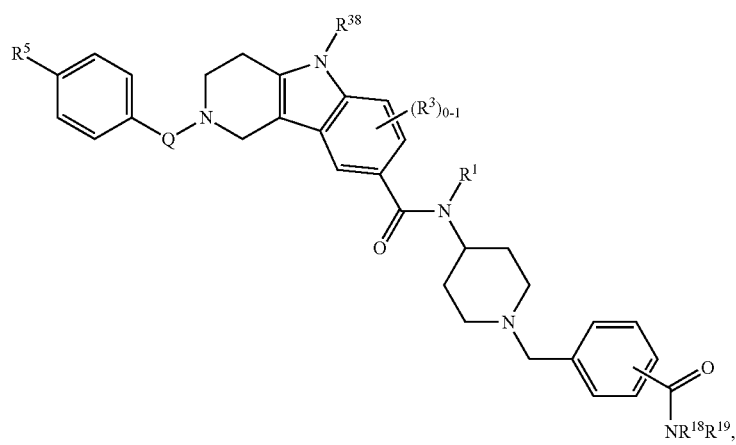

in which Q, $R^1$, $R^3$, $R^5$ and $R^{38}$ are defined as described above with reference to any of structural formulae (2-I), (2-III), (2-XIII) and (2-XXII), and $R^{18}$ and $R^{19}$ are defined as described above with reference to structural formula (2-XLIV).

In another embodiment, the presently disclosed compounds have the structural formula (2-XLVIII):

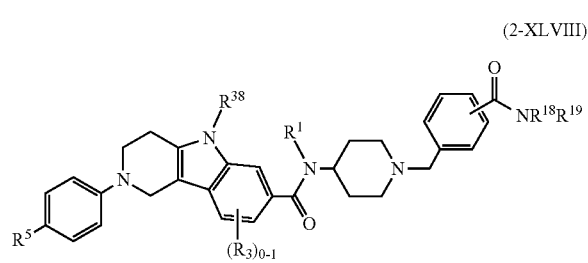

(2-XLVIII)

in which $R^1$, $R^3$, $R^5$ and $R^{38}$ are defined as described above with reference to any of structural formulae (2-I), (2-II), (2-XII) and (2-XXII), and $R^{18}$ and $R^{19}$ are defined as described above with reference to structural formula (2-XLIV).

In another embodiment, the presently disclosed compounds have the structural formula (2-XLIX):

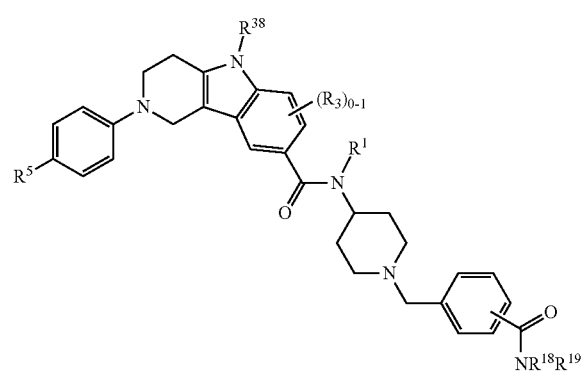

(2-XLIX)

in which $R^1$, $R^3$, $R^5$ and $R^{38}$ are defined as described above with reference to any of structural formulae (2-I), (2-III), (2-XIII) and (2-XXII), and $R^{18}$ and $R^{19}$ are defined as described above with reference to structural formula (2-XLIV).

In compounds according to any of structural formulae (2-I), (2-IV)-(2-$X^1$) and (2-XIV)-(2-XXI), T and $R^2$ can be defined as described above with reference to structural formulae (2-XLIV)-(2-XLIX).

In certain embodiments, the presently disclosed compounds have the structural formula (2-L):

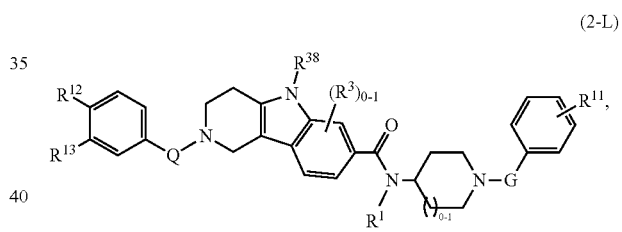

(2-L)

in which Q is —$CH_2$—, —C(O)— or a single bond; G is a single bond, —$CH_2$—, —C(O)—, —S(O)$_2$— or —C(O)—NH—; $R^1$, $R^3$ and $R^{38}$ are as described above with reference to any of structural formulae (2-I), (2-II), (2-XII) and (2-XXII); and $R^{11}$, $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, no $R^3$ is substituted on the benzo moiety. In another embodiment, one $R^3$ (e.g., —Cl, —F, —$CH_3$, —$C_2H_5$, —$C_3H_7$) is substituted on the benzo moiety.

In certain embodiments, the presently disclosed compounds have the structural formula (2-LI):

(2-LI)

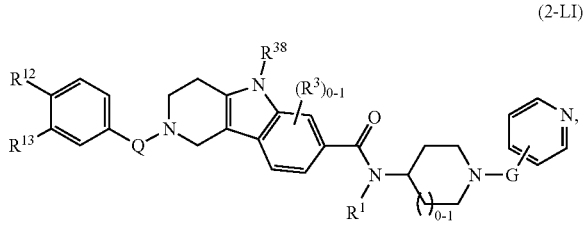

in which Q is —CH$_2$—, —C(O)— or a single bond; G is a single bond, —CH$_2$—, —C(O)—, —S(O)$_2$— or —C(O)—NH—; R$^1$, R$^3$ and R$^{38}$ are as described above with reference to any of structural formulae (2-I), (2-II), (2-XII) and (2-XXII); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyrido nitrogen is disposed in the para position relative to the G moiety; in another embodiment, the pyrido nitrogen is disposed in the meta position relative to the G moiety. In one embodiment, no R$^3$ is substituted on the benzo moiety. In another embodiment, one R$^3$ (e.g., —Cl, —F, —CH$_3$, —C$_2$H$_5$, —C$_3$H$_7$) is substituted on the benzo moiety.

In certain embodiments, the presently disclosed compounds have the structural formula (2-LII):

(2-LII)

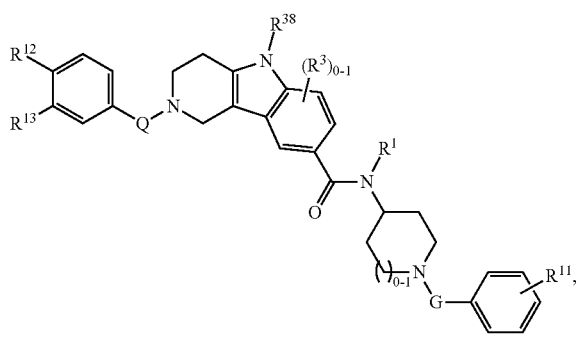

in which Q is —CH$_2$—, —C(O)— or a single bond; G is a single bond, —CH$_2$—, —C(O)—, —S(O)$_2$— or —C(O)—NH—; R$^1$, R$^3$ and R$^{38}$ are as described above with reference to any of structural formulae (2-I), (2 III) (2-XIII) and (2-XXII); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, no R$^3$ is substituted on the benzo moiety. In another embodiment, one R$^3$ (e.g., —Cl, —F, —CH$_3$, —C$_2$H$_5$, —C$_3$H$_7$) is substituted on the benzo moiety.

In certain embodiments, the presently disclosed compounds have the structural formula (2-LIII):

(2-LIII)

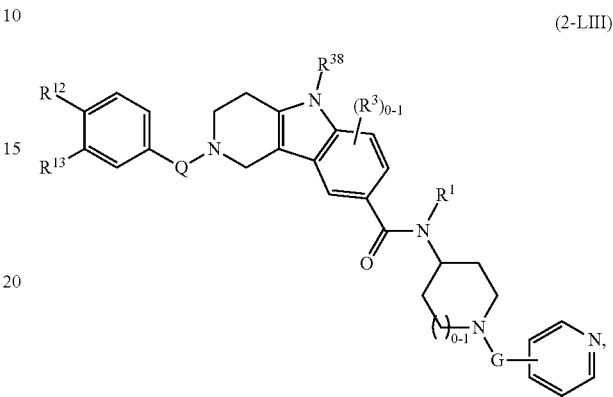

in which Q is —CH$_2$—, —C(O)— or a single bond; G is a single bond, —CH$_2$—, —C(O)—, —S(O)$_2$— or —C(O)—NH—; R$^1$, R$^3$ and R$^{38}$ are as described above with reference to any of structural formulae (2-I), (2-III), (2-XIII) and (2-XXII); R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyrido nitrogen is disposed in the para position relative to the G moiety; in another embodiment, the pyrido nitrogen is disposed in the meta position relative to the G moiety. In one embodiment, no R$^3$ is substituted on the benzo moiety. In another embodiment, one R$^3$ (e.g., —Cl, —F, —CH$_3$, —C$_2$H$_5$, —C$_3$H$_7$) is substituted on the benzo moiety.

In one embodiment, the presently disclosed compounds have the structural formula (2-LIV):

(2-LIV)

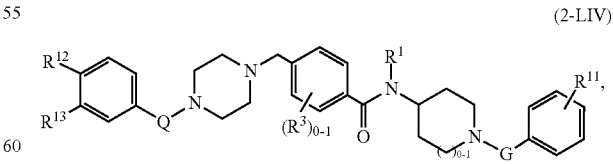

in which Q is —CH$_2$—, —C(O)— or a single bond; G is a single bond, —CH$_2$—, —C(O)—, —S(O)$_2$— or —C(O)—NH—; R$^1$ and R$^3$ are as described above with respect to any of structural formulae (2-I), (2-IV), (2 XIV) and (2-XXII);

and $R^{11}$, $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, no $R^3$ is substituted on the central phenyl moiety. In another embodiment, one $R^3$ (e.g., —Cl, —F, —$CH_3$, —$C_2H_5$, —$C_3H_7$) is substituted on the central phenyl moiety.

In certain embodiments, the presently disclosed compounds have the structural formula (2-LV):

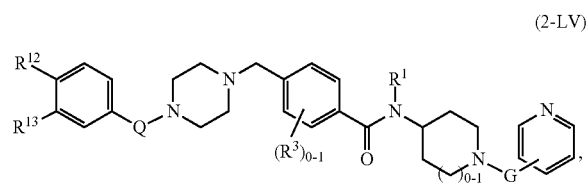

(2-LV)

in which Q is —$CH_2$—, —C(O)— or a single bond; G is a single bond, —$CH_2$—, —C(O)—, —S(O)$_2$— or —C(O)—NH—; $R^1$ and $R^3$ are as described above with reference to any of structural formulae (2-I), (2-IV), (2-XIV) and (2-XXII); and $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H. In one embodiment, the pyrido nitrogen is disposed in the para position relative to the G moiety; in another embodiment, the pyrido nitrogen is disposed in the meta position relative to the G moiety. In one embodiment, no $R^3$ is substituted on the central phenyl moiety. In another embodiment, one $R^3$ (e.g., —Cl, —F, —$CH_3$, —$C_2H_5$, —$C_3H_7$) is substituted on the central phenyl moiety.

In certain embodiments, the presently disclosed compounds have the structural formula (2-LVI):

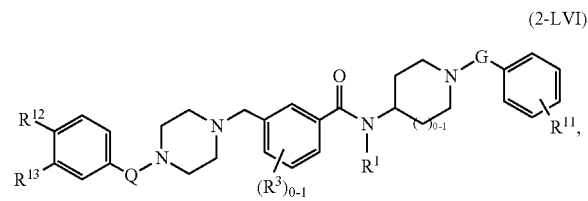

(2-LVI)

in which Q is —$CH_2$—, —C(O)— or a single bond; G is a single bond, —$CH_2$—, —C(O)—, —S(O)$_2$— or —C(O)—NH—; $R^1$ and $R^3$ are as described above with respect to any of structural formulae (2-I), (2-V), (2-XV) and (2-XXII); and $R^{11}$, $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, no $R^3$ is substituted on the central phenyl moiety. In another embodiment, one $R^3$ (e.g., —Cl, —F, —$CH_3$, —$C_2H_5$, —$C_3H_7$) is substituted on the central phenyl moiety.

In certain embodiments, the presently disclosed compounds have the structural formula (2-LVII):

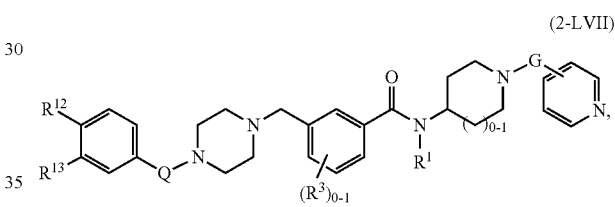

(2-LVII)

in which Q is —$CH_2$—, —C(O)— or a single bond; G is a single bond, —$CH_2$—, —C(O)—, —S(O)$_2$— or —C(O)—NH—; $R^1$ and $R^3$ are as described above with reference to any of structural formulae (2-I), (2-V), (2-XV) and (2-XXII); and $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H. In one embodiment, the pyrido nitrogen is disposed in the para position relative to the G moiety; in another embodiment, the pyrido nitrogen is disposed in the meta position relative to the G moiety. In one embodiment, no $R^3$ is substituted on the central phenyl moiety. In another embodiment, one $R^3$ (e.g., —Cl, —F, —$CH_3$, —$C_2H_5$, —$C_3H_7$) is substituted on the central phenyl moiety.

In certain embodiments, the presently disclosed compounds have the structural formula (2-LVIII):

(2-LVIII)

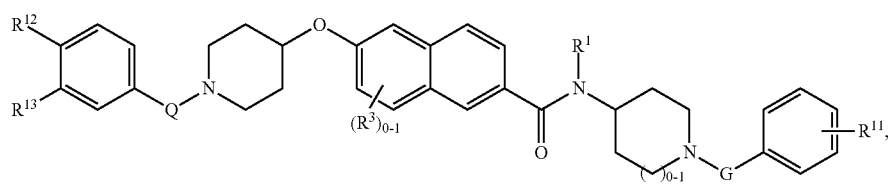

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (2-I), (2-VI), (2-XVI) and (2-XXII); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, no R$^3$ is substituted on the naphthyl moiety. In another embodiment, one R$^3$ (e.g., —Cl, —F, —CH$_3$, —C$_2$H$_5$, —C$_3$H$_7$) is substituted on the naphthyl moiety.

In certain embodiments, the presently disclosed compounds have the structural formula (2-LIX):

(2-LIX)

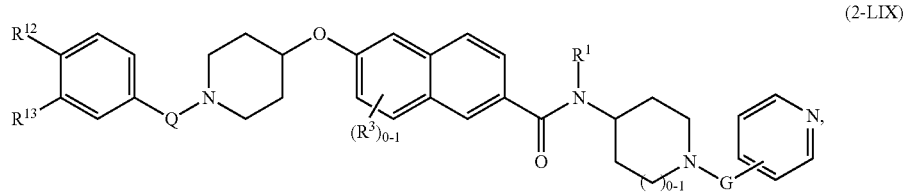

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to structural formulae (2-I), (2-VI), (2-XVI) and (2-XXII); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyrido nitrogen is disposed in the para position relative to the G moiety; in another embodiment, the pyrido nitrogen is disposed in the meta position relative to the G moiety. In one embodiment, no R$^3$ is substituted on the naphthyl moiety. In another embodiment, one R$^3$ (e.g., —Cl, —F, —CH$_3$, —C$_2$H$_5$, —C$_3$H$_7$) is substituted on the naphthyl moiety.

In certain embodiments, the presently disclosed compounds have the structural formula (2-LX):

(2-LX)

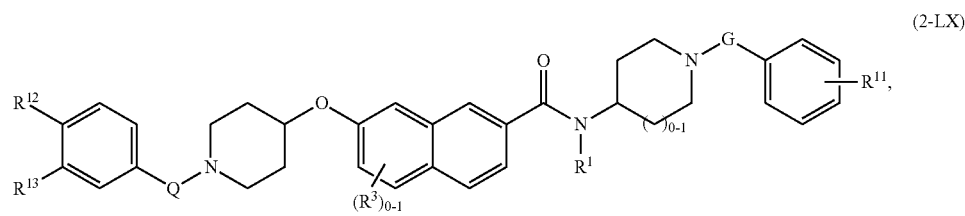

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (2-I), (2-VII), (2-XVII) and (2-XXII); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, no R$^3$ is substituted on the naphthyl moiety. In another embodiment, one R$^3$ (e.g., —Cl, —F, —CH$_3$, —C$_2$H$_5$, —C$_3$H$_7$) is substituted on the naphthyl moiety.

In certain embodiments, the presently disclosed compounds have the structural formula (2-LXI):

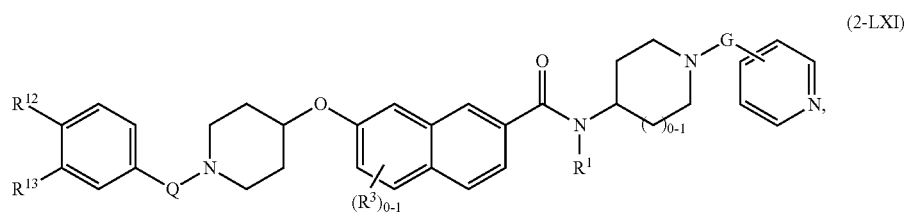

(2-LXI)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to structural formulae (2-I), (2-VII), (2-XVII) and (2-XXII); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyrido nitrogen is disposed in the para position relative to the G moiety; in another embodiment, the pyrido nitrogen is disposed in the meta position relative to the G moiety. In one embodiment, no R$^3$ is substituted on the naphthyl moiety. In another embodiment, one R$^3$ (e.g., —Cl, —F, —CH$_3$, —C$_2$H$_5$, —C$_3$H$_7$) is substituted on the naphthyl moiety.

In certain embodiments, the presently disclosed compounds have the structural formula (2-LXII):

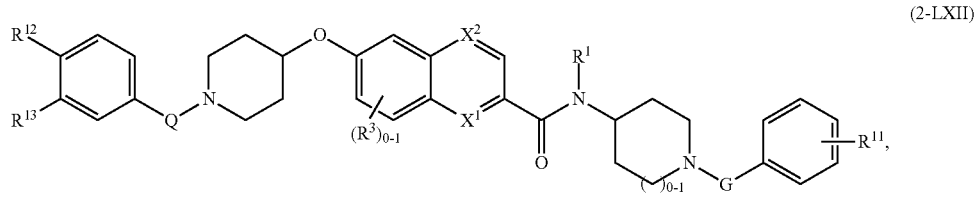

(2-LXII)

in which one of $X^1$ and $X^2$ is N and the other is a carbon; Q is —$CH_2$—, —C(O)— or a single bond; G is a single bond, —$CH_2$—, —C(O)—, —$S(O)_2$— or —C(O)—NH—; $R^1$ and $R^3$ are as described above with reference to any of structural formulae (2-I), (2-VIII), (2-XVIII) and (2-XXII); and $R^{11}$, $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, no $R^3$ is substituted on the quinolinyl moiety. In another embodiment, one $R^3$ (e.g., —Cl, —F, —$CH_3$, —$C_2H_5$, —$C_3H_7$) is substituted on the quinolinyl moiety.

In certain embodiments, the presently disclosed compounds have the structural formula (2-LXIII):

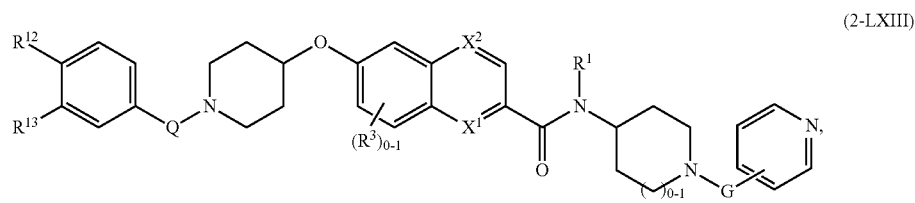

(2-LXIII)

in which one of $X^1$ and $X^2$ is N and the other is a carbon; Q is —$CH_2$—, —C(O)— or a single bond; G is a single bond, —$CH_2$—, —C(O)—, —$S(O)_2$— or —C(O)—NH—; $R^1$ and $R^3$ are as described above with reference to structural formulae (2-I), (2-VIII), (2-XVIII) and (2-XXII); and $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H. In one embodiment, the pyrido nitrogen is disposed in the para position relative to the G moiety; in another embodiment, the pyrido nitrogen is disposed in the meta position relative to the G moiety. In one embodiment, no $R^3$ is substituted on the quinolinyl moiety. In another embodiment, one $R^3$ (e.g., —Cl, —F, —$CH_3$, —$C_2H_5$, —$C_3H_7$) is substituted on the quinolinyl moiety.

In certain embodiments, the presently disclosed compounds have the structural formula (2-LXIV):

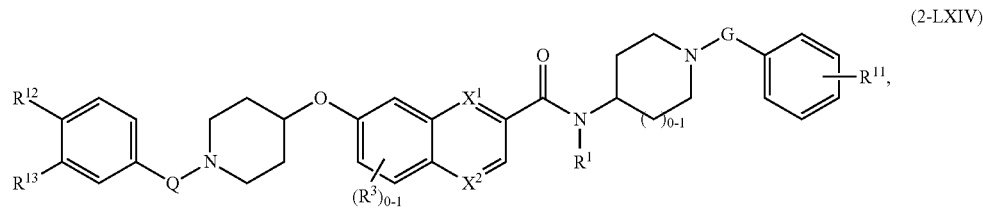

(2-LXIV)

in which one of $X^1$ and $X^2$ is N and the other is a carbon; Q is —$CH_2$—, —C(O)— or a single bond; G is a single bond, —$CH_2$—, —C(O)—, —$S(O)_2$— or —C(O)—NH—; $R^1$ and $R^3$ are as described above with reference to any of structural formulae (2-I), (2-IX), (2-XIX) and (2-XXII); and $R^{11}$, $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, no $R^3$ is substituted on the quinolinyl moiety. In another embodiment, one $R^3$ (e.g., —Cl, —F, —$CH_3$, —$C_2H_5$, —$C_3H_7$) is substituted on the quinolinyl moiety.

In certain embodiments, the presently disclosed compounds have the structural formula (2-LXV):

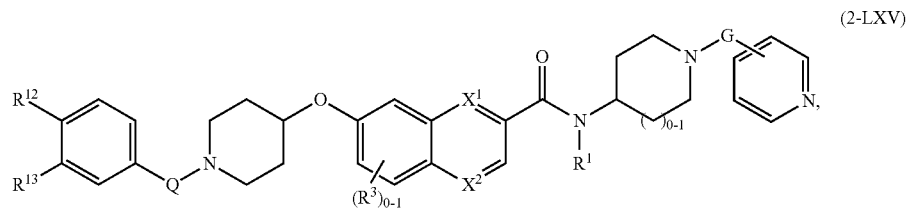

(2-LXV)

in which one of $X^1$ and $X^2$ is N and the other is a carbon; Q is —$CH_2$—, —C(O)— or a single bond; G is a single bond, —$CH_2$—, —C(O)—, —$S(O)_2$— or —C(O)—NH—; $R^1$ and $R^3$ are as described above with reference to structural formulae (2-I), (2-IX), (2-XIX) and (2-XXII); and $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H. In one embodiment, the pyrido nitrogen is disposed in the para position relative to the G moiety; in another embodiment, the pyrido nitrogen is disposed in the meta position relative to the G moiety. In one embodiment, no $R^3$ is substituted on the quinolinyl moiety. In another embodiment, one $R^3$ (e.g., —Cl, —F, —$CH_3$, —$C_2H_5$, —$C_3H_7$) is substituted on the quinolinyl moiety.

In certain embodiments, the presently disclosed compounds have the structural formula (2-LXVI):

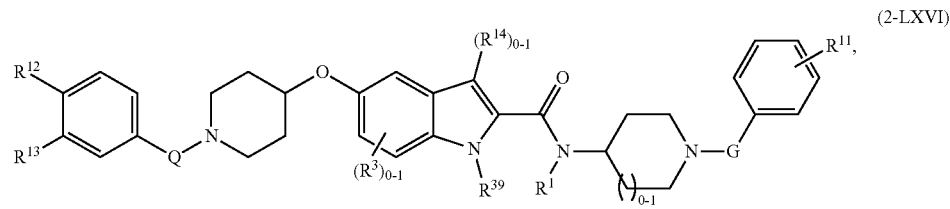

(2-LXVI)

in which Q is —CH$_2$—, —C(O)— or a single bond; G is a single bond, —CH$_2$—, —C(O)—, —S(O)$_2$— or —C(O)—NH—; R$^1$, R$^3$ and R$^{39}$ are as described above with reference to any of structural formulae (2-I), (2-X), (2-XX) and (2-XXII); R$^{14}$ is as described above with reference to structural formulae (2-I), (2-X), (2-XX) and (2-XXII) (e.g., absent, methyl or halo); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, no R$^3$ is substituted on the benzo moiety. In another embodiment, one R$^3$ (e.g., —Cl, —F, —CH$_3$, —C$_2$H$_5$, —C$_3$H$_7$) is substituted on the benzo moiety.

In certain embodiments, the presently disclosed compounds have the structural formula (2-LXVII):

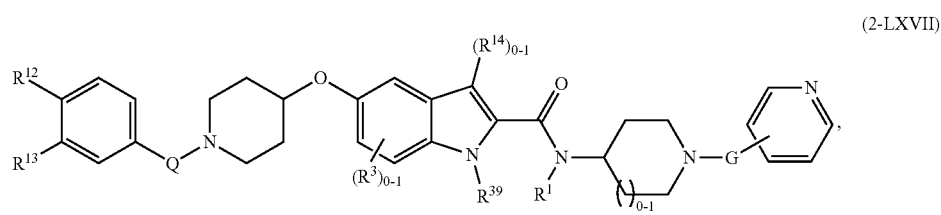

(2-LXVII)

in which Q is —CH$_2$—, —C(O)— or a single bond; G is a single bond, —CH$_2$—, —C(O)—, —S(O)$_2$— or —C(O)—NH—; R$^1$, R$^3$ and R$^{39}$ are as described above with reference to any of structural formulae (2-I), (2-X), (2-XX) and (2-XXII); R$^{14}$ is as described above with reference to structural formulae (2-I), (2-X), (2-XX) and (2-XXII) (e.g., absent, methyl or halo); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyrido nitrogen is disposed in the para position relative to the G moiety; in another embodiment, the pyrido nitrogen is disposed in the meta position relative to the G moiety. In one embodiment, no R$^3$ is substituted on the benzo moiety. In another embodiment, one R$^3$ (e.g., —Cl, —F, —CH$_3$, —C$_2$H$_5$, —C$_3$H$_7$) is substituted on the benzo moiety.

In certain embodiments, the presently disclosed compounds have the structural formula (2-LXVIII):

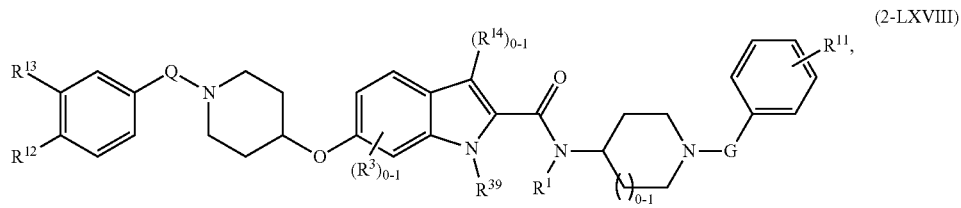

(2-LXVIII)

in which Q is —CH₂—, —C(O)— or a single bond; G is a single bond, —CH₂—, —C(O)—, —S(O)₂— or —C(O)—NH—; $R^1$, $R^3$ and $R^{39}$ are as described above with reference to any of structural formulae (2-I), (2-XI), (2-XXI) and (2-XXII); $R^{14}$ is as described above with reference to structural formulae (2-I), (2-XI), (2-XXI) and (2-XXII) (e.g., absent, methyl or halo); and $R^{11}$, $R^{12}$ and $R^{13}$ are independently selected from H, halo, cyano, —(C₁-C₄ haloalkyl), —O—(C₁-C₄ haloalkyl), —(C₁-C₄ alkyl), —O—(C₁-C₄ alkyl), —C(O)—(C₀-C₄ alkyl), —C(O)O—(C₀-C₄ alkyl), —C(O)N(C₀-C₄ alkyl)(C₀-C₄ alkyl), NO₂ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, no $R^3$ is substituted on the benzo moiety. In another embodiment, one $R^3$ (e.g., —Cl, —F, —CH₃, —C₂H₅, —C₃H₇) is substituted on the benzo moiety.

In certain embodiments, the presently disclosed compounds have the structural formula (2-LXIX):

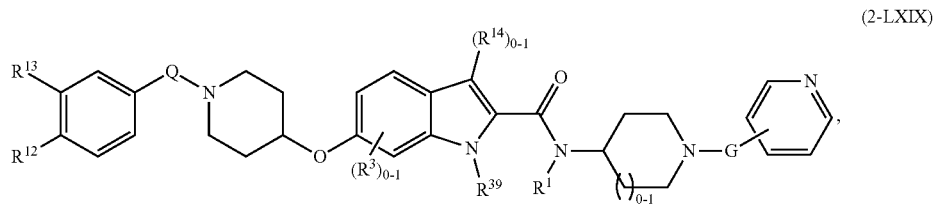

(2-LXIX)

in which Q is —CH₂—, —C(O)— or a single bond; G is a single bond, —CH₂—, —C(O)—, —S(O)₂— or —C(O)—NH—; $R^1$, $R^3$ and $R^{39}$ are as described above with reference to any of structural formulae (2-I), (2-X), (2-XX) and (2-XXII); $R^{14}$ is as described above with reference to structural formulae (2-I), (2-X), (2-XX) and (2-XXII) (e.g., absent, methyl or halo); and $R^{12}$ and $R^{13}$ are independently selected from H, halo, cyano, —(C₁-C₄ haloalkyl), —O—(C₁-C₄ haloalkyl), —(C₁-C₄ alkyl), —O—(C₁-C₄ alkyl), —C(O)—(C₀-C₄ alkyl), —C(O)O—(C₀-C₄ alkyl), —C(O)N(C₀-C₄ alkyl)(C₀-C₄ alkyl), NO₂ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H. In one embodiment, the pyrido nitrogen is disposed in the para position relative to the G moiety; in another embodiment, the pyrido nitrogen is disposed in the meta position relative to the G moiety. In one embodiment, no $R^3$ is substituted on the benzo moiety. In another embodiment, one $R^3$ (e.g., —Cl, —F, —CH₃, —C₂H₅, —C₃H₇) is substituted on the benzo moiety.

Examples of compounds according to structural formula (2-I) include those listed in Table 2. These compounds can be made, for example using a procedure analogous to those described in U.S. Patent Application Publications nos. 2009/0163511, 2009/0170829, 2009/0186894 and 2009/0275609, and in U.S. patent application Ser. No. 12/695,861, each of which is hereby incorporated by reference in its entirety.

TABLE 2

| No. | Name | Structure |
|---|---|---|
| 2-1 | benzyl 8-(1-(4-cyanobenzyl)piperidin-4-ylcarbamoyl)-3,4-dihydro-1H-pyrido[4,3-b]indole-2(5H)-carboxylate | 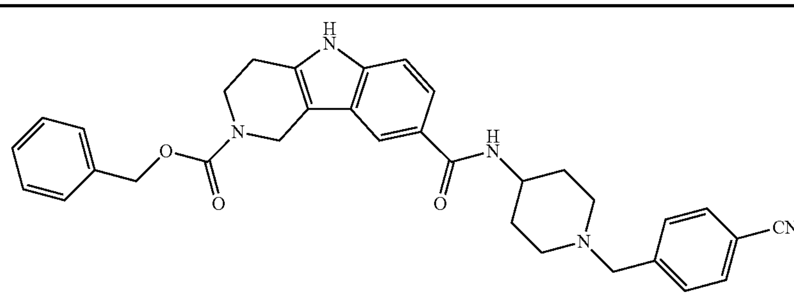 |

TABLE 2-continued

| No. | Name | Structure |
|---|---|---|
| 2-2 | benzyl 8-(1-(4-benzyl)piperidin-4-ylcarbamoyl)-3,4-dihydro-1H-pyrido[4,3-b]indole-2(5H)-carboxylate | 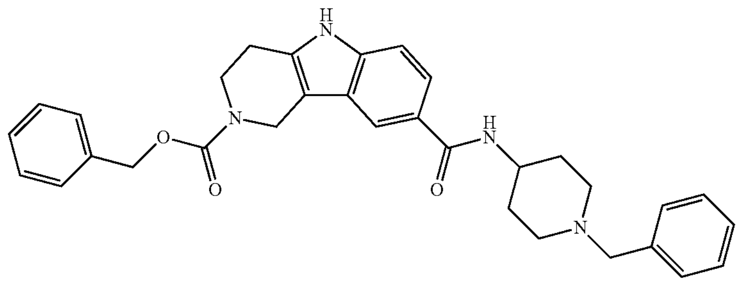 [SMILES: O=C(NC1CCN(Cc2ccccc2)CC1)c1ccc2[nH]c3c(c2c1)CN(C(=O)OCc1ccccc1)CC3] |
| 2-3 | benzyl 8-(1-(tert-butoxycarbonyl)piperidin-4-ylcarbamoyl)-3,4-dihydro-1H-pyrido[4,3-b]indole-2(5H)-carboxylate | 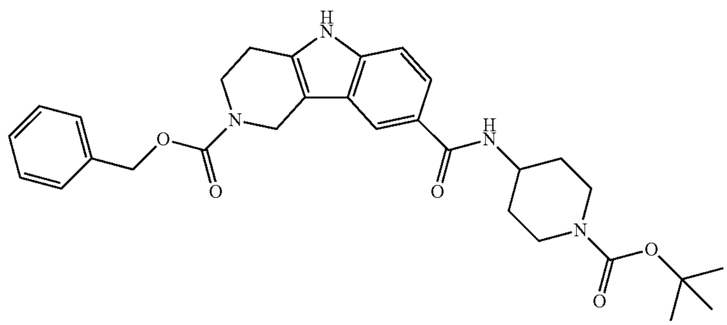 [SMILES: CC(C)(C)OC(=O)N1CCC(NC(=O)c2ccc3[nH]c4c(c3c2)CN(C(=O)OCc2ccccc2)CC4)CC1] |
| 2-4 | 2-benzyl-N-(1-(4-cyanobenzyl)piperidin-4-yl)-2,3,4,5-tetrahydro-1H-pyrido[4,3-b]indole-8-carboxamide | 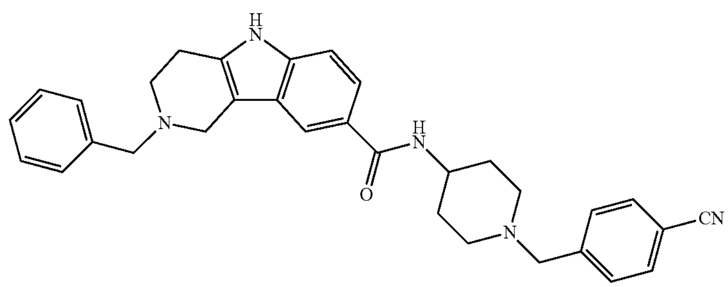 [SMILES: N#Cc1ccc(CN2CCC(NC(=O)c3ccc4[nH]c5c(c4c3)CN(Cc3ccccc3)CC5)CC2)cc1] |
| 2-5 | 2-benzyl-N-(1-(4-trifluoromethylbenzyl)piperidin-4-yl)-2,3,4,5-tetrahydro-1H-pyrido[4,3-b]indole-8-carboxamide | 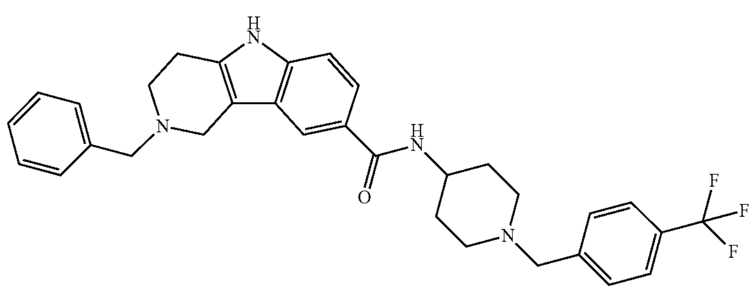 [SMILES: O=C(NC1CCN(Cc2ccc(C(F)(F)F)cc2)CC1)c1ccc2[nH]c3c(c2c1)CN(Cc1ccccc1)CC3] |
| 2-6 | tert-butyl 4-(2-(4-(trifluoromethyl)benzyl)-2,3,4,5-tetrahydro-1H-pyrido[4,3-b]indole-8-carboxamido)piperidine-1-carboxylate | 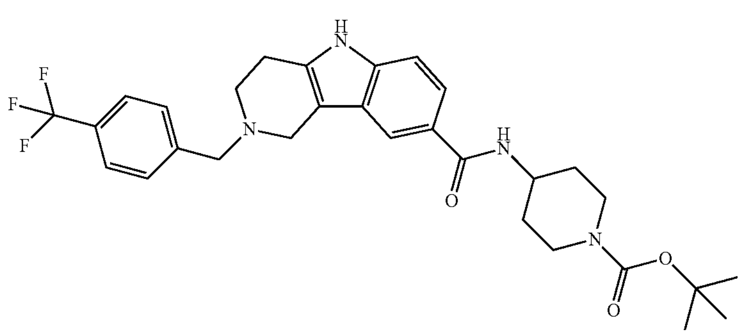 [SMILES: CC(C)(C)OC(=O)N1CCC(NC(=O)c2ccc3[nH]c4c(c3c2)CN(Cc2ccc(C(F)(F)F)cc2)CC4)CC1] |

TABLE 2-continued

| No. | Name | Structure |
|---|---|---|
| 2-7 | 2-benzyl-N-(1-(pyridin-4-ylmethyl)piperidin-4-yl)-2,3,4,5-tetrahydro-1H-pyrido[4,3-b]indole-8-carboxamide | 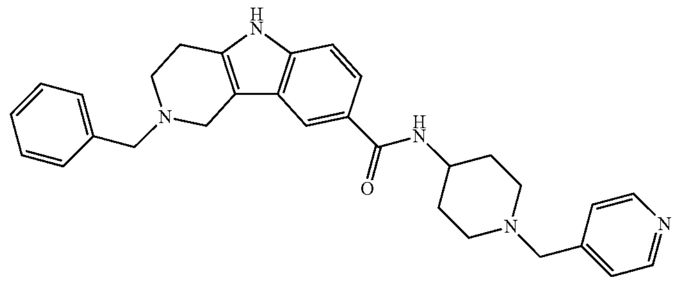 [SMILES: O=C(NC1CCN(Cc2ccncc2)CC1)c1ccc2[nH]c3c(c2c1)CN(Cc1ccccc1)CC3] |
| 2-8 | 2-(4-fluorobenzyl)-N-(1-(pyridin-3-ylmethyl)piperidin-4-yl)-2,3,4,5-tetrahydro-1H-pyrido[4,3-b]indole-8-carboxamide | 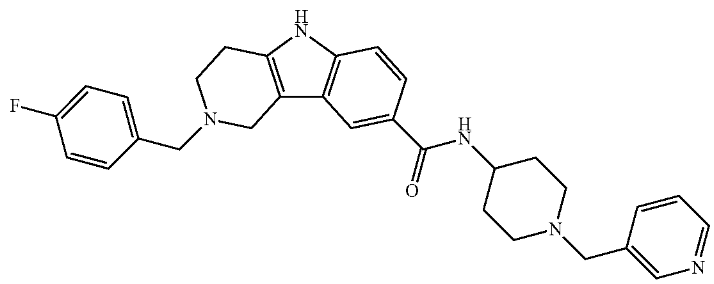 [SMILES: O=C(NC1CCN(Cc2cccnc2)CC1)c1ccc2[nH]c3c(c2c1)CN(Cc1ccc(F)cc1)CC3] |
| 2-9 | N-(1-(4-cyanobenzyl)piperidin-4-yl)-2-(4-fluorobenzyl)-2,3,4,5-tetrahydro-1H-pyrido[4,3-b]indole-8-carboxamide | 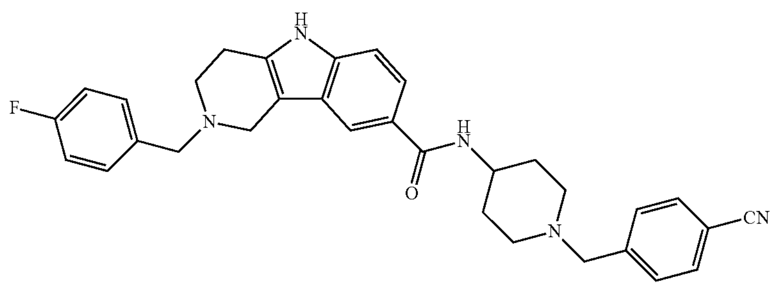 [SMILES: N#Cc1ccc(CN2CCC(NC(=O)c3ccc4[nH]c5c(c4c3)CN(Cc3ccc(F)cc3)CC5)CC2)cc1] |
| 2-10 | N-(1-(4-trifluoromethylbenzyl)piperidin-4-yl)-2-(4-fluorobenzyl)-2,3,4,5-tetrahydro-1H-pyrido[4,3-b]indole-8-carboxamide | 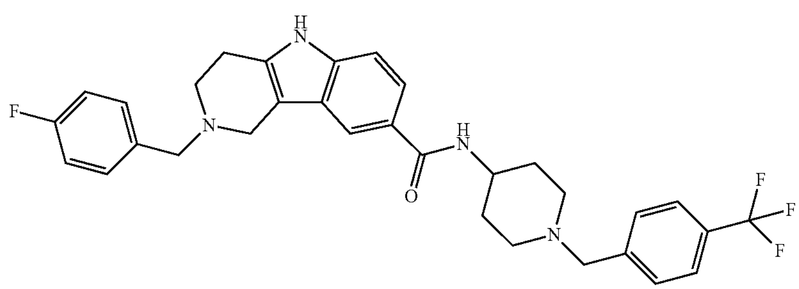 [SMILES: O=C(NC1CCN(Cc2ccc(C(F)(F)F)cc2)CC1)c1ccc2[nH]c3c(c2c1)CN(Cc1ccc(F)cc1)CC3] |
| 2-11 | N-(1-(pyridin-3-ylmethyl)piperidin-4-yl)-2-(4-(trifluoromethyl)benzyl)-2,3,4,5-tetrahydro-1H-pyrido[4,3-b]indole-8-carboxamide | 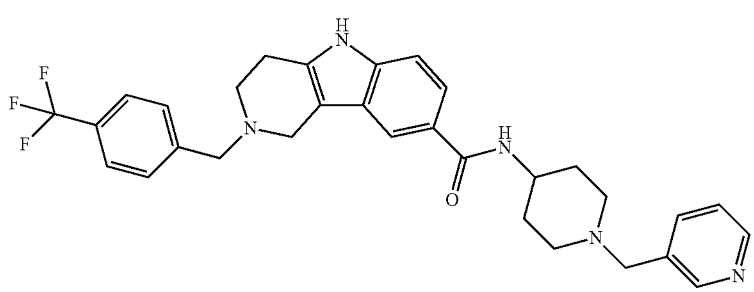 [SMILES: O=C(NC1CCN(Cc2cccnc2)CC1)c1ccc2[nH]c3c(c2c1)CN(Cc1ccc(C(F)(F)F)cc1)CC3] |

TABLE 2-continued

| No. | Name | Structure |
|---|---|---|
| 2-12 | N-(1-(4-cyanobenzyl)piperidin-4-yl)-2-(4-(trifluoromethyl)benzyl)-2,3,4,5-tetrahydro-1H-pyrido[4,3-b]indole-8-carboxamide | 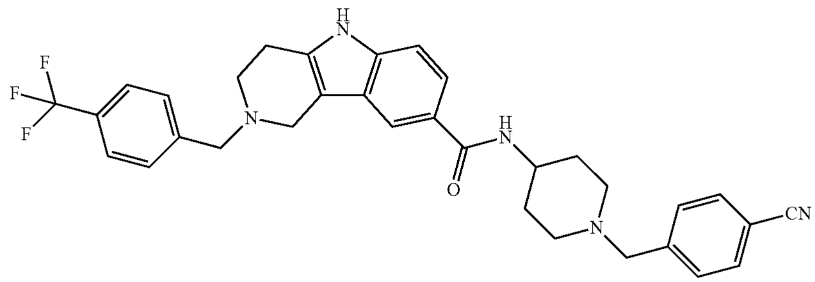 [SMILES: N#Cc1ccc(CN2CCC(NC(=O)c3ccc4[nH]c5c(c4c3)CN(Cc3ccc(C(F)(F)F)cc3)CC5)CC2)cc1] |
| 2-13 | N-(1-(4-trifluoromethyl-benzyl)piperidin-4-yl)-2-(4-(trifluoromethyl)benzyl)-2,3,4,5-tetrahydro-1H-pyrido[4,3-b]indole-8-carboxamide | 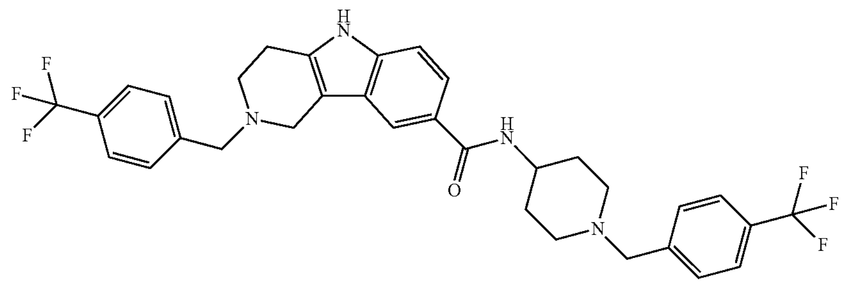 [SMILES: O=C(NC1CCN(Cc2ccc(C(F)(F)F)cc2)CC1)c1ccc2[nH]c3c(c2c1)CN(Cc1ccc(C(F)(F)F)cc1)CC3] |
| 2-14 | N-(1-phenethyl-piperidin-4-yl)-2-(4-(trifluoromethyl)benzyl)-2,3,4,5-tetrahydro-1H-pyrido[4,3-b]indole-8-carboxamide | 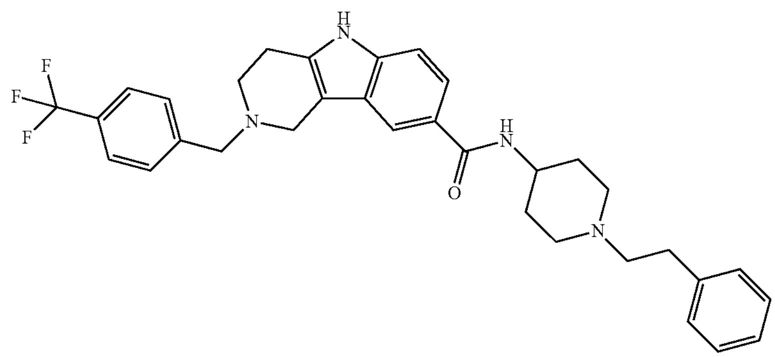 [SMILES: O=C(NC1CCN(CCc2ccccc2)CC1)c1ccc2[nH]c3c(c2c1)CN(Cc1ccc(C(F)(F)F)cc1)CC3] |
| 2-15 | N-(1-(4-fluorophenyl)piperidin-4-yl)-2-(4-(trifluoromethyl)benzyl)-2,3,4,5-tetrahydro-1H-pyrido[4,3-b]indole-8-carboxamide | 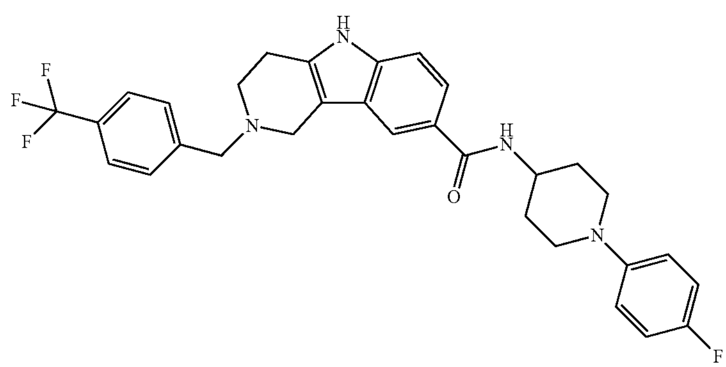 [SMILES: O=C(NC1CCN(c2ccc(F)cc2)CC1)c1ccc2[nH]c3c(c2c1)CN(Cc1ccc(C(F)(F)F)cc1)CC3] |
| 2-16 | N-(1-cyanobenzyl)piperidin-4-yl)-5-methyl-2-(4-(trifluoromethyl)benzyl)-2,3,4,5-tetrahydro-1H-pyrido[4,3-b]indole-8-carboxamide | 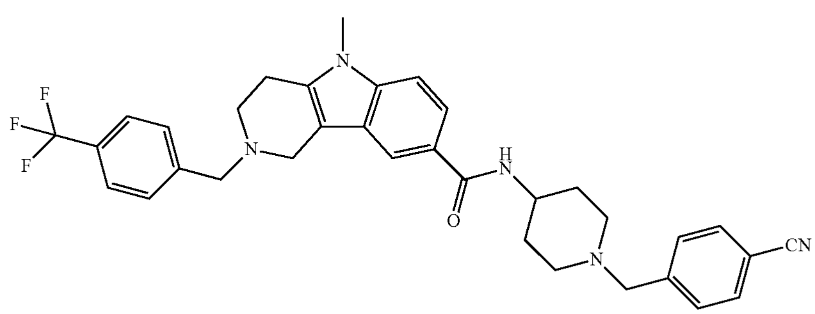 [SMILES: Cn1c2c(c3cc(C(=O)NC4CCN(Cc5ccc(C#N)cc5)CC4)ccc31)CN(Cc1ccc(C(F)(F)F)cc1)CC2] |

TABLE 2-continued

| No. | Name | Structure |
|---|---|---|
| 2-17 | N-(1-(4-trifluoromethylbenzyl)piperidin-4-yl)-5-methyl-2-(4-(trifluoromethyl)benzyl)-2,3,4,5-tetrahydro-1H-pyrido[4,3-b]indole-8-carboxamide | 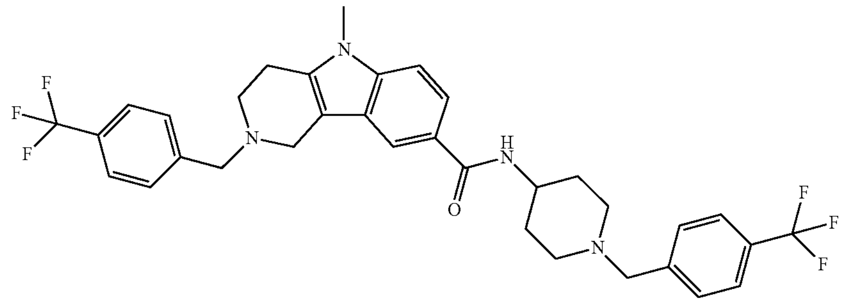 [SMILES: Cn1c2c(c3cc(C(=O)NC4CCN(Cc5ccc(C(F)(F)F)cc5)CC4)ccc31)CN(Cc1ccc(C(F)(F)F)cc1)CC2] |
| 2-18 | 5-methyl-N-(1-(pyridin-3-ylmethyl)piperidin-4-yl)-2-(4-(trifluoromethyl)benzyl)-2,3,4,5-tetrahydro-1H-pyrido[4,3-b]indole-8-carboxamide | 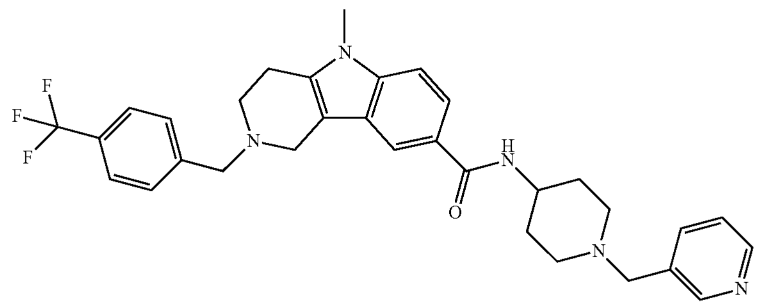 [SMILES: Cn1c2c(c3cc(C(=O)NC4CCN(Cc5cccnc5)CC4)ccc31)CN(Cc1ccc(C(F)(F)F)cc1)CC2] |
| 2-19 | N-(1-benzylpiperidin-4-yl)-2-(4-(trifluoromethyl)phenylsulfonyl)-2,3,4,5-tetrahydro-1H-pyrido[4,3-b]indole-8-carboxamide | 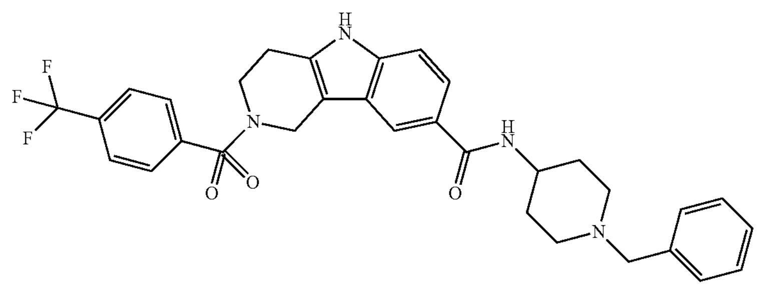 |
| 2-20 | 5-acetyl-N-(1-(pyridin-3-ylmethyl)piperidin-4-yl)-2-(4-(trifluoromethyl)benzyl)-2,3,4,5-tetrahydro-1H-pyrido[4,3-b]indole-8-carboxamide | 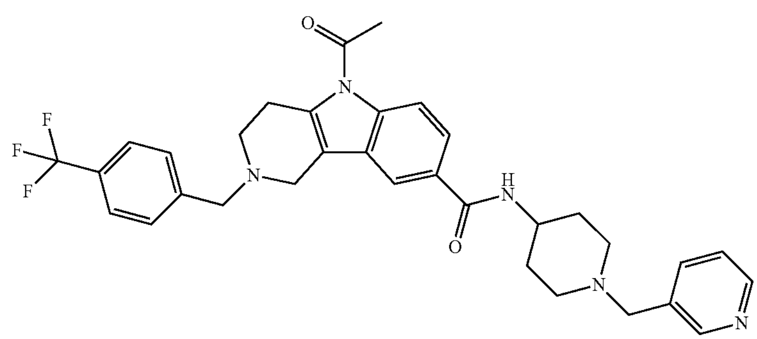 [SMILES: CC(=O)n1c2c(c3cc(C(=O)NC4CCN(Cc5cccnc5)CC4)ccc31)CN(Cc1ccc(C(F)(F)F)cc1)CC2] |
| 2-21 | N-(1-(4-cyanophenylsulfonyl)piperidin-4-yl)-2-(4-(trifluoromethyl)benzyl)-2,3,4,5-tetrahydro-1H-pyrido[4,3-b]indole-8-carboxamide | 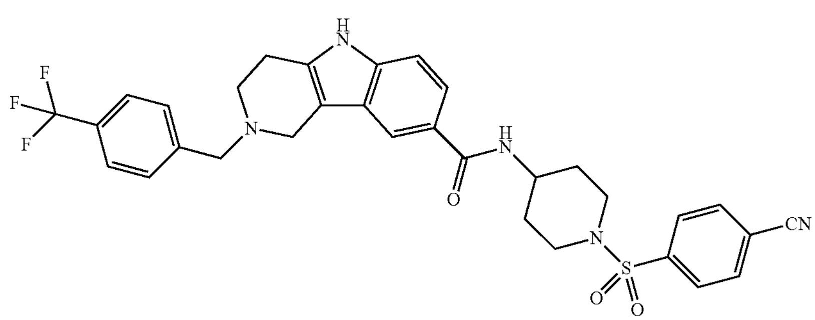 [SMILES: N#Cc1ccc(S(=O)(=O)N2CCC(NC(=O)c3ccc4[nH]c5c(c4c3)CN(Cc3ccc(C(F)(F)F)cc3)CC5)CC2)cc1] |

TABLE 2-continued

| No. | Name | Structure |
|---|---|---|
| 2-22 | N-(1-(pyridin-3-ylsulfonyl)piperidin-4-yl)-2-(4-(trifluoromethyl)benzyl)-2,3,4,5-tetrahydro-1H-pyrido[4,3-b]indole-8-carboxamide | 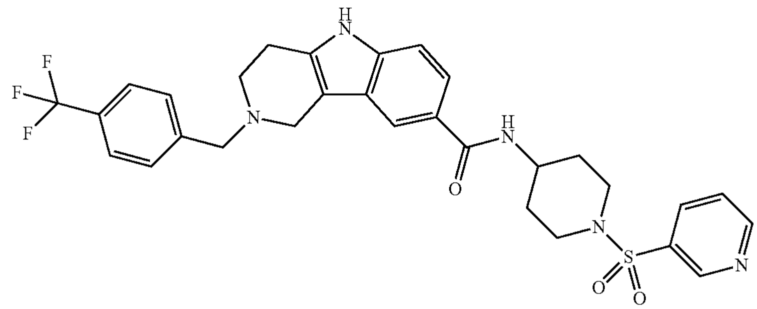 [SMILES: O=C(NC1CCN(S(=O)(=O)c2cccnc2)CC1)c1ccc2[nH]c3c(c2c1)CN(Cc1ccc(C(F)(F)F)cc1)CC3] |
| 2-23 | 2-(4-(trifluoromethyl)benzyl)-N-(1-(4-(trifluoromethyl)phenylsulfonyl)piperidin-4-yl)-2,3,4,5-tetrahydro-1H-pyrido[4,3-b]indole-8-carboxamide | 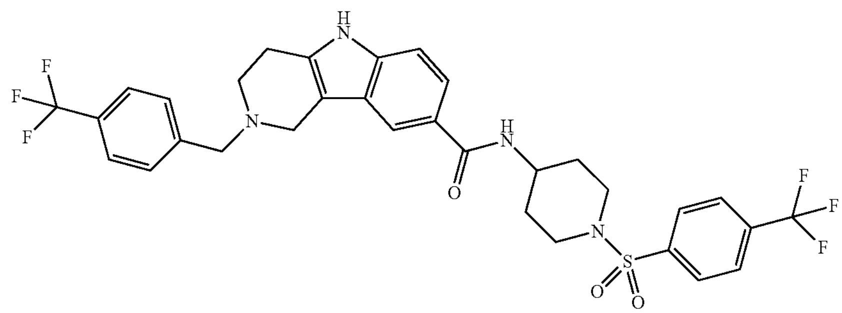 [SMILES: O=C(NC1CCN(S(=O)(=O)c2ccc(C(F)(F)F)cc2)CC1)c1ccc2[nH]c3c(c2c1)CN(Cc1ccc(C(F)(F)F)cc1)CC3] |
| 2-24 | N-(1-(4-cyanobenzyl)piperidin-4-yl)-2-(4-(trifluoromethyl)phenylsulfonyl)-2,3,4,5-tetrahydro-1H-pyrido[4,3-b]indole-8-carboxamide | 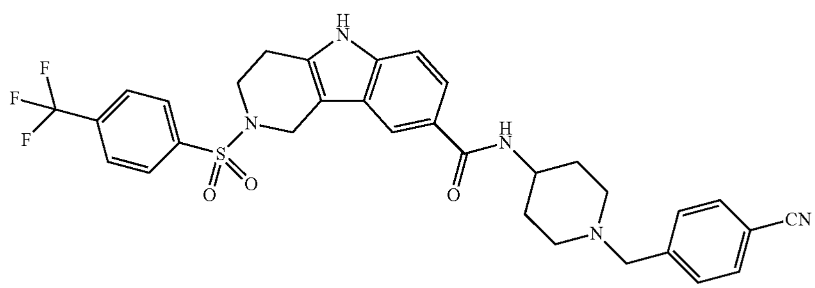 [SMILES: N#Cc1ccc(CN2CCC(NC(=O)c3ccc4[nH]c5c(c4c3)CN(S(=O)(=O)c3ccc(C(F)(F)F)cc3)CC5)CC2)cc1] |
| 2-25 | N-(1-(4-cyanobenzyl)piperidin-4-yl)-2-(4-cyanophenylsulfonyl)-2,3,4,5-tetrahydro-1H-pyrido[4,3-b]indole-8-carboxamide | 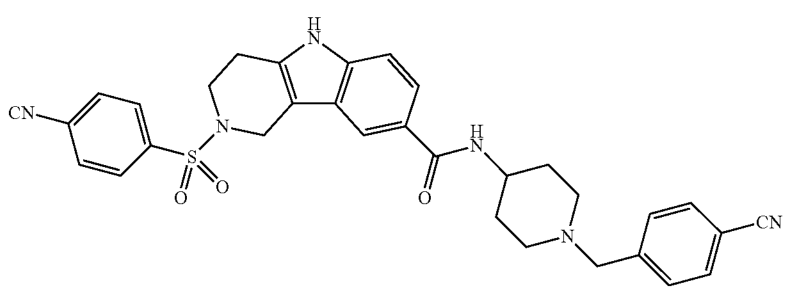 |
| 2-26 | N-(1-(4-cyanobenzyl)piperidin-4-yl)-2-(pyridin-3-ylsulfonyl)-2,3,4,5-tetrahydro-1H-pyrido[4,3-b]indole-8-carboxamide | 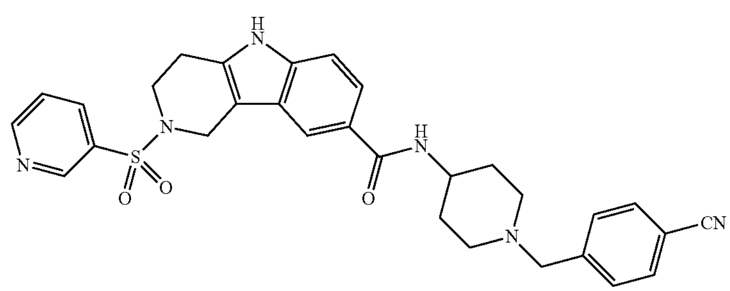 [SMILES: N#Cc1ccc(CN2CCC(NC(=O)c3ccc4[nH]c5c(c4c3)CN(S(=O)(=O)c3cccnc3)CC5)CC2)cc1] |

TABLE 2-continued

| No. | Name | Structure |
|---|---|---|
| 2-27 | N-(1-(4-cyanophenyl-carbamoyl)piperidin-4-yl)-2-(4-(trifluoromethyl)benzyl)-2,3,4,5-tetrahydro-1H-pyrido[4,3-b]indole-8-carboxamide | 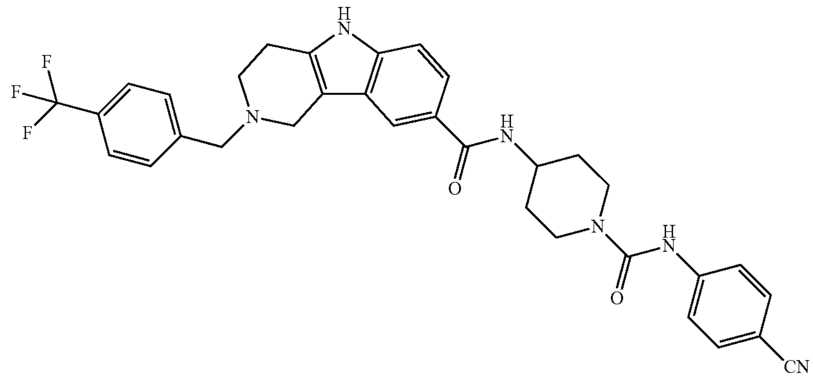 [SMILES: N#Cc1ccc(NC(=O)N2CCC(NC(=O)c3ccc4[nH]c5c(c4c3)CN(Cc3ccc(C(F)(F)F)cc3)CC5)CC2)cc1] |
| 2-28 | N-(1-(4-fluorophenyl-sulfonyl)piperidin-4-yl)-2-(4-(trifluoro-methyl)benzyl)-2,3,4,5-tetrahydro-1H-pyrido[4,3-b]indole-8-carboxamide | 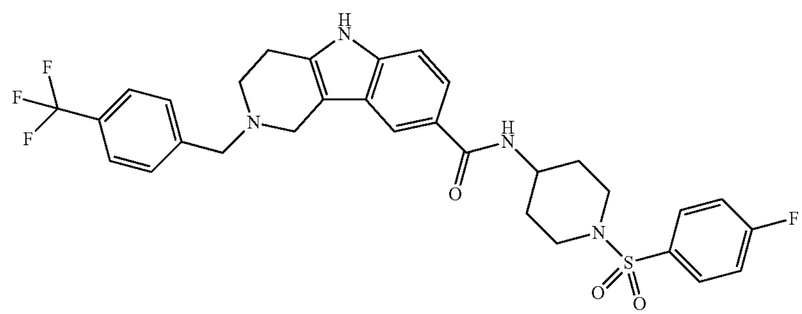 [SMILES: O=C(NC1CCN(S(=O)(=O)c2ccc(F)cc2)CC1)c1ccc2[nH]c3c(c2c1)CN(Cc1ccc(C(F)(F)F)cc1)CC3] |
| 2-29 | N-(1-(3-cyanophenyl-sulfonyl)piperidin-4-yl)-2-(4-(trifluoro-methyl)benzyl)-2,3,4,5-tetrahydro-1H-pyrido[4,3-b]indole-8-carboxamide | 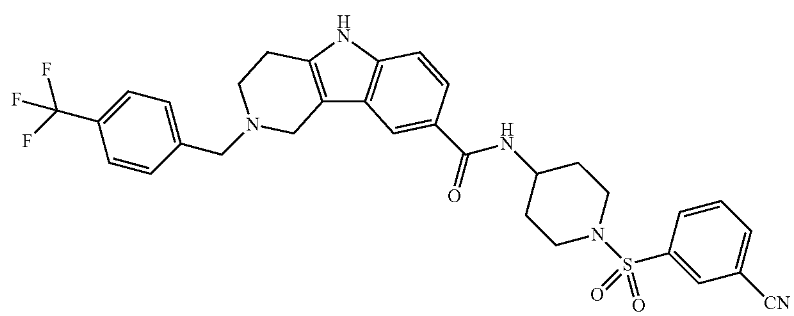 [SMILES: N#Cc1cccc(S(=O)(=O)N2CCC(NC(=O)c3ccc4[nH]c5c(c4c3)CN(Cc3ccc(C(F)(F)F)cc3)CC5)CC2)c1] |
| 2-30 | 2-(4-(trifluoromethyl)benzyl)-N-(1-(3-(trifluoromethyl)phenylsulfonyl)piperidin-4-yl)-2,3,4,5-tetrahydro-1H-pyrido[4,3-b]indole-8-carboxamide | 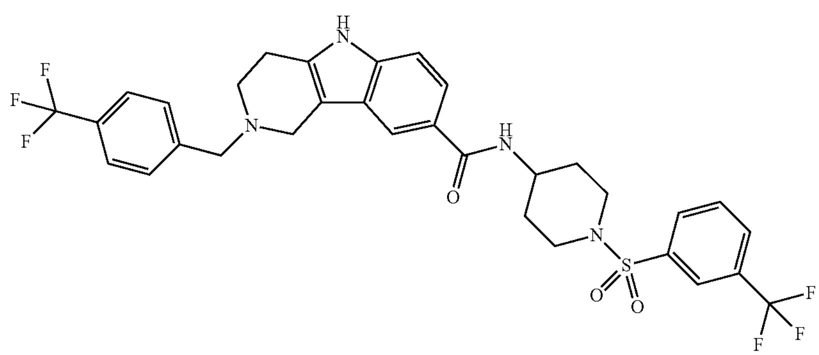 [SMILES: O=C(NC1CCN(S(=O)(=O)c2cccc(C(F)(F)F)c2)CC1)c1ccc2[nH]c3c(c2c1)CN(Cc1ccc(C(F)(F)F)cc1)CC3] |

TABLE 2-continued

| No. | Name | Structure |
|---|---|---|
| 2-31 | N-(1-(3-fluorophenyl-carbamoyl)piperidin-4-yl)-2-(4-(trifluoro-methyl)benzyl)-2,3,4,5-tetrahydro-1H-pyrido[4,3-b]indole-8-carboxamide | 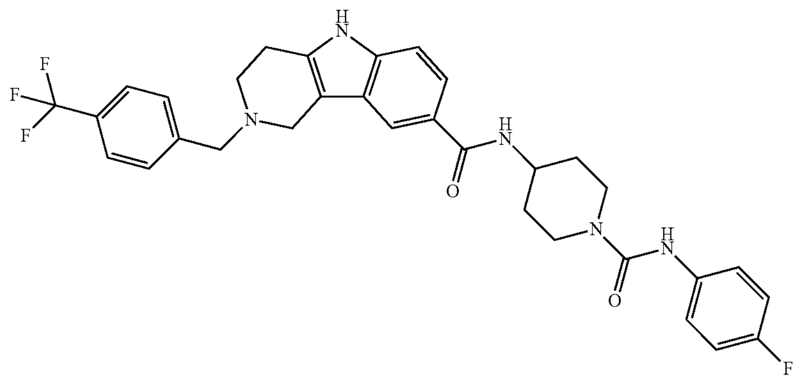 [SMILES: O=C(NC1CCN(C(=O)Nc2ccc(F)cc2)CC1)c1ccc2[nH]c3c(c2c1)CN(Cc1ccc(C(F)(F)F)cc1)CC3] |
| 2-32 | N-(1-(4-chlorophenyl-sulfonyl)piperidin-4-yl)-2-(4-(trifluoro-methyl)benzyl)-2,3,4,5-tetrahydro-1H-pyrido[4,3-b]indole-8-carboxamide | 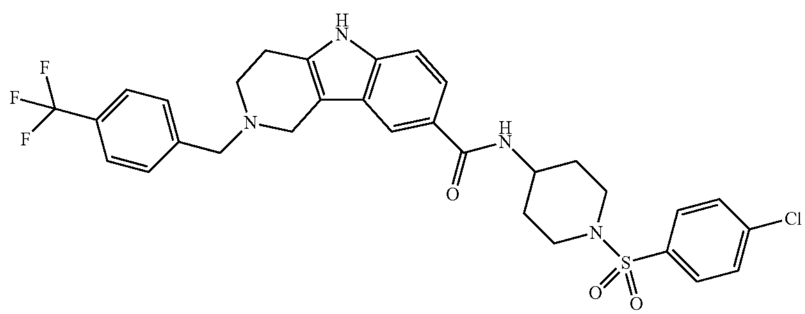 [SMILES: O=C(NC1CCN(S(=O)(=O)c2ccc(Cl)cc2)CC1)c1ccc2[nH]c3c(c2c1)CN(Cc1ccc(C(F)(F)F)cc1)CC3] |
| 2-33 | 2-(4-(trifluoromethyl)benzyl)-N-(1-(4-(trifluoromethyl)phenylcarbamoyl)piperidin-4-yl)-2,3,4,5-tetrahydro-1H-pyrido[4,3-b]indole-8-carboxamide | 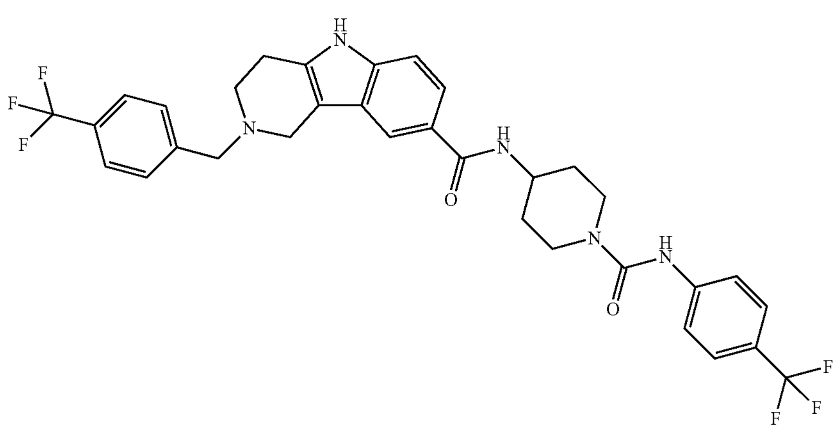 [SMILES: O=C(NC1CCN(C(=O)Nc2ccc(C(F)(F)F)cc2)CC1)c1ccc2[nH]c3c(c2c1)CN(Cc1ccc(C(F)(F)F)cc1)CC3] |
| 2-34 | N-(1-(4-cyanobenzyl)piperidin-4-yl)-2-(4-fluorophenyl)-2,3,4,5-tetrahydro-1H-pyrido[4,3-b]indole-8-carboxamide | 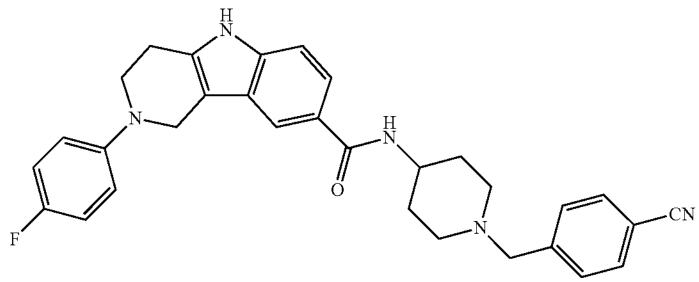 [SMILES: N#Cc1ccc(CN2CCC(NC(=O)c3ccc4[nH]c5c(c4c3)CN(c3ccc(F)cc3)CC5)CC2)cc1] |

TABLE 2-continued

| No. | Name | Structure |
|---|---|---|
| 2-35 | 2-(4-fluorophenyl)-N-(1-(4-fluorophenylsulfonyl)piperidin-4-yl)-2,3,4,5-tetrahydro-1H-pyrido[4,3-b]indole-8-carboxamide | 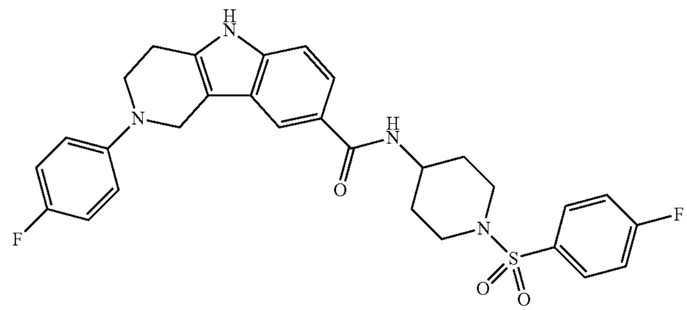 [SMILES: O=C(NC1CCN(S(=O)(=O)c2ccc(F)cc2)CC1)c1ccc2[nH]c3c(c2c1)CN(c1ccc(F)cc1)CC3] |
| 2-36 | 2-(4-fluorophenyl)-N-(1-(pyridin-3-ylmethyl)piperidin-4-yl)-2,3,4,5-tetrahydro-1H-pyrido[4,3-b]indole-8-carboxamide | 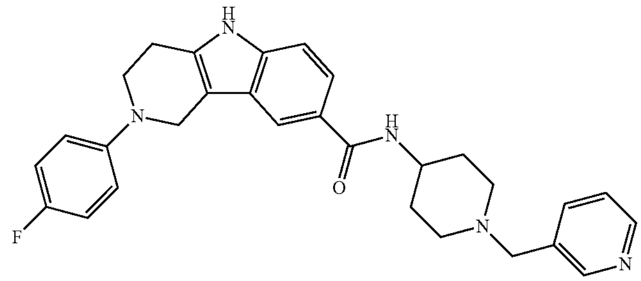 [SMILES: O=C(NC1CCN(Cc2cccnc2)CC1)c1ccc2[nH]c3c(c2c1)CN(c1ccc(F)cc1)CC3] |
| 2-37 | 2-(4-fluorophenyl)-N-(1-(4-(trifluoromethyl)benzyl)piperidin-4-yl)-2,3,4,5-tetrahydro-1H-pyrido[4,3-b]indole-8-carboxamide | 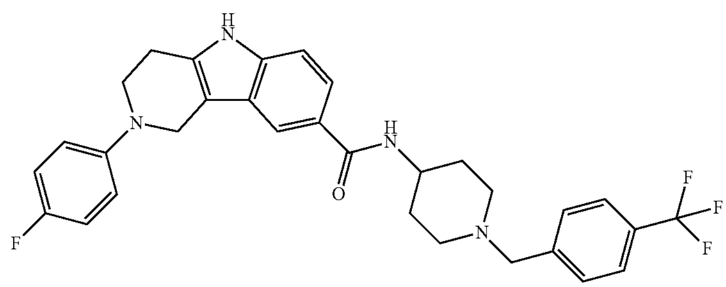 [SMILES: O=C(NC1CCN(Cc2ccc(C(F)(F)F)cc2)CC1)c1ccc2[nH]c3c(c2c1)CN(c1ccc(F)cc1)CC3] |
| 2-38 | tert-butyl 4-(2-(4-fluorophenyl)-2,3,4,5-tetrahydro-1H-pyrido[4,3-b]indole-8-carboxamido)piperidine-1-carboxylate | 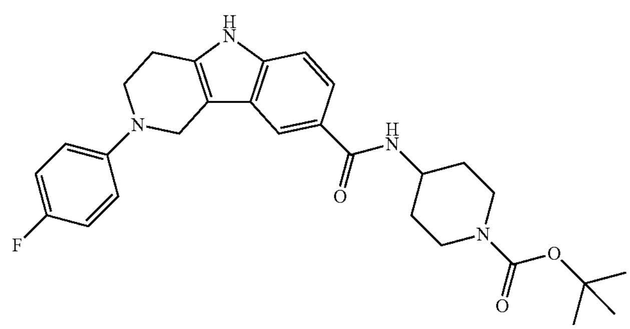 [SMILES: CC(C)(C)OC(=O)N1CCC(NC(=O)c2ccc3[nH]c4c(c3c2)CN(c2ccc(F)cc2)CC4)CC1] |
| 2-39 | N-(1-(4-fluorobenzoyl)piperidin-4-yl)-2-(4-fluorophenyl)-2,3,4,5-tetrahydro-1H-pyrido[4,3-b]indole-8-carboxamide | 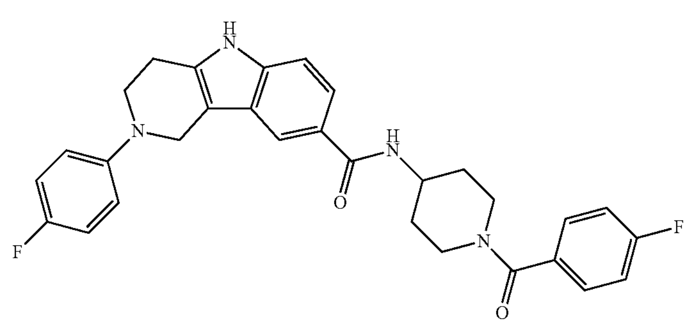 [SMILES: O=C(NC1CCN(C(=O)c2ccc(F)cc2)CC1)c1ccc2[nH]c3c(c2c1)CN(c1ccc(F)cc1)CC3] |

TABLE 2-continued

| No. | Name |
|---|---|
| 2-40 | 2-(4-fluorophenyl)-N-(1-nicotinoylpiperidin-4-yl)-2,3,4,5-tetrahydro-1H-pyrido[4,3-b]indole-8-carboxamide |
| 2-41 | 2-(4-fluorophenyl)-N-(1-(4-(trifluoromethyl)benzoyl)piperidin-4-yl)-2,3,4,5-tetrahydro-1H-pyrido[4,3-b]indole-8-carboxamide |
| 2-42 | N-(1-nicotinoylpiperidin-4-yl)-2-(4-(trifluoromethyl)benzyl)-2,3,4,5-tetrahydro-1H-pyrido[4,3-b]indole-8-carboxamide |
| 2-43 | tert-butyl 4-(2-(4-carbamoylbenzyl)-2,3,4,5-tetrahydro-1H-pyrido[4,3-b]indole-8-carboxamido)piperidine-1-carboxylate |
| 2-44 | 2-(4-carbamoylbenzyl)-N-(1-(4-cyanobenzyl)piperidin-4-yl)-2,3,4,5-tetrahydro-1H-pyrido[4,3-b]indole-8-carboxamide |

TABLE 2-continued

| No. | Name | Structure |
|---|---|---|
| 2-45 | 2-(4-carbamoylbenzyl)-N-(1-(pyridin-4-ylmethyl)piperidin-4-yl)-2,3,4,5-tetrahydro-1H-pyrido[4,3-b]indole-8-carboxamide | 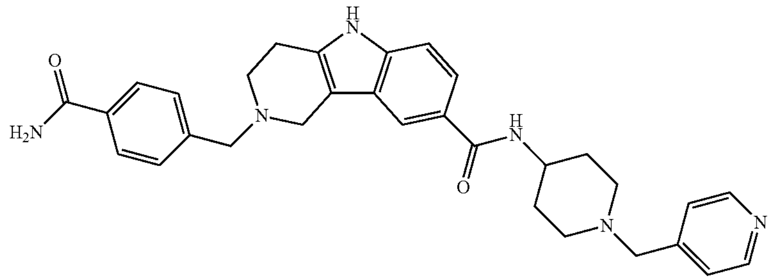 [SMILES: NC(=O)c1ccc(CN2CCc3[nH]c4ccc(C(=O)NC5CCN(Cc6ccncc6)CC5)cc4c3C2)cc1] |
| 2-46 | 2-(4-carbamoylbenzyl)-N-(1-isonicotinoylpiperidin-4-yl)-2,3,4,5-tetrahydro-1H-pyrido[4,3-b]indole-8-carboxamide | 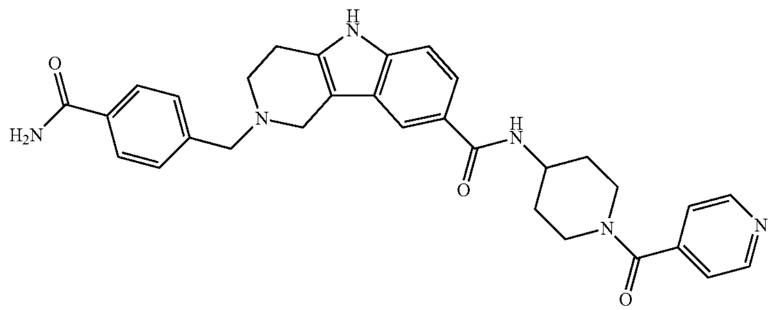 [SMILES: NC(=O)c1ccc(CN2CCc3[nH]c4ccc(C(=O)NC5CCN(C(=O)c6ccncc6)CC5)cc4c3C2)cc1] |
| 2-47 | 2-(4-carbamoylbenzyl)-N-(1-(4-(trifluoromethyl)benzyl)piperidin-4-yl)-2,3,4,5-tetrahydro-1H-pyrido[4,3-b]indole-8-carboxamide | 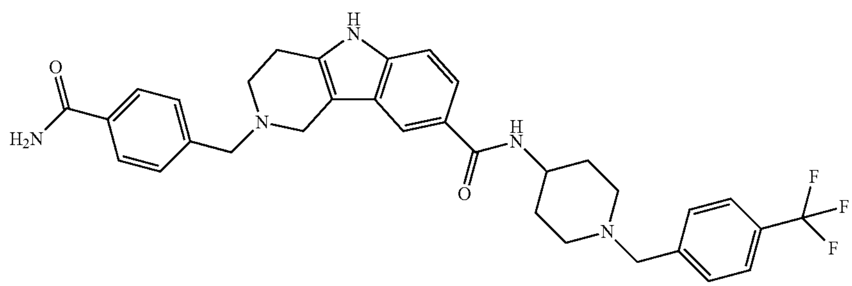 [SMILES: NC(=O)c1ccc(CN2CCc3[nH]c4ccc(C(=O)NC5CCN(Cc6ccc(C(F)(F)F)cc6)CC5)cc4c3C2)cc1] |
| 2-48 | 2-(4-carbamoylbenzyl)-N-(1-(4-fluorobenzyl)piperidin-4-yl)-2,3,4,5-tetrahydro-1H-pyrido[4,3-b]indole-8-carboxamide | 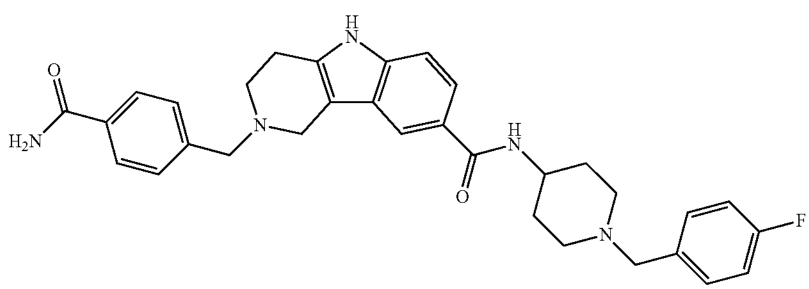 [SMILES: NC(=O)c1ccc(CN2CCc3[nH]c4ccc(C(=O)NC5CCN(Cc6ccc(F)cc6)CC5)cc4c3C2)cc1] |
| 2-49 | 2-(4-carbamoylbenzyl)-N-(1-(4-carbamoylbenzyl)piperidin-4-yl)-2,3,4,5-tetrahydro-1H-pyrido[4,3-b]indole-8-carboxamide | 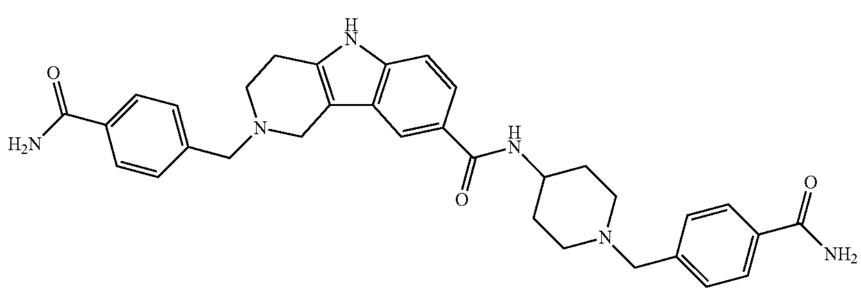 [SMILES: NC(=O)c1ccc(CN2CCC(NC(=O)c3ccc4[nH]c5c(c4c3)CN(Cc3ccc(C(N)=O)cc3)CC5)CC2)cc1] |

TABLE 2-continued

| No. | Name | Structure |
|---|---|---|
| 2-50 | N-(1-(pyridin-4-ylmethyl)piperidin-4-yl)-2-(4-(trifluoromethyl)benzyl)-2,3,4,5-tetrahydro-1H-pyrido[4,3-b]indole-8-carboxamide | 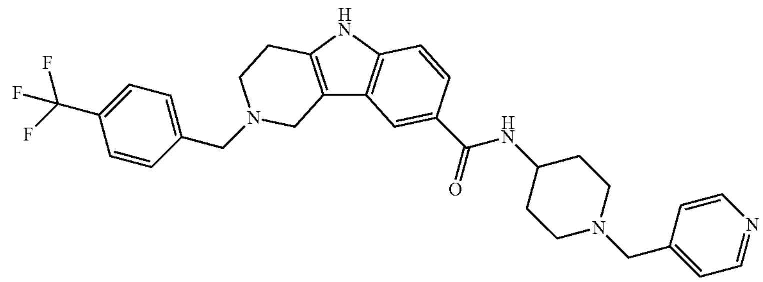 [SMILES: O=C(NC1CCN(Cc2ccncc2)CC1)c1ccc2[nH]c3c(c2c1)CN(Cc1ccc(C(F)(F)F)cc1)CC3] |
| 2-51 | N-(1-isonicotinoyl-piperidin-4-yl)-2-(4-(trifluoromethyl)benzyl)-2,3,4,5-tetrahydro-1H-pyrido[4,3-b]indole-8-carboxamide | 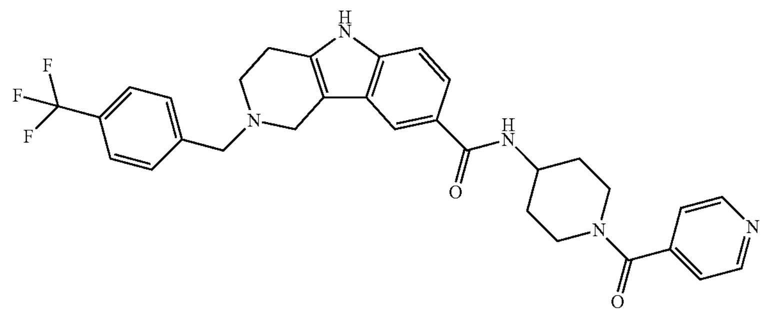 [SMILES: O=C(NC1CCN(C(=O)c2ccncc2)CC1)c1ccc2[nH]c3c(c2c1)CN(Cc1ccc(C(F)(F)F)cc1)CC3] |
| 2-52 | N-(1-(4-carbamoyl-benzyl)piperidin-4-yl)-2-(4-(trifluoromethyl)benzyl)-2,3,4,5-tetrahydro-1H-pyrido[4,3-b]indole-8-carboxamide | 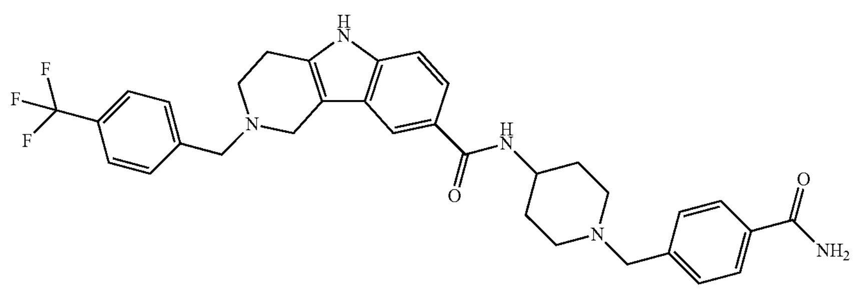 [SMILES: NC(=O)c1ccc(CN2CCC(NC(=O)c3ccc4[nH]c5c(c4c3)CN(Cc3ccc(C(F)(F)F)cc3)CC5)CC2)cc1] |
| 2-53 | N-(1-((1-methyl-1H-imidazol-4-yl)methyl)piperidin-4-yl)-2-(4-(trifluoromethyl)benzyl)-2,3,4,5-tetrahydro-1H-pyrido[4,3-b]indole-8-carboxamide | 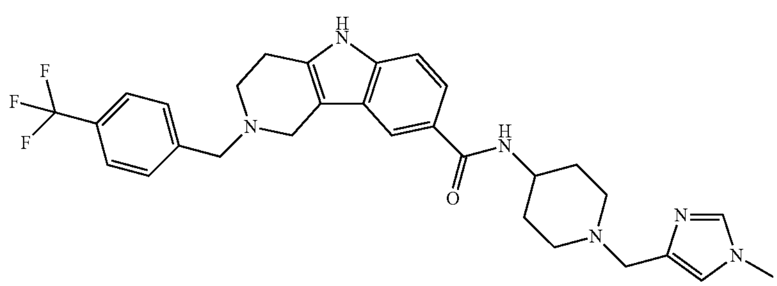 [SMILES: Cn1cnc(CN2CCC(NC(=O)c3ccc4[nH]c5c(c4c3)CN(Cc3ccc(C(F)(F)F)cc3)CC5)CC2)c1] |
| 2-54 | N-(1-(oxazol-4-ylmethyl)piperidin-4-yl)-2-(4-(trifluoromethyl)benzyl)-2,3,4,5-tetrahydro-1H-pyrido[4,3-b]indole-8-carboxamide | 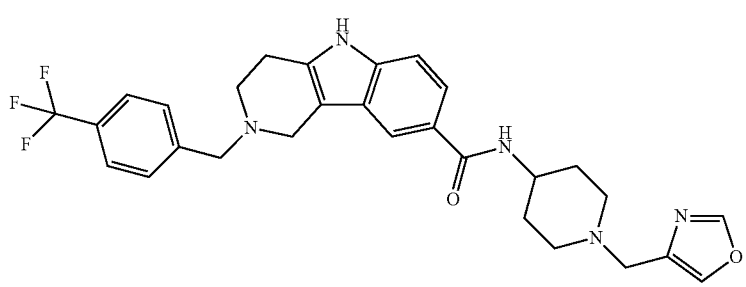 [SMILES: O=C(NC1CCN(Cc2cocn2)CC1)c1ccc2[nH]c3c(c2c1)CN(Cc1ccc(C(F)(F)F)cc1)CC3] |

TABLE 2-continued

| No. | Name | Structure |
|---|---|---|
| 2-55 | 4-((4-benzylpiperazin-1-yl)methyl)-N-(1-benzylpiperidin-4-yl)benzamide | 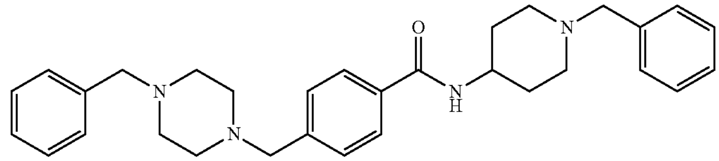 [SMILES: O=C(NC1CCN(Cc2ccccc2)CC1)c1ccc(CN2CCN(Cc3ccccc3)CC2)cc1] |
| 2-56 | N-(1-benzylpiperidin-4-yl)-4-((4-(cyclohexylmethyl)piperazin-1-yl)methyl)benzamide | 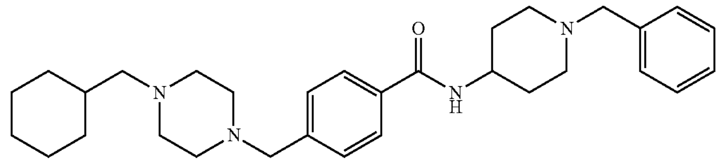 [SMILES: O=C(NC1CCN(Cc2ccccc2)CC1)c1ccc(CN2CCN(CC3CCCCC3)CC2)cc1] |
| 2-57 | N-(1-benzylpiperidin-4-yl)-4-((4-(5-(trifluoromethyl)pyridin-2-yl)piperazin-1-yl)methyl)benzamide | 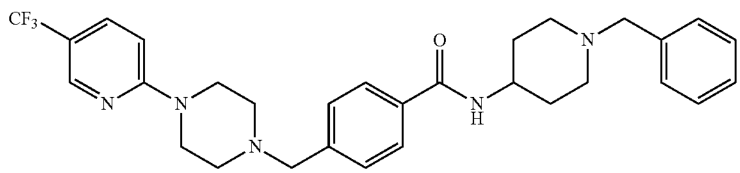 [SMILES: O=C(NC1CCN(Cc2ccccc2)CC1)c1ccc(CN2CCN(c3ccc(C(F)(F)F)cn3)CC2)cc1] |
| 2-58 | N-(1-benzylpiperidin-4-yl)-4-((4-(pyridin-2-yl)piperazin-1-yl)methyl)benzamide | 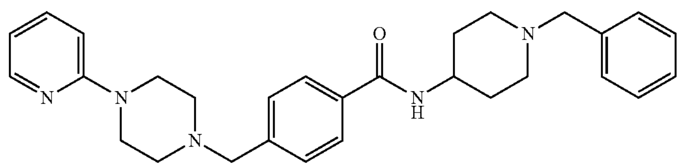 [SMILES: O=C(NC1CCN(Cc2ccccc2)CC1)c1ccc(CN2CCN(c3ccccn3)CC2)cc1] |
| 2-59 | 4-((4-benzylpiperazin-1-yl)methyl)-N-(1-(pyridin-4-ylmethyl)piperidin-4-yl)benzamide | 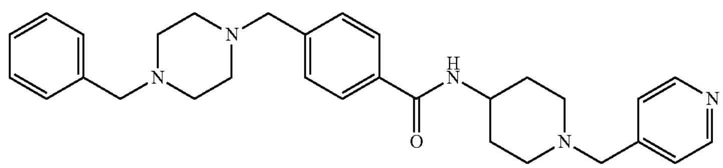 [SMILES: O=C(NC1CCN(Cc2ccncc2)CC1)c1ccc(CN2CCN(Cc3ccccc3)CC2)cc1] |
| 2-60 | 4-((4-benzylpiperazin-1-yl)methyl)-N-(1-(pyridin-3-ylmethyl)piperidin-4-yl)benzamide | 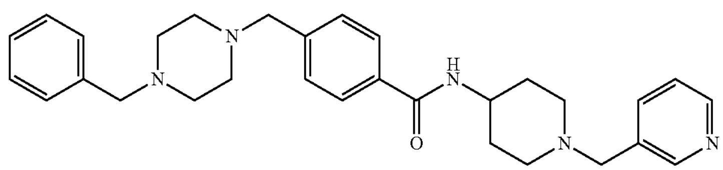 [SMILES: O=C(NC1CCN(Cc2cccnc2)CC1)c1ccc(CN2CCN(Cc3ccccc3)CC2)cc1] |
| 2-61 | 4-((4-benzylpiperazin-1-yl)methyl)-N-(1-(4-cyanobenzyl)piperidin-4-yl)benzamide | 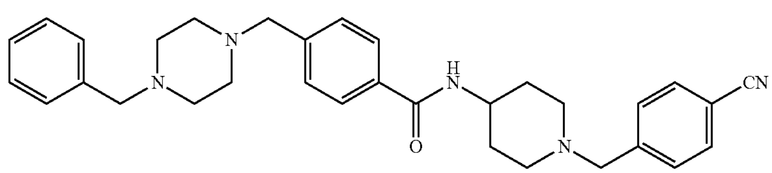 [SMILES: N#Cc1ccc(CN2CCC(NC(=O)c3ccc(CN4CCN(Cc5ccccc5)CC4)cc3)CC2)cc1] |
| 2-62 | 4-((4-benzylpiperazin-1-yl)methyl)-N-(1-(4-trifluoromethylbenzyl)piperidin-4-yl)benzamide | 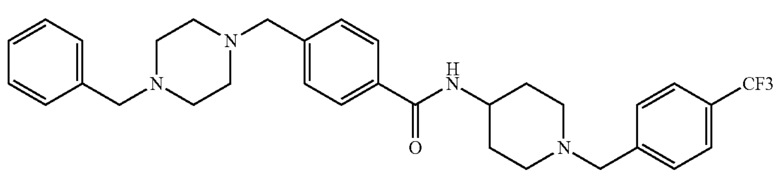 [SMILES: O=C(NC1CCN(Cc2ccc(C(F)(F)F)cc2)CC1)c1ccc(CN2CCN(Cc3ccccc3)CC2)cc1] |
| 2-63 | N-(1-benzylpiperidin-4-yl)-6-(1-(4-(trifluoromethyl)benzyl)piperidin-4-yloxy)-2-naphthamide | 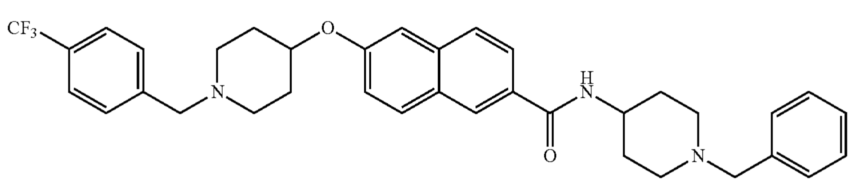 [SMILES: O=C(NC1CCN(Cc2ccccc2)CC1)c1ccc2cc(OC3CCN(Cc4ccc(C(F)(F)F)cc4)CC3)ccc2c1] |

TABLE 2-continued

| No. | Name | Structure |
|---|---|---|
| 2-64 | N-(1-benzylpiperidin-4-yl)-6-(1-(4-cyanobenzyl)piperidin-4-yloxy)-2-naphthamide | 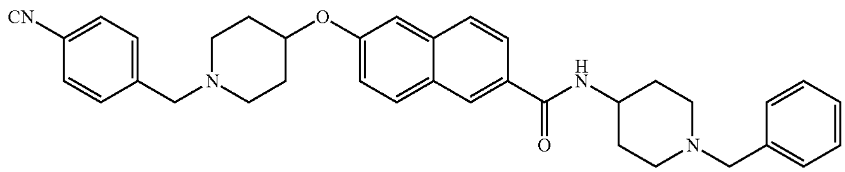 |
| 2-65 | N-(1-benzylpiperidin-4-yl)-6-(1-(4-(trifluoromethyl)phenyl)piperidin-4-yloxy)-2-naphthamide | 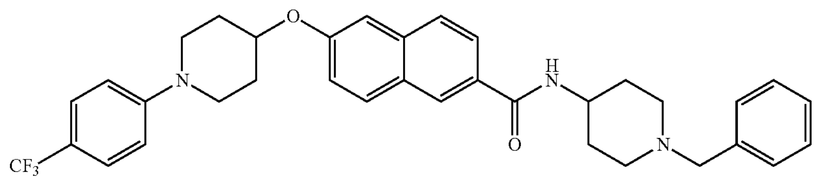 [SMILES: O=C(NC1CCN(Cc2ccccc2)CC1)c1ccc2cc(OC3CCN(c4ccc(C(F)(F)F)cc4)CC3)ccc2c1] |
| 2-66 | tert-butyl 4-(7-(1-(4-(trifluoromethyl)phenyl)piperidin-4-yloxy)-2-naphthamido)piperidine-1-carboxylate | 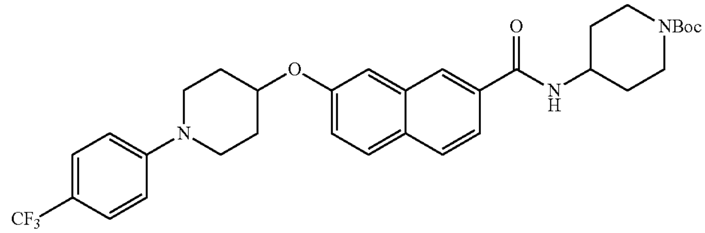 [SMILES: CC(C)(C)OC(=O)N1CCC(NC(=O)c2ccc3ccc(OC4CCN(c5ccc(C(F)(F)F)cc5)CC4)cc3c2)CC1] |
| 2-67 | tert-butyl 4-(6-(1-(4-(trifluoromethyl)phenyl)piperidin-4-yloxy)quinoline-3-carboxamido)piperidine-1-carboxylate | 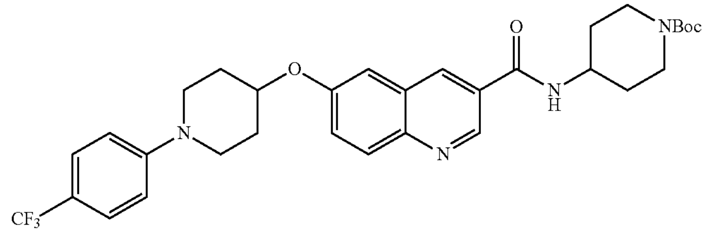 [SMILES: CC(C)(C)OC(=O)N1CCC(NC(=O)c2cnc3ccc(OC4CCN(c5ccc(C(F)(F)F)cc5)CC4)cc3c2)CC1] |
| 2-68 | N-(piperidin-4-yl)-6-(1-(4-(trifluoromethyl)phenyl)piperidin-4-yloxy)quinoline-3-carboxamide | 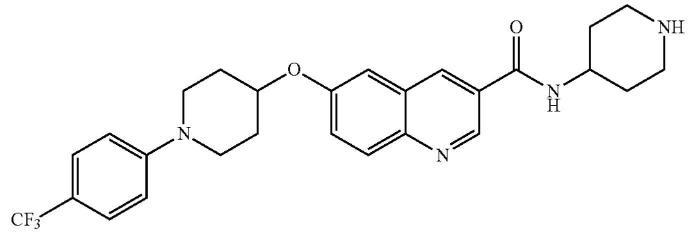 [SMILES: O=C(NC1CCNCC1)c1cnc2ccc(OC3CCN(c4ccc(C(F)(F)F)cc4)CC3)cc2c1] |
| 2-69 | N-(1-(4-cyanobenzyl)piperidin-4-yl)-6-(1-(4-(trifluoromethyl)phenyl)piperidin-4-yloxy)quinoline-3-carboxamide | 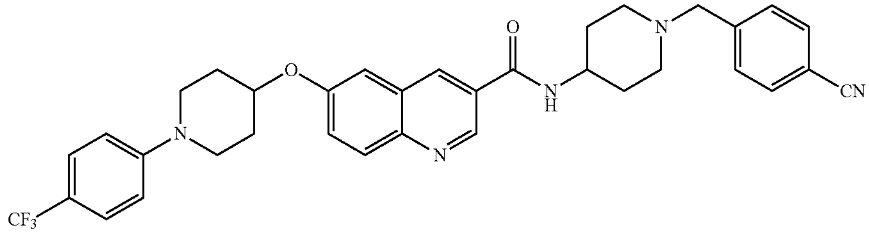 [SMILES: N#Cc1ccc(CN2CCC(NC(=O)c3cnc4ccc(OC5CCN(c6ccc(C(F)(F)F)cc6)CC5)cc4c3)CC2)cc1] |
| 2-70 | N-(1-(4-(trifluoromethyl)benzyl)piperidin-4-yl)-6-(1-(4-(trifluoromethyl)phenyl)piperidin-4-yloxy)quinoline-3-carboxamide | 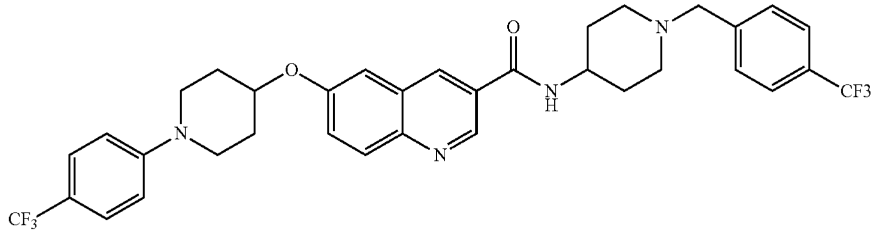 [SMILES: O=C(NC1CCN(Cc2ccc(C(F)(F)F)cc2)CC1)c1cnc2ccc(OC3CCN(c4ccc(C(F)(F)F)cc4)CC3)cc2c1] |

TABLE 2-continued

| No. | Name | Structure |
|---|---|---|
| 2-71 | N-(1-benzylpiperidin-4-yl)-6-(1-(4-(trifluoromethyl)phenyl)piperidin-4-yloxy)quinoline-3-carboxamide | 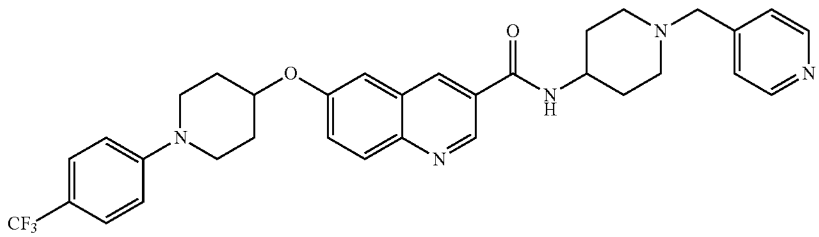 [SMILES: O=C(NC1CCN(Cc2ccncc2)CC1)c1cnc2ccc(OC3CCN(c4ccc(C(F)(F)F)cc4)CC3)cc2c1] |
| 2-72 | N-(1-benzylpiperidin-4-yl)-5-(1-(4-(trifluoromethyl)phenyl)piperidin-4-yloxy)-1H-indole-2-carboxamide | 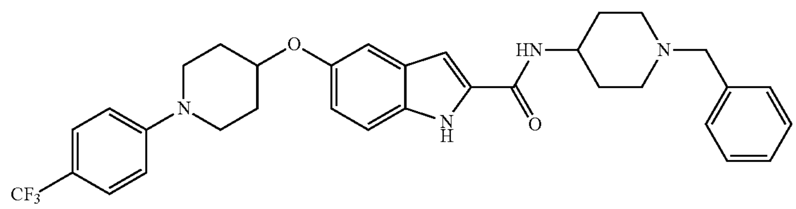 [SMILES: O=C(NC1CCN(Cc2ccccc2)CC1)c1cc2cc(OC3CCN(c4ccc(C(F)(F)F)cc4)CC3)ccc2[nH]1] |

Another aspect of the disclosure provides a method for treating or ameliorating a disorder or condition related to oxidative stress, mitochondrial dysfunction, free radical damage and/or metabolic inefficiency in a subject, the method including administering to the subject an effective amount of a compound having structural formula (3-I):

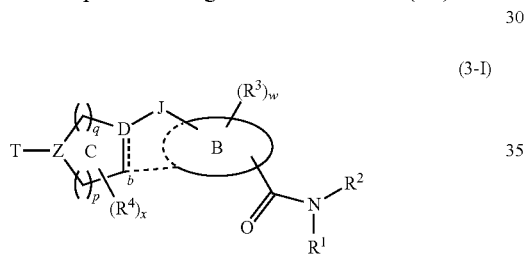

(3-I)

or a pharmaceutically acceptable salt, prodrug or N-oxides thereof (or a solvate or hydrate thereof), wherein
ring system "B" is -(aryl or heteroaryl)-;
ring system "C" is an azacycloalkyl ring in which D is C, CH, $CR^4$, or N,
Z is CH, $CR^4$ or N, provided that at least one of D and Z is N, and
the bond between D and the carbon at the position denoted by "b" is a single bond or a double bond;
J is —O—, —N($R^{38}$)—C(O)—, —C(O)— or absent, provided that:
(a) when J is —O— or —N($R^{38}$)—C(O)—, D is CH or $CR^4$, Z is N, J links ring systems "B" and "C", the dotted line connecting ring system "B" to the carbon denoted by "b" in ring system "C" is absent, and the bond between D and the carbon atom at the position denoted by "b" is a single bond,
(b) when J is —C(O)—, J links ring systems "B" and "C", the dotted line connecting ring "B" to the carbon denoted by "b" in ring system "C" is absent, and the bond between D and the carbon atom at the position denoted by "b" is a single bond,
(c) when J is absent, the dotted line connecting ring system "B" to the carbon denoted by "b" in ring system "C" signifies that ring systems "B" and "C" are fused through the bond connecting D and the carbon atom denoted by "b" in ring system "C", and (d) when J is —O—, the ring system denoted by "B" is other than phenyl, that is, the compound does not have the formula

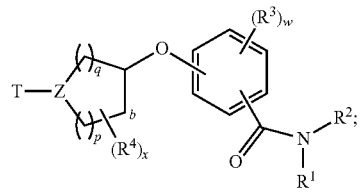

$R^1$ is H, —($C_1$-$C_4$ alkyl), —C(O)—($C_1$-$C_4$ alkyl) or —C(O)O—($C_1$-$C_4$ alkyl), and
$R^2$ is -Hca, -Cak-N($R^9$)-G-$R^{22}$ or —($C_2$-$C_8$ alkyl)-N($R^9$)—$R^{24}$ in which one or two (e.g., non-adjacent) carbons of the ($C_2$-$C_8$ alkyl) are optionally replaced by —O—, —S— or —N($R^9$)—, and $R^{24}$ is —$R^{23}$, -G-$R^{23}$ or —C(O)O—($C_1$-$C_6$ alkyl), provided that two consecutive carbons of the ($C_2$-$C_8$ alkyl) are not replaced by —O—, or
$R^1$ and $R^2$ together with the nitrogen to which they are attached come together to form -Hca;
each $R^3$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-N$R^8R^9$, —($C_0$-$C_6$ alkyl)-O$R^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN;
w is 0, 1, 2, 3 or 4;
each $R^4$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-N$R^8R^9$, —($C_0$-$C_6$ alkyl)-O$R^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, and two $R^4$ on the same carbon optionally combine to form oxo;
p is 0, 1, 2, 3 or 4;
q is 0, 1, 2, 3 or 4, provided that the sum of p and q is 1, 2, 3 or 4;
x is 0 or an integer ≤p+q, wherein when D or Z is $CR^4$, the $R^4$ of D or Z is one of the x $R^4$ groups on ring system "C";

T is —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$ or

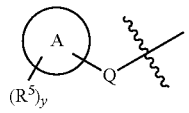

in which
Q is —S(O)$_2$—, L, or ($C_0$-$C_3$ alkyl)-, in which each carbon of the —($C_0$-$C_3$ alkyl)- is optionally and independently substituted with one or two $R^{16}$;
the ring denoted by "A" is heteroaryl, aryl, cycloalkyl or heterocycloalkyl;
each $R^5$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN; and
y is 0, 1, 2, 3 or 4;
in which
each L is independently selected from —$NR^9$C(O)O—, —OC(O)$NR^9$—, —$NR^9$C(O)—$NR^9$—, —$NR^9$C(O)S—, —SC(O)$NR^9$—, —$NR^9$C(O)—, —C(O)—$NR^9$—, —$NR^9$C(S)O—, —OC(S)$NR^9$—, —$NR^9$C(S)—$NR^9$—, —$NR^9$C(S)S—, —SC(S)$NR^9$—, —$NR^9$C(S)—, —C(S)$NR^9$—, —SC(O)$NR^9$—, —$NR^9$C(S)—, —S(O)$_{0-2}$—, —C(O)O, —OC(O)—, —C(S)O—, —OC(S)—, —C(O)S—, —SC(O)—, —C(S)S—, —SC(S)—, —OC(O)O—, —SC(O)O—, —OC(O)S—, —SC(S)O—, —OC(S)S—, —$NR^9$C($NR^2$)$NR^9$—, —$NR^9$SO$_2$—, —SO$_2$$NR^9$— and —$NR^9$SO$_2$$NR^9$—,
each $R^6$, $R^7$, $R^8$ and $R^{10}$ is independently selected from H, —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-($C_0$-$C_6$ alkyl), —($C_0$-$C_6$ alkyl)-$NR^9$—($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl),
each $R^9$ is independently selected from —H, —($C_1$-$C_4$ alkyl), —C(O)—($C_1$-$C_4$ alkyl) and —C(O)O—($C_1$-$C_4$ alkyl),
each G is independently —S(O)$_2$—, L, or —($C_0$-$C_3$ alkyl)-, in which each carbon of the —($C_0$-$C_3$ alkyl)- is optionally and independently substituted with one or two $R^{16}$,
each $R^{16}$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, or two $R^{16}$ on the same carbon combine to form oxo,
$R^{38}$ is independently selected from —H, —($C_1$-$C_4$ alkyl), —C(O)—($C_1$-$C_4$ alkyl) and —C(O)O—($C_1$-$C_4$ alkyl),
$R^{22}$ and $R^{23}$ are each independently Ar or Het,
each Ar is an optionally substituted aryl,
each Het is an optionally substituted heteroaryl,
each Cak is an optionally substituted cycloalkyl,
each Hca is an optionally substituted heterocycloalkyl, and
each alkyl is optionally substituted.

Various embodiments of compounds of structural formula (2-I) suitable for use in the methods described herein are described below. Information regarding these compounds can also be found in U.S. Patent Application Publication no. 2009/0275609, which is hereby incorporated by reference in its entirety.

In certain embodiments of the presently disclosed compounds of structural formula (3-I), J is —O— or —N($R^{38}$)—C(O)— and D is CH or C— substituted with one of the x $R^4$ groups. In other embodiments of the presently disclosed compounds of structural formula (3-I), J is —C(O)—. In certain such embodiments, D is N.

In certain embodiments of the presently disclosed compounds of structural formula (3-I), Z is N and D is C, CH or C— substituted with one of the x $R^4$ groups. In other embodiments, D is N and Z is CH or C— substituted with one of the x $R^4$ groups. In further embodiments, D is N and Z is N.

In certain embodiments of the presently disclosed compounds of structural formula (3-I), $R^{38}$ is —H. In other embodiments, $R^{38}$ is —($C_1$-$C_4$ alkyl), for example methyl, ethyl or propyl. In other embodiments, $R^{38}$ is —C(O)—($C_1$-$C_4$ alkyl), for example acetyl. In other embodiments, $R^{38}$ is —C(O)—O—($C_1$-$C_4$ alkyl)-, for example —C(O)—O-t-butyl. In certain embodiments, no alkyl of $R^{38}$ is substituted with an aryl-, heteroaryl-, cycloalkyl- or heterocycloalkyl-containing group.

In certain embodiments of the presently disclosed compounds of structural formula (3-I) as described above, ring system "B" is not fused to ring system "C" at the position denoted by "b," so that the compounds have structural formula (3-II):

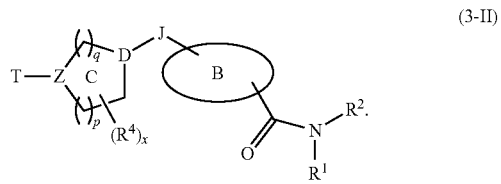

In other embodiments, ring system "B" is fused to ring system "C" at the position denoted by "b"; for example, the compounds can have structural formula (3-III):

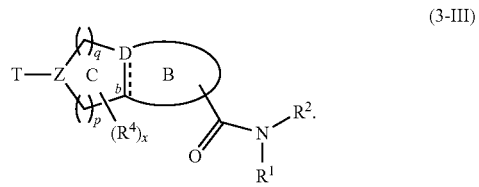

In certain embodiments of the presently disclosed compounds of structural formula (3-I), "B" represents

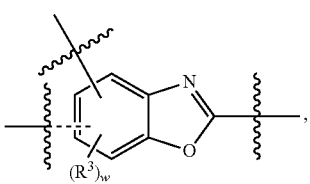

in which the benzo ring is linked or fused to ring system "C" and the dotted line is not a bond but merely indicates that the benzo ring is fused to ring system "C" or not. Examples of such compounds wherein ring system "B" is not fused to ring system "C" are represented by the formula

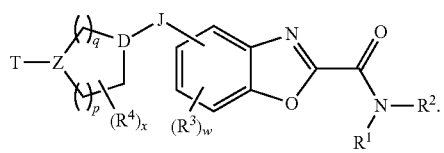

In certain such embodiments, J is —O—, Z is N and D is CH or C— substituted by one of the x $R^4$.

In other embodiments of the presently disclosed compounds of structural formula (3-I), "B" represents

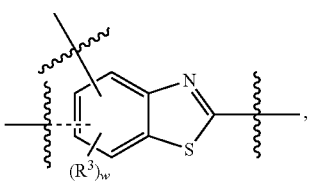

in which the benzo ring is linked or fused to ring system "C" and the dotted line is not a bond but merely indicates that the benzo ring is fused to ring system "C" or not. Examples of such compounds wherein ring system "B" is not fused to ring system "C" are represented by the formula

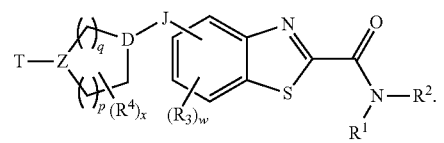

In certain such embodiments, J is —O—, Z is N and D is CH or C— substituted by one of the x $R^4$.

In other embodiments of the presently disclosed compounds of structural formula (3-I), "B" represents

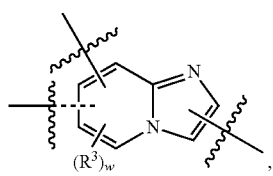

in which the pyrido ring is linked or fused to ring system "C" and the dotted line is not a bond but merely indicates that the pyrido ring is fused to ring system "C" or not. Examples of such compounds wherein ring system "B" is not fused to ring system "C" are represented by the formula

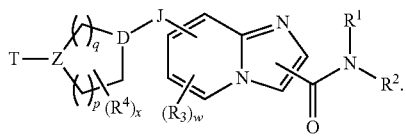

In certain such embodiments, J is —O—, Z is N and D is CH or C— substituted by one of the x $R^4$. Floating bonds indicate attachment on any carbon of the imidazo[1,2-a]pyridine ring system. In some embodiments, for example, the J moiety is on the pyridine ring of the imidazo[1,2-a]pyridine ring system, and the carboxamide (3-I.e., —C(O)—$NR^1R^2$) moiety is on the imidazo ring of the imidazo[1,2-a]pyridine ring system, and any $R^3$ groups can be on either ring of the imidazo[1,2-a]pyridine ring system.

In other embodiments of the presently disclosed compounds of structural formula (3-I), "B" represents

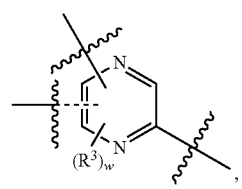

in which the pyrazine ring is linked or fused to ring system "C" and the dotted line is not a bond but merely indicates that the pyrazine ring is fused to ring system "C" or not. Examples of such compounds wherein ring system "B" is not fused to ring system "C" are represented by the formula

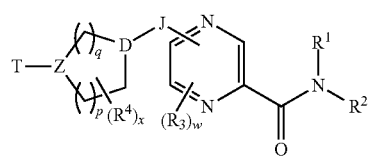

In certain such embodiments, J is —O—, Z is N and D is CH or C— substituted by one of the x $R^4$.

In other embodiments of the presently disclosed compounds of structural formula (3-I), "B" represents

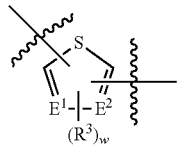

and is not fused to ring system "C", one of $E^1$ and $E^2$ is N and the other is CH, C substituted with the $R^3$, C substituted with the -J-(ring system "C"), or C substituted with the —C(O)—$NR^1R^2$), w is 0 or 1. In certain such embodiments, J is —O—, Z is N and D is CH or C— substituted by one of the x $R^4$.

In other embodiments of the presently disclosed compounds of structural formula (3-I), ring system "B" is

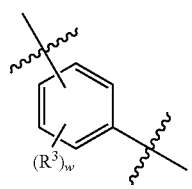

and is not fused to ring system "C". In such embodiments, J is other than O. In certain such embodiments, J is —C(O)—, Z is N, CH or C-substituted by one of the x $R^4$ and D is N. In other such embodiments, J is —N($R^{38}$)—C(O)—, Z is N and D is CH or C— substituted by one of the x $R^4$.

In certain embodiments according to structural formulae (3-I)-(3-III), the sum of p and q is 2 or 3. For example, in one embodiment, the sum of p and q is 2 (e.g., p is 1 and q is 1). In another embodiment, the sum of p and q is 3 (e.g., p is 1 and q is 2).

In other embodiments of the presently disclosed compounds of structural formula (3-I), ring system "B" is a phenyl and is fused to ring system "C" (3-I.e., J is absent), Z is N, D is C, q is 2 and p is 1, such that the compound has structural formula (3-IV):

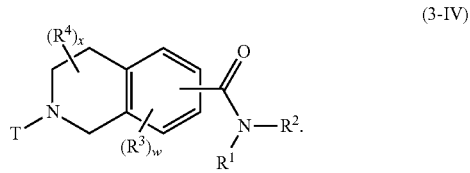

(3-IV)

In certain embodiments of the presently disclosed compounds of structural formulae (3-I)-(3-IV), T is

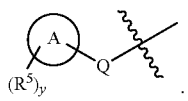

In such embodiments, Q is —S(O)$_2$—, L or —(C$_0$-C$_3$ alkyl)- in which each carbon of the (C$_0$-C$_3$ alkyl) is optionally and independently substituted with one or two $R^{16}$, in which each $R^{16}$ is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-$R^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, and optionally two of $R^{16}$ on the same carbon combine to form oxo. In certain embodiments, each $R^{16}$ is independently selected from —(C$_1$-C$_6$ alkyl), —(C$_1$-C$_6$ haloalkyl) (e.g., difluoromethyl, trifluoromethyl and the like), —(C$_0$-C$_6$ alkyl)-L-$R^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, and two $R^{16}$ on the same carbon optionally combine to form an oxo, in which each $R^7$, $R^8$ and $R^{10}$ is independently selected from H, —(C$_1$-C$_6$ alkyl), —(C$_1$-C$_6$ haloalkyl), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl), and —(C$_0$-C$_6$ alkyl)-S(O)$_{0-2}$—(C$_0$-C$_6$ alkyl), and in which no alkyl or haloalkyl is substituted with an aryl-, heteroaryl-, cycloalkyl- or heterocycloalkyl-containing group. For example, in particular compounds, each $R^{16}$ is —(C$_1$-C$_3$ alkyl), —(C$_1$-C$_3$ haloalkyl), —(C$_0$-C$_3$ alkyl)-L-$R^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN, and two $R^{16}$ on the same carbon optionally combine to form an oxo, in which each $R^7$, $R^8$ and $R^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group. In certain embodiments, Q has at most one $R^{16}$ or oxo substituted thereon. Q can be, for example, an unsubstituted —(C$_0$-C$_3$ alkyl)-. In other embodiments, Q is a (C$_1$-C$_3$ alkyl) having as its only substitution a single oxo group. For example, in certain embodiments, Q is —CH$_2$—; a single bond; —S(O)$_2$—; —C(O)—; or —CH(CH$_3$)—.

In certain embodiments of the compounds of structural formulae (3-I)-(3-IV), the

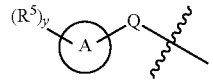

moiety is

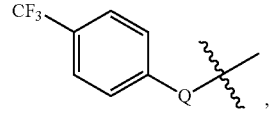

for example, p-(trifluoromethyl)phenyl. In other embodiments, the

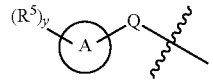

moiety is

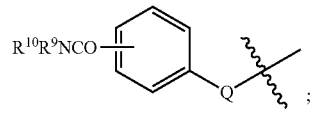

in one such embodiment, Q is a single bond.

The number of substituents on the ring system denoted by "A", y, is 0, 1, 2, 3 or 4. For example, in some embodiments of the presently disclosed compounds of structural formulae (3-I)-(3-IV), y is 0, 1, 2 or 3, such as 1. In one embodiment, y is not zero and at least one $R^5$ is halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ or —C(O)-Hca wherein the Hca contains a ring nitrogen atom through which it is bound to the —C(O)—, and wherein no alkyl, haloalkyl or heterocycloalkyl is substituted by an aryl, heteroaryl, cycloalkyl or heterocycloalkyl-containing group.

In certain embodiments of the presently disclosed compounds of structural formulae (3-I)-(3-IV), each $R^5$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-$S(O)_{0-2}R^{10}$, -halogen, —$NO_2$ and —CN, in which each $R^7$, $R^8$ and $R^{10}$ is independently selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-$S(O)_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^5$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-$S(O)_{0-2}R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-$S(O)_{0-2}$—($C_0$-$C_2$ alkyl), and in which no alkyl or haloalkyl is substituted with an aryl-, heteroaryl-, cycloalkyl- or heterocycloalkyl-containing group.

In one embodiment of the compounds of structural formulae (3-I)-(3-IV), y is 0.

In the presently disclosed compounds of structural formulae (3-I)-(3-IV), the ring system denoted by "A" is heteroaryl, aryl, cycloalkyl or heterocycloalkyl. For example, in one embodiment, the ring system denoted by "A" is an aryl or a heteroaryl. The ring system denoted by "A" can be, for example, a monocyclic aryl or heteroaryl. In one embodiment, when the "A" ring system is aryl, Q is a —($C_0$-$C_3$ alkyl)- optionally substituted with oxo, and optionally substituted with one or more $R^{16}$. For example, Q can be a —($C_1$-$C_3$ alkyl)- having its only substitution a single oxo, or an unsubstituted —($C_0$-$C_3$ alkyl)-. For example, in certain embodiments, Q is —$CH_2$—; a single bond; —$S(O)_2$—; —C(O)—; or —CH($CH_3$)—.

For example, in certain embodiments of the presently disclosed compounds of structural formulae (3-I)-(3-IV), the ring system denoted by "A" is a phenyl. In one embodiment, y is 1 and $R^5$ is attached to the phenyl in the para position relative to Q. In another embodiment, y is 1 and $R^5$ is selected from the group consisting of halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, and in which no ($C_0$-$C_4$ alkyl) or ($C_1$-$C_4$ alkyl) is substituted by an aryl, heteroaryl, cycloalkyl or heterocycloalkyl-containing group. $R^5$ can be, for example, —Cl, —F, cyano, —C(O)$CH_3$, —C(O)OH, —C(O)$NH_2$, trifluoromethyl, difluoromethyl, difluoromethoxy or trifluoromethoxy. In another embodiment, the

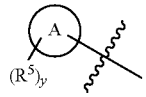

moiety is a 3,4-dihalophenyl.

In another embodiment of the presently disclosed compounds of structural formulae (3-I)-(3-IV), the ring system denoted by "A" is a heteroaryl. For example, in certain embodiments, the ring system denoted by "A" is a pyridyl, a thienyl, or a furanyl. In one embodiment, when the "A" ring system is heteroaryl, Q is a —($C_0$-$C_3$ alkyl)- optionally substituted with oxo, and optionally substituted with one or more $R^{16}$. For example, Q can be a —($C_1$-$C_3$ alkyl)- having its only substitution a single oxo, or an unsubstituted —($C_0$-$C_3$ alkyl)-. In certain embodiments, Q is —$CH_2$—; a single bond; —$S(O)_2$—; —C(O)—; or —CH($CH_3$)—.

In certain embodiments (e.g., when ring system "B" is a phenyl and is fused to ring system "C", J is absent, Z is N, D is carbon, q is 2 and p is 1), T is not —C(O)O—($C_0$-$C_6$ alkyl).

In certain embodiments (e.g., when ring system "B" is a phenyl and is fused to ring system "C", J is absent, Z is N, D is carbon, q is 2 and p is 1), T is not is not —$CH_2$C(O)OH; —NH—$CH_2$—C(O)OH; —O—$CH_2$—C(O)OH; —$CH_2$—$CH_2$—C(O)OH; —CH=CH—C(O)OH; —N(C(O)$CH_3$)—$CH_2$—C(O)OH; =CH—C(O)OH or =CH—$CH_2$—$CH_2$—C(O)OH.

In one embodiment of the presently disclosed compounds, the compound has structural formula (3-V):

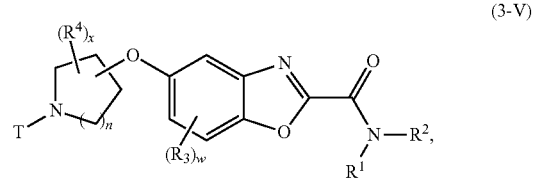

(3-V)

in which n is 1, 2, 3 or 4, and all other variables are defined as described above with reference to structural formulae (3-I)-(3-IV).

In one embodiment of the presently disclosed compounds, the compound has structural formula (3-VI):

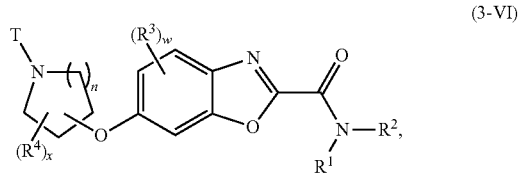

(3-VI)

in which n is 1, 2, 3 or 4, and all other variables are defined as described above with reference to structural formulae (3-I)-(3-IV).

In one embodiment of the presently disclosed compounds, the compound has structural formula (3-VII):

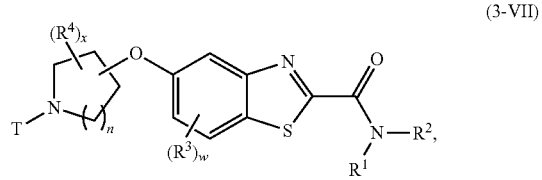

(3-VII)

in which n is 1, 2, 3 or 4, and all other variables are defined as described above with reference to structural formulae (3-I)-(3-IV).

In one embodiment of the presently disclosed compounds, the compound has structural formula (3-VIII):

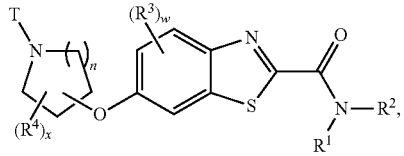

(3-VIII)

in which n is 1, 2, 3 or 4, and all other variables are defined as described above with reference to structural formulae (3-I)-(3-IV).

In one embodiment of the presently disclosed compounds, the compound has structural formula (3-IX):

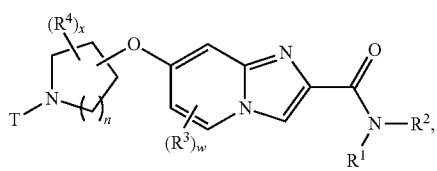

(3-IX)

in which n is 1, 2, 3 or 4, and all other variables are defined as described above with reference to structural formulae (3-I)-(3-IV).

In one embodiment of the presently disclosed compounds, the compound has structural formula (2-X):

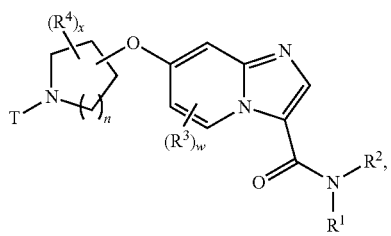

(3-X)

in which n is 1, 2, 3 or 4, and all other variables are defined as described above with reference to structural formulae (3-I)-(3-IV).

In one embodiment of the presently disclosed compounds, the compound has structural formula (3-XI):

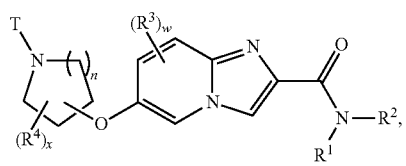

(3-XI)

in which n is 1, 2, 3 or 4, and all other variables are defined as described above with reference to structural formulae (3-I)-(3-IV).

In one embodiment of the presently disclosed compounds, the compound has structural formula (3-XII):

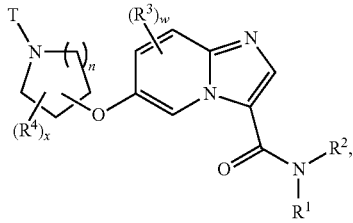

(3-XII)

in which n is 1, 2, 3 or 4, and all other variables are defined as described above with reference to structural formulae (3-I)-(3-IV).

In one embodiment of the presently disclosed compounds, the compound has structural formula (3-XIII):

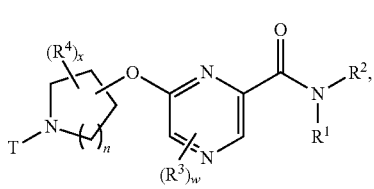

(3-XIII)

in which n is 1, 2, 3 or 4, and all other variables are defined as described above with reference to structural formulae (3-I)-(3-IV).

In one embodiment of the presently disclosed compounds, the compound has structural formula (3-XIV):

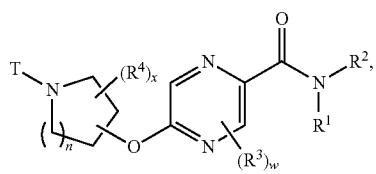

(3-XIV)

in which n is 1, 2, 3 or 4, and all other variables are defined as described above with reference to structural formulae (3-I)-(3-IV).

In one embodiment of the presently disclosed compounds, the compound has structural formula (3-XV):

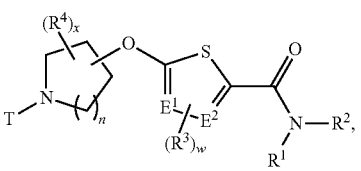

(3-XV)

in which n is 1, 2, 3 or 4, w is 0 or 1, and all other variables are defined as described above with reference to structural formulae (3-I)-(3-IV). For example, in one embodiment, $E^1$ is N and $E^2$ is —CH— or —$CR^3$—. In another embodiment, $E^1$ is —CH— or —$CR^3$— and $E^2$ is N.

In one embodiment of the presently disclosed compounds, the compound has structural formula (3-XVI):

(3-XVI)

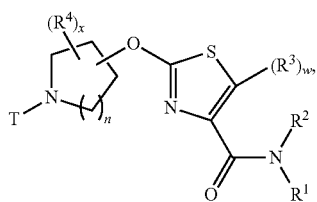

in which n is 1, 2, 3 or 4, w is 0 or 1, and all other variables are defined as described above with reference to structural formulae (3-I)-(3-IV). When w is 0, the ring position shown occupied by $R^3$ bears a hydrogen atom.

In one embodiment of the presently disclosed compounds, the compound has structural formula (3-XVII):

(3-XVII)

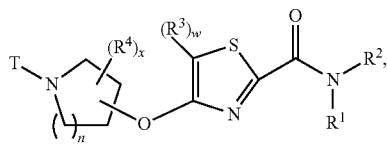

in which n is 1, 2, 3 or 4, w is 0 or 1, and all other variables are defined as described above with reference to structural formulae (3-I)-(3-IV). When w is 0, the ring position shown occupied by $R^3$ bears a hydrogen atom.

In certain embodiments of the compounds disclosed with reference to structural formulae (3-V)-(3-XVII), n is 1 or 2. For example, in one embodiment, n is 2. In another embodiment, n is 1.

For example, in one embodiment of the presently disclosed compounds, the compound has structural formula (3-XVIII):

(3-XVIII)

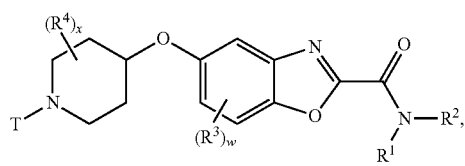

in which all variables are defined as described above with reference to structural formulae (3-I)-(3-IV).

In another embodiment of the presently disclosed compounds, the compound has structural formula (3-XIX):

(3-XIX)

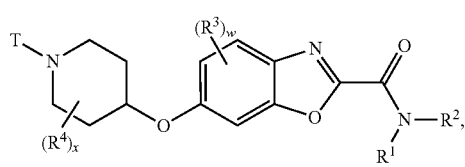

in which all variables are defined as described above with reference to structural formulae (3-I)-(3-IV).

In another embodiment of the presently disclosed compounds, the compound has structural formula (3-XX):

(3-XX)

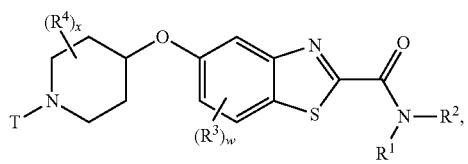

in which all variables are defined as described above with reference to structural formulae (3-I)-(3-IV).

In another embodiment of the presently disclosed compounds, the compound has structural formula (3-XXI):

(3-XXI)

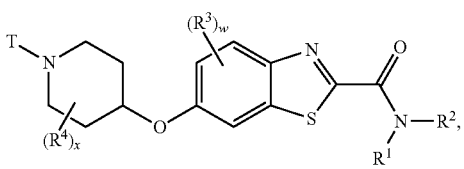

in which all variables are defined as described above with reference to structural formulae (3-I)-(3-IV).

In another embodiment of the presently disclosed compounds, the compound has structural formula (3-XXII):

(3-XXII)

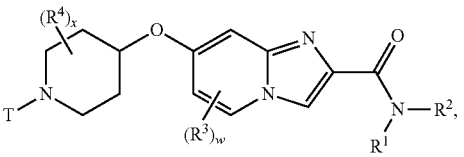

in which all variables are defined as described above with reference to structural formulae (3-I)-(3-IV).

In another embodiment of the presently disclosed compounds, the compound has structural formula (3-XXIII):

(3-XXIII)

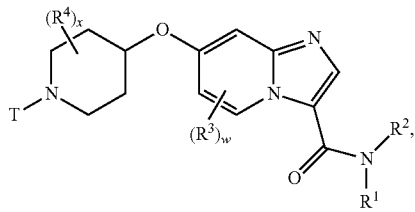

in which all variables are defined as described above with reference to structural formulae (3-I)-(3-IV).

In another embodiment of the presently disclosed compounds, the compound has structural formula (3-XXIV):

(3-XXIV)

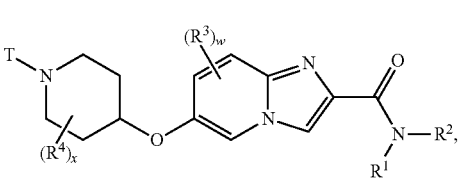

in which all variables are defined as described above with reference to structural formulae (3-I)-(3-IV).

In another embodiment of the presently disclosed compounds, the compound has structural formula (3-XXV):

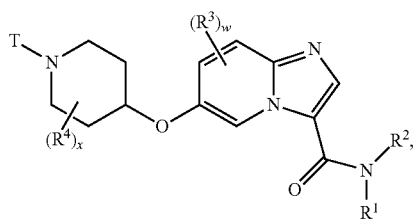

(3-XXV)

in which all variables are defined as described above with reference to structural formulae (3-I)-(3-IV).

In another embodiment of the presently disclosed compounds, the compound has structural formula (3-XXVI):

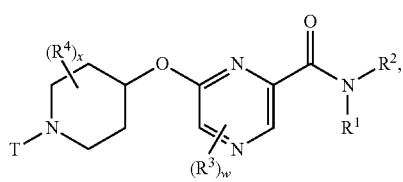

(3-XXVI)

in which all variables are defined as described above with reference to structural formulae (3-I)-(3-IV).

In another embodiment of the presently disclosed compounds, the compound has structural formula (3-XXVII):

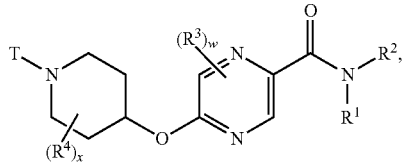

(3-XXVII)

in which all variables are defined as described above with reference to structural formulae (3-I)-(3-IV).

In another embodiment of the presently disclosed compounds, the compound has structural formula (3-XXVIII):

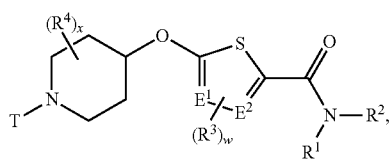

(3-XXVIII)

in which w is 0 or 1 and all other variables are defined as described above with reference to structural formulae (3-I)-(3-IV). When w is 0, the ring position shown occupied by $R^3$ bears a hydrogen atom. In one embodiment, $E^1$ is —CH— or —CR$^3$— and $E^2$ is N. In another embodiment, $E^1$ is N and $E^2$ is —CH— or —CR$^3$—.

In another embodiment of the presently disclosed compounds, the compound has structural formula (3-XXIX):

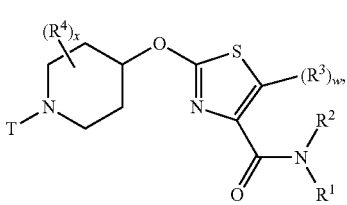

(3-XXIX)

in which w is 0 or 1 and all other variables are defined as described above with reference to structural formulae (3-I)-(3-IV). When w is 0, the ring position shown occupied by $R^3$ bears a hydrogen atom.

In another embodiment of the presently disclosed compounds, the compound has structural formula (3-XXX):

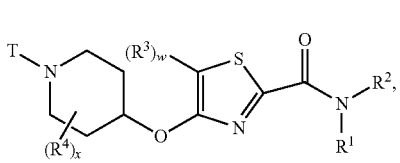

(3-XXX)

in which w is 0 or 1 and all other variables are defined as described above with reference to structural formulae (3-I)-(3-IV). When w is 0, the ring position shown occupied by $R^3$ bears a hydrogen atom.

In one embodiment of the presently disclosed compounds, the compound has structural formula (3-XXXI):

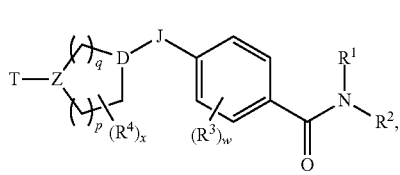

(3-XXXI)

in which all variables are defined as described above with reference to structural formulae (3-I)-(3-IV). In one such embodiment, J is —C(O)—, Z is CH or C substituted with one of the x $R^4$ and D is N. In another such embodiment, J is —C(O)—, Z is N and D is N. In a further such embodiment, J is —N($R^{38}$)—C(O)— (e.g., —NH—C(O)—), Z is N and D is CH or C substituted with one of the x $R^4$.

In another embodiment of the presently disclosed compounds, the compound has structural formula (3-XXXII):

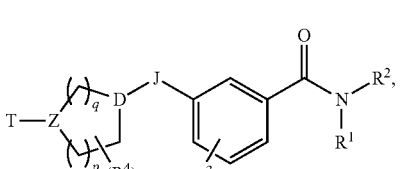

(3-XXXII)

in which all variables are defined as described above with reference to structural formulae (3-I)-(3-IV). In one such embodiment, J is —C(O)—, Z is CH or C substituted with one of the x R⁴ and D is N. In another such embodiment, J is —C(O)—, Z is N and D is N. In a further such embodiment, J is —N(R³⁸)—C(O)— (e.g., —NH—C(O)—), Z is N and D is CH or C substituted with one of the x R⁴.

In another embodiment of the presently disclosed compounds, the compound has structural formula (3-XXXIII):

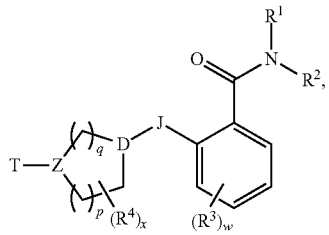
(3-XXXIII)

in which all variables are defined as described above with reference to structural formulae (3-I)-(3-IV). In one such embodiment, J is —C(O)—, Z is CH or C substituted with one of the x R⁴ and D is N. In another such embodiment, J is —C(O)—, Z is N and D is N. In a further such embodiment, J is —N(R³⁸)—C(O)— (e.g., —NH—C(O)—), Z is N and D is CH or C substituted with one of the x R⁴.

In certain embodiments according to structural formulae (3-XXXI)-(3-XXXIII), the sum of p and q is 2 or 3. For example, in one embodiment, the sum of p and q is 2 (e.g., p is 1 and q is 1). In another embodiment, the sum of p and q is 3 (e.g., p is 1 and q is 2).

For example, in one embodiment of the presently disclosed compounds, the compound has structural formula (3-XXXIV):

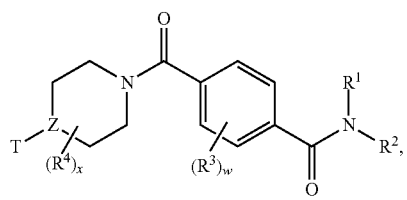
(3-XXXIV)

in which all variables are defined as described above with reference to structural formulae (3-I)-(3-IV). In one such embodiment, Z is N. In another such embodiment, Z is CH or C substituted with one of the x R⁴.

In another embodiment of the presently disclosed compounds, the compound has structural formula (3-XXXV):

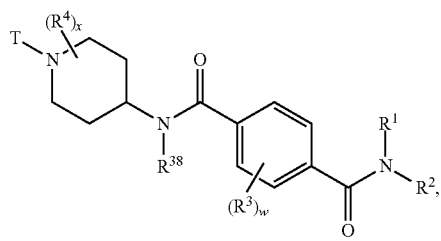
(3-XXXV)

in which all variables are defined as described above with reference to structural formulae (3-I)-(3-IV).

In another embodiment of the presently disclosed compounds, the compound has structural formula (3-XXXVI):

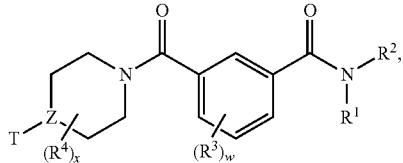
(3-XXXVI)

in which all variables are defined as described above with reference to structural formulae (3-I)-(3-IV). In one such embodiment, Z is N. In another such embodiment, Z is CH or C substituted with one of the x R⁴.

For example, in one embodiment of the presently disclosed compounds, the compound has structural formula (3-XXXVII):

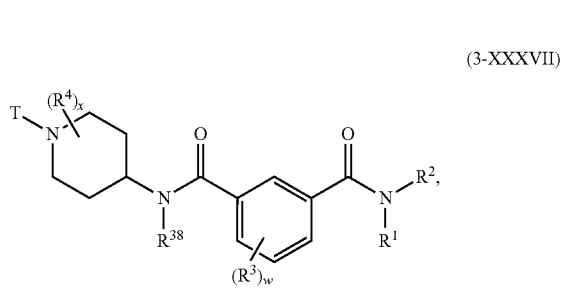
(3-XXXVII)

in which all variables are defined as described above with reference to structural formulae (3-I)-(3-IV).

For example, in one embodiment of the presently disclosed compounds, the compound has structural formula (3-XXXVIII):

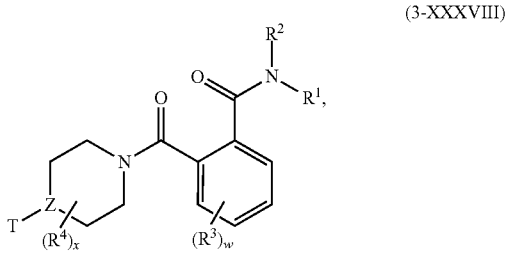
(3-XXXVIII)

in which all variables are defined as described above with reference to structural formulae (3-I)-(3-IV). In one such embodiment, Z is N. In another such embodiment, Z is CH or C substituted with one of the x R⁴.

In another embodiment of the presently disclosed compounds, the compound has structural formula (3-XXXIX):

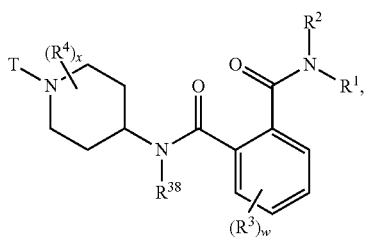
(3-XXXIX)

in which all variables are defined as described above with reference to structural formulae (3-I)-(3-IV).

In one embodiment of the presently disclosed compounds, the compound has structural formula (3-XL):

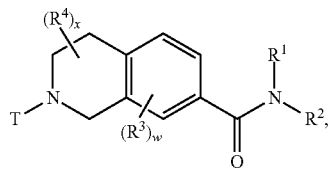
(3-XL)

in which all variables are defined as described above with reference to structural formulae (3-I)-(3-IV).

In one embodiment of the presently disclosed compounds, the compound has structural formula (3-XLI):

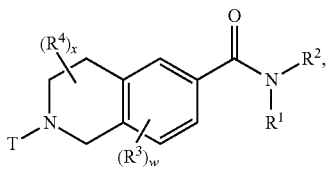
(3-XLI)

in which all variables are defined as described above with reference to structural formulae (3-I)-(3-IV).

In one embodiment of the presently disclosed compounds, the compound has structural formula (3-XLII):

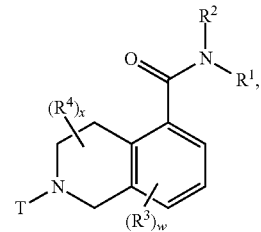
(3-XLII)

in which all variables are defined as described above with reference to structural formulae (3-I)-(3-IV).

In one embodiment of the presently disclosed compounds, the compound has structural formula (3-XLIII):

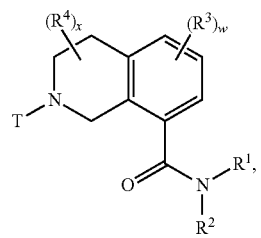
(3-XLIII)

in which all variables are defined as described above with reference to structural formulae (34)-(3-IV).

In certain embodiments of the presently disclosed compounds of structural formulae (3-I)-(3-XLIII), $R^1$ is H, —($C_1$-$C_4$ alkyl), —C(O)—($C_1$-$C_4$ alkyl) or —C(O)O—($C_1$-$C_4$ alkyl), and $R^2$ is -Hca, -Cak-N($R^9$)-G-$R^{22}$ or —($C_2$-$C_8$ alkyl)-N($R^9$)—$R^{24}$ in which one or two (for example, non-adjacent) carbons of the ($C_2$-$C_8$ alkyl) are optionally replaced by —O—, —S— or —N($R^9$)—, and $R^{24}$ is —$R^{23}$, -G-$R^{23}$ or —C(O)O—($C_1$-$C_6$ alkyl), provided that two consecutive carbons of the ($C_2$-$C_8$ alkyl) are not replaced by —O—. For example, in one embodiment, $R^1$ is H, —($C_1$-$C_4$ alkyl), —C(O)—($C_1$-$C_4$ alkyl) or —C(O)O—($C_1$-$C_4$ alkyl), and $R^2$ is -Hca.

In certain embodiments of the presently disclosed compounds of any of structural formulae (3-I)-(3-XLIII), $R^1$ is —H. In other embodiments, $R^1$ is ($C_1$-$C_4$ alkyl), for example methyl, ethyl, n-propyl or isopropyl.

In certain embodiments of the presently disclosed compounds of any structural formulae (3-I)-(3-XLIII), $R^2$ is -Hca. In certain embodiments, $R^2$ is an optionally-substituted monocyclic heterocycloalkyl.

In certain of the presently disclosed compounds of any structural formulae (3-I)-(3-XLIII), $R^2$ is -(optionally-substituted azetidinyl), -(optionally-substituted pyrrolidinyl), -(optionally-substituted piperidinyl) or -(optionally-substituted azepanyl). For example, $R^2$ can be -(optionally substituted piperidinyl) or -(optionally substituted pyrrolidinyl). In one embodiment, $R^2$ is -(optionally substituted piperidinyl). In another embodiment, $R^2$ is -(optionally substituted pyrrolidinyl).

In certain particular embodiments of the presently disclosed compounds of any of structural formulae (3-I)-(3-XLIII), $R^2$ is -(optionally-substituted azetidin-3-yl), -(optionally substituted piperidin-4-yl), -(optionally substituted pyrrolidin-3-yl) or -(optionally-substituted azepan-4-yl). For example, in one embodiment, $R^2$ is -(optionally substituted piperidin-4-yl). In another embodiment, $R^2$ is -(optionally substituted pyrrolidin-3-yl).

In certain embodiments of the presently disclosed compounds of any of structural formulae (3-I)-(3-XLIII), the azetidinyl, pyrrolidinyl, piperidinyl and azepanyl $R^2$ moieties described above are substituted at their 1-positions. For example, in one embodiment, $R^2$ is substituted at its 1-position with —($C_0$-$C_3$ alkyl)-Ar or —($C_0$-$C_3$ alkyl)-Het, for example -(unsubstituted $C_0$-$C_3$ alkyl)-Ar or -(unsubstituted $C_0$-$C_3$ alkyl)-Het. For example, in one particular embodiment, the azetidinyl, pyrrolidinyl, piperidinyl or azepanyl $R^2$ moiety is substituted at its 1-position with an optionally substituted benzyl or an optionally substituted phenyl. In another embodiment, the azetidinyl, pyrrolidinyl, piperidinyl or azepanyl $R^2$ moiety is substituted at its 1-position with a benzyl substituted with an electron withdrawing group; or with a pyridinylmethyl optionally substituted with an electron withdrawing group. For example, the benzyl or pyridinylmethyl can be substituted with an electron withdrawing group selected from the group consisting of halo, cyano, —($C_1$-$C_4$ fluoroalkyl), —O—($C_1$-$C_4$ fluoroalkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), —S(O)$_2$O—($C_0$-$C_4$ alkyl), $NO_2$ and —C(O)-Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group. In other embodiments, the azetidinyl, pyrrolidinyl, piperidinyl or azepanyl $R^2$ moiety is substituted at its 1-position with an unsubstituted benzyl or an unsubstituted phenyl.

In other embodiments of the compounds disclosed herein having any of structural formulae (3-I)-(3-XLIII), the azetidinyl, pyrrolidinyl, piperidinyl or azepanyl $R^2$ moiety is substituted at its 1-position with an optionally substituted pyridinylmethyl, an optionally substituted furanylmethyl, an optionally substituted thienylmethyl, an optionally substituted oxazolylmethyl, or an optionally substituted imidazolylmethyl. For example, the azetidinyl, pyrrolidinyl, piperidinyl or azepanyl $R^2$ moiety can be substituted with an unsubstituted pyridinylmethyl, an unsubstituted furanylmethyl, an unsubstituted thienylmethyl, an unsubstituted oxazolylmethyl, or an unsubstituted imidazolylmethyl. In other embodiments, the azetidinyl, pyrrolidinyl, piperidinyl or azepanyl $R^2$ moiety can be substituted with an pyridinylmethyl, furanylmethyl, thienylmethyl, oxazolylmethyl or imidazolylmethyl substituted with an electron withdrawing group as described above.

In certain embodiments of the compounds disclosed herein having any of structural formulae (3-I)-(3-XLIII), the azetidinyl, pyrrolidinyl, piperidinyl or azepanyl $R^2$ moiety is substituted at its 1-position with -L-Ar or -L-Het, in which Ar and Het can be, for example, as described above with reference to —($C_0$-$C_3$ alkyl)-Ar or —($C_0$-$C_3$ alkyl)-Het. In one such embodiment, L is —C(O)—$NR^9$—, such as —C(O)—NH—.

In other embodiments of the presently disclosed compounds of any of structural formulae (3-I)-(3-XLIII), the azetidinyl, pyrrolidinyl, piperidinyl or azepanyl $R^2$ moiety is substituted at its 1-position with —C(O)—O($C_0$-$C_6$ alkyl), —C(O)—Het, —C(O)—Ar, —$S(O)_2$-Het, —$S(O)_2$—Ar or —$S(O)_{2-0}$($C_0$-$C_6$ alkyl), in which Ar and Het can be, for example, as described above with reference to —($C_0$-$C_3$ alkyl)-Ar or —($C_0$-$C_3$ alkyl)-Het. In one embodiment, the azetidinyl, pyrrolidinyl, piperidinyl or azepanyl $R^2$ moiety is substituted at its 1-position with —C(O)—Het or —C(O)—Ar; in another embodiment, it is substituted at its 1-position with —$S(O)_2$-Het or —$S(O)_2$—Ar. For example, in certain embodiments, the azetidinyl, pyrrolidinyl, piperidinyl or azepanyl $R^2$ moiety is substituted at its 1-position with an optionally-substituted benzoyl (e.g., substituted with an electron withdrawing group as described above); or with an optionally-substituted nicotinyl, isonicotinyl or picolinyl (e.g., optionally substituted with an electron withdrawing group as described above). In other embodiments, the azetidinyl, pyrrolidinyl, piperidinyl or azepanyl $R^2$ moiety is substituted at its 1-position with an unsubstituted benzoyl; or an unsubstituted nicotinoyl, isonicotinoyl or picolinoyl.

In certain embodiments, $R^2$ is an optionally-substituted bridged azacycloalkyl or diazacycloalkyl, for example, a bridged azabicyclohexyl, a bridged azabicycloheptyl, a bridged azabicyclooctyl, a bridged diazabicyclohexyl, a bridged diazabicycloheptyl or a bridged diazabicyclooctyl. Particular examples of such $R^2$ moieties include optionally substituted azabicyclo[2.2.2]octyl, optionally substituted azabicyclo[3.2.1]octyl, and optionally substituted 2,5-diazabicyclo[2.2.1]heptyl.

When $R^2$ is a bridged azacycloalkyl or diazacycloalkyl, it can be substituted as described above with reference to the azetidinyl, pyrrolidinyl, piperidinyl and azepanyl $R^2$ moieties. For example, a bridged azacycloalkyl or diazacycloalkyl $R^2$ moiety can be substituted (e.g., at a nitrogen) with —($C_0$-$C_3$ alkyl)-Ar, —($C_0$-$C_3$ alkyl)-Het, -L-Ar, -L-Het, —C(O)—O($C_0$-$C_6$ alkyl), —C(O)—Het, —C(O)—Ar, —$S(O)_2$-Het, —$S(O)_2$—Ar or —$S(O)_2$—O($C_0$-$C_6$ alkyl), as described above.

In certain embodiments of the compounds of any of structural formulae (3-I)-(3-XLIII), $R^2$ is -Cak-N($R^9$)-G-$R^{22}$, as described above. For example, in one embodiment of the disclosed compounds, $R^2$ has the structure

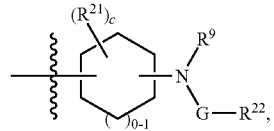

in which c is 0, 1, 2, 3 or 4, and each $R^{21}$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-$S(O)_{0-2}R^{10}$, -halogen, —$NO_2$ and —CN, and two $R^{21}$ on the same carbon optionally combine to form oxo. In certain embodiments of the presently disclosed compounds, each $R^{21}$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-$S(O)_{0-2}R^{10}$, -halogen, —$NO_2$ and —CN and two $R^{21}$ on the same carbon optionally combine to form oxo, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-$S(O)_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^{21}$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-$S(O)_{0-2}R^{10}$, -halogen, —$NO_2$ and —CN and two $R^{21}$ on the same carbon optionally combine to form oxo, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-$S(O)_{0-2}$—($C_0$-$C_2$ alkyl), and in which no alkyl or haloalkyl is substituted with an aryl-, heteroaryl-, cycloalkyl- or heterocycloalkyl-containing group. In certain embodiments, c is 1 or 2. In other embodiments, c is 0. In certain embodiments, $R^9$ is H. In certain embodiments, G is a single bond. In certain embodiments of the presently disclosed compounds, $R^{22}$ is not substituted with an aryl-, heteroaryl-, cycloalkyl- or heterocycloalkyl-containing group. In certain embodiments of the presently disclosed compounds, $R^{23}$ is not substituted with an aryl-, heteroaryl-, cycloalkyl- or heterocycloalkyl-containing group.

In one embodiment of compounds of any of structural formulae (3-I)-(3-XLIII), $R^2$ has the structure

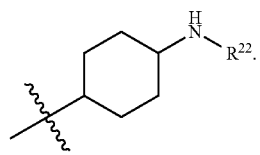

In certain embodiments of the compounds of any of structural formulae (3-I)-(3-XLIII), $R^2$ is —($C_2$-$C_8$ alkyl)-N($R^9$)—$R^{24}$ in which one or two carbons of the ($C_2$-$C_8$ alkyl) are optionally replaced by —O— or —N($R^9$)— and $R^{24}$ is —$R^{23}$, -$GR^{23}$ or —C(O)O—($C_1$-$C_6$ alkyl). In certain embodiments, the ($C_2$-$C_8$ alkyl) is unsubstituted and no carbon is replaced by —O— or —N($R^9$)—. For example, in one embodiment, $R^2$ is —$CH_2$—$CH_2$—$CH_2$—N($R^9$)—$R^{24}$ or —$CH_2$—$CH_2$—$CH_2$—$CH_2$—N($R^9$)—$R^{24}$. In other embodiments, the ($C_2$-$C_8$ alkyl) is substituted and/or one or two carbons are replaced by —O— or —N($R^9$)—. For example, in one embodiment, $R^2$ is —$CH_2$—$CH_2$—O—$CH_2$—$CH_2$—N($R^9$)—$R^{24}$; —$CH_2$—$CH(CH_3)$—N($R^9$)—$R^{24}$; or —$CH_2$—$CH_2$—O—$CH_2$—$C(O)$—N($R^9$)—$R^{24}$. In certain embodiments, $R^9$ is H. In certain embodiments, $R^{24}$ is Ar or Het. In certain embodiments, $R^{24}$ is not substituted with an aryl-, heteroaryl-, cycloalkyl- or heterocycloalkyl-containing group. In certain embodiments, the ($C_2$-$C_8$ alkyl) is a ($C_2$-$C_5$ alkyl).

In certain embodiments (e.g., when rings system "B" is

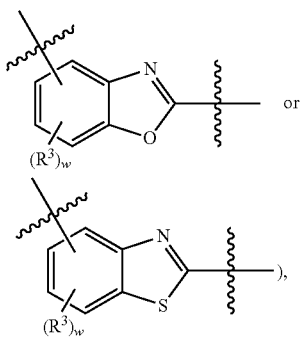

when $R^2$ is an azabicycloalkyl moiety (e.g., a 1-azabicycloheptyl, a 1-azabicyclooctyl, a 1-azabicyclononyl or a 1-azabicyclodecyl), $R^2$ is not vicinally substituted (3-I.e., at the position next to the amide nitrogen) with —($C_0$-$C_4$)-Het.

In certain embodiments (e.g., when rings system "B" is

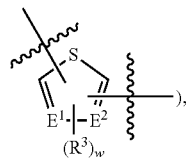

$R^2$ is not a benzo-, pyrido-, pyrimido-, pyrazino- or pyridazino-fused azacycloalkyl. In other embodiments, $R^2$ is not 7-azabicyclo[2.2.1]hept-2-yl. In other embodiments, $R^2$ is not a quinuclidin-3-yl moiety.

In certain embodiments (e.g., when "B" represents

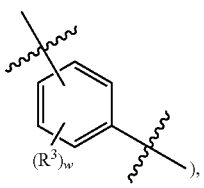

$R^2$ is not a 4,5-dihydroisoxazol-4-yl moiety or an optionally substituted optionally ring-fused azetidin-2-on-3-yl moiety. In one embodiment, $R^2$ is not an oxo-substituted heterocycloalkyl.

In certain embodiments of the presently disclosed compounds, $R^1$ and $R^2$ together with the nitrogen to which they are attached (3-I.e., the carboxamide nitrogen) come together to form Hca. $R^1$, $R^2$ and the nitrogen can come together to form, for example, an optionally-substituted monocyclic azacycloalkyl or monocyclic diazacycloalkyl, such as a piperidine, a pyrrolidine, a piperazine or an imidazolidine. In other embodiments, $R^1$ and $R^2$ come together to form an optionally-substituted bridged azacycloalkyl or diazacycloalkyl, for example, a bridged azabicyclohexyl, a bridged azabicycloheptyl, a bridged azabicyclooctyl, a bridged diazabicyclohexyl, a bridged diazabicycloheptyl or a bridged diazabicyclooctyl. Particular examples of such $R^2$ moieties include azabicyclo[2.2.2]octyl, azabicyclo[3.2.1]octyl, and 2,5-diazabicyclo[2.2.1]heptyl.

When $R^1$, $R^2$ and the nitrogen come together to form Hca, the Hca can be substituted as described above with reference to the azetidinyl, pyrrolidinyl, piperidinyl and azepanyl $R^2$ moieties. For example, the heterocycloalkyl can be substituted with —($C_0$-$C_3$ alkyl)-Ar, —($C_0$-$C_3$ alkyl)-Het, -L-Ar, -L-Het, —C(O)—O($C_0$-$C_6$ alkyl), —C(O)—Het, —C(O)—Ar, —S(O)$_2$-Het, —S(O)$_2$—Ar or —S(O)$_{2\text{-}0}$($C_0$-$C_6$ alkyl), as described above. When $R^1$ and $R^2$ come together to form a diazacycloalkyl, it can be substituted at a nitrogen atom.

For example, in certain embodiments, the —C(O)—$NR^1R^2$ moiety is

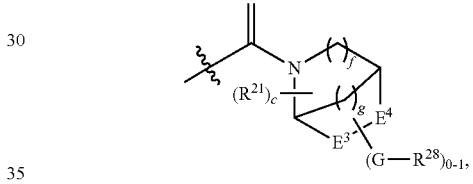

in which f is 0 or 1; g is 0, 1 or 2; c is 0, 1, 2, 3 or 4; $R^{28}$ is Ar or Het; $E^3$ is NH, N substituted by one of the c $R^{21}$, N substituted by the -G-$R^{28}$, $CH_2$, CH substituted by one of the c $R^{21}$, CH substituted by the -G-$R^{28}$, or C substituted by one of the c $R^{21}$ and the -G-$R^{28}$; and $E^4$ is absent, NH, N substituted by one of the c $R^{21}$, N substituted by the -G-$R^{28}$, $CH_2$, CH substituted by one of the c $R^{21}$, CH substituted by the -G-$R^{28}$, or C substituted by one of the c $R^{21}$ and the -G-$R^{28}$, provided that both $E^3$ and $E^4$ are not N. When g is 0, $R^1$, $R^2$ and the nitrogen come together to form a monocyclic azacycloalkyl or diazacycloalkyl. In other embodiments, when g is 1 or 2, $R^1$, $R^2$ and the nitrogen come together to form a bridged bicyclic azacycloalkyl or diazacycloalkyl. The c $R^{21}$ moieties can be disposed anywhere on the azacycloalkyl or diazacycloalkyl ring system. Each $R^{21}$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-N$R^8R^9$, —($C_0$-$C_6$ alkyl)-O$R^{10}$, —($C_0$-$C_6$ alkyl)-C(O)$R^{10}$, —($C_0$-$C_6$ alkyl)-S(O)$_{0\text{-}2}R^{10}$, -halogen, —$NO_2$ and —CN, and two $R^{21}$ on the same carbon optionally combine to form oxo. In certain embodiments of the presently disclosed compounds, each $R^{21}$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-N$R^8R^9$, —($C_0$-$C_6$ alkyl)-O$R^{10}$, ($C_0$-$C_6$ alkyl)-C(O)$R^{10}$, —($C_0$-$C_6$ alkyl)-S(O)$_{0\text{-}2}R^{10}$, -halogen, —$NO_2$ and —CN and two $R^{21}$ on the same carbon optionally combine to form oxo, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_0$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^{21}$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, ($C_0$-$C_3$ alkyl)-S(O)$_{0-2}R^{10}$, -halogen, —$NO_2$ and —CN and two $R^{21}$ on the same carbon optionally combine to form oxo, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. In certain embodiments, c is 1 or 2. In other embodiments, c is 0. In certain embodiments, G is a single bond, $CH_2$, or C(O). In certain embodiments of the presently disclosed compounds, $R^{28}$ is not substituted with an aryl-, heteroaryl-, cycloalkyl- or heterocycloalkyl-containing group. In one embodiment, $R^{28}$ is monocyclic aryl or heteroaryl substituted with 0-3 substitutents selected from halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl) and $NO_2$, in which each alkyl is not further substituted. The -G-$R^{28}$ moiety, when present, can in some embodiments be as described below for -G-$R^{17}$.

For example, in certain embodiments, the —C(O)—$NR^1R^2$ moiety is

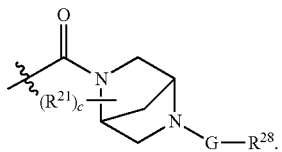

In the compounds of any of structural formulae (3-I)-(3-XLIII), the number of substituents on ring system "B", w, is 0, 1, 2 or 3. For example, in one embodiment, w is 0, 1 or 2. In another embodiment, w is 0. In other embodiments, w is at least 1, and at least one $R^3$ is selected from the group consisting of halo, cyano, —($C_1$-$C_4$ fluoroalkyl), —O—($C_1$-$C_4$ fluoroalkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), —S(O)$_2$O—($C_0$-$C_4$ alkyl), $NO_2$ and —C(O)-Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group. For example, in certain embodiments, at least one $R^3$ is halo (e.g., chloro) or —($C_1$-$C_4$ alkyl) (e.g., methyl, ethyl or propyl). In certain embodiments, an $R^3$ is substituted on the "B" ring system at a 6-membered aromatic ring position in the meta position relative to the J moiety.

In certain embodiments of the compounds of any of structural formulae (3-I)-(3-XLIII), each $R^3$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl), and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^3$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. For example, in certain embodiments, each $R^3$ is halo (e.g., chloro) or —($C_1$-$C_4$ alkyl) (e.g., methyl, ethyl or propyl).

In certain embodiments of the compounds of any of structural formulae (3-I)-(3-XLIII), w is at least one, and at least one $R^3$ is —$NR^8R^9$. For example, in one embodiment, w is 1. In certain such embodiments, $R^3$ is substituted on the "B" ring system at a 6-membered aromatic ring position in the meta position relative to the J moiety.

In other embodiments of the compounds of any of structural formulae (3-I)-(3-XLIII), w is at least one, and at least one $R^3$ is —($C_0$-$C_3$ alkyl)-$Y^1$—($C_1$-$C_3$ alkyl)-$Y^2$—($C_0$-$C_3$ alkyl), in which each of $Y^1$ and $Y^2$ is independently L, —O—, —S— or —$NR^9$—. For example, in one embodiment, w is 1. In certain such embodiments, $R^3$ is substituted on the "B" ring system at a 6-membered aromatic ring position in the meta position relative to the J moiety. In one particular embodiment, $R^3$ is —$CH_2$—N($CH_3$)—$CH_2$—C(O)—$OCH_3$.

In certain embodiments in which ring system "B" is

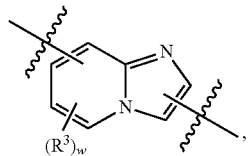

the imidazo portion of the central imidazo[1,2-a]pyridine ring system has no substitutions other than the carboxamide substitution. In another embodiment, no $R^3$ at the 2-position of the imidazo[1,2-a]pyridine core is —($C_1$ alkyl)-N($R^8$)-(5,6,7,8-tetrahydroquinolin-8-yl); —($C_1$ alkyl)-N($R^8$)-(6,7-dihydro-5H-cyclopenta[b]pyridin-7-yl); —($C_1$ alkyl)-N($R^8$)-(6,7,8,9-tetrahydro-5H-cyclohepta[b]pyridin-9-yl); —($C_1$ alkyl)-N($R^8$)-(2,3-dihydrofuro[3,2-b]pyridin-3-yl); —($C_1$ alkyl)-N($R^8$)-(3,4-dihydro-2H-pyrano[3,2-b]pyridin-4-yl); or —($C_1$ alkyl)-N($R^8$)-(6,7,8,9-tetrahydrooxepino[3,2-b]pyridin-9-yl). In another embodiment, the compound does not have two $R^3$ moieties that include Ar or Het as part of each of the moieties' structure. In another embodiment, no $R^3$ at the 3-position of the imidazo[1,2-a]pyridine core is Het.

In certain embodiments in which ring system "B" is

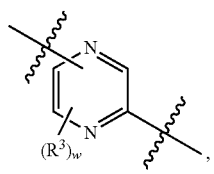

the compound does not have two $R^3$ moieties that include Ar or Het in the moieties' structure. In another embodiment, when an $R^3$ is —$NR^9$—($C_0$-$C_6$ alkyl)-Ar, —$NR^9$—($C_0$-$C_6$ alkyl)-Het, —$NR^9$—Hca, —O—($C_0$-$C_6$ alkyl)-Ar or —O—($C_0$-$C_6$ alkyl)-Het, it is not substituted on the pyrazine core at a position ortho to (3-I.e., on the carbon adjacent to) the amide. In another embodiment, when an $R^3$ is —Ar or -Het, it is substituted on the pyrazine core at a position para to (3-I.e., directly across the ring from) the amide.

In certain embodiments in which ring system "B" is

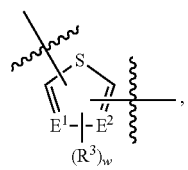

when $R^3$ is ($C_0$-$C_4$ alkyl)-O—($C_0$-$C_4$ alkyl)-(optionally-substituted phenyl); ($C_0$-$C_4$ alkyl)-S(O)$_{0-2}$—($C_0$-$C_4$ alkyl)-(optionally-substituted phenyl) or ($C_0$-$C_4$ alkyl)-S(O)$_{0-2}$—($C_0$-$C_4$ alkyl)-O-(optionally-substituted phenyl), it is not at the 2 position of the thiazole core (3-I.e., not on the carbon between the N and the S of the thiazole). In one embodiment, the compound does not have two $R^3$ moieties that include Ar or Het in the moieties' structure.

In the presently disclosed compounds of any of structural formulae (3-I)-(3-XLIII), the number of substituents on ring system "C", x, is 0 or an integer less than or equal to the sum of p and q. when D or Z is $CR^4$, the $R^4$ of D or Z is one of the x $R^4$ groups on ring system "C". In one embodiment, x is 0, 1, 2 or 3. For example, x can be 0, or can be 1 or 2.

In certain embodiments of the presently disclosed compounds of any of structural formula (3-I)-(3-XLIII), two $R^4$ groups combine to form an oxo. The oxo can be bound, for example, at the position alpha to a nitrogen of ring system "C". In other embodiments, no two $R^4$ groups combine to form an oxo.

In certain embodiments of the presently disclosed compounds of any of structural formulae (3-I)-(3-XLIII), when x is 4, not all four $R^4$ groups are ($C_1$-$C_6$ alkyl).

In certain embodiments of the presently disclosed compounds of any of structural formulae (3-I)-(3-XLIII), each $R^4$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-$NR^8R^9$, ($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^4$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O) $R^{10}$, —($C_0$-$C_3$ alkyl)-S(O)$_{0-2}R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group.

In certain embodiments, the presently disclosed compounds have the structural formula (3-XLIV):

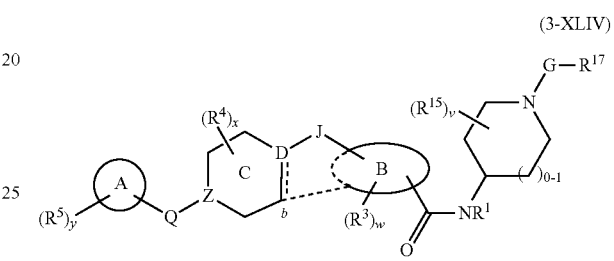

(3-XLIV)

in which Q and G are each independently a bond, —$CH_2$—, —C(H)($R^{16}$)—, —C($R^{16}$)$_2$—, L (e.g., —C(O)—$NR^9$— or —$NR^9$—C(O)—) or —S(O)$_2$—; v is 0, 1, 2, 3 or 4; each $R^{15}$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, and two $R^{15}$ on the same carbon optionally combine to form oxo; $R^{17}$ is Het or Ar, and all other variables are defined as described above with reference to any of structural formula (3-I)-(3-XLIII). In one embodiment, Q is a single bond. In another embodiment, Q is —$CH_2$—. In other embodiments, Q is —C(O)— or —S(O)$_2$—. In certain embodiments, G is —$CH_2$—. In other embodiments, G is —C(O)— or —S(O)$_2$—. In other embodiments, G is —$CH(CH_3)$—. In other embodiments, G is —C(O)—NH—. The above-recited Q and G moieties can be combined in any possible combination. For example, in one embodiment, Q is a single bond and G is —$CH_2$— or —C(O)—. As described above, in certain embodiments, the ring system denoted by "A" is aryl or heteroaryl. In one embodiment, the ring system denoted by "A" is substituted with one or more electron-withdrawing groups as described above. In another embodiment, $R^{17}$ is substituted with one or more electron-withdrawing groups as described above. In certain embodiments, the ring system denoted by "A", $R^{17}$ or both are not substituted with an aryl, heteroaryl, cycloalkyl or heterocycloalkyl-containing group. In certain embodiments, the azacycloalkyl to which -G-$R^{17}$ is bound is a piperidinyl; in other embodiments, it is a pyrrolidinyl.

In the presently disclosed compounds of structural formula (3-XLIV), v is 0, 1, 2, 3 or 4. In one embodiment, v is 0, 1, 2 or 3. For example, v can be 0, or can be 1 or 2.

In certain embodiments of the presently disclosed compounds of structural formula (3-XLIV), two $R^{15}$ groups combine to form an oxo. The oxo can be bound, for example, at the position alpha relative to the nitrogen of the azacycloalkyl ring. In other embodiments, no two $R^{15}$ groups combine to form an oxo.

In certain embodiments of the presently disclosed compounds of structural formula (3-XLIV), when v is 4, not all four $R^{15}$ moieties are ($C_1$-$C_6$ alkyl).

In certain embodiments of the presently disclosed compounds of structural formula (3-XLIV), each $R^{15}$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN and two $R^{15}$ on the same carbon optionally combine to form oxo, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^{15}$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}R^{10}$, -halogen, —$NO_2$ and —CN and two $R^{15}$ on the same carbon optionally combine to form oxo, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. In some embodiments, one $R^{15}$ is —C(O)$NR^9R^7$, which can be bound, for example, at a position alpha relative to the piperidine nitrogen, or at the position linked to the —N($R^1$)—.

In certain embodiments of the presently disclosed compounds of structural formula (3-XLIV), $R^{17}$ is an unsubstituted aryl or heteroaryl. In other embodiments, the $R^{17}$ Ar or Het is substituted with 1, 2 or 3 substituents independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, the $R^{17}$ Ar or Het is substituted with 1, 2 or 3 substituents independently selected from —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. In certain embodiments, $R^{17}$ is substituted with 1, 2 or 3 substituents selected from halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca. $R^{17}$ can be substituted with, for example, one such substituent, or two such substituents.

For example, in certain embodiments, the presently disclosed compounds have the structural formula (3-XLV):

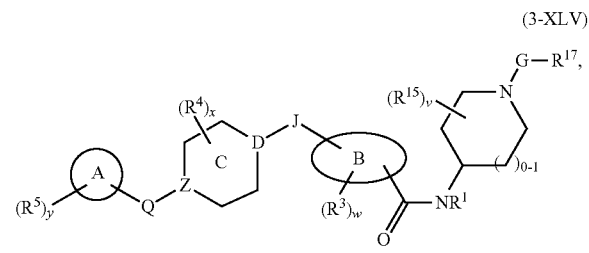

(3-XLV)

in which all variables are as defined above with reference to any of structural formulae (3-I)-(3-XLIV).

In other embodiments, the presently disclosed compounds have structural formula (3-XLVI):

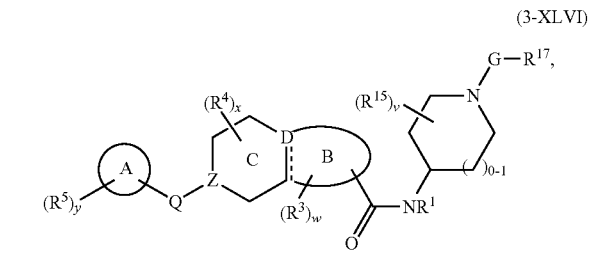

(3-XLVI)

in which all variables are as defined above with reference to any of structural formulae (3-I)-(3-XLIV).

In certain embodiments, the presently disclosed compounds have the structural formula (3-XLVII):

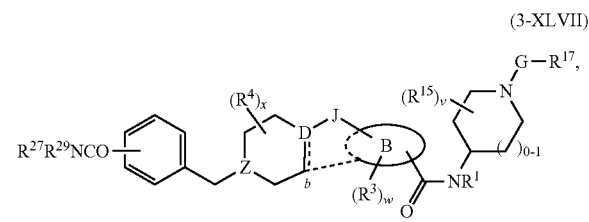

(3-XLVII)

in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —C(O)—($C_1$-$C_4$ alkyl) or —C(O)—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (3-I)-(3-XLVI). In one embodiment, $R^{27}$ and $R^{29}$ are both H.

In certain embodiments, the presently disclosed compounds have the structural formula (3-XLVIII):

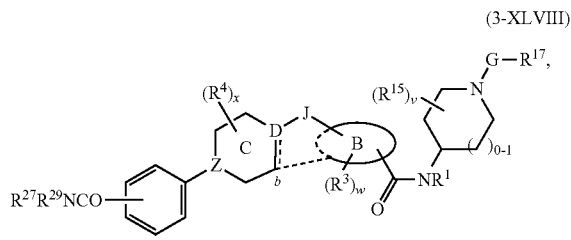

(3-XLVIII)

in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$ ($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —C(O)— ($C_1$-$C_4$ alkyl) or —C(O)—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (3-I)-(3-XLVI). In one embodiment, $R^{27}$ and $R^{29}$ are both H.

In certain embodiments, the presently disclosed compounds have the structural formula (3-XLIX):

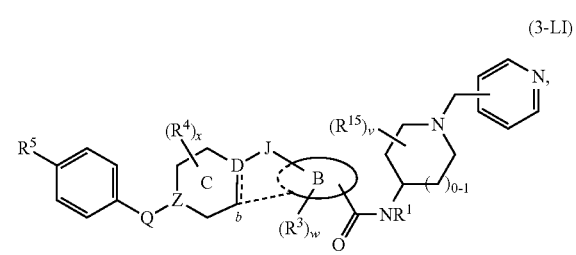

(3-XLIX)

in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$ ($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —C(O)—($C_1$-$C_4$ alkyl) or —C(O)—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (3-I)-(3-XLVI). In one embodiment, $R^{27}$ and $R^{29}$ are both H.

In certain embodiments, the presently disclosed compounds have the structural formula (3-L):

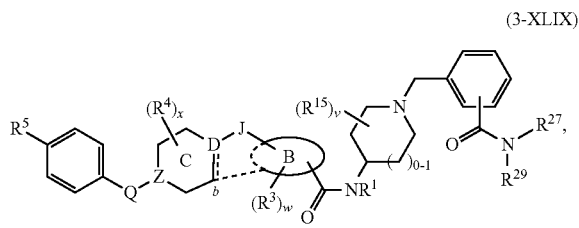

(3-L)

in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$ ($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —C(O)—($C_1$-$C_4$ alkyl) or —C(O)—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (3-I)-(3-XLVI). In one embodiment, $R^{27}$ and $R^{29}$ are both H.

In certain embodiments, the presently disclosed compounds have the structural formula (3-LI):

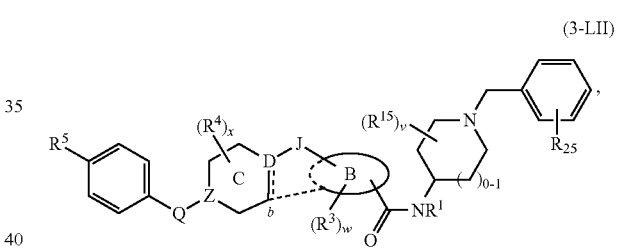

(3-LI)

in which all variables are as described above with reference to any of structural formulae (3-I)-(3-XLVI).

In certain embodiments, the presently disclosed compounds have the structural formula (3-LII):

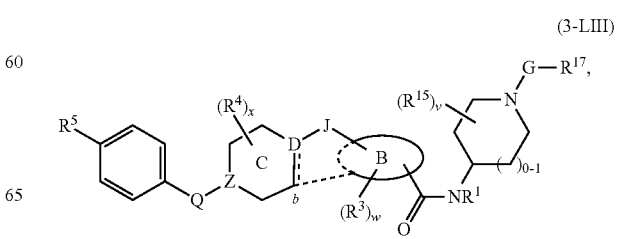

(3-LII)

in which $R^{25}$ is selected from halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), NO$_2$ and —C(O)-Hca in which the Hca contains a ring nitrogen atom through which it is bound to the —C(O)—, in which no alkyl or haloalkyl is substituted by an aryl, heteroaryl, cycloalkyl or heterocycloalkyl-containing group; and all other variables are as described above with reference to any of structural formulae (3-I)-(3-XLVI). $R^{25}$ can be, for example, —Cl, —F, cyano, —C(O)CH$_3$, —C(O)OH, —C(O)NH$_2$, trifluoromethyl, difluoromethyl, difluoromethoxy or trifluoromethoxy.

In certain embodiments, the presently disclosed compounds have the structural formula (3-LIII):

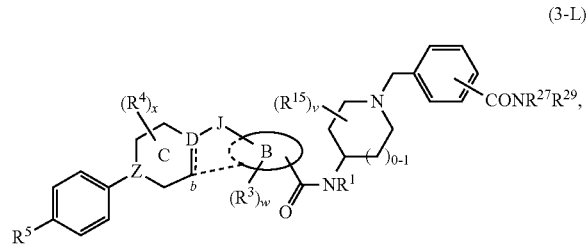

(3-LIII)

in which G is —C(O)—, —S(O)$_2$— or —C(O)—NH— and all other variables are as described above with reference to any of structural formulae (3-I)-(3-XLVI).

In certain embodiments, the presently disclosed compounds have the structural formula (3-LIV):

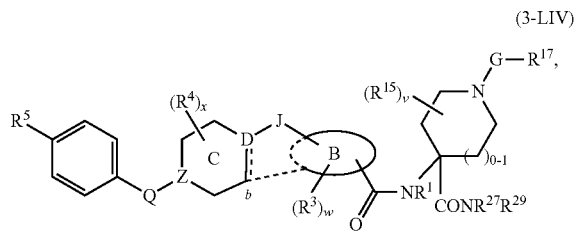

(3-LIV)

in which R$^{27}$ is selected from H, —(C$_1$-C$_6$ alkyl), —(C$_1$-C$_6$ haloalkyl) (e.g., difluoromethyl, trifluoromethyl and the like), —(C$_0$-C$_6$ alkyl)-L-(C$_0$-C$_6$ alkyl), —(C$_0$-C$_6$ alkyl)-NR$^9$ (C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl)-(C$_0$-C$_6$ alkyl)-S(O)$_{0-2}$—(C$_0$-C$_6$ alkyl), in which no heterocycloalkyl, alkyl or haloalkyl is substituted with an aryl-, heteroaryl-, cycloalkyl- or heterocycloalkyl-containing group, and R$^{29}$ is —H, —(C$_1$-C$_4$ alkyl), —C(O)—(C$_1$-C$_4$ alkyl) or —C(O)—O—(C$_1$-C$_4$ alkyl) in which no (C$_1$-C$_4$ alkyl) is substituted by an aryl, heteroaryl, cycloalkyl or heterocycloalkyl-containing group, or R$^{27}$ and R$^{29}$ together with the nitrogen to which they are bound form Hca, and all other variables are as described above with reference to any of structural formulae (3-I)-(3-XLVI). In one embodiment, R$^{27}$ and R$^{29}$ are both H. In some embodiments, the compounds of structural formula (3-LIV) are present as racemic mixtures or scalemic mixtures. In other embodiments, the compounds of structural formula (3-LIV) are present in an enantiomerically-enriched form, for example as a substantially pure stereoisomer.

In certain embodiments, the presently disclosed compounds have the structural formula (3-LV):

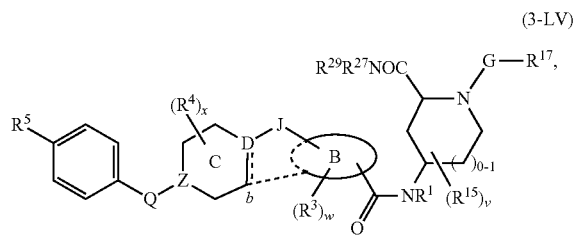

(3-LV)

in which R$^{27}$ is selected from H, —(C$_1$-C$_6$ alkyl), —(C$_1$-C$_6$ haloalkyl) (e.g., difluoromethyl, trifluoromethyl and the like), —(C$_0$-C$_6$ alkyl)-L-(C$_0$-C$_6$ alkyl), —(C$_0$-C$_6$ alkyl)-NR$^9$ (C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl)-(C$_0$-C$_6$ alkyl)-S(O)$_{0-2}$—(C$_0$-C$_6$ alkyl), in which no heterocycloalkyl, alkyl or haloalkyl is substituted with an aryl-, heteroaryl-, cycloalkyl- or heterocycloalkyl-containing group, and R$^{29}$ is —H, —(C$_1$-C$_4$ alkyl), —C(O)—(C$_1$-C$_4$ alkyl) or —C(O)—O—(C$_1$-C$_4$ alkyl) in which no (C$_1$-C$_4$ alkyl) is substituted by an aryl, heteroaryl, cycloalkyl or heterocycloalkyl-containing group, or R$^{27}$ and R$^{29}$ together with the nitrogen to which they are bound form Hca, and all other variables are as described above with reference to any of structural formulae (3-I)-(3-XLVI). In one embodiment, R$^{27}$ and R$^{29}$ are both H. In some embodiments, the compounds of structural formula (3-LV) are present as racemic mixtures or scalemic mixtures. In other embodiments, the compounds of structural formula (3-LV) are present in an enantiomerically-enriched form, for example as a substantially pure stereoisomer.

In certain embodiments, the presently disclosed compounds have the structural formula (3-LVI):

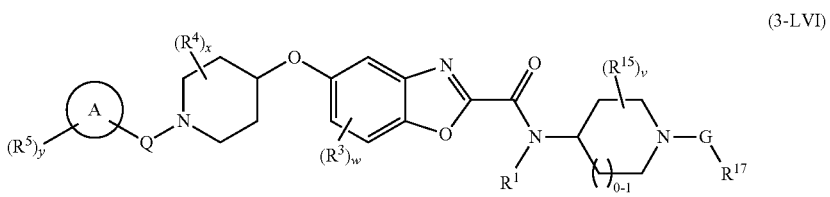

(3-LVI)

in which G, v, R$^{15}$ and R$^{17}$ are defined as described above with reference to structural formula (3-XLIV), and all other variables are defined as described above with reference to structural formulae (3-I)-(3-IV) and (3-XVIII). R$^5$, y, v, R$^{15}$, R$^{17}$, Q, G and the ring denoted by "A" can be defined, for example, as described with reference to any of structural formulae (3-XLVII)-(3-LV).

In certain embodiments, the presently disclosed compounds have the structural formula (3-LVII):

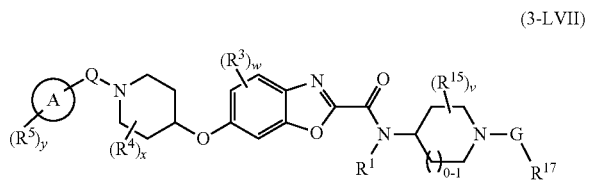

(3-LVII)

in which G, v, R$^{15}$ and R$^{17}$ are defined as described above with reference to structural formula (3-XLIV), and all other variables are defined as described above with reference to structural formulae (3-I)-(3-IV) and (3-XIX). R$^5$, y, v, R$^{15}$, R$^{17}$, Q, G and the ring denoted by "A" can be defined, for example, as described with reference to any of structural formulae (3-XLVII)-(3-LV).

In certain embodiments, the presently disclosed compounds have the structural formula (3-LVIII):

(3-LVIII)

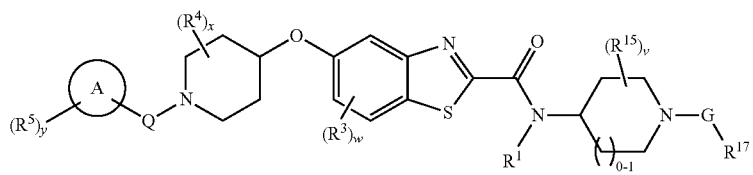

in which G, v, $R^{15}$ and $R^{17}$ are defined as described above with reference to structural formula (3-XLIV), and all other variables are defined as described above with reference to structural formulae (3-I)-(3-IV) and (3-XX). $R^5$, y, v, $R^{15}$, $R^{17}$, Q, G and the ring denoted by "A" can be defined, for example, as described with reference to any of structural formulae (3-XLVII)-(3-LV).

In certain embodiments, the presently disclosed compounds have the structural formula (3-LIX):

(3-LIX)

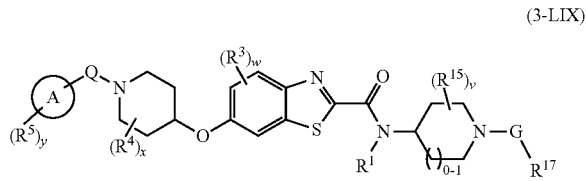

in which G, v, $R^{15}$ and $R^{17}$ are defined as described above with reference to structural formula (3-XLIV), and all other variables are defined as described above with reference to structural formulae (3-I)-(3-IV) and (3-XXI). $R^5$, y, v, $R^{15}$, $R^{17}$, Q, G and the ring denoted by "A" can be defined, for example, as described with reference to any of structural formulae (3-XLVII)-(3-LV).

In certain embodiments, the presently disclosed compounds have the structural formula (3-LX):

(3-LX)

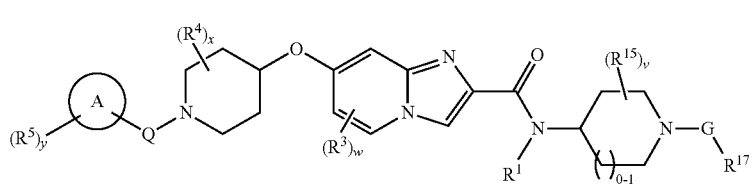

in which G, v, $R^{15}$ and $R^{17}$ are defined as described above with reference to structural formula (3-XLVII), and all other variables are defined as described above with reference to structural formulae (3-I)-(3-IV) and (3-XXII). $R^5$, y, v, $R^{15}$, $R^{17}$, Q, G and the ring denoted by "A" can be defined, for example, as described with reference to any of structural formulae (3-XLVIII)-(3-LV).

In certain embodiments, the presently disclosed compounds have the structural formula (3-LXI):

(3-LXI)

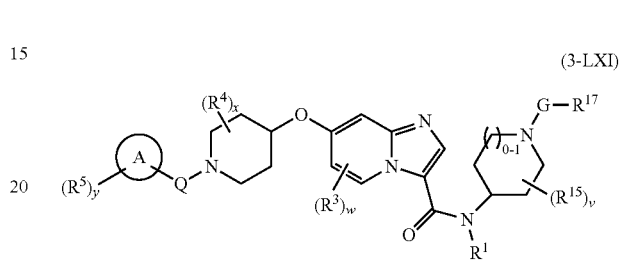

in which G, v, $R^{15}$ and $R^{17}$ are defined as described above with reference to structural formula (3-XLIV), and all other variables are defined as described above with reference to structural formulae (3-I)-(3-IV) and (3-XXIII). $R^5$, y, v, $R^{15}$, $R^{17}$, Q, G and the ring denoted by "A" can be defined, for example, as described with reference to any of structural formulae (3-XLVII)-(3-LV).

In certain embodiments, the presently disclosed compounds have the structural formula (3-LXII):

(3-LXII)

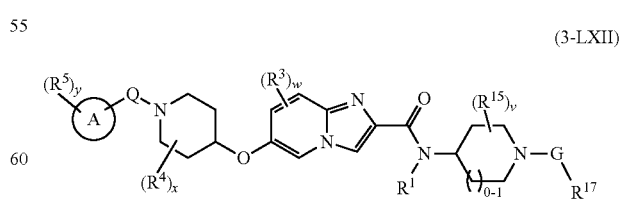

in which G, v, $R^{15}$ and $R^{17}$ are defined as described above with reference to structural formula (3-XLIV), and all other variables are defined as described above with reference to structural formulae (3-I)-(3-IV) and (3-XXIV). $R^5$, y, v, $R^{15}$, $R^{17}$, Q, G and the ring denoted by "A" can be defined, for example, as described with reference to any of structural formulae (3-XLVII)-(3-LV).

In certain embodiments, the presently disclosed compounds have the structural formula (3-LXIII):

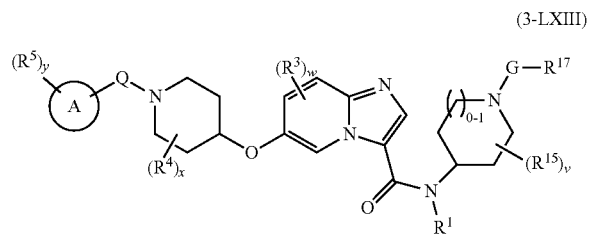

(3-LXIII)

in which G, v, $R^{15}$ and $R^{17}$ are defined as described above with reference to structural formula (3-XLIV), and all other variables are defined as described above with reference to structural formulae (3-I)-(3-IV) and (3-XXV). $R^5$, y, v, $R^{15}$, $R^{17}$, Q, G and the ring denoted by "A" can be defined, for example, as described with reference to any of structural formulae (3-XLVII)-(3-LV).

In certain embodiments, the presently disclosed compounds have the structural formula (3-LXIV):

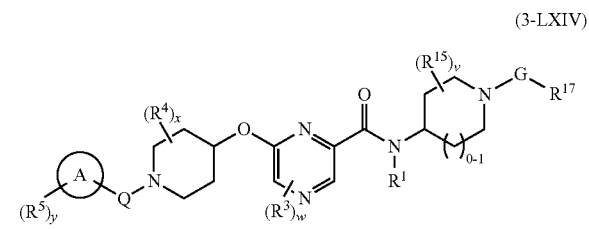

(3-LXIV)

in which G, v, $R^{15}$ and $R^{17}$ are defined as described above with reference to structural formula (3-XLIV), and all other variables are defined as described above with reference to structural formulae (3-I)-(3-IV) and (3-XXVI). $R^5$, y, v, $R^{15}$, $R^{17}$, Q, G and the ring denoted by "A" can be defined, for example, as described with reference to any of structural formulae (3-XLVII)-(3-LV).

In certain embodiments, the presently disclosed compounds have the structural formula (3-LXV):

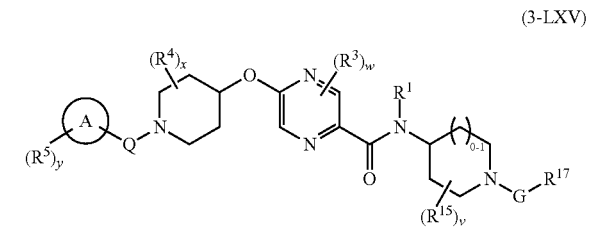

(3-LXV)

in which G, v, $R^{15}$ and $R^{17}$ are defined as described above with reference to structural formula (3-XLIV), and all other variables are defined as described above with reference to structural formulae (3-I)-(3-IV) and (3-XXVII). $R^5$, y, v, $R^{15}$, $R^{12}$, Q, G and the ring denoted by "A" can be defined, for example, as described with reference to any of structural formulae (3-XLVII)-(3-LV).

In certain embodiments, the presently disclosed compounds have the structural formula (3-LXVI):

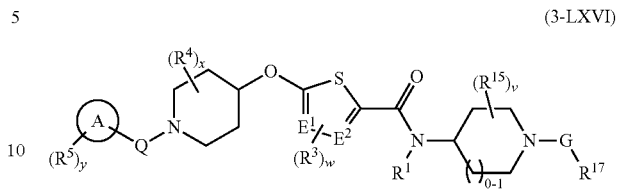

(3-LXVI)

in which G, v, $R^{15}$ and $R^{17}$ are defined as described above with reference to structural formula (3-XLIV), and all other variables are defined as described above with reference to structural formulae (3-I)-(3-IV) and (3-XXVIII). $R^5$, y, v, $R^{15}$, $R^{12}$, Q, G and the ring denoted by "A" can be defined, for example, as described with reference to any of structural formulae (3-XLVII)-(3-LV). In one embodiment, $E^1$ is carbon and $E^2$ is N. In another embodiment, $E^1$ is N and $E^2$ is carbon.

In certain embodiments, the presently disclosed compounds have the structural formula (3-LXVII):

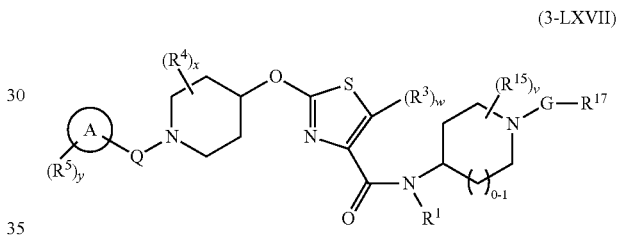

(3-LXVII)

in which G, v, $R^{15}$ and $R^{17}$ are defined as described above with reference to structural formula (3-XLIV), and all other variables are defined as described above with reference to structural formulae (3-I)-(3-IV) or (3-XXIX). $R^5$, y, v, $R^{15}$, $R^{17}$, Q, G and the ring denoted by "A" can be defined, for example, as described with reference to any of structural formulae (3-XLVII)-(3-LV). When w is 0, the ring position shown occupied by $R^3$ bears a hydrogen atom.

In certain embodiments, the presently disclosed compounds have the structural formula (3-LXVIII):

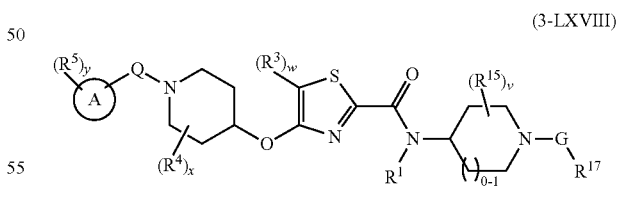

(3-LXVIII)

in which G, v, $R^{15}$ and $R^{17}$ are defined as described above with reference to structural formula (3-XLIV), and all other variables are defined as described above with reference to structural formulae (3-I)-(3-IV) and (3-XXX). $R^5$, y, v, $R^{15}$, $R^{17}$, Q, G and the ring denoted by "A" can be defined, for example, as described with reference to any of structural formulae (3-XLVII)-(3-LV). When w is 0, the ring position shown occupied by $R^3$ bears a hydrogen atom.

In certain embodiments, the presently disclosed compounds have the structural formula (3-LXIX):

(3-LXIX)

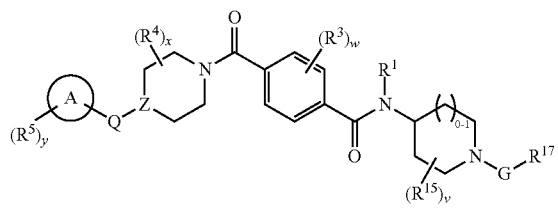

in which G, v, $R^{15}$ and $R^{17}$ are defined as described above with reference to structural formula (3-XLIV), and all other variables are defined as described above with reference to structural formulae (3-I)-(3-IV) and (3-XXXIV). $R^5$, y, v, $R^{15}$, $R^{17}$, Q, G and the ring denoted by "A" can be defined, for example, as described with reference to any of structural formulae (3-XLVII)-(3-LV). In certain embodiments, Z is N. In other embodiments, Z is CH or C substituted with one of the x $R^4$.

In certain embodiments, the presently disclosed compounds have the structural formula (3-LXX):

(3-LXX)

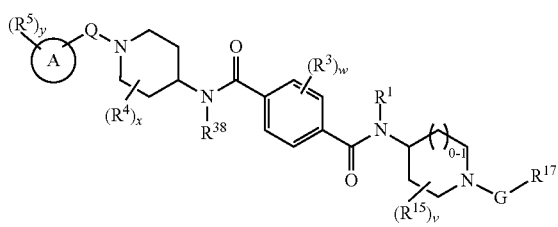

in which G, v, $R^{15}$ and $R^{17}$ are defined as described above with reference to structural formula (3-XLIV), and all other variables are defined as described above with reference to structural formulae (3-I)-(3-IV) and (3-XXXV). $R^5$, y, v, $R^{15}$, $R^{17}$, Q, G and the ring denoted by "A" can be defined, for example, as described with reference to any of structural formulae (3-XLVII)-(3-LV).

In certain embodiments, the presently disclosed compounds have the structural formula (3-LXXI):

(3-LXXI)

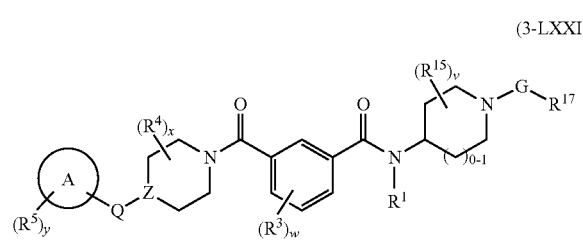

in which G, v, $R^{15}$ and $R^{17}$ are defined as described above with reference to structural formula (3-XLIV), and all other variables are defined as described above with reference to structural formulae (3-I)-(3-IV) and (3-XXXVI). $R^5$, y, v, $R^{15}$, $R^{17}$, Q, G and the ring denoted by "A" can be defined, for example, as described with reference to any of structural formulae (3-XLVII)-(3-LV). In certain embodiments, Z is N. In other embodiments, Z is CH or C substituted with one of the x $R^4$.

In certain embodiments, the presently disclosed compounds have the structural formula (3-LXXII):

(3-LXXII)

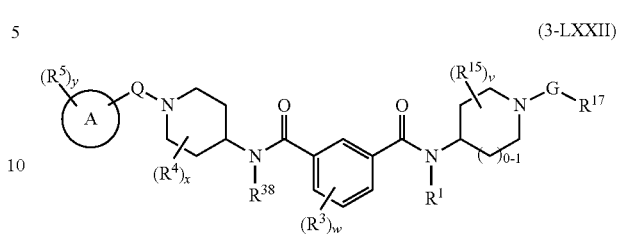

in which G, v, $R^{15}$ and $R^{17}$ are defined as described above with reference to structural formula (3-XLIV), and all other variables are defined as described above with reference to structural formulae (3-I)-(3-IV) and (3-XXXVII). $R^5$, y, v, $R^{15}$, $R^{17}$, Q, G and the ring denoted by "A" can be defined, for example, as described with reference to any of structural formulae (3-XLVII)-(3-LV).

In certain embodiments, the presently disclosed compounds have the structural formula (3-LXXIII):

(3-LXXIII)

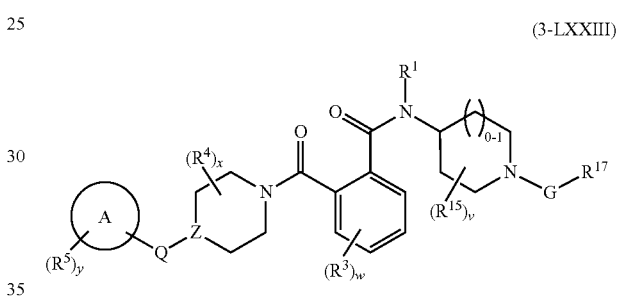

in which G, v, $R^{15}$ and $R^{17}$ are defined as described above with reference to structural formula (3-XLIV), and all other variables are defined as described above with reference to structural formulae (3-I)-(3-IV) and (3-XXXVIII). $R^5$, y, v, $R^{15}$, $R^{17}$, Q, G and the ring denoted by "A" can be defined, for example, as described with reference to any of structural formulae (3-XLVII)-(3-LV). In certain embodiments, Z is N. In other embodiments, Z is carbon (e.g., CH or C substituted with one of the x $R^4$).

In certain embodiments, the presently disclosed compounds have the structural formula (3-LXXIV):

(3-LXXIV)

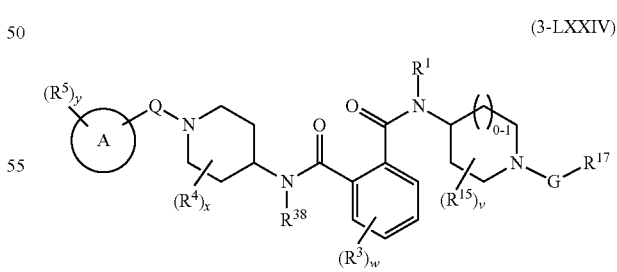

in which G, v, $R^{15}$ and $R^{17}$ are defined as described above with reference to structural formula (3-XLIV), and all other variables are defined as described above with reference to structural formulae (3-I)-(3-IV) and (3-XXXIX). $R^5$, y, v, $R^{15}$, $R^{17}$, Q, G and the ring denoted by "A" can be defined, for example, as described with reference to any of structural formulae (3-XLVII)-(3-LV).

In certain embodiments, the presently disclosed compounds have the structural formula (3-LXXV):

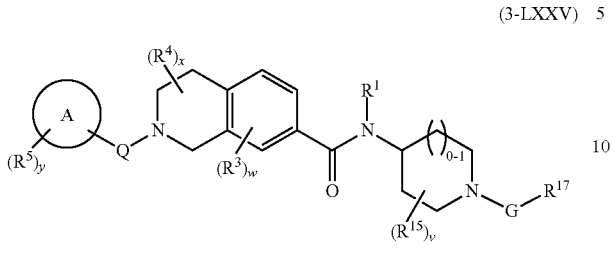

(3-LXXV)

in which G, v, $R^{15}$ and $R^{17}$ are defined as described above with reference to structural formula (3-XLIV), and all other variables are defined as described above with reference to structural formulae (3-I)-(3-IV) and (3-XL). $R^5$, y, v, $R^{15}$, $R^{17}$, Q, G and the ring denoted by "A" can be defined, for example, as described with reference to any of structural formulae (3-XLVII)-(3-LV).

In certain embodiments, the presently disclosed compounds have the structural formula (3-LXXVI):

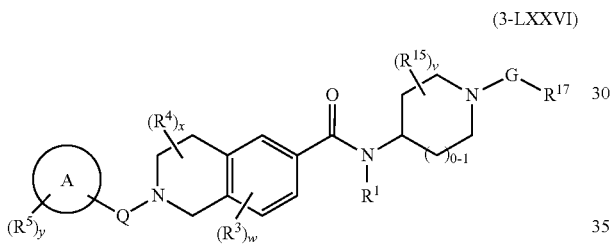

(3-LXXVI)

in which G, v, $R^{15}$ and $R^{17}$ are defined as described above with reference to structural formula (3-XLIV), and all other variables are defined as described above with reference to structural formulae (3-I)-(3-IV) and (3-XLI). $R^5$, y, v, $R^{15}$, $R^{17}$, Q, G and the ring denoted by "A" can be defined, for example, as described with reference to any of structural formulae (3-XLVII)-(3-LV).

In certain embodiments, the presently disclosed compounds have the structural formula (3-LXXVII):

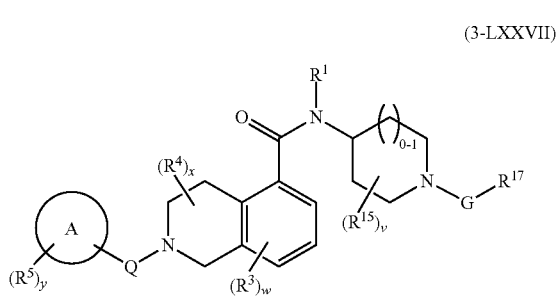

(3-LXXVII)

in which G, v, $R^{15}$ and $R^{17}$ are defined as described above with reference to structural formula (3-XLIV), and all other variables are defined as described above with reference to structural formulae (3-I)-(3-IV) and (3-XLII). $R^5$, y, v, $R^{15}$, $R^{17}$, Q, G and the ring denoted by "A" can be defined, for example, as described with reference to any of structural formulae (3-XLVII)-(3-LV).

In certain embodiments, the presently disclosed compounds have the structural formula (3-LXXVIII):

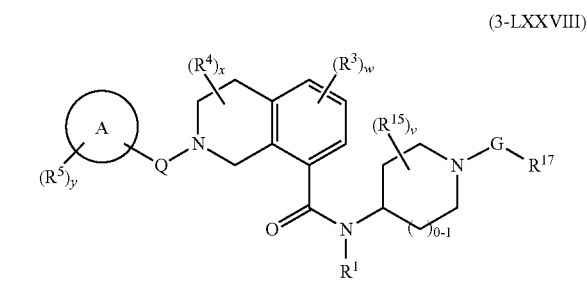

(3-LXXVIII)

in which G, v, $R^{15}$ and $R^{17}$ are defined as described above with reference to structural formula (3-XLIV), and all other variables are defined as described above with reference to structural formulae (3-I)-(3-IV) and (3-XLIII). $R^5$, y, v, $R^{15}$, $R^{17}$, Q, G and the ring denoted by "A" can be defined, for example, as described with reference to any of structural formulae (3-XLVII)-(3-LV).

In certain embodiments of compounds having structural formulae (3-XLIV)-(3-XLVIII), (3-LIII) and (3-LVI)-(3-LXXVIII), the

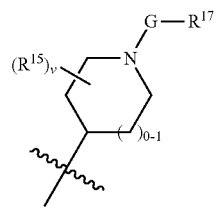

moiety has the structure

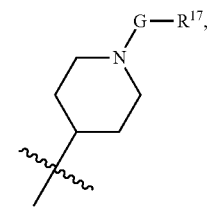

in which G is —$CH_2$—, —$CH(CH_3)$—, —C(O)—, —$S(O)_2$— or —C(O)—NH—. For example, in one embodiment, G is —$CH_2$—. In another embodiment, G is —C(O)— or —$S(O)_2$—. In another embodiment, G is —C(O)—NH—.

In other embodiments of compounds having structural formulae (3-XLIV)-(3-XLVIII), (3-LIII) and (3-LVI)-(3-LXXVIII), the

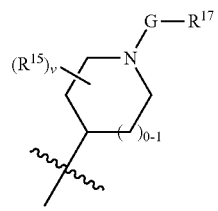

moiety has the structure

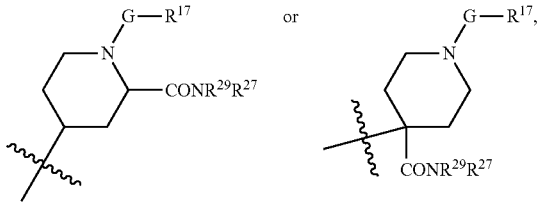

in which G is —CH$_2$—, —C(O)—, —S(O)$_2$— or —C(O)—NH—, R$^{27}$ is selected from H, —(C$_1$-C$_6$ alkyl), —(C$_1$-C$_6$ haloalkyl) (e.g., difluoromethyl, trifluoromethyl and the like), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl) —(C$_0$-C$_6$ alkyl)-S(O)$_{0-2}$—(C$_0$-C$_6$ alkyl), in which no heterocycloalkyl, alkyl or haloalkyl is substituted with an aryl-, heteroaryl-, cycloalkyl- or heterocycloalkyl-containing group, and R$^{29}$ is —H, —(C$_1$-C$_4$ alkyl), —CO—(C$_1$-C$_4$ alkyl) or —CO—O—(C$_1$-C$_4$ alkyl) in which no (C$_1$-C$_4$ alkyl) is substituted by an aryl, heteroaryl, cycloalkyl or heterocycloalkyl-containing group, or R$^{27}$ and R$^{29}$ together with the nitrogen to which they are bound form Hca. In such embodiments, the compounds can be present as racemic mixtures or scalemic mixtures, or in an enantiomerically-enriched form, for example as a substantially pure stereoisomer.

In other embodiments of compounds having structural formulae (3-XLIV)-(3-XLVIII), (3-LIII) and (3-LVI)-(3-LXXVIII), the

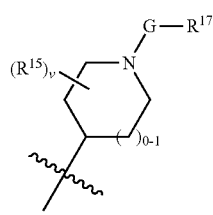

moiety has the structure

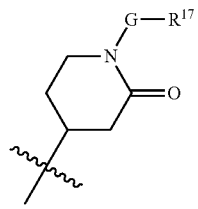

in which G is —CH$_2$—, —C(O)—, —S(O)$_2$— or —C(O)—NH—.

In certain embodiments of compounds having structural formulae (3-XLIV)-(3-XLVIII), (3-LIII) and (3-LVI)-(3-LXXVIII), the R$^{17}$ moiety has the structure

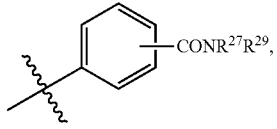

in which R$^{27}$ is selected from H, —(C$_1$-C$_6$ alkyl), —(C$_1$-C$_6$ haloalkyl) (e.g., difluoromethyl, trifluoromethyl and the like), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl) —(C$_0$-C$_6$ alkyl)-S(O)$_{0-2}$—(C$_0$-C$_6$ alkyl), in which no heterocycloalkyl, alkyl or haloalkyl is substituted with an aryl-, heteroaryl-, cycloalkyl- or heterocycloalkyl-containing group, and R$^{29}$ is —H, —(C$_1$-C$_4$ alkyl), —CO—(C$_1$-C$_4$ alkyl) or —CO—O—(C$_1$-C$_4$ alkyl) in which no (C$_1$-C$_4$ alkyl) is substituted by an aryl, heteroaryl, cycloalkyl or heterocycloalkyl-containing group, or R$^{27}$ and R$^{29}$ together with the nitrogen to which they are bound form Hca.

In certain embodiments of compounds having structural formulae (3-XLIV)-(3-LXXVIII), w is 1, and R$^3$ is —NR$^8$R$^9$. In certain such embodiments, R$^3$ is substituted at a 6-membered aromatic ring position in the meta position relative to the J moiety.

In other embodiments of compounds having structural formulae (3-XLIV)-(3-LXXVIII), w is 1, and R$^3$ is —(C$_0$-C$_3$ alkyl)-Y$^1$—(C$_1$-C$_3$ alkyl)-Y$^2$—(C$_0$-C$_3$ alkyl), in which each of Y$^1$ and Y$^2$ is independently L, —O—, —S— or —NR$^9$—. In certain such embodiments, R$^3$ is substituted at a 6-membered aromatic ring position in the meta position relative to the J moiety.

In certain embodiments described above, each R$^{27}$ is selected from —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN and two R$^{21}$ on the same carbon optionally combine to form oxo, in which each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group, and each R$^{29}$ is H, methyl or ethyl, or R$^{27}$ and R$^{29}$ together with the nitrogen to which they are bound form Hca.

In certain embodiments of compounds having structural formulae (3-XLIV)-(3-XLVI) and (3-XLIX)-(3-LXXVIII), at least one R$^5$ moiety is a haloalkyl group, and in exemplary embodiments of these formulae the

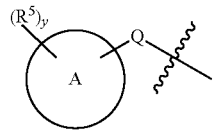

moiety is p-(trifluoromethyl)phenyl.

In one embodiment, the presently disclosed compounds of any of structural formulae (3-I)-(3-XLIII) have a T moiety having the structural formula

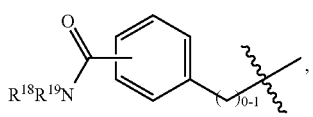

and an R² moiety having the structural formula

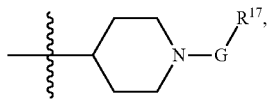

in which G and $R^{17}$ are as described above with reference to any of structural formulae (3-I)-(3-LXXVIII), $R^{18}$ is H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), in which no alkyl or haloalkyl is substituted with an aryl-, heteroaryl-, cycloalkyl- or heterocycloalkyl-containing group and $R^{19}$ is —H, —($C_1$-$C_4$ alkyl), —CO—($C_1$-$C_4$ alkyl) or —CO—O—($C_1$-$C_4$ alkyl) in which no alkyl is substituted by an aryl, heteroaryl, cycloalkyl or heterocycloalkyl-containing group, or $R^{18}$ and $R^{19}$ together with the nitrogen to which they are bound form Hca. In one embodiment, $R^{18}$ and $R^{19}$ are both H.

In another embodiment, the presently disclosed compounds of any of structural formulae (3-I)-(3-XLIII) have a T moiety having the structural formula

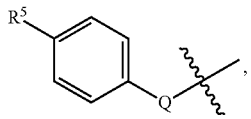

and an R² moiety having the structural formula

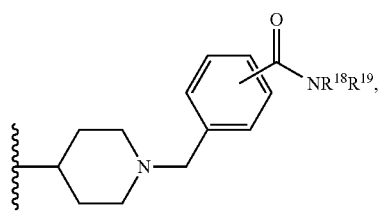

in which Q and $R^5$ are defined as described above with reference to any of structural formulae (3-I)-(3-LXXVIII), $R^{18}$ is H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), in which no alkyl or haloalkyl is substituted with an aryl-, heteroaryl-, cycloalkyl- or heterocycloalkyl-containing group and $R^{19}$ is —H, —($C_1$-$C_4$ alkyl), —CO—($C_1$-$C_4$ alkyl) or —CO—O—($C_1$-$C_4$ alkyl) in which no alkyl is substituted by an aryl, heteroaryl, cycloalkyl or heterocycloalkyl-containing group, or $R^{18}$ and $R^{19}$ together with the nitrogen to which they are bound form Hca. In one embodiment, $R^{18}$ and $R^{19}$ are both H.

In another embodiment, the presently disclosed compounds of any of structural formulae (3-I)-(3-XLIII) have a T moiety having the structural formula

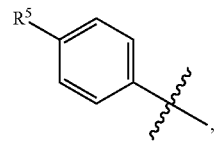

and an R² moiety having the structural formula

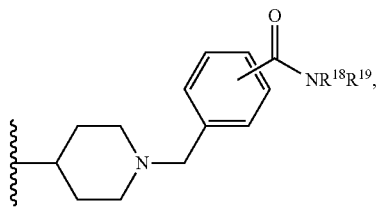

in which Q and $R^5$ are defined as described above with reference to any of structural formulae (3-I)-(3-LXXVIII), $R^{18}$ is H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), in which no alkyl or haloalkyl is substituted with an aryl-, heteroaryl-, cycloalkyl- or heterocycloalkyl-containing group and $R^{19}$ is —H, —($C_1$-$C_4$ alkyl), —CO—($C_1$-$C_4$ alkyl) or —CO—O—($C_1$-$C_4$ alkyl) in which no alkyl is substituted by an aryl, heteroaryl, cycloalkyl or heterocycloalkyl-containing group, or $R^{18}$ and $R^{19}$ together with the nitrogen to which they are bound form Hca. In one embodiment, $R^{18}$ and $R^{19}$ are both H.

In certain embodiments, the presently disclosed compounds have the structural formula (3-LXXIX):

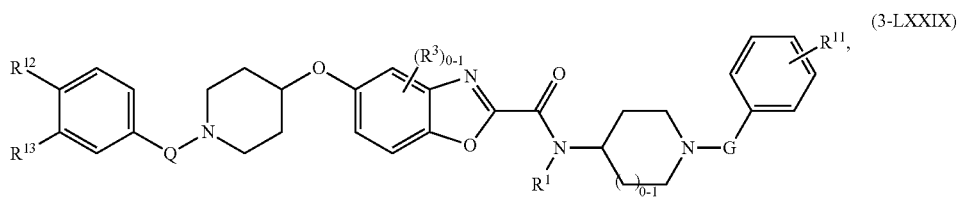

(3-LXXIX)

in which Q is —$CH_2$—, —C(O)— or a single bond; G is a single bond, —$CH_2$—, —C(O)—, —S(O)$_2$— or —C(O)—

NH—; $R^1$ and $R^3$ are as described above with reference to any of structural formulae (3-I)-(3-IV) and (3-LVI); and $R^{11}$, $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, $R^1$ is H. In another embodiment, $R^1$ is methyl, ethyl, propyl or butyl. In one embodiment, no $R^3$ is substituted on the benzo moiety of the central benzo[d]oxazole. In another embodiment, one $R^3$ (e.g., —Cl, —F, —$CH_3$, —$C_2H_5$, —$C_3H_7$) is substituted on the benzo moiety of the central benzo[d]oxazole.

In certain embodiments, the presently disclosed compounds have the structural formula (3-LXXX):

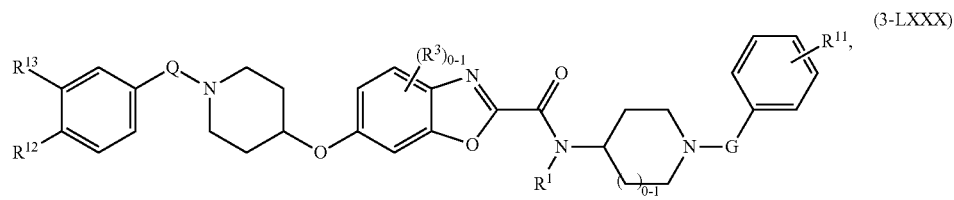

(3-LXXX)

in which Q is —$CH_2$—, —C(O)— or a single bond; G is a single bond, —$CH_2$—, —C(O)—, —S(O)$_2$— or —C(O)—NH—; $R^1$ and $R^3$ are as described above with reference to any of structural formulae (3-I)-(3-IV) and (3-LVII); and $R^{11}$, $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, $R^1$ is H. In another embodiment, $R^1$ is methyl, ethyl, propyl or butyl. In one embodiment, no $R^3$ is substituted on the benzo moiety of the central benzo[d]oxazole. In another embodiment, one $R^3$ (e.g., —Cl, —F, —$CH_3$, —$C_2H_5$, —$C_3H_7$) is substituted on the benzo moiety of the central benzo[d]oxazole.

In certain embodiments, the presently disclosed compounds have the structural formula (3-LXXXI):

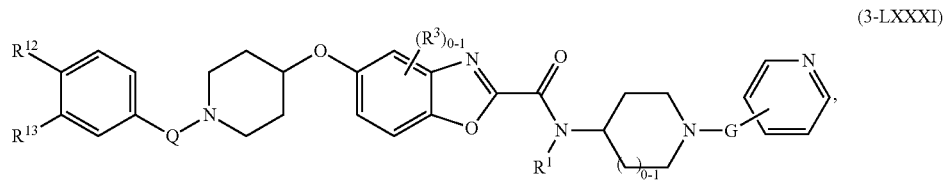

(3-LXXXI)

in which Q is —CH₂—, —C(O)— or a single bond; G is a single bond, —CH₂—, —C(O)—, —S(O)₂— or —C(O)—NH—; R¹ and R³ are as described above with reference to any of structural formulae (3-I)-(3-IV) and (3-LVI); and R¹² and R¹³ are independently selected from H, halo, cyano, —(C₁-C₄ haloalkyl), —O—(C₁-C₄ haloalkyl), —(C₁-C₄ alkyl), —O—(C₁-C₄ alkyl), —C(O)—(C₀-C₄ alkyl), —C(O)O—(C₀-C₄ alkyl), —C(O)N(C₀-C₄ alkyl)(C₀-C₄ alkyl), NO₂ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R¹² and R¹³ is not H. In one embodiment, the pyridine nitrogen is positioned in the para position relative to the G moiety; in another embodiment, the pyridine nitrogen is positioned in the meta position relative to the G moiety. In one embodiment, R¹ is H. In another embodiment, R¹ is methyl, ethyl, propyl or butyl. In one embodiment, no R³ is substituted on the benzo moiety of the central benzo[d]oxazole. In another embodiment, one R³ (e.g., —Cl, —F, —CH₃, —C₂H₅, —C₃H₇) is substituted on the benzo moiety of the central benzo[d]oxazole.

In certain embodiments, the presently disclosed compounds have the structural formula (3-LXXXII):

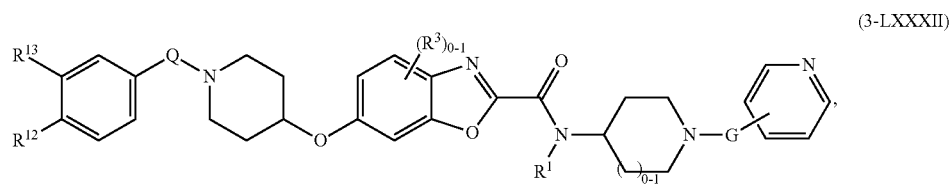

(3-LXXXII)

in which Q is —CH₂—, —C(O)— or a single bond; G is a single bond, —CH₂—, —C(O)—, —S(O)₂— or —C(O)—NH—; R¹ and R³ are as described above with reference to any of structural formulae (3-I)-(3-IV) and (3-LVI); and R¹² and R¹³ are independently selected from H, halo, cyano, —(C₁-C₄ haloalkyl), —O—(C₁-C₄ haloalkyl), —(C₁-C₄ alkyl), —O—(C₁-C₄ alkyl), —C(O)—(C₀-C₄ alkyl), —C(O)O—(C₀-C₄ alkyl), —C(O)N(C₀-C₄ alkyl)(C₀-C₄ alkyl), NO₂ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R¹² and R¹³ is not H. In one embodiment, the pyridine nitrogen is positioned in the para position relative to the G moiety; in another embodiment, the pyridine nitrogen is positioned in the meta position relative to the G moiety. In one embodiment, R¹ is H. In another embodiment, R¹ is methyl, ethyl, propyl or butyl. In one embodiment, no R³ is substituted on the benzo moiety of the central benzo[d]oxazole. In another embodiment, one R³ (e.g., —Cl, —F, —CH₃, —C₂H₅, —C₃H₇) is substituted on the benzo moiety of the central benzo[d]oxazole.

In certain embodiments, the presently disclosed compounds have the structural formula (3-LXXXIII):

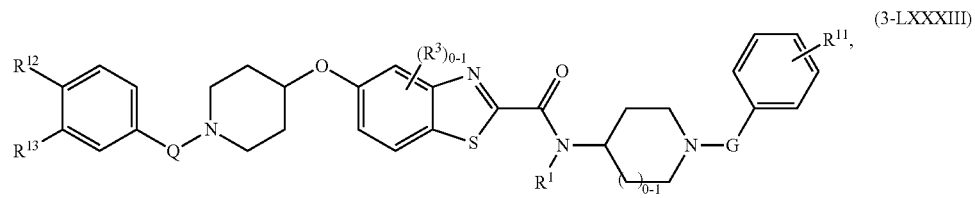

(3-LXXXIII)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (3-I)-(3-IV) and (3-LVIII); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, R$^1$ is H. In another embodiment, R$^1$ is methyl, ethyl, propyl or butyl. In one embodiment, no R$^3$ is substituted on the benzo moiety of the central benzo[d]thiazole. In another embodiment, one R$^3$ (e.g., —Cl, —F, —CH$_3$, —C$_2$H$_5$, —C$_3$H$_7$) is substituted on the benzo moiety of the central benzo[d]thiazole.

In certain embodiments, the presently disclosed compounds have the structural formula (3-LXXXIV):

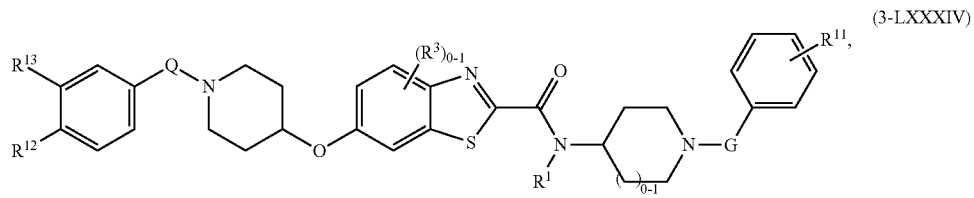

(3-LXXXIV)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (3-I)-(3-IV) and (3-LIX); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, R$^1$ is H. In another embodiment, R$^1$ is methyl, ethyl, propyl or butyl. In one embodiment, no R$^3$ is substituted on the benzo moiety of the central benzo[d]thiazole. In another embodiment, one R$^3$ (e.g., —Cl, —F, —CH$_3$, —C$_2$H$_5$, —C$_3$H$_7$) is substituted on the benzo moiety of the central benzo[d]thiazole.

In certain embodiments, the presently disclosed compounds have the structural formula (3-LXXXV):

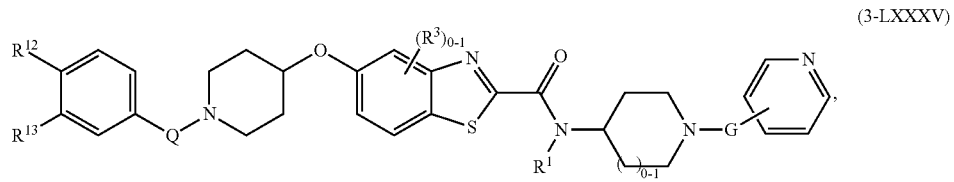

(3-LXXXV)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (3-I)-(3-IV) and (3-LVIII); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyridine nitrogen is positioned in the para position relative to the G moiety; in another embodiment, the pyridine nitrogen is positioned in the meta position relative to the G moiety. In one embodiment, R$^1$ is H. In another embodiment, R$^1$ is methyl, ethyl, propyl or butyl. In one embodiment, no R$^3$ is substituted on the benzo moiety of the central benzo[d]thiazole. In another embodiment, one R$^3$ (e.g., —Cl, —F, —CH$_3$, —C$_2$H$_5$, —C$_3$H$_7$) is substituted on the benzo moiety of the central benzo[d]thiazole.

In certain embodiments, the presently disclosed compounds have the structural formula (3-LXXXVI):

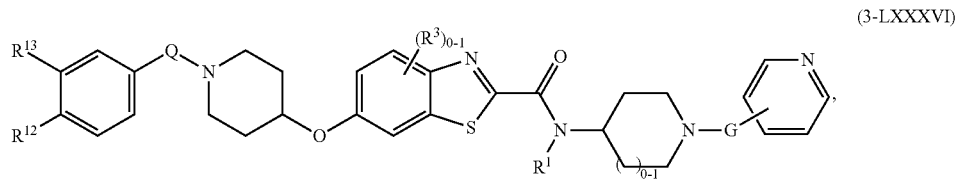

(3-LXXXVI)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (3-I)-(3-IV) and (3-LIX); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyridine nitrogen is positioned in the para position relative to the G moiety; in another embodiment, the pyridine nitrogen is positioned in the meta position relative to the G moiety. In one embodiment, R$^1$ is H. In another embodiment, R$^1$ is methyl, ethyl, propyl or butyl. In one embodiment, no R$^3$ is substituted on the benzo moiety of the central benzo[d]thiazole. In another embodiment, one R$^3$ (e.g., —Cl, —F, —CH$_3$, —C$_2$H$_5$, —C$_3$H$_7$) is substituted on the benzo moiety of the central benzo[d]thiazole.

In certain embodiments, the presently disclosed compounds have the structural formula (3-LXXXVII):

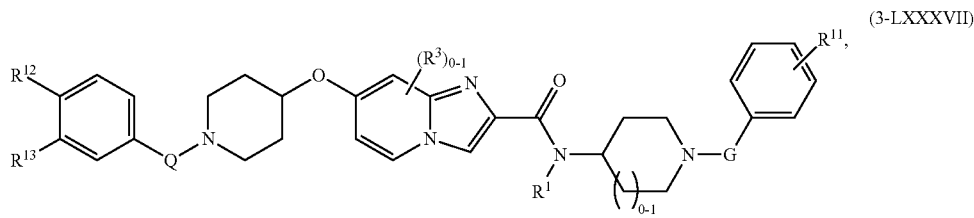

(3-LXXXVII)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (3-I)-(3-IV) and (3-LX); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, $R^1$ is H. In another embodiment, $R^1$ is methyl, ethyl, propyl or butyl. In one embodiment, no $R^3$ is substituted on the central imidazo[1,2-a]pyridine. In another embodiment, one $R^3$ (e.g., —Cl, —F, —CH$_3$, —C$_2$H$_5$, —C$_3$H$_7$) is substituted on the central imidazo[1,2-a]pyridine.

In certain embodiments, the presently disclosed compounds have the structural formula (3-LXXXVIII):

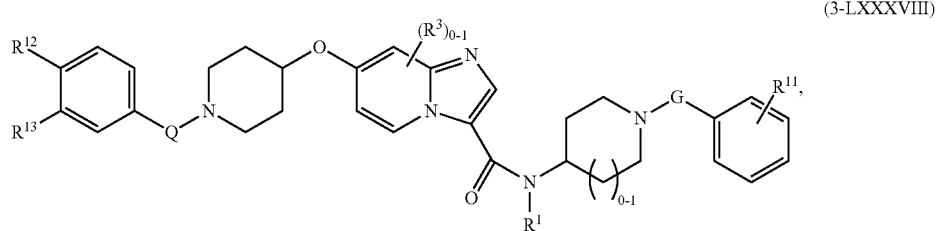

(3-LXXXVIII)

in which Q is —CH$_2$—, —C(O)— or a single bond; G is a single bond, —CH$_2$—, —C(O)—, —S(O)$_2$— or —C(O)—NH—; $R^1$ and $R^3$ are as described above with reference to any of structural formulae (3-I)-(3-IV) and (3-LXI); and $R^{11}$, $R^{12}$ and $R^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, $R^1$ is H. In another embodiment, $R^1$ is methyl, ethyl, propyl or butyl. In one embodiment, no $R^3$ is substituted on the central imidazo[1,2-a]pyridine. In another embodiment, one $R^3$ (e.g., —Cl, —F, —CH$_3$, —C$_2$H$_5$, —C$_3$H$_7$) is substituted on the central imidazo[1,2-a]pyridine.

In certain embodiments, the presently disclosed compounds have the structural formula (3-LXXXIX):

in which Q is —CH$_2$—, —C(O)— or a single bond; G is a single bond, —CH$_2$—, —C(O)—, —S(O)$_2$— or —C(O)—NH—; $R^1$ and $R^3$ are as described above with reference to any of structural formulae (3-I)-(3-IV) and (3-LXII); and $R^{11}$, $R^{12}$ and $R^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, $R^1$ is H. In another embodiment, $R^1$ is methyl, ethyl, propyl or butyl. In one embodiment, no $R^3$ is substituted on the central imidazo[1,2-a]pyridine. In another embodiment, one $R^3$ (e.g., —Cl, —F, —CH$_3$, —C$_2$H$_5$, —C$_3$H$_7$) is substituted on the central imidazo[1,2-a]pyridine.

In certain embodiments, the presently disclosed compounds have the structural formula (3-XC):

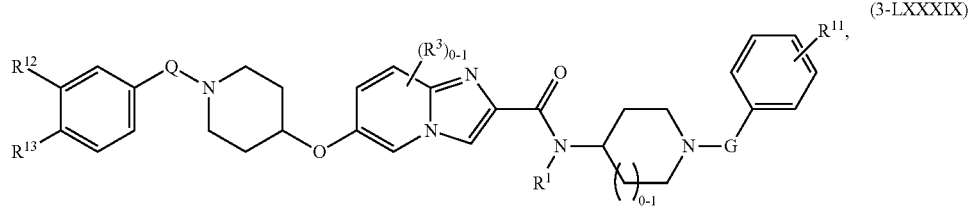

(3-LXXXIX)

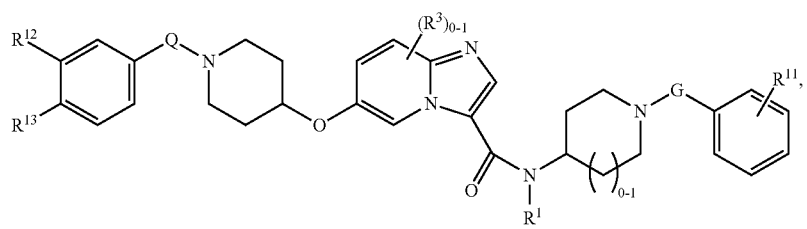

(3-XC)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (3-I)-(3-IV) and (3-LXIII); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, R$^1$ is H. In another embodiment, R$^1$ is methyl, ethyl, propyl or butyl. In one embodiment, no R$^3$ is substituted on the central imidazo[1,2-a]pyridine. In another embodiment, one R$^3$ (e.g., —Cl, —F, —CH$_3$, —C$_2$H$_5$, —C$_3$H$_7$) is substituted on the central imidazo[1,2-a]pyridine.

In certain embodiments, the presently disclosed compounds have the structural formula (3-XCI):

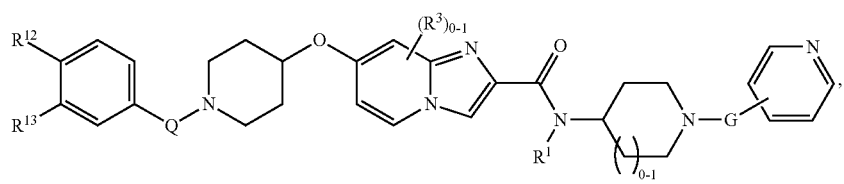

(3-XCI)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (3-I)-(3-IV) and (3-LX); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyridine nitrogen is positioned in the para position relative to the G moiety; in another embodiment, the pyridine nitrogen is positioned in the meta position relative to the G moiety. In one embodiment, R$^1$ is H. In another embodiment, R$^1$ is methyl, ethyl, propyl or butyl. In one embodiment, no R$^3$ is substituted on the central imidazo[1,2-a]pyridine. In another embodiment, one R$^3$ (e.g., —Cl, —F, —CH$_3$, —C$_2$H$_5$, —C$_3$H$_7$) is substituted on the central imidazo[1,2-a]pyridine.

In certain embodiments, the presently disclosed compounds have the structural formula (3-XCII):

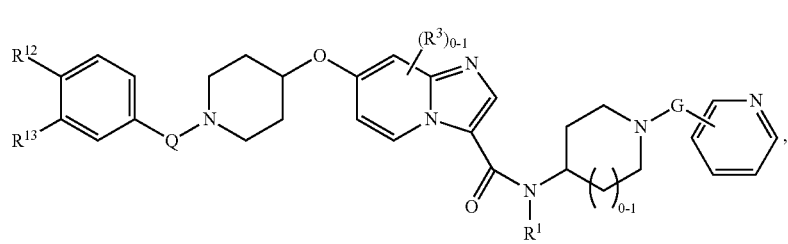

(3-XCII)

in which Q is —CH₂—, —C(O)— or a single bond; G is a single bond, —CH₂—, —C(O)—, —S(O)₂— or —C(O)—NH—; $R^1$ and $R^3$ are as described above with reference to any of structural formulae (3-I)-(3-IV) and (3-LXI); and $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), NO₂ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H. In one embodiment, the pyridine nitrogen is positioned in the para position relative to the G moiety; in another embodiment, the pyridine nitrogen is positioned in the meta position relative to the G moiety. In one embodiment, $R^1$ is H. In another embodiment, $R^1$ is methyl, ethyl, propyl or butyl. In one embodiment, no $R^3$ is substituted on the central imidazo[1,2-a]pyridine. In another embodiment, one $R^3$ (e.g., —Cl, —F, —CH₃, —C₂H₅, —C₃H₇) is substituted on the central imidazo[1,2-a]pyridine.

In certain embodiments, the presently disclosed compounds have the structural formula (3-XCIII):

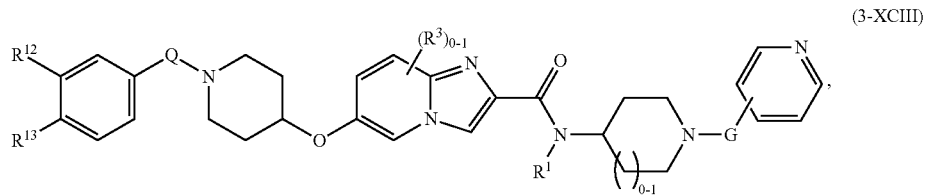

(3-XCIII)

in which Q is —CH₂—, —C(O)— or a single bond; G is a single bond, —CH₂—, —C(O)—, —S(O)₂— or —C(O)—NH—; $R^1$ and $R^3$ are as described above with reference to any of structural formulae (3-I)-(3-IV) and (3-LXII); and $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), NO₂ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H. In one embodiment, the pyridine nitrogen is positioned in the para position relative to the G moiety; in another embodiment, the pyridine nitrogen is positioned in the meta position relative to the G moiety. In one embodiment, $R^1$ is H. In another embodiment, $R^1$ is methyl, ethyl, propyl or butyl. In one embodiment, no $R^3$ is substituted on the central imidazo[1,2-a]pyridine. In another embodiment, one $R^3$ (e.g., —Cl, —F, —CH₃, —C₂H₅, —C₃H₇) is substituted on the central imidazo[1,2-a]pyridine.

In certain embodiments, the presently disclosed compounds have the structural formula (3-XCIV):

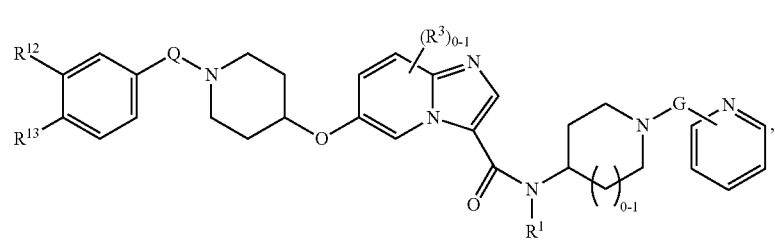

(3-XCIV)

in which Q is —CH₂—, —C(O)— or a single bond; G is a single bond, —CH₂—, —C(O)—, —S(O)₂— or —C(O)—NH—; $R^1$ and $R^3$ are as described above with reference to any of structural formulae (3-I)-(3-IV) and (3-LXIII); and $R^{12}$ and $R^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyridine nitrogen is positioned in the para position relative to the G moiety; in another embodiment, the pyridine nitrogen is positioned in the meta position relative to the G moiety. In one embodiment, R$^1$ is H. In another embodiment, R$^1$ is methyl, ethyl, propyl or butyl. In one embodiment, no R$^3$ is substituted on the central imidazo[1,2-a]pyridine. In another embodiment, one R$^3$ (e.g., —Cl, —F, —CH$_3$, —C$_2$H$_5$, —C$_3$H$_7$) is substituted on the central imidazo[1,2-a]pyridine.

In certain embodiments, the presently disclosed compounds have the structural formula (3-XCV):

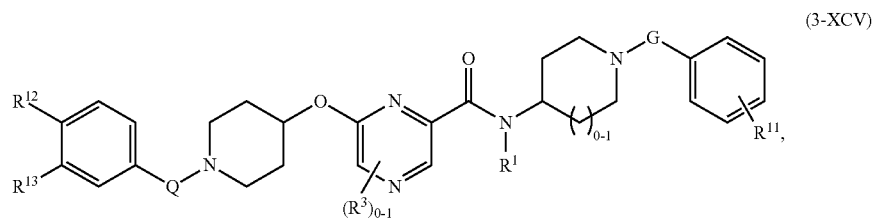

(3-XCV)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (3-I)-(3-IV) and (3-LXIV); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, R$^1$ is H. In another embodiment, R$^1$ is methyl, ethyl, propyl or butyl. In one embodiment, no R$^3$ is substituted on the central pyrazine. In another embodiment, one R$^3$ (e.g., —Cl, —F, —CH$_3$, —C$_2$H$_5$, —C$_3$H$_7$) is substituted on the central pyrazine.

In certain embodiments, the presently disclosed compounds have the structural formula (3-XCVI):

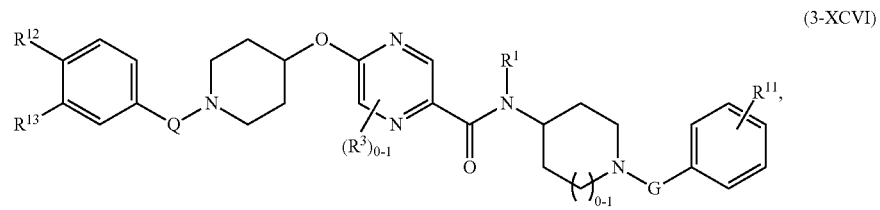

(3-XCVI)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (3-I)-(3-IV) and (3-LXV); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, $R^1$ is H. In another embodiment, $R^1$ is methyl, ethyl, propyl or butyl. In one embodiment, no $R^3$ is substituted on the central pyrazine. In another embodiment, one $R^3$ (e.g., —Cl, —F, —CH$_3$, —C$_2$H$_5$, —C$_3$H$_7$) is substituted on the central pyrazine.

In certain embodiments, the presently disclosed compounds have the structural formula (3-XCVII):

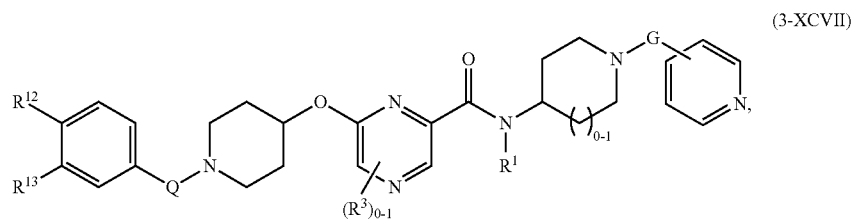

(3-XCVII)

in which Q is —CH$_2$—, —C(O)— or a single bond; G is a single bond, —CH$_2$—, —C(O)—, —S(O)$_2$— or —C(O)—NH—; $R^1$ and $R^3$ are as described above with reference to any of structural formulae (3-I) and (3-LXIV); and $R^{12}$ and $R^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group.

In one particular such embodiment, at least one of $R^{12}$ and $R^{13}$ is not H. In one embodiment, the pyridine nitrogen is positioned in the para position relative to the G moiety; in another embodiment, the pyridine nitrogen is positioned in the meta position relative to the G moiety. In one embodiment, $R^1$ is H. In another embodiment, $R^1$ is methyl, ethyl, propyl or butyl. In one embodiment, no $R^3$ is substituted on the central pyrazine. In another embodiment, one $R^3$ (e.g., —Cl, —F, —CH$_3$, —C$_2$H$_5$, —C$_3$H$_7$) is substituted on the central pyrazine.

In certain embodiments, the presently disclosed compounds have the structural formula (3-XCVIII):

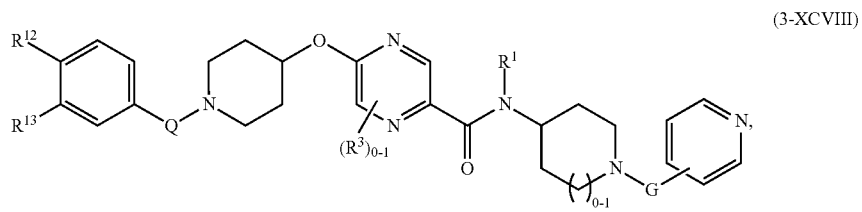

(3-XCVIII)

in which Q is —CH$_2$—, —C(O)— or a single bond; G is a single bond, —CH$_2$—, —C(O)—, —S(O)$_2$— or —C(O)—NH—; $R^1$ and $R^3$ are as described above with reference to any of structural formulae (3-I)-(3-IV) and (3-LXV); and $R^{12}$ and $R^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H. In one embodiment, the pyridine nitrogen is positioned in the para position relative to the G moiety; in another embodiment, the pyridine nitrogen is positioned in the meta position relative to the G moiety. In one embodiment, $R^1$ is H. In another embodiment, $R^1$ is methyl, ethyl, propyl or butyl. In one embodiment, no $R^3$ is substituted on the central pyrazine. In another embodiment, one $R^3$ (e.g., —Cl, —F, —CH$_3$, —C$_2$H$_5$, —C$_3$H$_7$) is substituted on the central pyrazine.

In certain embodiments, the presently disclosed compounds have the structural formula (3-XCIX):

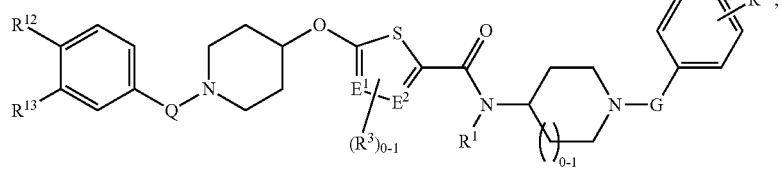
(3-XCIX)

in which Q is —CH$_2$—, —C(O)— or a single bond; G is a single bond, —CH$_2$—, —C(O)—, —S(O)$_2$— or —C(O)—NH—; $E^1$, $E^2$, $R^1$ and $R^3$ are as described above with reference to any of structural formulae (3-I)-(3-IV) and (3-LXVI); and $R^{11}$, $R^{12}$ and $R^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, $R^1$ is H. In another embodiment, $R^1$ is methyl, ethyl, propyl or butyl. In one embodiment, no $R^3$ is substituted on the central thiazole. In another embodiment, one $R^3$ (e.g., —Cl, —F, —CH$_3$, —C$_2$H$_5$, —C$_3$H$_7$) is substituted on the central thiazole. In one embodiment, $E^1$ is carbon and $E^2$ is N. In another embodiment, $E^1$ is N and $E^2$ is carbon.

In certain embodiments, the presently disclosed compounds have the structural formula (3-C):

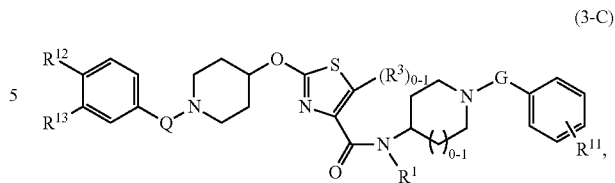
(3-C)

in which Q is —CH$_2$—, —C(O)— or a single bond; G is a single bond, —CH$_2$—, —C(O)—, —S(O)$_2$— or —C(O)—NH—; $R^1$ and $R^3$ are as described above with reference to any of structural formulae (3-I)-(3-IV) and (3-LXVII); and $R^{11}$, $R^{12}$ and $R^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, $R^1$ is H. In another embodiment, $R^1$ is methyl, ethyl, propyl or butyl. In one embodiment, no $R^3$ is substituted on the central thiazole (3-I.e., the ring position shown occupied by $R^3$ bears a hydrogen atom). In another embodiment, one $R^3$ (e.g., —Cl, —F, —CH$_3$, —C$_2$H$_5$, —C$_3$H$_7$) is substituted on the central thiazole.

In certain embodiments, the presently disclosed compounds have the structural formula (3-CI):

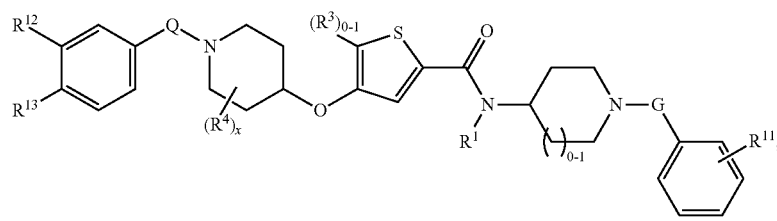
(3-CI)

in which Q is —CH$_2$—, —C(O)— or a single bond; G is a single bond, —CH$_2$—, —C(O)—, —S(O)$_2$— or —C(O)—NH—; $R^1$ and $R^3$ are as described above with reference to any of structural formulae (3-I)-(3-IV) and (3-LXVIII); and $R^{11}$, $R^{12}$ and $R^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, $R^1$ is H. In another embodiment, $R^1$ is methyl, ethyl, propyl or butyl. In one embodiment, no $R^3$ is substituted on the central thiazole (3-I.e., the ring position shown occupied by $R^3$ bears a hydrogen atom). In another embodiment, one $R^3$ (e.g., —Cl, —F, —CH$_3$, —C$_2$H$_5$, —C$_3$H$_7$) is substituted on the central thiazole.

In certain embodiments, the presently disclosed compounds have the structural formula (3-CII):

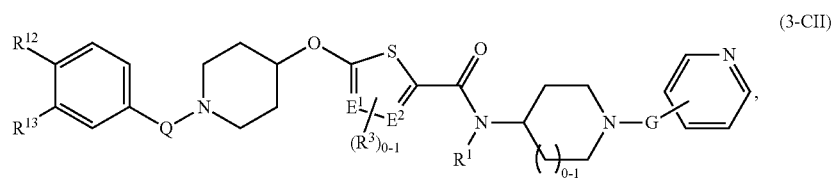

(3-CII)

in which Q is —CH$_2$—, —C(O)— or a single bond; G is a single bond, —CH$_2$—, —C(O)—, —S(O)$_2$— or —C(O)—NH—; $E^1$, $E^2$, $R^1$ and $R^3$ are as described above with reference to any of structural formulae (3-I)-(3-IV) and (3-LXVI); and $R^{11}$, $R^{12}$ and $R^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one embodiment, the pyridine nitrogen is positioned in the para position relative to the G moiety; in another embodiment, the pyridine nitrogen is positioned in the meta position relative to the G moiety. In one embodiment, $R^1$ is H. In another embodiment, $R^1$ is methyl, ethyl, propyl or butyl. In one embodiment, no $R^3$ is substituted on the central thiazole. In another embodiment, one $R^3$ (e.g., —Cl, —F, —CH$_3$, —C$_2$H$_5$, —C$_3$H$_7$) is substituted on the central thiazole. In one embodiment, $E^1$ is carbon and $E^2$ is N. In another embodiment, $E^1$ is N and $E^2$ is carbon.

In certain embodiments, the presently disclosed compounds have the structural formula (3-CIII):

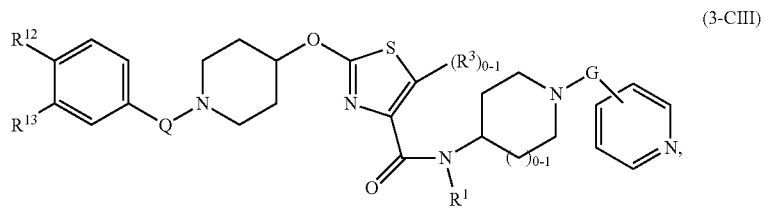

(3-CIII)

in which Q is —CH$_2$—, —C(O)— or a single bond; G is a single bond, —CH$_2$—, —C(O)—, —S(O)$_2$— or —C(O)—NH—; $R^1$ and $R^3$ are as described above with reference to any of structural formulae (3-I)-(3-IV) and (3-LXVII); and $R^{11}$, $R^{12}$ and $R^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one embodiment, the pyridine nitrogen is positioned in the para position relative to the G moiety; in another embodiment, the pyridine nitrogen is positioned in the meta position relative to the G moiety. In one embodiment, $R^1$ is H. In another embodiment, $R^1$ is methyl, ethyl, propyl or butyl. In one embodiment, no $R^3$ is substituted on the central thiazole (3-I.e., the ring position shown occupied by $R^3$ bears a hydrogen atom). In another embodiment, one $R^3$ (e.g., —Cl, —F, —CH$_3$, —C$_2$H$_5$, —C$_3$H$_7$) is substituted on the central thiazole.

In certain embodiments, the presently disclosed compounds have the structural formula (3-CIV):

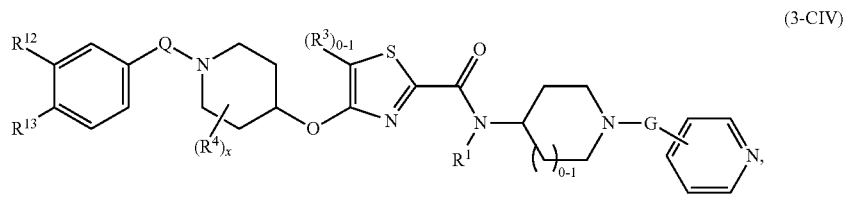

(3-CIV)

in which Q is —CH$_2$—, —C(O)— or a single bond; G is a single bond, —CH$_2$—, —C(O)—, —S(O)$_2$— or —C(O)—NH—; $R^1$ and $R^3$ are as described above with reference to any of structural formulae (3-I)-(3-IV) and (3-LXVIII); and $R^{11}$, $R^{12}$ and $R^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one embodiment, the pyridine nitrogen is positioned in the para position relative to the G moiety; in another embodiment, the pyridine nitrogen is positioned in the meta position relative to the G moiety. In one embodiment, $R^1$ is H. In another embodiment, $R^1$ is methyl, ethyl, propyl or butyl. In one embodiment, no $R^3$ is substituted on the central thiazole (3-I.e., the ring position shown occupied by $R^3$ bears a hydrogen atom). In another embodiment, one $R^3$ (e.g., —Cl, —F, —CH$_3$, —C$_2$H$_5$, —C$_3$H$_7$) is substituted on the central thiazole.

In certain embodiments, the presently disclosed compounds have the structural formula (3-CV):

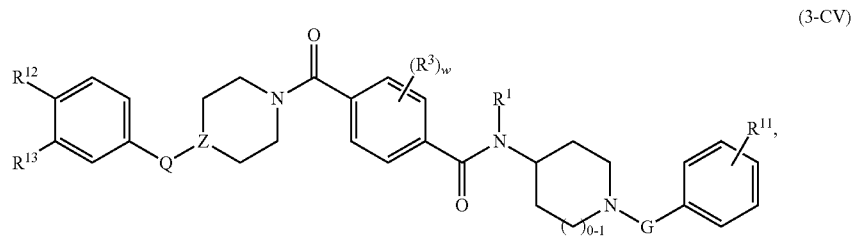

(3-CV)

in which Q is —CH$_2$—, —C(O)— or a single bond; G is a single bond, —CH$_2$—, —C(O)—, —S(O)$_2$— or —C(O)—NH—; Z, $R^1$ and $R^3$ are as described above with reference to any of structural formulae (3-I)-(3-IV) and (3-LXIX); and $R^{11}$, $R^{12}$ and $R^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, $R^1$ is H. In another embodiment, $R^1$ is methyl, ethyl, propyl or butyl. In one embodiment, no $R^3$ is substituted on the central phenyl ring. In another embodiment, one $R^3$ (e.g., —Cl, —F, —CH$_3$, —C$_2$H$_5$, —C$_3$H$_7$) is substituted on the central phenyl ring. In one embodiment, Z is N. In another embodiment, Z is CH.

In certain embodiments, the presently disclosed compounds have the structural formula (3-CVI):

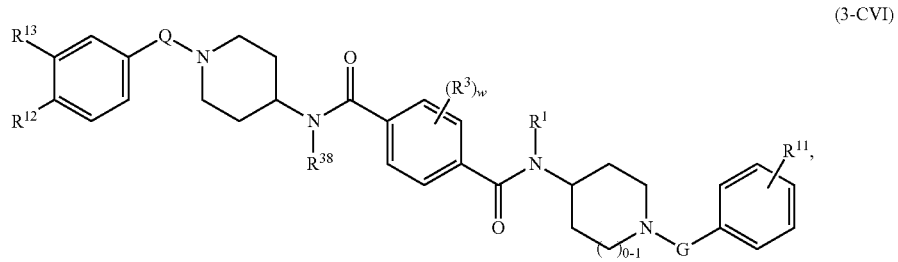

(3-CVI)

in which Q is —CH$_2$—, —C(O)— or a single bond; G is a single bond, —CH$_2$—, —C(O)—, —S(O)$_2$— or —C(O)—NH—; $R^1$, $R^3$ and $R^{38}$ are as described above with reference to any of structural formulae (3-I)-(3-IV) and (3-LXX); and $R^{11}$, $R^{12}$ and $R^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, $R^1$ is H. In another embodiment, $R^1$ is methyl, ethyl, propyl or butyl. In one embodiment, no $R^3$ is substituted on the central phenyl ring. In another embodiment, one $R^3$ (e.g., —Cl, —F, —CH$_3$, —C$_2$H$_5$, —C$_3$H$_7$) is substituted on the central phenyl ring. In one embodiment, $R^{38}$ is H. In another embodiment, $R^{38}$ is methyl, ethyl, propyl or butyl.

In certain embodiments, the presently disclosed compounds have the structural formula (3-CVII):

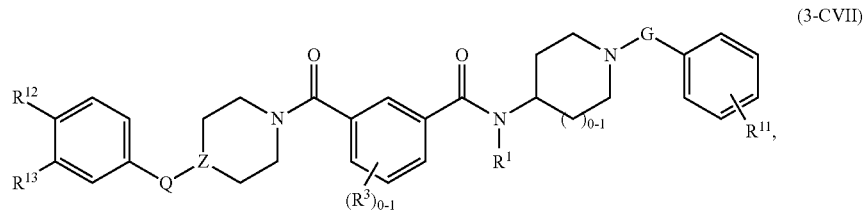

(3-CVII)

in which Q is —CH$_2$—, —C(O)— or a single bond; G is a single bond, —CH$_2$—, —C(O)—, —S(O)$_2$— or —C(O)—NH—; Z, $R^1$ and $R^3$ are as described above with reference to any of structural formulae (3-I)-(3-IV) and (3-LXXI); and $R^{11}$, $R^{12}$ and $R^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, $R^1$ is H. In another embodiment, $R^1$ is methyl, ethyl, propyl or butyl. In one embodiment, no $R^3$ is substituted on the central phenyl ring. In another embodiment, one $R^3$ (e.g., —Cl, —F, —CH$_3$, —C$_2$H$_5$, —C$_3$H$_7$) is substituted on the central phenyl ring. In one embodiment, Z is N. In another embodiment, Z is CH.

In certain embodiments, the presently disclosed compounds have the structural formula (3-CVIII):

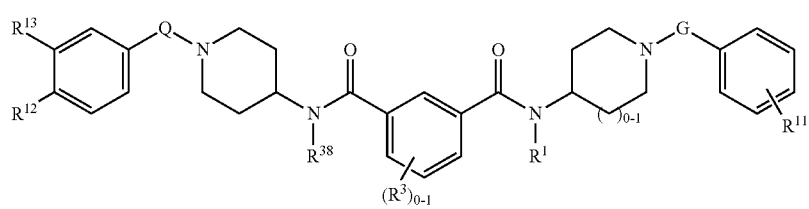

(3-CVIII)

in which Q is —CH$_2$—, —C(O)— or a single bond; G is a single bond, —CH$_2$—, —C(O)—, —S(O)$_2$— or —C(O)—NH—; $R^1$, $R^3$ and $R^{38}$ are as described above with reference to any of structural formulae (3-I)-(3-IV) and (3-LXXII); and $R^{11}$, $R^{12}$ and $R^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, $R^1$ is H. In another embodiment, $R^1$ is methyl, ethyl, propyl or butyl. In one embodiment, no $R^3$ is substituted on the central phenyl ring. In another embodiment, one $R^3$ (e.g., —Cl, —F, —CH$_3$, —C$_2$H$_5$, —C$_3$H$_7$) is substituted on the central phenyl ring. In one embodiment, $R^{38}$ is H. In another embodiment, $R^{38}$ is methyl, ethyl, propyl or butyl.

In certain embodiments, the presently disclosed compounds have the structural formula (3-CIX):

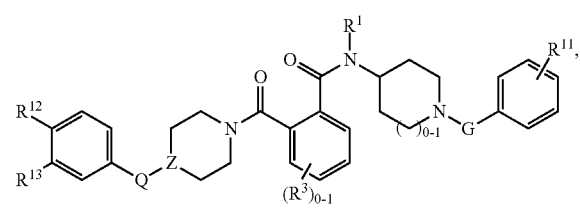

(3-CIX)

in which Q is —CH$_2$—, —C(O)— or a single bond; G is a single bond, —CH$_2$—, —C(O)—, —S(O)$_2$— or —C(O)—NH—; Z, $R^1$ and $R^3$ are as described above with reference to any of structural formulae (3-I)-(3-IV) and (3-LXXIII); and $R^{11}$, $R^{12}$ and $R^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, $R^1$ is H. In another embodiment, $R^1$ is methyl, ethyl, propyl or butyl. In one embodiment, no $R^3$ is substituted on the central phenyl ring. In another embodiment, one $R^3$ (e.g., —Cl, —F, —CH$_3$, —C$_2$H$_5$, —C$_3$H$_7$) is substituted on the central phenyl ring. In one embodiment, Z is N. In another embodiment, Z is CH.

In certain embodiments, the presently disclosed compounds have the structural formula (3-CX):

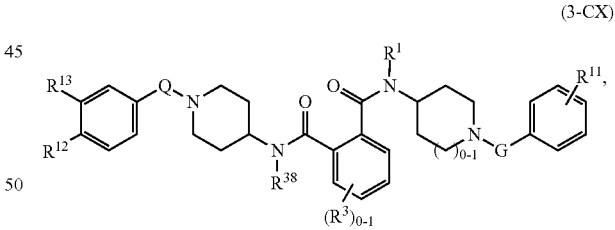

(3-CX)

in which Q is —CH$_2$—, —C(O)— or a single bond; G is a single bond, —CH$_2$—, —C(O)—, —S(O)$_2$— or —C(O)—NH—; $R^1$, $R^3$ and $R^{38}$ are as described above with reference to any of structural formulae (3-I)-(3-IV) and (3-LXXIV); and $R^{11}$, $R^{12}$ and $R^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, $R^1$ is H. In another embodiment, $R^1$ is methyl, ethyl, propyl or butyl. In one embodiment, no $R^3$ is substituted on the central phenyl ring. In another embodiment, one $R^3$ (e.g., —Cl, —F, —CH$_3$, —C$_2$H$_5$, —C$_3$H$_7$) is substituted on the central phenyl ring. In one embodiment, $R^{38}$ is H. In another embodiment, $R^{38}$ is methyl, ethyl, propyl or butyl.

In certain embodiments, the presently disclosed compounds have the structural formula (3-CXI):

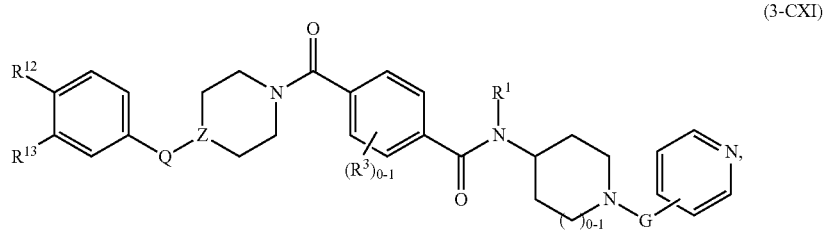

(3-CXI)

in which Q is —CH$_2$—, —C(O)— or a single bond; G is a single bond, —CH$_2$—, —C(O)—, —S(O)$_2$— or —C(O)—NH—; Z, $R^1$ and $R^3$ are as described above with reference to any of structural formulae (3-I)-(3-IV) and (3-LXIX); and $R^{12}$ and $R^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H. In one embodiment, the pyridine nitrogen is positioned in the para position relative to the G moiety; in another embodiment, the pyridine nitrogen is positioned in the meta position relative to the G moiety. In one embodiment, $R^1$ is H. In another embodiment, $R^1$ is methyl, ethyl, propyl or butyl. In one embodiment, no $R^3$ is substituted on the central phenyl ring. In another embodiment, one $R^3$ (e.g., —Cl, —F, —CH$_3$, —C$_2$H$_5$, —C$_3$H$_7$) is substituted on the central phenyl ring. In one embodiment, Z is N. In another embodiment, Z is CH.

In certain embodiments, the presently disclosed compounds have the structural formula (3-CXII):

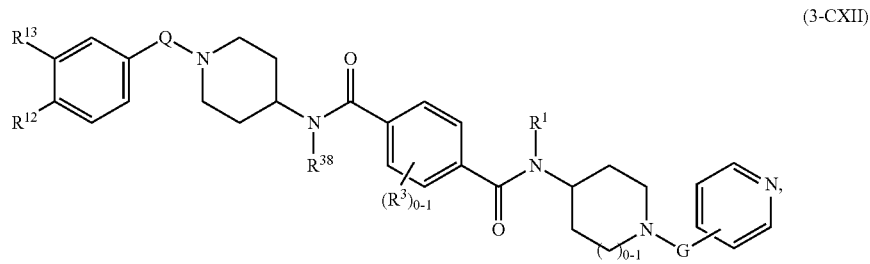

(3-CXII)

in which Q is —CH$_2$—, —C(O)— or a single bond; G is a single bond, —CH$_2$—, —C(O)—, —S(O)$_2$— or —C(O)—NH—; $R^1$, $R^3$ and $R^{38}$ are as described above with reference to any of structural formulae (3-I)-(3-IV) and (3-LXX); and $R^{12}$ and $R^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)

N(C₀-C₄ alkyl)(C₀-C₄ alkyl), NO₂ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H. In one embodiment, the pyridine nitrogen is positioned in the para position relative to the G moiety; in another embodiment, the pyridine nitrogen is positioned in the meta position relative to the G moiety. In one embodiment, $R^1$ is H. In another embodiment, $R^1$ is methyl, ethyl, propyl or butyl. In one embodiment, no $R^3$ is substituted on the central phenyl ring. In another embodiment, one $R^3$ (e.g., —Cl, —F, —CH₃, —C₂H₅, —C₃H₇) is substituted on the central phenyl ring. In one embodiment, $R^{38}$ is H. In another embodiment, $R^{38}$ is methyl, ethyl, propyl or butyl.

In certain embodiments, the presently disclosed compounds have the structural formula (3-CXIII):

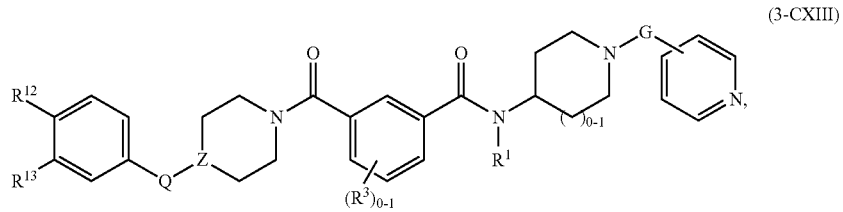

(3-CXIII)

in which Q is —CH₂—, —C(O)— or a single bond; G is a single bond, —CH₂—, —C(O)—, —S(O)₂— or —C(O)—NH—; Z, $R^1$ and $R^3$ are as described above with reference to any of structural formulae (3-I)-(3-IV) and (3-LXXI); and $R^{12}$ and $R^{13}$ are independently selected from H, halo, cyano, —(C₁-C₄ haloalkyl), —O—(C₁-C₄ haloalkyl), —(C₁-C₄ alkyl), —O—(C₁-C₄ alkyl), —C(O)—(C₀-C₄ alkyl), —C(O)O—(C₀-C₄ alkyl), —C(O)N(C₀-C₄ alkyl)(C₀-C₄ alkyl), NO₂ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H. In one embodiment, the pyridine nitrogen is positioned in the para position relative to the G moiety; in another embodiment, the pyridine nitrogen is positioned in the meta position relative to the G moiety. In one embodiment, $R^1$ is H. In another embodiment, $R^1$ is methyl, ethyl, propyl or butyl. In one embodiment, no $R^3$ is substituted on the central phenyl ring. In another embodiment, one $R^3$ (e.g., —Cl, —F, —CH₃, —C₂H₅, —C₃H₇) is substituted on the central phenyl ring. In one embodiment, Z is N. In another embodiment, Z is CH.

In certain embodiments, the presently disclosed compounds have the structural formula (3-CXIV):

in which Q is —CH₂—, —C(O)— or a single bond; G is a single bond, —CH₂—, —C(O)—, —S(O)₂— or —C(O)—NH—; $R^1$, $R^3$ and $R^{38}$ are as described above with reference to any of structural formulae (3-I)-(3-IV) and (3-LXXII); and $R^{12}$ and $R^{13}$ are independently selected from H, halo, cyano, —(C₁-C₄ haloalkyl), —O—(C₁-C₄ haloalkyl), —(C₁-C₄ alkyl), —O—(C₁-C₄ alkyl), —C(O)—(C₀-C₄ alkyl), —C(O)O—(C₀-C₄ alkyl), —C(O)N(C₀-C₄ alkyl)(C₀-C₄ alkyl), NO₂ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H. In one embodiment, the pyridine nitrogen is positioned in the para position relative to the G moiety; in another embodiment, the pyridine nitrogen is positioned in the meta position relative to the G moiety. In one embodiment, $R^1$ is H. In another embodiment, $R^1$ is methyl, ethyl, propyl or butyl. In one embodiment, no $R^3$ is substituted on the central phenyl ring. In another embodiment, one $R^3$ (e.g., —Cl, —F, —CH₃, —C₂H₅, —C₃H₇) is substituted on the central phenyl ring. In one embodiment, $R^{38}$ is H. In another embodiment, $R^{38}$ is methyl, ethyl, propyl or butyl.

In certain embodiments, the presently disclosed compounds have the structural formula (3-CXV):

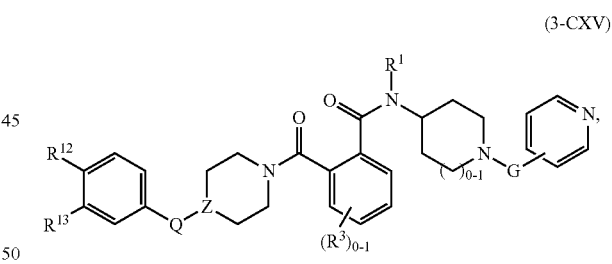

(3-CXV)

in which Q is —CH₂—, —C(O)— or a single bond; G is a single bond, —CH₂—, —C(O)—, —S(O)₂— or —C(O)—NH—; Z, $R^1$ and $R^3$ are as described above with reference to any of structural formulae (3-I)-(3-IV) and (3-LXXIII);

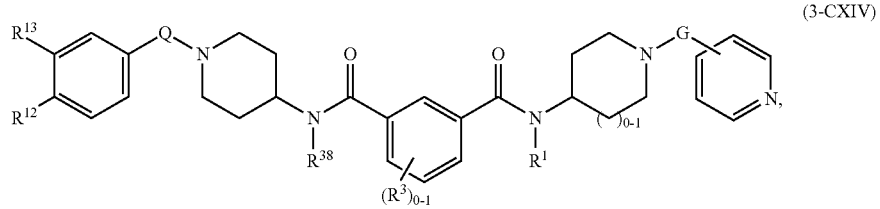

(3-CXIV)

and $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H. In one embodiment, the pyridine nitrogen is positioned in the para position relative to the G moiety; in another embodiment, the pyridine nitrogen is positioned in the meta position relative to the G moiety. In one embodiment, $R^1$ is H. In another embodiment, $R^1$ is methyl, ethyl, propyl or butyl. In one embodiment, no $R^3$ is substituted on the central phenyl ring. In another embodiment, one $R^3$ (e.g., —Cl, —F, —$CH_3$, —$C_2H_5$, —$C_3H_7$) is substituted on the central phenyl ring. In one embodiment, Z is N. In another embodiment, Z is CH.

In certain embodiments, the presently disclosed compounds have the structural formula (3-CXVI):

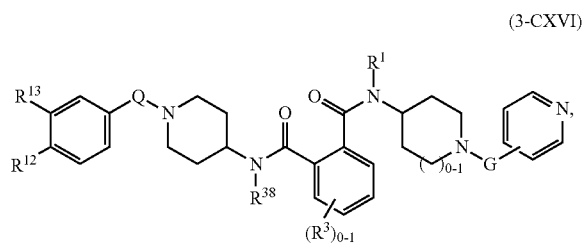

(3-CXVI)

in which Q is —$CH_2$—, —C(O)— or a single bond; G is a single bond, —$CH_2$—, —C(O)—, —S(O)$_2$— or —C(O)—NH—; $R^1$, $R^3$ and $R^{38}$ are as described above with reference to any of structural formulae (3-I)-(3-IV) and (3-LXXIV); and $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H. In one embodiment, the pyridine nitrogen is positioned in the para position relative to the G moiety; in another embodiment, the pyridine nitrogen is positioned in the meta position relative to the G moiety. In one embodiment, $R^1$ is H. In another embodiment, $R^1$ is methyl, ethyl, propyl or butyl. In one embodiment, no $R^3$ is substituted on the central phenyl ring. In another embodiment, one $R^3$ (e.g., —Cl, —F, —$CH_3$, —$C_2H_5$, —$C_3H_7$) is substituted on the central phenyl ring. In one embodiment, $R^{38}$ is H. In another embodiment, $R^{38}$ is methyl, ethyl, propyl or butyl.

In certain embodiments, the presently disclosed compounds have the structural formula (3-CXVII):

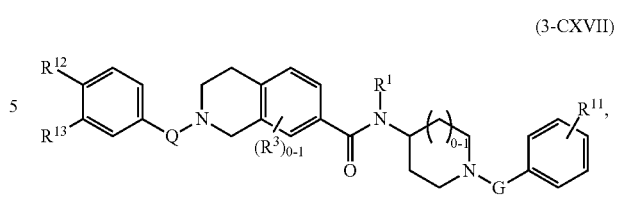

(3-CXVII)

in which Q is —$CH_2$—, —C(O)— or a single bond; G is a single bond, —$CH_2$—, —C(O)—, —S(O)$_2$— or —C(O)—NH—; $R^1$ and $R^3$ are as described above with reference to any of structural formulae (3-I)-(3-IV) and (3-LXXV); and $R^{11}$, $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, $R^1$ is H. In another embodiment, $R^1$ is methyl, ethyl, propyl or butyl. In one embodiment, no $R^3$ is substituted on the central benzo moiety. In another embodiment, one $R^3$ (e.g., —Cl, —F, —$CH_3$, —$C_2H_5$, —$C_3H_7$) is substituted on the central benzo moiety.

In certain embodiments, the presently disclosed compounds have the structural formula (3-CXVIII):

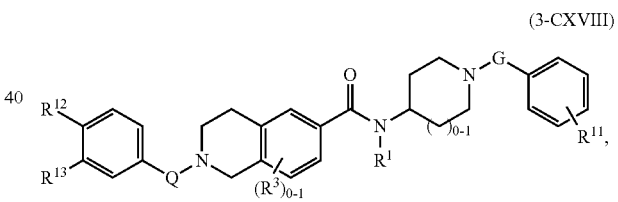

(3-CXVIII)

in which Q is —$CH_2$—, —C(O)— or a single bond; G is a single bond, —$CH_2$—, —C(O)—, —S(O)$_2$— or —C(O)—NH—; $R^1$ and $R^3$ are as described above with reference to any of structural formulae (3-I)-(3-IV) and (3-LXXVI); and $R^{11}$, $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, $R^1$ is H. In another embodiment, $R^1$ is methyl, ethyl, propyl or butyl. In one embodiment, no $R^3$ is substituted on the central benzo moiety. In another embodiment, one $R^3$ (e.g., —Cl, —F, —$CH_3$, —$C_2H_5$, —$C_3H_7$) is substituted on the central benzo moiety.

In certain embodiments, the presently disclosed compounds have the structural formula (3-CXIX):

(3-CXIX)

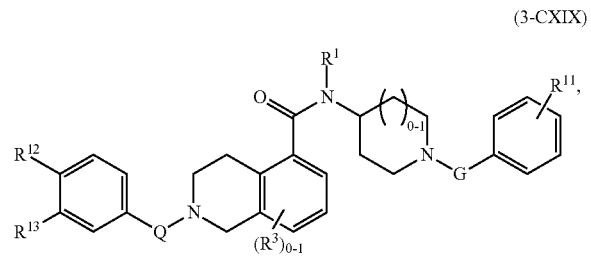

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (3-I)-(3-IV) and (3-LXXVII); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, R$^1$ is H. In another embodiment, R$^1$ is methyl, ethyl, propyl or butyl. In one embodiment, no R$^3$ is substituted on the central benzo moiety. In another embodiment, one R$^3$ (e.g., —Cl, —F, —CH$_3$, —C$_2$H$_5$, —C$_3$H$_7$) is substituted on the central benzo moiety.

In certain embodiments, the presently disclosed compounds have the structural formula (3-CXX):

(3-CXX)

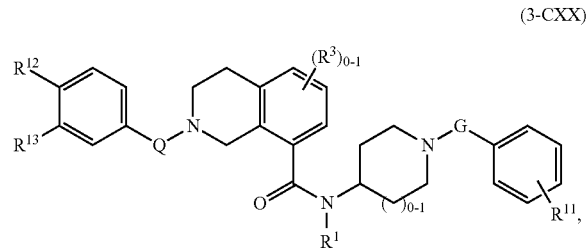

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (3-I)-(3-IV) and (3-LXXVIII); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, R$^1$ is H. In another embodiment, R$^1$ is methyl, ethyl, propyl or butyl. In one embodiment, no R$^3$ is substituted on the central benzo moiety. In another embodiment, one R$^3$ (e.g., —Cl, —F, —CH$_3$, —C$_2$H$_5$, —C$_3$H$_7$) is substituted on the central benzo moiety.

In certain embodiments, the presently disclosed compounds have the structural formula (3-CXXI):

(3-CXXI)

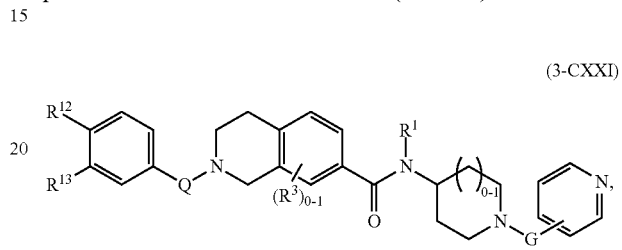

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (3-I)-(3-IV) and (3-LXXV); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyridine nitrogen is positioned in the para position relative to the G moiety; in another embodiment, the pyridine nitrogen is positioned in the meta position relative to the G moiety. In one embodiment, R$^1$ is H. In another embodiment, R$^1$ is methyl, ethyl, propyl or butyl. In one embodiment, no R$^3$ is substituted on the central benzo moiety. In another embodiment, one R$^3$ (e.g., —Cl, —F, —CH$_3$, —C$_2$H$_5$, —C$_3$H$_7$) is substituted on the central benzo moiety.

In certain embodiments, the presently disclosed compounds have the structural formula (3-CXXII):

(3-CXXII)

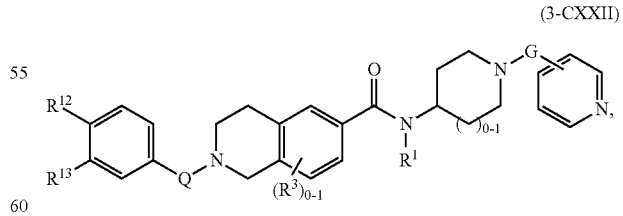

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (3-I)-(3-IV) and (3-LXXVI); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyridine nitrogen is positioned in the para position relative to the G moiety; in another embodiment, the pyridine nitrogen is positioned in the meta position relative to the G moiety. In one embodiment, R$^1$ is H. In another embodiment, R$^1$ is methyl, ethyl, propyl or butyl. In one embodiment, no R$^3$ is substituted on the central benzo moiety. In another embodiment, one R$^3$ (e.g., —Cl, —F, —CH$_3$, —C$_2$H$_5$, —C$_3$H$_7$) is substituted on the central benzo moiety.

In certain embodiments, the presently disclosed compounds have the structural formula (3-CXXIII):

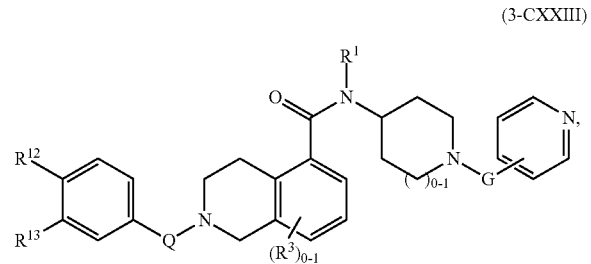

(3-CXXIII)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (3-I)-(3-IV) and (3-LXXVII); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyridine nitrogen is positioned in the para position relative to the G moiety; in another embodiment, the pyridine nitrogen is positioned in the meta position relative to the G moiety. In one embodiment, R$^1$ is H. In another embodiment, R$^1$ is methyl, ethyl, propyl or butyl. In one embodiment, no R$^3$ is substituted on the central benzo moiety. In another embodiment, one R$^3$ (e.g., —Cl, —F, —CH$_3$, —C$_2$H$_5$, —C$_3$H$_7$) is substituted on the central benzo moiety.

In certain embodiments, the presently disclosed compounds have the structural formula (3-CXXIV):

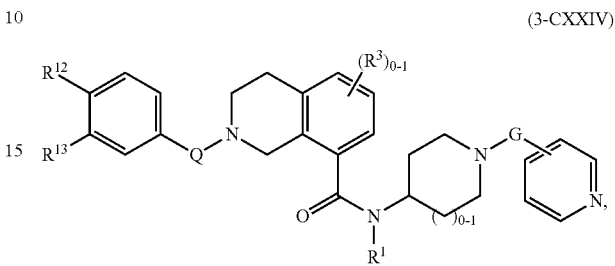

(3-CXXIV)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (3-I)-(3-IV) and (3-LXXVIII); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyridine nitrogen is positioned in the para position relative to the G moiety; in another embodiment, the pyridine nitrogen is positioned in the meta position relative to the G moiety. In one embodiment, R$^1$ is H. In another embodiment, R$^1$ is methyl, ethyl, propyl or butyl. In one embodiment, no R$^3$ is substituted on the central benzo moiety. In another embodiment, one R$^3$ (e.g., —Cl, —F, —CH$_3$, —C$_2$H$_5$, —C$_3$H$_7$) is substituted on the central benzo moiety.

Examples of compounds according to structural formula (3-I) include those listed below in Table 3. These compounds can be made, for example using a procedure analogous to those described in U.S. Patent Application Publications nos. 2009/0163511, 2009/0170829, 2009/0186894 and 2009/0275609, and in U.S. patent application Ser. No. 12/695,861, each of which is hereby incorporated by reference in its entirety.

TABLE 3

| No. | Name | Structure |
| --- | --- | --- |
| 3-1 | tert-butyl 4-(6-(1-(4-(trifluoromethyl)phenyl)piperidin-4-yloxy)benzo[d]oxazole-2-carboxamido)piperidine-1-carboxylate | 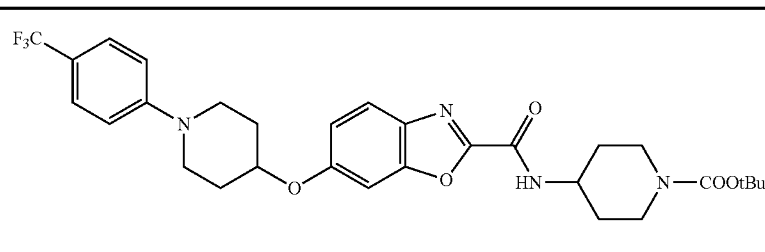 |

TABLE 3-continued

| No. | Name |
|---|---|
| 3-2 | N-(1-(4-cyanobenzyl)piperidin-4-yl)-6-(1-(4-(trifluoromethyl)phenyl)piperidin-4-yloxy)benzo[d]oxazole-2-carboxamide |
| 3-3 | N-(1-(pyridin-4-ylmethyl)piperidin-4-yl)-6-(1-(4-(trifluoromethyl)phenyl)piperidin-4-yloxy)benzo[d]oxazole-2-carboxamide |
| 3-4 | N-(1-(4-fluorobenzoyl)piperidin-4-yl)-6-(1-(4-(trifluoromethyl)phenyl)piperidin-4-yloxy)benzo[d]oxazole-2-carboxamide |
| 3-5 | N-(piperidin-4-yl)-6-(1-(4-(trifluoromethyl)phenyl)piperidin-4-yloxy)benzo[d]oxazole-2-carboxamide |
| 3-6 | N-(1-(4-cyanobenzoyl)piperidin-4-yl)-6-(1-(4-(trifluoromethyl)phenyl)piperidin-4-yloxy)benzo[d]oxazole-2-carboxamide |
| 3-7 | N-(4-isonicotinoylcyclohexyl)-6-(1-(4-(trifluoromethyl)phenyl)piperidin-4-yloxy)benzo[d]oxazole-2-carboxamide |
| 3-8 | (5-(pyridin-4-ylmethyl)-2,5-diazabicyclo[2.2.1]heptan-2-yl)(6-(1-(4-(trifluoromethyl)phenyl)piperidin-4-yloxy)benzo[d]oxazol-2-yl)methanone |

TABLE 3-continued

| No. | Name | Structure |
|---|---|---|
| 3-9 | 4-((5-(6-(1-(4-(trifluoromethyl)phenyl)piperidin-4-yloxy)benzo[d]oxazole-2-carbonyl)-2,5-diazabicyclo[2.2.1]heptan-2-yl)methyl)benzamide | 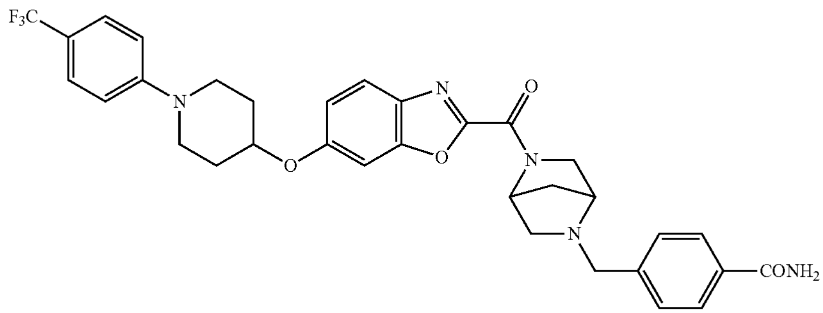 [SMILES: NC(=O)c1ccc(CN2CC3CC2CN3C(=O)c2nc3ccc(OC4CCN(c5ccc(C(F)(F)F)cc5)CC4)cc3o2)cc1] |
| 3-10 | 4-((5-(6-(1-(4-(trifluoromethyl)phenyl)piperidin-4-yloxy)benzo[d]oxazole-2-carbonyl)-2,5-diazabicyclo[2.2.1]heptan-2-yl)methyl)benzonitrile | 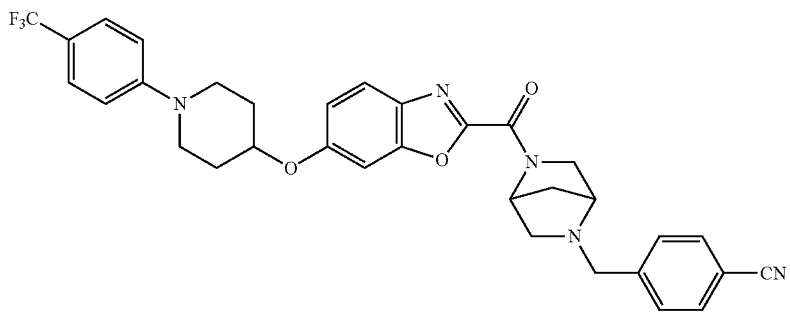 [SMILES: N#Cc1ccc(CN2CC3CC2CN3C(=O)c2nc3ccc(OC4CCN(c5ccc(C(F)(F)F)cc5)CC4)cc3o2)cc1] |
| 3-11 | (5-isonicotinoyl-2,5-diazabicyclo[2.2.1]heptan-2-yl)(6-(1-(4-(trifluoromethyl)phenyl)piperidin-4-yloxy)benzo[d]oxazol-2-yl)methanone | 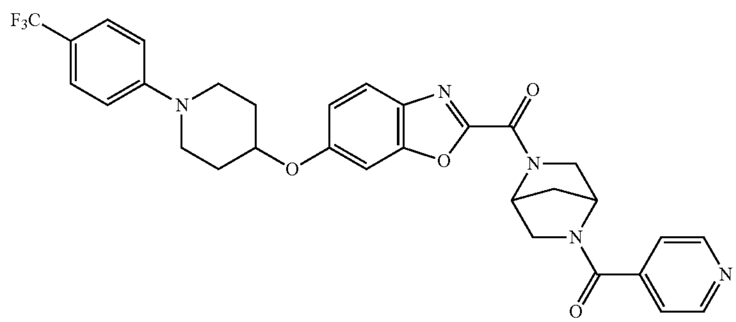 [SMILES: O=C(c1ccncc1)N1CC2CC1CN2C(=O)c1nc2ccc(OC3CCN(c4ccc(C(F)(F)F)cc4)CC3)cc2o1] |
| 3-12 | 4-(5-(6-(1-(4-(trifluoromethyl)phenyl)piperidin-4-yloxy)benzo[d]oxazole-2-carbonyl)-2,5-diazabicyclo[2.2.1]heptane-2-carbonyl)benzonitrile | 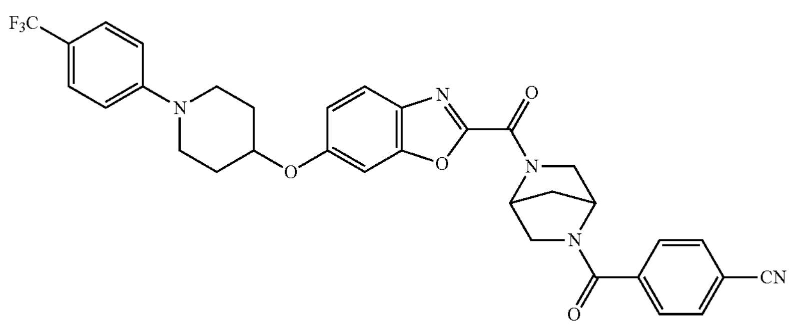 [SMILES: N#Cc1ccc(C(=O)N2CC3CC2CN3C(=O)c2nc3ccc(OC4CCN(c5ccc(C(F)(F)F)cc5)CC4)cc3o2)cc1] |
| 3-13 | (5-(4-fluorobenzoyl)-2,5-diazabicyclo[2.2.1]heptan-2-yl)(6-(1-(4-(trifluoromethyl)phenyl)piperidin-4-yloxy)benzo[d]oxazol-2-yl)methanone | 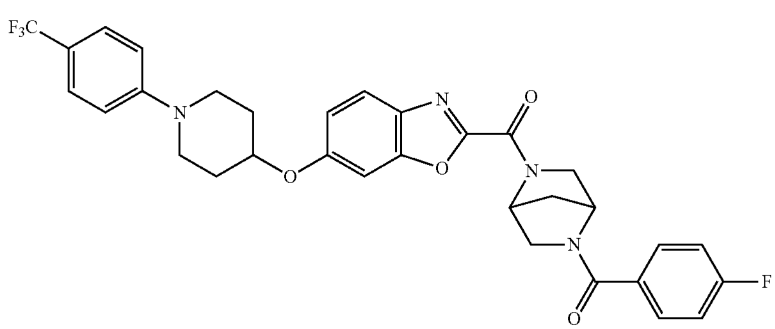 [SMILES: O=C(c1ccc(F)cc1)N1CC2CC1CN2C(=O)c1nc2ccc(OC3CCN(c4ccc(C(F)(F)F)cc4)CC3)cc2o1] |

TABLE 3-continued

| No. | Name | Structure |
|---|---|---|
| 3-14 | tert-butyl 4-(6-(1-(4-(trifluoromethyl)phenyl)piperidin-4-yloxy)benzo[d]thiazole-2-carboxamido)piperidine-1-carboxylate | 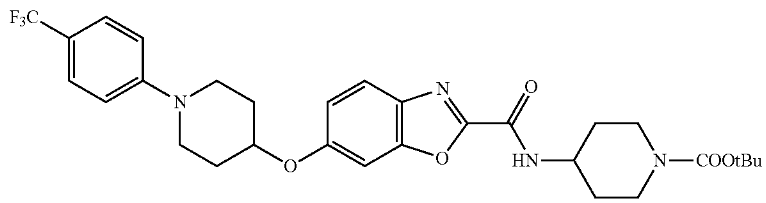 |
| 3-15 | N-(1-(pyridin-4-ylmethyl)piperidin-4-yl)-6-(1-(4-(trifluoromethyl)phenyl)piperidin-4-yloxy)benzo[d]thiazole-2-carboxamide | 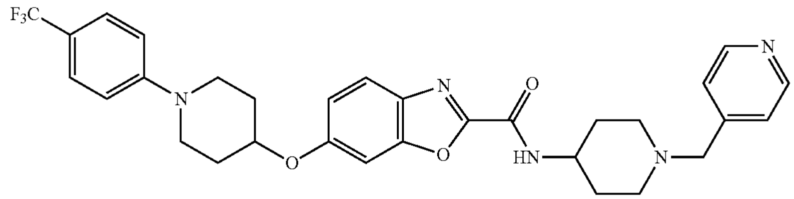 [SMILES: O=C(NC1CCN(Cc2ccncc2)CC1)c1nc2ccc(OC3CCN(c4ccc(C(F)(F)F)cc4)CC3)cc2o1] |
| 3-16 | N-(1-(4-cyanobenzyl)piperidin-4-yl)-6-(1-(4-(trifluoromethyl)phenyl)piperidin-4-yloxy)benzo[d]thiazole-2-carboxamide | 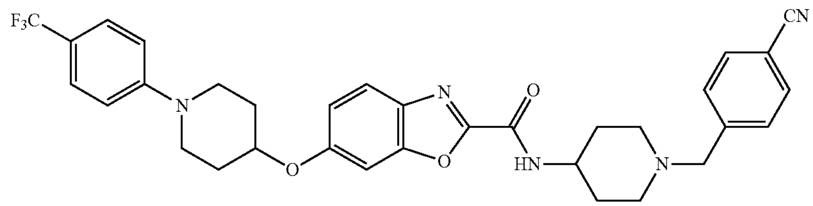 [SMILES: N#Cc1ccc(CN2CCC(NC(=O)c3nc4ccc(OC5CCN(c6ccc(C(F)(F)F)cc6)CC5)cc4o3)CC2)cc1] |
| 3-17 | N-(1-(pyridin-4-ylmethyl)piperidin-4-yl)-7-(1-(4-(trifluoromethyl)phenyl)piperidin-4-yloxy)imidazo[1,2-a]pyridine-2-carboxamide | 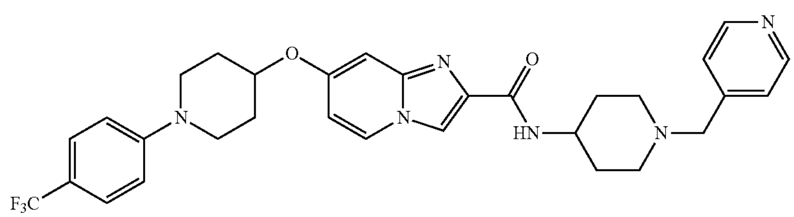 [SMILES: O=C(NC1CCN(Cc2ccncc2)CC1)c1cn2ccc(OC3CCN(c4ccc(C(F)(F)F)cc4)CC3)cc2n1] |
| 3-18 | N-(1-(4-cyanobenzyl)piperidin-4-yl)-7-(1-(4-(trifluoromethyl)phenyl)piperidin-4-yloxy)imidazo[1,2-a]pyridine-2-carboxamide | 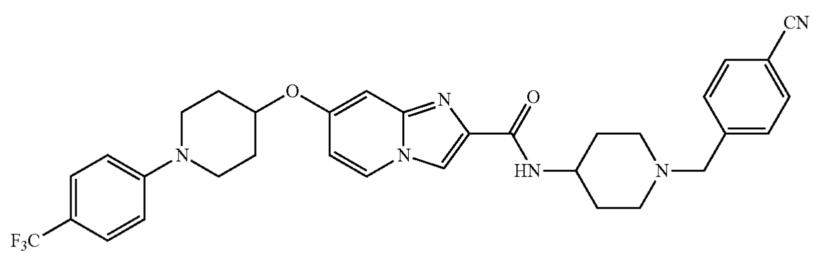 [SMILES: N#Cc1ccc(CN2CCC(NC(=O)c3cn4ccc(OC5CCN(c6ccc(C(F)(F)F)cc6)CC5)cc4n3)CC2)cc1] |
| 3-19 | tert-butyl 4-(5-(1-(4-(trifluoromethyl)phenyl)piperidin-4-yloxy)pyrazine-2-carboxamido)piperidine-1-carboxylate | 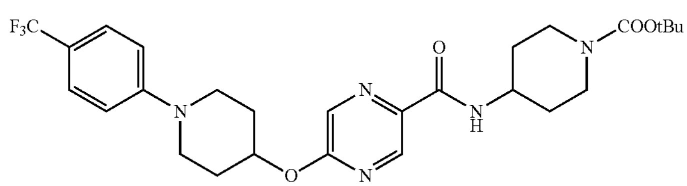 |
| 3-20 | N-(piperidin-4-yl)-5-(1-(4-(trifluoromethyl)phenyl)piperidin-4-yloxy)pyrazine-2-carboxamide | 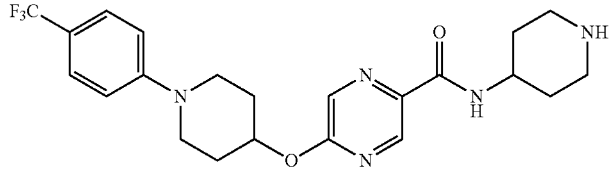 [SMILES: O=C(NC1CCNCC1)c1cnc(OC2CCN(c3ccc(C(F)(F)F)cc3)CC2)cn1] |

TABLE 3-continued

| No. | Name |
|---|---|
| 3-21 | N-(1-(pyridin-4-ylmethyl)piperidin-4-yl)-5-(1-(4-(trifluoromethyl)phenyl)piperidin-4-yloxy)pyrazine-2-carboxamide |
| 3-22 | N-(1-(4-cyanobenzyl)piperidin-4-yl)-5-(1-(4-(trifluoromethyl)phenyl)piperidin-4-yloxy)pyrazine-2-carboxamide |
| 3-23 | N-(1-(4-cyanobenzyl)piperidin-4-yl)-2-(1-(4-(trifluoromethyl)phenyl)piperidin-4-yloxy)thiazole-5-carboxamide |
| 3-24 | N-(1-(4-cyanobenzyl)piperidin-4-yl)-2-(1-(4-cyanophenyl)piperidin-4-yloxy)thiazole-5-carboxamide |
| 3-25 | N-(1-(4-cyanobenzyl)piperidin-4-yl)-2-(1-(4-(trifluoromethyl)benzyl)piperidin-4-yloxy)thiazole-5-carboxamide |
| 3-26 | tert-butyl 4-(5-(1-(4-cyanobenzyl)piperidin-4-ylcarbamoyl)thiazol-2-yloxy)piperidine-1-carboxylate |
| 3-27 | N-(1-(4-cyanobenzyl)piperidin-4-yl)-4-(1-(4-ethoxybenzyl)piperidine-4-carbonyl)benzamide |

TABLE 3-continued

| No. | Name | Structure |
|---|---|---|
| 3-28 | 4-(4-(4-chlorobenzyl)piperazine-1-carbonyl)-N-(1-(4-cyanobenzyl)piperidin-4-yl)benzamide | 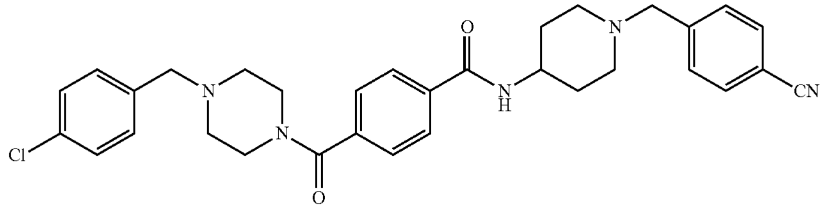 [SMILES: N#Cc1ccc(CN2CCC(NC(=O)c3ccc(C(=O)N4CCN(Cc5ccc(Cl)cc5)CC4)cc3)CC2)cc1] |
| 3-29 | 4-(4-(4-chlorophenyl)piperazine-1-carbonyl)-N-(1-(4-cyanobenzyl)piperidin-4-yl)benzamide | 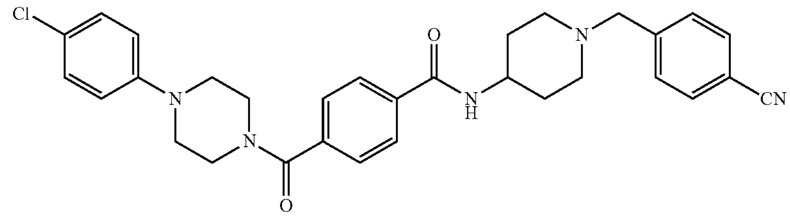 [SMILES: N#Cc1ccc(CN2CCC(NC(=O)c3ccc(C(=O)N4CCN(c5ccc(Cl)cc5)CC4)cc3)CC2)cc1] |
| 3-30 | N-(1-(4-cyanobenzyl)piperidin-4-yl)-4-(4-(5-(trifluoromethyl)pyridin-2-yl)piperazine-1-carbonyl)benzamide | 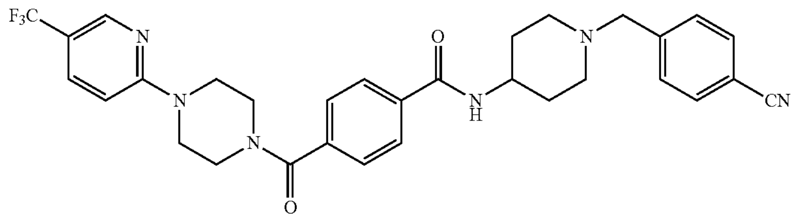 [SMILES: N#Cc1ccc(CN2CCC(NC(=O)c3ccc(C(=O)N4CCN(c5ccc(C(F)(F)F)cn5)CC4)cc3)CC2)cc1] |
| 3-31 | $N^1$-(1-(4-cyanobenzyl)piperidin-4-yl)-$N^4$-(1-(4-(trifluoromethyl)benzyl)piperidin-4-yl)terephthalamide | 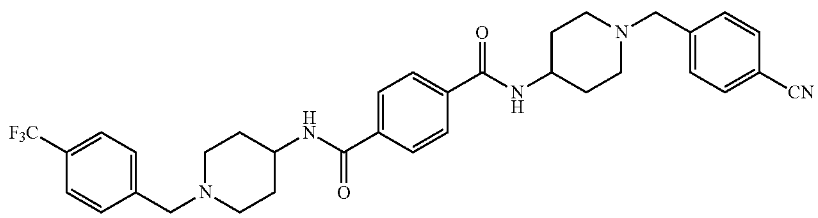 [SMILES: N#Cc1ccc(CN2CCC(NC(=O)c3ccc(C(=O)NC4CCN(Cc5ccc(C(F)(F)F)cc5)CC4)cc3)CC2)cc1] |
| 3-32 | $N^1$-(1-(4-cyanobenzyl)piperidin-4-yl)-$N^4$-(1-phenylpiperidin-4-yl)terephthalamide | 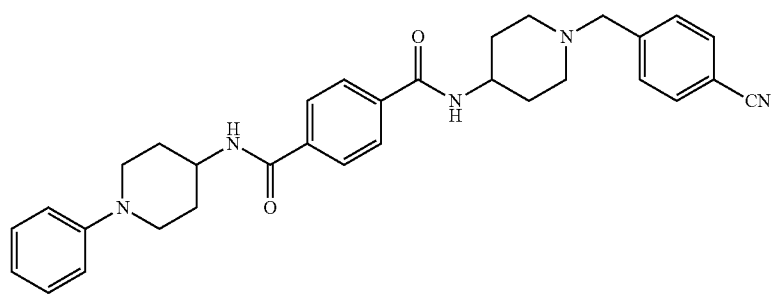 [SMILES: N#Cc1ccc(CN2CCC(NC(=O)c3ccc(C(=O)NC4CCN(c5ccccc5)CC4)cc3)CC2)cc1] |
| 3-33 | $N^1$-(1-benzylpiperidin-4-yl)-$N^4$-(1-(4-cyanobenzyl)piperidin-4-yl)terephthalamide | 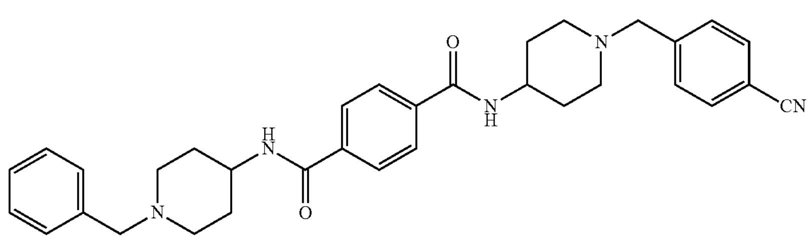 [SMILES: N#Cc1ccc(CN2CCC(NC(=O)c3ccc(C(=O)NC4CCN(Cc5ccccc5)CC4)cc3)CC2)cc1] |
| 3-34 | N-(1-(4-cyanobenzyl)piperidin-4-yl)-2-(4-fluorobenzyl)-1,2,3,4-tetrahydroisoquinoline-7-carboxamide | 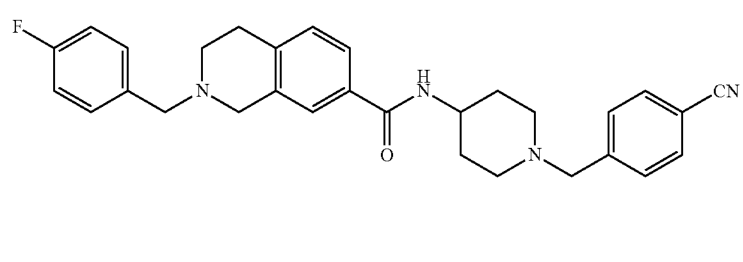 [SMILES: N#Cc1ccc(CN2CCC(NC(=O)c3ccc4c(c3)CN(Cc3ccc(F)cc3)CC4)CC2)cc1] |

TABLE 3-continued

| No. | Name | Structure |
|---|---|---|
| 3-35 | 2-(4-fluorobenzyl)-N-(1-(pyridin-3-ylmethyl)piperidin-4-yl)-1,2,3,4-tetrahydroisoquinoline-7-carboxamide | 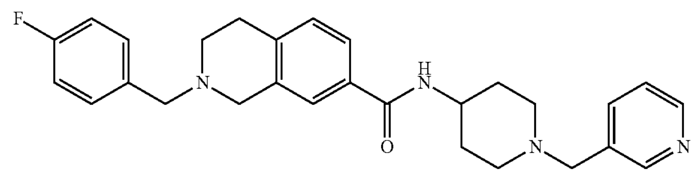 [SMILES: O=C(NC1CCN(Cc2cccnc2)CC1)c1ccc2c(c1)CN(Cc1ccc(F)cc1)CC2] |
| 3-36 | 2-(4-fluorobenzyl)-N-(1-(4-(trifluoromethyl)benzyl)piperidin-4-yl)-1,2,3,4-tetrahydroisoquinoline-7-carboxamide | 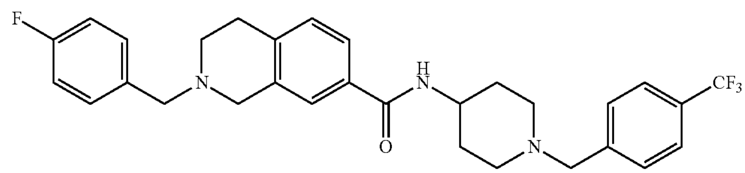 [SMILES: O=C(NC1CCN(Cc2ccc(C(F)(F)F)cc2)CC1)c1ccc2c(c1)CN(Cc1ccc(F)cc1)CC2] |
| 3-37 | 2-(4-cyanobenzyl)-N-(1-(4-cyanobenzyl)piperidin-4-yl)-1,2,3,4-tetrahydroisoquinoline-7-carboxamide | 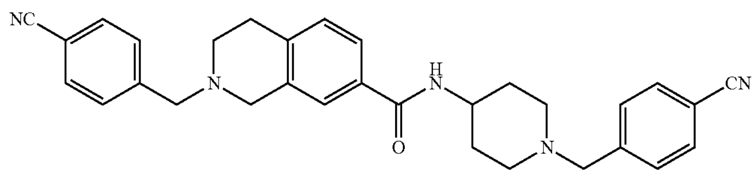 [SMILES: N#Cc1ccc(CN2CCC(NC(=O)c3ccc4c(c3)CN(Cc3ccc(C#N)cc3)CC4)CC2)cc1] |
| 3-38 | 2-(4-cyanobenzyl)-N-(1-(pyridin-3-ylmethyl)piperidin-4-yl)-1,2,3,4-tetrahydroisoquinoline-7-carboxamide | 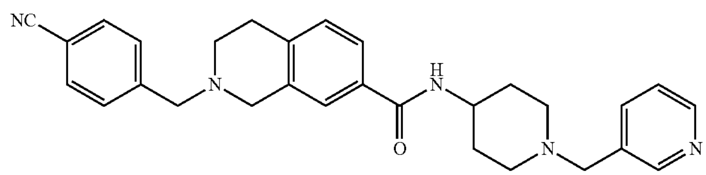 [SMILES: N#Cc1ccc(CN2CCc3ccc(C(=O)NC4CCN(Cc5cccnc5)CC4)cc3C2)cc1] |
| 3-39 | 2-(4-cyanobenzyl)-N-(1-(4-(trifluoromethyl)benzyl)piperidin-4-yl)-1,2,3,4-tetrahydroisoquinoline-7-carboxamide | 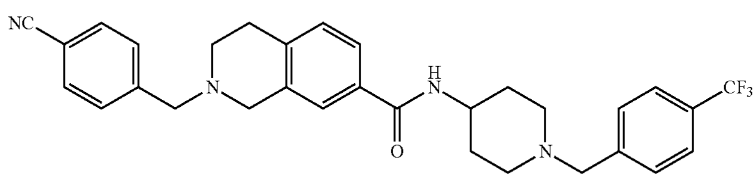 [SMILES: N#Cc1ccc(CN2CCc3ccc(C(=O)NC4CCN(Cc5ccc(C(F)(F)F)cc5)CC4)cc3C2)cc1] |
| 3-40 | N-(1-(4-cyanobenzyl)piperidin-4-yl)-2-(4-fluorobenzyl)-1,2,3,4-tetrahydroisoquinoline-7-carboxamide | 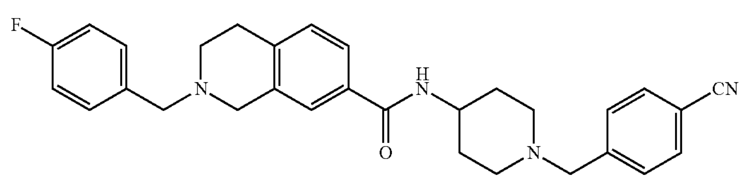 [SMILES: N#Cc1ccc(CN2CCC(NC(=O)c3ccc4c(c3)CN(Cc3ccc(F)cc3)CC4)CC2)cc1] |
| 3-41 | 2-(4-fluorobenzyl)-N-(1-(pyridine-3-ylmethyl)piperidin-4-yl)-1,2,3,4-tetrahydroisoquinoline-7-carboxamide | 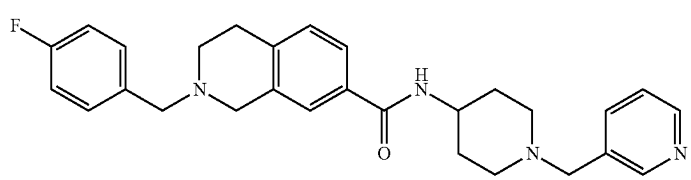 [SMILES: O=C(NC1CCN(Cc2cccnc2)CC1)c1ccc2c(c1)CN(Cc1ccc(F)cc1)CC2] |
| 3-42 | 2-(4-fluorobenzyl)-N-(1-(4-(trifluoromethyl)benzyl)piperidin-4-yl)-1,2,3,4-tetrahydroisoquinoline-7-carboxamide | 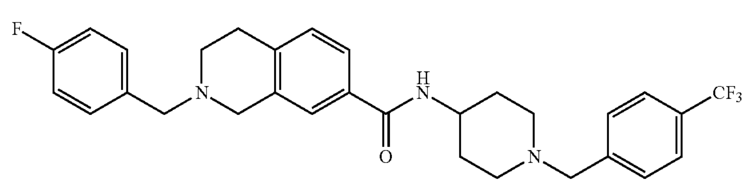 [SMILES: O=C(NC1CCN(Cc2ccc(C(F)(F)F)cc2)CC1)c1ccc2c(c1)CN(Cc1ccc(F)cc1)CC2] |

Another aspect of the disclosure provides a method for treating or ameliorating a disorder or condition related to oxidative stress, mitochondrial dysfunction, free radical damage and/or metabolic inefficiency in a subject, the method including administering to the subject an effective amount of a compound having structural formula (4-I):

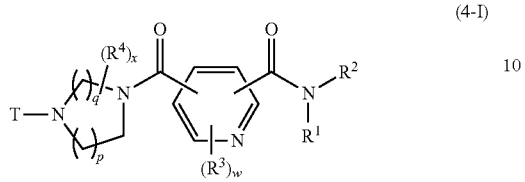
(4-I)

or a pharmaceutically acceptable salt, prodrug or N-oxide thereof (or a solvate or hydrate thereof), in which $R^1$ is H, —($C_1$-$C_4$ alkyl), —C(O)—($C_1$-$C_4$ alkyl) or —C(O)O—($C_1$-$C_4$ alkyl);

$R^2$ is -Hca, -Cak-N($R^9$)-G-$R^{22}$ or —($C_2$-$C_8$ alkyl)-N($R^9$)—$R^{24}$ in which one or two carbons of the ($C_2$-$C_8$ alkyl) are optionally replaced by —O—, —S— or —N($R^9$)— and $R^{24}$ is —$R^{23}$, -G-$R^{23}$ or —C(O)O—($C_1$-$C_6$ alkyl), provided that two consecutive carbons of the ($C_2$-$C_8$ alkyl) are not replaced by —O—;

each $R^3$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-NR$^8$R$^9$, —($C_0$-$C_6$ alkyl)-OR$^{10}$, —($C_0$-$C_6$ alkyl)-C(O)R$^{10}$, —($C_0$-$C_6$ alkyl)-S(O)$_{0-2}$R$^{10}$, -halogen, —NO$_2$ and —CN;

w is 0, 1, 2 or 3;

each $R^4$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-NR$^8$R$^9$, —($C_0$-$C_6$ alkyl)-OR$^{10}$, —($C_0$-$C_6$ alkyl)-C(O)R$^{10}$, —($C_0$-$C_6$ alkyl)-S(O)$_{0-2}$R$^{10}$, -halogen, —NO$_2$ and —CN, and two $R^4$ on the same carbon optionally combine to form oxo;

x is 0, 1, 2, 3 or 4;

p is 0, 1, 2, 3 or 4;

q is 2, 3 or 4;

the sum of p and q is 2, 3, 4, 5 or 6;

T is —($C_0$-$C_6$ alkyl)-L-$R^7$, —($C_0$-$C_6$ alkyl)-NR$^8$R$^9$, —($C_0$-$C_6$ alkyl)-OR$^{10}$, —($C_0$-$C_6$ alkyl)-C(O)R$^{10}$, —($C_0$-$C_6$ alkyl)-S(O)$_{0-2}$R$^{10}$ or

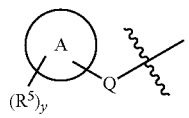

in which

Q is —S(O)$_2$—, L or ($C_0$-$C_3$ alkyl)-, in which each carbon of the —($C_0$-$C_3$ alkyl)- is optionally and independently substituted with one or two $R^{16}$;

the ring system denoted by "A" is heteroaryl, aryl, cycloalkyl or heterocycloalkyl;

each $R^5$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-NR$^8$R$^9$, —($C_0$-$C_6$ alkyl)-OR$^{10}$, —($C_0$-$C_6$ alkyl)-C(O)R$^{10}$, —($C_0$-$C_6$ alkyl)-S(O)$_{0-2}$R$^{10}$, -halogen, —NO$_2$ and —CN; and y is 0, 1, 2, 3 or 4;

in which each L is independently selected from —NR$^9$C(O)O—, —OC(O)NR$^9$—, —NR$^9$C(O)—NR$^9$—, —NR$^9$C(O)S—, —SC(O)NR$^9$—, —NR$^9$C(O)—, —C(O)NR$^9$—, —NR$^9$C(S)O—, —OC(S)NR$^9$—, —NR$^9$C(S)—NR$^9$—, —NR$^9$C(S)S—, —SC(S)NR$^9$—, —NR$^9$C(S)—, —C(S)NR$^9$—, —SC(O)NR$^9$—, —NR$^9$C(S)—, —S(O)$_{0-2}$—, —C(O)O, —OC(O)—, —C(S)O—, —OC(S)—, —C(O)S—, —SC(O)—, —C(S)S—, —SC(S)—, —OC(O)O—, —SC(O)O—, —OC(O)S—, —SC(S)O—, —OC(S)S—, —NR$^9$C(NR$^2$)NR$^9$—, —NR$^9$SO$_2$—, —SO$_2$NR$^9$— and —NR$^9$SO$_2$NR$^9$—, each $R^6$, $R^7$, $R^8$ and $R^{10}$ is independently selected from H, —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-($C_0$-$C_6$ alkyl), —($C_0$-$C_6$ alkyl)-NR$^9$—($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), each $R^9$ is independently selected from —H, —($C_1$-$C_4$ alkyl), —C(O)—($C_1$-$C_4$ alkyl) and —C(O)O—($C_1$-$C_4$ alkyl), each G is independently —S(O)$_2$—, L or —($C_0$-$C_3$ alkyl)-, in which each carbon of the —($C_0$-$C_3$ alkyl)- is optionally and independently substituted with one or two $R^{16}$, each $R^{16}$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-NR$^8$R$^9$, —($C_0$-$C_6$ alkyl)-OR$^{10}$, —($C_0$-$C_6$ alkyl)-C(O)R$^{10}$, —($C_0$-$C_6$ alkyl)-S(O)$_{0-2}$R$^{10}$, -halogen, —NO$_2$ and —CN, and optionally two of $R^{16}$ on the same carbon combine to form oxo, each $R^{22}$ and $R^{23}$ is independently Ar or Het, each Ar is an optionally substituted aryl, each Het is an optionally substituted heteroaryl, each Cak is an optionally substituted cycloalkyl, each Hca is an optionally substituted heterocycloalkyl, and each alkyl is optionally substituted.

Various embodiments of compounds of structural formula (2-I) suitable for use in the methods described herein are described below. Information regarding these compounds can also be found in U.S. patent application Ser. No. 12/695,861, which is hereby incorporated by reference in its entirety.

In certain embodiments of the presently disclosed compounds of structural formula (4-I), T is

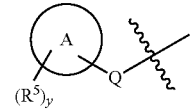

In such embodiments, Q is —S(O)$_2$—, L or —($C_0$-$C_3$ alkyl)- in which each carbon of the ($C_0$-$C_3$ alkyl) is optionally and independently substituted with one or two $R^{16}$, in which each $R^{16}$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-NR$^8$R$^9$, —($C_0$-$C_6$ alkyl)-OR$^{10}$, —($C_0$-$C_6$ alkyl)-C(O)R$^{10}$, —($C_0$-$C_6$ alkyl)-S(O)$_{0-2}$R$^{10}$, -halogen, —NO$_2$ and —CN, and optionally two of $R^{16}$ on the same carbon combine to form oxo. In certain embodiments, each $R^{16}$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, and two $R^{16}$ on the same carbon optionally combine to form an oxo, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl), and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in particular compounds, each $R^{16}$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}R^{10}$, -halogen, —$NO_2$ and —CN, and two $R^{16}$ on the same carbon optionally combine to form an oxo, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. In certain embodiments, Q has at most one $R^{16}$ or an oxo substituted thereon. Q can be, for example, an unsubstituted —($C_0$-$C_3$ alkyl)-. In other embodiments, Q is a ($C_1$-$C_3$ alkyl) having as its only substitution a single oxo group. For example, in certain embodiments, Q is —$CH_2$—; a single bond; —S(O)$_2$—; —C(O)—; or —CH(CH$_3$)—.

In certain embodiments of the compounds of structural formula (4-I), the

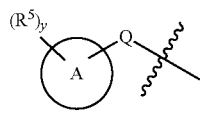

moiety is

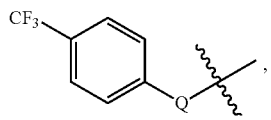

for example, p-(trifluoromethyl)phenyl. In other embodiments, the

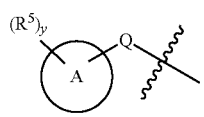

moiety is

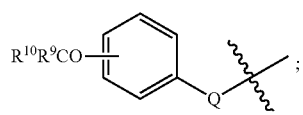

in one such embodiment, Q is a single bond.

The number of substituents on the ring system denoted by "A", y, is 0, 1, 2, 3 or 4. For example, in some embodiments of the presently disclosed compounds of structural formula (4-I), y is 0, 1, 2 or 3, such as 1. In one embodiment, y is not zero and at least one $R^5$ is halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ or —C(O)-Hca wherein the Hca contains a ring nitrogen atom through which it is bound to the —C(O)—, and wherein no alkyl, haloalkyl or heterocycloalkyl is substituted by an aryl, heteroaryl, cycloalkyl or heterocycloalkyl-containing group.

In certain embodiments of the presently disclosed compounds of structural formula (4-I), each $R^5$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, in which each $R^7$, $R^8$ and $R^{10}$ is independently selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^5$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group.

In one embodiment of the compounds of structural formula (4-I), y is 0.

In the presently disclosed compounds of structural formula (4-I), the ring system denoted by "A" is heteroaryl, aryl, cycloalkyl or heterocycloalkyl. For example, in one embodiment, the ring system denoted by "A" is an aryl or a heteroaryl. The ring system denoted by "A" can be, for example, a monocyclic aryl or heteroaryl. In one embodiment, when the "A" ring system is aryl, Q is a —($C_0$-$C_3$ alkyl)- optionally substituted with oxo, and optionally substituted with one or more $R^{16}$. For example, Q can be a —($C_1$-$C_3$ alkyl)- having its only substitution a single oxo, or an unsubstituted —($C_0$-$C_3$ alkyl)-. For example, in certain embodiments, Q is —$CH_2$—; a single bond; —S(O)$_2$—; —C(O)—; or —CH(CH$_3$)—.

For example, in certain embodiments of the presently disclosed compounds of structural formula (4-I), the ring system denoted by "A" is a phenyl. In one embodiment, y is 1 and $R^5$ is attached to the phenyl in the para position relative to Q. In another embodiment, y is 1 and $R^5$ is selected from the group consisting of halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, and in which no ($C_0$-$C_4$ alkyl) or ($C_1$-$C_4$ alkyl) is substituted by an aryl, heteroaryl, cycloalkyl or heterocycloalkyl-containing group. $R^5$ can be, for example, —Cl, —F, cyano, —C(O)CH$_3$, —C(O)OH, —C(O)NH$_2$, trifluoromethyl, difluoromethyl, difluoromethoxy or trifluoromethoxy. In another embodiment, the

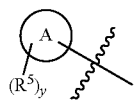

moiety is a 3,4-dihalophenyl.

In another embodiment of the presently disclosed compounds of structural formula (4-I), the ring system denoted by "A" is a heteroaryl. For example, in certain embodiments, the ring system denoted by "A" is a pyridyl, a thienyl, or a furanyl. In one embodiment, when the "A" ring system is heteroaryl, Q is a —(C$_0$-C$_3$ alkyl)- optionally substituted with oxo, and optionally substituted with one or more $R^{16}$. For example, Q can be a —(C$_1$-C$_3$ alkyl)- having its only substitution a single oxo, or an unsubstituted —(C$_0$-C$_3$ alkyl)-. In certain embodiments, Q is —CH$_2$—; a single bond; —S(O)$_2$—; —C(O)—; or —CH(CH$_3$)—.

In one embodiment of the presently disclosed compounds, the compound has structural formula (4-II):

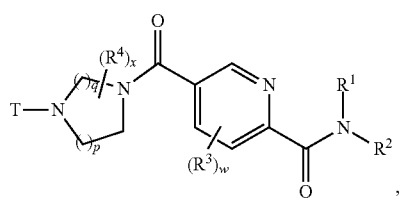

(4-II)

in which the variables are defined as described above with reference to structural formula (4-I).

In one embodiment of the presently disclosed compounds, the compound has structural formula (4-III):

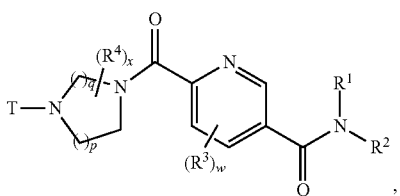

(4-III)

in which the variables are defined as described above with reference to structural formula (4-I).

In another embodiment of the presently disclosed compounds, the compound has structural formula (4-IV):

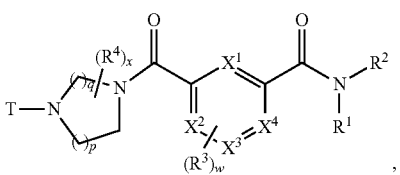

(4-IV)

in which one of $X^1$, $X^2$, $X^3$ and $X^4$ are N, and the others are carbons (for example, independently CH or C substituted with one of the w $R^3$ groups), and all other variables are defined as described above with reference to structural formula (4-I). For example, in one embodiment, $X^1$ is N and $X^2$, $X^3$ and $X^4$ are carbons. In another embodiment, $X^2$ is N and $X^1$, $X^3$ and $X^4$ are carbons. In another embodiment, $X^3$ is N and $X^1$, $X^2$ and $X^4$ are carbons. In another embodiment, $X^4$ is N and $X^1$, $X^2$ and $X^3$ are carbons.

In compounds according to structural formulae (4-I)-(4-IV), p is 0, 1, 2, 3 or 4 and q is 2, 3 or 4. For example, in one embodiment, q is 2. In certain embodiments, p is 1.

In certain embodiments according to structural formulae (4-I)-(4-IV), the sum of p and q is 2 or 3. For example, in one embodiment, the sum of p and q is 2 (e.g., p is 0 and q is 2). In another embodiment, the sum of p and q is 3 (e.g., p is 1 and q is 2). In other embodiments the sum of p and q is 4, 5, or 6. Accordingly the ring containing the p and q carbon atoms can be a 5, 6, 7, 8 or 9-membered ring.

In one embodiment of the presently disclosed compounds, the compound has structural formula (4-V):

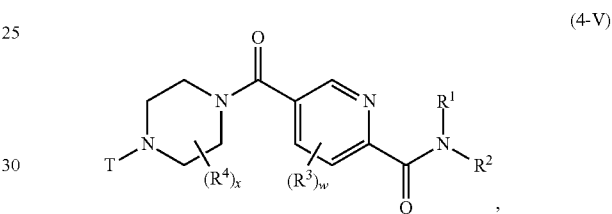

(4-V)

in which the variables are defined as described above with reference to structural formula (4-I).

In another embodiment of the presently disclosed compounds, the compound has structural formula (4-VI):

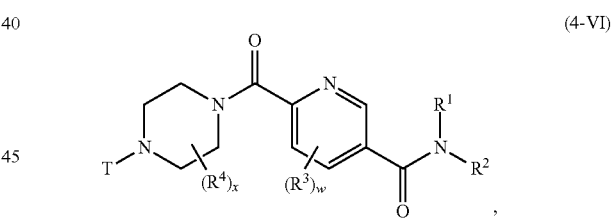

(4-VI)

in which the variables are defined as described above with reference to structural formula (4-I).

In another embodiment of the presently disclosed compounds, the compound has structural formula (4-VII):

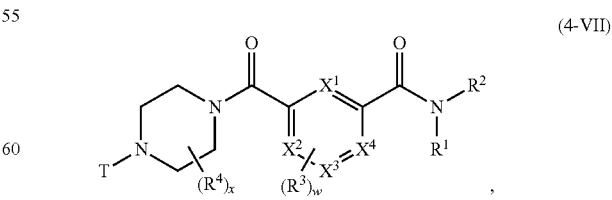

(4-VII)

in which one of $X^1$, $X^2$, $X^3$ and $X^4$ are N, and the others are carbons (for example, independently CH or C substituted with one of the w $R^3$ groups), and all other variables are defined as described above with reference to structural formula (4-I). For example, in one embodiment, $X^1$ is N and $X^2$, $X^3$ and $X^4$ are carbons. In another embodiment, $X^2$ is N and $X^1$, $X^3$ and $X^4$ are carbons. In another embodiment, $X^3$ is N and $X^1$, $X^2$ and $X^4$ are carbons. In another embodiment, $X^4$ is N and $X^1$, $X^2$ and $X^3$ are carbons.

In certain embodiments of the presently disclosed compounds of any of structural formulae (4-I)-(4-VII), $R^1$ is —H. In other embodiments, $R^1$ is ($C_1$-$C_4$ alkyl), for example methyl, ethyl, n-propyl or isopropyl. In still other embodiments, $R^1$ is —C(O)—O—($C_1$-$C_4$ alkyl), for example —C(O)—O-t-butyl. In certain embodiments, no alkyl of $R^1$ is substituted with an aryl-, heteroaryl-, cycloalkyl- or heterocycloalkyl-containing group.

In certain embodiments of the presently disclosed compounds of any structural formulae (4-I)-(4-VII), $R^2$ is -Hca. In certain embodiments, $R^2$ is an optionally-substituted monocyclic heterocycloalkyl. In one embodiment, $R^2$ is not an oxo-substituted heterocycloalkyl.

In certain of the presently disclosed compounds of any structural formulae (4-I)-(4-VII), $R^2$ is -(optionally-substituted azetidinyl), -(optionally-substituted pyrrolidinyl), -(optionally-substituted piperidinyl), or -(optionally-substituted azepanyl). For example, $R^2$ can be -(optionally substituted piperidinyl) or -(optionally substituted pyrrolidinyl). In one embodiment, $R^2$ is -(optionally substituted piperidinyl). In another embodiment, $R^2$ is -(optionally substituted pyrrolidinyl).

In certain particular embodiments of the presently disclosed compounds of any of structural formulae (4-I)-(4-VII), $R^2$ is -(optionally-substituted azetidin-3-yl), -(optionally substituted piperidin-4-yl), -(optionally substituted pyrrolidin-3-yl) or -(optionally-substituted azepan-4-yl). For example, in one embodiment, $R^2$ is -(optionally substituted piperidin-4-yl). In another embodiment, $R^2$ is -(optionally substituted pyrrolidin-3-yl).

In certain embodiments of the presently disclosed compounds of any of structural formulae (4-I)-(4-VII), the azetidinyl, pyrrolidinyl, piperidinyl and azepanyl $R^2$ moieties described above are substituted at their 1-positions. For example, in one embodiment, $R^2$ is substituted at its 1-position with —($C_0$-$C_3$ alkyl)-Ar or —($C_0$-$C_3$ alkyl)-Het, for example -(unsubstituted $C_0$-$C_3$ alkyl)-Ar or -(unsubstituted $C_0$-$C_3$ alkyl)-Het. For example, in one particular embodiment, the azetidinyl, pyrrolidinyl, piperidinyl or azepanyl $R^2$ moiety is substituted at its 1-position with an optionally substituted benzyl or an optionally substituted phenyl. In another embodiment, the azetidinyl, pyrrolidinyl, piperidinyl or azepanyl $R^2$ moiety is substituted at its 1-position with a benzyl substituted with an electron withdrawing group; or with a pyridinylmethyl optionally substituted with an electron withdrawing group. For example, the benzyl or pyridinylmethyl can be substituted with an electron withdrawing group selected from the group consisting of halo, cyano, —($C_1$-$C_4$ fluoroalkyl), —O—($C_1$-$C_4$ fluoroalkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), —S(O)$_2$O—($C_0$-$C_4$ alkyl), NO$_2$ and —C(O)-Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group. In other embodiments, the azetidinyl, pyrrolidinyl, piperidinyl or azepanyl $R^2$ moiety is substituted at its 1-position with an unsubstituted benzyl or an unsubstituted phenyl.

In other embodiments of the compounds disclosed herein having any of structural formulae (4-I)-(4-VII), the azetidinyl, pyrrolidinyl, piperidinyl or azepanyl $R^2$ moiety is substituted at its 1-position with an optionally substituted pyridinylmethyl, an optionally substituted furanylmethyl, an optionally substituted thienylmethyl, an optionally substituted oxazolylmethyl, or an optionally substituted imidazolylmethyl. For example, the azetidinyl, pyrrolidinyl, piperidinyl or azepanyl $R^2$ moiety can be substituted with an unsubstituted pyridinylmethyl, an unsubstituted furanylmethyl, an unsubstituted thienylmethyl, an unsubstituted oxazolylmethyl, or an unsubstituted imidazolylmethyl. In other embodiments, the azetidinyl, pyrrolidinyl, piperidinyl or azepanyl $R^2$ moiety can be substituted with an pyridinylmethyl, furanylmethyl, thienylmethyl, oxazolylmethyl or imidazolylmethyl substituted with an electron withdrawing group as described above.

In certain embodiments of the compounds disclosed herein having any of structural formulae (4-I)-(4-VII), the azetidinyl, pyrrolidinyl, piperidinyl or azepanyl $R^2$ moiety is substituted at its 1-position with -L-Ar or -L-Het, in which Ar and Het can be, for example, as described above with reference to —($C_0$-$C_3$ alkyl)-Ar or —($C_0$-$C_3$ alkyl)-Het. In one such embodiment, L is —C(O)—NR$^9$—, such as —C(O)—NH—.

In other embodiments of the presently disclosed compounds of any of structural formulae (4-I)-(4-VII), the azetidinyl, pyrrolidinyl, piperidinyl or azepanyl $R^2$ moiety is substituted at its 1-position with —C(O)—O($C_0$-$C_6$ alkyl), —C(O)—Het, —C(O)—Ar, —S(O)$_2$-Het, —S(O)$_2$—Ar or —S(O)$_{2-0}$($C_0$-$C_6$ alkyl), in which Ar and Het can be, for example, as described above with reference to —($C_0$-$C_3$ alkyl)-Ar or —($C_0$-$C_3$ alkyl)-Het. In one embodiment, the azetidinyl, pyrrolidinyl, piperidinyl or azepanyl $R^2$ moiety is substituted at its 1-position with —C(O)—Het or —C(O)—Ar; in another embodiment, it is substituted at its 1-position with —S(O)$_2$-Het or —S(O)$_2$—Ar. For example, in certain embodiments, the azetidinyl, pyrrolidinyl, piperidinyl or azepanyl $R^2$ moiety is substituted at its 1-position with an optionally-substituted benzoyl (e.g., substituted with an electron withdrawing group as described above); or with an optionally-substituted nicotinyl, isonicotinyl or picolinyl (e.g., optionally substituted with an electron withdrawing group as described above). In other embodiments, the azetidinyl, pyrrolidinyl, piperidinyl or azepanyl $R^2$ moiety is substituted at its 1-position with an unsubstituted benzoyl; or an unsubstituted nicotinoyl, isonicotinoyl or picolinoyl.

In certain embodiments of the compounds of any of structural formulae (4-I)-(4-VII), $R^2$ is -Cak-N($R^9$)-G-$R^{22}$, as described above. For example, in one embodiment of the disclosed compounds, $R^2$ has the structure

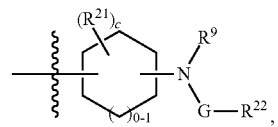

in which c is 0, 1, 2, 3 or 4, and each $R^{21}$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-NR$^8$R$^9$, —($C_0$-$C_6$ alkyl)-OR$^{10}$, —($C_0$-$C_6$ alkyl)-C(O)R$^{10}$, —($C_0$-$C_6$ alkyl)-S(O)$_{0-2}$R$^{10}$, -halogen, —NO$_2$ and —CN, and two $R^{21}$ on the same carbon optionally combine to form oxo. In certain embodiments of the presently disclosed compounds, each $R^{21}$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-

$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN and two $R^{21}$ on the same carbon optionally combine to form oxo, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^{21}$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}R^{10}$, -halogen, —$NO_2$ and —CN and two $R^{21}$ on the same carbon optionally combine to form oxo, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. In certain embodiments, c is 1 or 2. In other embodiments, c is 0. In certain embodiments, $R^9$ is H. In certain embodiments, G is a single bond. In certain embodiments of the presently disclosed compounds, each $R^{22}$ is not substituted with an aryl-, heteroaryl-, cycloalkyl- or heterocycloalkyl-containing group. In certain embodiments of the presently disclosed compounds, each $R^{23}$ is not substituted with an aryl-, heteroaryl-, cycloalkyl- or heterocycloalkyl-containing group.

In one embodiment of compounds of any of structural formulae (4-I)-(4-VII), $R^2$ has the structure

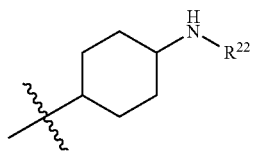

In certain embodiments of the compounds of any of structural formulae (4-I)-(4-VII), $R^2$ is —($C_2$-$C_8$ alkyl)-N($R^9$)—$R^{24}$ in which one or two carbons of the ($C_2$-$C_8$ alkyl) are optionally replaced by —O— or —N($R^9$)— and $R^{24}$ is —$R^{23}$, -$GR^{23}$ or —C(O)O—($C_1$-$C_6$ alkyl). In certain embodiments, the ($C_2$-$C_8$ alkyl) is unsubstituted and no carbon is replaced by —O— or —N($R^9$)—. For example, in one embodiment, $R^2$ is —$CH_2$—$CH_2$—$CH_2$—N($R^9$)—$R^{24}$ or –$CH_2$—$CH_2$—$CH_2$—$CH_2$—N($R^9$)—$R^{24}$. In other embodiments, the ($C_2$-$C_8$ alkyl) is substituted and/or one or two carbons are replaced by —O— or —N($R^9$)—. For example, in one embodiment, $R^2$ is —$CH_2$—$CH_2$—O—$CH_2$—$CH_2$—N($R^9$)—$R^{24}$; —$CF_{12}$—CH($CH_3$)—N($R^9$)—$R^{24}$; or —$CH_2$—$CH_2$—O—$CH_2$—C(O)—N($R^9$)—$R^{24}$. In certain embodiments, $R^9$ is H. In certain embodiments, $R^{24}$ is Ar or Het. In certain embodiments, $R^{24}$ is not substituted with an aryl-, heteroaryl-, cycloalkyl- or heterocycloalkyl-containing group. In certain embodiments, the ($C_2$-$C_8$ alkyl) is a ($C_2$-$C_5$ alkyl).

In the compounds of any of structural formulae (4-I)-(4-VII), the number of substituents on the central pyridine, w, is 0, 1, 2 or 3. For example, in one embodiment, w is 0, 1 or 2. In another embodiment, w is 0. In other embodiments, w is at least 1, and at least one $R^3$ is selected from the group consisting of halo, cyano, —($C_1$-$C_4$ fluoroalkyl), —O—($C_1$-$C_4$ fluoroalkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), —S(O)$_2$O—($C_0$-$C_4$ alkyl), $NO_2$ and —C(O)-Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group. For example, in certain embodiments, at least one $R^3$ is halo (e.g., chloro) or —($C_1$-$C_4$ alkyl) (e.g., methyl, ethyl or propyl). In certain embodiments, an $R^3$ is substituted on the central pyridine in the meta position relative to the carbonyl bearing the diazacycloalkyl moiety.

In certain embodiments of the compounds of any of structural formulae (4-I)-(4-VII), each $R^3$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl), and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^3$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. For example, in certain embodiments, each $R^3$ is halo (e.g., chloro) or —($C_1$-$C_4$ alkyl) (e.g., methyl, ethyl or propyl).

In certain embodiments of the compounds of any of structural formulae (4-I)-(4-VII), w is at least one, and at least one $R^3$ is —$NR^8R^9$. For example, in one embodiment, w is 1. In certain such embodiments, an $R^3$ is substituted on the central pyridine in the meta position relative to the carbonyl bearing the diazacycloalkyl moiety.

In other embodiments of the compounds of any of structural formulae (4-I)-(4-VII), w is at least one, and at least one $R^3$ is —($C_0$-$C_3$ alkyl)-$Y^1$—($C_1$-$C_3$ alkyl)-$Y^2$—($C_0$-$C_3$ alkyl), in which each of $Y^1$ and $Y^2$ is independently L, —O—, —S— or —$NR^9$—.

For example, in one embodiment, w is 1. In certain such embodiments, $R^3$ is substituted on the central pyridine in the meta position relative to the carbonyl bearing the diazacycloalkyl moiety. In one particular embodiment, $R^3$ is —$CH_2$—N($CH_3$)—$CH_2$—C(O)—$OCH_3$.

In the presently disclosed compounds of any of structural formulae (4-I)-(4-VII), the number of substituents on the diazacycloalkyl ring, x, is 0, 1, 2, 3 or 4. In one embodiment, x is 0, 1, 2 or 3. For example, x can be 0, or can be 1 or 2.

In certain embodiments of the presently disclosed compounds of any of structural formula (4-I)-(4-VII), two $R^4$ groups combine to form an oxo. The oxo can be bound, for example, at the position alpha to a nitrogen of the diazacycloalkyl ring. In other embodiments, no two $R^4$ groups combine to form an oxo.

In certain embodiments of the presently disclosed compounds of any of structural formulae (4-I)-(4-VII), when x is 4, not all four $R^4$ groups are ($C_1$-$C_6$ alkyl).

In certain embodiments of the presently disclosed compounds of any of structural formulae (4-I)-(4-VII), each $R^4$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-$C(O)R^{10}$, —($C_0$-$C_6$ alkyl)-$S(O)_{0-2}R^{10}$, -halogen, —$NO_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-$S(O)_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^4$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-$C(O)R^{10}$, —($C_0$-$C_3$ alkyl)-$S(O)_{0-2}R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-$S(O)_{0-2}$—($C_0$-$C_2$ alkyl), and in which no alkyl or haloalkyl is substituted with an aryl-, heteroaryl-, cycloalkyl- or heterocycloalkyl-containing group.

In certain embodiments, the presently disclosed compounds have the structural formula (4-VIII):

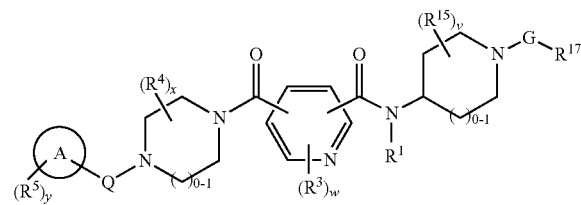

(4-VIII)

in which Q and G are each independently a bond, —$CH_2$—, —C(H)($R^{16}$)—, —C($R^{16}$)$_2$—, L (e.g., —C(O)—$NR^9$— or —$NR^9$—C(O)—) or —$S(O)_2$—; v is 0, 1, 2, 3 or 4; each $R^{15}$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-$C(O)R^{10}$, —($C_0$-$C_6$ alkyl)-$S(O)_{0-2}R^{10}$, -halogen, —$NO_2$ and —CN, and two $R^{15}$ on the same carbon optionally combine to form oxo; $R^{17}$ is Het or Ar, and all other variables are defined as described above with reference to any of structural formula (4-I)-(4-VII). In one embodiment, Q is a single bond. In another embodiment, Q is —$CH_2$—. In other embodiments, Q is —C(O)— or —$S(O)_2$—. In certain embodiments, G is —$CH_2$—. In other embodiments, G is —C(O)— or —$S(O)_2$—. In other embodiments, G is —CH($CH_3$)—. In other embodiments, G is —C(O)—NH—. The above-recited Q and G moieties can be combined in any possible combination. For example, in one embodiment, Q is a single bond and G is —$CH_2$— or —C(O)—. As described above, in certain embodiments, the ring system denoted by "A" is aryl or heteroaryl. In one embodiment, the ring system denoted by "A" is substituted with one or more electron-withdrawing groups as described above. In another embodiment, $R^{17}$ is substituted with one or more electron-withdrawing groups as described above. In certain embodiments, the ring system denoted by "A", $R^{17}$ or both are not substituted with an aryl, heteroaryl, cycloalkyl or heterocycloalkyl-containing group. In certain embodiments, the azacycloalkyl to which -G-$R^{17}$ is bound is a piperidinyl; in other embodiments, it is a pyrrolidinyl.

In the presently disclosed compounds of structural formula (4-VIII), v is 0, 1, 2, 3 or 4. In one embodiment, v is 0, 1, 2 or 3. For example, v can be 0, or can be 1 or 2.

In certain embodiments of the presently disclosed compounds of structural formula (4-VIII), two $R^{15}$ groups combine to form an oxo. The oxo can be bound, for example, at the position alpha relative to the nitrogen of the azacycloalkyl ring. In other embodiments, no two $R^{15}$ groups combine to form an oxo.

In certain embodiments of the presently disclosed compounds of structural formula (4-VIII), when v is 4, not all four $R^{15}$ moieties are ($C_1$-$C_6$ alkyl).

In certain embodiments of the presently disclosed compounds of structural formula (4-VIII), each $R^{15}$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-$C(O)R^{10}$, —($C_0$-$C_6$ alkyl)-$S(O)_{0-2}R^{10}$, -halogen, —$NO_2$ and —CN and two $R^{15}$ on the same carbon optionally combine to form oxo, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-$S(O)_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^{15}$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-$C(O)R^{10}$, —($C_0$-$C_3$ alkyl)-$S(O)_{0-2}R^{10}$, -halogen, —$NO_2$ and —CN and two $R^{15}$ on the same carbon optionally combine to form oxo, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-$S(O)_{0-2}$—($C_0$-$C_2$ alkyl), and in which no alkyl or haloalkyl is substituted with an aryl-, heteroaryl-, cycloalkyl- or heterocycloalkyl-containing group. In some embodiments, one $R^{15}$ is —$C(O)NR^9R^7$, which can be bound, for example, at a position alpha relative to the piperidine nitrogen, or at the position linked to the —N($R^1$)—.

In certain embodiments of the presently disclosed compounds of structural formula (4-VIII), $R^{17}$ is an unsubstituted aryl or heteroaryl. In other embodiments, the $R^{17}$ Ar or Het is substituted with 1, 2 or 3 substituents independently selected from —($C_1$-$C_6$ alkyl), —($C_1$-$C_6$ haloalkyl) (e.g., difluoromethyl, trifluoromethyl and the like), —($C_0$-$C_6$—($C_0$-$C_6$ alkyl)-$NR^8R^9$, —($C_0$-$C_6$ alkyl)-$OR^{10}$, —($C_0$-$C_6$ alkyl)-$C(O)R^{10}$, —($C_0$-$C_6$ alkyl)-$S(O)_{0-2}R^{10}$, -halogen, —$NO_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-$S(O)_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, the R¹⁷ Ar or Het is substituted with 1, 2 or 3 substituents independently selected from —($C_1$-$C_3$ alkyl), —($C_1$-$C_3$ haloalkyl), —($C_0$-$C_3$ alkyl)-L-R⁷, —($C_0$-$C_3$ alkyl)-NR⁸R⁹, —($C_0$-$C_3$ alkyl)-OR¹⁰, —($C_0$-$C_3$ alkyl)-C(O) R¹⁰, —($C_0$-$C_3$ alkyl)-S(O)$_{0-2}$R¹⁰, -halogen, —NO$_2$ and —CN, in which each R⁷, R⁸ and R¹⁰ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-NR⁹($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. In certain embodiments, R¹⁷ is substituted with 1, 2 or 3 substituents selected from halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), NO$_2$ and —C(O)-Hca. R¹⁷ can be substituted with, for example, one such substituent, or two such substituents.

In certain embodiments, the presently disclosed compounds have the structural formula (4-IX):

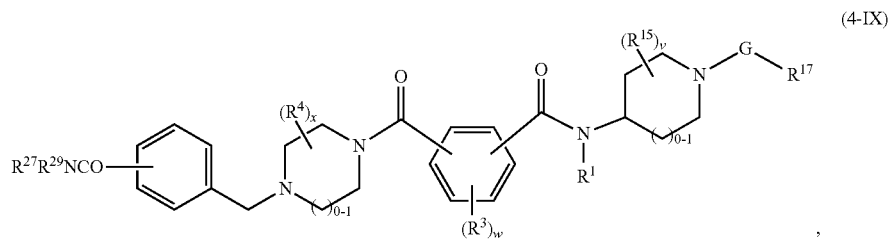

(4-IX)

in which R²⁷ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-NR⁹ ($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and R²⁹ is —H, —($C_1$-$C_4$ alkyl), —C(O)—($C_1$-$C_4$ alkyl) or —C(O)—O—($C_1$-$C_4$ alkyl) in which no ($C_1$-$C_4$ alkyl) is substituted by an aryl, heteroaryl, cycloalkyl or heterocycloalkyl-containing group, or R²⁷ and R²⁹ together with the nitrogen to which they are bound form Hca, and all other variables are as described above with reference to any of structural formulae (4-I)-(4-VIII). In one embodiment, R²⁷ and R²⁹ are both H.

In certain embodiments, the presently disclosed compounds have the structural formula (4-X):

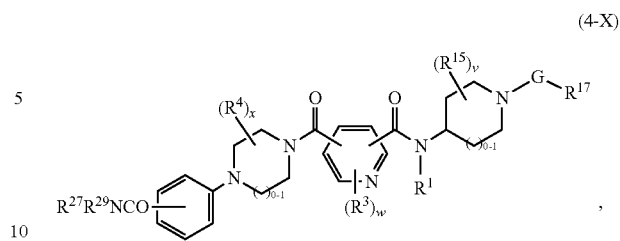

(4-X)

in which R²⁷ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-NR⁹ ($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and R²⁹ is —H, —($C_1$-$C_4$ alkyl), —CO—O—($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or R²⁷ and R²⁹ together with the nitrogen to which they are bound form Hca, and all other variables are as described above with reference to any of structural formulae (4-I)-(4-VIII). In one embodiment, R²⁷ and R²⁹ are both H.

In certain embodiments, the presently disclosed compounds have the structural formula (4-XI):

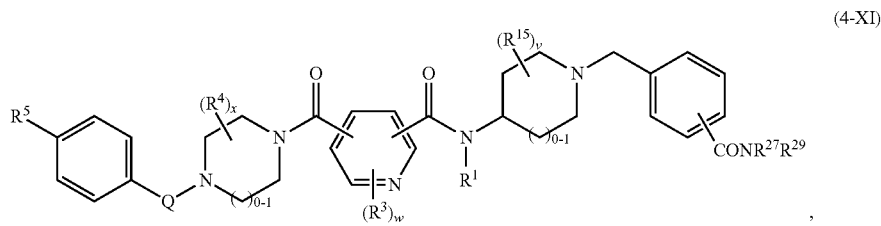

(4-XI)

in which R²⁷ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-NR⁹ ($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and R²⁹ is —H, —($C_1$-$C_4$ alkyl), —CO—O—($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (4-I)-(4-VIII). In one embodiment, $R^{27}$ and $R^{29}$ are both H.

In certain embodiments, the presently disclosed compounds have the structural formula (4-XII):

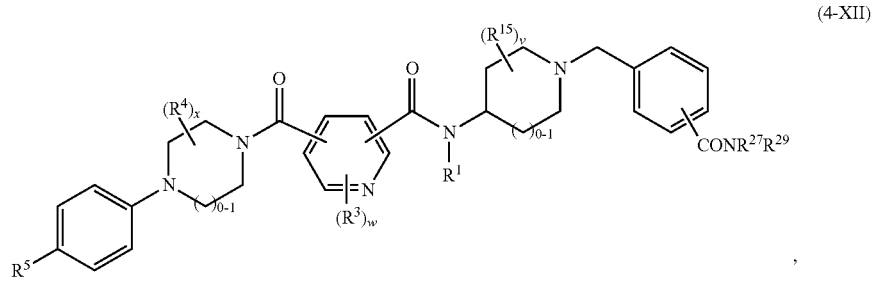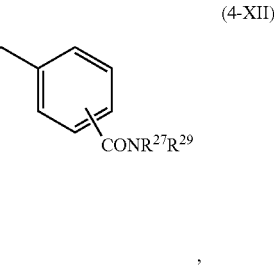

(4-XII)

in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —CO—O—($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (4-I)-(4-VIII). In one embodiment, $R^{27}$ and $R^{29}$ are both H.

In certain embodiments, the presently disclosed compounds have the structural formula (4-XIII):

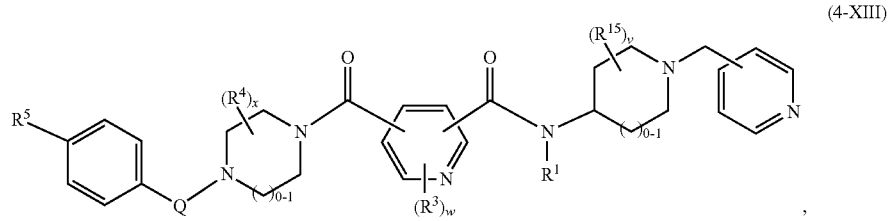

(4-XIII)

in which all variables are as described above with reference to any of structural formulae (4-I)-(4-VIII).

In certain embodiments, the presently disclosed compounds have the structural formula (4-XIV):

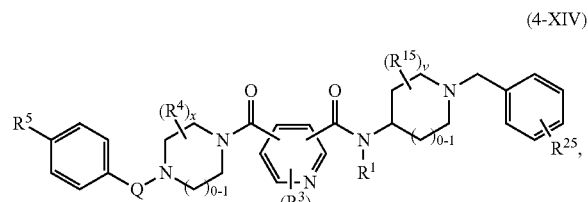

(4-XIV)

in which $R^{25}$ is selected from halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, in which no alkyl or haloalkyl is substituted by an aryl, heteroaryl, cycloalkyl or heterocycloalkyl-containing group; and all other variables are as described above with reference to any of structural formulae (4-I)-(4-VIII). $R^{25}$ can be, for example, —Cl, —F, cyano, —C(O)$CH_3$, —C(O)OH, —C(O)$NH_2$, trifluoromethyl, difluoromethyl, difluoromethoxy or trifluoromethoxy.

In certain embodiments, the presently disclosed compounds have the structural formula (4-XV):

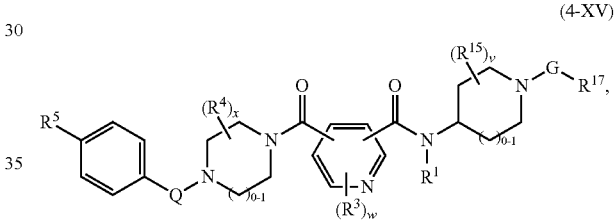

(4-XV)

in which G is —C(O)—, —S(O)$_2$— or —C(O)—NH— and all other variables are as described above with reference to any of structural formulae (4-I)-(4-VIII).

In certain embodiments, the presently disclosed compounds have the structural formula (4-XVI):

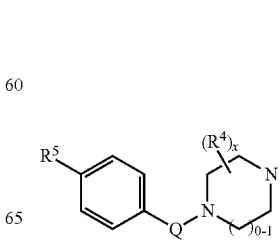

(4-XVI)

in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$ ($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —CO—O—($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (4-I)-(4-VIII). In one embodiment, $R^{27}$ and $R^{29}$ are both H. In some embodiments, the compounds of structural formula (4-VIII) are present as racemic mixtures or scalemic mixtures. In other embodiments, the compounds of structural formula (4-XVI) are present in an enantiomerically-enriched form, for example as a substantially pure stereoisomer.

In certain embodiments, the presently disclosed compounds have the structural formula (4-XVII):

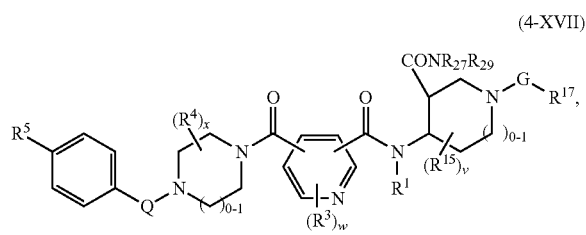

(4-XVII)

in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$ ($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —CO—O—($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (4-I)-(4-VIII). In one embodiment, $R^{27}$ and $R^{29}$ are both H. In some embodiments, the compounds of structural formula (4-VIII) are present as racemic mixtures or scalemic mixtures. In other embodiments, the compounds of structural formula (4-XVII) are present in an enantiomerically-enriched form, for example as a substantially pure stereoisomer.

In certain embodiments, the presently disclosed compounds have the structural formula (4-XVIII):

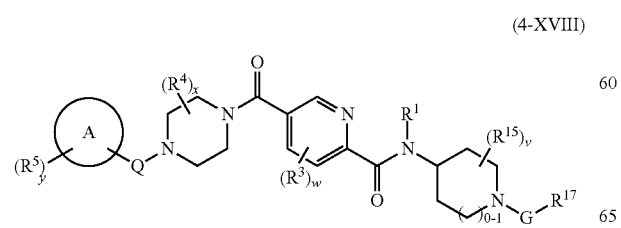

(4-XVIII)

in which G, v, $R^{15}$ and $R^{17}$ are defined as described above with reference to structural formula (4-VIII), and all other variables are defined as described above with reference to structural formulae (4-I) or (4-II). $R^5$, y, v, $R^{15}$, $R^{12}$, Q, G and the ring denoted by "A" can be defined, for example, as described with reference to any of structural formulae (4-IX)-(4-XVII).

In certain embodiments, the presently disclosed compounds have the structural formula (4-XIX):

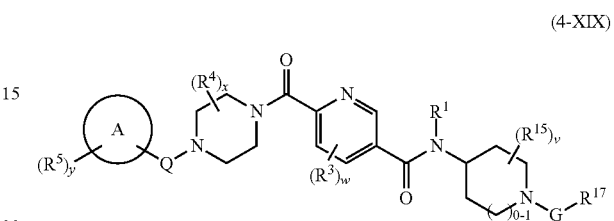

(4-XIX)

in which G, v, $R^{15}$ and $R^{17}$ are defined as described above with reference to structural formula (4-VIII), and all other variables are defined as described above with reference to structural formulae (4-I) or (4-III). $R^5$, y, v, $R^{15}$, $R^{12}$, Q, G and the ring denoted by "A" can be defined, for example, as described with reference to any of structural formulae (4-IX)-(4-XVII).

In certain embodiments, the presently disclosed compounds have the structural formula (4-XX):

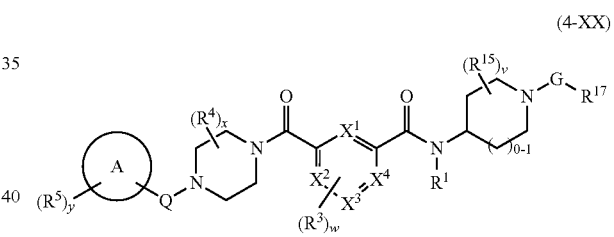

(4-XX)

in which one of $X^1$, $X^2$, $X^3$ and $X^4$ are N, and the others are carbons (for example, independently CH or C substituted with one of the w $R^3$ groups), as described above with reference to structural formulae (4-IV) and (4-VII); G, v, $R^{15}$ and $R^{12}$ are defined as described above with reference to structural formula (4-VIII), and all other variables are defined as described above with reference to structural formulae (4-I) or (4-IV). $R^5$, y, v, $R^{15}$, $R^{17}$, Q, G and the ring denoted by "A" can be defined, for example, as described with reference to any of structural formulae (4-IX)-(4-XVII).

In certain embodiments of compounds having structural formulae (4-VIII)-(4-XX), the

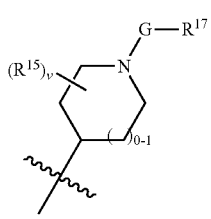

moiety has the structure

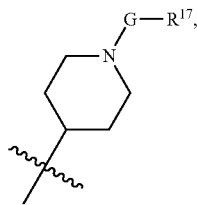

in which G is —CH$_2$—, —CH(CH$_3$)—, —C(O)—, —S(O)$_2$— or —C(O)—NH—. For example, in one embodiment, G is —CH$_2$—. In another embodiment, G is —C(O)— or —S(O)$_2$—. In another embodiment, G is —C(O)—NH—.

In other embodiments of compounds having structural formulae (4-VIII)-(4-XX), the

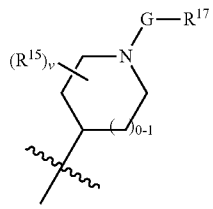

moiety has the structure

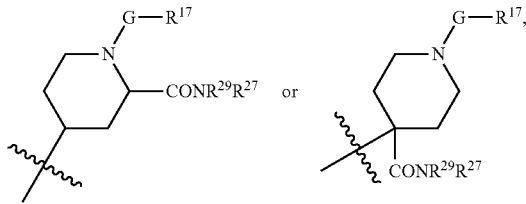

in which G is —CH$_2$—, —C(O)—, —S(O)$_2$— or —C(O)—NH—, R$^{27}$ is selected from H, —(C$_1$-C$_6$ alkyl), —(C$_1$-C$_6$ haloalkyl) (e.g., difluoromethyl, trifluoromethyl and the like), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl)-(C$_0$-C$_6$ alkyl)-S(O)$_{0-2}$—(C$_0$-C$_6$ alkyl), in which no heterocycloalkyl, alkyl or haloalkyl is substituted with an aryl-, heteroaryl-, cycloalkyl- or heterocycloalkyl-containing group, and R$^{29}$ is —H, —(C$_1$-C$_4$ alkyl), —CO—(C$_1$-C$_4$ alkyl) or —CO—O—(C$_1$-C$_4$ alkyl) in which no (C$_1$-C$_4$ alkyl) is substituted by an aryl, heteroaryl, cycloalkyl or heterocycloalkyl-containing group, or R$^{27}$ and R$^{29}$ together with the nitrogen to which they are bound form Hca. In such embodiments, the compounds can be present as racemic mixtures or scalemic mixtures, or in an enantiomerically-enriched form, for example as a substantially pure stereoisomer.

In other embodiments of compounds having structural formulae (4-VIII)-(4-XX), the

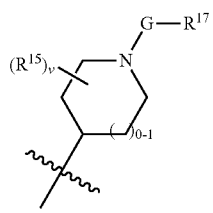

moiety has the structure

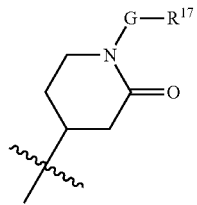

in which G is —CH$_2$—, —C(O)—, —S(O)$_2$— or —C(O)—NH—.

In certain embodiments of compounds having structural formulae (4-VIII)-(4-XX), the R$^{17}$ moiety has the structure

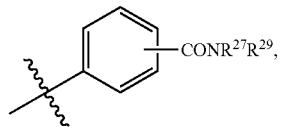

in which R$^{27}$ is selected from H, —(C$_1$-C$_6$ alkyl), —(C$_1$-C$_6$ haloalkyl) (e.g., difluoromethyl, trifluoromethyl and the like), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl)-(C$_0$-C$_6$ alkyl)-S(O)$_{0-2}$—(C$_0$-C$_6$ alkyl), in which no heterocycloalkyl, alkyl or haloalkyl is substituted with an aryl-, heteroaryl-, cycloalkyl- or heterocycloalkyl-containing group, and R$^{29}$ is —H, —(C$_1$-C$_4$ alkyl), —CO—(C$_1$-C$_4$ alkyl) or —CO—O—(C$_1$-C$_4$ alkyl) in which no (C$_1$-C$_4$ alkyl) is substituted by an aryl, heteroaryl, cycloalkyl or heterocycloalkyl-containing group, or R$^{27}$ and R$^{29}$ together with the nitrogen to which they are bound form Hca.

In certain embodiments of compounds having structural formulae (4-VIII)-(4-XX), w is 1, and R$^3$ is —NR$^8$R$^9$. In certain such embodiments, R$^3$ is substituted on the central pyridine in a meta position relative to the —C(O)— bearing the diazacycloalkyl moiety.

In other embodiments of compounds having structural formulae (4-VIII)-(4-XX), w is 1, and R$^3$ is —(C$_0$-C$_3$ alkyl)-Y$^1$—(C$_1$-C$_3$ alkyl)-Y$^2$—(C$_0$-C$_3$ alkyl), in which each of Y$^1$ and Y$^2$ is independently L, —O—, —S— or —NR$^9$—. In certain such embodiments, R$^3$ is substituted on the central pyridine in a meta position relative to the —C(O)— bearing the diazacycloalkyl moiety.

In certain embodiments described above, each R$^{27}$ is selected from —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN and two R$^{21}$ on the same carbon optionally combine to form oxo, in which each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group, and each R$^{29}$ is H, methyl or ethyl, or R$^{27}$ and R$^{29}$ together with the nitrogen to which they are bound form Hca.

In certain embodiments of compounds having structural formulae (4-VIII)-(4-XX), at least one R$^5$ moiety is a haloalkyl group, and in exemplary embodiments of these formulae the

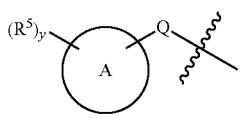

moiety is p-(trifluoromethyl)phenyl, p-fluorophenyl or p-cyanophenyl. By way of further illustration, certain exemplary compounds including such

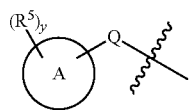

moieties have structural formula (4-XXI), (4-XXII) or (4-XXIII):

(4-XXI)

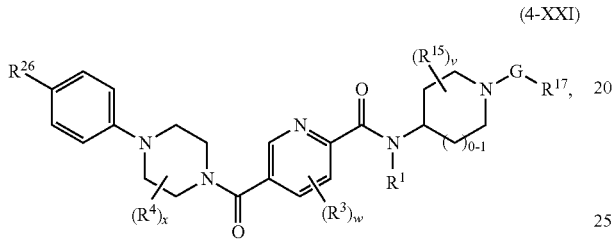

(4-XXII)

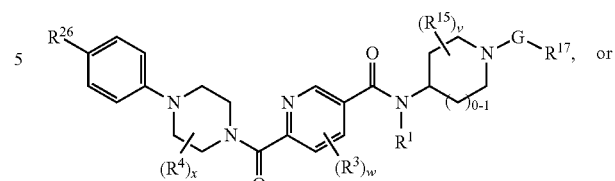

(4-XXIII)

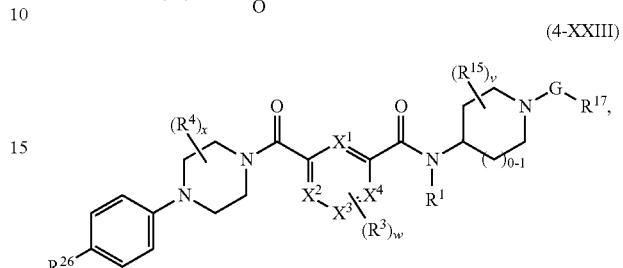

in which $R^{26}$ is trifluoromethyl, chloro, fluoro or cyano and all other variables are as described above with reference to structural formulae (4-XVIII), (4-XIX) and (4-XX).

In certain embodiments, the presently disclosed compounds have the structural formula (4-XXIV):

(4-XXIV)

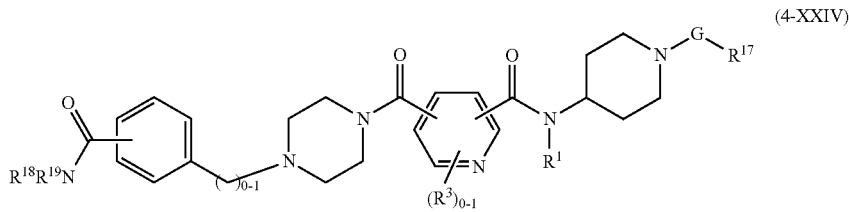

in which G, $R^1$, $R^3$ and $R^{17}$ are as described above with reference to any of structural formulae (4-I)-(4-XXIII), $R^{18}$ is H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), in which no alkyl or haloalkyl is substituted with an aryl-, heteroaryl-, cycloalkyl- or heterocycloalkyl-containing group and $R^{19}$ is —H, —($C_1$-$C_4$ alkyl), —CO—($C_1$-$C_4$ alkyl) or —CO—O—($C_1$-$C_4$ alkyl) in which no alkyl is substituted by an aryl, heteroaryl, cycloalkyl or heterocycloalkyl-containing group, or $R^{18}$ and $R^{19}$ together with the nitrogen to which they are bound form Hca. In one embodiment, $R^{18}$ and $R^{19}$ are both H.

For example, in one embodiment, the presently disclosed compounds have the structural formula (4-XXV):

(4-XXV)

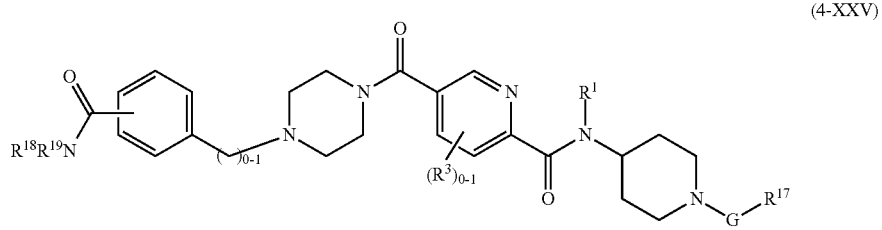

in which G, $R^1$, $R^3$ and $R^{17}$ are as described above with reference to any of structural formulae (4-I), (4-VIII), (4-XIII), (4-XIV), (4-XVI) or (4-XXII), and $R^{18}$ and $R^{19}$ are defined as described above with reference to structural formula (4-XXIV).

In certain embodiments, the presently disclosed compounds have the structural formula (4-XXVI):

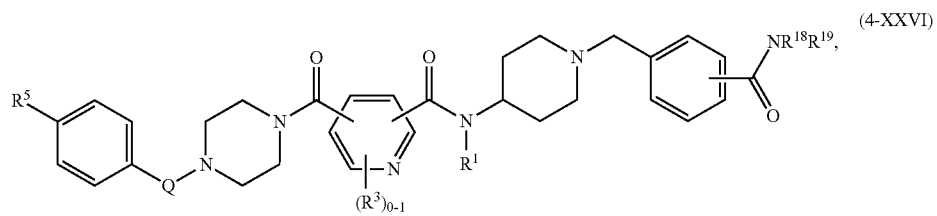

(4-XXVI)

in which Q, $R^1$, $R^3$ and $R^5$ are defined as described above with reference to any of structural formulae (4-I)-(4-XXIII), and $R^{18}$ and $R^{19}$ are defined as described above with reference to structural formula (4-XXIV).

For example, in one embodiment, the presently disclosed compounds have the structural formula (4-XXVII):

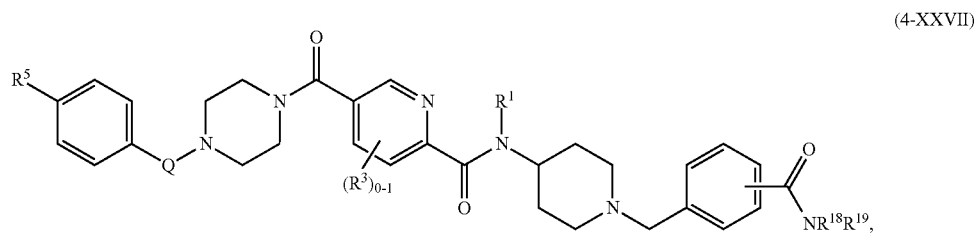

(4-XXVII)

in which Q, $R^1$, $R^3$ and $R^5$ are defined as described above with reference to any of structural formulae (4-I)-(4-XXIII), and $R^{18}$ and $R^{19}$ are defined as described above with reference to structural formula (4-XXIV).

In certain embodiments, the presently disclosed compounds have the structural formula (4-XXVIII):

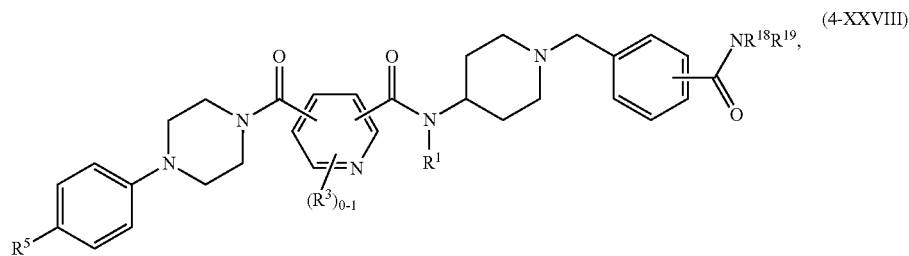

(4-XXVIII)

in which $R^1$, $R^3$ and $R^5$ are defined as described above with reference to any of structural formulae (4-I)-(4-XXIII), and $R^{18}$ and $R^{19}$ are defined as described above with reference to structural formula (4-XXIV).

For example, in one embodiment, the presently disclosed compounds have the structural formula (4-XXIX):

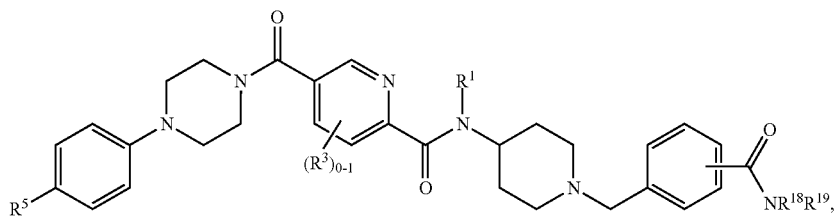

(4-XXIX)

in which $R^1$, $R^3$ and $R^5$ are defined as described above with reference to any of structural formulae (4-I)-(4-XXIII), and $R^{18}$ and $R^{19}$ are defined as described above with reference to structural formula (4-XXIV).

In compounds according to any of structural formulae (4-I)-(4-VII), T and $R^2$ can be defined as described above with reference to structural formulae (4-VIII)-(4-XXIX).

In certain embodiments, the presently disclosed compounds have the structural formula (4-XXX):

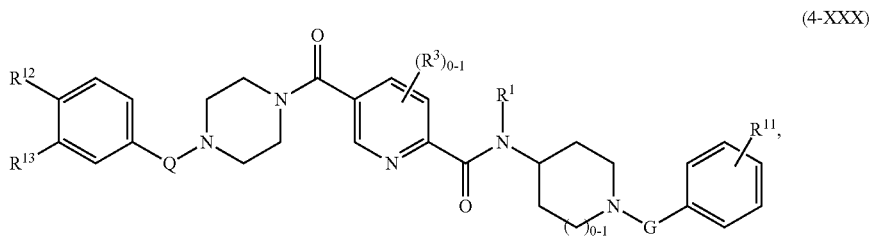

(4-XXX)

in which Q is —CH$_2$—, —C(O)— or a single bond; G is a single bond, —CH$_2$—, —C(O)—, —S(O)$_2$— or —C(O)—NH—; $R^1$ and $R^3$ are as described above with reference to any of structural formulae (4-I), (4-II), and (4-VIII); and $R^{11}$, $R^{12}$ and $R^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, no $R^3$ is substituted on the central pyridine. In another embodiment, one $R^3$ (e.g., —Cl, —F, —CH$_3$, —C$_2$H$_5$, —C$_3$H$_7$) is substituted on the central pyridine.

In certain embodiments, the presently disclosed compounds have the structural formula (4-XXXI):

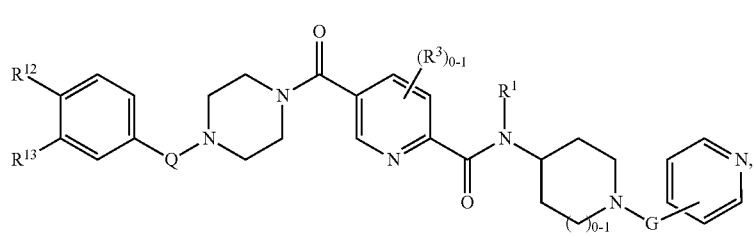

(4-XXXI)

in which Q is —CH₂—, —C(O)— or a single bond; G is a single bond, —CH₂—, —C(O)—, —S(O)₂— or —C(O)—NH—; R¹ and R³ are as described above with reference to any of structural formulae (4-I), (4-II) and (4-VIII); and R¹² and R¹³ are independently selected from H, halo, cyano, —(C₁-C₄ haloalkyl), —O—(C₁-C₄ haloalkyl), —(C₁-C₄ alkyl), —O—(C₁-C₄ alkyl), —C(O)—(C₀-C₄ alkyl), —C(O)O—(C₀-C₄ alkyl), —C(O)N(C₀-C₄ alkyl)(C₀-C₄ alkyl), NO₂ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R¹² and R¹³ is not H. In one embodiment, the pyrido nitrogen is disposed in the para position relative to the G moiety; in another embodiment, the pyrido nitrogen is disposed in the meta position relative to the G moiety. In one embodiment, no R³ is substituted on the central pyridine. In another embodiment, one R³ (e.g., —Cl, —F, —CH₃, —C₂H₅, —C₃H₇) is substituted on the central pyridine.

In certain embodiments, the presently disclosed compounds have the structural formula (4-XXXII):

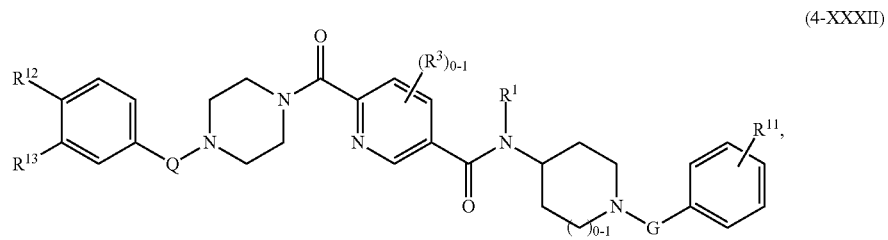

(4-XXXII)

in which Q is —CH₂—, —C(O)— or a single bond; G is a single bond, —CH₂—, —C(O)—, —S(O)₂— or —C(O)—NH—; R¹ and R³ are as described above with reference to any of structural formulae (4-I), (4-III), and (4-VIII); and R¹¹, R¹² and R¹³ are independently selected from H, halo, cyano, —(C₁-C₄ haloalkyl), —O—(C₁-C₄ haloalkyl), —(C₁-C₄ alkyl), —O—(C₁-C₄ alkyl), —C(O)—(C₀-C₄ alkyl), —C(O)O—(C₀-C₄ alkyl), —C(O)N(C₀-C₄ alkyl)(C₀-C₄ alkyl), NO₂ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R¹¹, R¹² and R¹³ is not H. In one embodiment, R¹¹ is attached in the para position relative to the G moiety; in another embodiment, R¹¹ is attached in the meta position relative to the G moiety. In one embodiment, no R³ is substituted on the central pyridine. In another embodiment, one R³ (e.g., —Cl, —F, —CH₃, —C₂H₅, —C₃H₇) is substituted on the central pyridine.

In certain embodiments, the presently disclosed compounds have the structural formula (4-XXXIII):

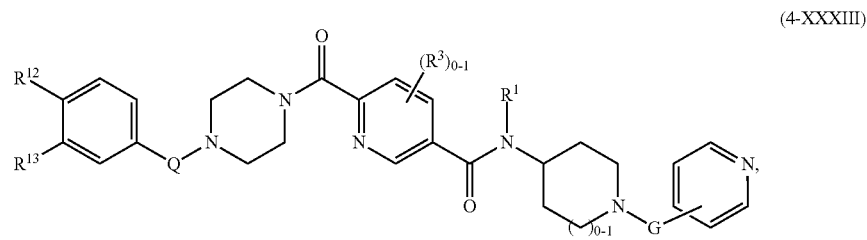

(4-XXXIII)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (4-I), (4-III) and (4-VIII); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyrido nitrogen is disposed in the para position relative to the G moiety; in another embodiment, the pyrido nitrogen is disposed in the meta position relative to the G moiety. In one embodiment, no R$^3$ is substituted on the central pyridine. In another embodiment, one R$^3$ (e.g., —Cl, —F, —CH$_3$, —C$_2$H$_5$, —C$_3$H$_7$) is substituted on the central pyridine.

In certain embodiments, the presently disclosed compounds have the structural formula (4-XXXIV):

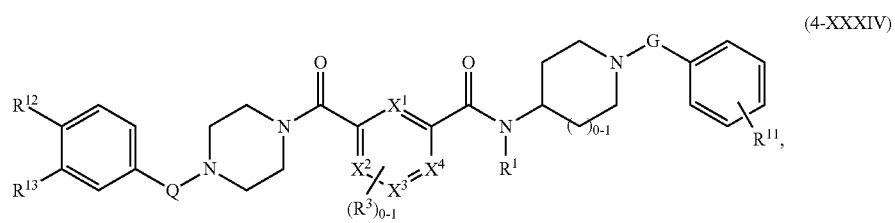

(4-XXXIV)

in which one of X$^1$, X$^2$, X$^3$ and X$^4$ are N, and the others are carbons (for example, independently CH or C substituted with one of the w R$^3$ groups), as described above with reference to structural formulae (4-IV) and (4-VII); Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (4-I), (4-IV), and (4-VIII); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, no R$^3$ is substituted on the central pyridine. In another embodiment, one R$^3$ (e.g., —Cl, —F, —CH$_3$, —C$_2$H$_5$, —C$_3$H$_7$) is substituted on the central pyridine.

In certain embodiments, the presently disclosed compounds have the structural formula (4-XXXV):

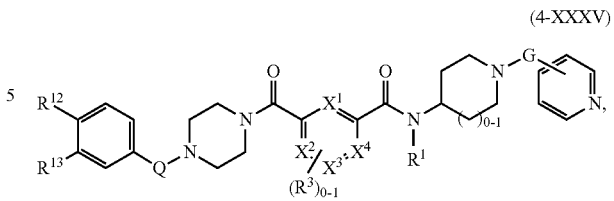

(4-XXXV)

in which one of X$^1$, X$^2$, X$^3$ and X$^4$ are N, and the others are carbons (for example, independently CH or C substituted with one of the w R$^3$ groups), as described above with reference to structural formulae (4-IV) and (4-VII); Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (4-I), (4-IV) and (4-VIII); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyrido nitrogen is disposed in the para position relative to the G moiety; in another embodiment, the pyrido nitrogen is disposed in the meta position relative to the G moiety. In one embodiment, no R$^3$ is substituted on the central pyridine. In another embodiment, one R$^3$ (e.g., —Cl, —F, —CH$_3$, —C$_2$H$_5$, —C$_3$H$_7$) is substituted on the central pyridine.

As the person of skill in the art will recognize, the various embodiments described above can be combined to form other embodiments of the disclosure. For example, in one embodiment, Q is —CH$_2$—, as described above, and G is —CH$_2$—, as described above.

Examples of compounds according to structural formula (4-I) include those listed in Table 4. These compounds can be made, for example using a procedure analogous to those described in U.S. Patent Application Publications nos. 2009/0163511, 2009/0170829, 2009/0186894 and 2009/0275609, and in U.S. patent application Ser. No. 12/695,861, each of which is hereby incorporated by reference in its entirety.

TABLE 4

| No. | Name | Structure |
|---|---|---|
| 4-1 | 5-(4-(4-cyanobenzyl)piperazine-1-carbonyl)-N-(1-(4-cyanobenzyl)piperidin-4-yl)picolinamide | 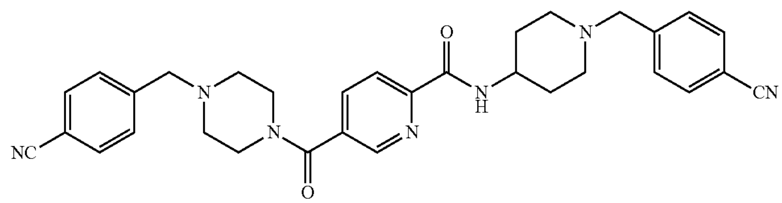 [SMILES: N#Cc1ccc(CN2CCC(NC(=O)c3ccc(C(=O)N4CCN(Cc5ccc(C#N)cc5)CC4)cn3)CC2)cc1] |
| 4-2 | N-(1-(4-cyanobenzyl)piperidin-4-yl)-5-(4-(4-fluorobenzyl)piperazine-1-carbonyl)picolinamide | 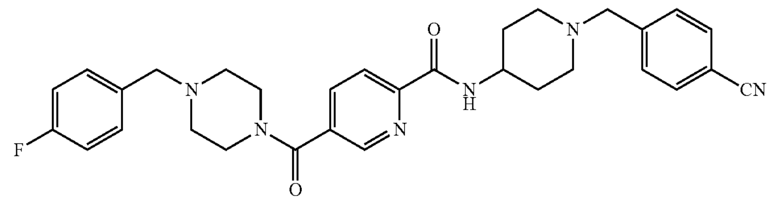 [SMILES: N#Cc1ccc(CN2CCC(NC(=O)c3ccc(C(=O)N4CCN(Cc5ccc(F)cc5)CC4)cn3)CC2)cc1] |
| 4-3 | N-(1-(4-cyanobenzyl)piperidin-4-yl)-5-(4-(4-(trifluoromethyl)benzyl)piperazine-1-carbonyl)picolinamide | 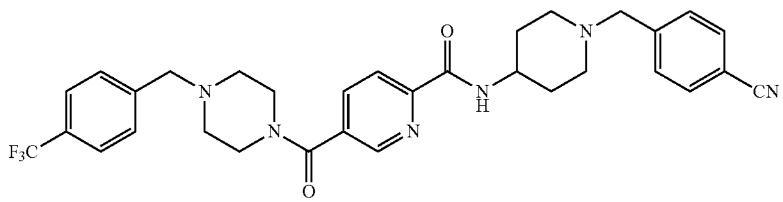 [SMILES: N#Cc1ccc(CN2CCC(NC(=O)c3ccc(C(=O)N4CCN(Cc5ccc(C(F)(F)F)cc5)CC4)cn3)CC2)cc1] |
| 4-4 | (S)-5-(4-(4-chlorophenyl)piperazine-1-carbonyl)-N-(1-(4-fluorobenzyl)pyrrolidin-3-yl)picolinamide | 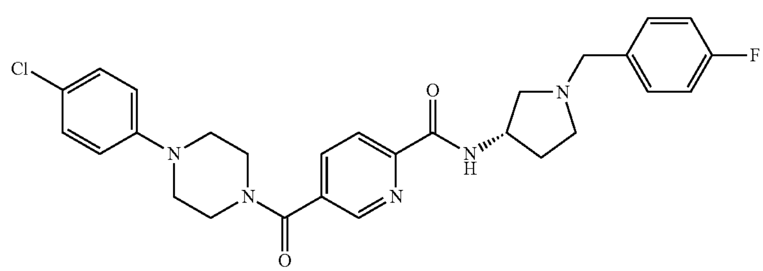 [SMILES: O=C(N[C@H]1CCN(Cc2ccc(F)cc2)C1)c1ccc(C(=O)N2CCN(c3ccc(Cl)cc3)CC2)cn1] |
| 4-5 | (S)-5-(4-(4-chlorophenyl)piperazine-1-carbonyl)-N-(1-(pyridin-4-ylmethyl)pyrrolidin-3-yl)picolinamide | 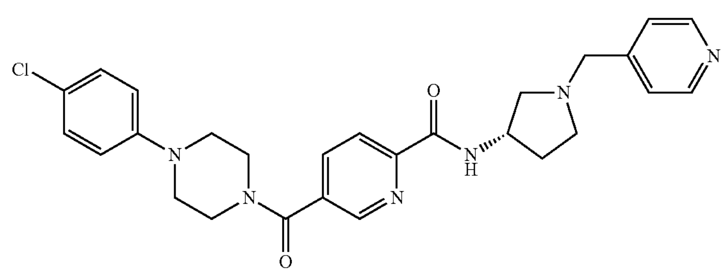 [SMILES: O=C(N[C@H]1CCN(Cc2ccncc2)C1)c1ccc(C(=O)N2CCN(c3ccc(Cl)cc3)CC2)cn1] |
| 4-6 | (S)-5-(4-(4-chlorophenyl)piperazine-1-carbonyl)-N-(1-(4-cyanobenzyl)pyrrolidin-3-yl)picolinamide | 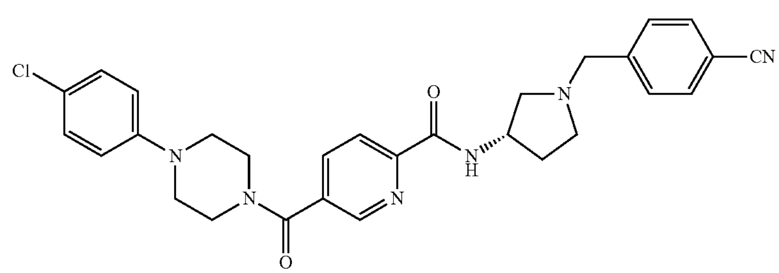 [SMILES: N#Cc1ccc(CN2CC[C@H](NC(=O)c3ccc(C(=O)N4CCN(c5ccc(Cl)cc5)CC4)cn3)C2)cc1] |

TABLE 4-continued

| No. | Name | Structure |
|---|---|---|
| 4-7 | N-(1-(4-chlorobenzyl)pyrrolidin-3-yl)-5-(4-(4-chlorophenyl)piperazine-1-carbonyl)picolinamide | 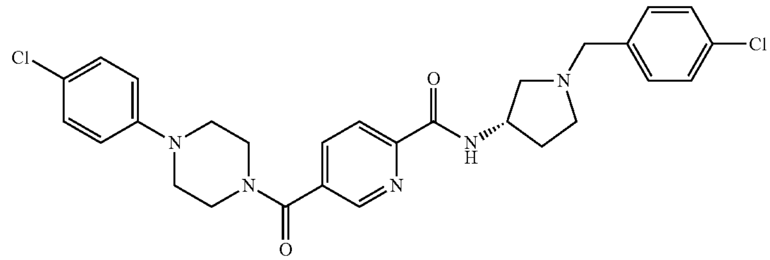 [SMILES: O=C(N[C@H]1CCN(Cc2ccc(Cl)cc2)C1)c1ccc(C(=O)N2CCN(c3ccc(Cl)cc3)CC2)cn1] |
| 4-8 | 5-(4-(4-chlorophenyl)piperazine-1-carbonyl)-N-(1-(4-(trifluoromethyl)benzyl)pyrrolidin-3-yl)picolinamide | 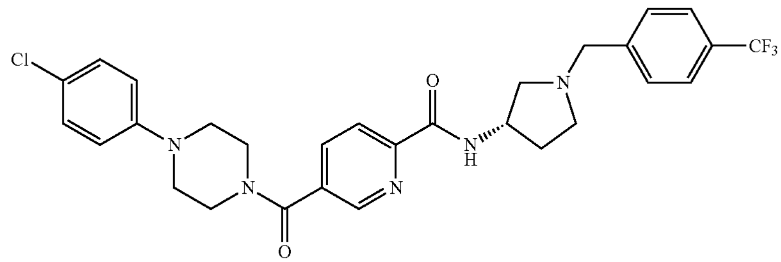 [SMILES: O=C(N[C@H]1CCN(Cc2ccc(C(F)(F)F)cc2)C1)c1ccc(C(=O)N2CCN(c3ccc(Cl)cc3)CC2)cn1] |

Another aspect of the disclosure provides a method for treating or ameliorating a disorder or condition related to oxidative stress, mitochondrial dysfunction, free radical damage and/or metabolic inefficiency in a subject, the method including administering to the subject an effective amount of a compound having structural formula (5-I):

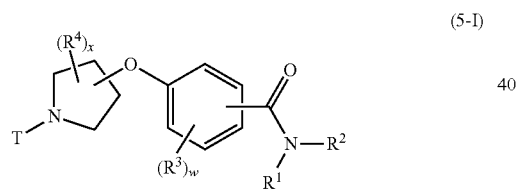

(5-I)

or a pharmaceutically acceptable salt, solvate, hydrate, or N-oxide thereof (or a solvate or hydrate thereof), in which
$R^1$ is H;
$R^2$ is —Hca;
each $R^3$ is independently selected from —($C_1$-$C_6$ alkyl), —($C_1$-$C_6$ fluoroalkyl), —($C_0$-$C_6$ alkyl)-Ar; —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-S(O)$_{0-2}R^{10}$, -halogen, —$NO_2$ and —CN;
w is 0, 1, 2, or 3;
n is 0, 1 2 or 3;
each $R^4$ is independently selected from —($C_1$-$C_6$ alkyl), —($C_1$-$C_6$ fluoroalkyl), —($C_0$-$C_6$ alkyl)-Ar; —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-S(O)$_{0-2}R^{10}$, -halogen, —$NO_2$ and —CN, and two $R^4$ on the same carbon optionally combine to form oxo;
x is 0, 1, 2, 3 or 4;
T is —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-S(O)$_{0-2}R^{10}$; or

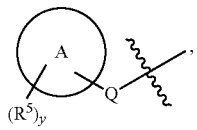

n which
Q is —($C_0$-$C_3$ alkyl)-, in which each carbon of the —($C_0$-$C_3$ alkyl)- is optionally and independently substituted with one or two $R^{16}$;
each $R^{16}$ is independently selected from —($C_1$-$C_6$ alkyl), —($C_1$-$C_6$ fluoroalkyl), —($C_0$-$C_6$ alkyl)-Ar; —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-S(O)$_{0-2}R^{10}$, -halogen, —$NO_2$ and —CN, and two $R^{16}$ on the same carbon optionally combine to form oxo;
the ring system denoted by "A" is heteroaryl, aryl, cycloalkyl or heterocycloalkyl;
each $R^5$ is independently selected from —($C_1$-$C_6$ alkyl), —($C_1$-$C_6$ fluoroalkyl), —($C_0$-$C_6$ alkyl)-Ar; —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-S(O)$_{0-2}R^{10}$, -halogen, —$NO_2$ and —CN; and
y is 0, 1, 2, 3 or 4;
in which
each L is independently selected from —$NR^9$C(O)O—, —$NR^9$C(O)—$NR^9$—, —$NR^9$C(O)S—, —$NR^9$C(O)—, —$NR^9$C(S)O—, —$NR^9$C(S)—$NR^9$—, —$NR^9$C(S)S—, —$NR^9$C(S)—, —OC(O)$NR^9$—, —SC(O)$NR^9$—, —C(S)$NR^9$—, —OC(S)$NR^9$—, —SC(S)$NR^9$—, —C(S)$NR^9$—, —S(O)$_{0-2}$—, —C(O)O—, —OC(O)—, —C(S)O—, —OC(S)—, —C(O)S—, —SC(O)—, —C(S)S—, —SC(S)—, —OC(O)O—, —SC(O)O—, —OC(O)S—, —SC(S)

O—, —OC(S)S—, —NR$^9$C(NR$^2$)NR$^9$—, —NR$^9$SO$_2$—, —SO$_2$NR$^9$— and —NR$^9$SO$_2$NR$^9$—, each R$^6$, R$^7$, R$^8$ and R$^{10}$ is independently selected from H, —(C$_1$-C$_6$ alkyl), —(C$_1$-C$_6$ fluoroalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl) and —(C$_0$-C$_6$ alkyl)-S(O)$_{0-2}$—(C$_0$-C$_6$ alkyl), each R$^9$ is independently selected from —H, —(C$_1$-C$_4$ alkyl) and —C(O)—(C$_1$-C$_4$ alkyl), each Ar is an optionally substituted aryl, each Het is an optionally substituted heteroaryl, each Cak is an optionally substituted cycloalkyl, each Hca is an optionally substituted heterocycloalkyl, and each alkyl is optionally substituted.

Various embodiments of compounds of structural formula (5-I) suitable for use in the methods described herein are described below. Information regarding these compounds can also be found in U.S. Patent Application Publication no. 2009/0186894, which is hereby incorporated by reference in its entirety.

R$^1$, R$^2$, R$^3$, R$^4$, T, w, x and n may alternatively be as described above with respect to structural formulae (3-I)-(3-CXX).

In one embodiment of compounds of structural formula (5-I), two R$^4$s combine to form an oxo. The oxo can be bound, for example, at the position alpha to the nitrogen of the azacycloalkyl.

In certain embodiments of the compounds of formula (5-I), T is

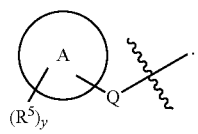

In these embodiments, Q is —(C$_0$-C$_3$ alkyl)-, in which each carbon of the (C$_0$-C$_3$ alkyl) is optionally and independently substituted with one or two R$^{16}$, in which each R$^{16}$ is independently selected from —(C$_1$-C$_6$ alkyl), —(C$_1$-C$_6$ fluoroalkyl), —(C$_0$-C$_6$ alkyl)-Ar; —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-S(O)$_{0-2}$R$^{10}$, -halogen, —NO$_2$ and —CN, and two R$^{16}$ on the same carbon optionally combine to form an oxo. Q can be, for example, an unsubstituted (C$_1$-C$_3$ alkyl). In other embodiments, Q is a (C$_1$-C$_3$ alkyl) having as its only substitution a single oxo group. For example, in certain embodiments, Q is —CH$_2$—; a single bond; or —C(O)— or —CH(CH$_3$)—.

The number of substituents on the ring system denoted by "A", y, in these embodiments is 0, 1, 2, 3 or 4. For example, in some embodiments, y is 0, 1, 2 or 3, for example 0, or 1. In one embodiment, y is not zero and at least one R$^5$ is halo, cyano, trifluoromethyl or trifluoromethoxy.

The ring system denoted by "A" is heteroaryl, aryl, cycloalkyl or heterocycloalkyl. For example, of the compounds of structural formula (5-I), the ring system denoted by "A" is an aryl or a heteroaryl. In one embodiment of the compounds of structural formula (5-I), the ring system denoted by "A" is an aryl. The ring system denoted by "A" can be, for example, a monocyclic aryl or heteroaryl.

For example, in one embodiment of the compounds of structural formula (5-I), the ring system denoted by "A" is an aryl, such as a phenyl. In one embodiment of the compounds of structural formula (5-I), y is 1 and R$^5$ is attached to the phenyl para to Q. In another embodiment of the compounds of structural formula (5-I), y is 1 and R$^5$ is selected from the group consisting of halo, cyano, —(C$_1$-C$_4$ fluoroalkyl), —O—(C$_1$-C$_4$ fluoroalkyl), acyl, carboxylate, carboxamide and nitro. R$^5$ can be, for example, —Cl, —F, cyano, trifluoromethyl or trifluoromethoxy. In another embodiment of the compounds of structural formula (5-I), the

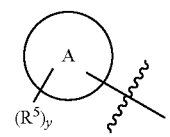

moiety is a 3,4-dihalophenyl.

In another embodiment of the compounds of structural formula (5-I), the ring system denoted by "A" is a heteroaryl. For example, in certain embodiments of the compounds of structural formula (5-I), the ring system denoted by "A" is a pyridiyl, a thienyl, or a furanyl.

In one embodiment of the compounds of structural formula (5-I), the compound has structural formula (5-II):

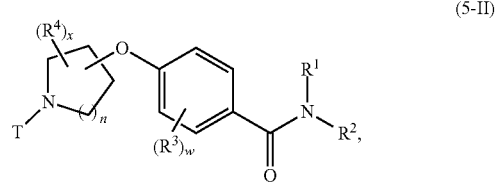

(5-II)

in which the variables are defined as described above with reference to formula (5-I).

In another embodiment of the compounds of structural formula (5-I), the compound has the structural formula (5-III):

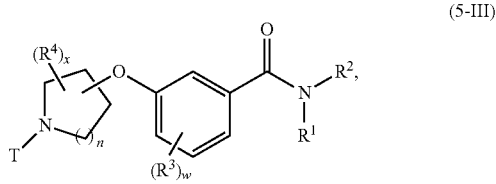

(5-III)

in which the variables are defined as described above with reference to formula (5-I).

For example, compounds according to certain embodiments of the compounds of structural formula (5-I) have structural formula (5-IV):

(5-IV)

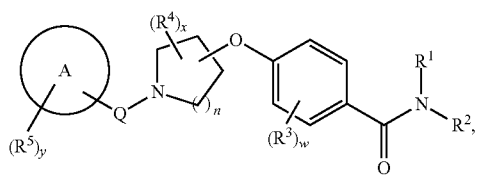

in which the variables are defined as described above with reference to formula (5-I).

In other embodiments of the compounds of structural formula (5-I) have structural formula (5-V):

(5-V)

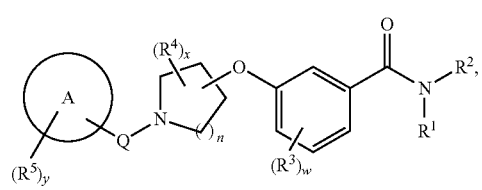

in which the variables are defined as described above with reference to formula (5-I).

In certain embodiments of the compounds of structural formula (5-I), n is 1 or 2. For example, in one embodiment of the compounds of structural formula (5-I), n is 2.

In one embodiment of the compounds of structural formula (5-I), the compound has structural formula (5-VI):

(5-VI)

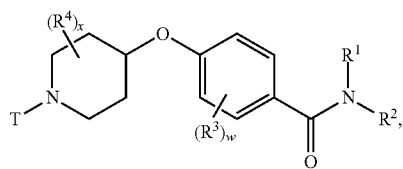

in which the variables are defined as described above with reference to formula (5-I).

In another embodiment, the compound has the structural formula (5-VII):

(5-VII)

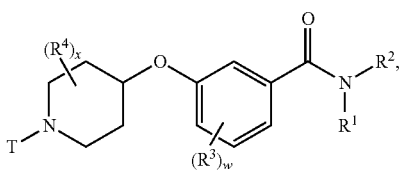

in which the variables are defined as described above with reference to formula (5-I).

For example, compounds of structural formula (5-I) can have structural formula (5-VIII):

(5-VIII)

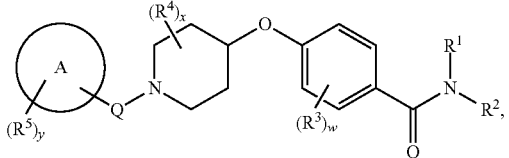

in which the variables are defined as described above with reference to formula (5-I).

In other embodiments of the compounds of structural formula (5-I), compounds of have structural formula (5-IX):

(5-IX)

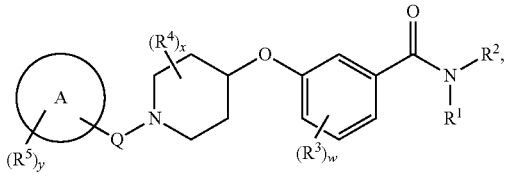

in which the variables are defined as described above with reference to formula (5-I).

According to structural formula (5-I), $R^1$ is —H and $R^2$ is -Hca. In certain embodiments of the compounds of structural formula (5-I), $R^2$ is substituted with ($C_0$-$C_3$ alkyl)-Het or ($C_0$-$C_3$ alkyl)-Ar. In one embodiment of the compounds of structural formula (5-I), $R^2$ is -(optionally-substituted azetidinyl), -(optionally-substituted pyrrolidinyl), -(optionally-substituted piperidinyl), or -(optionally-substituted azepanyl). For example, $R^2$ can be -(optionally substituted piperidinyl) or -(optionally substituted pyrrolidinyl).

In one embodiment of the compounds of structural formula (5-I), $R^1$ is —H and $R^2$ is -(optionally-substituted azetidin-3-yl), -(optionally substituted piperidin-4-yl), -(optionally substituted pyrrolidin-3-yl) or -(optionally-substituted azepan-4-yl). For example, in one embodiment of the compounds of structural formula (5-I), $R^2$ is -(optionally substituted piperidin-4-yl). In another embodiment of the compounds of structural formula (5-I), $R^2$ is -(optionally substituted pyrrolidin-3-yl).

In certain embodiments of the compounds of structural formula (5-I), the azetidinyl, pyrrolidinyl, piperidinyl and azepanyl $R^2$ moieties described above are substituted at their 1-positions. For example, in one embodiment of the compounds of structural formula (5-I), $R^2$ is substituted at its 1-position with ($C_0$-$C_3$ alkyl)-Ar or ($C_0$-$C_3$ alkyl)-Het. For example, in one embodiment of the compounds of structural formula (5-I), the azetidinyl, pyrrolidinyl, piperidinyl or azepanyl $R^2$ moiety is substituted at its 1-position with an optionally substituted benzyl or an optionally substituted phenyl. In another embodiment of the compounds of structural formula (5-I), the azetidinyl, pyrrolidinyl, piperidinyl or azepanyl $R^2$ moiety is substituted at its 1-position with a benzyl substituted with an electron withdrawing group; or with a pyridinylmethyl substituted with an electron withdrawing group. For example, the benzyl or pyridinylmethyl can be substituted with an electron withdrawing group selected from the group consisting of halo, cyano, —($C_1$-$C_4$ fluoroalkyl), —O—($C_1$-$C_4$ fluoroalkyl), acyl groups, carboxylate groups, carboxamide groups, cyano groups, sulfonate groups, and nitro groups. In other embodiments of the compounds of structural formula (5-I), the azetidinyl, pyrrolidinyl, piperidinyl or azepanyl R² moiety is substituted at its 1-position with an unsubstituted benzyl or an unsubstituted phenyl.

In other embodiments of the compounds of structural formula (5-I), the azetidinyl, pyrrolidinyl, piperidinyl or azepanyl R² moiety is substituted at its 1-position with an optionally substituted pyridinylmethyl, an optionally substituted furanylmethyl or an optionally substituted thienylmethyl. For example, the azetidinyl, pyrrolidinyl, piperidinyl or azepanyl R² moiety can be substituted with an unsubstituted pyridinylmethyl, an unsubstituted furanylmethyl, or an unsubstituted thienylmethyl.

In other embodiments of the compounds of structural formula (5-I), the azetidinyl, pyrrolidinyl, piperidinyl or azepanyl R² moiety is substituted at its 1-position with —CO—O—($C_0$-$C_6$ alkyl), —CO-Het, —CO—Ar or —$SO_2$—($C_0$-$C_6$ alkyl).

According to structural formula (5-I), the number of substituents on the central phenyl ring, w, is 0, 1, 2, 3 or 4. For example, in one embodiment of the compounds of structural formula (5-I), w is 0, 1 or 2. In another embodiment of the compounds of structural formula (5-I), w is 0. In other embodiments of the compounds of structural formula (5-I), w is at least 1, and at least one R³ is selected from the group consisting of halo, cyano, —($C_1$-$C_4$ fluoroalkyl), —O—($C_1$-$C_4$ fluoroalkyl), acyl, carboxylate, carboxamide and nitro.

In certain embodiments of the compounds of structural formula (5-I), R³ is selected from the group consisting of halo, cyano, —($C_1$-$C_4$ fluoroalkyl), —O—($C_1$-$C_4$ fluoroalkyl), acyl, carboxylate, carboxamide and nitro. R³ can be, for example, —Cl or —F. For example, compounds according to these embodiments can have structural formula (5-X):

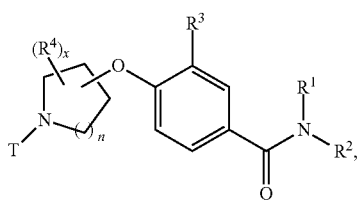

in which the remaining variables are defined as described above with reference to formula (5-I).

Certain other compounds according to these embodiments have structural formula (5-XI):

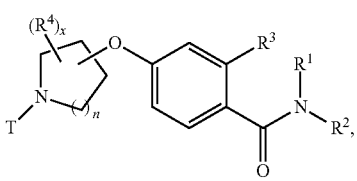

in which the remaining variables are defined as described above with reference to formula (5-I).

According to the compounds of structural formula (5-I), the number of substituents on the ethereal azacycloalkane ring, x, is 0, 1, 2, 3 or 4. In one embodiment of the compounds of structural formula (5-I), x is 0, 1, 2 or 3. For example, x can be 0, or can be 1 or 2.

Compounds according to one embodiment of the compounds of structural formula (5-I) have the structural formula (5-XII):

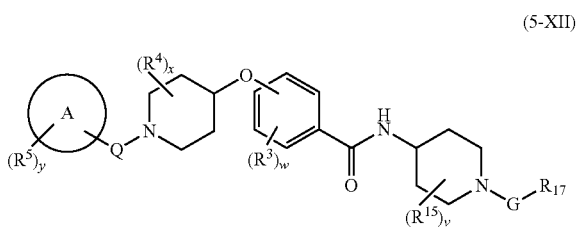

in which Q and G are each independently a bond, —$CH_2$—, —C(H)($R^{16}$)— or —C($R^{16}$)$_2$—; v is 0, 1, 2, 3 or 4; each $R^{15}$ is independently selected from —($C_1$-$C_6$ alkyl), —($C_1$-$C_6$ fluoroalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-N$R^8R^9$, —($C_0$-$C_6$ alkyl)-O$R^{10}$, —($C_0$-$C_6$ alkyl)-S(O)$_{0-2}R^{10}$, -halogen, —$NO_2$ and —CN, and two $R^{15}$ on the same carbon optionally combine to form oxo; $R^{17}$ is Het or Ar, and all other variables are defined as described above with reference to formula (5-I). In one embodiment of the compounds of structural formula (5-I), v is 0. In one embodiment of the compounds of structural formula (5-I), Q is a single bond. In another embodiment, G is —$CH_2$— or —CO—. For example, in one embodiment of the compounds of structural formula (5-I), Q is a single bond and G is —$CH_2$— or —CO—. The ethereal linkage of the piperidine to the benzamide can be at any aryl carbon. For example, the ether can be substituted at the 3-position or the 4-position of the benzamide. In one embodiment of the compounds of structural formula (5-I), two $R^{15}$s combine to form an oxo, which can be bound, for example, at a position alpha to the piperidine nitrogen. As described above, in certain embodiments of the compounds of structural formula (5-I), the ring system denoted by "A" is aryl or heteroaryl. In one embodiment of the compounds of structural formula (5-I), the ring system denoted by "A" is substituted with one or more electron-withdrawing groups. In another embodiment, $R^{17}$ is substituted with one or more electron-withdrawing groups.

Compounds according to certain embodiments have the structural formula (5-XIII):

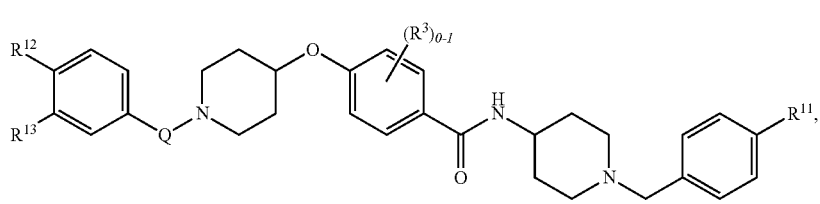

in which Q is —CH₂— or a single bond; R³ is halo; R¹¹ is H, halo, cyano, or a carboxylate; and R¹² and R¹³ are independently H, trifluoromethyl, trifluoromethoxy, halo or cyano.

Compounds according to other embodiments have structural formula (5-XIV):

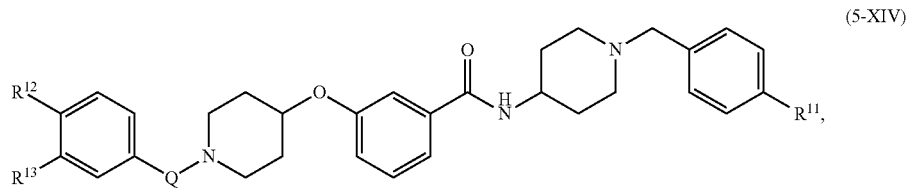

(5-XIV)

in which Q is —CH₂— or a single bond; R¹¹ is H, halo, cyano, or a carboxylate; and R¹² and R¹³ are independently H, trifluoromethyl, trifluoromethoxy, halo or cyano.

Compounds according to certain embodiments have the structural formula (5-XV):

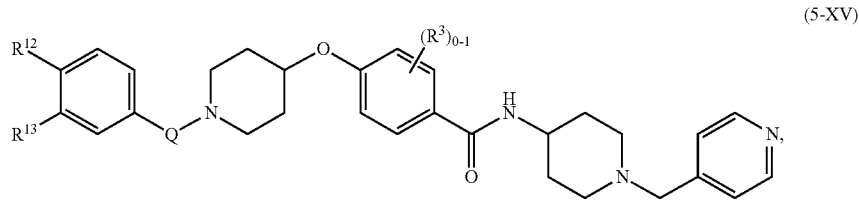

(5-XV)

in which Q is —CH₂— or a single bond; R³ is halo; and R¹² and R¹³ are independently H, trifluoromethyl, trifluoromethoxy, halo or cyano.

Compounds according to other embodiments have the structural formula (5-XVI):

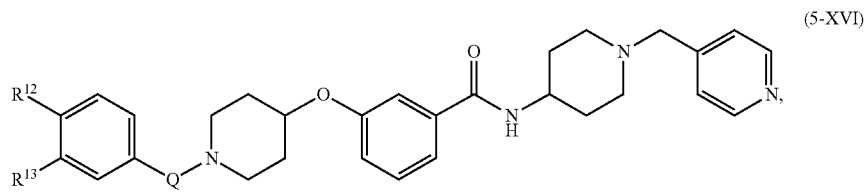

(5-XVI)

in which Q is —CH₂— or a single bond; and R¹² and R¹³ are independently H, trifluoromethyl, trifluoromethoxy, halo or cyano.

Another aspect of the disclosure provides a method for treating or ameliorating a disorder or condition related to oxidative stress, mitochondrial dysfunction, free radical damage and/or metabolic inefficiency in a subject, the method including administering to the subject an effective amount of a compound having structural formula (5-XVII):

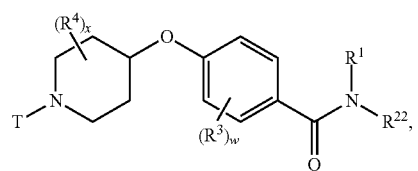

(5-XVII)

or a pharmaceutically acceptable salt, solvate, hydrate, or N-oxide thereof (or a solvate or hydrate thereof), wherein
$R^1$ and $R^{22}$, together with the nitrogen to which they are attached, form an optionally substituted monocyclic heterocycloalkyl; or
$R^1$ is H and $R^{22}$ is selected from —($C_2$-$C_4$ alkyl)-(morpholin-4-yl) and —($C_2$-$C_4$ alkyl)-NH—C(O)O—($C_1$-$C_6$ alkyl), and
all other variables are as described above with reference to structural formulae (5-I)-(5-XVI).

In one embodiment of the compounds according to structural formula (5-XVII), $R^1$ and $R^{22}$, together with the nitrogen to which they are attached, form an optionally substituted monocyclic heterocycloalkyl. The heterocycloalkyl can be, for example, piperidine or piperazine. In certain embodiments of the compounds of structural formula (5-XVII), the heterocycloalkyl is piperazine substituted at its 4-position with —C(O)O—($C_1$-$C_6$ alkyl), —($C_0$-$C_4$)-Het or —($C_0$-$C_4$)—Ar. For example, the piperazine may be substituted at its 4-position with —C(O)O-tBu, -optionally-substituted pyridinylmethyl, optionally-substituted phenyl or optionally-substituted pyridinyl.

In another embodiment of the compounds according to structural formula (5-XVII), $R^1$ is H and $R^{22}$ is selected from —($C_2$-$C_4$ alkyl)-(morpholin-4-yl) and —($C_2$-$C_4$ alkyl)-NH—C(O)O—($C_1$-$C_6$ alkyl). However, in certain embodiments, when w and x are zero, y is 1 and $R^5$ is methoxy substituted para to the benzyl methylene, $R^{22}$ is not —($C_2$-$C_4$ alkyl)-(morpholin-4-yl); and when w is 1, x and y are zero, and $R^3$ is methoxy substituted ortho to the ether oxygen, $R^{22}$ is not —($C_2$-$C_4$ alkyl)-(morpholin-4-yl). In certain embodiments, $R^{22}$ is —($C_2$-$C_4$ alkyl)-NH—C(O)O—($C_1$-$C_6$ alkyl). The $C_1$-$C_6$ alkyl can be, for example, a tert-butyl group.

Examples of compounds according to structural formulae (5-I) and (5-XVII) include those listed in Table 5. These compounds can be made, for example using a procedure analogous to those described in U.S. Patent Application Publications nos. 2009/0163511, 2009/0170829, 2009/0186894 and 2009/0275609, and in U.S. patent application Ser. No. 12/695,861, each of which is hereby incorporated by reference in its entirety.

TABLE 5

| Cpd | Name | Structure |
|---|---|---|
| 5-1 | N-(1-benzylpiperidin-4-yl)-3-chloro-4-(1-(4-methoxybenzyl)piperidin-4-yloxy)benzamide | 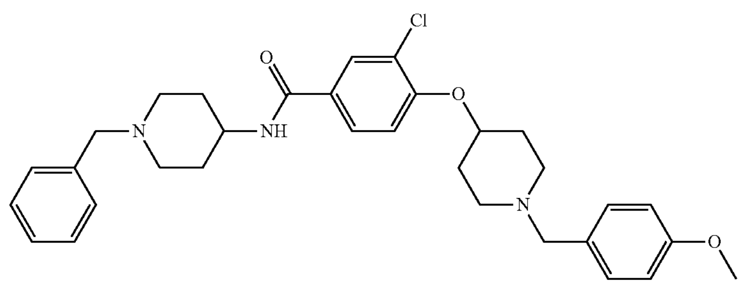 [SMILES: COc1ccc(CN2CCC(Oc3ccc(C(=O)NC4CCN(Cc5ccccc5)CC4)cc3Cl)CC2)cc1] |
| 5-2 | N-(1-benzylpiperidin-4-yl)-4-(1-benzylpiperidin-4-yloxy)-3-methoxybenzamide | 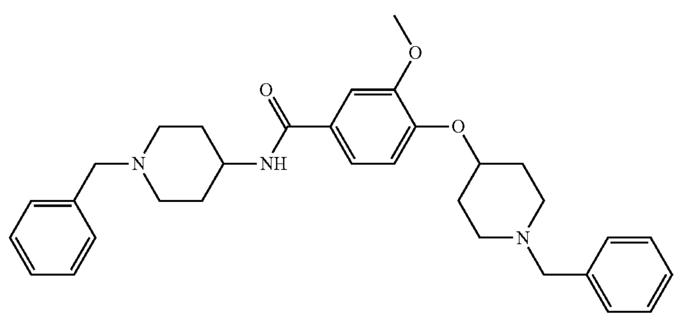 [SMILES: COc1cc(C(=O)NC2CCN(Cc3ccccc3)CC2)ccc1OC1CCN(Cc2ccccc2)CC1] |
| 5-3 | N-(1-benzylpiperidin-4-yl)-4-(1-(furan-2-ylmethyl)piperidin-4-yloxy)benzamide | 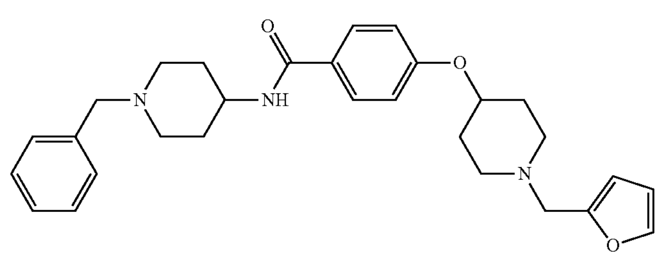 [SMILES: O=C(NC1CCN(Cc2ccccc2)CC1)c1ccc(OC2CCN(Cc3ccco3)CC2)cc1] |

TABLE 5-continued

| Cpd | Name | Structure |
|---|---|---|
| 5-4 | N-(1-benzylpiperidin-4-yl)-4-(1-((1-methyl-1H-imidazol-5-yl)methyl)piperidin-4-yloxy)benzamide | 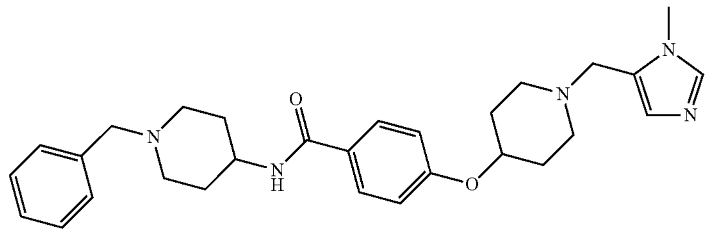 [SMILES: Cn1cncc1CN1CCC(Oc2ccc(C(=O)NC3CCN(Cc4ccccc4)CC3)cc2)CC1] |
| 5-5 | N-(1-benzylpiperidin-4-yl)-3-chloro-4-(1-((1-methyl-1H-imidazol-5-yl)methyl)piperidin-4-yloxy)benzamide | 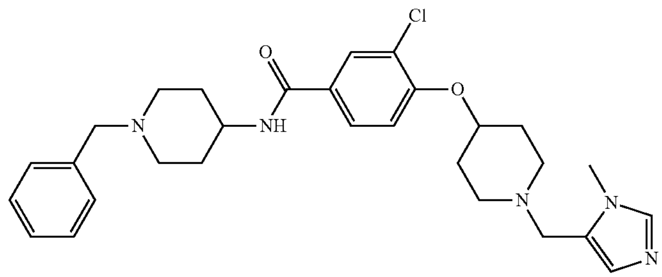 [SMILES: Cn1cncc1CN1CCC(Oc2ccc(C(=O)NC3CCN(Cc4ccccc4)CC3)cc2Cl)CC1] |
| 5-6 | N-(1-benzylpiperidin-4-yl)-3-chloro-4-(1-(pyridin-4-ylmethyl)piperidin-4-yloxy)benzamide | 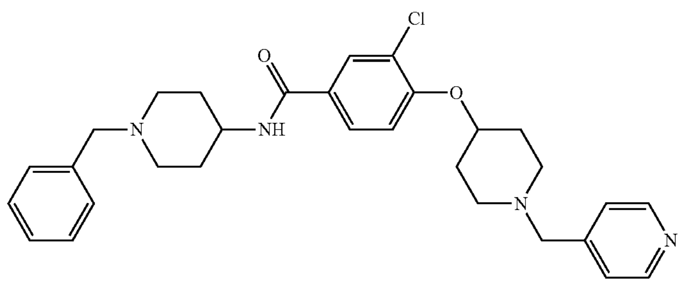 [SMILES: O=C(NC1CCN(Cc2ccccc2)CC1)c1ccc(OC2CCN(Cc3ccncc3)CC2)c(Cl)c1] |
| 5-7 | N-(1-benzylpiperidin-4-yl)-3-methoxy-4-(1-(3-phenylpropyl)piperidin-4-yloxy)benzamide | 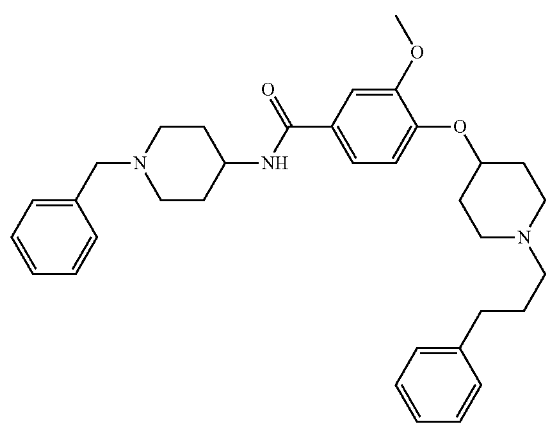 [SMILES: COc1cc(C(=O)NC2CCN(Cc3ccccc3)CC2)ccc1OC1CCN(CCCc2ccccc2)CC1] |
| 5-8 | N-(1-benzylpiperidin-4-yl)-3-methoxy-4-(1-(thiophen-2-yl)piperidin-4-yloxy)benzamide | 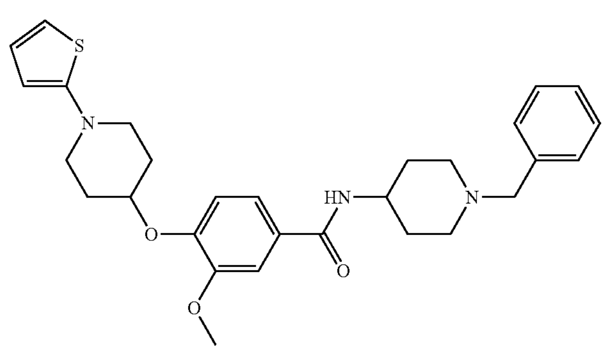 [SMILES: COc1cc(C(=O)NC2CCN(Cc3ccccc3)CC2)ccc1OC1CCN(c2cccs2)CC1] |

TABLE 5-continued

| Cpd | Name | Structure |
|---|---|---|
| 5-9 | N-(1-benzylpiperidin-4-yl)-3-methoxy-4-(1-(methylsulfonyl)piperidin-4-yloxy)benzamide | 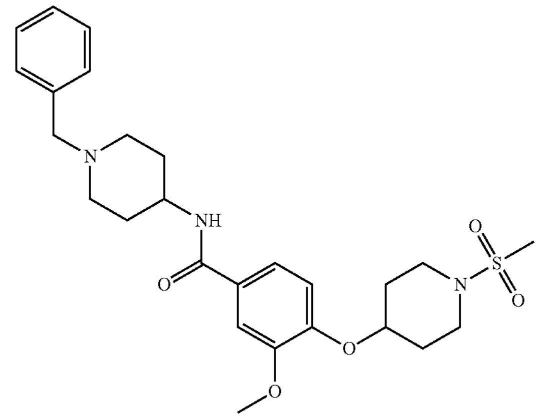 [SMILES: COc1cc(C(=O)NC2CCN(Cc3ccccc3)CC2)ccc1OC1CCN(S(C)(=O)=O)CC1] |
| 5-10 | N-(1-benzylpiperidin-4-yl)-3-chloro-4-(1-(thiophen-2-yl)piperidin-4-yloxy)benzamide | 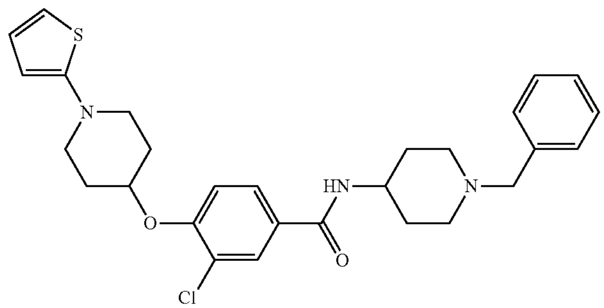 [SMILES: O=C(NC1CCN(Cc2ccccc2)CC1)c1ccc(OC2CCN(c3cccs3)CC2)c(Cl)c1] |
| 5-11 | N-(1-benzylpiperidin-4-yl)-3-chloro-4-(1-(furan-2-yl)piperidin-4-yloxy)benzamide | 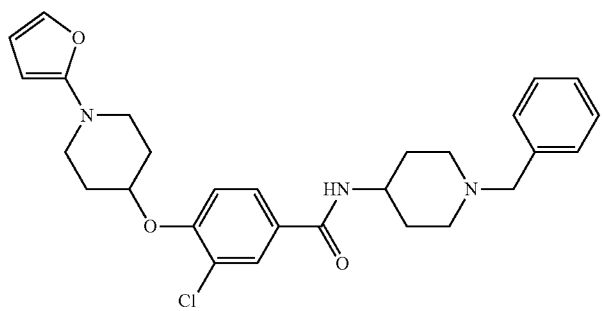 [SMILES: O=C(NC1CCN(Cc2ccccc2)CC1)c1ccc(OC2CCN(c3ccco3)CC2)c(Cl)c1] |
| 5-12 | N-(1-benzylpiperidin-4-yl)-3-methoxy-4-(1-(furan-2-yl)piperidin-4-yloxy)benzamide | 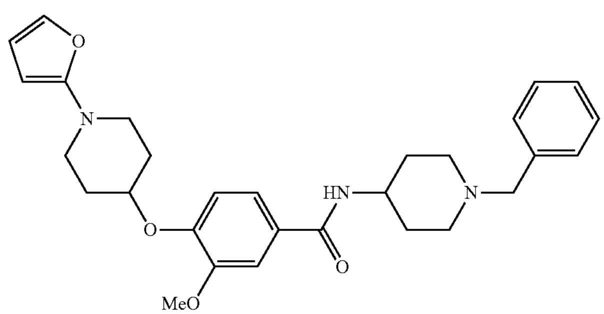 [SMILES: COc1cc(C(=O)NC2CCN(Cc3ccccc3)CC2)ccc1OC1CCN(c2ccco2)CC1] |
| 5-13 | N-(1-benzylpiperidin-4-yl)-3-(1-benzylpiperidin-4-yloxy)benzamide | 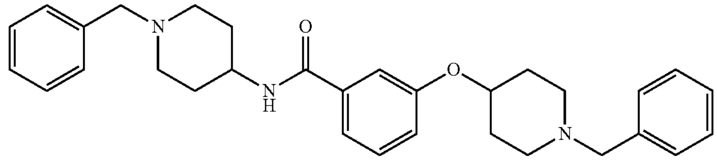 [SMILES: O=C(NC1CCN(Cc2ccccc2)CC1)c1cccc(OC2CCN(Cc3ccccc3)CC2)c1] |

TABLE 5-continued

| Cpd | Name | Structure |
|---|---|---|
| 5-14 | N-(1-benzylpiperidin-4-yl)-4-(1-benzylpiperidin-4-yloxy)-3-chlorobenzamide | 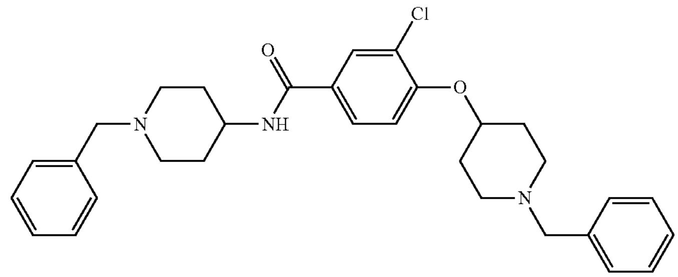 [SMILES: O=C(NC1CCN(Cc2ccccc2)CC1)c1ccc(OC2CCN(Cc3ccccc3)CC2)c(Cl)c1] |
| 5-15 | N-(1-benzylpiperidin-4-yl)-3-chloro-4-(1-((2,3-dihydrobenzo[b][1,4]dioxin-6-yl)methyl)piperidin-4-yloxy)benzamide | 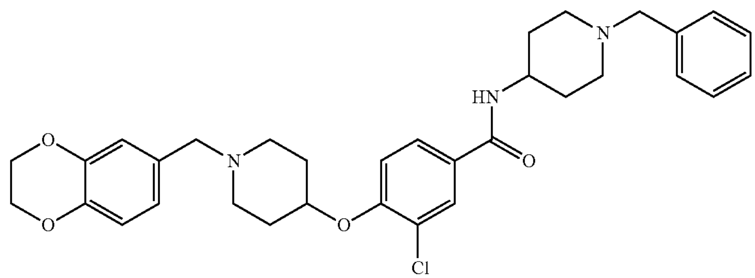 [SMILES: O=C(NC1CCN(Cc2ccccc2)CC1)c1ccc(OC2CCN(Cc3ccc4c(c3)OCCO4)CC2)c(Cl)c1] |
| 5-16 | N-(1-benzylpiperidin-4-yl)-4-(1-(4-tert-butylbenzyl)piperidin-4-yloxy)-3-chlorobenzamide | 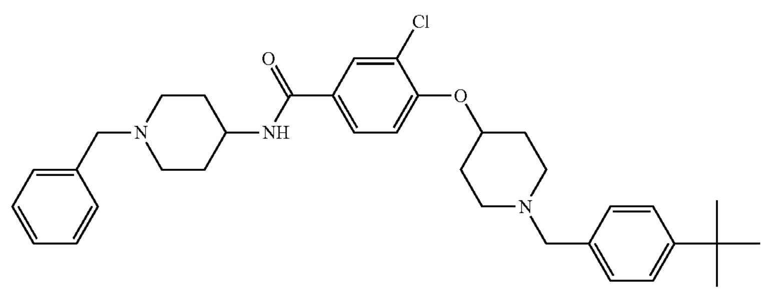 [SMILES: CC(C)(C)c1ccc(CN2CCC(Oc3ccc(C(=O)NC4CCN(Cc5ccccc5)CC4)cc3Cl)CC2)cc1] |
| 5-17 | N-(1-benzylpiperidin-4-yl)-3-chloro-4-(1-(4-(trifluoromethyl)phenyl)piperidin-4-yloxy)benzamide | 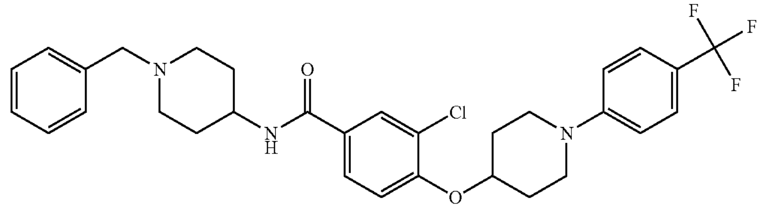 [SMILES: O=C(NC1CCN(Cc2ccccc2)CC1)c1ccc(OC2CCN(c3ccc(C(F)(F)F)cc3)CC2)c(Cl)c1] |
| 5-18 | N-(1-benzylpiperidin-4-yl)-3-chloro-4-(1-(4-(trifluoromethyl)benzoyl)piperidin-4-yloxy)benzamide | 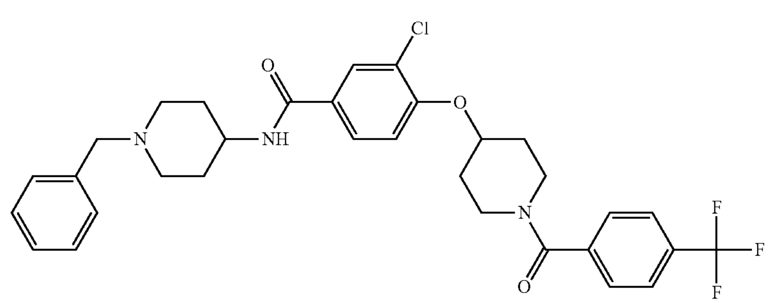 [SMILES: O=C(NC1CCN(Cc2ccccc2)CC1)c1ccc(OC2CCN(C(=O)c3ccc(C(F)(F)F)cc3)CC2)c(Cl)c1] |

TABLE 5-continued

| Cpd | Name | Structure |
|---|---|---|
| 5-19 | N-(1-benzylpiperidin-4-yl)-3-chloro-4-(1-(4-fluorobenzyl)piperidin-4-yloxy)benzamide | 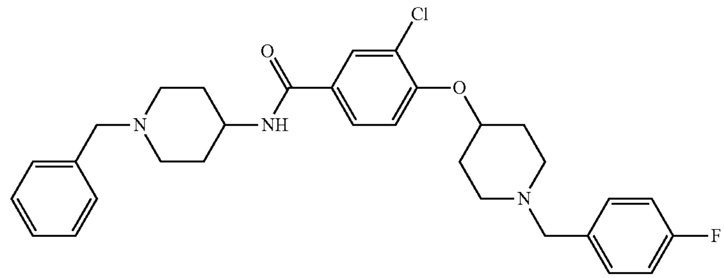 |
| 5-20 | N-(1-benzylpiperidin-4-yl)-3-fluoro-4-(1-(4-tert-butylbenzyl)piperidin-4-yloxy)benzamide | 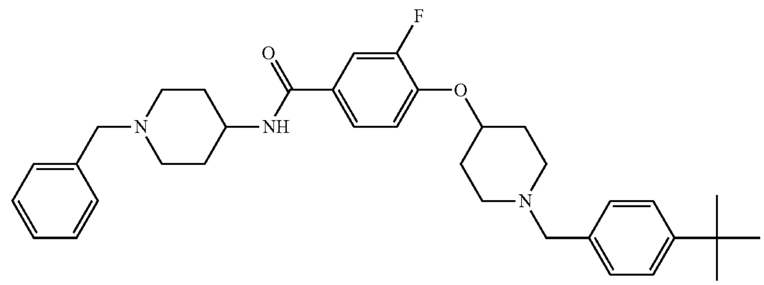 [SMILES: CC(C)(C)c1ccc(CN2CCC(Oc3ccc(C(=O)NC4CCN(Cc5ccccc5)CC4)cc3F)CC2)cc1] |
| 5-21 | N-(1-benzylpiperidin-4-yl)-3-fluoro-4-(1-(1-phenylethyl)piperidin-4-yloxy)benzamide | 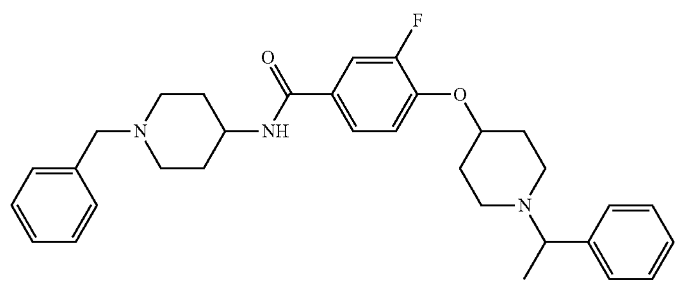 [SMILES: CC(c1ccccc1)N1CCC(Oc2ccc(C(=O)NC3CCN(Cc4ccccc4)CC3)cc2F)CC1] |
| 5-22 | N-(1-benzylpiperidin-4-yl)-3-chloro-4-(1-(4-fluorobenzoyl)piperidin-4-yloxy)benzamide | 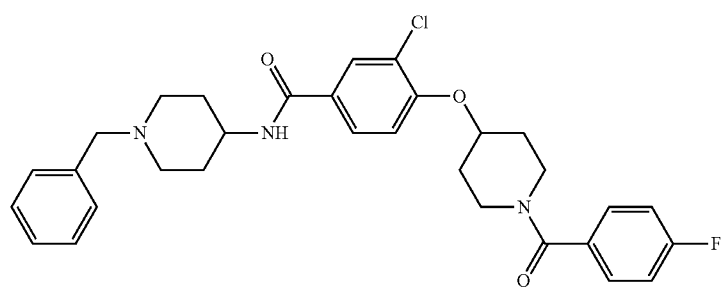 [SMILES: O=C(NC1CCN(Cc2ccccc2)CC1)c1ccc(OC2CCN(C(=O)c3ccc(F)cc3)CC2)c(Cl)c1] |
| 5-23 | N-(1-benzylpiperidin-4-yl)-3-fluoro-4-(1-(4-(trifluoromethyl)phenyl)piperidin-4-yloxy)benzamide | 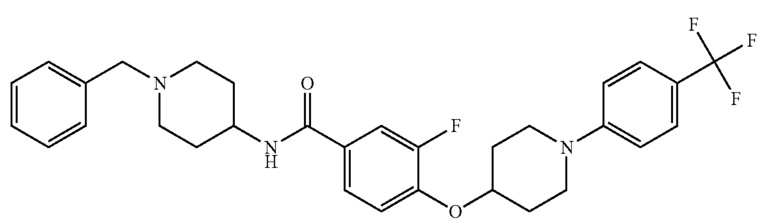 [SMILES: O=C(NC1CCN(Cc2ccccc2)CC1)c1ccc(OC2CCN(c3ccc(C(F)(F)F)cc3)CC2)c(F)c1] |
| 5-24 | N-(1-benzylpiperidin-4-yl)-3-chloro-4-(1-(2-(trifluoromethyl)benzyl)piperidin-4-yloxy)benzamide | 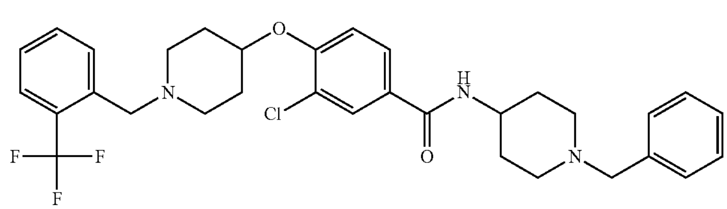 [SMILES: O=C(NC1CCN(Cc2ccccc2)CC1)c1ccc(OC2CCN(Cc3ccccc3C(F)(F)F)CC2)c(Cl)c1] |

TABLE 5-continued

| Cpd | Name | Structure |
|---|---|---|
| 5-25 | 3-fluoro-N-(1-phenylpiperidin-4-yl)-4-(1-(4-(trifluoromethyl)phenyl)piperidin-4-yloxy)benzamide | 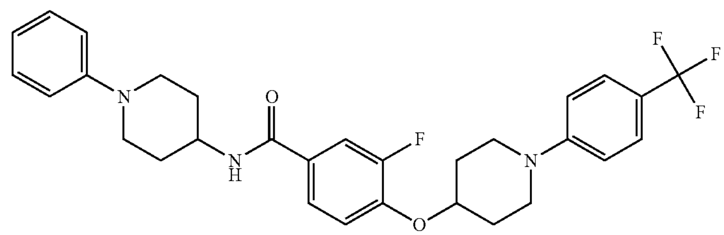 [SMILES: O=C(NC1CCN(c2ccccc2)CC1)c1ccc(OC2CCN(c3ccc(C(F)(F)F)cc3)CC2)c(F)c1] |
| 5-26 | tert-butyl 4-(3-fluoro-4-(1-(4-(trifluoromethyl)phenyl)piperidin-4-yloxy)benzamido)piperidine-1-carboxylate | 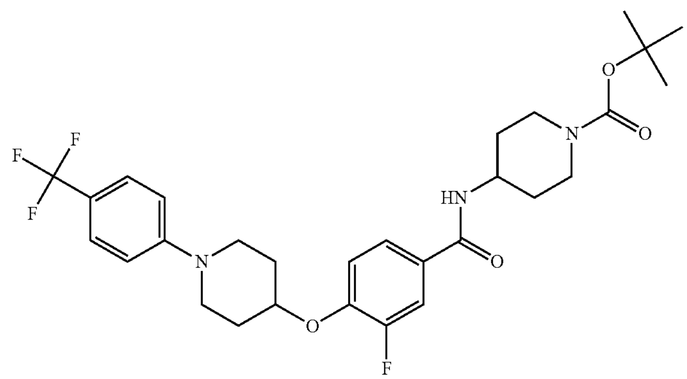 [SMILES: CC(C)(C)OC(=O)N1CCC(NC(=O)c2ccc(OC3CCN(c4ccc(C(F)(F)F)cc4)CC3)c(F)c2)CC1] |
| 5-27 | 3-fluoro-N-(1-(4-fluorobenzyl)piperidin-4-yl)-4-(1-(4-(trifluoromethyl)phenyl)piperidin-4-yloxy)benzamide | 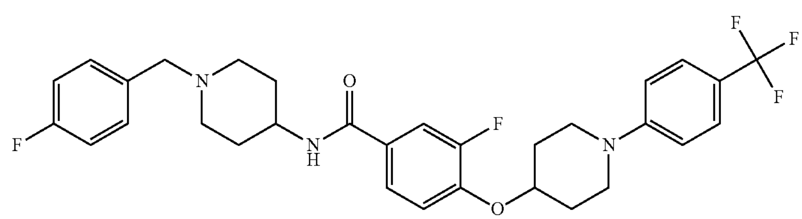 [SMILES: O=C(NC1CCN(Cc2ccc(F)cc2)CC1)c1ccc(OC2CCN(c3ccc(C(F)(F)F)cc3)CC2)c(F)c1] |
| 5-28 | 3-fluoro-N-(1-(pyridin-4-ylmethyl)piperidin-4-yl)-4-(1-(4-(trifluoromethyl)phenyl)piperidin-4-yloxy)benzamide | 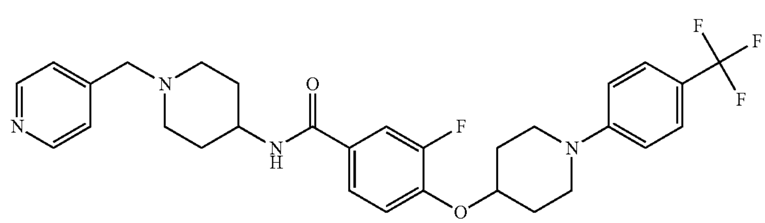 [SMILES: O=C(NC1CCN(Cc2ccncc2)CC1)c1ccc(OC2CCN(c3ccc(C(F)(F)F)cc3)CC2)c(F)c1] |
| 5-29 | 3-fluoro-N-(1-(pyridin-3-ylmethyl)piperidin-4-yl)-4-(1-(4-(trifluoromethyl)phenyl)piperidin-4-yloxy)benzamide | 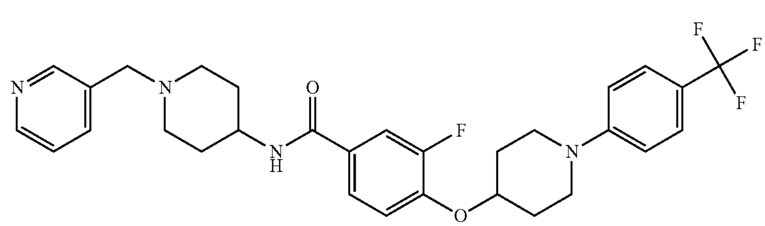 [SMILES: O=C(NC1CCN(Cc2cccnc2)CC1)c1ccc(OC2CCN(c3ccc(C(F)(F)F)cc3)CC2)c(F)c1] |

TABLE 5-continued

| Cpd | Name | Structure |
|---|---|---|
| 5-30 | 3-fluoro-N-(1-pivaloylpiperidin-4-yl)-4-(1-(4-(trifluoromethyl)phenyl)piperidin-4-yloxy)benzamide | 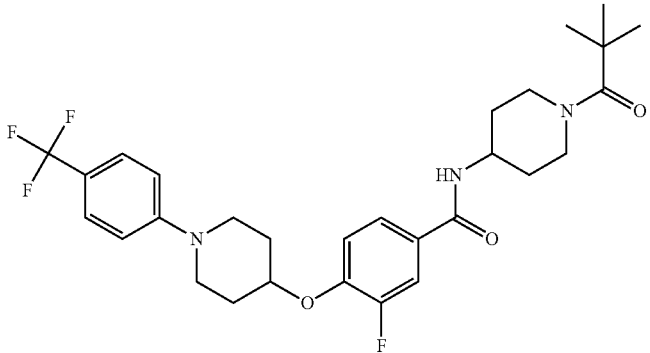 [SMILES: CC(C)(C)C(=O)N1CCC(NC(=O)c2ccc(OC3CCN(c4ccc(C(F)(F)F)cc4)CC3)c(F)c2)CC1] |
| 5-31 | 3-fluoro-N-(1-(4-fluorobenzoyl)piperidin-4-yl)-4-(1-(4-(trifluoromethyl)phenyl)piperidin-4-yloxy)benzamide | 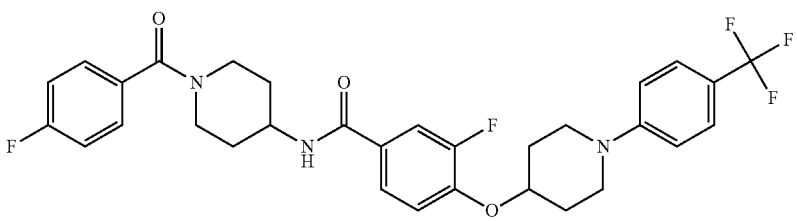 [SMILES: O=C(NC1CCN(C(=O)c2ccc(F)cc2)CC1)c1ccc(OC2CCN(c3ccc(C(F)(F)F)cc3)CC2)c(F)c1] |
| 5-32 | 3-fluoro-N-(1-(pyridin-2-ylmethyl)piperidin-4-yl)-4-(1-(4-(trifluoromethyl)phenyl)piperidin-4-yloxy)benzamide | 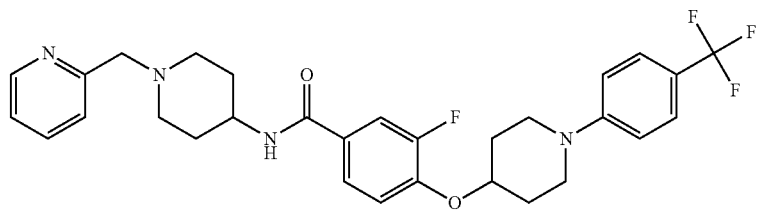 [SMILES: O=C(NC1CCN(Cc2ccccn2)CC1)c1ccc(OC2CCN(c3ccc(C(F)(F)F)cc3)CC2)c(F)c1] |
| 5-33 | methyl 4-((4-(3-fluoro-4-(1-(4-(trifluoromethyl)phenyl)piperidin-4-yloxy)benzamido)piperidin-1-yl)methyl)benzoate | 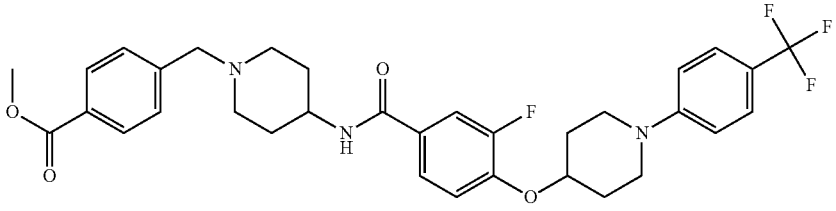 [SMILES: COC(=O)c1ccc(CN2CCC(NC(=O)c3ccc(OC4CCN(c5ccc(C(F)(F)F)cc5)CC4)c(F)c3)CC2)cc1] |
| 5-34 | 3-fluoro-N-(1-(isopropylsulfonyl)piperidin-4-yl)-4-(1-(4-(trifluoromethyl)phenyl)piperidin-4-yloxy)benzamide | 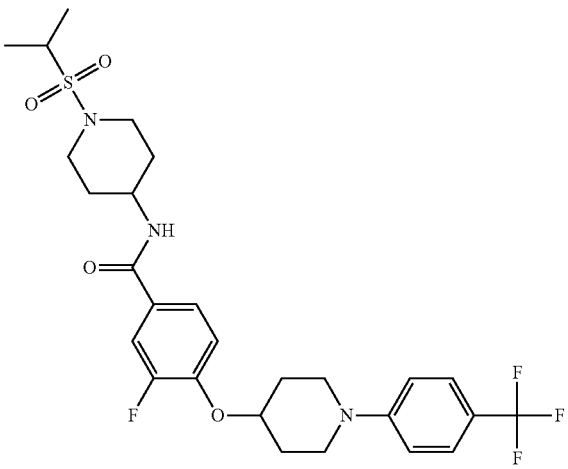 [SMILES: CC(C)S(=O)(=O)N1CCC(NC(=O)c2ccc(OC3CCN(c4ccc(C(F)(F)F)cc4)CC3)c(F)c2)CC1] |

TABLE 5-continued

| Cpd | Name | Structure |
|---|---|---|
| 5-35 | 4-((4-(3-fluoro-4-(1-(4-(trifluoromethyl)phenyl)piperidin-4-yloxy)benzamido)piperidin-1-yl)methyl)benzoic acid | 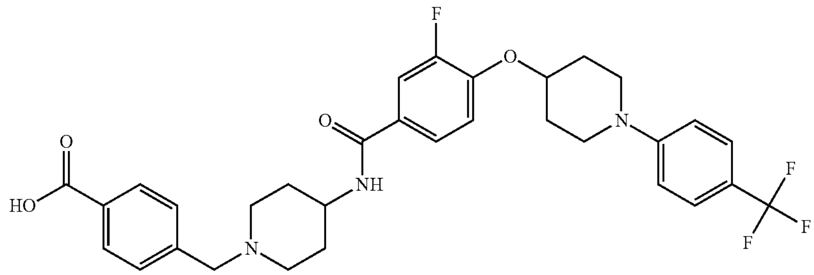 [SMILES: O=C(O)c1ccc(CN2CCC(NC(=O)c3ccc(OC4CCN(c5ccc(C(F)(F)F)cc5)CC4)c(F)c3)CC2)cc1] |
| 5-36 | 4-(1-(4-tert-butylbenzyl)piperidin-4-yloxy)-3-fluoro-N-(1-phenylpiperidin-4-yl)benzamide | 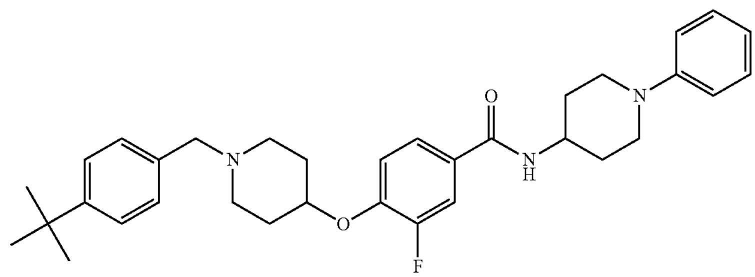 [SMILES: CC(C)(C)c1ccc(CN2CCC(Oc3ccc(C(=O)NC4CCN(c5ccccc5)CC4)cc3F)CC2)cc1] |
| 5-37 | N-(1-benzylpiperidin-4-yl)-3-fluoro-4-(1-(pyridin-4-ylmethyl)piperidin-4-yloxy)benzamide | 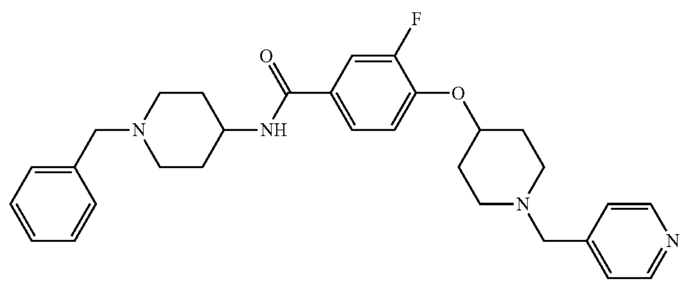 |
| 5-38 | N-(1-benzylpiperidin-4-yl)-3-fluoro-4-(1-(pyridin-3-ylmethyl)piperidin-4-yloxy)benzamide | 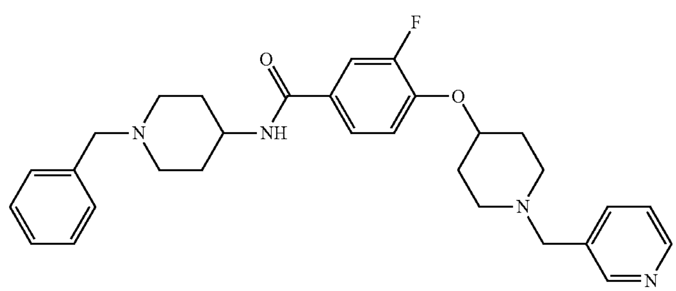 [SMILES: O=C(NC1CCN(Cc2ccccc2)CC1)c1ccc(OC2CCN(Cc3cccnc3)CC2)c(F)c1] |
| 5-39 | N-(1-benzylpiperidin-4-yl)-3-fluoro-4-(1-(pyridin-2-ylmethyl)piperidin-4-yloxy)benzamide | 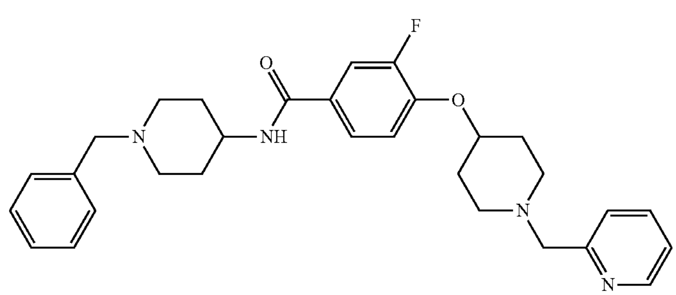 [SMILES: O=C(NC1CCN(Cc2ccccc2)CC1)c1ccc(OC2CCN(Cc3ccccn3)CC2)c(F)c1] |

TABLE 5-continued

| Cpd | Name | Structure |
|---|---|---|
| 5-40 | 3-fluoro-N-(1-isonicotinoylpiperidin-4-yl)-4-(1-(4-(trifluoromethyl)phenyl)piperidin-4-yloxy)benzamide | 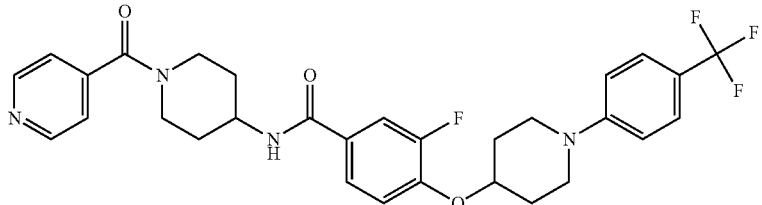 |
| 5-41 | N-(1-benzylpiperidin-4-yl)-4-(1-(4-cyanobenzyl)piperidin-4-yloxy)-3-fluorobenzamide | 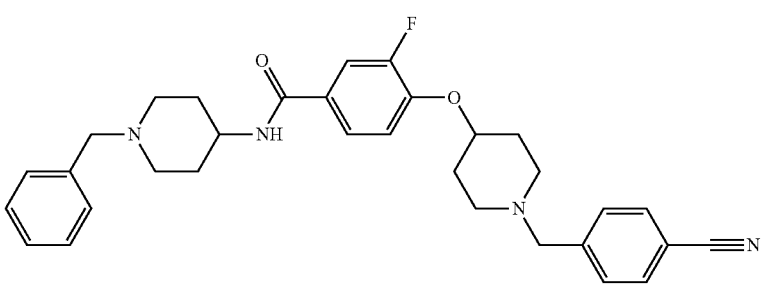 [SMILES: N#Cc1ccc(CN2CCC(Oc3ccc(C(=O)NC4CCN(Cc5ccccc5)CC4)cc3F)CC2)cc1] |
| 5-42 | N-(1-benzylpiperidin-4-yl)-3-fluoro-4-(1-(4-methylbenzyl)piperidin-4-yloxy)benzamide | 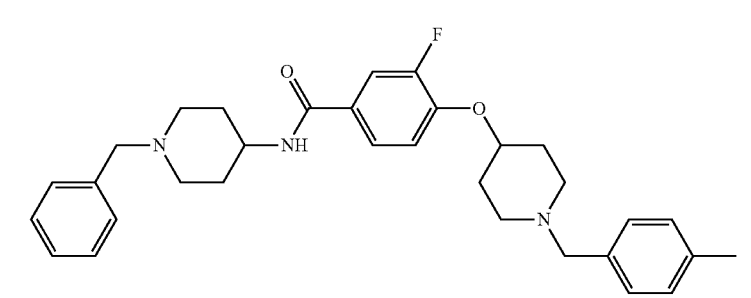 [SMILES: Cc1ccc(CN2CCC(Oc3ccc(C(=O)NC4CCN(Cc5ccccc5)CC4)cc3F)CC2)cc1] |
| 5-43 | N-(1-(4-cyanobenzyl)piperidin-4-yl)-3-fluoro-4-(1-(4-(trifluoromethyl)phenyl)piperidin-4-yloxy)benzamide | 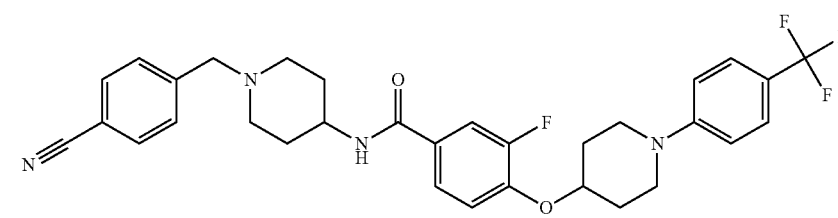 |
| 5-44 | 4-(1-(4-cyanophenyl)piperidin-4-yloxy)-3-fluoro-N-(1-(pyridin-4-ylmethyl)piperidin-4-yl)benzamide | 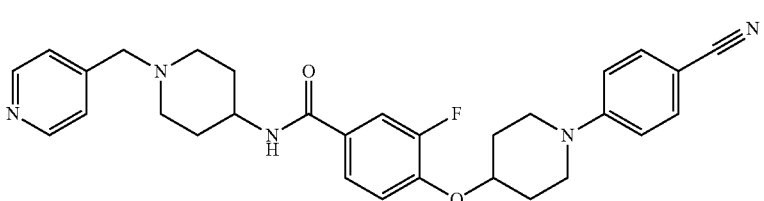 |
| 5-45 | N-(1-(4-cyanobenzyl)piperidin-4-yl)-4-(1-(4-cyanophenyl)piperidin-4-yloxy)-3-fluorobenzamide | 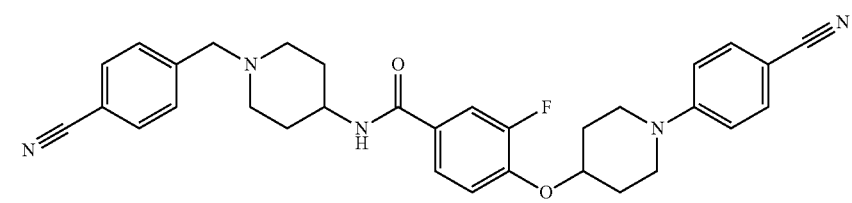 [SMILES: N#Cc1ccc(CN2CCC(NC(=O)c3ccc(OC4CCN(c5ccc(C#N)cc5)CC4)c(F)c3)CC2)cc1] |

TABLE 5-continued

| Cpd | Name | Structure |
|---|---|---|
| 5-46 | N-(1-benzylpiperidin-4-yl)-3-(1-(4-(trifluoromethyl)phenyl)piperidin-4-yloxy)benzamide | 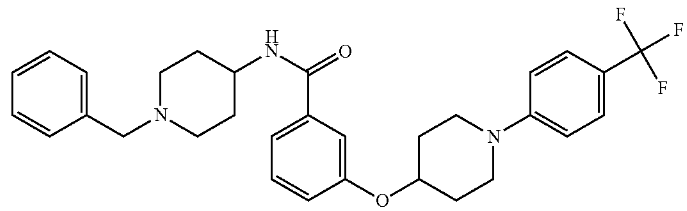 [SMILES: O=C(NC1CCN(Cc2ccccc2)CC1)c1cccc(OC2CCN(c3ccc(C(F)(F)F)cc3)CC2)c1] |
| 5-47 | N-(1-benzylpiperidin-4-yl)-2-chloro-4-(1-(4-(trifluoromethyl)phenyl)piperidin-4-yloxy)benzamide | 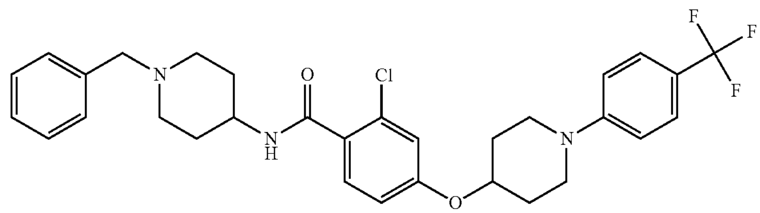 [SMILES: O=C(NC1CCN(Cc2ccccc2)CC1)c1ccc(OC2CCN(c3ccc(C(F)(F)F)cc3)CC2)cc1Cl] |
| 5-48 | N-(1-benzylpiperidin-4-yl)-3-(1-(4-cyanophenyl)piperidin-4-yloxy)benzamide | 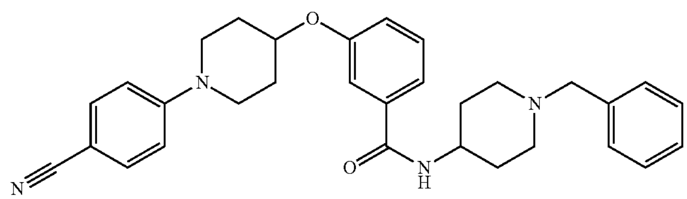 [SMILES: N#Cc1ccc(N2CCC(Oc3cccc(C(=O)NC4CCN(Cc5ccccc5)CC4)c3)CC2)cc1] |
| 5-49 | N-(1-benzylpiperidin-4-yl)-2-chloro-4-(1-(4-cyanophenyl)piperidin-4-yloxy)benzamide | 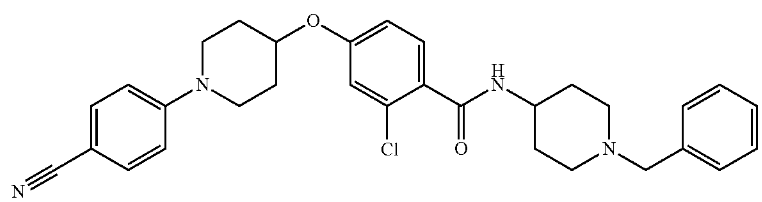 [SMILES: N#Cc1ccc(N2CCC(Oc3ccc(C(=O)NC4CCN(Cc5ccccc5)CC4)c(Cl)c3)CC2)cc1] |
| 5-50 | N-(1-benzylpiperidin-4-yl)-3-(1-(4-cyanobenzyl)piperidin-4-yloxy)benzamide | 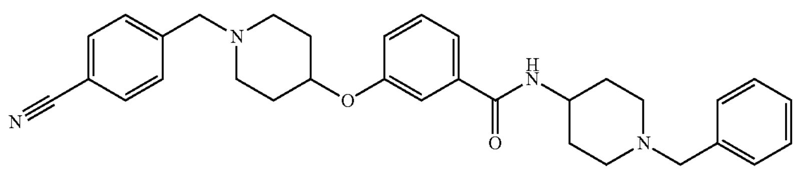 [SMILES: N#Cc1ccc(CN2CCC(Oc3cccc(C(=O)NC4CCN(Cc5ccccc5)CC4)c3)CC2)cc1] |
| 5-51 | N-(1-benzylpiperidin-4-yl)-2-chloro-4-(1-(4-cyanobenzyl)piperidin-4-yloxy)benzamide | 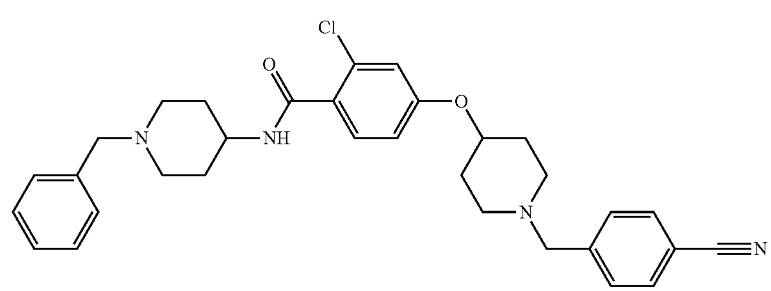 [SMILES: N#Cc1ccc(CN2CCC(Oc3ccc(C(=O)NC4CCN(Cc5ccccc5)CC4)c(Cl)c3)CC2)cc1] |
| 5-52 | N-(1-benzylpiperidin-4-yl)-3-(1-(4-(trifluoromethyl)benzyl)piperidin-4-yloxy)benzamide | 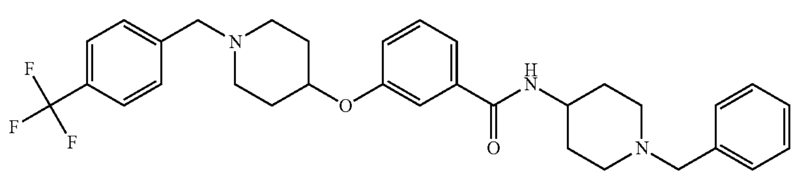 [SMILES: O=C(NC1CCN(Cc2ccccc2)CC1)c1cccc(OC2CCN(Cc3ccc(C(F)(F)F)cc3)CC2)c1] |

TABLE 5-continued

| Cpd | Name | Structure |
|---|---|---|
| 5-53 | N-(1-benzylpiperidin-4-yl)-3-(1-(pyridin-4-yl)piperidin-4-yloxy)benzamide | 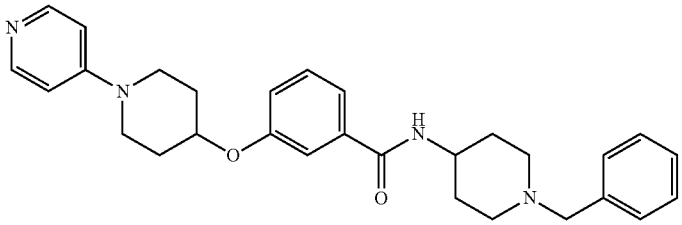 [SMILES: O=C(NC1CCN(Cc2ccccc2)CC1)c1cccc(OC2CCN(c3ccncc3)CC2)c1] |
| 5-54 | N-(1-benzylpiperidin-4-yl)-3-chloro-4-(1-(4-(trifluoromethoxy)benzyl)piperidin-4-yloxy)benzamide | 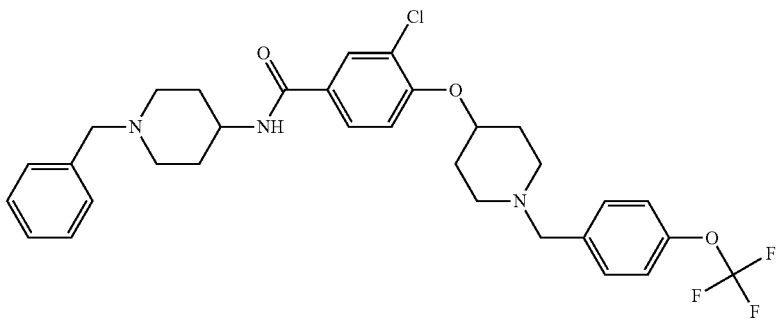 |
| 5-55 | N-(1-benzylpiperidin-4-yl)-3-fluoro-4-(1-(4-(trifluoromethyl)benzyl)piperidin-4-yloxy)benzamide | 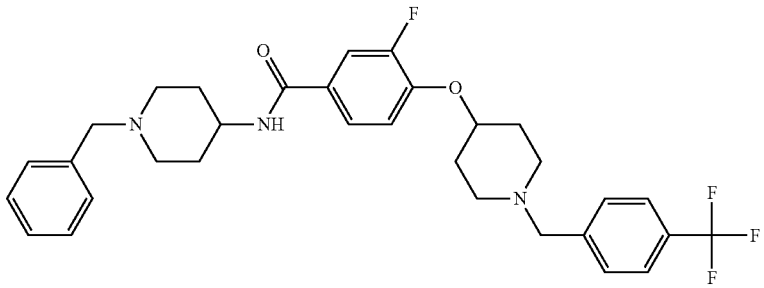 [SMILES: O=C(NC1CCN(Cc2ccccc2)CC1)c1ccc(OC2CCN(Cc3ccc(C(F)(F)F)cc3)CC2)c(F)c1] |
| 5-56 | N-(1-benzylpiperidin-4-yl)-3-chloro-4-(1-(4-(trifluoromethyl)benzyl)piperidin-4-yloxy)benzamide | 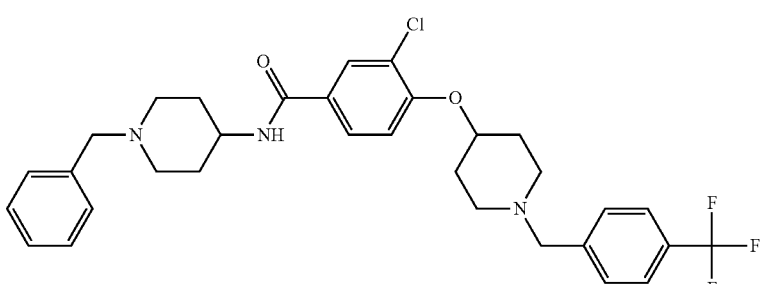 |
| 5-57 | N-(1-benzylpiperidin-4-yl)-3-fluoro-4-(1-(4-(trifluoromethoxy)benzyl)piperidin-4-yloxy)benzamide | 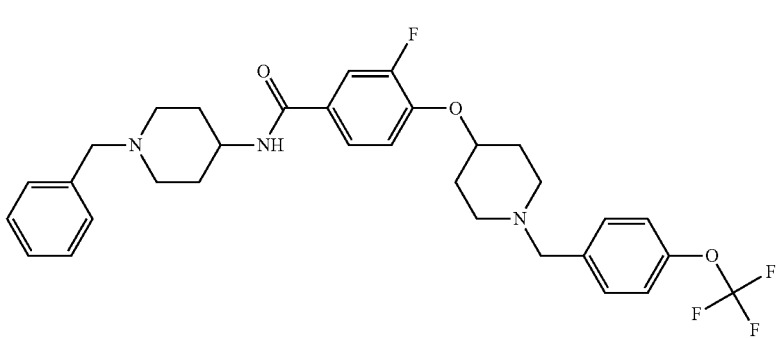 [SMILES: O=C(NC1CCN(Cc2ccccc2)CC1)c1ccc(OC2CCN(Cc3ccc(OC(F)(F)F)cc3)CC2)c(F)c1] |

TABLE 5-continued

| Cpd | Name | Structure |
|---|---|---|
| 5-58 | 3-chloro-N-(1-methylpiperidin-4-yl)-4-(1-(4-(trifluoromethyl)benzyl)piperidin-4-yloxy)benzamide | 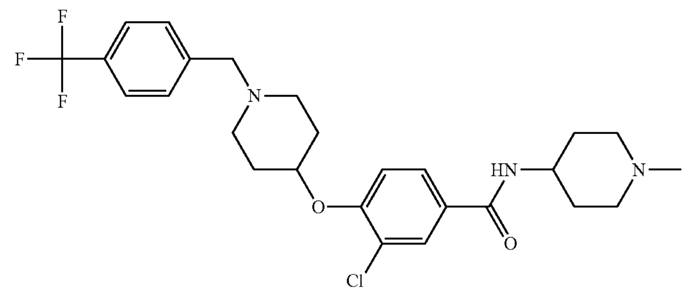 [SMILES: CN1CCC(NC(=O)c2ccc(OC3CCN(Cc4ccc(C(F)(F)F)cc4)CC3)c(Cl)c2)CC1] |
| 5-59 | N-(1-benzylpiperidin-4-yl)-3-fluoro-4-(1-(3-(trifluoromethyl)benzyl)piperidin-4-yloxy)benzamide | 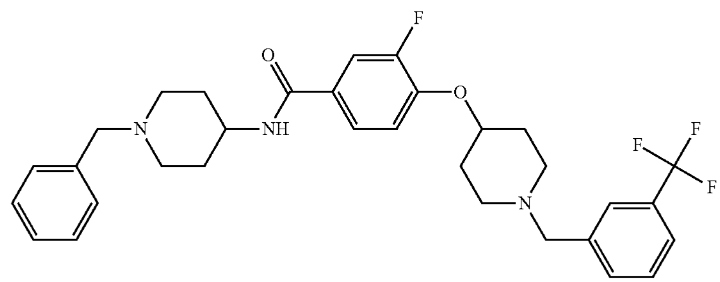 [SMILES: O=C(NC1CCN(Cc2ccccc2)CC1)c1ccc(OC2CCN(Cc3cccc(C(F)(F)F)c3)CC2)c(F)c1] |
| 5-60 | N-(1-benzylpiperidin-4-yl)-3-chloro-4-(1-(3-(trifluoromethyl)benzyl)piperidin-4-yloxy)benzamide | 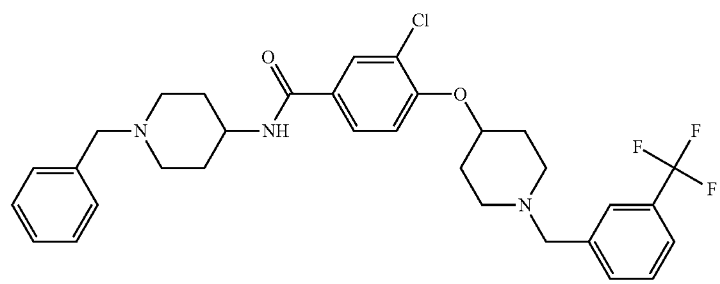 [SMILES: O=C(NC1CCN(Cc2ccccc2)CC1)c1ccc(OC2CCN(Cc3cccc(C(F)(F)F)c3)CC2)c(Cl)c1] |
| 5-61 | N-(1-benzylpiperidin-4-yl)-3-fluoro-4-(1-(4-fluorobenzyl)piperidin-4-yloxy)benzamide | 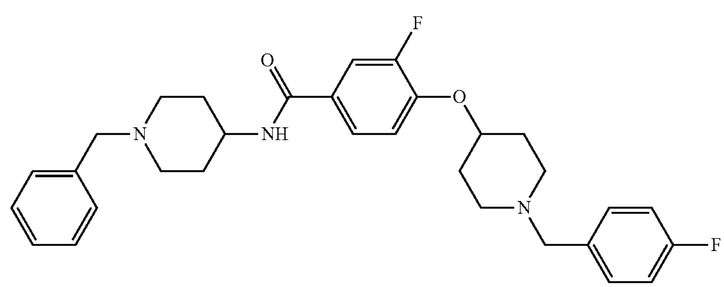 [SMILES: O=C(NC1CCN(Cc2ccccc2)CC1)c1ccc(OC2CCN(Cc3ccc(F)cc3)CC2)c(F)c1] |
| 5-62 | N-(1-benzylpiperidin-4-yl)-3,5-dichloro-4-(1-(3-(trifluoromethyl)benzyl)piperidin-4-yloxy)benzamide | 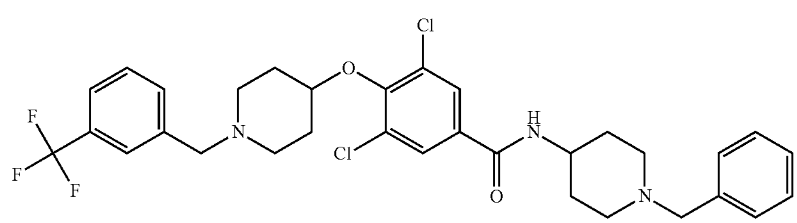 [SMILES: O=C(NC1CCN(Cc2ccccc2)CC1)c1cc(Cl)c(OC2CCN(Cc3cccc(C(F)(F)F)c3)CC2)c(Cl)c1] |
| 5-63 | N-(1-benzylpiperidin-4-yl)-4-(1-(4-(trifluoromethoxy)benzyl)piperidin-4-yloxy)benzamide | 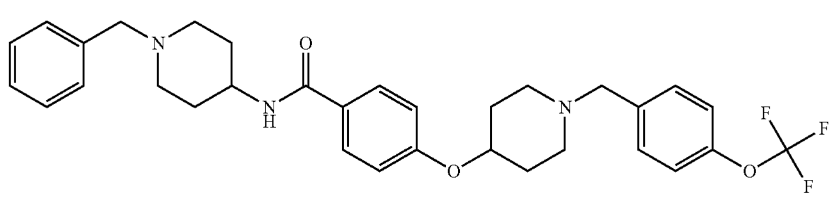 [SMILES: O=C(NC1CCN(Cc2ccccc2)CC1)c1ccc(OC2CCN(Cc3ccc(OC(F)(F)F)cc3)CC2)cc1] |

TABLE 5-continued

| Cpd | Name | Structure |
|---|---|---|
| 5-64 | N-(1-benzylpiperidin-4-yl)-4-(1-(4-chlorobenzyl)piperidin-4-yloxy)-3-fluorobenzamide | 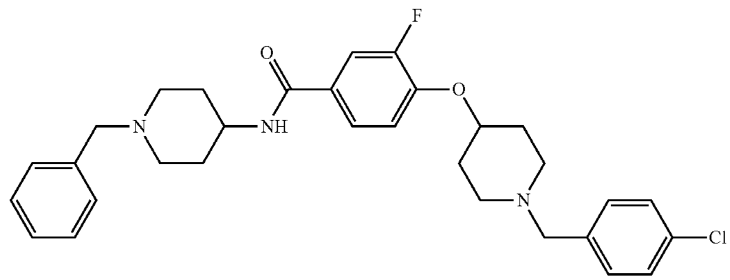 [SMILES: O=C(NC1CCN(Cc2ccccc2)CC1)c1ccc(OC2CCN(Cc3ccc(Cl)cc3)CC2)c(F)c1] |
| 5-65 | N-(1-benzylpiperidin-4-yl)-3-chloro-4-(1-(4-chlorobenzyl)piperidin-4-yloxy)benzamide | 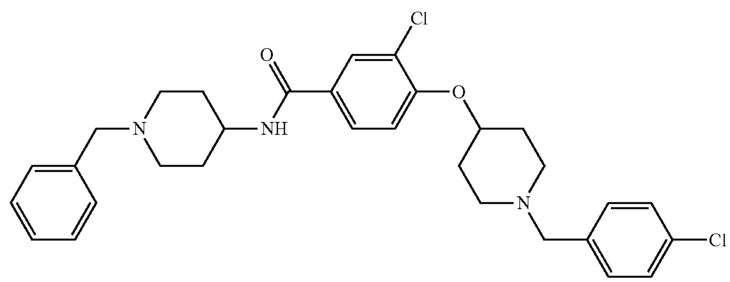 [SMILES: O=C(NC1CCN(Cc2ccccc2)CC1)c1ccc(OC2CCN(Cc3ccc(Cl)cc3)CC2)c(Cl)c1] |
| 5-66 | 3-chloro-4-(1-(4-chlorobenzyl)piperidin-4-yloxy)-N-(1-(4-fluorobenzyl)piperidin-4-yl)benzamide | 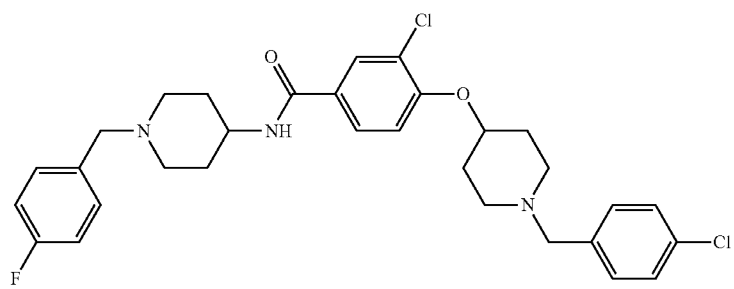 [SMILES: O=C(NC1CCN(Cc2ccc(F)cc2)CC1)c1ccc(OC2CCN(Cc3ccc(Cl)cc3)CC2)c(Cl)c1] |
| 5-67 | N-(1-benzylpiperidin-4-yl)-3-chloro-4-(1-(4-cyanobenzyl)piperidin-4-yloxy)benzamide | 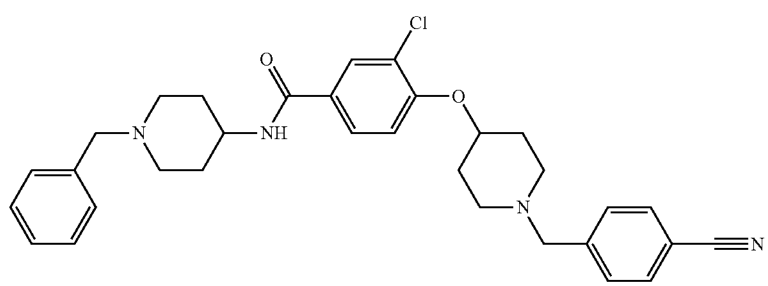 [SMILES: N#Cc1ccc(CN2CCC(Oc3ccc(C(=O)NC4CCN(Cc5ccccc5)CC4)cc3Cl)CC2)cc1] |
| 5-68 | 3-chloro-N-(1-(4-fluorobenzyl)piperidin-4-yl)-4-(1-(4-methylbenzyl)piperidin-4-yloxy)benzamide | 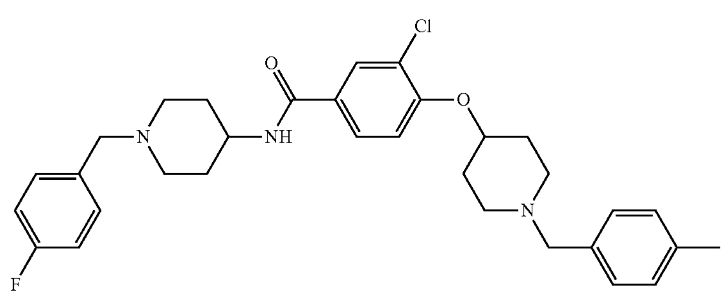 [SMILES: Cc1ccc(CN2CCC(Oc3ccc(C(=O)NC4CCN(Cc5ccc(F)cc5)CC4)cc3Cl)CC2)cc1] |

TABLE 5-continued

| Cpd | Name | Structure |
|---|---|---|
| 5-69 | N-(1-benzylpiperidin-4-yl)-4-(1-(3,4-difluorobenzyl)piperidin-4-yloxy)-3-fluorobenzamide | 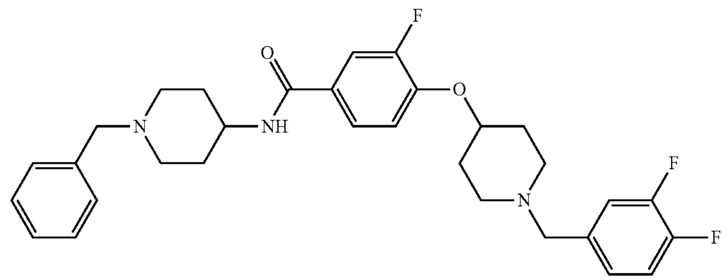 [SMILES: O=C(NC1CCN(Cc2ccccc2)CC1)c1ccc(OC2CCN(Cc3ccc(F)c(F)c3)CC2)c(F)c1] |
| 5-70 | N-(1-(4-chlorobenzyl)piperidin-4-yl)-4-(1-(4-cyanobenzyl)piperidin-4-yloxy)-3-fluorobenzamide | 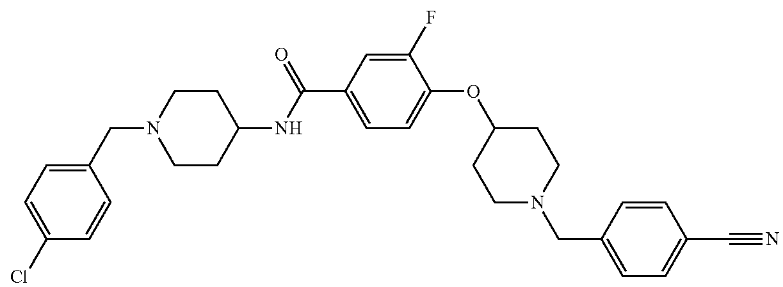 [SMILES: N#Cc1ccc(CN2CCC(Oc3ccc(C(=O)NC4CCN(Cc5ccc(Cl)cc5)CC4)cc3F)CC2)cc1] |
| 5-71 | N-(1-(4-chlorobenzyl)piperidin-4-yl)-4-(1-(3,4-difluorobenzyl)piperidin-4-yloxy)-3-fluorobenzamide | 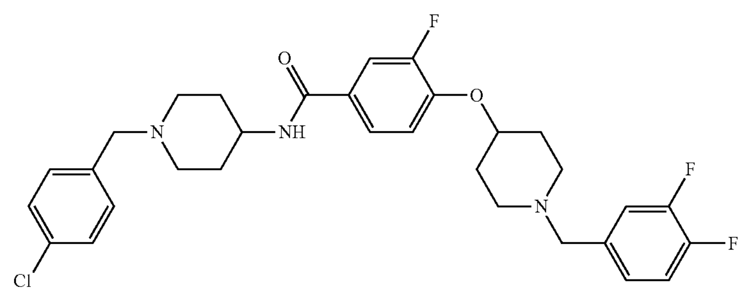 [SMILES: O=C(NC1CCN(Cc2ccc(Cl)cc2)CC1)c1ccc(OC2CCN(Cc3ccc(F)c(F)c3)CC2)c(F)c1] |
| 5-72 | N-(1-(4-chlorobenzyl)piperidin-4-yl)-4-(1-(4-chlorobenzyl)piperidin-4-yloxy)-3-fluorobenzamide | 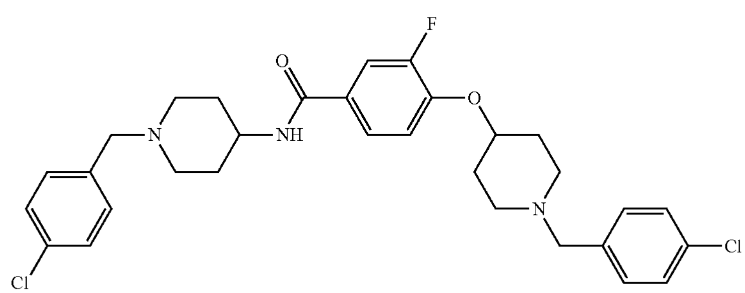 [SMILES: O=C(NC1CCN(Cc2ccc(Cl)cc2)CC1)c1ccc(OC2CCN(Cc3ccc(Cl)cc3)CC2)c(F)c1] |
| 5-73 | N-(1-(4-chlorobenzyl)piperidin-4-yl)-3-fluoro-4-(1-(4-methylbenzyl)piperidin-4-yloxy)benzamide | 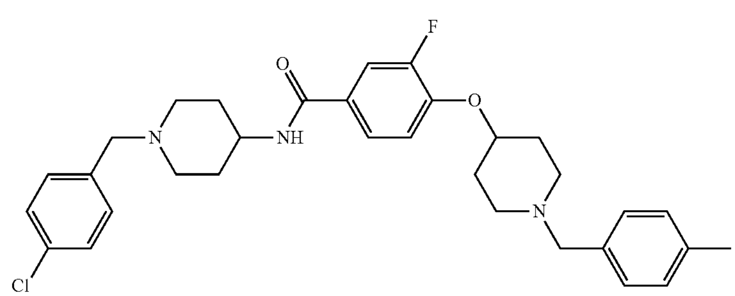 [SMILES: Cc1ccc(CN2CCC(Oc3ccc(C(=O)NC4CCN(Cc5ccc(Cl)cc5)CC4)cc3F)CC2)cc1] |

TABLE 5-continued

| Cpd | Name | Structure |
|---|---|---|
| 5-74 | N-(1-benzylpiperidin-4-yl)-3-chloro-4-(1-(3,4-difluorobenzyl)piperidin-4-yloxy)benzamide | 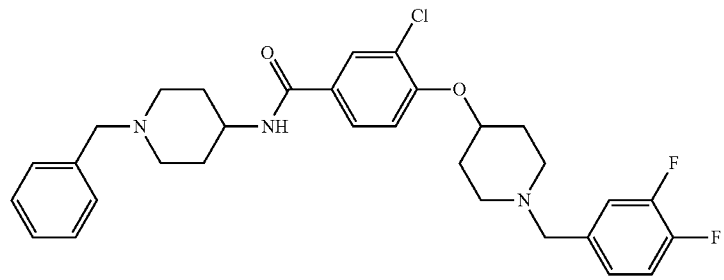 [SMILES: O=C(NC1CCN(Cc2ccccc2)CC1)c1ccc(OC2CCN(Cc3ccc(F)c(F)c3)CC2)c(Cl)c1] |
| 5-75 | N-(1-benzylpiperidin-4-yl)-3,5-dichloro-4-(1-(4-chlorobenzyl)piperidin-4-yloxy)benzamide | 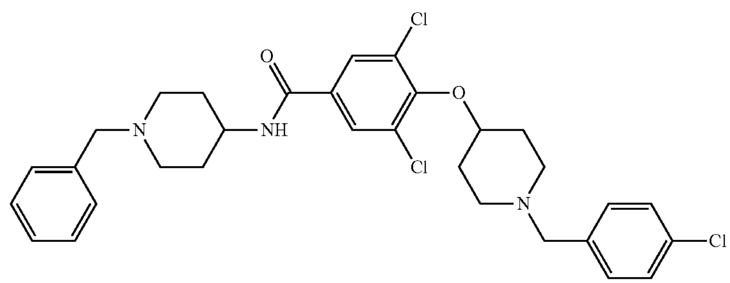 [SMILES: O=C(NC1CCN(Cc2ccccc2)CC1)c1cc(Cl)c(OC2CCN(Cc3ccc(Cl)cc3)CC2)c(Cl)c1] |
| 5-76 | N-(1-benzylpiperidin-4-yl)-3,5-dichloro-4-(1-(3,4-difluorobenzyl)piperidin-4-yloxy)benzamide | 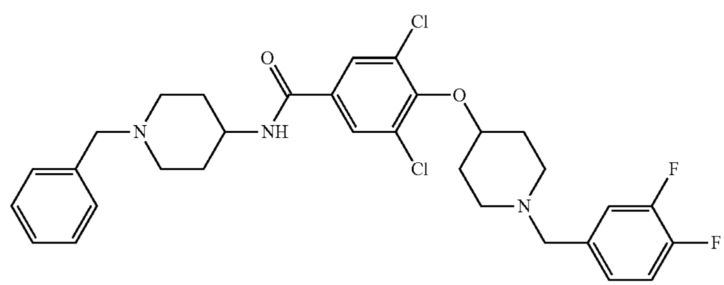 [SMILES: O=C(NC1CCN(Cc2ccccc2)CC1)c1cc(Cl)c(OC2CCN(Cc3ccc(F)c(F)c3)CC2)c(Cl)c1] |
| 5-77 | N-(1-benzylpiperidin-4-yl)-3,5-dichloro-4-(1-(4-cyanobenzyl)piperidin-4-yloxy)benzamide | 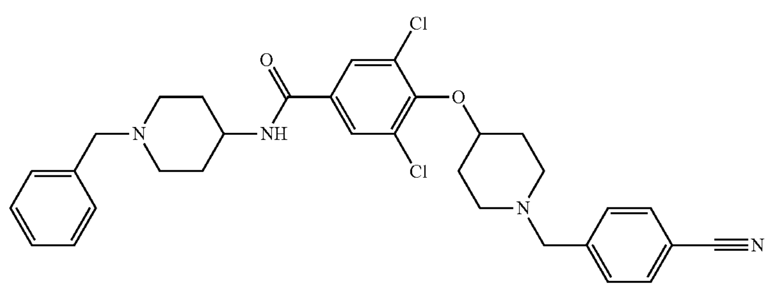 [SMILES: N#Cc1ccc(CN2CCC(Oc3c(Cl)cc(C(=O)NC4CCN(Cc5ccccc5)CC4)cc3Cl)CC2)cc1] |
| 5-78 | tert-butyl 4-(4-(1-(4-cyanobenzyl)piperidin-4-yloxy)benzamido)piperidine-1-carboxylate | 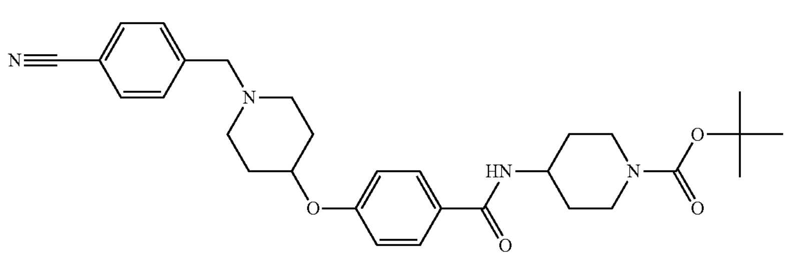 [SMILES: CC(C)(C)OC(=O)N1CCC(NC(=O)c2ccc(OC3CCN(Cc4ccc(C#N)cc4)CC3)cc2)CC1] |

TABLE 5-continued

| Cpd | Name | Structure |
|---|---|---|
| 5-79 | 4-(1-(4-cyanobenzyl)piperidin-4-yloxy)-N-(piperidin-4-yl)benzamide | 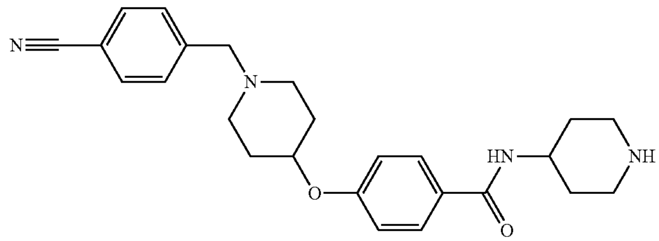 [SMILES: N#Cc1ccc(CN2CCC(Oc3ccc(C(=O)NC4CCNCC4)cc3)CC2)cc1] |
| 5-80 | N-(1-(4-chlorobenzyl)piperidin-4-yl)-4-(1-(3,4-dichlorobenzyl)piperidin-4-yloxy)-3-fluorobenzamide | 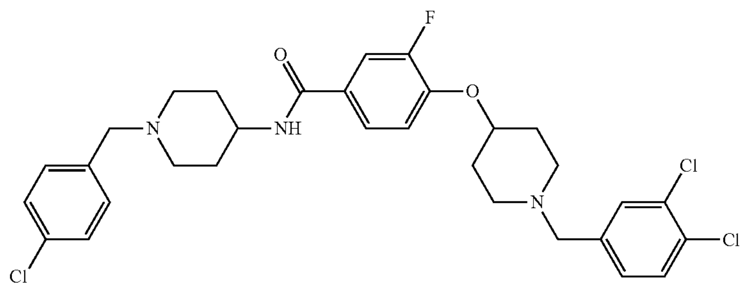 [SMILES: O=C(NC1CCN(Cc2ccc(Cl)cc2)CC1)c1ccc(OC2CCN(Cc3ccc(Cl)c(Cl)c3)CC2)c(F)c1] |
| 5-81 | N-(1-(4-chlorobenzyl)piperidin-4-yl)-4-(1-(4-cyanophenyl)piperidin-4-yloxy)-3-fluorobenzamide | 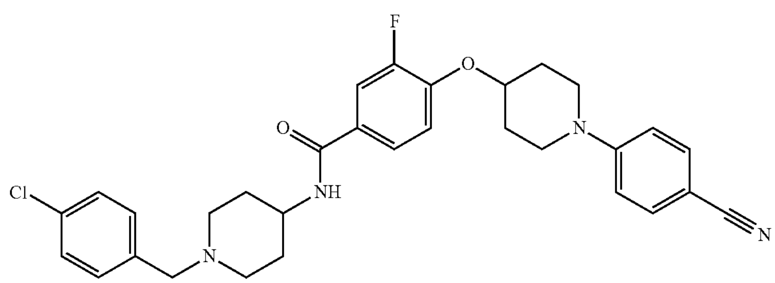 [SMILES: N#Cc1ccc(N2CCC(Oc3ccc(C(=O)NC4CCN(Cc5ccc(Cl)cc5)CC4)cc3F)CC2)cc1] |
| 5-82 | N-(1-benzylpiperidin-4-yl)-4-(1-(3,4-dichlorobenzyl)piperidin-4-yloxy)-3-fluorobenzamide | 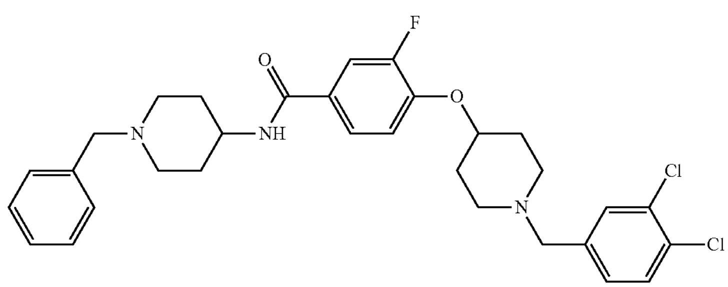 [SMILES: O=C(NC1CCN(Cc2ccccc2)CC1)c1ccc(OC2CCN(Cc3ccc(Cl)c(Cl)c3)CC2)c(F)c1] |
| 5-83 | 4-(1-(4-cyanobenzyl)piperidin-4-yloxy)-N-(1-(pyridin-4-ylmethyl)piperidin-4-yl)benzamide | 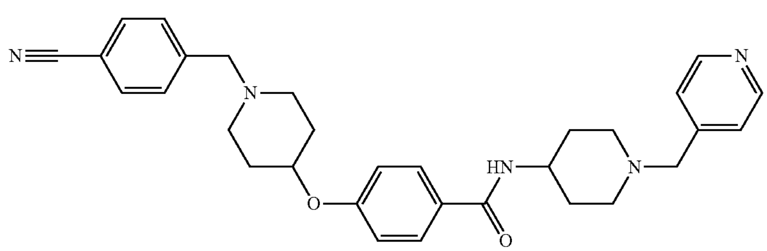 [SMILES: N#Cc1ccc(CN2CCC(Oc3ccc(C(=O)NC4CCN(Cc5ccncc5)CC4)cc3)CC2)cc1] |

TABLE 5-continued

| Cpd | Name | Structure |
|---|---|---|
| 5-84 | N-(1-benzylpiperidin-4-yl)-3-chloro-4-(1-(3,4-dichlorobenzyl)piperidin-4-yloxy)benzamide | 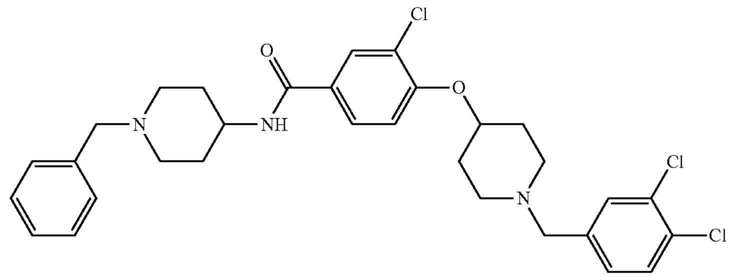 [SMILES: O=C(NC1CCN(Cc2ccccc2)CC1)c1ccc(OC2CCN(Cc3ccc(Cl)c(Cl)c3)CC2)c(Cl)c1] |
| 5-85 | 4-(1-(4-cyanobenzyl)piperidin-4-yloxy)-N-(1-(pyridin-2-ylmethyl)piperidin-4-yl)benzamide | 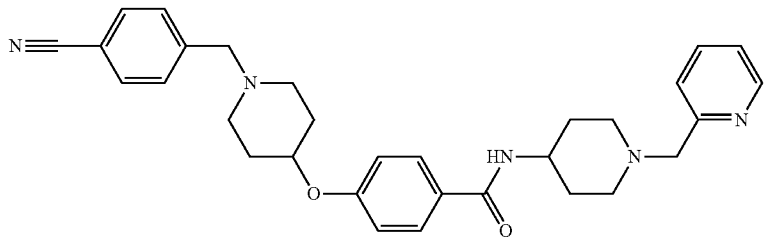 [SMILES: N#Cc1ccc(CN2CCC(Oc3ccc(C(=O)NC4CCN(Cc5ccccn5)CC4)cc3)CC2)cc1] |
| 5-86 | N-(1-benzylpiperidin-4-yl)-3-(1-(pyridin-2-yl)piperidin-4-yloxy)benzamide | 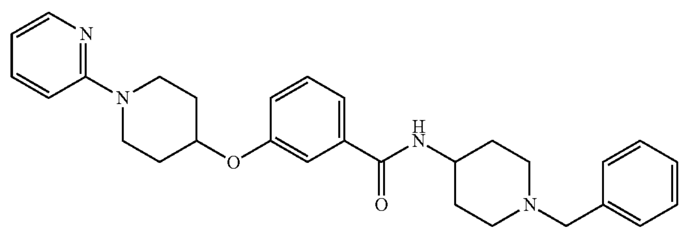 [SMILES: O=C(NC1CCN(Cc2ccccc2)CC1)c1cccc(OC2CCN(c3ccccn3)CC2)c1] |
| 5-87 | N-(1-(pyridin-4-ylmethyl)piperidin-4-yl)-3-(1-(4-(trifluoromethyl)phenyl)piperidin-4-yloxy)benzamide | 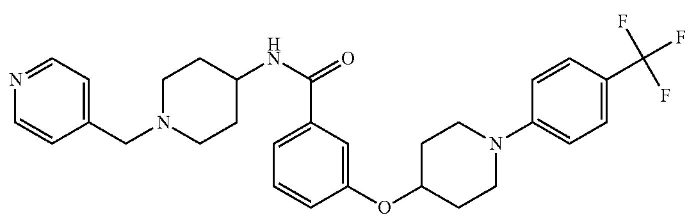 [SMILES: O=C(NC1CCN(Cc2ccncc2)CC1)c1cccc(OC2CCN(c3ccc(C(F)(F)F)cc3)CC2)c1] |
| 5-88 | N-(1-(pyridin-4-ylmethyl)piperidin-4-yl)-3-(1-(4-cyanophenyl)piperidin-4-yloxy)benzamide | 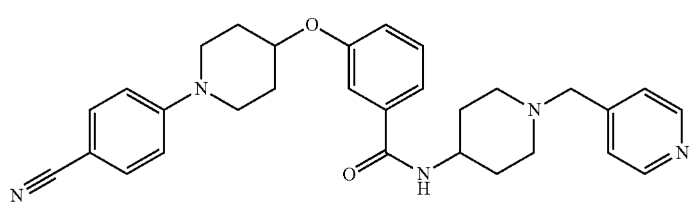 [SMILES: N#Cc1ccc(N2CCC(Oc3cccc(C(=O)NC4CCN(Cc5ccncc5)CC4)c3)CC2)cc1] |
| 5-89 | N-(1-benzylpiperidin-4-yl)-3-(1-(3-cyanobenzyl)piperidin-4-yloxy)benzamide | 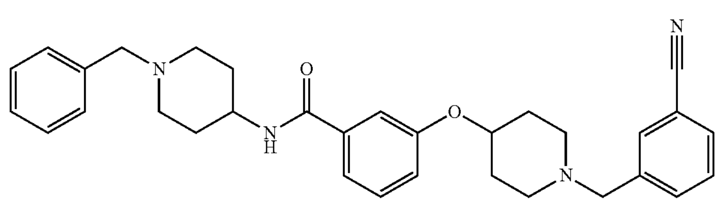 [SMILES: N#Cc1cccc(CN2CCC(Oc3cccc(C(=O)NC4CCN(Cc5ccccc5)CC4)c3)CC2)c1] |
| 5-90 | tert-butyl 4-(4-(1-benzylpiperidin-4-ylcarbamoyl)-2-chlorophenoxy)piperidine-1-carboxylate | 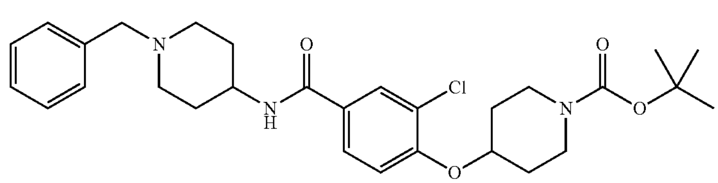 [SMILES: CC(C)(C)OC(=O)N1CCC(Oc2ccc(C(=O)NC3CCN(Cc4ccccc4)CC3)cc2Cl)CC1] |

TABLE 5-continued

| Cpd | Name | Structure |
|---|---|---|
| 5-91 | N-(1-benzylpiperidin-4-yl)-3-chloro-4-(1-pivaloylpiperidin-4-yloxy)benzamide | 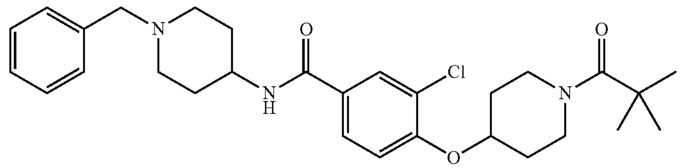 [SMILES: CC(C)(C)C(=O)N1CCC(Oc2ccc(C(=O)NC3CCN(Cc4ccccc4)CC3)cc2Cl)CC1] |
| 5-92 | tert-butyl 4-(4-(1-benzylpiperidin-4-ylcarbamoyl)-2-fluorophenoxy)piperidine-1-carboxylate | 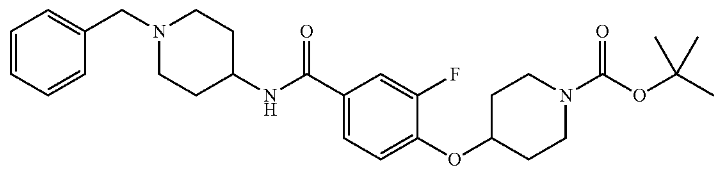 [SMILES: CC(C)(C)OC(=O)N1CCC(Oc2ccc(C(=O)NC3CCN(Cc4ccccc4)CC3)cc2F)CC1] |
| 5-93 | N-(1-benzylpiperidin-4-yl)-3-chloro-4-(piperidin-4-yloxy)benzamide | 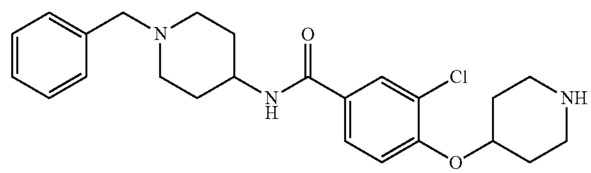 [SMILES: O=C(NC1CCN(Cc2ccccc2)CC1)c1ccc(OC2CCNCC2)c(Cl)c1] |
| 5-94 | tert-butyl 3-(3-methoxy-4-(1-(4-(trifluoromethyl)benzyl)piperidin-4-yloxy)benzamido)propylcarbamate | 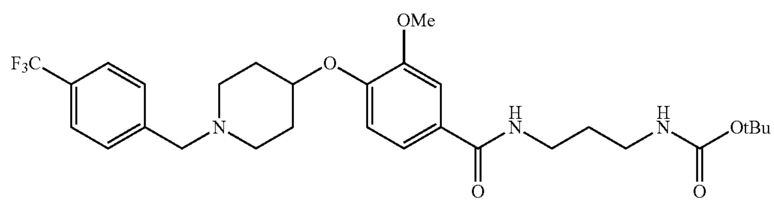 [SMILES: COc1cc(C(=O)NCCCNC(=O)OC(C)(C)C)ccc1OC1CCN(Cc2ccc(C(F)(F)F)cc2)CC1] |
| 5-95 | tert-butyl 3-(4-(1-(4-(trifluoromethyl)benzyl)piperidin-4-yloxy)benzamido)propylcarbamate | 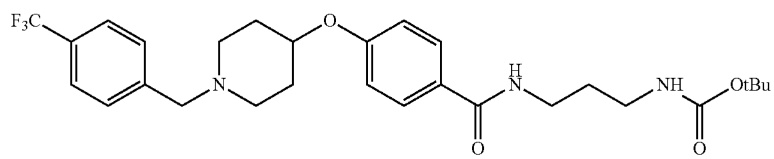 [SMILES: CC(C)(C)OC(=O)NCCCNC(=O)c1ccc(OC2CCN(Cc3ccc(C(F)(F)F)cc3)CC2)cc1] |
| 5-96 | tert-butyl 4-(4-(1-(4-methoxybenzyl)piperidin-4-yloxy)benzoyl)piperazine-1-carboxylate | 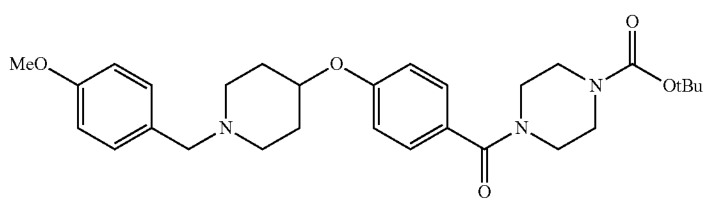 [SMILES: COc1ccc(CN2CCC(Oc3ccc(C(=O)N4CCN(C(=O)OC(C)(C)C)CC4)cc3)CC2)cc1] |
| 5-97 | tert-butyl 3-(3-chloro-4-(1-(4-methoxybenzyl)piperidin-4-yloxy)benzamido)propylcarbamate | 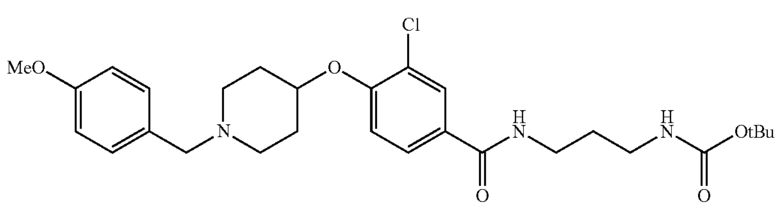 [SMILES: COc1ccc(CN2CCC(Oc3ccc(C(=O)NCCCNC(=O)OC(C)(C)C)cc3Cl)CC2)cc1] |
| 5-98 | 4-(1-(4-chlorobenzyl)piperidin-4-yloxy)-4-methoxy-N-(3-morpholinopropyl)benzamide | 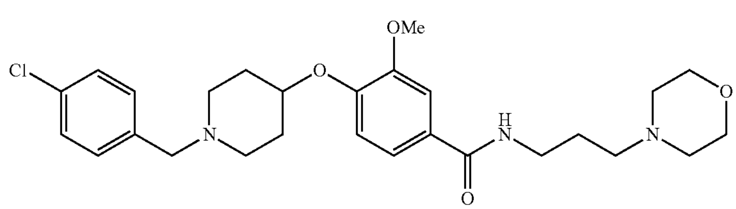 [SMILES: COc1cc(C(=O)NCCCN2CCOCC2)ccc1OC1CCN(Cc2ccc(Cl)cc2)CC1] |

TABLE 5-continued

| Cpd | Name | Structure |
|---|---|---|
| 5-99 | tert-butyl 4-(4-(1-benzylpiperidin-4-yloxy)benzoyl)piperazine-1-carboxylate | 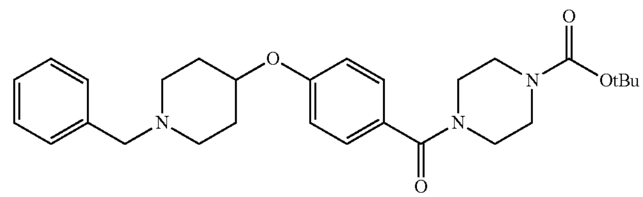 [SMILES: CC(C)(C)OC(=O)N1CCN(C(=O)c2ccc(OC3CCN(Cc4ccccc4)CC3)cc2)CC1] |
| 5-100 | 4-(1-(4-chlorobenzyl)piperidin-4-yloxy)-N-(3-morpholinopropyl)benzamide | 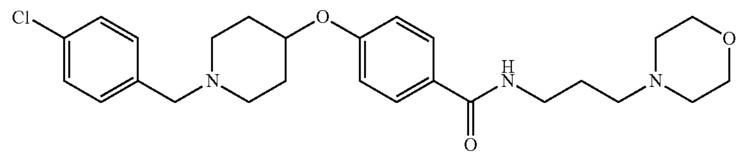 [SMILES: O=C(NCCCN1CCOCC1)c1ccc(OC2CCN(Cc3ccc(Cl)cc3)CC2)cc1] |
| 5-101 | 3-chloro-4-(1-(4-methoxybenzyl)piperidin-4-yloxy)-N-(3-morpholinopropyl)benzamide | 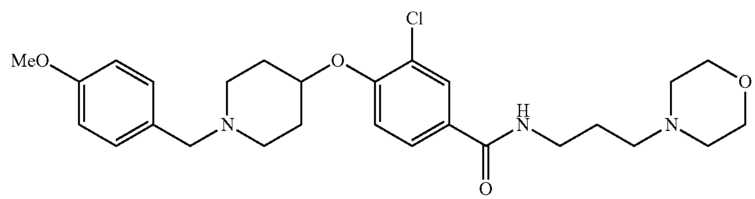 [SMILES: COc1ccc(CN2CCC(Oc3ccc(C(=O)NCCCN4CCOCC4)cc3Cl)CC2)cc1] |
| 5-102 | tert-butyl 3-(4-(1-benzylpiperidin-4-yloxy)-3-chlorobenzamido)propylcarbamate | 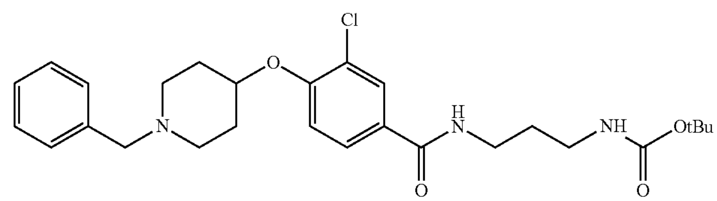 [SMILES: CC(C)(C)OC(=O)NCCCNC(=O)c1ccc(OC2CCN(Cc3ccccc3)CC2)c(Cl)c1] |
| 5-103 | (4-(1-benzylpiperidin-4-yloxy)phenyl)(4-phenylpiperazin-1-yl)methanone | 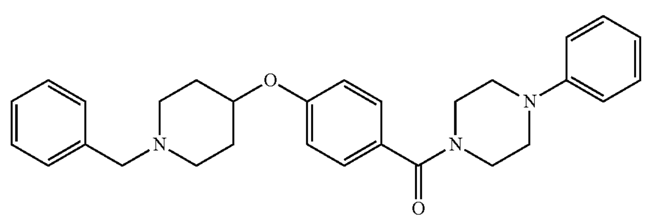 [SMILES: O=C(c1ccc(OC2CCN(Cc3ccccc3)CC2)cc1)N1CCN(c2ccccc2)CC1] |
| 5-104 | 4-(1-(4-methylbenzyl)piperidin-4-yloxy)-N-(3-morpholinopropyl)benzamide | 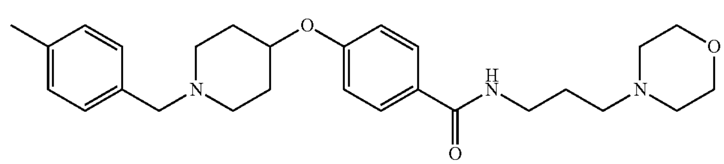 [SMILES: Cc1ccc(CN2CCC(Oc3ccc(C(=O)NCCCN4CCOCC4)cc3)CC2)cc1] |
| 5-105 | (4-(1-benzylpiperidin-4-yloxy)phenyl)(4-(pyridin-2-ylmethyl)piperazin-1-yl)methanone | 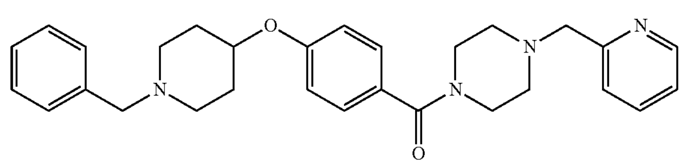 [SMILES: O=C(c1ccc(OC2CCN(Cc3ccccc3)CC2)cc1)N1CCN(Cc2ccccn2)CC1] |

The present disclosure contemplates combinations of particularly described embodiments. For example, certain embodiments of ring system "B" and certain embodiments of T are described in separate paragraphs; also contemplated are embodiments in which ring system "B" is as described in a relevant paragraph, and T is as described in a relevant paragraph. This disclosure contemplates all such combinations, to the extent the definitions of the various structural features do not conflict with one another.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety can refer to a monovalent radical (e.g. $CH_3$—$CH_2$—), in some circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for O, and 2, 4, or 6 for S, depending on the oxidation state of the S). Nitrogens in the presently disclosed compounds can be hypervalent, e.g., an N-oxide or tetrasubstituted ammonium salt. On occasion a moiety may be defined, for example, as $(A)_a$-B—, wherein a is 0 or 1. In such instances, when a is 0 the moiety is B— and when a is 1 the moiety is A-B—.

As used herein, the term "alkyl" includes alkyl, alkenyl and alkynyl groups of a designed number of carbon atoms, desirably from 1 to about 12 carbons (i.e., inclusive of 1 and 12). The term "$C_m$—$C_n$ alkyl" means an alkyl group having from m to n carbon atoms (i.e., inclusive of m and n). The term "$C_m$—$C_n$ alkyl" means an alkyl group having from m to n carbon atoms. For example, "$C_1$-$C_6$ alkyl" is an alkyl group having from one to six carbon atoms. Alkyl and alkyl groups may be straight or branched and depending on context, may be a monovalent radical or a divalent radical (i.e., an alkylene group). In the case of an alkyl or alkyl group having zero carbon atoms (i.e., "$C_0$ alkyl"), the group is simply a single covalent bond if it is a divalent radical or is a hydrogen atom if it is a monovalent radical. For example, the moiety "—($C_0$-$C_0$ alkyl)-Ar" signifies connection of an optionally substituted aryl through a single bond or an alkylene bridge having from 1 to 6 carbons. Examples of "alkyl" include, for example, methyl, ethyl, propyl, isopropyl, butyl, iso-, sec- and tert-butyl, pentyl, hexyl, heptyl, 3-ethylbutyl, 3-hexenyl and propargyl. If the number of carbon atoms is not specified, the subject "alkyl" or "alkyl" moiety has from 1 to 12 carbons.

The term "haloalkyl" is an alkyl group substituted with one or more halogen atoms, e.g. F, Cl, Br and I. A more specific term, e.g., "fluoroalkyl" is an alkyl group substituted with one or more fluorine atoms. Examples of "fluoroalkyl" include fluoromethyl, difluoromethyl, trifluoromethyl, pentafluoroethyl, hexafluoroisopropyl and the like. In certain embodiments of the compounds disclosed herein, each haloalkyl is a fluoroalkyl.

The term "aryl" represents an aromatic ring system having a single ring (e.g., phenyl) which is optionally fused to other aromatic hydrocarbon rings or non-aromatic hydrocarbon rings. "Aryl" includes ring systems having multiple condensed rings and in which at least one is carbocyclic and aromatic, (e.g., 1,2,3,4-tetrahydronaphthyl, naphthyl). Examples of aryl groups include phenyl, 1-naphthyl, 2-naphthyl, indanyl, indenyl, dihydronaphthyl, fluorenyl, tetralinyl, and 6,7,8,9-tetrahydro-5H-benzo[a]cycloheptenyl. In certain examples, aryl groups include those having a first carbocyclic, aromatic ring fused to an aromatic or aliphatic heterocycle, for example, 2,3-dihydrobenzofuranyl. The aryl groups herein are unsubstituted or, when specified as "optionally substituted", can unless stated otherwise be substituted in one or more substitutable positions with various groups, as described below.

The term "heteroaryl" refers to an aromatic ring system containing at least one heteroatom selected from nitrogen, oxygen and sulfur in an aromatic ring. The heteroaryl may be fused to one or more cycloalkyl or heterocycloalkyl rings. Examples of heteroaryl groups include, for example, pyridyl, pyrimidinyl, quinolinyl, benzothienyl, indolyl, indolinyl, pyridazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, benzo[1,4]oxazinyl, triazolyl, tetrazolyl, isothiazolyl, naphthyridinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. Preferred heteroaryl groups include pyridyl, pyrimidyl, quinolinyl, indolyl, pyrrolyl, furanyl, thienyl and imidazolyl, pyrazolyl, indazolyl, thiazolyl and benzothiazolyl. In certain embodiments, each heteroaryl is selected from pyridyl, pyrimidinyl, pyridazinyl, pyrazinyl, imidazolyl, isoxazolyl, pyrazolyl, oxazolyl, thiazolyl, furanyl, thienyl, pyrrolyl, oxadiazolyl, thiadiazolyl, triazolyl, tetrazolyl, isothiazolyl, pyridinyl-N-oxide, pyrrolyl N-oxide, pyrimidinyl N-oxide, pyridazinyl N-oxide, pyrazinyl N-oxide, imidazolyl N-oxide, isoxazolyl N-oxide, oxazolyl N-oxide, thiazolyl N-oxide, pyrrolyl N-oxide, oxadiazolyl N-oxide, thiadiazolyl N-oxide, triazolyl N-oxide, and tetrazolyl N-oxide. Preferred heteroaryl groups include pyridyl, pyrimidyl, quinolinyl, indolyl, pyrrolyl, furanyl, thienyl, imidazolyl, pyrazolyl, indazolyl, thiazolyl and benzothiazolyl. The heteroaryl groups herein are unsubstituted or, when specified as "optionally substituted", can unless stated otherwise be substituted in one or more substitutable positions with various groups, as described below.

The term "heterocycloalkyl" refers to a non-aromatic ring or ring system containing at least one heteroatom that is preferably selected from nitrogen, oxygen and sulfur, wherein said heteroatom is in a non-aromatic ring. The heterocycloalkyl may be saturated (i.e., a heterocycloalkyl) or partially unsaturated (i.e., a heterocycloalkenyl). Heterocycloalkyl includes monocyclic groups as well as bicyclic and polycyclic ring systems, including bridged and fused systems. The heterocycloalkyl ring is optionally fused to other heterocycloalkyl rings and/or non-aromatic hydrocarbon rings and/or phenyl rings. In certain embodiments, the heterocycloalkyl groups have from 3 to 7 members in a single ring. In other embodiments, heterocycloalkyl groups have 5 or 6 members in a single ring. Examples of heterocycloalkyl groups include, for example, azabicyclo[2.2.2]octyl (in each case also "quinuclidinyl" or a quinuclidine derivative), azabicyclo[3.2.1]octyl, 2,5-diazabicyclo[2.2.1]heptyl, morpholinyl, thiomorpholinyl, thiomorpholinyl S-oxide, thiomorpholinyl S,S-dioxide, 2-oxazolidonyl, piperazinyl, homopiperazinyl, piperazinonyl, pyrrolidinyl, azepanyl, azetidinyl, pyrrolinyl, tetrahydropyranyl, piperidinyl, tetrahydrofuranyl, tetrahydrothienyl, 3,4-dihydroisoquinolin-2(1H)-yl, isoindolindionyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, imidazolidonyl, tetrahydrothienyl S-oxide, tetrahydrothienyl S,S-dioxide and homothiomorpholinyl S-oxide. Especially desirable heterocycloalkyl groups include morpholinyl, 3,4-dihydroisoquinolin-2(1H)-yl, tetrahydropyranyl, piperidinyl, aza-bicyclo[2.2.2]octyl, γ-butyrolactonyl (i.e., an oxo-substituted tetrahydrofuranyl), γ-butryolactamyl (i.e., an oxo-substituted pyrrolidine), pyrrolidinyl, piperazinyl, azepanyl, azetidinyl, thiomorpholinyl, thiomorpholinyl S,S-dioxide, 2-oxazolidonyl, imidazolidonyl, isoindolindionyl, piperazinonyl. The heterocycloalkyl groups herein are unsubstituted or, when specified as "optionally substituted", can unless stated otherwise be substituted in one or more substitutable positions with various groups, as described below.

The term "cycloalkyl" refers to a non-aromatic carbocyclic ring or ring system, which may be saturated (i.e., a cycloalkyl) or partially unsaturated (i.e., a cycloalkenyl). The cycloalkyl ring optionally fused to or otherwise attached (e.g., bridged systems) to other cycloalkyl rings. Certain examples of cycloalkyl groups present in the disclosed compounds have from 3 to 7 members in a single ring, such as having 5 or 6 members in a single ring. Examples of cycloalkyl groups include, for example, cyclohexyl, cyclopentyl, cyclobutyl, cyclopropyl, tetrahydronaphthyl and bicyclo[2.2.1]heptane. The cycloalkyl groups herein are unsubstituted or, when specified as "optionally substituted", may be substituted in one or more substitutable positions with various groups.

The term "ring system" encompasses monocycles, as well as fused and/or bridged polycycles.

The term "oxa" means a divalent oxygen radical in a chain, sometimes designated as —O—.

The term "oxo" means a doubly bonded oxygen, sometimes designated as =O or for example in describing a carbonyl "C(O)" may be used to show an oxo substituted carbon.

The term "electron withdrawing group" means a group that withdraws electron density from the structure to which it is attached than would a similarly-attached hydrogen atom. For example, electron withdrawing groups can be selected from the group consisting of halo, cyano, —($C_1$-$C_4$ fluoroalkyl), —O—($C_1$-$C_4$ fluoroalkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), —S(O)$_2$O—($C_0$-$C_4$ alkyl), NO$_2$ and —C(O)-Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group.

The term "substituted," when used to modify a specified group or radical, means that one or more hydrogen atoms of the specified group or radical are each, independently of one another, replaced with the same or different substituent groups as defined below.

Substituent groups for substituting for hydrogens on saturated carbon atoms in the specified group or radical are, unless otherwise specified, —$R^{60}$, halo, —O$^-$M$^+$, =O, —OR$^{70}$, —SR$^{70}$, —S$^-$M$^+$, =S, —NR$^{80}$R$^{80}$, =NR$^{70}$, =N—OR$^{70}$, trihalomethyl, —CF$_3$, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, NR$^{70}$C(NR$^{70}$)R$^{70}$ and —NR$^{70}$C(NR$^{70}$)NR$^{80}$R$^{80}$. Each $R^{60}$ is independently selected from the group consisting of alkyl, heteroalkyl, cycloalkyl, heterocycloalkyl, heterocycloalkylalkyl, cycloalkylalkyl, aryl, arylalkyl, heteroaryl and heteroarylalkyl, each of which is optionally substituted with 1, 2, 3, 4 or 5 groups selected from the group consisting of halo, —O$^-$M$^+$, =O, —OR$^{71}$, —SR$^{71}$, —S$^-$M$^+$, =S, —NR$^{81}$R$^{81}$, =NR$^{71}$, =N—OR$^{71}$, trihalomethyl, —CF$_3$, —CN, —OCN, —SCN, —NO, —NO$_2$, =N$_2$, —N$_3$, —SO$_2$R$^{71}$, —SO$_2$O$^-$M$^+$, —SO$_2$OR$^{71}$, —OSO$_2$R$^{71}$, —OSO$_2$O$^-$M$^+$, —OSO$_2$OR$^{71}$, —P(O)(O$^-$)$_2$(M$^+$)$_2$, —P(O)(OR$^{71}$)O$^-$M$^+$, —P(O)(OR$^{71}$)$_2$, —C(O)R$^{71}$, —C(S)R$^{71}$, —C(NR$^{71}$)R$^{71}$, —C(O)O$^-$M$^+$, —C(O)OR$^{71}$, —C(S)OR$^{71}$, —C(O)NR$^{81}$R$^{81}$, —C(NR$^{71}$)NR$^{81}$R$^{81}$, —OC(O)R$^{71}$, —OC(S)R$^{71}$, —OC(O)O$^-$M$^{30}$, —OC(O)OR$^{71}$, —OC(S)OR$^{71}$, —NR$^{71}$C(O)R$^{71}$, —NR$^{71}$C(S)R$^{71}$, —NR$^{71}$CO$_2^-$M$^+$, —NR$^{71}$CO$_2$R$^{71}$, —NR$^{71}$C(S)OR$^{71}$, —NR$^{71}$C(O)NR$^{81}$R$^{81}$, NR$^{71}$C(NR$^{71}$)R$^{71}$ and —NR$^{71}$C(NR$^{71}$)NR$^{81}$R$^{81}$. Each $R^{70}$ is independently hydrogen or $R^{60}$; each $R^{80}$ is independently $R^{70}$ or alternatively, two $R^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution; and each M$^+$ is a counter ion with a net single positive charge. Each $R^{71}$ is independently hydrogen or $R^{61}$, in which $R^{61}$ is alkyl, heteroalkyl, cycloalkyl, heterocycloalkyl, heterocycloalkylalkyl, cycloalkylalkyl, aryl, arylalkyl, heteroaryl and heteroarylalkyl, each of which is optionally substituted with 1, 2, 3, 4 or 5 groups selected from the group consisting of halo, —O$^-$M$^+$, =O, —OR$^{72}$, —SR$^{72}$, —S$^-$M$^+$, =S, —NR$^{82}$R$^{82}$, =NR$^{72}$, =N—OR$^{72}$, trihalomethyl, —CF$_3$, —CN, —OCN, —SCN, —NO, —NO$_2$, =N$_2$, —N$_3$, —SO$_2$R$^{71}$, —SO$_2$O$^-$M$^+$, —SO$_2$OR$^{72}$, —OSO$_2$R$^{72}$, —OSO$_2$O$^-$M$^+$, —OSO$_2$OR$^{72}$, —P(O)(O$^-$)$_2$(M$^+$)$_2$, —P(O)(OR$^{72}$)O$^-$M$^+$, —P(O)(OR$^{72}$)$_2$, —C(O)R$^{72}$, —C(S)R$^{72}$, —C(NR$^{72}$)R$^{72}$, —C(O)O$^-$M$^+$, —C(O)OR$^{72}$, —C(S)OR$^{72}$, —C(O)NR$^{82}$R$^{82}$, —C(NR$^{72}$)NR$^{82}$R$^{82}$, —OC(O)R$^{72}$, —OC(S)R$^{72}$, —OC(O)O$^-$M$^+$, —OC(O)OR$^{72}$, —OC(S)OR$^{72}$, —NR$^{72}$C(O)R$^{72}$, —NR$^{72}$C(S)R$^{72}$, —NR$^{72}$CO$_2^-$M$^+$, —NR$^{72}$CO$_2$R$^{72}$, —NR$^{72}$C(S)OR$^{72}$, —NR$^{72}$C(O)NR$^{82}$R$^{82}$, —NR$^{72}$C(NR$^{72}$)R$^{72}$ and —NR$^{72}$C(NR$^{72}$)NR$^{82}$R$^{82}$; and each $R^{81}$ is independently $R^{71}$ or alternatively, two $R^{81}$s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution. Each $R^{72}$ is independently hydrogen, ($C_1$-$C_6$ alkyl) or ($C_1$-$C_6$ fluoroalkyl); each $R^{82}$ is independently $R^{72}$ or alternatively, two $R^{82}$s, taken together with the nitrogen atom to which they are bonded, form a 5-, 6- or 7-membered heterocycloalkyl which may optionally include 1, 2, 3 or 4 of the same or different additional heteroatoms selected from the group consisting of O, N and S, of which N may have —H or $C_1$-$C_3$ alkyl substitution. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means e.g. that one of the counter ions for such divalent alkali earth ions can be an ionized form of a presently disclosed compound and the other a typical counter ion such as chloride, or two ionized presently disclosed molecules can serve as counter ions for such divalent alkali earth ions, or a doubly ionized compound can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4-methyl-piperazin-1-yl and N-morpholinyl.

Substituent groups for hydrogens on unsaturated carbon atoms in "substituted" alkene, alkyne, aryl and heteroaryl groups are, unless otherwise specified, —$R^{60}$, halo, —O$^-$M$^+$, —OR$^{70}$, —SR$^{70}$, —S$^-$M$^+$, —NR$^{80}$R$^{80}$, trihalomethyl, —CF$_3$, —CN, —OCN, —SCN, —NO, —NO$_2$, —N$_3$, —$SO_2R^{70}$, —$SO_3^-M^+$, —$SO_3R^{70}$, —$OSO_2R^{70}$, —$OSO_3^-M^+$, —$OSO_3R^{70}$, —$PO_3^{-2}(M^+)_2$, —$P(O)(OR^{70})O^-M^+$, —$P(O)(OR^{70})_2$, —$C(O)R^{70}$, —$C(S)R^{70}$, —$C(NR^{70})R^{70}$, —$CO_2^-M^+$, —$CO_2R^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OCO_2^-M^+$, —$OCO_2R^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined.

Substituent groups for hydrogens on nitrogen atoms in "substituted" heteroalkyl and heterocycloalkyl groups are, unless otherwise specified, —$R^{60}$, —$O^-M^+$, —$OR^{70}$, —$SR^{70}$, —$S^-M^+$, —$NR^{80}R^{80}$, trihalomethyl, —$CF_3$, —CN, —NO, —$NO_2$, —$S(O)_2R^{70}$, —$S(O)_2O^-M^+$, —$S(O)_2OR^{70}$, —$OS(O)_2R^{70}$, $OS(O)_2O^-M^+$, —$OS(O)_2OR^{70}$, —$P(O)(O^-)_2(M^+)_2$, —$P(O)(OR^{70})O^-M^+$, —$P(O)(OR^{70})(OR^{70})$, —$C(O)R^{70}$, —$C(S)R^{70}$, —$C(NR^{70})R^{70}$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)OR^{70}$, —$OC(S)OR^{70}$, —$NR^{70}C(O)R^{70}$, —$NR^{70}C(S)R^{70}$, —$NR^{70}C(O)OR^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined.

In certain embodiments of the compounds disclosed herein, a group that is substituted has 1, 2, 3, or 4 substituents, 1, 2, or 3 substituents, 1 or 2 substituents, or 1 substituent.

In certain preferred embodiments, substituent groups on "substituted" alkyl, cycloalkyl, heterocycloalkyl, aryl and heteroaryl groups are -halo, —OH, —O—($C_1$-$C_4$ alkyl), —O—($C_1$-$C_4$ haloalkyl), —N($C_0$-$C_4$ alkyl)($C_0$-$C_4$ alkyl), —SH, —S(O)$_{0-2}$—($C_1$-$C_4$ alkyl), —($C_1$-$C_4$ alkyl), —($C_1$-$C_4$ haloalkyl), —C(O)—($C_0$-$C_4$ alkyl), —C(O)N($C_0$-$C_4$ alkyl)($C_0$-$C_4$ alkyl), —N($C_0$-$C_4$ alkyl)C(O)($C_0$-$C_4$ alkyl)($C_0$-$C_4$ alkyl), —C(O)O—($C_0$-$C_4$ alkyl), —OC(O)—($C_0$-$C_4$ alkyl), $S(O)_2$—O($C_0$-$C_4$ alkyl), and —$NO_2$, in which no alkyl is further substituted.

The compounds disclosed herein can also be provided as pharmaceutically acceptable salts. The term "pharmaceutically acceptable salts" or "a pharmaceutically acceptable salt thereof" refer to salts prepared from pharmaceutically acceptable non-toxic acids or bases including inorganic acids and bases and organic acids and bases. If the compound is basic, salts may be prepared from pharmaceutically acceptable non-toxic acids. Such salts may be, for example, acid addition salts of at least one of the following acids: benzenesulfonic acid, citric acid, α-glucoheptonic acid, D-gluconic acid, glycolic acid, lactic acid, malic acid, malonic acid, mandelic acid, phosphoric acid, propanoic acid, succinic acid, sulfuric acid, tartaric acid (d, l, or dl), tosic acid (toluenesulfonic acid), valeric acid, palmitic acid, pamoic acid, sebacic acid, stearic acid, lauric acid, acetic acid, adipic acid, carbonic acid, 4-chlorobenzenesulfonic acid, ethanedisulfonic acid, ethylsuccinic acid, fumaric acid, galactaric acid (mucic acid), D-glucuronic acid, 2-oxoglutaric acid, glycerophosphoric acid, hippuric acid, isethionic acid (ethanolsulfonic acid), lactobionic acid, maleic acid, 1,5-naphthalene-disulfonic acid, 2-naphthalene-sulfonic acid, pivalic acid, terephthalic acid, thiocyanic acid, cholic acid, n-dodecyl sulfate, 3-hydroxy-2-naphthoic acid, 1-hydroxy-2-naphthoic acid, oleic acid, undecylenic acid, ascorbic acid, (+)-camphoric acid, d-camphorsulfonic acid, dichloroacetic acid, ethanesulfonic acid, formic acid, hydriodic acid, hydrobromic acid, hydrochloric acid, methanesulfonic acid, nicotinic acid, nitric acid, orotic acid, oxalic acid, picric acid, L-pyroglutamic acid, saccharine, salicylic acid, gentisic acid, and/or 4-acetamidobenzoic acid.

The compounds described herein can also be provided in prodrug form. "Prodrug" refers to a derivative of an active compound (drug) that undergoes a transformation under the conditions of use, such as within the body, to release the active drug. Prodrugs are frequently, but not necessarily, pharmacologically inactive until converted into the active drug. Prodrugs are typically obtained by masking a functional group in the drug believed to be in part required for activity with a progroup (defined below) to form a promoiety which undergoes a transformation, such as cleavage, under the specified conditions of use to release the functional group, and hence the active drug. The cleavage of the promoiety can proceed spontaneously, such as by way of a hydrolysis reaction, or it can be catalyzed or induced by another agent, such as by an enzyme, by light, by acid, or by a change of or exposure to a physical or environmental parameter, such as a change of temperature. The agent can be endogenous to the conditions of use, such as an enzyme present in the cells to which the prodrug is administered or the acidic conditions of the stomach, or it can be supplied exogenously. A wide variety of progroups, as well as the resultant promoieties, suitable for masking functional groups in the active drugs to yield prodrugs are well-known in the art. For example, a hydroxyl functional group can be masked as a sulfonate, ester or carbonate promoiety, which can be hydrolyzed in vivo to provide the hydroxyl group. An amino functional group can be masked as an amide, carbamate, imine, urea, phosphenyl, phosphoryl or sulfenyl promoiety, which can be hydrolyzed in vivo to provide the amino group. A carboxyl group can be masked as an ester (including silyl esters and thioesters), amide or hydrazide promoiety, which can be hydrolyzed in vivo to provide the carboxyl group. Specific examples of suitable progroups and their respective promoieties will be apparent to those of skill in the art.

The compounds disclosed herein can also be provided as N-oxides.

The presently disclosed compounds, salts, prodrugs and N-oxides can be provided, for example, in solvate or hydrate form.

One of ordinary skill in the art of medicinal chemistry also will appreciate that the disclosed structures are intended to include isotopically enriched forms of the present compounds. As used herein "isotopes" includes those atoms having the same atomic number but different mass numbers. As will be apparent to those of skill in the art upon consideration of the present compounds, certain atoms can be enriched an isotope of that atom. For example, compounds having a fluorine atom, may be synthesized in a form enriched in the radioactive fluorine isotope $^{18}$F. Similarly, compounds may be enriched in the heavy isotopes of hydrogen, deuterium and tritium, and can be enriched in a radioactive isotope of carbon, such as $^{13}$C. Such compounds can be useful, for example, in studying the AMPK pathway and its role in metabolism.

Compounds can be assayed for binding to a membrane-bound adiponectin receptor by performing a competitive binding assay with adiponectin. In one such procedure, HEK 293 cellular membrane is coated onto a COSTAR 384 plate, which is then blocked with 1% casein. Polyhistidine-tagged globular adiponectin and a candidate compound is incubated with the membrane in HEPES buffer. Unbound ligands are washed away and the degree of binding of the adiponectin is determined using horseradish peroxidase-conjugated anti-polyhistidine. Compounds that compete with adiponectin binding to the membrane (i.e., give a reduced signal compared to a control performed without a candidate compound) can be chosen as hits and further screened using the below-described functional assays to identify adiponectin receptor agonists.

An in-cell western assay can be performed to demonstrate the activation of AMPK in human liver cells by globular adiponectin using glutathione S-transferase (GST). AMPK activity can be measured by the relative concentration of phosphorylated acetyl Co-A carboxylase, which is one of the products of AMPK. An increase in pACC correlates with an increase in the rate of fatty acid oxidation.

The compounds disclosed herein can be administered, for example, orally, topically, parenterally, by inhalation or spray or rectally in dosage unit formulations containing one or more pharmaceutically acceptable carriers, diluents or excipients. The term parenteral as used herein includes percutaneous, subcutaneous, intravascular (e.g., intravenous), intramuscular, or intrathecal injection or infusion techniques and the like.

Pharmaceutical compositions can be made using the presently disclosed compounds. For example, in one embodiment, a pharmaceutical composition includes a pharmaceutically acceptable carrier, diluent or excipient, and compound as described above.

In the pharmaceutical compositions disclosed herein, one or more of the presently disclosed compounds may be present in association with one or more pharmaceutically acceptable carriers, diluents or excipients, and, if desired, other active ingredients. The pharmaceutical compositions may be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any suitable method for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by suitable techniques to delay disintegration and absorption in the gastrointestinal tract and thereby provide a sustained action over a longer period. For example, a time delay material such as glyceryl monostearate or glyceryl distearate can be employed.

Formulations for oral use can also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use can also be presented as lozenges.

Aqueous suspensions contain the active materials in admixture with excipients suitable for the manufacture of aqueous suspensions. Such excipients can be suspending agents, for example sodium carboxymethylcellulose, methylcellulose, hydropropylmethylcellulose, sodium alginate, polyvinylpyrrolidone, gum tragacanth and gum acacia; dispersing or wetting agents such as a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative, flavoring, and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils can be employed as a solvent or suspending medium. For this purpose any bland fixed oil can be employed including synthetic mono- or diglycerides. In addition, fatty acids such as oleic acid find use in the preparation of injectables.

The presently disclosed compounds can also be administered in the form of suppositories, e.g., for rectal administration of the drug. These compositions can be prepared by mixing the compound with a suitable non-irritating excipient that is solid at ordinary temperatures but liquid at the rectal temperature and will therefore melt in the rectum to release the drug. Such materials include cocoa butter and polyethylene glycols.

The presently disclosed compounds can also be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

The compounds disclosed herein can be made using procedures familiar to the person of ordinary skill in the art and as described, for example, in U.S. Patent Application Publications nos. 2009/0163511, 2009/0170829, 2009/0186894 and 2009/0275609, and in U.S. patent application Ser. No. 12/695,861, each of which is hereby incorporated by reference in its entirety. One of skill in the art can adapt the reaction sequences described therein to fit the desired target molecule. Of course, in certain situations one of skill in the art will use different reagents to affect one or more of the individual steps or to use protected versions of certain of the substituents. Additionally, one skilled in the art would recognize that the presently disclosed compounds can be synthesized using different routes altogether.

Compounds suitable for use in the presently disclosed pharmaceutical compositions include compounds of Tables 1-5, above.

Without being limited to any particular theory, it currently is believed that the presently disclosed compounds exert their therapeutic benefits as adiponectin receptor agonists, AMPK activators, or both. For convenience, and without limitation to theory, the present compounds are referred to as "adiponectin receptor agonists" or AMPK activators interchangeably throughout the specification. The presently disclosed adiponectin receptor agonist compounds are useful for increasing metabolic efficiency, for example by increasing fiber oxidative capacity, endurance and aerobic workload. In particular, the present agonists are useful for treating and regulating disorders of mitochondrial function, including, without limitation, exercise intolerance, chronic fatigue syndrome, muscle weakness, myoclonus, myoclonus epilepsy, such as associated with ragged-red fibers syndrome, Kearns-Sayre syndrome, Leigh's syndrome, mitochondrial myopathy encephalopathy lactacidosis stroke (MELAS) syndrome and stroke like episodes. The disclosed agonists also are useful for treating muscular dystrophic states, such as Duchenne's and Becker's muscular dystrophies and Friedreich's ataxia.

The present agonists also function to reduce oxidative stress and secondary effects of such stress. Many diseases, including several of those listed above, have secondary effects caused by damage due to excessive oxidative stress which can be treated using the adiponectin receptor agonists disclosed herein. For example, free radical damage has been implicated in neurological disorders, such as Parkinson's disease, amyotrophic lateral sclerosis (Lou Gehrig's disease) and Alzheimers disease. Additional diseases in which excessive free radical damage occurs generally include hypoxic conditions and a variety of other disorders. More specifically, such disorders include ischemia, ischemic reperfusion injury (such as coronary or cerebral reperfusion injury), myocardial ischemia or infarction, cerebrovascular accidents (such as a thromboembolic or hemorrhagic stroke) that can lead to ischemia in the brain, operative ischemia, traumatic hemorrhage (for example, a hypovolemic stroke that can lead to CNS hypoxia or anoxia), resuscitation injury, spinal cord trauma, inflammatory diseases, autoimmune disorders (such as rheumatoid arthritis or systemic lupus erythematosis), Down's syndrome, Hallervorden-Spatz disease, Huntingtons chorea, Wilson's disease, diabetic angiopathy (such as peripheral vascular disease or retinal degeneration), uveitis, chronic obstructive pulmonary disease (COPD), including chronic bronchitis and emphysema, asthma, neoplasia, Crohn's disease, inflammatory bowel disease and pancreatitis. Free radical damage is also implicated in a variety of age-related disorders, particularly ophthalmic conditions such as cataracts and age-related macular degeneration.

In particular the present compounds are useful for treating neurological disorders associated with reduced mitochondrial function, oxidative stress, or both. For example, Alzheimer's disease, dementia and Parkinson's disease can be treated using the present adiponectin receptor agonists.

Metabolic efficiency is enhanced by the disclosed adiponectin receptor agonists. Thus the agonists can be administered to a subject to improve exercise efficiency and athletic performance. Moreover, conditions including, without limitation, hypoxic states, angina pectoris, coronary ischemia and organ damage secondary to coronary vessel occlusion, intermittent claudication, multi-infarct dementia, myocardial infarction, stroke, high altitude sickness and heart failure, including congestive heart failure can be treated using the disclosed compounds. In another aspect the present compounds are useful for treating conditions associated with chronic heart failure, including myopathy/muscle atrophy, chronic obstructive pulmonary disease (COPD) and kidney diseases.

In one aspect the present adiponectin receptor agonists stimulate increased nitric oxide production. Such compounds are useful for treating diseases associated with reduced circulation and reduced blood vessel function. For example, the present compounds are useful for the treatment of heart disease and cardiomyopathy.

In another aspect, the present compounds activate autophagy and/or apoptotic pathways. Accordingly the present compounds are useful in halting or slowing the progression of neurodegenerative diseases and hyperproliferative disorders, such as cancer.

Inflammatory disorders and effects can be treated using the present adiponectin receptor agonists. For example, in one aspect, the present compounds are particularly useful for treating lung inflammation, such as is involved in asthma, COPD and transplant rejection. Similarly, the present compounds are useful in reducing organ inflammation, particularly macrophage-associated inflammation, such as inflammation of the kidney, liver and other organs. The anti-inflammatory activity of the presently disclosed compounds can be assessed as is known to those of skill in the art, for example, by using the mixed lymphocyte response in vitro.

Accordingly, one aspect of the disclosure relates to a method for treating or ameliorating a disorder or condition related to oxidative stress, mitochondrial dysfunction, free radical damage and/or metabolic inefficiency in a subject in need thereof, the method including administering to the subject an effective amount of a compound, pharmaceutically acceptable salt, prodrug, N-oxide (or solvate or hydrate thereof) or pharmaceutical composition described above.

Another aspect of the present disclosure relates to a method for the treatment or amelioration of a disorder of mitochondrial dysfunction in a subject in need thereof, the method including administering to the subject an effective amount of a compound, pharmaceutically acceptable salt, prodrug, N-oxide (or solvate or hydrate thereof) or pharmaceutical composition described above. In certain embodiments, the disorder is selected from the group consisting of exercise intolerance, chronic fatigue syndrome, muscle weakness, myoclonus, myoclonus epilepsy (such as associated with ragged-red fibers syndrome), Kearns-Sayre syndrome, Leigh's syndrome, mitochondrial myopathy encephalopathy lactacidosis stroke (MELAS) syndrome and stroke like episodes.

Another aspect of the disclosure relates to a method of increasing metabolic efficiency in a subject in need thereof, the method including administering to the subject an effective amount of a compound, pharmaceutically acceptable salt, prodrug, N-oxide (or solvate or hydrate thereof) or pharmaceutical composition described above. Such methods can be used to increase fiber oxidative capacity, endurance, aerobic workload, or any combination thereof. These methods can be used, for example, to improve exercise efficiency, exercise endurance and/or athletic performance in a subject.

Another aspect of the present disclosure relates to methods for mimicking the effects of exercise in a subject in need thereof, the method including administering to the subject an effective amount of a compound, pharmaceutically acceptable salt, prodrug, N-oxide (or solvate or hydrate thereof) or pharmaceutical composition described above.

Another aspect of the disclosure relates to a method for treating or ameliorating a disorder in a subject in need thereof, the disorder being selected from the group consisting of hypoxic states, angina pectoris, coronary ischemia and organ damage secondary to coronary vessel occlusion, intermittent claudication, multi-infarct dementia, myocardial infarction, stroke, high altitude sickness and heart failure, including congestive heart failure, the method including administering to the subject an effective amount of a compound, pharmaceutically acceptable salt, prodrug, N-oxide (or solvate or hydrate thereof) or pharmaceutical composition described above.

Another aspect of the disclosure relates to a method for the treatment of amelioration of a muscular dystrophic state in a subject in need thereof, the method including administering to the subject an effective amount of a compound, pharmaceutically acceptable salt, prodrug, N-oxide (or solvate or hydrate thereof) or pharmaceutical composition described above. In certain embodiments, the muscular dystrophic state is Duchenne's muscular dystrophy, Becker's muscular dystrophy, or Freidreich's ataxia.

Another aspect of the disclosure relates to a method for increasing oxidative capacity of a muscle fiber, the method including contacting the muscle fiber with a compound, pharmaceutically acceptable salt, prodrug, N-oxide (or solvate or hydrate thereof) or pharmaceutical composition described above. The contacting may be performed in vitro or in vivo.

Another aspect of the disclosure relates to a method for reducing oxidative stress in a subject in need thereof, the method including administering to the subject an effective amount of a compound, pharmaceutically acceptable salt, prodrug, N-oxide (or solvate or hydrate thereof) or pharmaceutical composition described above.

Another aspect of the disclosure relates to a method for reducing free radical damage in a subject in need thereof, the method including administering to the subject an effective amount of a compound, pharmaceutically acceptable salt, prodrug, N-oxide (or solvate or hydrate thereof) or pharmaceutical composition described above.

Another aspect of the disclosure relates to a method for treating or ameliorating a disorder or condition in a subject in need thereof, the disorder or condition selected from the group consisting of neurological disorders, hypoxic conditions, ischemia, ischemic reperfusion injury, myocardial ischemia or infarction, cerebrovascular accidents, operative ischemia, traumatic hemorrhage, resuscitation injury, spinal cord trauma, inflammatory diseases, autoimmune disorders, Down's syndrome, Hallervorden-Spatz disease, Huntingtons chorea, Wilson's disease, diabetic angiopathy, uveitis, chronic obstructive pulmonary disease (COPD), asthma, neoplasia, Crohn's disease, inflammatory bowel disease, pancreatitis and age-related disorders, the method including administering to the subject an effective amount of a compound, pharmaceutically acceptable salt, prodrug, N-oxide (or solvate or hydrate thereof) or pharmaceutical composition described above. Particular examples of such disorders and conditions are discussed above.

Another aspect of the disclosure is a method for treating or ameliorating a neurological disorder in a subject in need thereof, the neurological disorder being associated with reduced mitochondrial function, oxidative stress, or both, the method including administering to the subject an effective amount of a compound, pharmaceutically acceptable salt, prodrug, N-oxide (or solvate or hydrate thereof) or pharmaceutical composition described above. Particular examples of such neurological disorders are discussed above.

Another aspect of the disclosure relates to a method for reducing oxidative stress in a cell, the method including contacting the cell with a compound, pharmaceutically acceptable salt, prodrug, N-oxide (or solvate or hydrate thereof) or pharmaceutical composition described above. The contacting may be performed in vitro or in vivo.

Another aspect of the disclosure relates to a method for reducing free radical damage in a cell, the method including contacting the cell with a compound, pharmaceutically acceptable salt, prodrug, N-oxide (or solvate or hydrate thereof) or pharmaceutical composition described above. The contacting may be performed in vitro or in vivo.

Another aspect of the disclosure is a method for treating an inflammatory disorder or effect in a subject in need thereof, the method including administering to the subject an effective amount of a compound, pharmaceutically acceptable salt, prodrug, N-oxide (or solvate or hydrate thereof) or pharmaceutical composition described above. For example, in one embodiment, the inflammatory disorder or effect is lung inflammation, such as is involved in asthma, COPD and transplant rejection. In another embodiment, the inflammatory disorder or effect is organ inflammation, particularly macrophage-associated inflammation, such as inflammation of the kidney, liver and other organs.

Other aspects of the disclosure relate to the use of a compound, pharmaceutically acceptable salt, prodrug, N-oxide (or solvate or hydrate thereof) or composition as described herein in the manufacture of a medicament for any of the therapeutic purposes described herein. Still other aspects of the disclosure relate to the use of a compound, pharmaceutically acceptable salt, prodrug, N-oxide (or solvate or hydrate thereof) or composition as described herein for the treatment of any of the therapeutic purposes described above. In certain embodiments, the compounds used in the methods and uses disclosed herein have $EC_{50}$ values for AMPK activation less than 10 µM, less than 5 µM, or even less than 1 µM.

EXAMPLES

AMPK Activation

Compounds of Table 1 were assayed for their ability to activate AMPK using an enzyme-linked immunosorbent assay. The EC$_{50}$ values for AMPK activation for the tested compounds are presented in Table 6 below, in which "A" is less than 0.1 μM; "B" is 0.1-0.5 μM; "C" is 0.5-1 μM; "D" is 1-5 μM; "E" is 5-10 μM; and "F" is >10 μM.

TABLE 6

| Cpd No. | AMPK EC$_{50}$ |
|---|---|
| 1-1 | B |
| 1-2 | A |
| 1-3 | A |
| 1-4 | A |
| 1-5 | A |
| 1-6 | B |
| 1-7 | A |
| 1-8 | A |
| 1-9 | B |
| 1-10 | A |
| 1-11 | A |
| 1-12 | C |
| 1-13 | B |
| 1-14 | A |
| 1-15 | D |
| 1-16 | A |
| 1-17 | A |
| 1-18 | A |
| 1-19 | D |
| 1-20 | C |
| 1-21 | B |
| 1-22 | D |
| 1-23 | B |
| 1-24 | E |
| 1-25 | B |
| 1-26 | B |
| 1-27 | F |
| 1-28 | A |
| 1-29 | B |
| 1-30 | A |
| 1-31 | A |
| 1-32 | B |
| 1-33 | C |
| 1-34 | C |
| 1-35 | B |
| 1-36 | C |
| 1-37 | C |
| 1-38 | D |
| 1-39 | B |
| 1-40 | A |
| 1-41 | B |
| 1-42 | D |
| 1-43 | D |
| 1-44 | B |
| 1-45 | F |
| 1-46 | D |
| 1-47 | D |
| 1-48 | D |
| 1-49 | A |
| 1-50 | D |
| 1-51 | B |
| 1-52 | B |
| 1-53 | B |
| 1-54 | D |
| 1-55 | D |
| 1-56 | E |
| 1-57 | C |
| 1-58 | A |
| 1-59 | B |
| 1-60 | F |
| 1-61 | B |
| 1-62 | E |
| 1-63 | A |
| 1-64 | A |
| 1-65 | A |
| 1-66 | A |
| 1-67 | A |
| 1-68 | A |
| 1-69 | A |
| 1-70 | A |
| 1-71 | A |
| 1-72 | B |

TABLE 6-continued

| Cpd No. | AMPK EC$_{50}$ |
|---|---|
| 1-73 | C |
| 1-74 | B |
| 1-75 | A |
| 1-76 | B |
| 1-77 | B |
| 1-78 | A |
| 1-79 | B |
| 1-80 | A |
| 1-81 | B |
| 1-82 | B |
| 1-83 | B |
| 1-84 | E |
| 1-85 | C |
| 1-86 | F |
| 1-87 | A |
| 1-88 | A |
| 1-89 | A |
| 1-90 | A |
| 1-91 | F |
| 1-92 | C |
| 1-93 | B |
| 1-94 | A |
| 1-95 | A |
| 1-96 | A |
| 1-97 | A |
| 1-98 | A |
| 1-99 | A |
| 1-100 | A |
| 1-101 | A |
| 1-102 | D |
| 1-103 | D |
| 1-104 | B |
| 1-105 | A |
| 1-106 | B |
| 1-107 | A |
| 1-108 | B |
| 1-109 | A |
| 1-110 | A |
| 1-111 | B |
| 1-112 | A |
| 1-113 | B |
| 1-114 | B |
| 1-115 | A |
| 1-116 | B |
| 1-117 | A |
| 1-118 | B |
| 1-119 | A |
| 1-120 | D |
| 1-121 | F |
| 1-122 | B |
| 1-123 | B |
| 1-124 | D |
| 1-125 | D |
| 1-126 | D |
| 1-127 | D |
| 1-128 | F |
| 1-129 | D |
| 1-130 | D |
| 1-131 | D |
| 1-137 | A |
| 1-138 | A |
| 1-139 | A |
| 1-140 | C |
| 1-141 | B |
| 1-144 | A |
| 1-145 | B |
| 1-146 | B |
| 1-147 | D |
| 1-148 | F |
| 1-149 | A |
| 1-150 | D |
| 1-151 | A |
| 1-152 | A |
| 1-153 | B |
| 1-154 | A |
| 1-155 | A |
| 1-156 | B |
| 1-157 | D |

TABLE 6-continued

| Cpd No. | AMPK EC$_{50}$ |
|---|---|
| 1-158 | B |
| 1-159 | B |
| 1-160 | A |

Compounds of Table 2 were assayed for their ability to activate AMPK using an enzyme-linked immunosorbent assay. The EC$_{50}$ values for AMPK activation for the tested compounds are presented in Table 7 below, in which "A" is less than 0.5 µM; "B" is 0.5-1 µM; "C" is 1-5 µM; and "D" is 5-10 µM; "E" is 10-50 µM; and "F" is >100 µM:

TABLE 7

| Cpd No. | AMPK EC$_{50}$ |
|---|---|
| 2-1 | C |
| 2-2 | E |
| 2-3 | E |
| 2-4 | C |
| 2-5 | C |
| 2-6 | B |
| 2-7 | D |
| 2-8 | D |
| 2-9 | A |
| 2-10 | B |
| 2-11 | A |
| 2-12 | A |
| 2-13 | A |
| 2-14 | A |
| 2-15 | A |
| 2-16 | A |
| 2-17 | B |
| 2-18 | C |
| 2-19 | F |
| 2-20 | C |
| 2-21 | B |
| 2-22 | B |
| 2-23 | C |
| 2-24 | C |
| 2-25 | E |
| 2-26 | E |
| 2-27 | C |
| 2-28 | C |
| 2-29 | C |
| 2-30 | C |
| 2-31 | C |
| 2-32 | C |
| 2-33 | C |
| 2-24 | C |
| 2-35 | E |
| 2-36 | F |
| 2-37 | D |
| 2-38 | E |
| 2-39 | E |
| 2-40 | F |
| 2-41 | E |
| 2-43 | F |
| 2-44 | E |
| 2-45 | F |
| 2-46 | F |
| 2-47 | E |
| 2-48 | F |
| 2-49 | F |
| 2-50 | A |
| 2-51 | B |
| 2-52 | C |
| 2-53 | E |
| 2-54 | A |

Compounds of Table 3 were assayed for their ability to activate AMPK using an enzyme-linked immunosorbent assay. The EC$_{50}$ values for AMPK activation for the tested compounds are presented in Table 8 below, in which "A" is less than 0.1 µM; "B" is 0.1-1 µM; "C" is 1-10 µM; and "D" is 10-100 µM:

TABLE 8

| Cpd No. | AMPK EC$_{50}$ |
|---|---|
| 3-1 | A |
| 3-2 | A |
| 3-3 | A |
| 3-4 | A |
| 3-5 | D |
| 3-6 | A |
| 3-7 | A |
| 3-8 | B |
| 3-9 | B |
| 3-10 | B |
| 3-11 | B |
| 3-12 | A |
| 3-13 | A |
| 3-14 | C |
| 3-15 | B |
| 3-16 | B |
| 3-17 | A |
| 3-18 | A |
| 3-19 | C |
| 3-20 | F |
| 3-21 | A |
| 3-22 | A |
| 3-23 | A |
| 3-24 | A |
| 3-25 | A |
| 3-26 | C |
| 3-27 | A |
| 3-28 | A |
| 3-29 | D |
| 3-30 | A |
| 3-31 | A |
| 3-32 | D |
| 3-33 | D |
| 3-34 | A |
| 3-35 | C |
| 3-36 | B |
| 3-37 | A |
| 3-38 | A |
| 3-39 | C |
| 3-40 | A |
| 3-41 | C |
| 3-42 | B |

Compounds of Table 4 were assayed for their ability to activate AMPK using an enzyme-linked immunosorbent assay. The EC$_{50}$ values for AMPK activation for the tested compounds are presented in Table 9 below, in which "A" is less than 0.5 µM; "B" is 0.5-1 µM; "C" is 1-5 µM; and "D" is 5-10 µM; "E" is 10-50 µM; and "F" is >100 µM:

TABLE 9

| Cpd No. | AMPK EC$_{50}$ |
|---|---|
| 1 | A |
| 2 | A |
| 3 | A |
| 4 | C |
| 5 | C |
| 6 | B |
| 7 | C |
| 8 | C |

Compounds of Table 5 were assayed for their ability to activate AMPK using an enzyme-linked immunosorbent assay. The EC$_{50}$ values for AMPK activation for the tested compounds are presented in Table 10 below, in which "A" is less than 1 µM; "B" is 1-10 µM; "C" is 10-20 µM; "D" is 20-50 µM; "E" is 50-100 µM, and "F" is >100 µM:

TABLE 10

| Cpd No. | AMPK EC$_{50}$ |
|---|---|
| 5-1 | A |
| 5-2 | A |
| 5-3 | B |
| 5-4 | F |
| 5-5 | E |
| 5-6 | A |
| 5-7 | A |
| 5-8 | B |
| 5-9 | D |
| 5-10 | B |
| 5-11 | B |
| 5-12 | B |
| 5-13 | D |
| 5-14 | A |
| 5-15 | A |
| 5-16 | A |
| 5-17 | A |
| 5-18 | A |
| 5-19 | A |
| 5-20 | A |
| 5-21 | B |
| 5-22 | B |
| 5-23 | A |
| 5-24 | C |
| 5-25 | F |
| 5-26 | A |
| 5-27 | A |
| 5-28 | A |
| 5-29 | A |
| 5-30 | A |
| 5-31 | A |
| 5-32 | A |
| 5-33 | A |
| 5-34 | A |
| 5-35 | B |
| 5-36 | A |
| 5-37 | A |
| 5-38 | B |
| 5-39 | B |
| 5-40 | A |
| 5-41 | A |
| 5-42 | A |
| 5-43 | A |
| 5-44 | A |
| 5-45 | A |
| 5-46 | A |
| 5-47 | A |
| 5-48 | A |
| 5-49 | A |
| 5-50 | B |
| 5-51 | A |
| 5-52 | B |
| 5-53 | C |
| 5-54 | A |
| 5-55 | A |
| 5-56 | A |
| 5-57 | A |
| 5-58 | B |
| 5-59 | A |
| 5-60 | A |
| 5-61 | A |
| 5-62 | A |
| 5-63 | A |
| 5-64 | A |
| 5-65 | A |
| 5-66 | A |
| 5-67 | A |
| 5-68 | A |
| 5-69 | A |
| 5-70 | A |
| 5-71 | A |
| 5-72 | A |
| 5-73 | A |
| 5-74 | A |
| 5-75 | A |
| 5-76 | A |
| 5-77 | A |
| 5-78 | A |
| 5-79 | F |
| 5-80 | A |
| 5-81 | A |
| 5-82 | A |
| 5-83 | A |
| 5-84 | A |
| 5-85 | A |
| 5-86 | A |
| 5-87 | A |
| 5-88 | B |
| 5-89 | B |
| 5-90 | B |
| 5-91 | A |
| 5-92 | B |
| 5-93 | F |
| 5-94 | A |
| 5-95 | A |
| 5-96 | B |
| 5-97 | B |
| 5-98 | B |
| 5-99 | B |
| 5-100 | B |
| 5-101 | C |
| 5-102 | C |
| 5-103 | D |
| 5-104 | C |
| 5-105 | C |

Endurance Testing

Male C57B/6J mice (8 weeks old) are randomly divided into at least four cohorts for exercise-trained and sedentary control and dosage groups.

Mice are acclimated to moderate treadmill running (10 m/min for 15 min) every other day for 1 week (day 1, 3, 5, 7). After acclimation, basal running endurances for the four groups are determined via a treadmill running test, where the speed is gradually increased from 0 to 15 m/min over the course of 15 min and then maintained constant until exhaustion. Treadmill to be used is 1012M-8-E52 Modular Enclosed Metabolic Treadmill for Mice, 8 Lanes w/ Shock for Mice w/ Shocker Detection & Software from Columbus Instruments or similar (with attached open-flow calorimeter for the measurement of respiratory metabolic performance while exercising). Exhaustion defined when mice are unable to avoid repetitive electrical shocks. Data are collected on total time and distance run as well as VO$_2$.

On day 8 dosing by gavage with the adiponectin receptor agonist begins for the sedentary and exercise-trained groups and dosing with vehicle only for the control sedentary and exercise-trained groups.

Beginning on day 9, the groups to be exercise-trained are subjected to 4 weeks (5 days/week) of exercise training. During all exercise sessions and treadmill tests, VO$_2$ is measured before, during, and after exercise by means of indirect calorimetry in metabolic treadmill chambers. The 5th day of training for each weekly exercise regime is used as a complete treadmill test where the speed is gradually increased from 0 to 15 m/min over the course of 15 min and then maintained constant until exhaustion. Day 9 exercise to consist of treadmill running of 10 m/min for 15 min with a treadmill incline of 5 degrees. Subsequent exercise-training is to be progressive with increasing intensity and time (also incline of 5 degrees on treadmill). Data are collected on total time and distance for each training session, with point of exhaustion noted for mice failing to complete exercise.

Treatment with the present adiponectin receptor agonists results in increased endurance for both the exercise-trained and sedentary groups.

What is claimed is:

1. A method for treating or ameliorating a disorder or condition selected from exercise intolerance resulting from mitochondrial dysfunction, chronic fatigue syndrome resulting from mitochondrial dysfunction, muscle weakness resulting from mitochondrial dysfunction, myoclonus resulting from mitochondrial dysfunction, myoclonus epilepsy, Kearns-Sayre syndrome, Leigh's syndrome, mitochondrial myopathy encephalopathy lactacidosis stroke (MELAS) syndrome, and intermittent claudication in a subject, the method comprising administering to the subject an effective amount of a compound having the structural formula

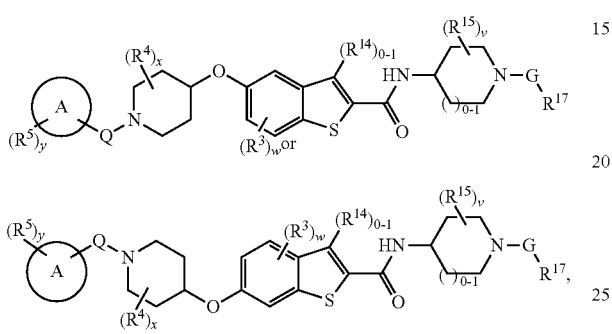

or a pharmaceutically acceptable salt or N-oxide thereof, wherein
- each $R^3$ is independently selected from —($C_1$-$C_3$ alkyl), —($C_1$-$C_3$ haloalkyl), —($C_0$-$C_3$alkyl)-L-$R^7$, —($C_0$-$C_3$ alkyl)-NR$^8$R$^9$, —($C_0$-$C_3$ alkyl)-OR$^{10}$, —($C_0$-$C_3$ alkyl)-C(O)R$^{10}$, —($C_0$-$C_3$ alkyl)-S(O)$_{0-2}$R$^{10}$, -halogen, —NO$_2$ and —CN;
- w is 0, 1, 2 or 3;
- $R^{14}$ is independently selected from —($C_1$-$C_3$ alkyl), —($C_1$-$C_3$ haloalkyl), —($C_0$-$C_3$ alkyl)-L-$R^7$, —($C_0$-$C_3$ alkyl)-NR$^8$R$^9$, —($C_0$-$C_3$ alkyl)-OR$^{10}$, —($C_0$-$C_3$ alkyl)-C(O)R$^{10}$, —($C_0$-$C_3$ alkyl)-S(O)$_{0-2}$R$^{10}$, -halogen, —NO$_2$ and —CN;
- each $R^4$ is independently selected from —($C_1$-$C_3$ alkyl), —($C_1$-$C_3$ haloalkyl), —($C_0$-$C_3$alkyl)-L-$R^7$, —($C_0$-$C_3$ alkyl)-NR$^8$R$^9$, —($C_0$-$C_3$ alkyl)-OR$^{10}$, —($C_0$-$C_3$ alkyl)-C(O)R$^{10}$, —($C_0$-$C_3$ alkyl)-S(O)$_{0-2}$R$^{10}$, -halogen, —NO$_2$ and —CN and two $R^4$ on the same carbon optionally combine to form oxo;
- x is 0, 1, 2, 3 or 4;
- each Q is —CH$_2$—, a single bond, —C(O)—, —S(O)$_2$— or —CH(CH$_3$)—;
- the ring system denoted by "A" is monocyclic heteroaryl or phenyl;
- each $R^5$ is independently selected from —($C_1$-$C_3$ alkyl), —($C_1$-$C_3$ haloalkyl), —($C_0$-$C_3$alkyl)-L-$R^7$, —($C_0$-$C_3$ alkyl)-NR$^8$R$^9$, —($C_0$-$C_3$ alkyl)-OR$^{10}$, —($C_0$-$C_3$ alkyl)-C(O)R$^{10}$, —($C_0$-$C_3$ alkyl)-S(O)$_{0-2}$R$^{10}$, -halogen, —NO$_2$ and —CN; and
- y is 0, 1, 2, 3 or 4;
- each $R^{15}$ is independently selected from —($C_1$-$C_3$ alkyl), —($C_1$-$C_3$ haloalkyl), —($C_0$-$C_3$alkyl)-L-$R^7$, —($C_0$-$C_3$ alkyl)-NR$^8$R$^9$, —($C_0$-$C_3$ alkyl)-OR$^{10}$, —($C_0$-$C_3$ alkyl)-C(O)R$^{10}$, —($C_0$-$C_3$ alkyl)-S(O)$_{0-2}$R$^{10}$, -halogen, —NO$_2$ and —CN, and two $R^{15}$ on the same carbon optionally combine to form oxo; and
- v is 0, 1, 2, 3 or 4;
- G is —CH$_2$—, —C(O)—, —S(O)$_2$— or —CH(CH$_3$)—; and
- $R^{17}$ is aryl or heteroaryl, optionally substituted with 1, 2 or 3 substituents independently selected from —($C_1$-$C_3$ alkyl), —($C_1$-$C_3$ haloalkyl), —($C_0$-$C_3$ alkyl)-L-$R^7$, —($C_0$-$C_3$ alkyl)-NR$^8$R$^9$, —($C_0$-$C_3$ alkyl)-OR$^{10}$, —($C_0$-$C_3$ alkyl)-C(O)R$^{10}$, —($C_0$-$C_3$ alkyl)-S(O)$_{0-2}$R$^{10}$, -halogen, —NO$_2$ and —CN;
- in which
  - each L is independently selected from —NR$^9$C(O)O—, —OC(O)NR$^9$—, —NR$^9$C(O)—NR$^9$—, —NR$^9$C(O)S—, —SC(O)NR$^9$—, —NR$^9$C(O)—, —C(O)NR$^9$—, —NR$^9$C(S)O—, —OC(S)NR$^9$—, —NR$^9$C(S)—NR$^9$—, —NR$^9$C(S)S—, —SC(S)NR$^9$—, —NR$^9$C(S)—, —C(S)NR$^9$—, —SC(O)NR$^9$—, —NR$^9$C(S)—, —S(O)$_{0-2}$—, —C(O)O, —OC(O)—, —C(S)O—, —OC(S)—, —C(O)S—, —SC(O)—, —C(S)S—, —SC(S)—, —OC(O)O—, —SC(O)O—, —OC(O)S—, —SC(S)O—, —OC(S)S—, —NR$^9$C(NR$^2$)NR$^9$—, —NR$^9$SO$_2$—, —SO$_2$NR$^9$— and —NR$^9$SO$_2$NR$^9$—,
  - each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-NR$^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and
  - each $R^9$ is independently selected from —H, —($C_1$-$C_4$ alkyl) and —C(O)O—($C_1$-$C_4$ alkyl) and wherein the subject does not have type 2 diabetes.

2. The method of claim 1, wherein the administration increases metabolic efficiency in the subject.

3. The method of claim 2, wherein the method is for treating intermittent claudication.

4. A method according to claim 1, wherein the ring system denoted by "A" is phenyl, pyridyl, thienyl or furanyl; and
$R^{17}$ is phenyl or pyridnyl, optionally substituted with 1, 2 or 3 substituents independently selected from —($C_1$-$C_3$ alkyl), —($C_1$-$C_3$ haloalkyl), —($C_0$-$C_3$ alkyl)-L-$R^7$, —($C_0$-$C_3$ alkyl)-NR$^8$R$^9$, —($C_0$-$C_3$—($C_0$-$C_3$ alkyl)-C(O)R$^{10}$, —($C_0$-$C_3$ alkyl)-S(O)$_{0-2}$R$^{10}$, -halogen, —NO$_2$ and —CN.

5. A method according to claim 1, wherein the ring system denoted by "A" is phenyl; and
$R^{17}$ is phenyl, optionally substituted with 1, 2 or 3 substituents independently selected from —($C_1$-$C_3$ alkyl), —($C_1$-$C_3$ haloalkyl), —($C_0$-$C_3$ alkyl)-L-$R^7$, —($C_0$-$C_3$ alkyl)-NR$^8$R$^9$, —($C_0$-$C_3$alkyl)-OR$^{10}$, —($C_0$-$C_3$ alkyl)-C(O)R$^{10}$, —($C_0$-$C_3$ alkyl)-S(O)$_{0-2}$R$^{10}$, -halogen, —NO$_2$ and —CN.

6. A method according to claim 1, wherein no $R^{14}$ is substituted on the furano carbon.

7. A method according to claim 1, wherein $R^{14}$ is halo, cyano, unsubstituted —($C_1$-$C_4$ alkyl) or unsubstituted —($C_1$-$C_4$ haloalkyl).

8. A method according to claim 1, wherein G is —CH$_2$—.

9. A method according to claim 1, wherein G is —C(O)— or —S(O)$_2$—.

10. A method according to claim 1, wherein
x is 0;
v is 0;
w is 0; and
no $R^{14}$ is substituted on the furano carbon, or $R^{14}$ is halo, cyano, unsubstituted —($C_1$-$C_4$ alkyl) or unsubstituted —($C_1$-$C_4$ haloalkyl).

11. A method according to claim 1, wherein
x is 0 or 1;
v is 0, 1 or 2; and
w is 0, 1 or 2.

12. A method according to claim 1, wherein the compound has the structural formula

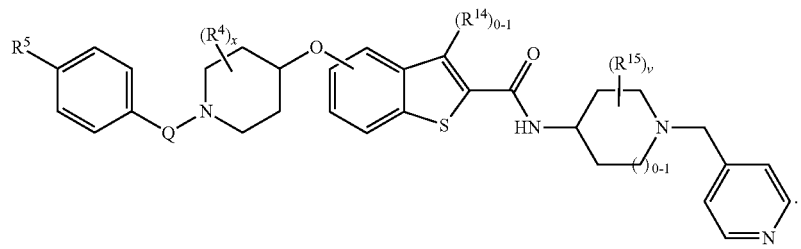

13. A method according to claim 1, wherein the compound has the structural formula

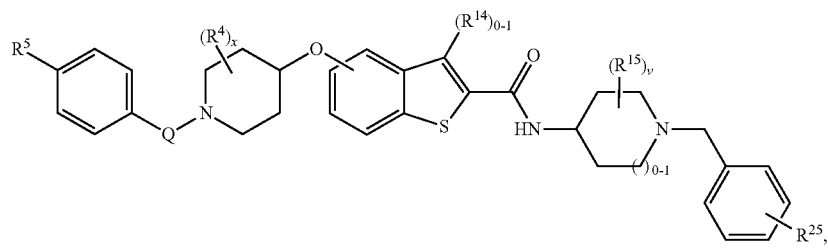

in which $R^{25}$ is selected from halo, cyano, —($C_1$-$C_3$ haloalkyl), —O—($C_1$-$C_2$ haloalkyl), —($C_1$-$C_3$ alkyl), —O—($C_1$-$C_2$ alkyl), —C(O)—($C_0$-$C_2$ alkyl), —C(O)O—($C_0$-$C_2$ alkyl), —C(O)N($C_0$-$C_4$ alkyl)($C_0$-$C_2$ alkyl) and $NO_2$.

14. A method according to claim 1, wherein the compound has the structural formula

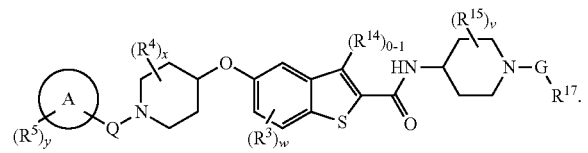

15. A method according to claim 14, wherein
x is 0;
v is 0;
w is 0; and
no $R^{14}$ is substituted on the furano carbon, or $R^{14}$ is halo, cyano, unsubstituted —($C_1$-$C_4$ alkyl) or unsubstituted —($C_1$-$C_4$ haloalkyl).

16. A method according to claim 1, wherein the compound has the structural formula

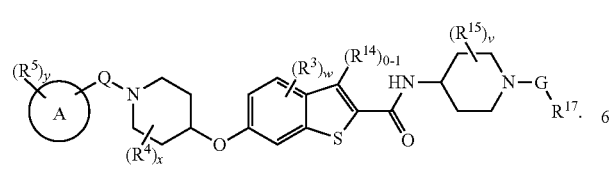

17. A method according to claim 16, wherein
x is 0;
v is 0;
w is 0; and
no $R^{14}$ is substituted on the furano carbon, or $R^{14}$ is halo, cyano, unsubstituted —($C_1$-$C_4$ alkyl) or unsubstituted —($C_1$-$C_4$ haloalkyl).

18. A method according to claim 1, wherein v is 0 and w is 0.

19. A method according to claim 1, wherein
x is 0;
v is 0;
w is 0;
Q is a single bond or —$CH_2$—;
G is —$CH_2$— or —C(O)—; and
no $R^{14}$ is substituted on the furano carbon, or $R^{14}$ is halo, cyano, unsubstituted —($C_1$-$C_4$ alkyl) or unsubstituted —($C_1$-$C_4$ haloalkyl).

20. A method according to claim 1, wherein
x is 0;
v is 0;
w is 0;
Q is a single bond;
G is —$CH_2$—; and
no $R^{14}$ is substituted on the furano carbon, or $R^{14}$ is halo, cyano, unsubstituted —($C_1$-$C_4$ alkyl) or unsubstituted —($C_1$-$C_4$ haloalkyl).

21. A method according to claim 1, wherein
Q is a single bond or —$CH_2$—; and
G is —$CH_2$— or —C(O)—.

22. A method according to claim 1, wherein
Q is a single bond; and
G is —$CH_2$—.

23. A method according to claim 1, wherein the compound is
N-(1-(pyridin-4-ylmethyl)piperidin-4-yl)-5-(1-(4-(trifluoromethoxy)phenyl)piperidin-4-yloxy)benzo[b]thiophene-2-carboxamide;
N-(1-(pyridin-4-ylmethyl)piperidin-4-yl)-5-(1-(4-(trifluoromethyl)phenyl)piperidin-4-yloxy)benzo[b]thiophene-2-carboxamide;

N-(1-(pyridin-4-ylmethyl)piperidin-4-yl)-5-(1-(4-chlorophenyl)piperidin-4-yloxy)benzo[b]thiophene-2-carboxamide;

N-(1-(pyridin-4-ylmethyl)piperidin-4-yl)-6-(1-(4-(trifluoromethyl)phenyl)piperidin-4-yloxy)benzo[b]thiophene-2-carboxamide;

N-(1-(pyridin-2-ylmethyl)piperidin-4-yl)-6-(1-(4-(trifluoromethyl)phenyl)piperidin-4-yloxy)benzo[b]thiophene-2-carboxamide;

N-(1-(4-cyanobenzyl)piperidin-4-yl)-6-(1-(4-(trifluoromethyl)phenyl)piperidin-4-yloxy)benzo[b]thiophene-2-carboxamide;

N-(1-(3-cyanobenzyl)piperidin-4-yl)-6-(1-(4-(trifluoromethyl)phenyl)piperidin-4-yloxy)benzo[b]thiophene-2-carboxamide;

N-(1-(2-cyanobenzyl)piperidin-4-yl)-6-(1-(4-(trifluoromethyl)phenyl)piperidin-4-yloxy)benzo[b]thiophene-2-carboxamide;

3-chloro-N-(1-(pyridin-4-ylmethyl)piperidin-4-yl)-6-(1-(4-(trifluoromethyl)phenyl)piperidin-4-yloxy)benzo[b]thiophene-2-carboxamide;

3-chloro-N-(1-(pyridin-3-ylmethyl)piperidin-4-yl)-6-(1-(4-(trifluoromethyl)phenyl)piperidin-4-yloxy)benzo[b]thiophene-2-carboxamide;

3-chloro-N-(1-(pyridin-2-ylmethyl)piperidin-4-yl)-6-(1-(4-(trifluoromethyl)phenyl)piperidin-4-yloxy)benzo[b]thiophene-2-carboxamide;

3-chloro-N-(1-(4-cyanobenzyl)piperidin-4-yl)-6-(1-(4-(trifluoromethyl)phenyl)piperidin-4-yloxy)benzo[b]thiophene-2-carboxamide; or 3-chloro-N-(1-isonicotinoylpiperidin-4-yl)-6-(1-(4-(trifluoromethyl)phenyl)piperidin-4-yloxy)benzo[b]thiophene-2-carboxamide.

24. The method of claim 1, wherein the disorder is exercise intolerance resulting from mitochondrial dysfunction.

25. The method of claim 1, wherein the method is for treating or ameliorating intermittent claudication in the subject.

* * * * *